(12) United States Patent
Numata et al.

(10) Patent No.: US 11,542,252 B2
(45) Date of Patent: Jan. 3, 2023

(54) HETEROCYCLIC COMPOUND, COMPOSITION INCLUDING THE SAME, AND ORGANIC LIGHT-EMITTING DEVICE INCLUDING THE HETEROCYCLIC COMPOUND

(71) Applicant: Samsung Electronics Co., Ltd., Suwon-si (KR)

(72) Inventors: Masaki Numata, Kanagawa-ken (JP); Rie Sakurai, Kanagawa-ken (JP); Keisuke Korai, Kanagawa-ken (JP); Mitsunori Ito, Kanagawa-ken (JP); Shiro Irisa, Kanagawa-ken (JP); Norihito Ishii, Kanagawa-ken (JP)

(73) Assignee: SAMSUNG ELECTRONICS CO., LTD., Gyeonggi-Do (KR)

(*) Notice: Subject to any disclaimer, the term of this patent is extended or adjusted under 35 U.S.C. 154(b) by 350 days.

(21) Appl. No.: 16/722,308

(22) Filed: Dec. 20, 2019

(65) Prior Publication Data

US 2020/0207739 A1 Jul. 2, 2020

(30) Foreign Application Priority Data

Dec. 28, 2018 (JP) .............................. JP2018-248437
Dec. 28, 2018 (JP) .............................. JP2018-248439
Oct. 30, 2019 (KR) ........................ 10-2019-0136945

(51) Int. Cl.
*C07D 403/04* (2006.01)
*C07D 403/10* (2006.01)
(Continued)

(52) U.S. Cl.
CPC ........ *C07D 403/04* (2013.01); *H01L 51/0052* (2013.01); *H01L 51/0072* (2013.01); *H01L 51/5016* (2013.01)

(58) Field of Classification Search
CPC .. C07D 403/04; C07D 403/10; H01L 51/5016
See application file for complete search history.

(56) References Cited

U.S. PATENT DOCUMENTS 8,324,403 B2 12/2012 Yabe et al.
8,847,141 B2 9/2014 Fukuzaki et al.
(Continued)

FOREIGN PATENT DOCUMENTS

CN 105968041 A 9/2016
EP 1972619 A1 * 9/2008 ........... C07D 209/58
(Continued)

OTHER PUBLICATIONS

Extended European search report issued by the European Patent Office dated Sep. 2, 2020 in the examination of the European Patent Application No. 19218584.1, which corresponds to the U.S. Application above.
(Continued)

*Primary Examiner* — Vu A Nguyen
(74) *Attorney, Agent, or Firm* — Cantor Colburn LLP

(57) ABSTRACT

A heterocyclic compound represented by Formula 1, a composition including the same, and an organic light-emitting device including the heterocyclic compound:
(Continued)

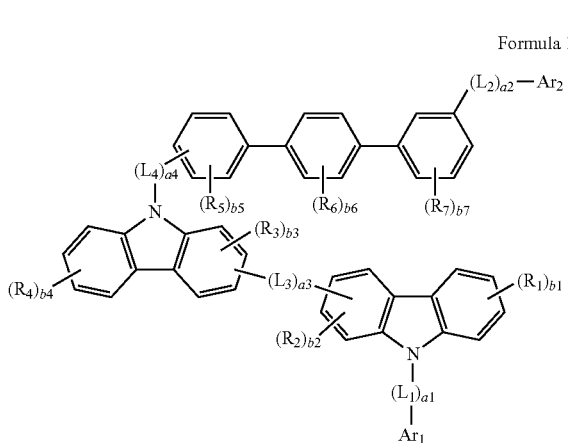

Formula 1

$L_1$ to $L_4$, $L_{11}$, a1 to a4, a11, $Ar_1$, $Ar_2$, $Ar_{11}$, $R_1$ to $R_7$, $R_{11}$ to $R_{12}$, b1 to b7, and b11 to b12 are described in the specification.

20 Claims, 5 Drawing Sheets

(51) Int. Cl.
  *H01L 51/00* (2006.01)
  *H01L 51/50* (2006.01)

(56) References Cited

U.S. PATENT DOCUMENTS

| | | |
|---|---|---|
| 9,000,421 B2 | 4/2015 | Yamamoto et al. |
| 9,680,111 B2 | 6/2017 | Feldman et al. |
| 9,944,846 B2 | 4/2018 | Wang et al. |
| 10,153,436 B2 | 12/2018 | Yu et al. |
| 10,193,081 B2 | 1/2019 | Kim et al. |
| 10,199,577 B2 | 2/2019 | Park et al. |
| 10,381,579 B2 | 8/2019 | Lin et al. |
| 2012/0175598 A1 | 7/2012 | Balaganesan et al. |
| 2014/0061629 A1 | 3/2014 | Murase et al. |
| 2015/0053938 A1 | 2/2015 | Zeng et al. |
| 2015/0115205 A1 | 4/2015 | Kang et al. |
| 2015/0221874 A1 | 8/2015 | Kim et al. |
| 2015/0243894 A1 | 8/2015 | Zeng et al. |
| 2015/0266863 A1 | 9/2015 | Dyatkin et al. |
| 2016/0093808 A1 | 3/2016 | Adamovich et al. |
| 2016/0315259 A1 | 10/2016 | Fennimore et al. |
| 2017/0047527 A1 | 2/2017 | Lee et al. |
| 2017/0263869 A1 | 9/2017 | Tada et al. |
| 2018/0155325 A1* | 6/2018 | Lee .............. H01L 51/0054 |
| 2019/0006590 A1 | 1/2019 | Park et al. |
| 2019/0393430 A1 | 12/2019 | Park et al. |

FOREIGN PATENT DOCUMENTS

| | | |
|---|---|---|
| EP | 1972619 A1 | 9/2008 |
| EP | 2259358 A2 | 12/2010 |
| EP | 3015527 A1 | 5/2016 |
| EP | 3336159 A1 | 6/2018 |
| JP | 2006199679 A | 8/2006 |
| JP | 2007126443 A | 5/2007 |
| JP | 2011509247 A | 3/2011 |
| JP | 2013183011 A | 9/2013 |
| JP | 2014509067 A | 4/2014 |
| JP | 2015532783 A | 11/2015 |
| KR | 1020130004780 A | 1/2013 |
| KR | 101507003 B1 | 7/2013 |
| KR | 1020130118059 A | 10/2013 |
| KR | 1020150010387 A | 1/2015 |
| KR | 1020150105201 A | 9/2015 |
| KR | 1020160086736 A | 7/2016 |
| WO | 2007029798 A1 | 3/2007 |
| WO | 2011159872 A1 | 12/2011 |
| WO | 2013077345 A1 | 5/2013 |
| WO | 2013094854 A1 | 6/2013 |
| WO | 2013165189 A1 | 11/2013 |
| WO | 2014017484 A1 | 1/2014 |
| WO | 2015009102 A1 | 1/2015 |
| WO | 2015167259 A1 | 11/2015 |
| WO | 2016033167 A1 | 3/2016 |
| WO | 2016036171 A1 | 3/2016 |
| WO | 2016204406 A1 | 12/2016 |
| WO | WO-2016204406 A1 * | 12/2016 ........... C07D 209/82 |
| WO | 2017034085 A1 | 3/2017 |
| WO | 2018117618 A1 | 6/2018 |

OTHER PUBLICATIONS

Partial European search report issued by the European Patent Office dated Apr. 22, 2020 in the examination of the European Patent Application No. 19218584.1, which corresponds to the U.S. Application above.

* cited by examiner

HETEROCYCLIC COMPOUND, COMPOSITION INCLUDING THE SAME, AND ORGANIC LIGHT-EMITTING DEVICE INCLUDING THE HETEROCYCLIC COMPOUND

CROSS-REFERENCE TO RELATED APPLICATIONS

This application claims priority to and the benefit of Korean Patent Application No. 10-2019-0136945, filed on Oct. 30, 2019, in the Korean Intellectual Property Office, and Japanese Patent Application No. 2018-248437, filed on Dec. 28, 2018, and Japanese Patent Application No. 2018-248439, filed on Dec. 28, 2018, in the Japanese Patent Office, and all of the benefits accruing therefrom under 35 U.S.C. § 119, the contents of which are incorporated herein in their entirety by reference.

BACKGROUND

1. Field

One or more embodiments relate to a heterocyclic compound, a material for an organic light-emitting device including the heterocyclic compound, and an organic light-emitting device including the heterocyclic compound.

2. Description of Related Art

Organic light-emitting devices are self-emission devices that produce full-color images, and also have wide viewing angles, high contrast ratios, short response times, as well as excellent characteristics in terms of brightness, driving voltage, and response speed.

In an example, an organic light-emitting device includes an anode, a cathode, and an organic layer between the anode and the cathode, wherein the organic layer includes an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

SUMMARY

One or more embodiments include a heterocyclic compound, a composition including the same, and an organic light-emitting device using the heterocyclic compound.

In manufacturing an organic light-emitting device, it is common to form an organic film constituting the organic light-emitting device by a dry film-forming method such as a vapor deposition method. However, when a film is formed by a dry film-forming method, such as a vapor deposition method, relatively long time and high costs are needed. Therefore, instead of such a dry film-forming method, wet film-forming methods, such as a solution coating method (henceforth a coating method), which may reduce the amount of time and the costs, are considered for use in the manufacturing process.

However, when wet film-forming methods are applied to conventional compounds, due to the low solubility of the compounds, the pot life (lifespan in solution) of the solution is short. After the film formation, aggregation of organic molecules may occur in an emission layer. Therefore, an organic light-emitting device formed by the coating method may not have sufficient current efficiency and light-emission lifespan.

Organic light-emitting devices using such conventional compounds have low efficiency and short lifespans.

Accordingly, the present disclosure provides a compound having high solubility and long solution pot life and an organic light emitting device having high efficiency and a long lifespan.

Specifically, an organic light-emitting device including the heterocyclic compound may have high luminescent efficiency and a long lifespan. In addition, the heterocyclic compound may have a low glass transition temperature and thus have high solubility, thereby increasing the pot life of the solution including the compound, and thus may be suitable for use in a solution coating method.

Additional aspects will be set forth in part in the description which follows and, in part, will be apparent from the description, or may be learned by practice of the presented embodiments of the disclosure.

According to an aspect of an embodiment, a heterocyclic compound represented by Formula 1 is provided.

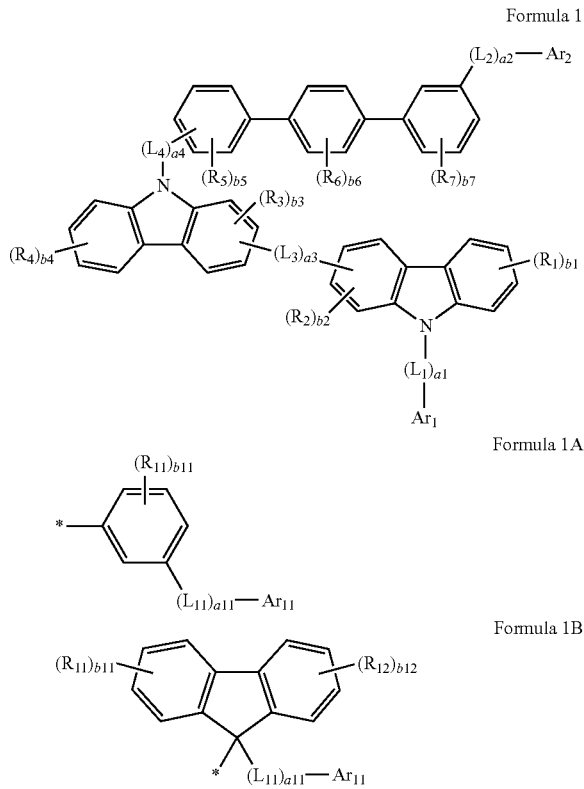

Formula 1

Formula 1A

Formula 1B

In Formulae 1, 1A, and 1B, $L_1$ to $L_4$ and $L_{11}$ may each independently be a single bond, a substituted or unsubstituted $C_5$-$C_{60}$ carbocyclic group, or a substituted or unsubstituted nitrogen-free $C_1$-$C_{60}$ heterocyclic group, a1 to a4 and a11 may each independently be an integer from 1 to 5, $Ar_1$ and $Ar_{11}$ may each independently be a substituted or unsubstituted $C_5$-$C_{60}$ carbocyclic group, or a substituted or unsubstituted nitrogen-free $C_1$-$C_{60}$ heterocyclic group, $Ar_2$ is a group represented by Formula 1A or Formula 1B, $R_1$ to $R_7$ and $R_{11}$ to $R_{12}$ may each independently be hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted nitrogen-free $C_1$-$C_{10}$ heterocycloalkyl group, a substituted or unsubstituted $C_3$-$C_{10}$ cycloalkenyl group, a substituted or unsubstituted nitrogen-free $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_7$-$C_{60}$ aryl alkyl group, a substituted or unsubstituted $C_7$-$C_{60}$ arylalkyloxy group, a substituted or unsubstituted $C_7$-$C_{60}$ arylalkylthio group, a substituted or unsubstituted $C_8$-$C_{30}$ arylalkenyl group, a substituted or unsubstituted $C_8$-$C_{30}$ arylalkynyl group, a substituted or unsubstituted $C_6$-$C_{60}$ aryloxy group, a substituted or unsubstituted $C_6$-$C_{60}$ arylthio group, a substituted or unsubstituted nitrogen-free $C_1$-$C_{60}$ heteroaryl group, a substituted or unsubstituted nitrogen-free $C_2$-$C_{60}$ alkylheteroaryl group, a substituted or unsubstituted nitrogen-free $C_1$-$C_{60}$ heteroaryloxy group, a substituted or unsubstituted nitrogen-free $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), or —N($Q_1$)($Q_2$), b2 and b3 may each independently be an integer from 0 to 3, b1, b4 to b7, b11, and b12 may each independently be an integer from 0 to 4, two adjacent $R_1$(s) in the number of b1, $R_2$(s) in the number of b2, $R_3$(s) in the number of b3, $R_4$(s) in the number of b4, $R_5$(s) in the number of b5, $R_6$(s) in the number of b6, $R_7$(s) in the number of b7, $R_{11}$(s) in the number of b11, and $R_{12}$(s) in the number of b12 may each optionally be linked to each other to form a substituted or unsubstituted $C_5$-$C_{30}$ carbocyclic group or a substituted or unsubstituted $C_1$-$C_{30}$ heterocyclic group, at least one substituent of the substituted $C_5$-$C_{60}$ carbocyclic group, the substituted nitrogen-free $C_1$-$C_{60}$ heterocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted nitrogen-free $C_1$-$C_{10}$ heterocycloalkyl group, the substituted $C_3$-$C_{10}$ cycloalkenyl group, the substituted nitrogen-free $C_1$-$C_{10}$ heterocycloalkenyl group, the substituted $C_6$-$C_{60}$ aryl group, the substituted $C_7$-$C_{60}$ alkylaryl group, the substituted $C_7$-$C_{60}$ aryl alkyl group, the substituted $C_7$-$C_{60}$ arylalkyloxy group, the substituted $C_7$-$C_{60}$ arylalkylthio group, the substituted $C_8$-$C_{30}$ arylalkenyl group, the substituted $C_8$-$C_{30}$ arylalkynyl group, the substituted $C_6$-$C_{60}$ aryloxy group, the substituted $C_6$-$C_{60}$ arylthio group, the substituted nitrogen-free $C_1$-$C_{60}$ heteroaryl group, the substituted nitrogen-free $C_2$-$C_{60}$ alkylheteroaryl group, the substituted nitrogen-free $C_1$-$C_{60}$ heteroaryloxy group, the substituted nitrogen-free $C_1$-$C_{60}$ heteroarylthio group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a nitrogen-free $C_1$-$C_{10}$ heterocycloalkyl group, a $C_3$-$C_{10}$ cycloalkenyl group, a nitrogen-free $C_1$-$C_{10}$ heterocycloalkenyl group, Si($Q_{11}$)($Q_{12}$)($Q_{13}$), —N($Q_{11}$)($Q_{12}$), —C(=O)($Q_{11}$), or any combination thereof;

a $C_3$-$C_{10}$ cycloalkyl group, a nitrogen-free $C_1$-$C_{10}$ heterocycloalkyl group, a $C_3$-$C_{10}$ cycloalkenyl group, or a nitrogen-free $C_1$-$C_{10}$ heterocycloalkenyl group;

a $C_3$-$C_{10}$ cycloalkyl group, a nitrogen-free $C_1$-$C_{10}$ heterocycloalkyl group, a $C_3$-$C_{10}$ cycloalkenyl group, or a nitrogen-free $C_1$-$C_{10}$ heterocycloalkenyl group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a nitrogen-free heterocycloalkyl group, a $C_3$-$C_{10}$ cycloalkenyl group, a nitrogen-free $C_1$-$C_{10}$ heterocycloalkenyl group, —Si($Q_{21}$)($Q_{22}$)($Q_{23}$), —N($Q_{21}$)($Q_{22}$), —C(=O)($Q_{21}$), or any combination thereof; or —Si($Q_{31}$)($Q_{32}$)($Q_{33}$), —N($Q_{31}$)($Q_{32}$), or —C(=O)($Q_{31}$), wherein $Q_1$ to $Q_3$, $Q_{11}$ to $Q_{13}$, $Q_{21}$ to $Q_{23}$ and $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* indicates a binding site to a neighboring atom.

Another aspect provides a composition including at least one heterocyclic compound represented by Formula 1.

Another aspect provides an organic light-emitting device including: a first electrode; a second electrode; and an organic layer placed between the first electrode and the second electrode and including an emission layer, wherein the organic light-emitting device includes at least one heterocyclic compound represented by Formula 1.

Another aspect provides a heterocyclic compound represented by Formula 2:

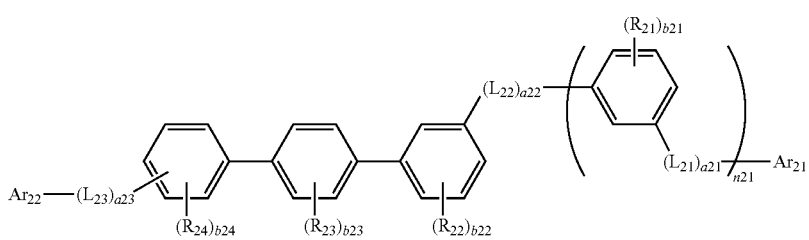

Formula 2

Formula 2A

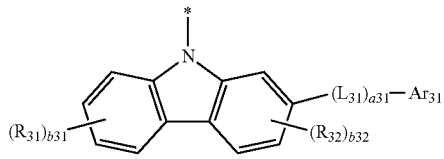

Formula 2B

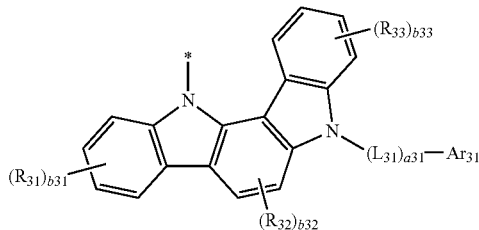

Formula 2C

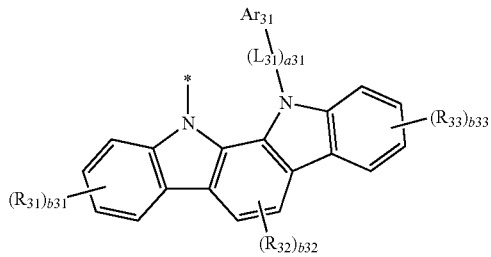

In Formulae 2 and 2A to 2C, $L_{21}$ to $L_{23}$ and $L_{31}$ may each independently be a single bond, a substituted or unsubstituted $C_5$-$C_{60}$ carbocyclic group, or a substituted or unsubstituted $C_1$-$C_{60}$ heterocyclic group, a21 to a23 and a31 may each independently be an integer from 1 to 5, $Ar_{21}$ and $Ar_{31}$ may each independently be a substituted or unsubstituted $C_5$-$C_{60}$ carbocyclic group, or a substituted or unsubstituted $C_1$-$C_{60}$ heterocyclic group, $Ar_{22}$ may be a group represented by one of Formulae 2A to 2C, the $C_1$-$C_{60}$ heterocyclic group of $A_{21}$ and $A_{31}$ is not an azine group, $R_{21}$ to $R_{24}$ and $R_{31}$ to $R_{33}$ may each independently be hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_7$-$C_{60}$ aryl alkyl group, a substituted or unsubstituted $C_7$-$C_{60}$ arylalkyloxy group, a substituted or unsubstituted $C_7$-$C_{60}$ arylalkylthio group, a substituted or unsubstituted $C_8$-$C_{30}$ arylalkenyl group, a substituted or unsubstituted $C_8$-$C_{30}$ arylalkynyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), or —N($Q_1$)($Q_2$), wherein the $C_1$-$C_{60}$ heteroaryl group $R_{21}$ to $R_{24}$ and $R_{31}$ to $R_{33}$ is not an azine group, b21 to b24 and b31 to b33 may each independently be an integer from 0 to 4, two adjacent $R_{21}$(s) in the number of b21, $R_{22}$(s) in the number of b22, $R_{23}$(s) in the number of b23, $R_{24}$(s) in the number of b24, $R_{31}$(s) in the number of b31, $R_{32}$(s) in the number of b32, and $R_{33}$(s) in the number of b33 may optionally be linked to each other to form a substituted or unsubstituted $C_5$-$C_{30}$ carbocyclic group or a substituted or unsubstituted $C_1$-$C_{30}$ heterocyclic group, n21 may be an integer from 1 to 5, at least one substituent of the substituted $C_5$-$C_{60}$ carbocyclic group, the substituted $C_1$-$C_{60}$ heterocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{30}$ cycloalkenyl group, the substituted $C_1$-$C_{10}$ heterocycloalkenyl group, the substituted $C_6$-$C_{60}$ aryl group, the substituted $C_7$-$C_{60}$ alkylaryl group, the substituted $C_7$-$C_{60}$ aryl alkyl group, the substituted $C_7$-$C_{60}$ arylalkyloxy group, the substituted $C_7$-$C_{60}$ arylalkylthio group, the substituted $C_8$-$C_{30}$ arylalkenyl group, the substituted $C_8$-$C_{30}$ arylalkynyl group, the substituted $C_6$-$C_{60}$ aryloxy group, the substituted $C_6$-$C_{60}$ arylthio group, the substituted $C_1$-$C_{60}$ heteroaryl group, the substituted $C_2$-$C_{60}$ alkylheteroaryl group, the substituted $C_1$-$C_{60}$ heteroaryloxy group, the substituted $C_1$-$C_{60}$ heteroarylthio group, the substituted monovalent non-aromatic condensed polycyclic group, or the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, $Si(Q_{11})(Q_{12})(Q_{13})$, —$N(Q_{11})(Q_{12})$, —$C(=O)(Q_{11})$, or any combination thereof;

a $C_3$-$C_{10}$ cycloalkyl group, a $C_1$-$C_{10}$ heterocycloalkyl group, a $C_3$-$C_{10}$ cycloalkenyl group, or a $C_1$-$C_{10}$ heterocycloalkenyl group;

a $C_3$-$C_{10}$ cycloalkyl group, a $C_1$-$C_{10}$ heterocycloalkyl group, a $C_3$-$C_{10}$ cycloalkenyl group, or a $C_1$-$C_{10}$ heterocycloalkenyl group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, —$Si(Q_{21})(Q_{22})(Q_{23})$, —$N(Q_{21})(Q_{22})$, —$C(=O)(Q_{21})$, or any combination thereof; or
–$Si(Q_{31})(Q_{32})(Q_{33})$, —$N(Q_{31})(Q_{32})$, or —$C(=O)(Q_{31})$, wherein $Q_1$ to $Q_3$, $Q_{11}$ to $Q_{13}$, $Q_{21}$ to $Q_{23}$, and $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* indicates a binding site to a neighboring atom.

Another aspect provides a composition including at least one heterocyclic compound represented by Formula 2.

Another aspect provides an organic light-emitting device including: a first electrode; a second electrode; and an organic layer placed between the first electrode and the second electrode and including an emission layer, and the organic light-emitting device includes at least one heterocyclic compound represented by Formula 2.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
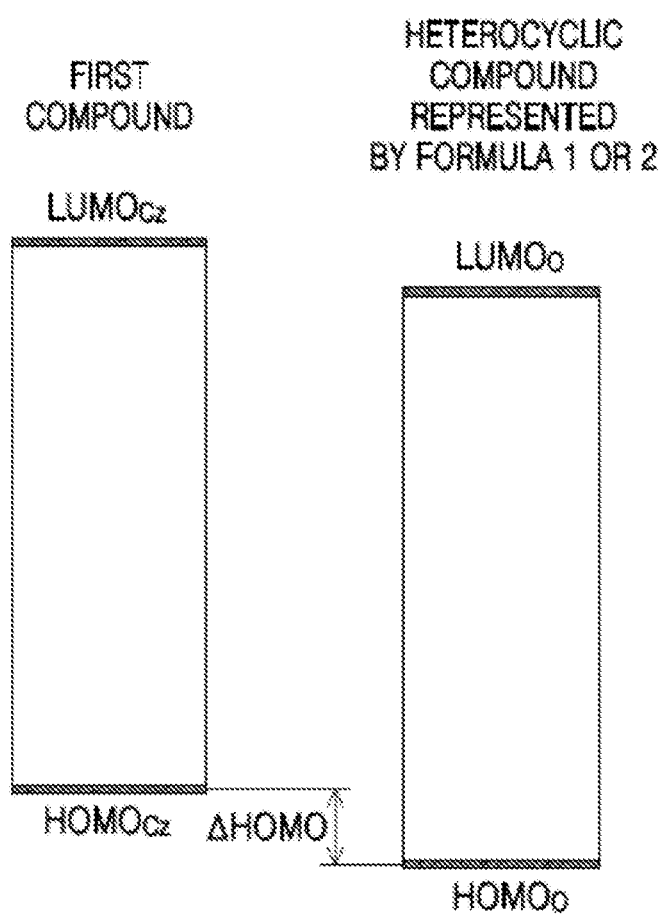
FIG. 1 shows a diagram illustrating an exemplary energy level relationship between a heterocyclic compound represented by Formula 1 or 2 and a first compound including a carbazole group in a composition according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Unless otherwise defined in the present specification, the handling and the measurement of physical properties are carried out under conditions of room temperature (about 20° C. to about 25° C.) and/or the relative humidity of about 40% RH to about 50% RH. In addition, throughout the present specification, the "compound for an organic light-emitting device" may be referred to as the "compound," the "material for an organic light-emitting device" may be referred to as the "material," and the "composition for an organic light-emitting device" may simply be called the " composition."

Heterocyclic Compound (1)

A heterocyclic compound represented by Formula 1 according to an embodiment of the present disclosure will be described in detail as follows:

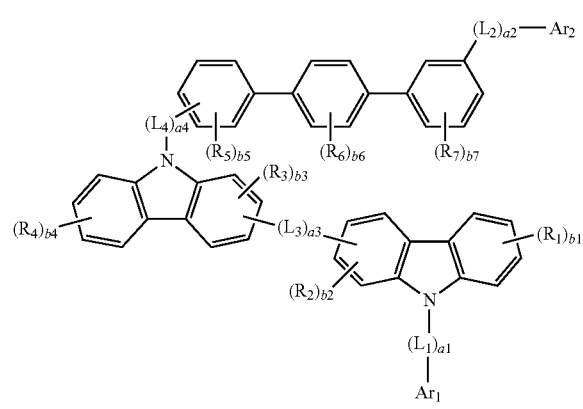

Formula 1

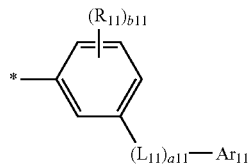

Formula 1A

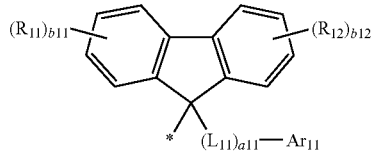

Formula 1B

In Formulae 1, 1A, and 1B, $L_1$ to $L_4$ and $L_{11}$ may each independently be a single bond, a substituted or unsubstituted $C_5$-$C_{60}$ carbocyclic group, or a substituted or unsubstituted nitrogen-free $C_1$-$C_{60}$ heterocyclic group.

$L_1$ to $L_4$ and $L_{11}$ may each independently be: a single bond, a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthylene group, a heptaphene group, a pyranthrene group, a benzoquinone group, a coumarin group, an anthraquinone group, a fluorenone group, a furan group, a thiene group, a silole group, a benzofuran group, a benzothiene group, a benzosilole group, a dibenzofuran group, a dibenzothiophene group, a dibenzosilole group, a xanthon group, or a thioxanthone group; or a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthylene group, a heptaphene group, a pyranthrene group, a benzoquinone group, a coumarin group, an anthraquinone group, a fluorenone group, a furan group, a thiene group, a silole group, a benzofuran group, a benzothiene group, a benzosilole group, a dibenzofuran group, a dibenzothiophene group, a dibenzosilole group, a xanthone group, or a thioxanthone group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a xanthonenyl group, a thioxanthonyl group, or any combination thereof.

For example, $L_1$ to $L_4$ and $L_{11}$ may each independently be: a single bond, a benzene group, a fluorene group, a biphenyl group, a terphenyl group, or a tetraphene group; or a benzene group, a fluorene group, a biphenyl group, a terphenyl group, or a tetraphene group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a biphenyl group, a terphenyl group, or any combination thereof.

For example, $L_2$ and $L_3$ may each be a single bond.

For example, $L_1$ to $L_4$ and $L_{11}$ may each independently be a single bond or a group represented by Formulae 3-1 to 3-7 below:

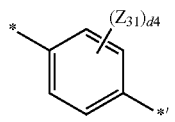

3-1

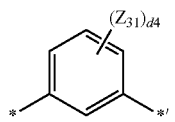

3-2

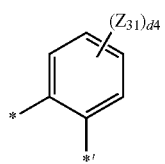

3-3

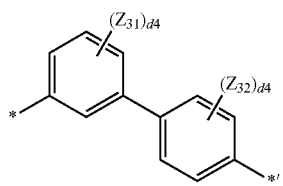

3-4

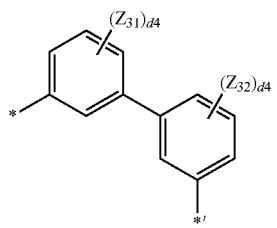

3-5

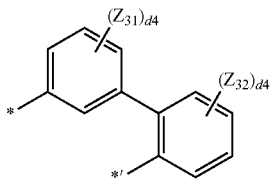

3-6

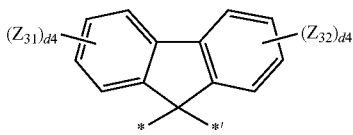

3-7

In Formulae 3-1 to 3-7, $Z_{31}$ and $Z_{32}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), d4 may be an integer from 0 to 4, $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* and *' each indicate a binding site to a neighboring atom.

The designations a1 to a4 and a11 in Formulae 1 and 1A to 1B may each independently be an integer from 1 to 5. a1 indicates the number of groups represented by $L_1$, and when a1 is 2 or more, $L_1$(s) in the number of a1 may be identical to or different from each other, a2 indicates the number of groups represented by $L_2$, and when a2 is 2 or more, $L_2$(s) in the number of a2 may be identical to or different from each other, a3 indicates the number of groups represented by $L_3$, and when a3 is 2 or more, $L_3$(s) in the number of a3 may be identical to or different from each other, a4 indicates the number of groups represented by $L_4$, and when a4 is 2 or more, $L_4$(s) in the number of a4 may be identical to or different from each other, and a11 indicates the number of groups represented by $L_{11}$, and when a11 is 2 or more, $L_{11}$ in the number of a11 may be identical to or different from each other.

For example, a2 and a11 may each be an integer from 1 to 4, and a3 and a4 may each be 1, but embodiments of the present disclosure are not limited thereto.

In Formulae 1, 1A, and 1B, $Ar_1$ and $Ar_{11}$ may each independently be a substituted or unsubstituted $C_5$-$C_{60}$ carbocyclic group or a substituted or unsubstituted nitrogen-free $C_1$-$C_{60}$ heterocyclic group, and $Ar_2$ may be a group represented by Formula 1A or 1B.

The term "nitrogen-free heterocyclic group" as used herein refers to a heterocyclic group not including a nitrogen atom.

For example, $Ar_1$ and $Ar_{11}$ may each independently be: a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a xanthonenyl group, or a thioxanthonyl group; or a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a xanthonenyl group, or a thioxanthonyl group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a xanthonenyl group, a thioxanthonyl group, or any combination thereof.

For example, $Ar_1$ and $Ar_{11}$ may each independently be: a phenyl group, a naphthyl group, a fluorenyl group, a biphenyl group, a terphenyl group, a tetraphenyl group, a dibenzofuranyl group, or a dibenzothiophenyl group; or a phenyl group, a naphthyl group, a fluorenyl group, a biphenyl group, a terphenyl group, a tetraphenyl group, a dibenzofuranyl group, or a dibenzothiophenyl group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a biphenyl group, a terphenyl group, or any combination thereof.

For example, a moiety represented by *—$(L_1)_{a1}$—$Ar_1$ may be a group represented by one of Formulae 4-1 to 4-17 below:

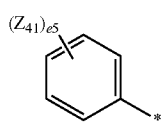
4-1

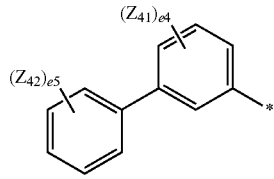
4-2

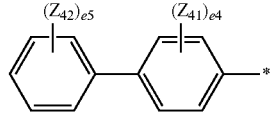
4-3

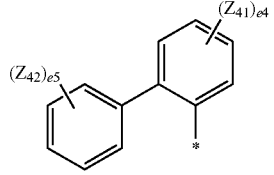
4-4

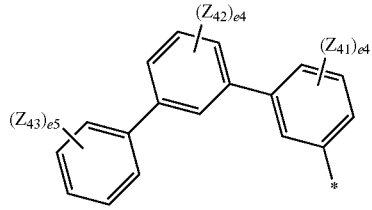
4-5

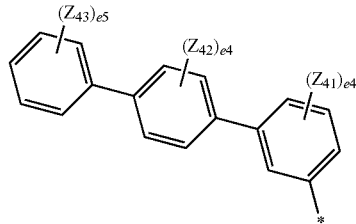
4-6

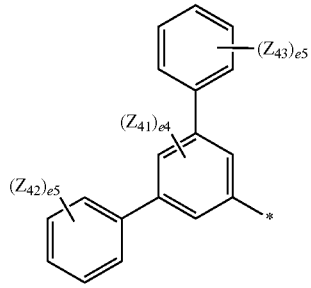
4-7

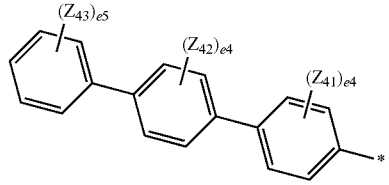
4-8

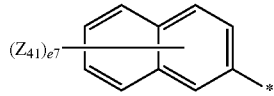
4-9

In Formulae 4-1 to 4-17,

Y$_{41}$ may be O, S, or C(Z$_{48}$)(Z$_{49}$),

Z$_{41}$ to Z$_{49}$ may each independently be hydrogen, deuterium, —F, —Cl, —Br, —I, a hydroxyl group, a cyano group, a C$_1$-C$_{20}$ alkyl group, a C$_1$-C$_{20}$ alkoxy group, a phenyl group, or —Si(Q$_{31}$)(Q$_{32}$)(Q$_{33}$), e3 may be an integer from 0 to 3, e4 may be an integer from 0 to 4, e5 may be an integer from 0 to 5, e7 may be an integer from 0 to 7, Q$_{31}$ to Q$_{33}$ may each independently be hydrogen, deuterium, a C$_1$-C$_{20}$ alkyl group, a C$_1$-C$_{20}$ alkoxy group, a phenyl group, or a biphenyl group, and

* indicates a binding site to a neighboring atom.

For example, a moiety represented by *-(L$_{11}$)$_{a11}$-Ar$_{11}$ may be a group represented by one of Formulae 5-1 to 5-13 below:

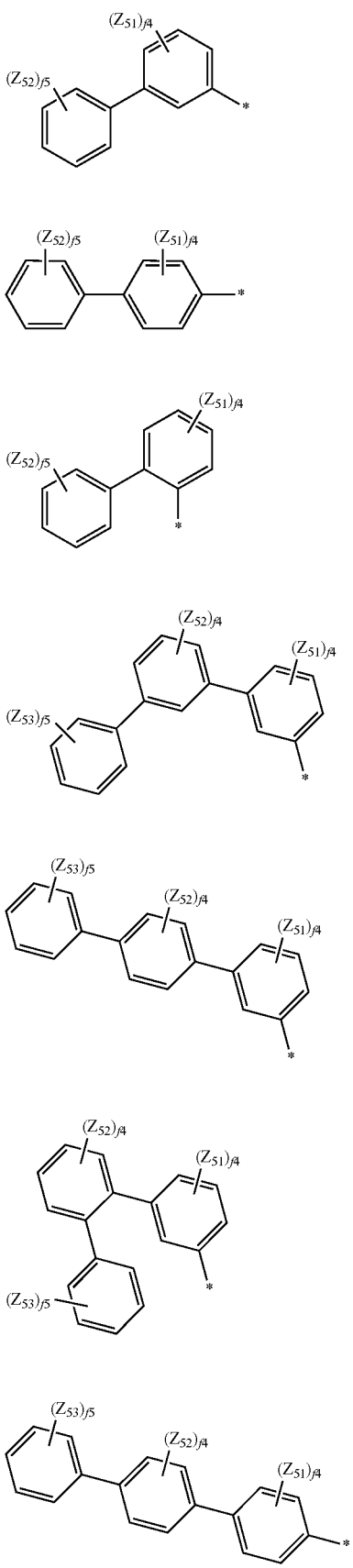
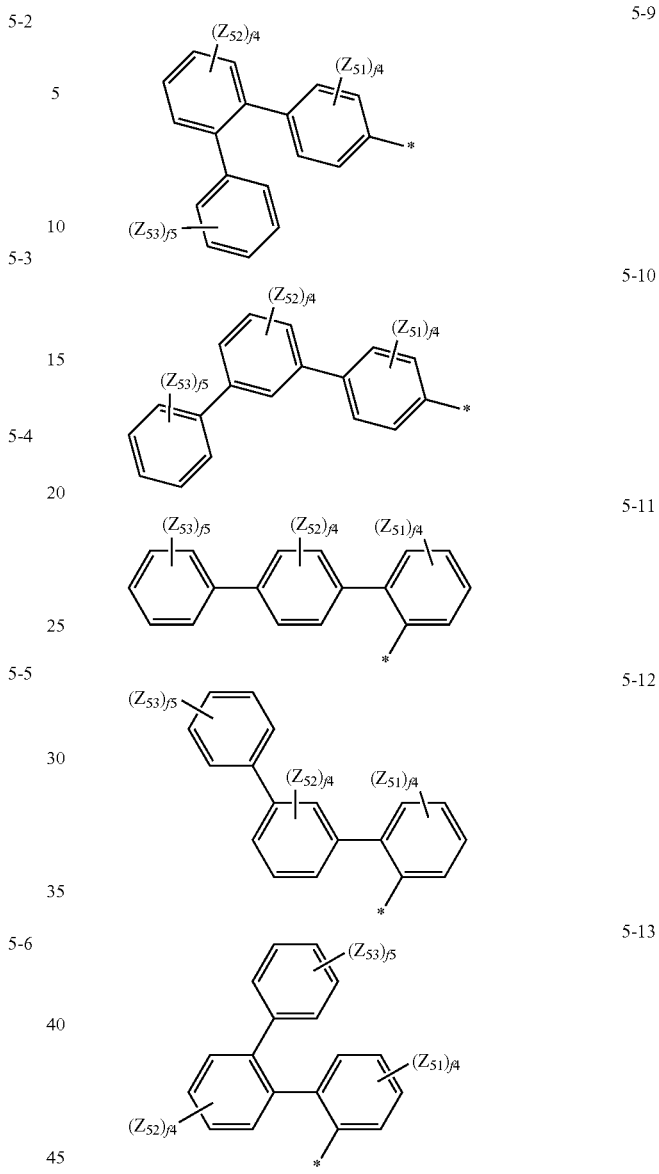

In Formulae 5-1 to 5-13, $Z_{51}$ to $Z_{53}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —Si($Q_{31}$)($Q_{32}$)($Q_{33}$), f4 may be an integer from 0 to 4, f5 may be an integer from 0 to 5, $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* indicates a binding site to a neighboring atom.

In Formulae 1, 1A, and 1B, $R_1$ to $R_7$, and $R_{11}$ to $R_{12}$ may each independently be: hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted nitrogen-free $C_1$-$C_{10}$ heterocycloalkyl group, a substituted or unsubstituted $C_3$-$C_{10}$ cycloalkenyl group, a substituted or unsubstituted nitrogen-free $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_7$-$C_{60}$ aryl alkyl group, a substituted or unsubstituted $C_7$-$C_{60}$ arylalkyloxy group, a substituted or unsubstituted $C_7$-$C_{60}$ arylalkylthio group, a substituted or unsubstituted $C_8$-$C_{30}$ arylalkenyl group, a substituted or unsubstituted $C_8$-$C_{30}$ arylalkynyl group, a substituted or unsubstituted $C_6$-$C_{60}$ aryloxy group, a substituted or unsubstituted $C_6$-$C_{60}$ arylthio group, a substituted or unsubstituted nitrogen-free $C_1$-$C_{60}$ heteroaryl group, a substituted or unsubstituted nitrogen-free $C_2$-$C_{60}$ alkylheteroaryl group, a substituted or unsubstituted nitrogen-free $C_1$-$C_{60}$ heteroaryloxy group, a substituted or unsubstituted nitrogen-free $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), or —N(Q$_1$)(Q$_2$), b2 and b3 may each independently be an integer from 0 to 3, b1, b4 to b7, and b11 to b12 may each independently be an integer from 0 to 4, any two adjacent groups among $R_1$(s) in the number of b1, $R_2$(s) in the number of b2, $R_3$(s) in the number of b3, $R_4$(s) in the number of b4, $R_5$(s) in the number of b5, $R_6$(s) in the number of b6, $R_7$(s) in the number of b7, $R_{11}$(s) in the number of b11, and $R_{12}$(s) in the number of b2 may optionally be linked to each other to form a substituted or unsubstituted $C_5$-$C_{30}$ carbocyclic group or a substituted or unsubstituted $C_1$-$C_{30}$ heterocyclic group.

For example, $R_1$ to $R_7$, $R_{11}$, and $R_{12}$ may each independently be: hydrogen, deuterium, —F, —Cl, —Br, —I, a cyano group, a $C_1$-$C_{20}$ alkyl group, a $C_2$-$C_{20}$ alkenyl group, a $C_2$-$C_{20}$ alkynyl group, or a $C_1$-$C_{20}$ alkoxy group; or a $C_1$-$C_{20}$ alkyl group, a $C_2$-$C_{20}$ alkenyl group, a $C_1$-$C_{20}$ alkynyl group, or $C_1$-$C_{20}$ alkoxy group, each substituted with at least one deuterium, —F, —Cl, —Br, —I, a cyano group, or any combination thereof.

For example, $R_1$ to $R_7$, $R_{11}$, and $R_{12}$ may each be hydrogen.

In one or more embodiments, the heterocyclic compound may be a compound represented by one of Formulae 1(1) to 1(3) below:

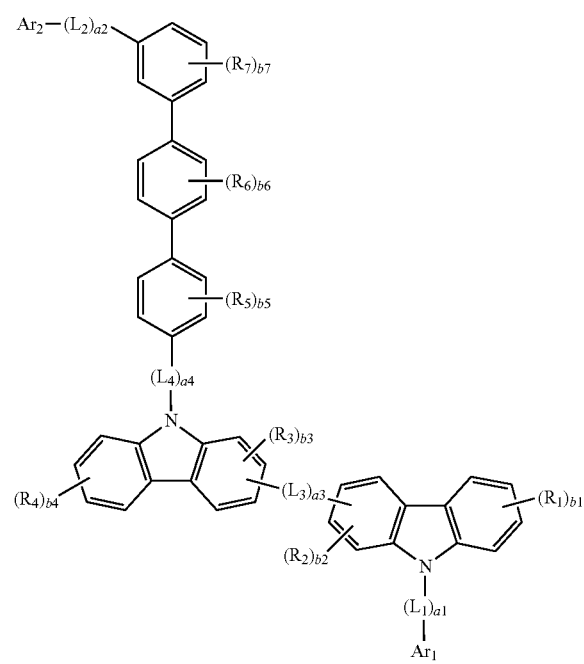

In Formulae 1(1) to 1(3), $L_1$ to $L_4$, a1 to a4, $Ar_1$, $Ar_2$, $R_1$ to $R_7$, and b1 to b7 may each be understood by referring to descriptions thereof provided herein.

In one or more embodiments, the heterocyclic compound may be a group represented by one of Formulae 1-1 to 1-16 below:

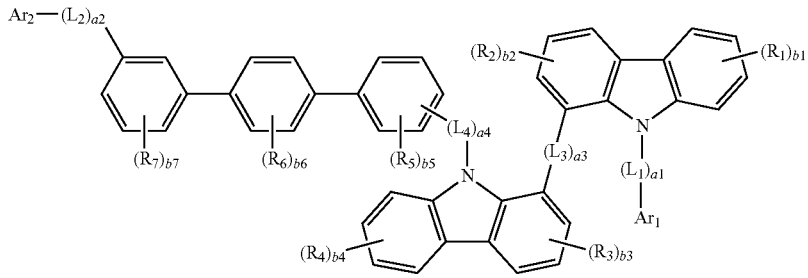
Formula 1-1
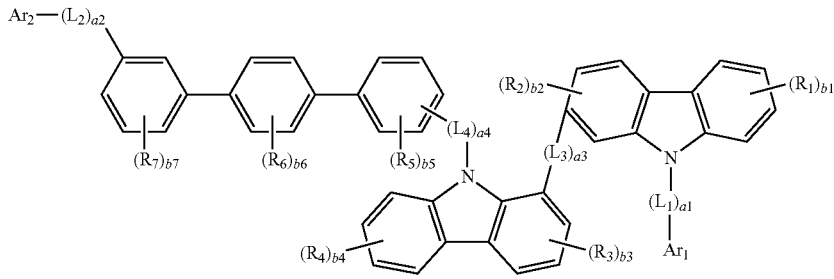
Formula 1-2
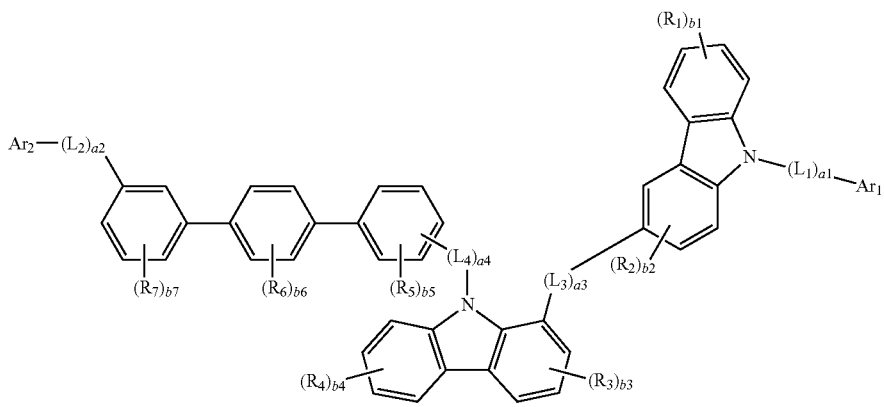
Formula 1-3
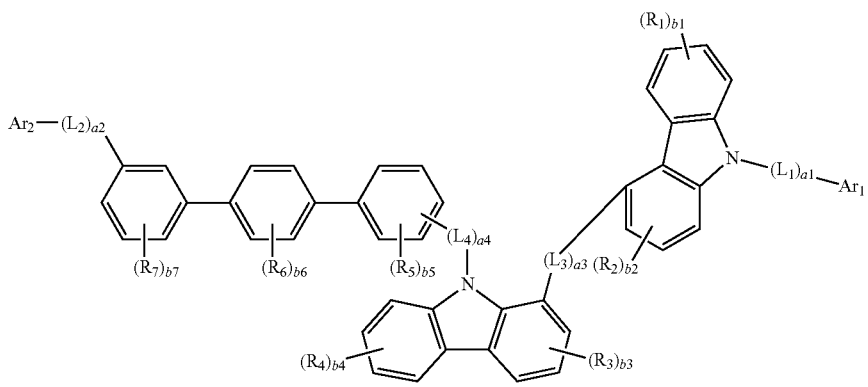
Formula 1-4
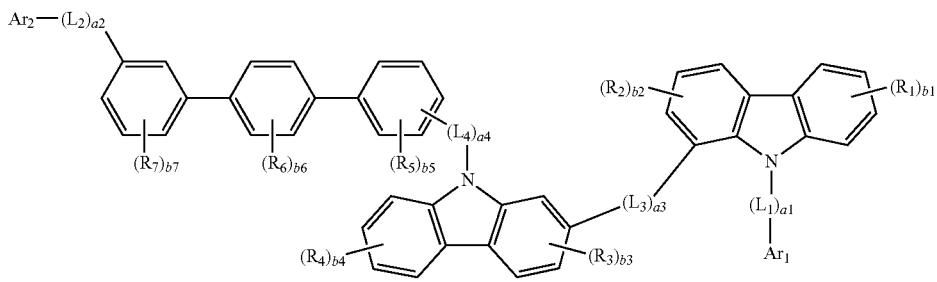
Formula 1-5

Formula 1-6
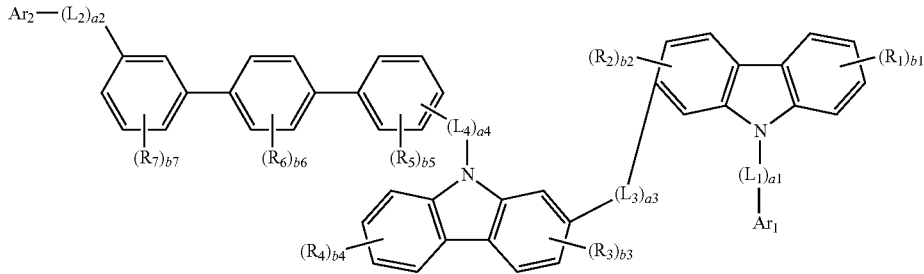
Formula 1-7
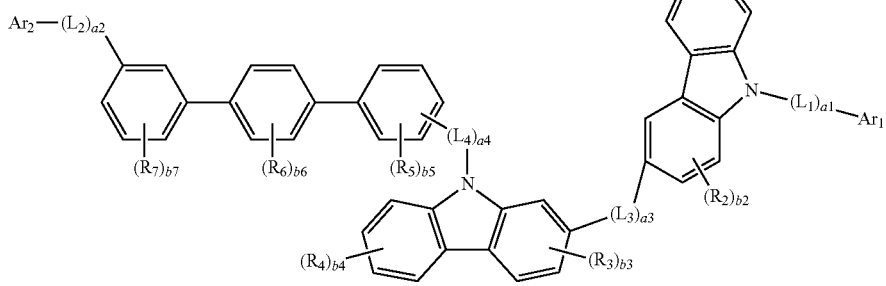
Formula 1-8
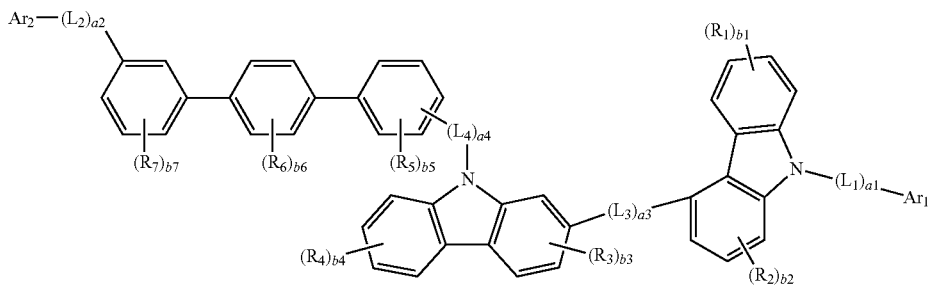
Formula 1-9
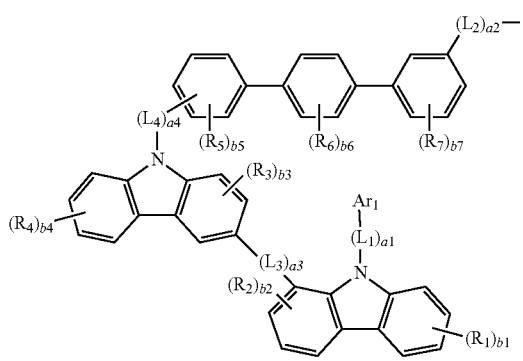
Formula 1-10
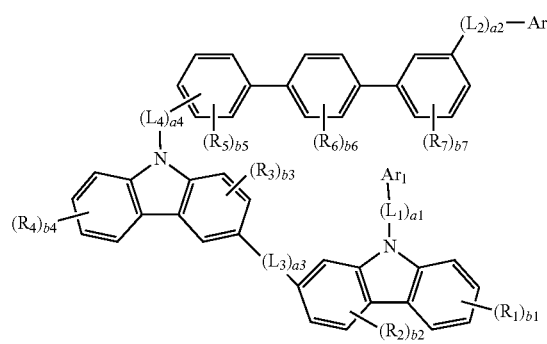

-continued
Formula 1-11
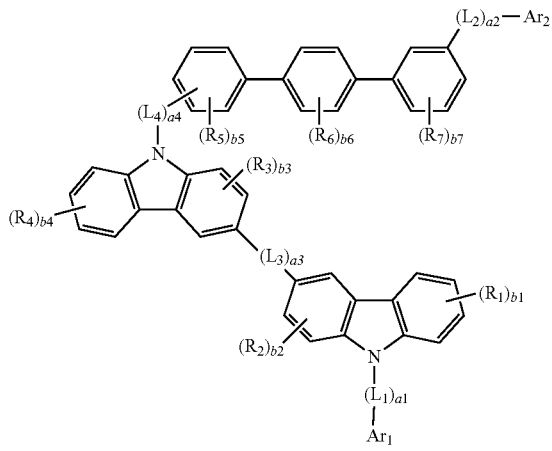
Formula 1-12
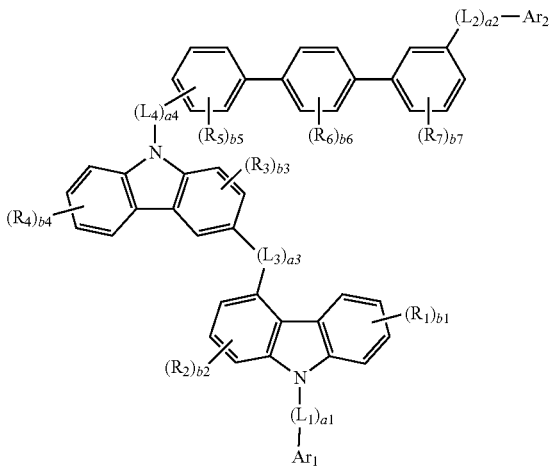
Formula 1-13
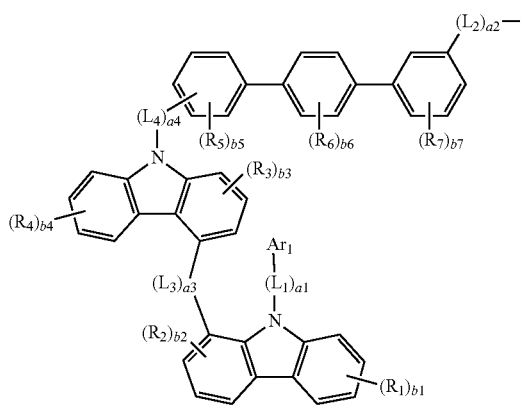
Formula 1-14
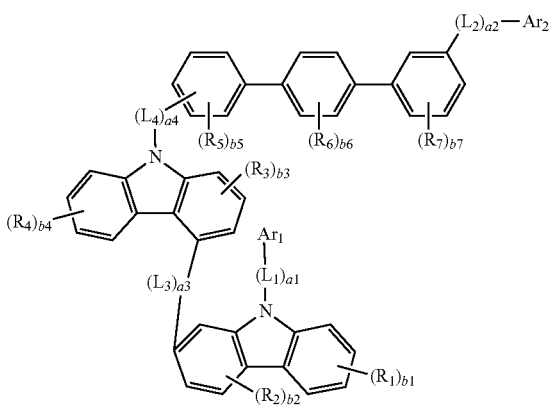
Formula 1-15
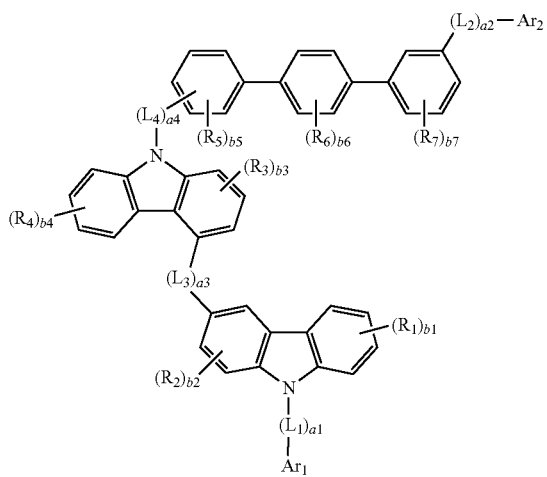
Formula 1-16
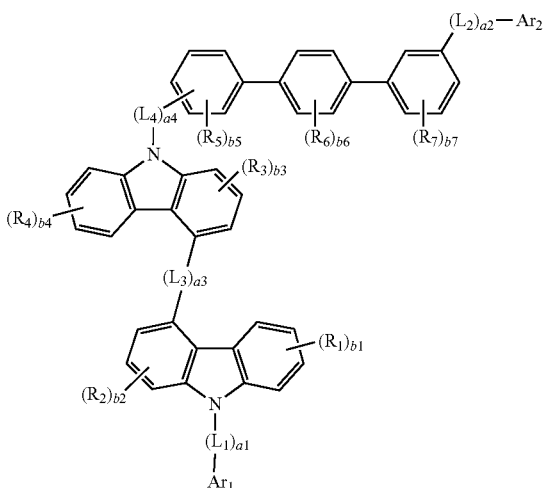
In Formulae 1-1 to 1-16,
$L_1$ to $L_4$, a1 to a4, $Ar_1$, $Ar_2$, $R_1$ to $R_7$, and b1 to b7 may each be understood by referring to descriptions thereof provided herein.
In one or more embodiments, the heterocyclic compound may have a lowest unoccupied molecular orbital (LUMO) energy level of −2.3 eV or less.

In one or more embodiments, the heterocyclic compound may be Compounds A1 to A496 below, but embodiments of the present disclosure are not limited thereto:
A1
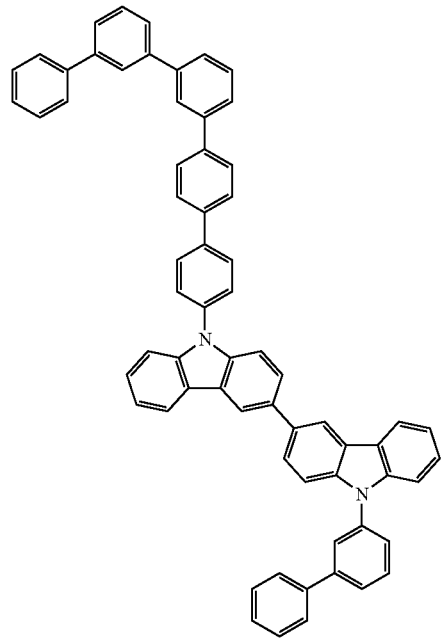
A2
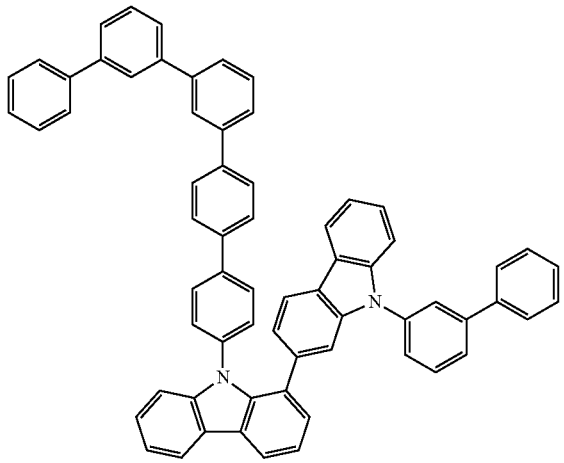
A3
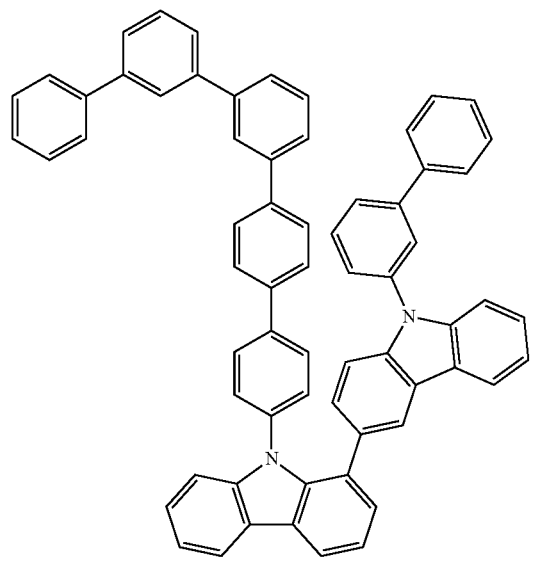
A4
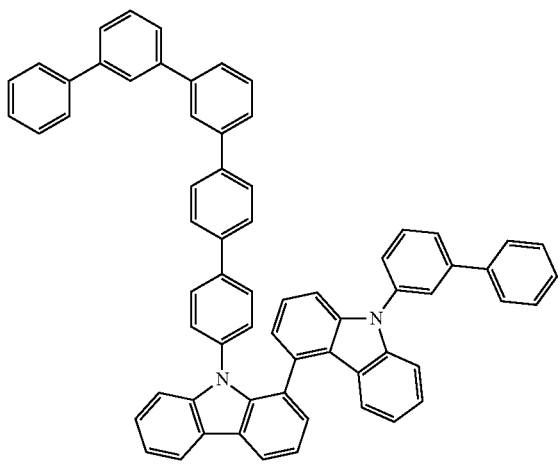

-continued
A5
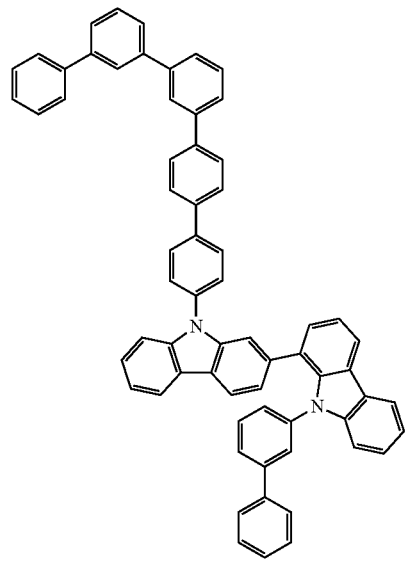
A6
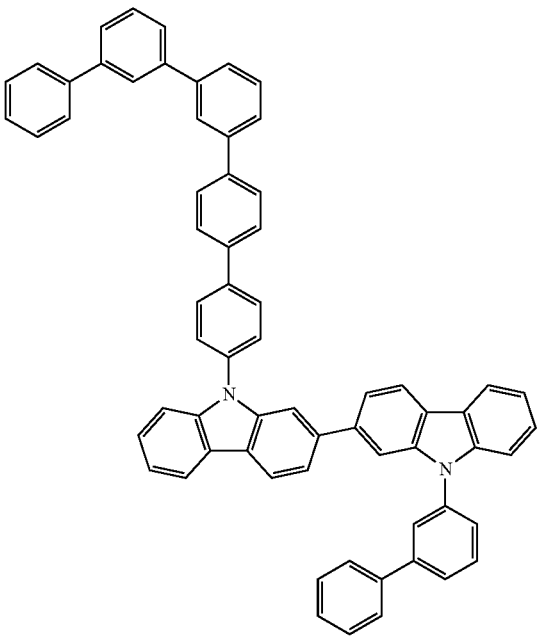
A7
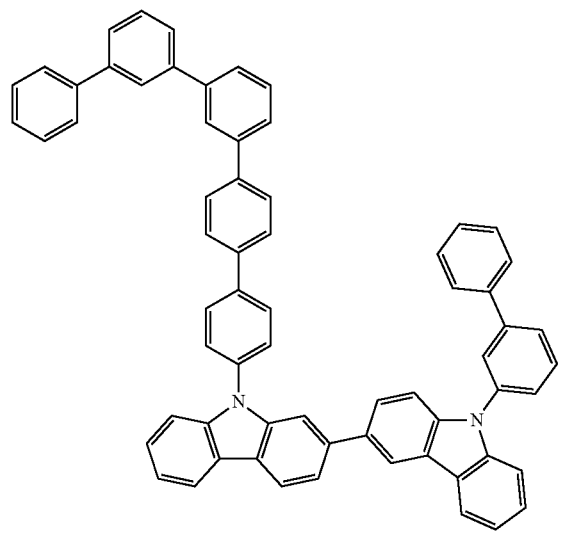
A8
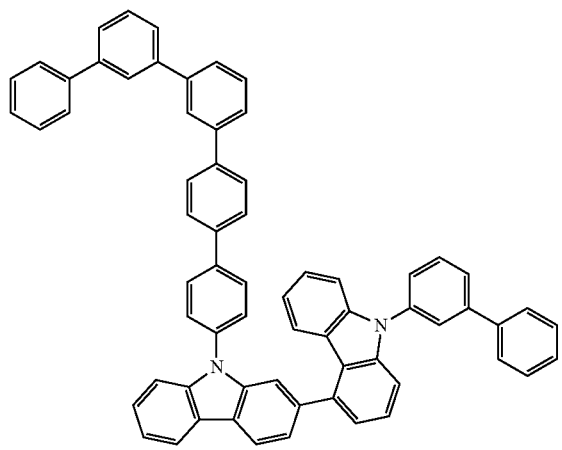

-continued
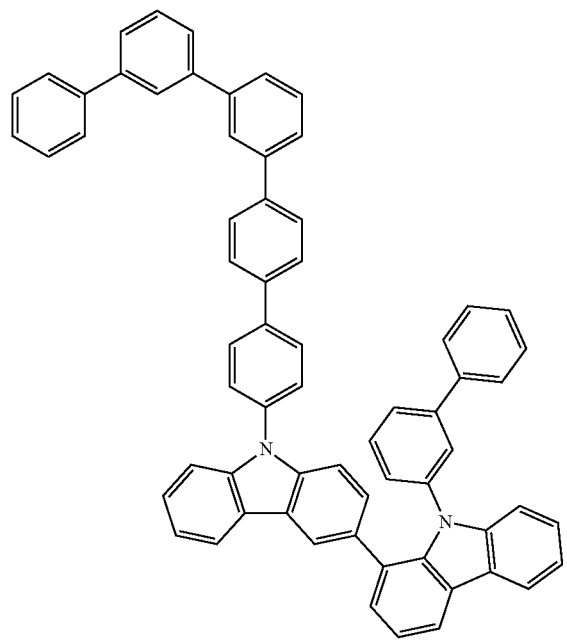
A9
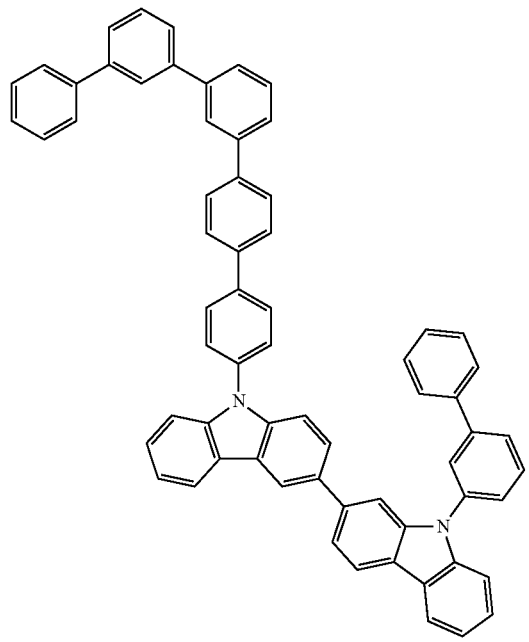
A10
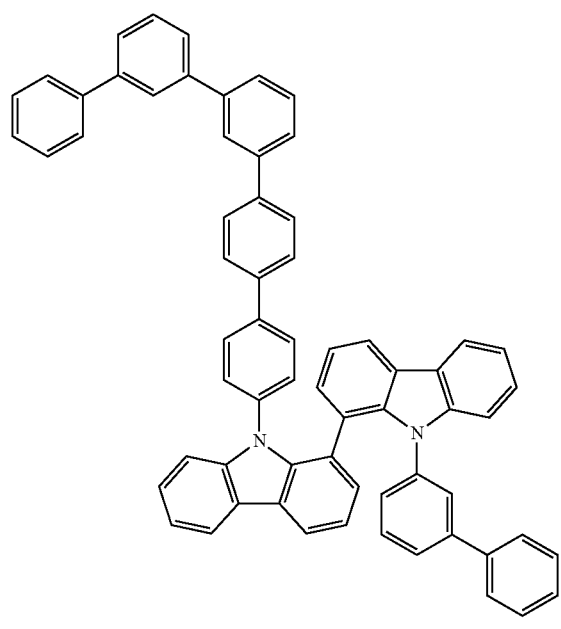
A11
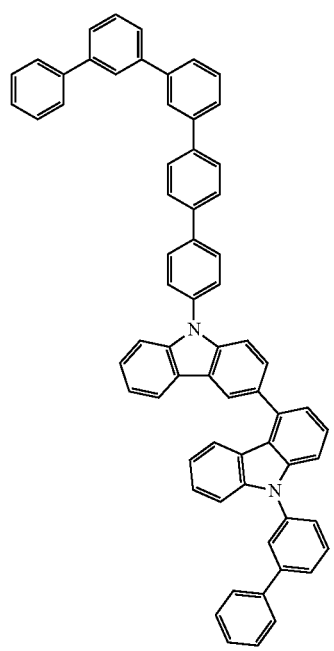
A12

-continued
A13
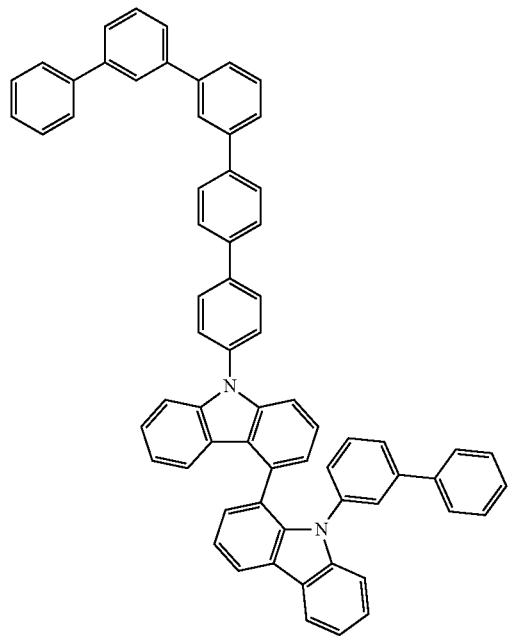
A14
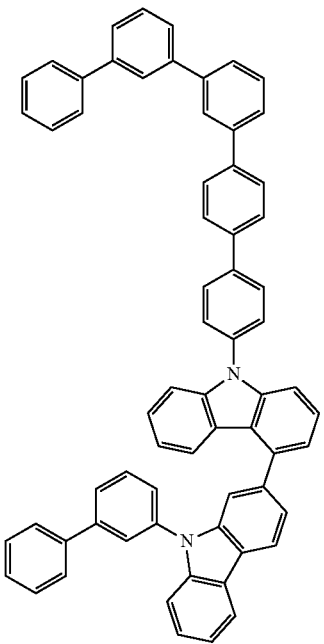
A15
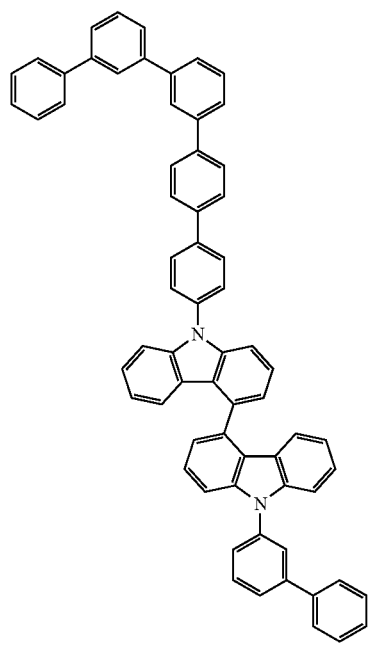
A16
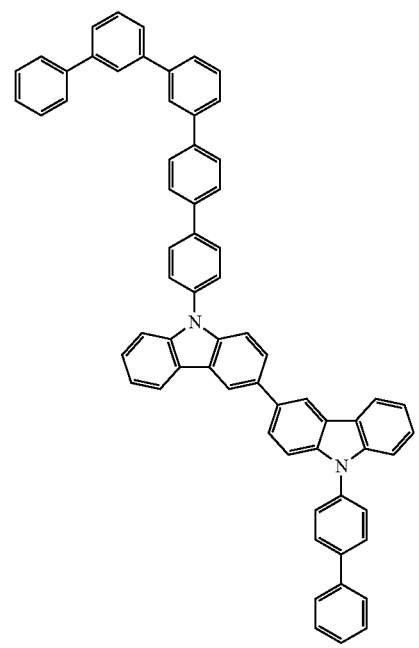

-continued
A17
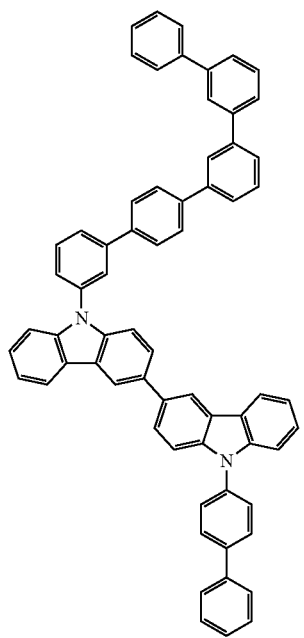
A18
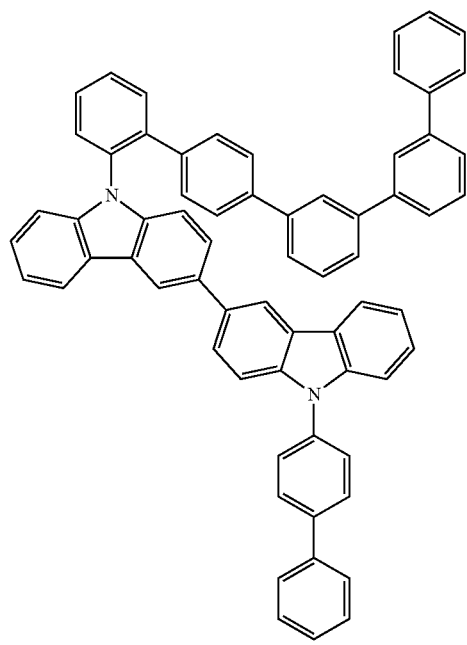
A19
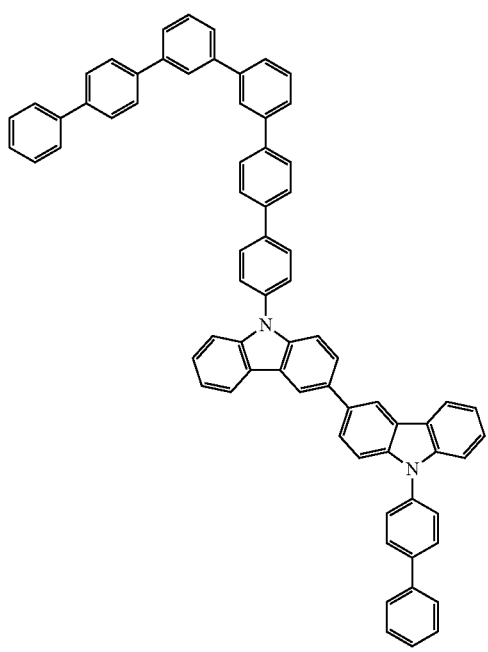
A20
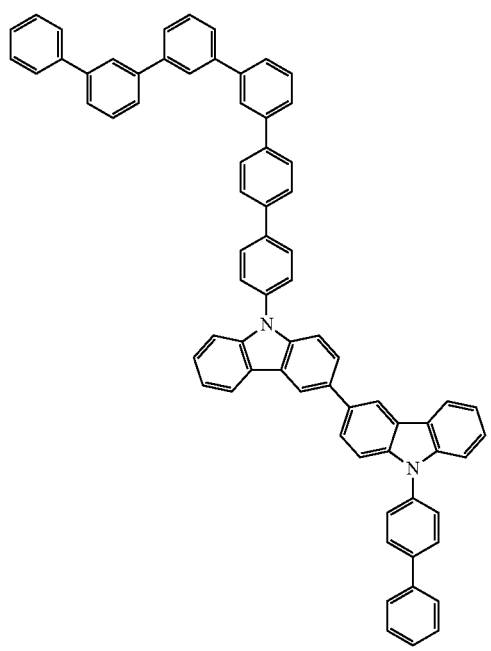

A21
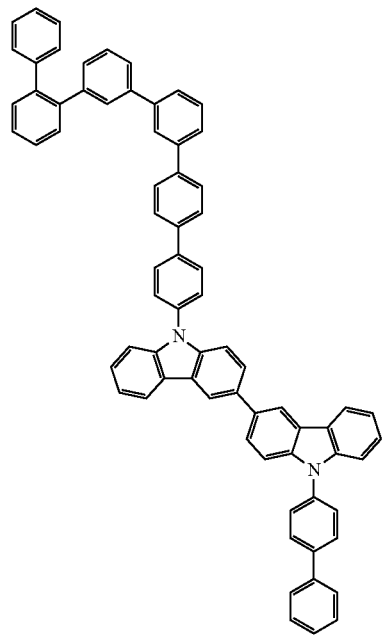
A22
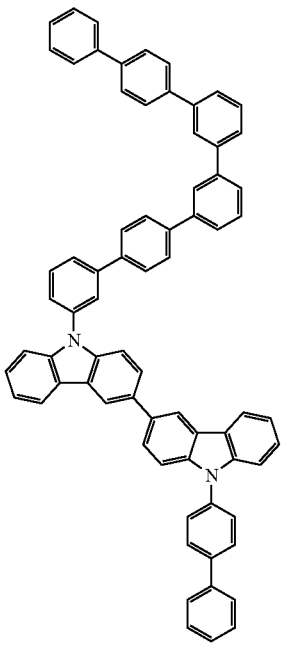
A23
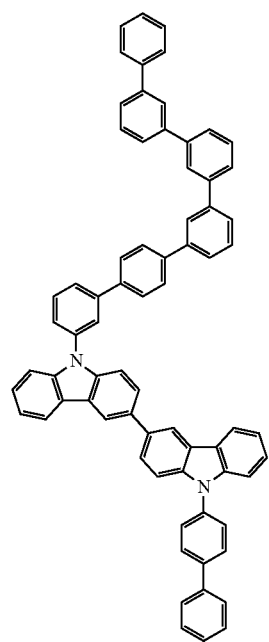
A24
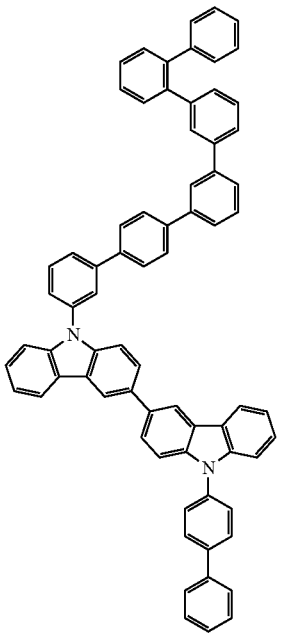

-continued
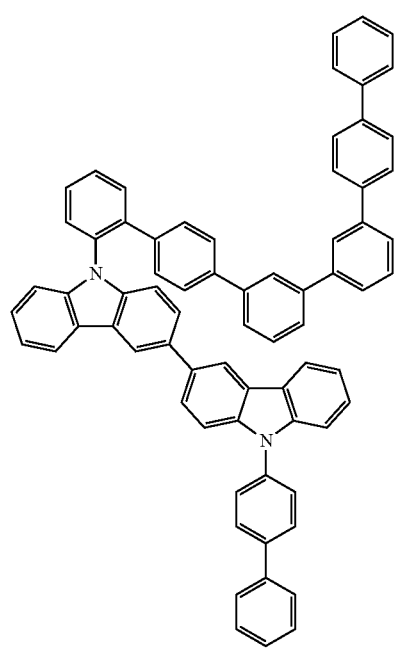
A25
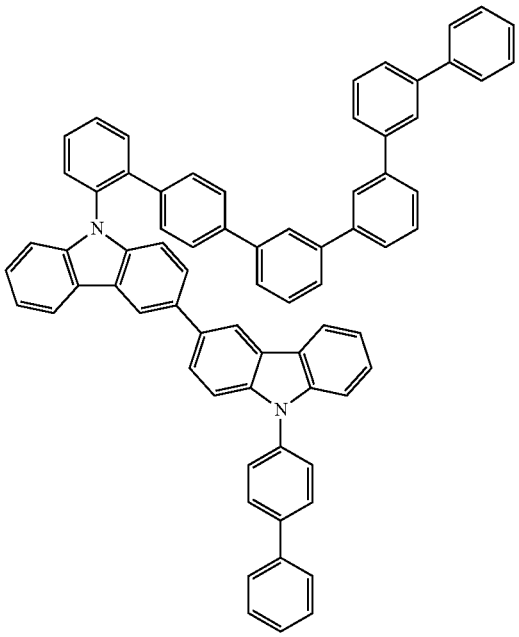
A26
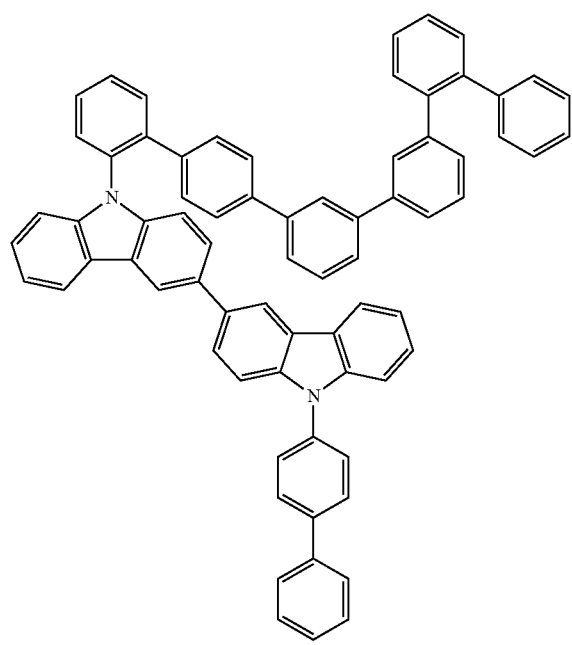
A27

-continued
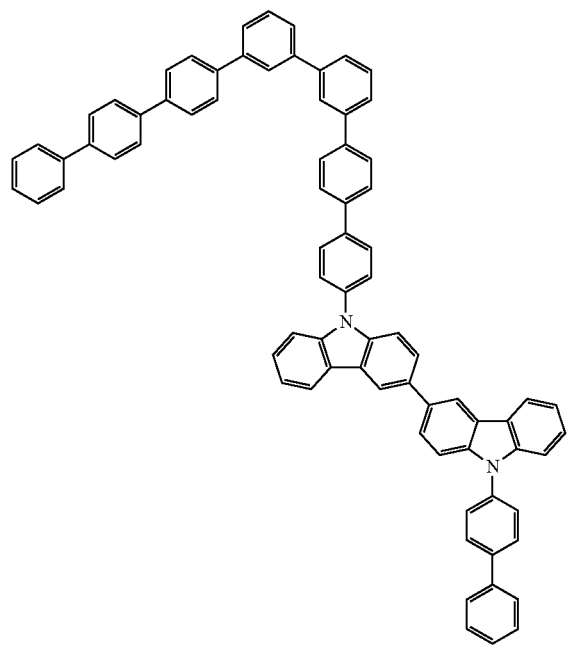
A28
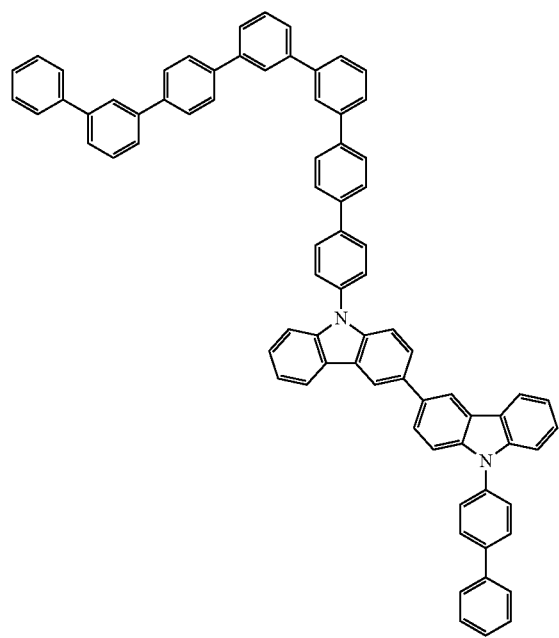
A29
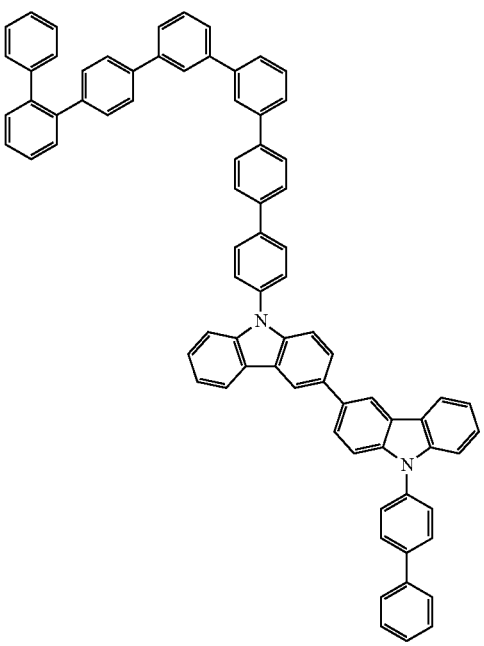
A30

-continued
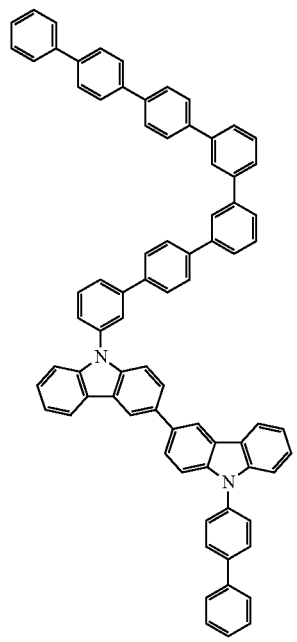
A31
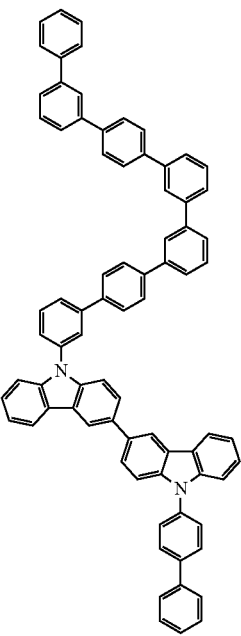
A32
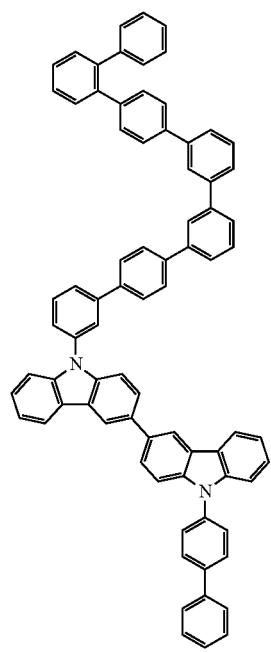
A33
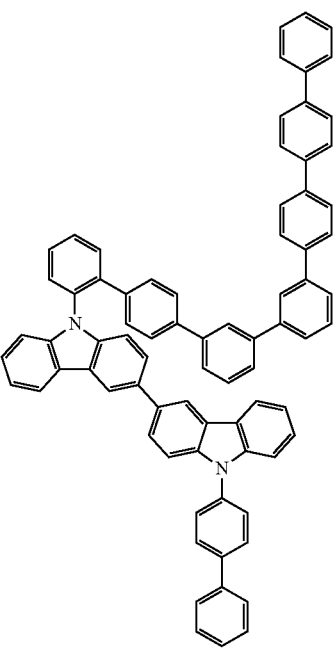
A34

-continued
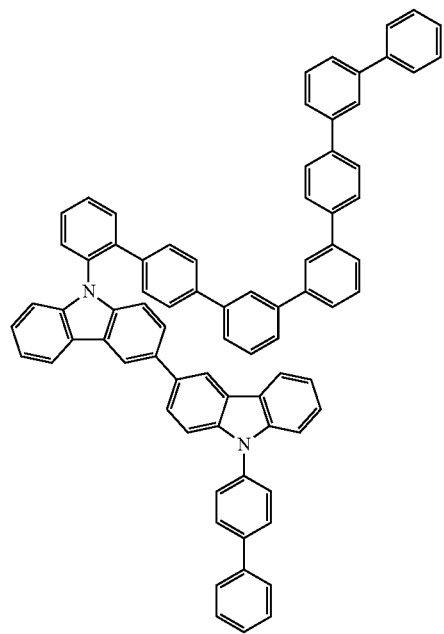
A35
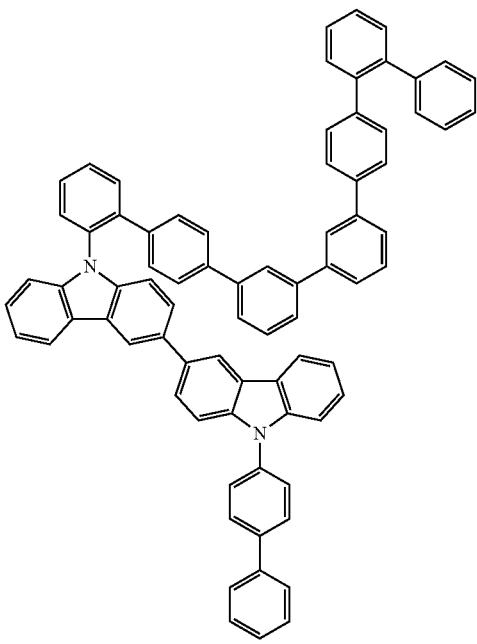
A36
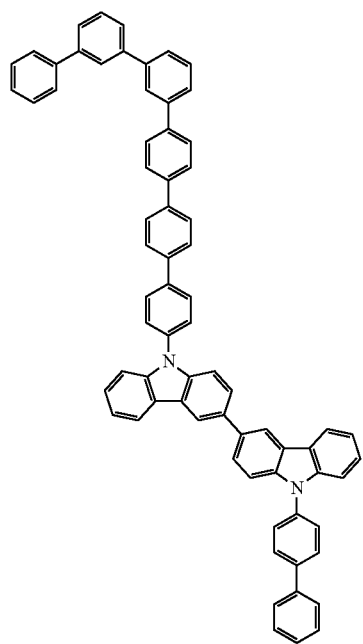
A37
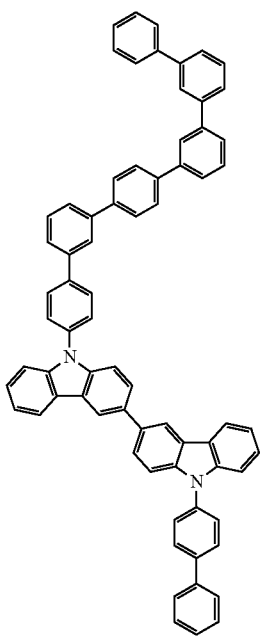
A38

-continued
A39
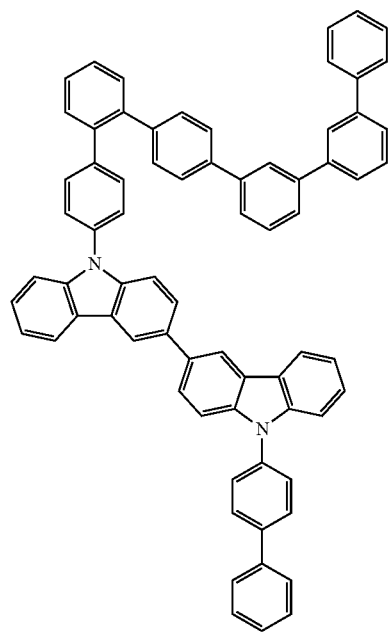
A40
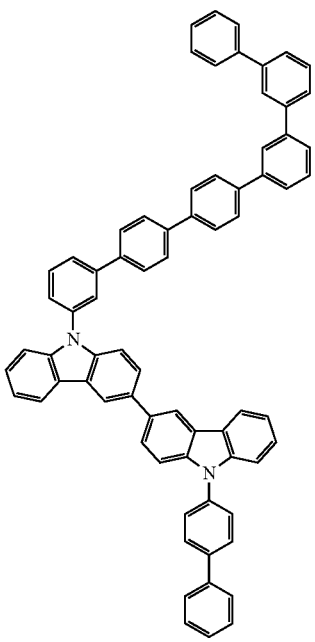
A41
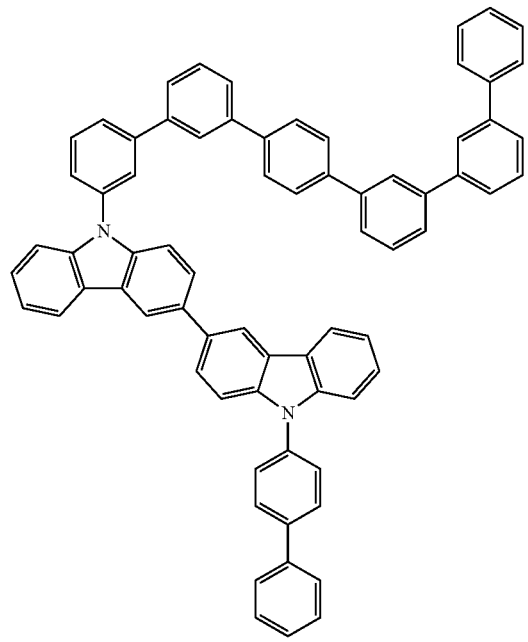
A42
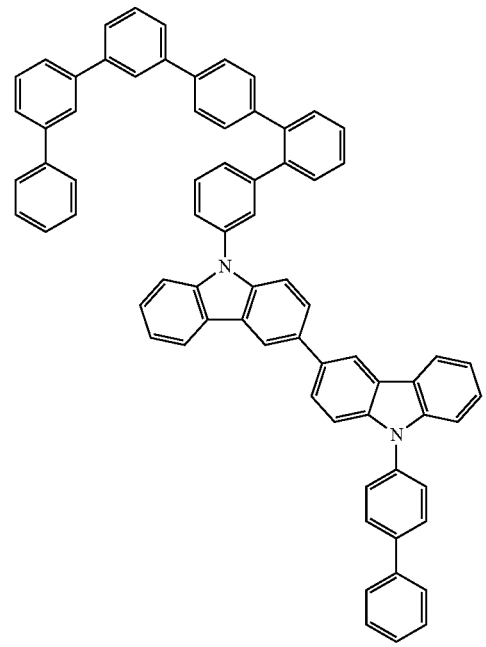

-continued
A43
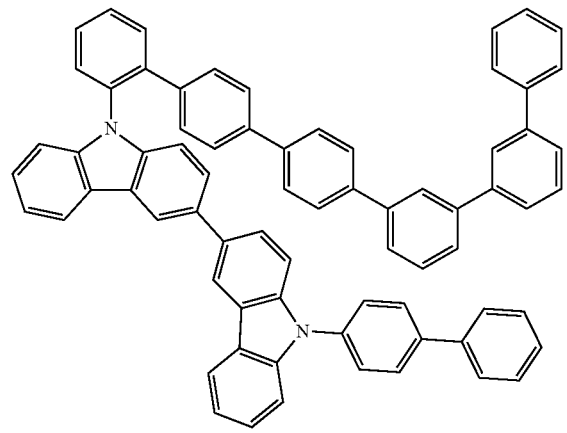
A44
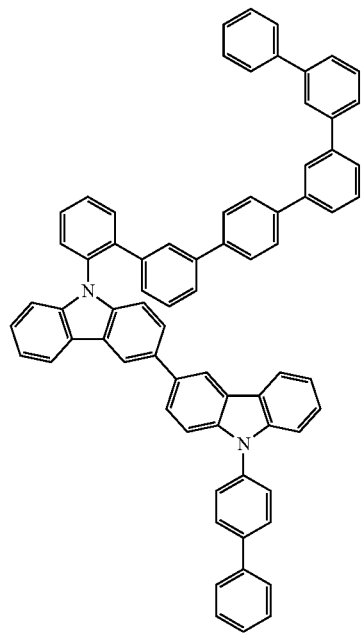
A45
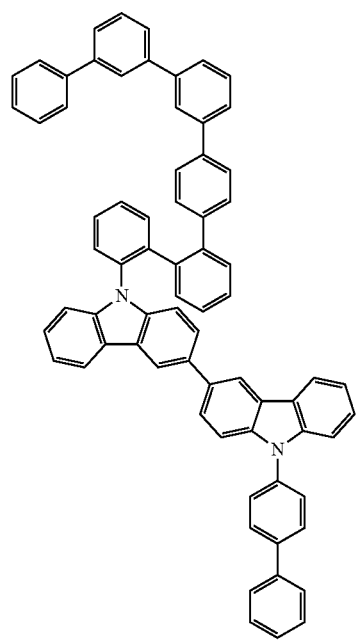
A46
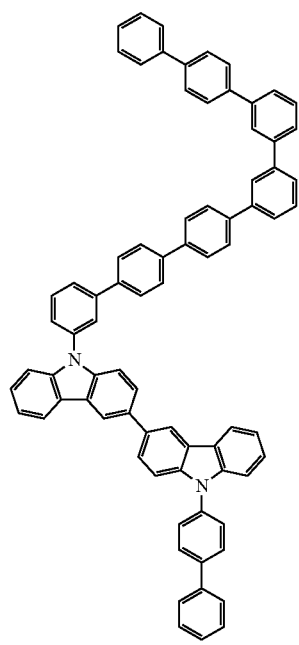

-continued
A47
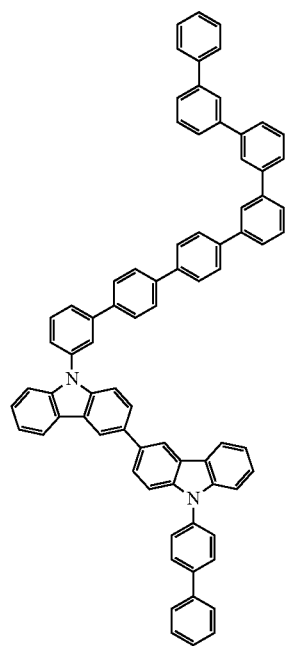
A48
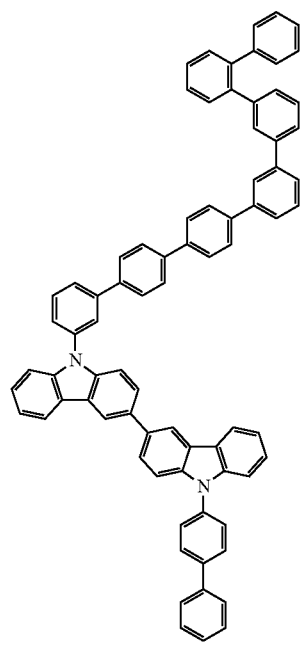
A49
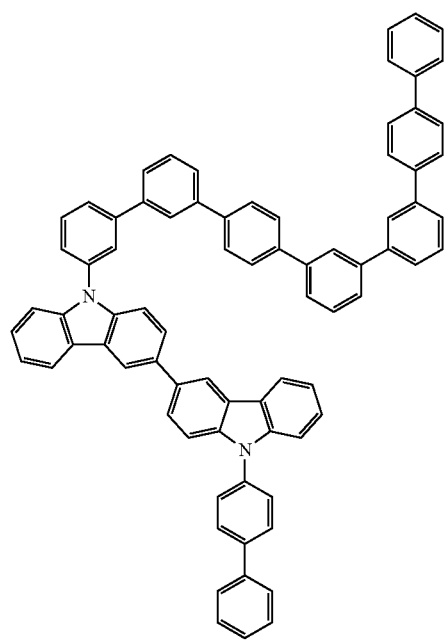
A50
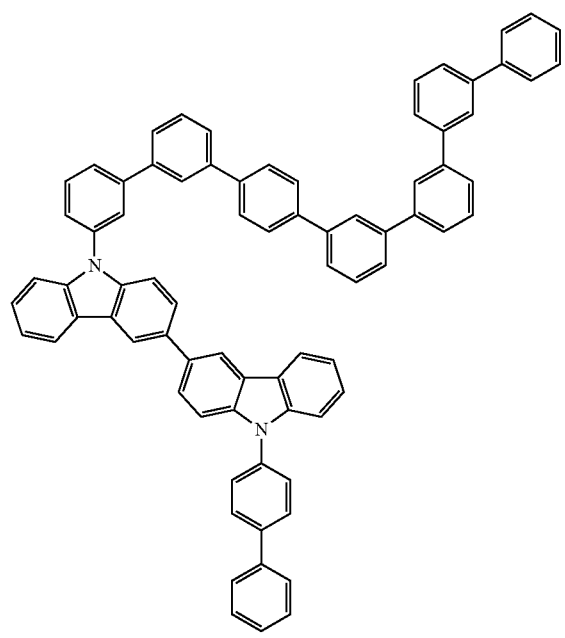

-continued
A51
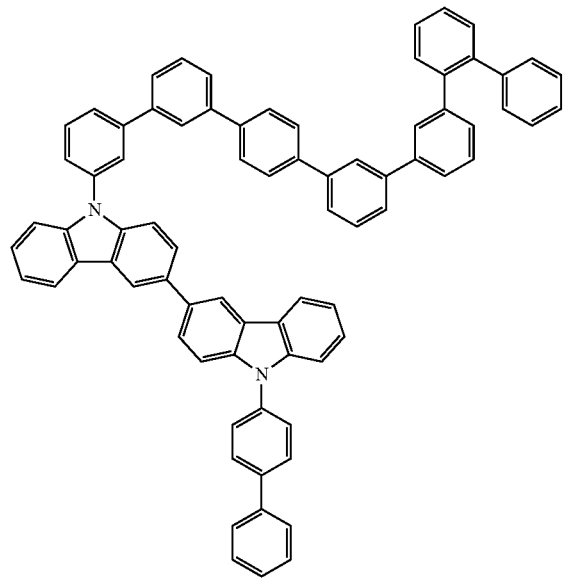
A52
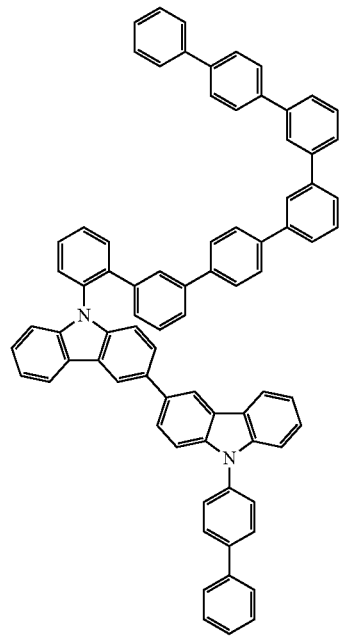
A53
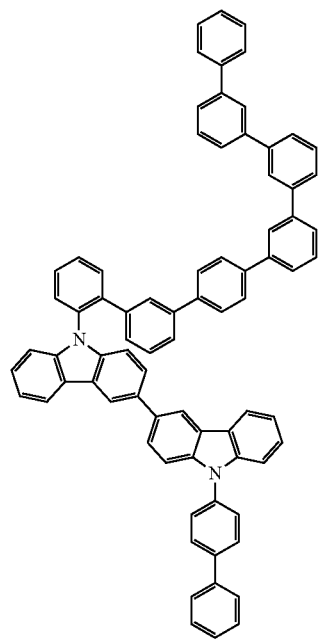
A54
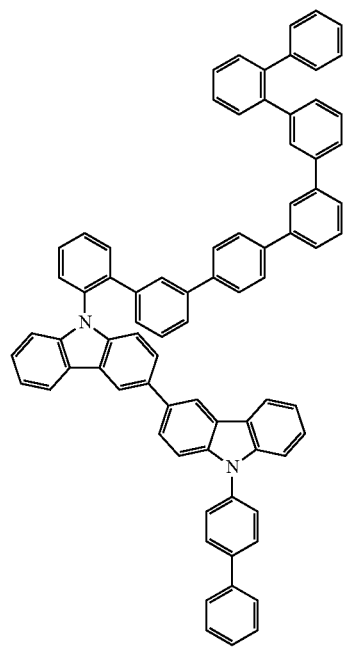

-continued
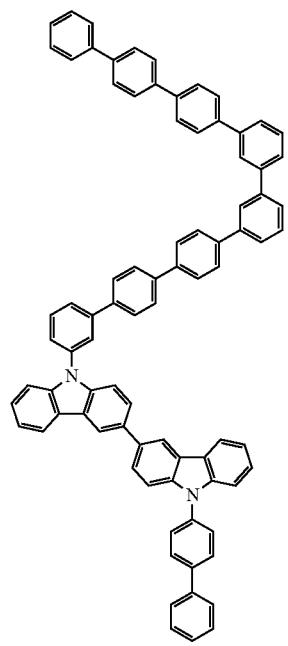
A55
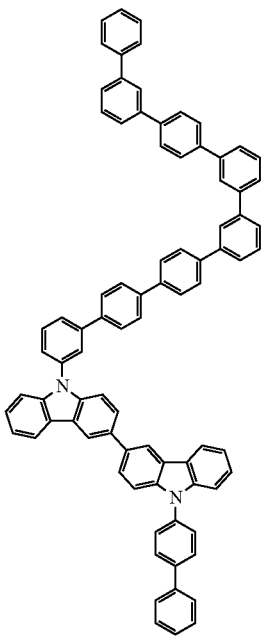
A56
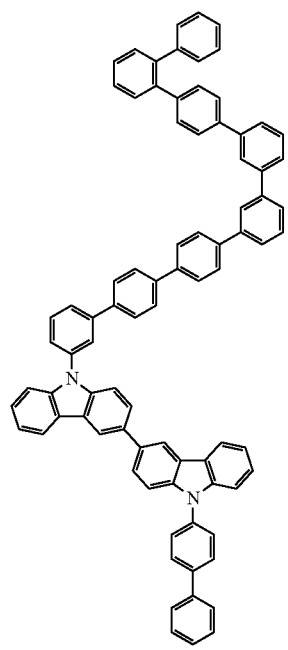
A57
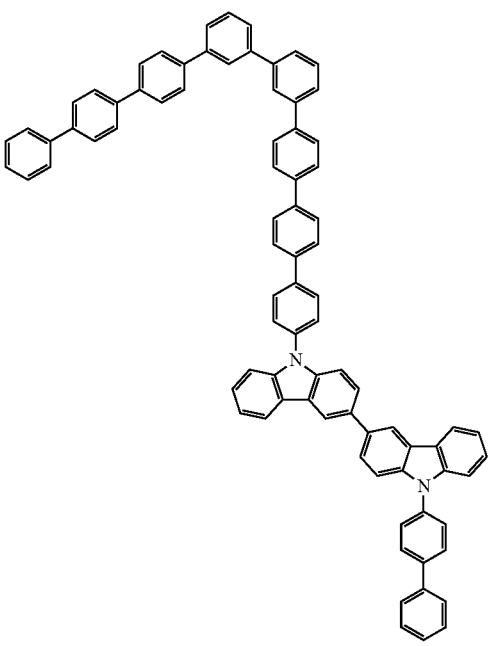
A58

-continued
A59
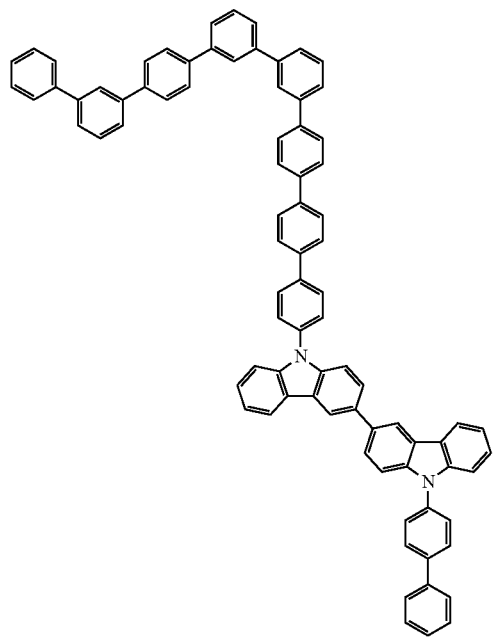
A60
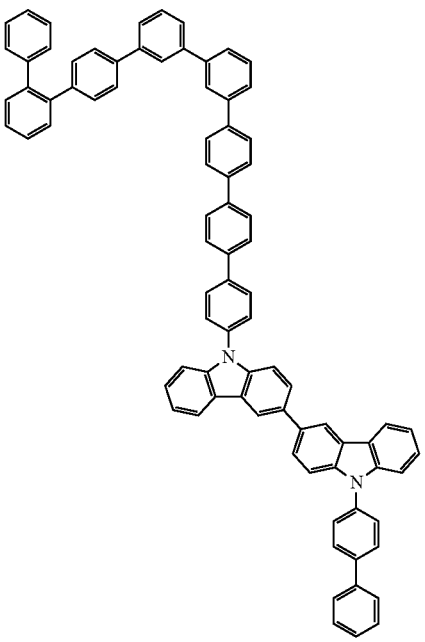
A61
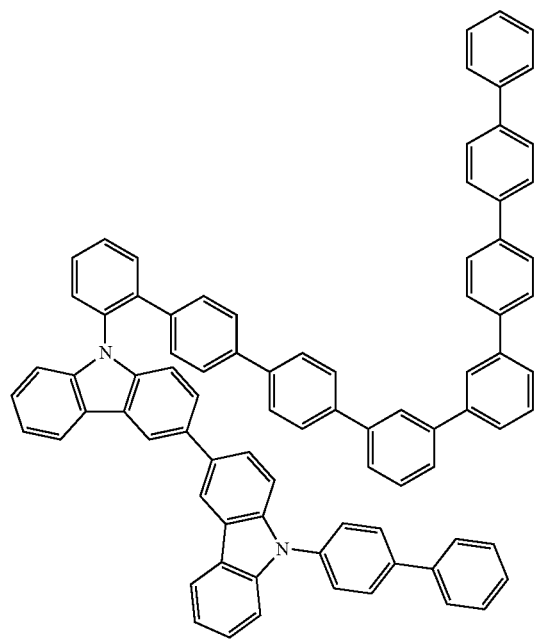
A62
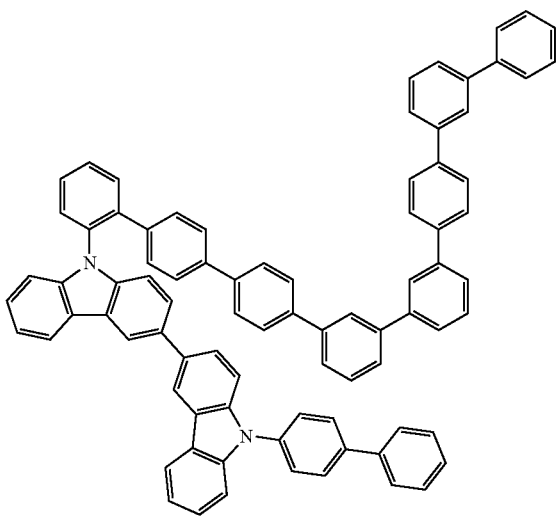

-continued
A63
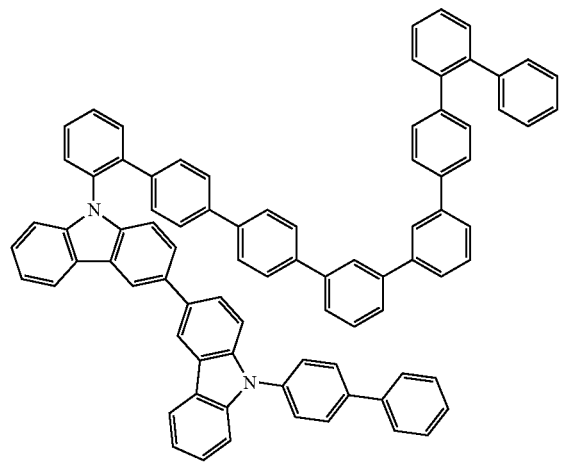
A64
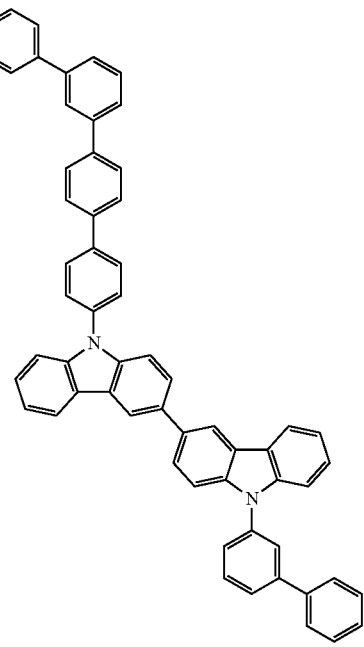
A65
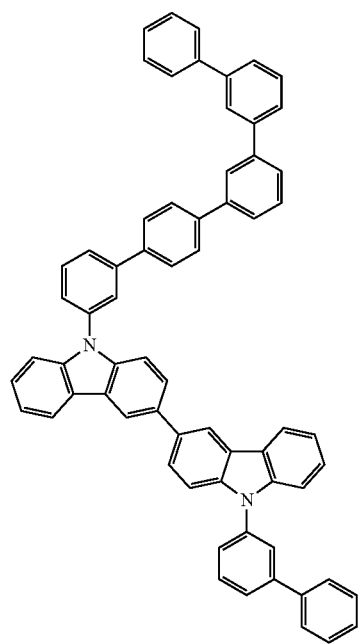
A66
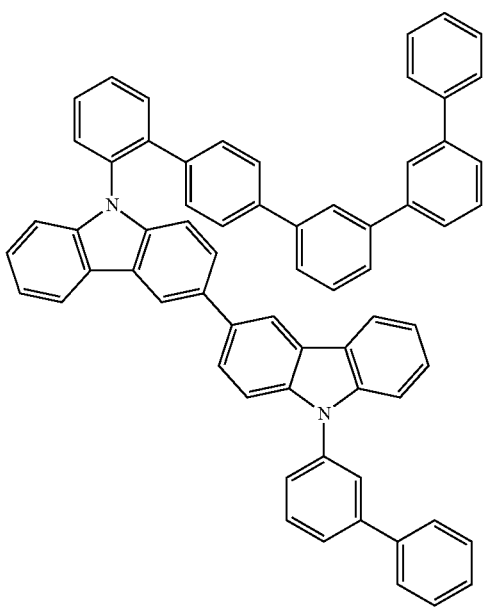

-continued
A67
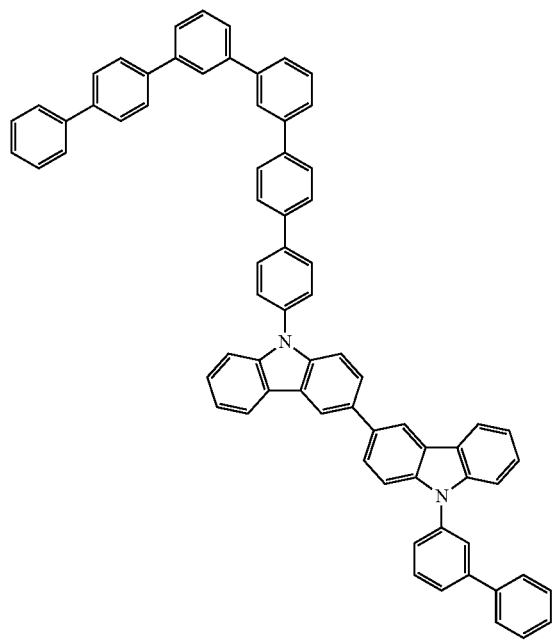
A68
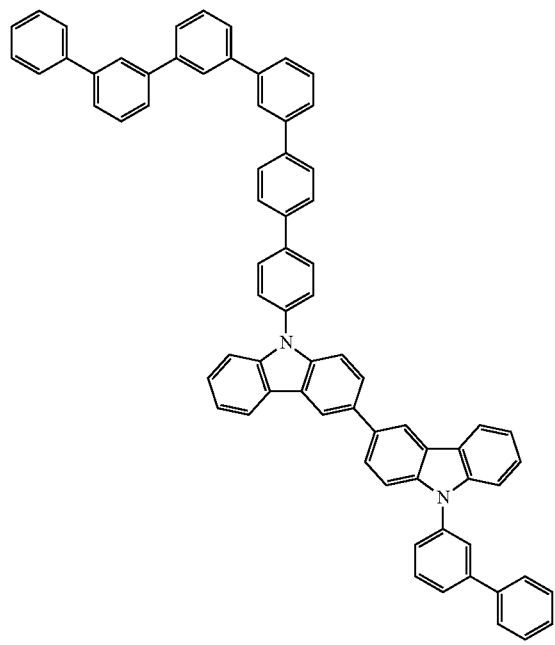
A69
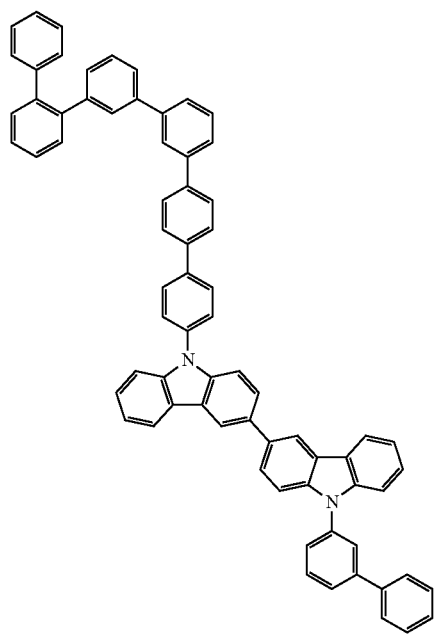
A70
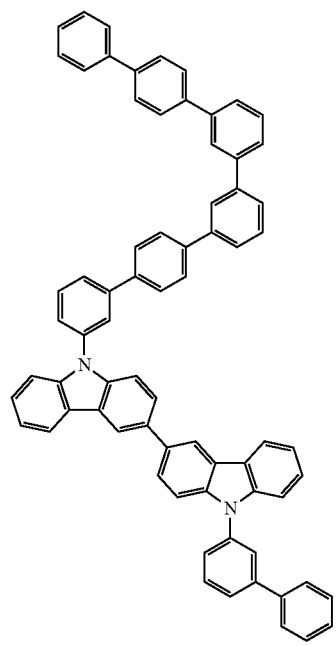

-continued
A71
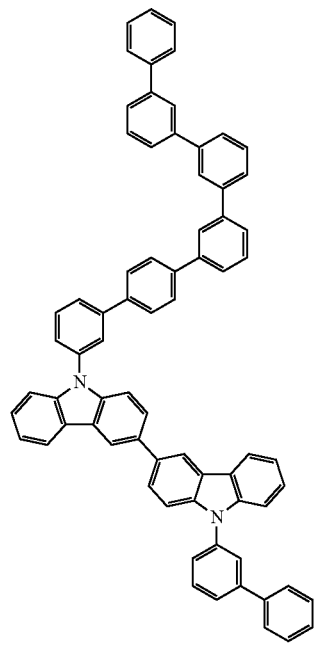
A72
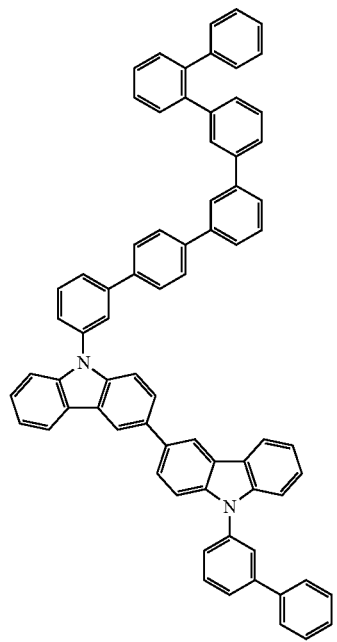
A73
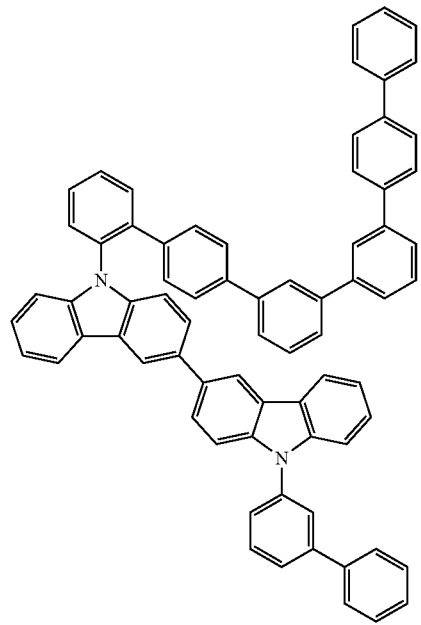
A74
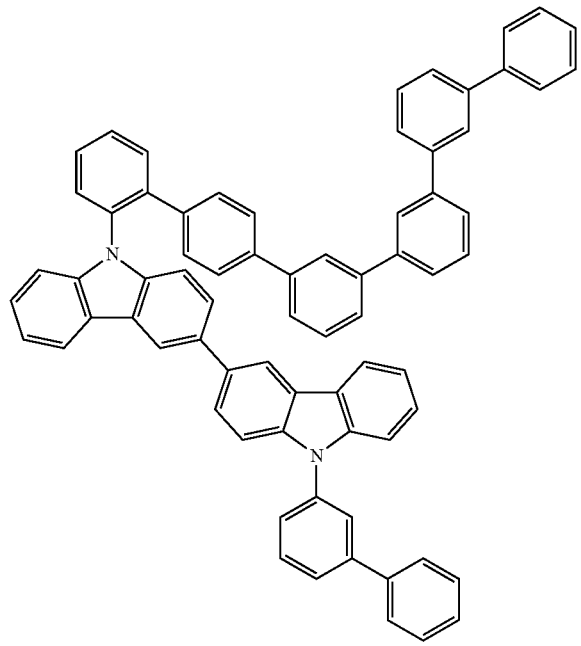

A75
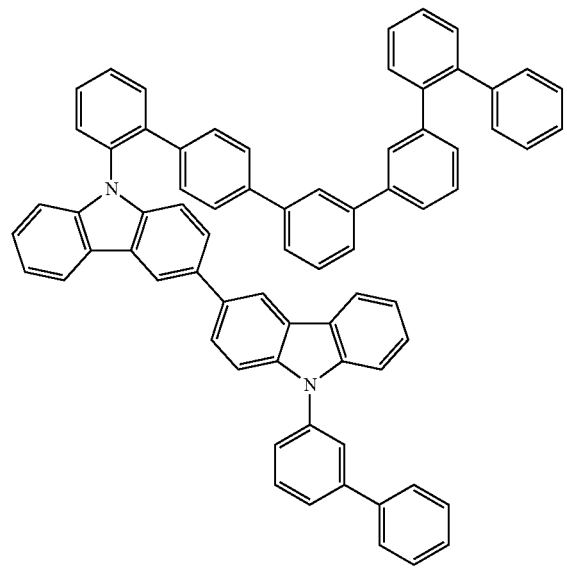
A76
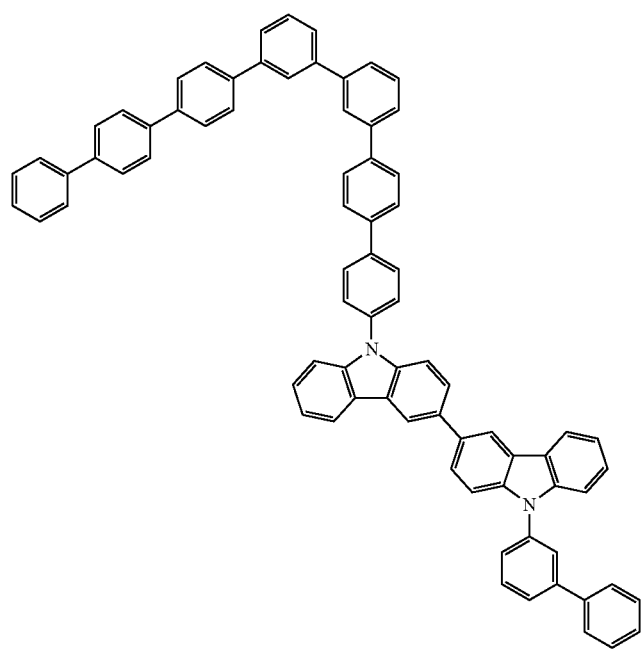

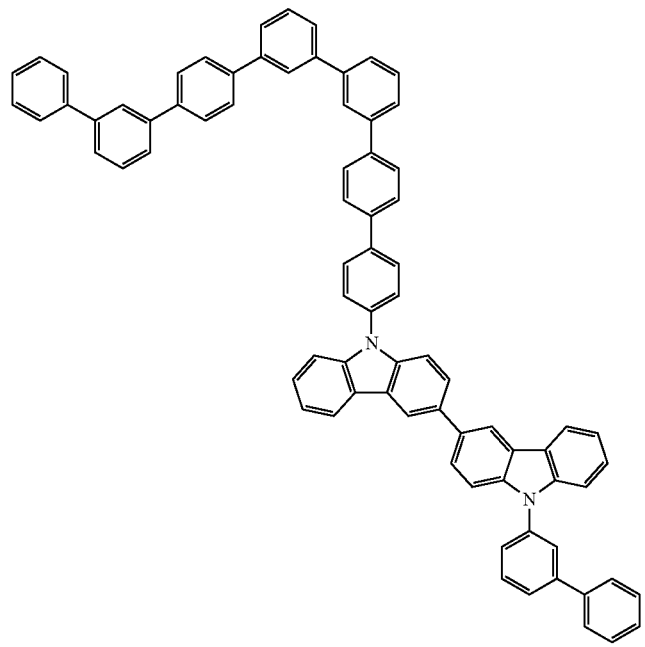
A77
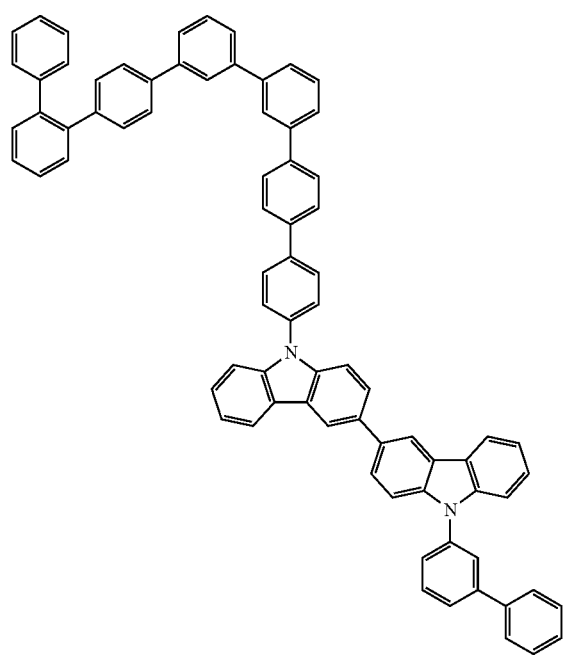
A78
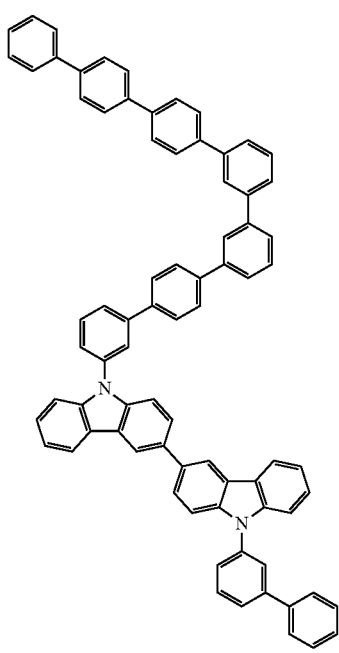
A79

-continued
A80
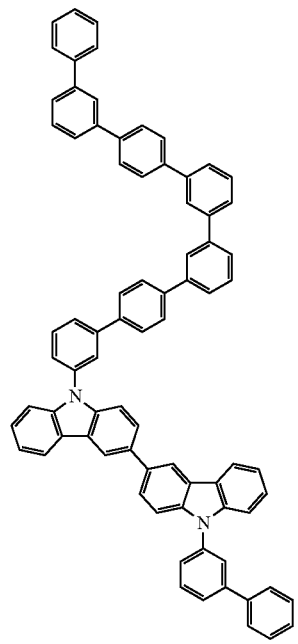
A81
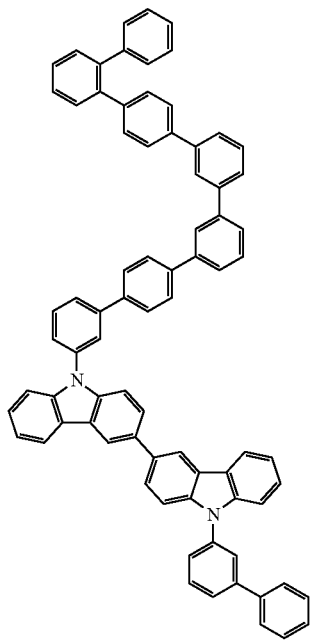
A82
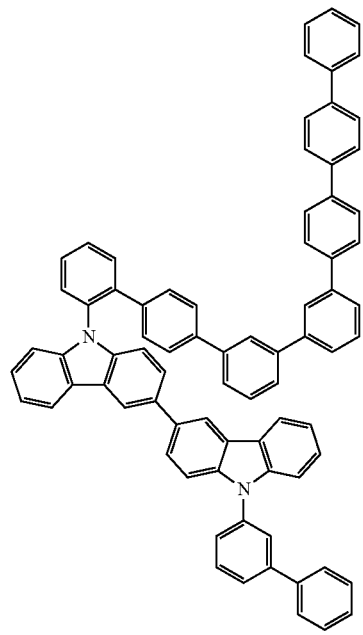
A83
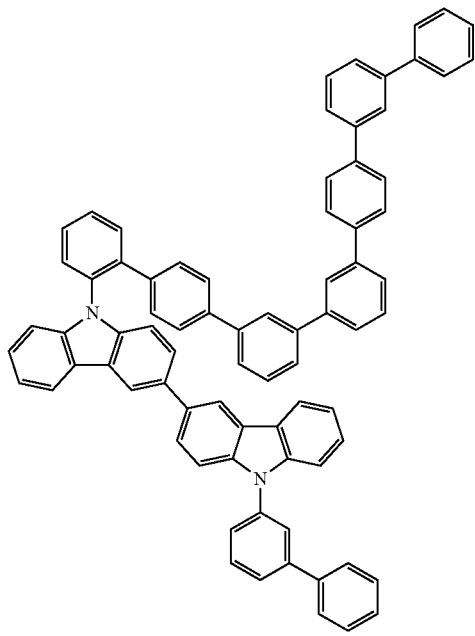

-continued
A84
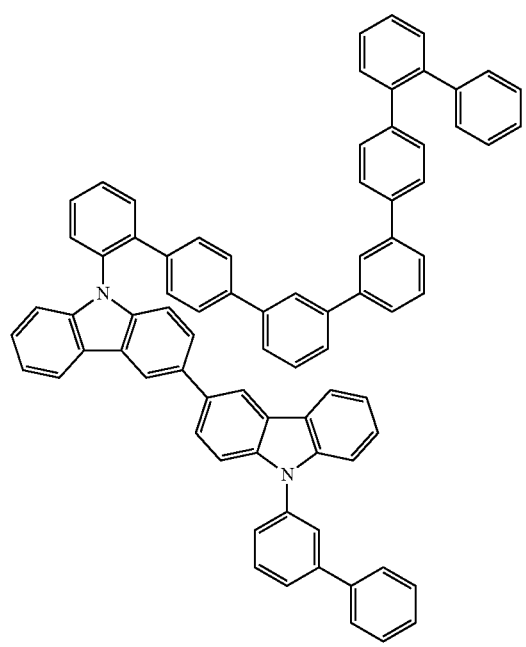
A85
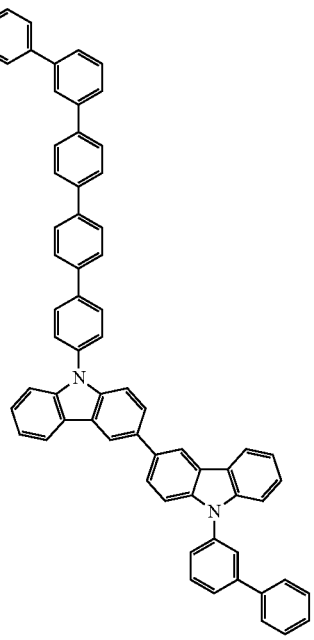
A86
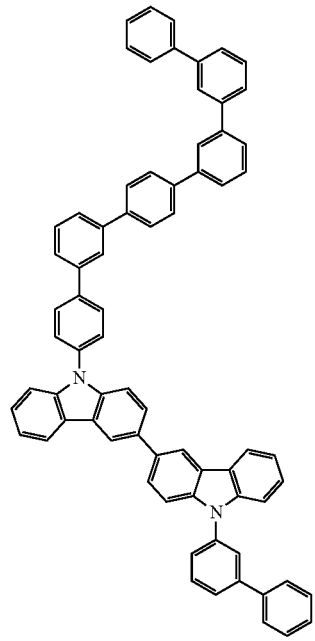
A87
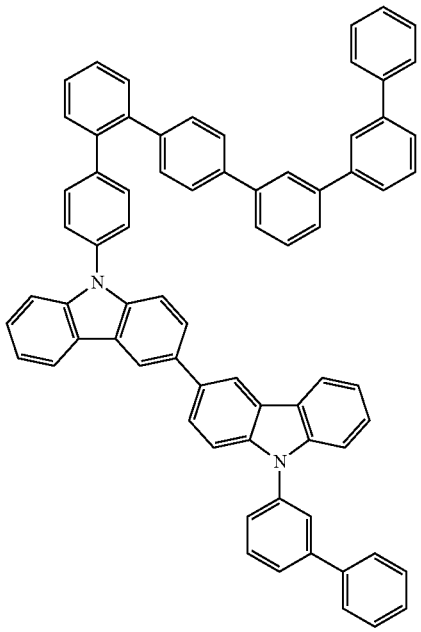

-continued
A88 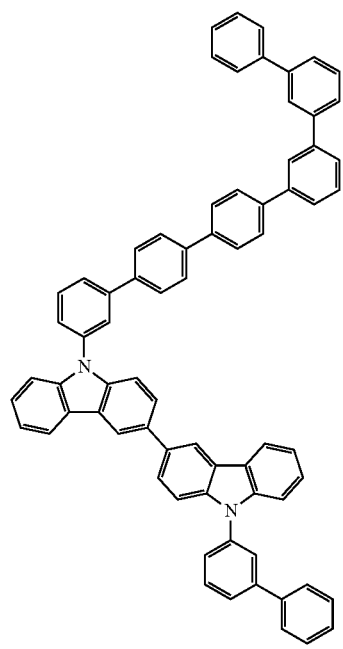
A89 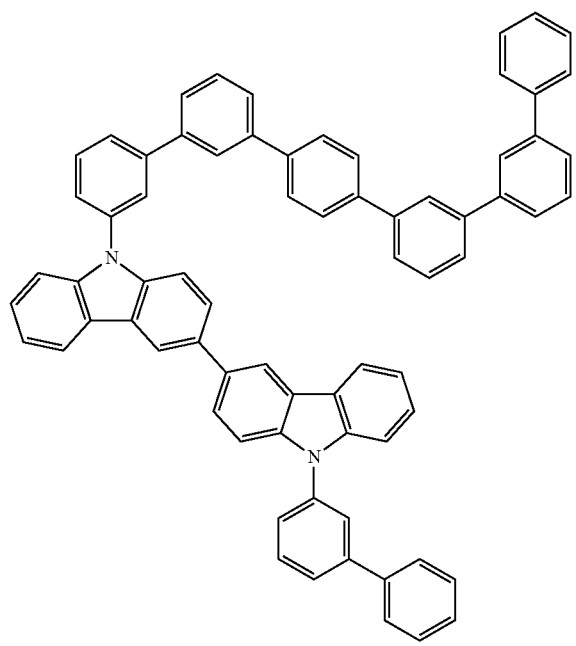
A90 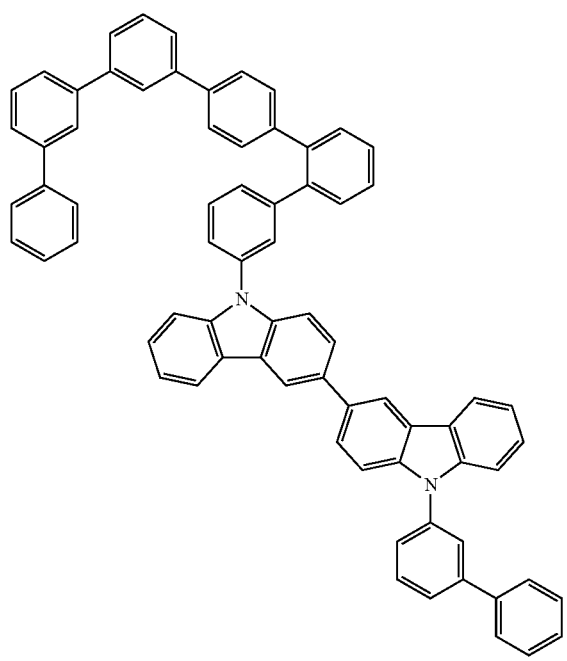
A91 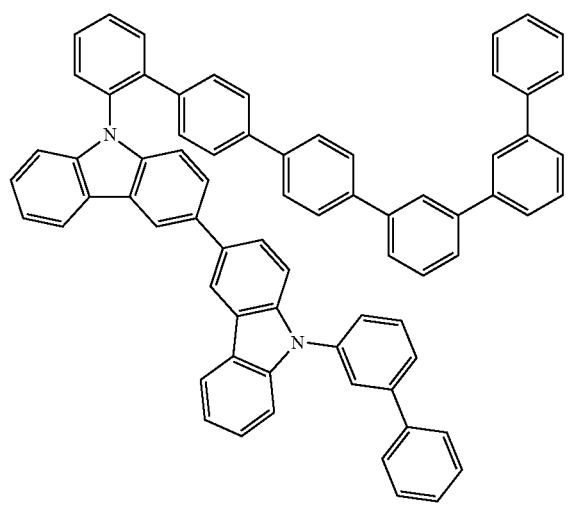

-continued
A92
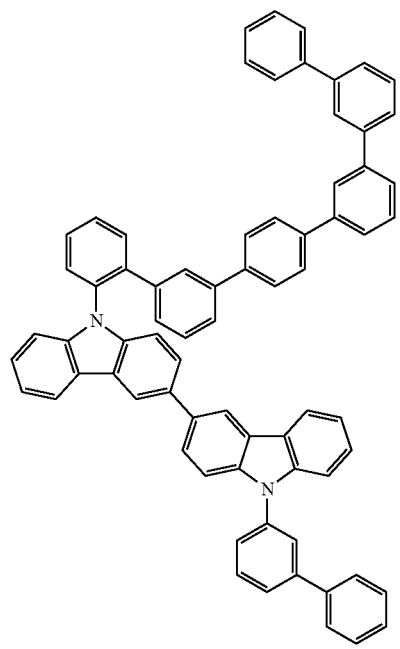
A93
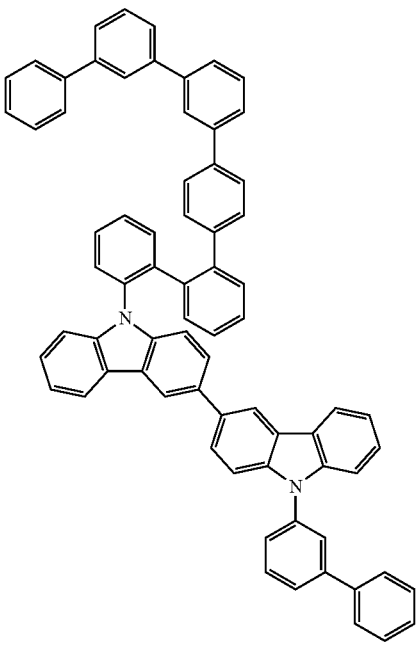
A94
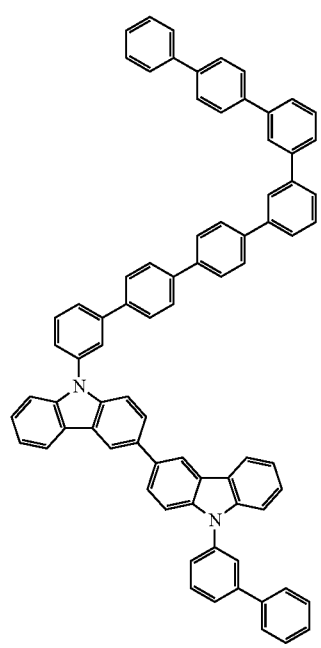
A95
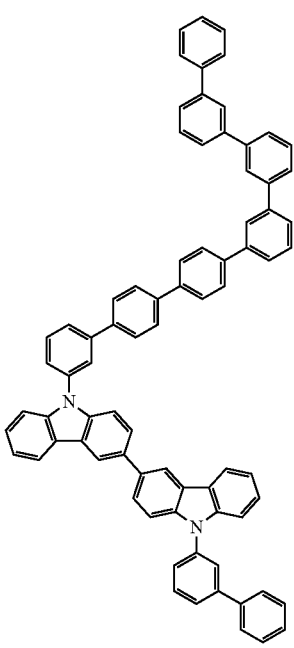

-continued
A96
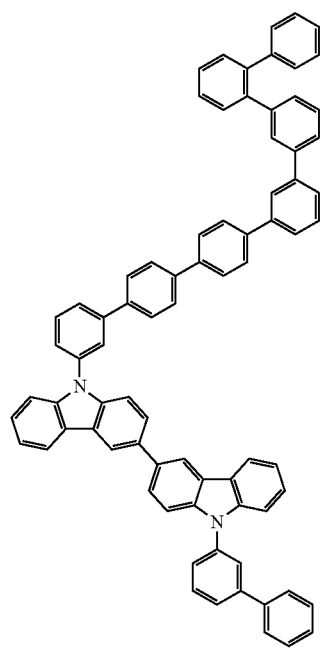
A97
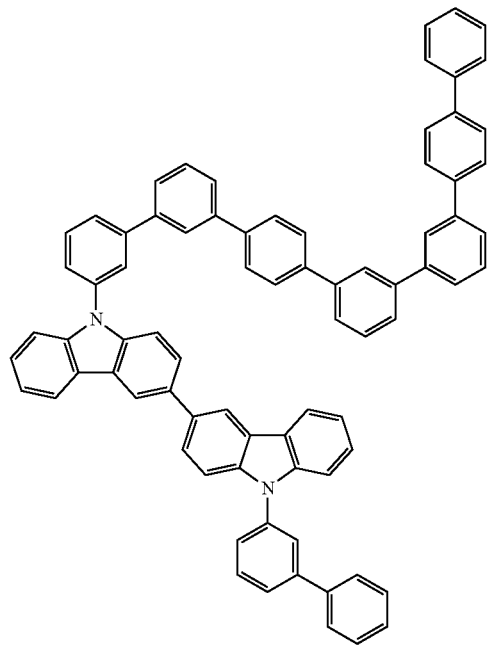
A98
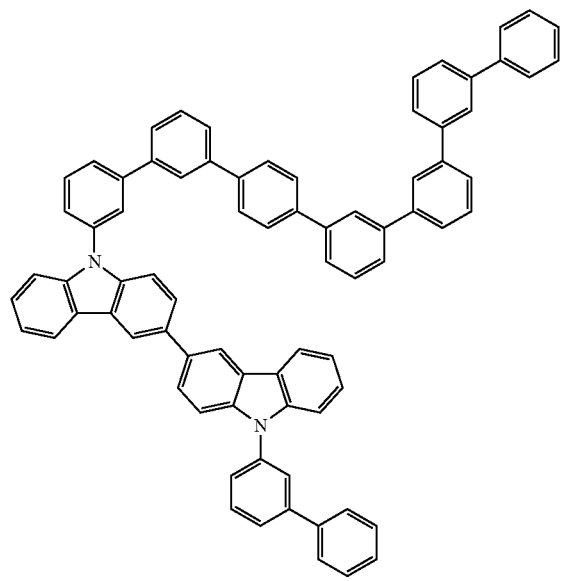
A99
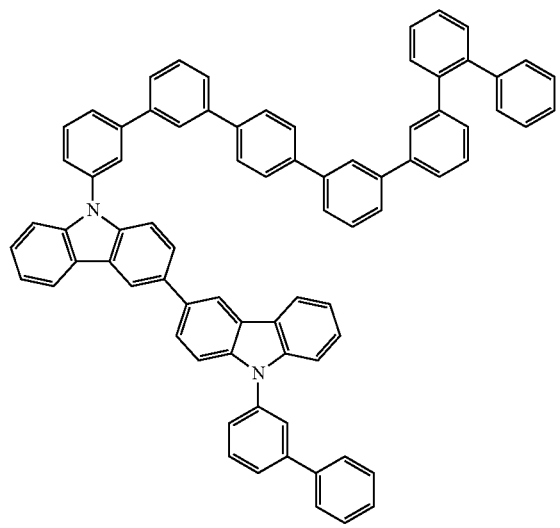

-continued
A100
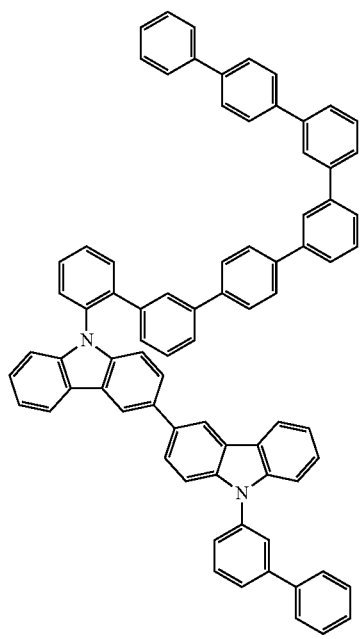
A101
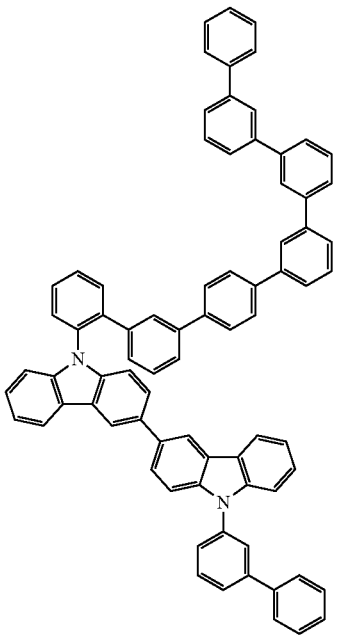
A102
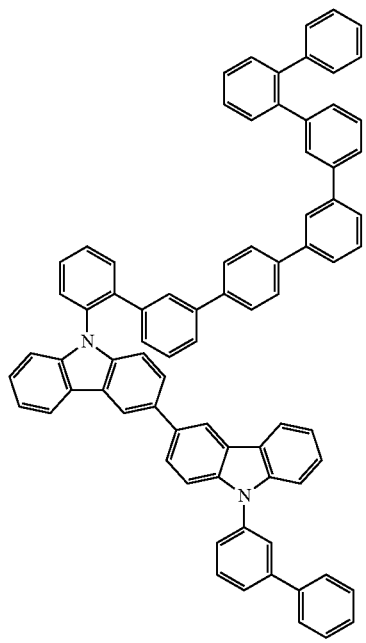
A103
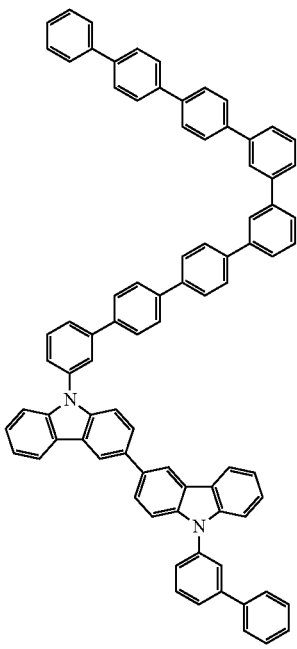

-continued
A104
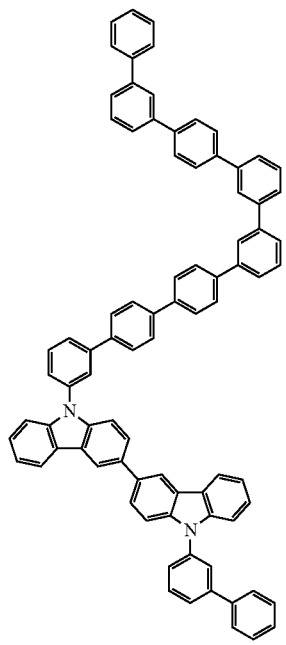
A105
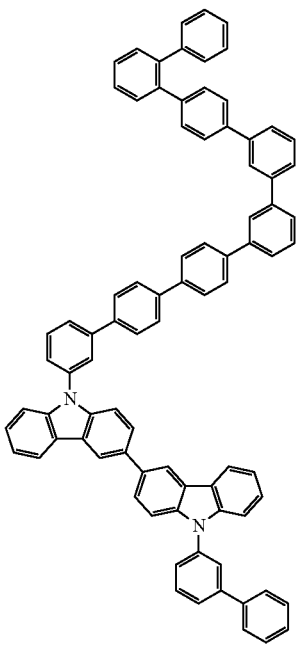
A106
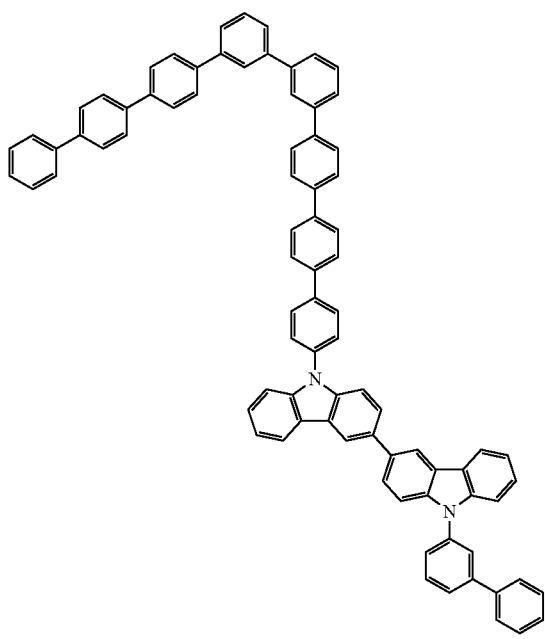

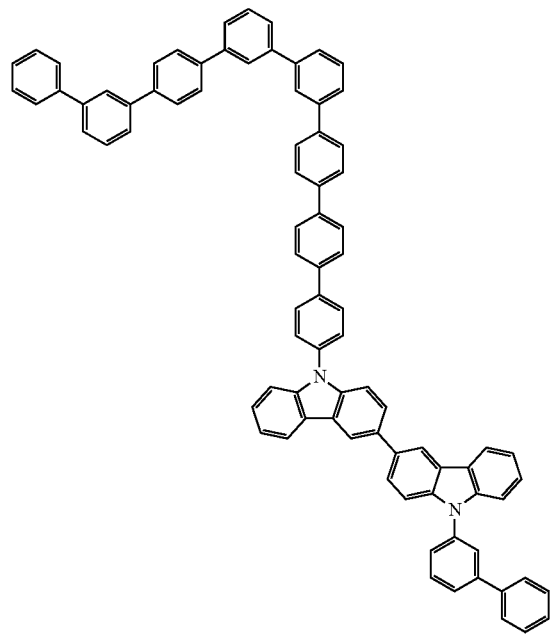
A107
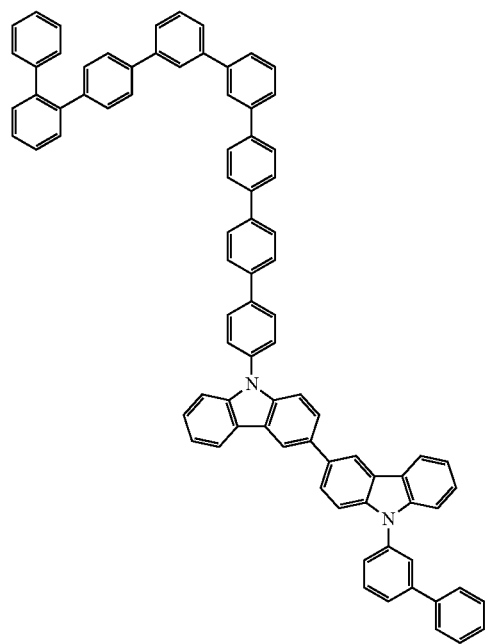
A108
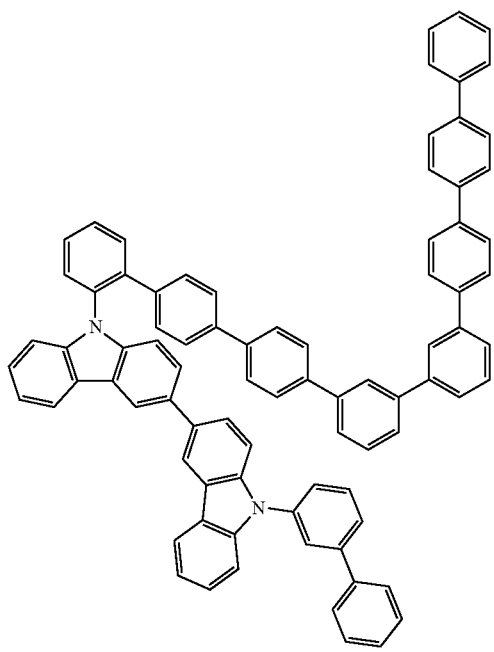
A109

-continued
A110
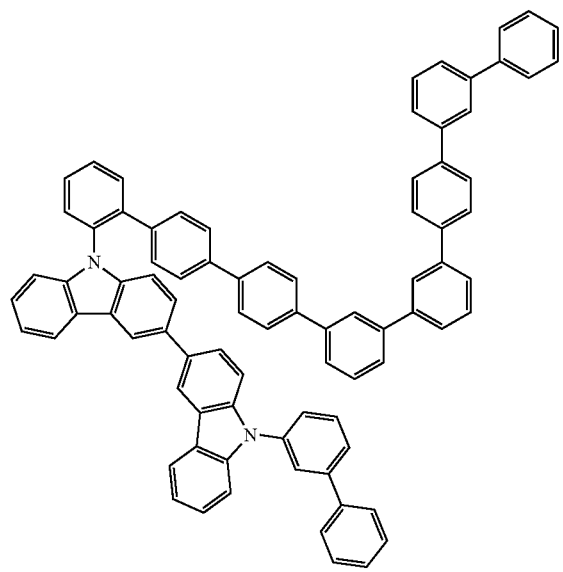
A111
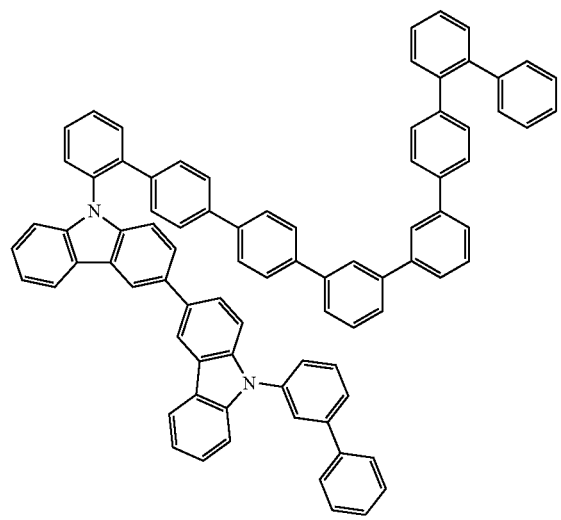
A112
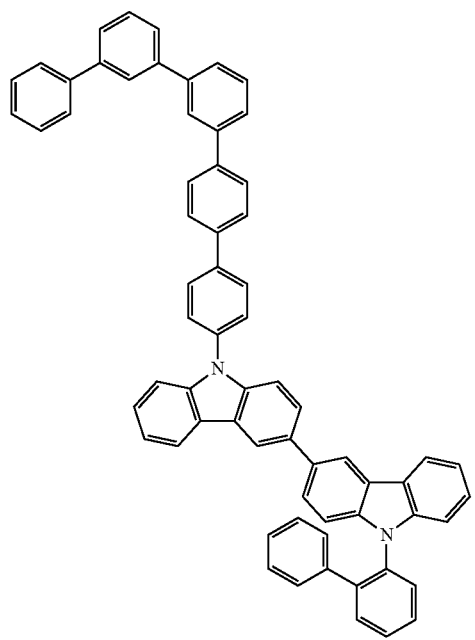
A113
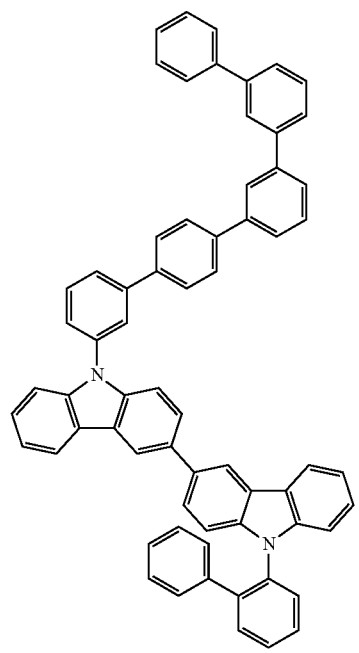

-continued
A114
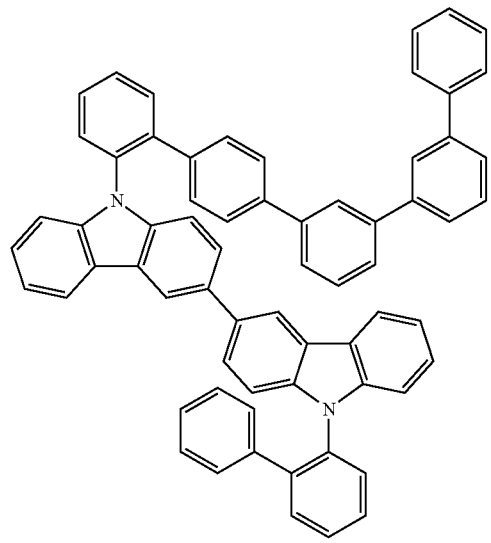
A115
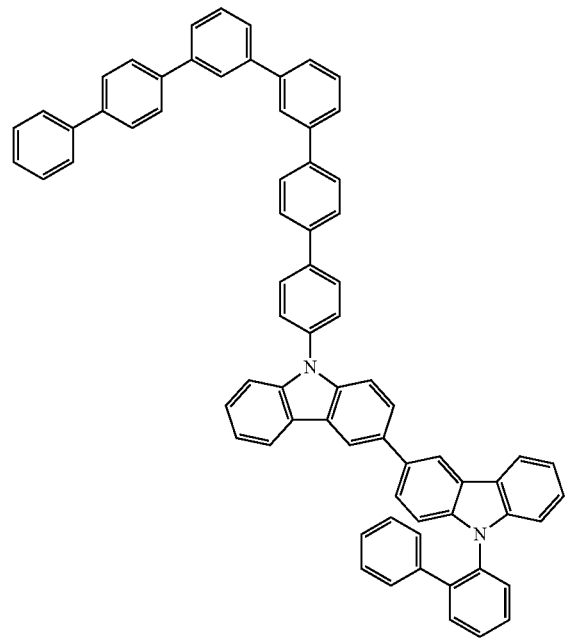
A116
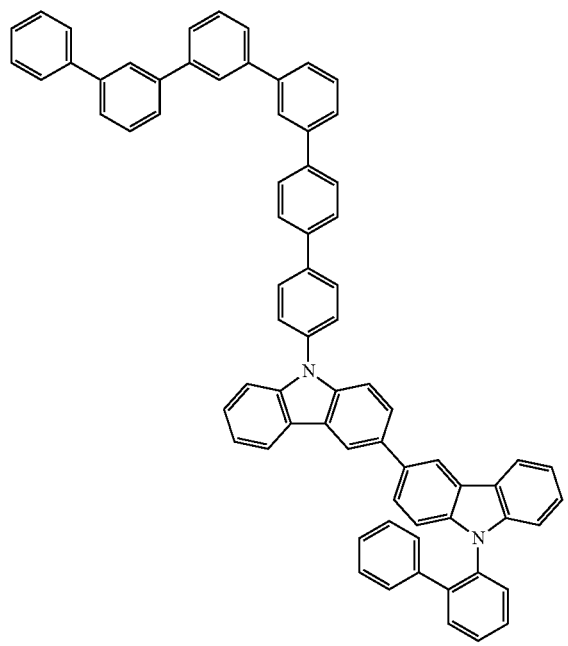
A117
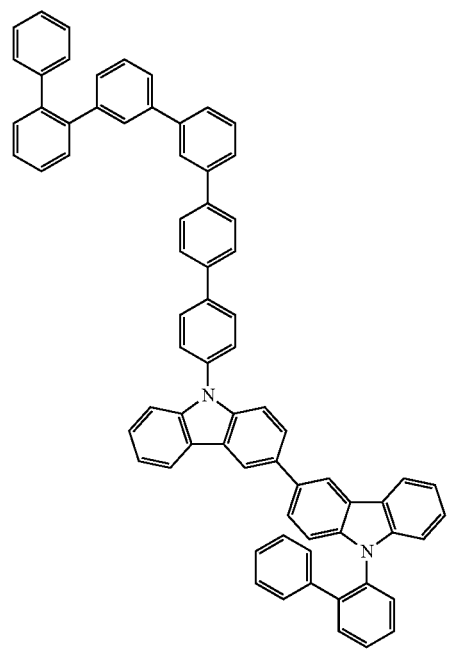

-continued
A118
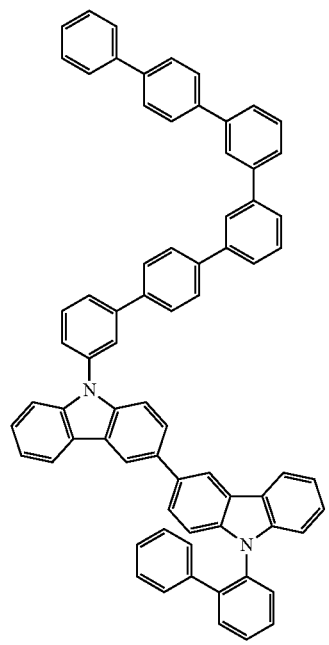
A119
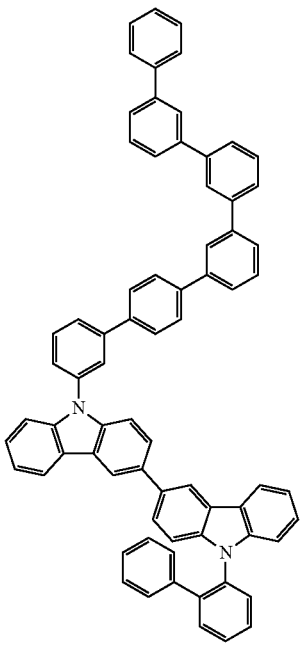
A120
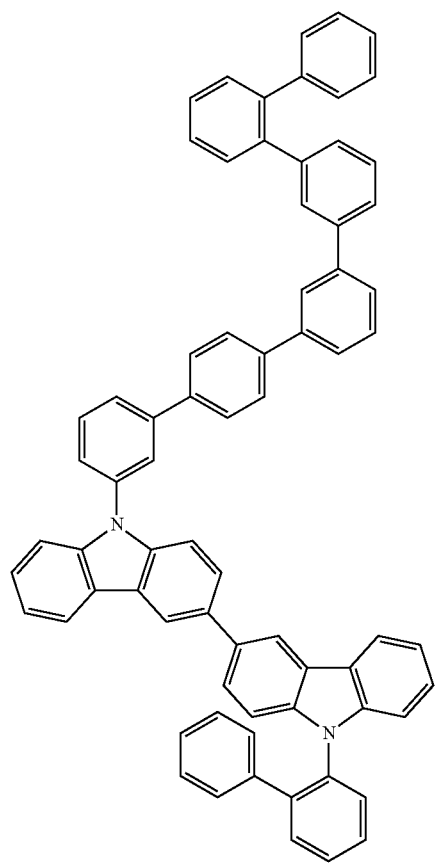
A121
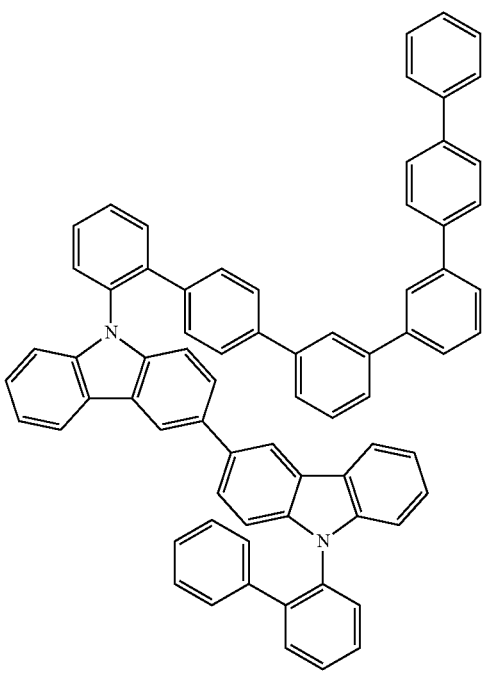

-continued
A122
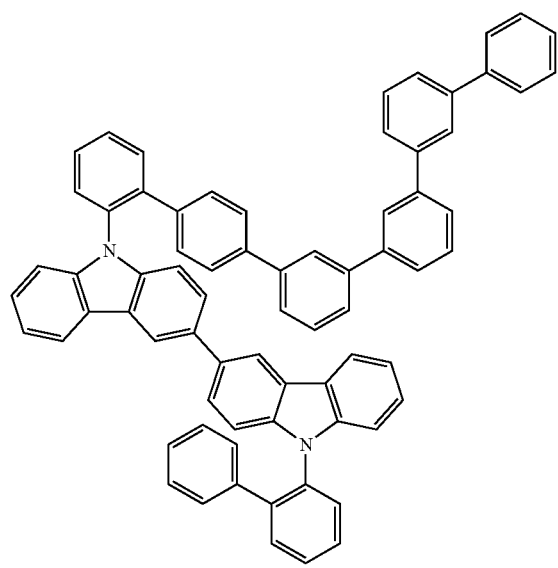
A123
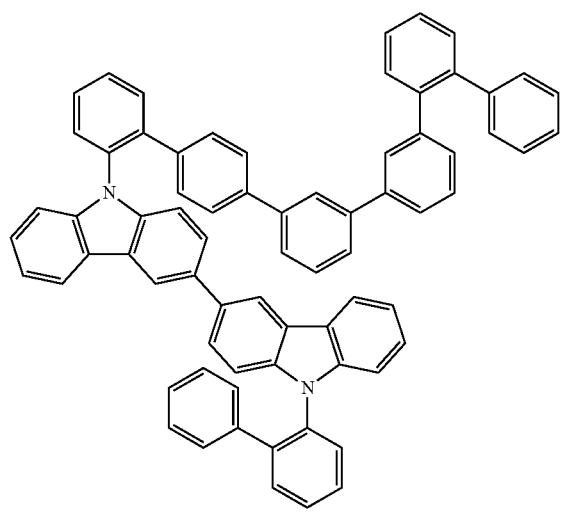
A124
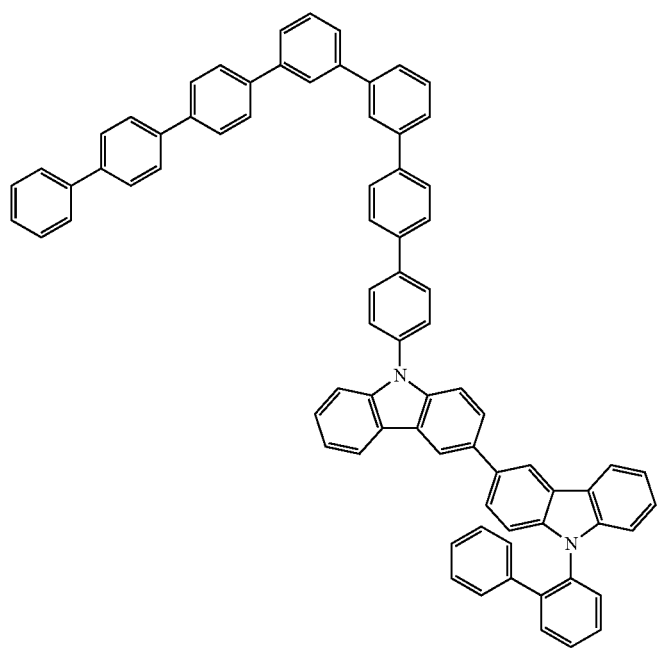

A125
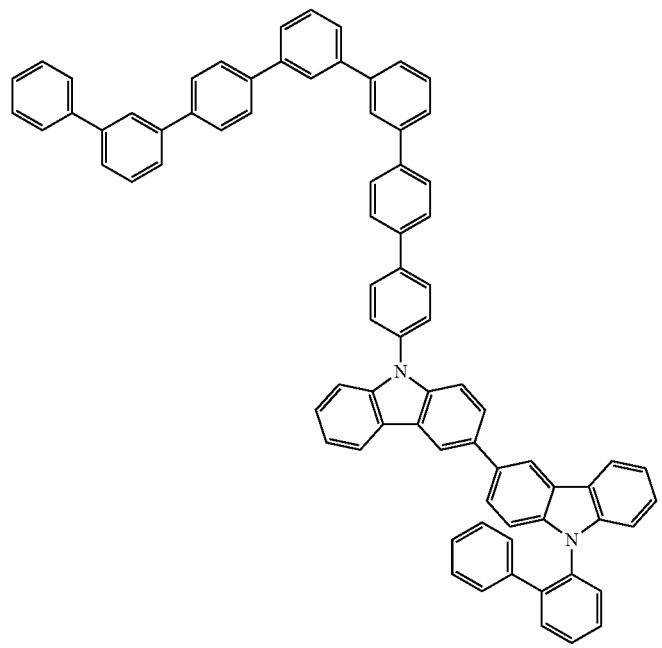
A126
A127
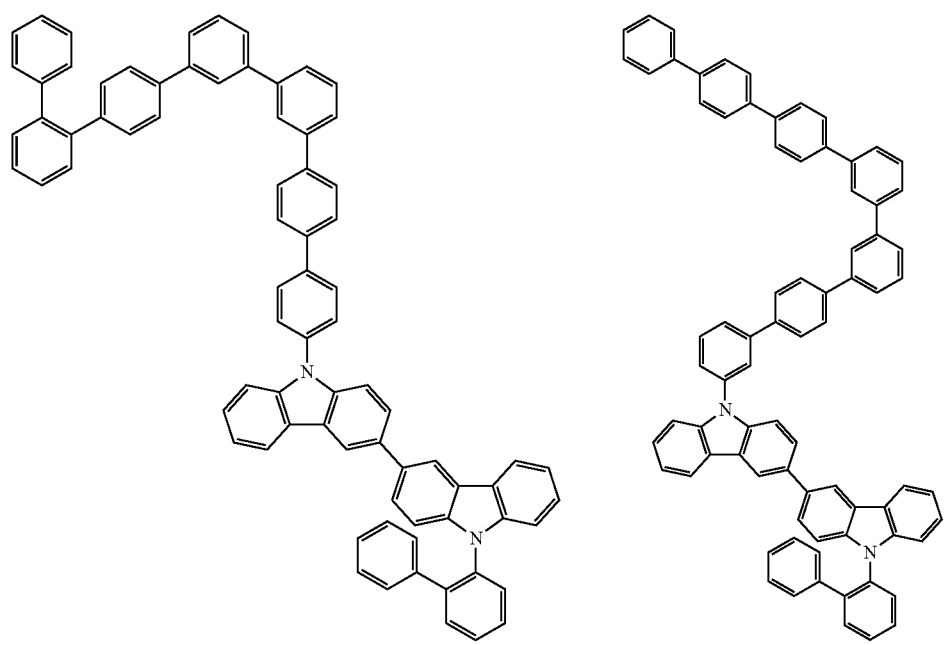

-continued
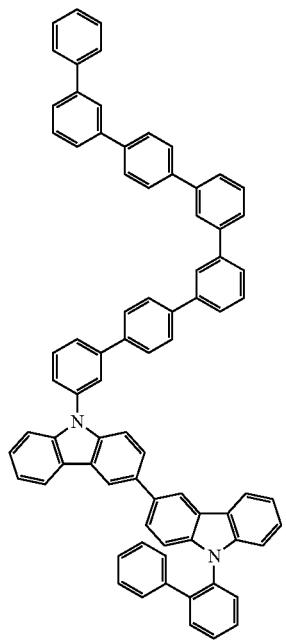
A128
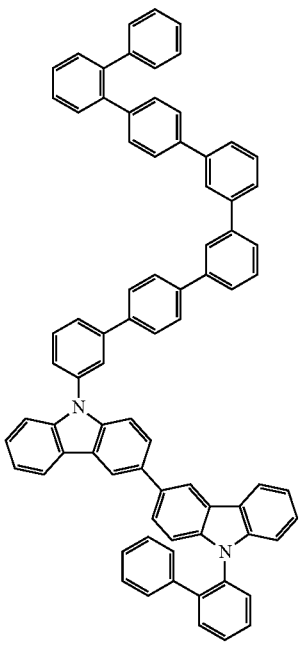
A129
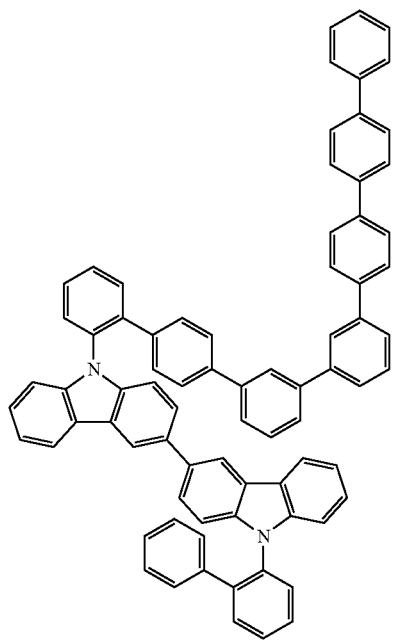
A130
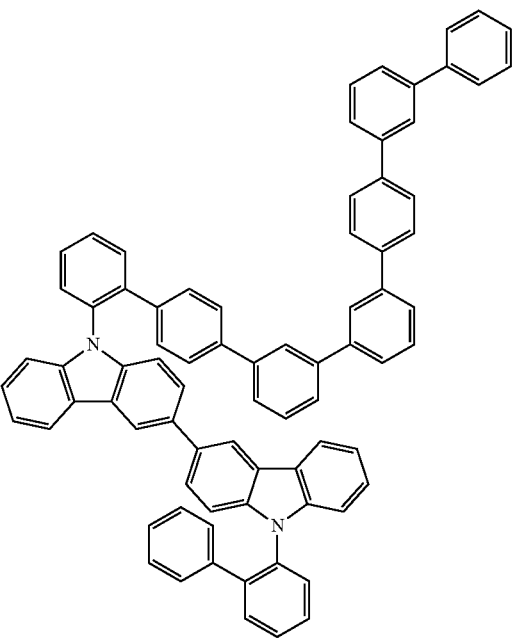
A131

-continued
A132
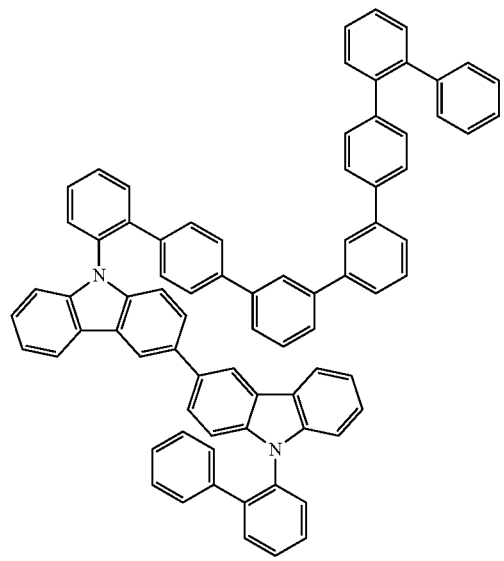
A133
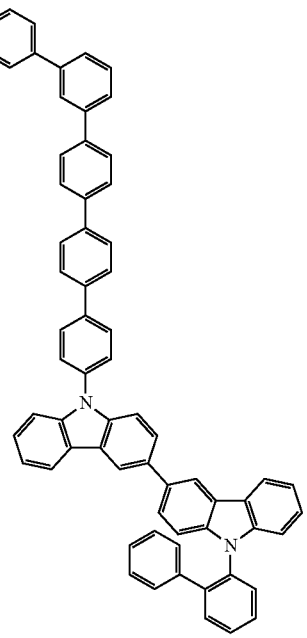
A134
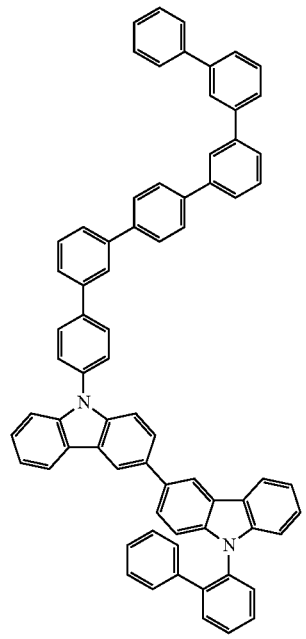
A135
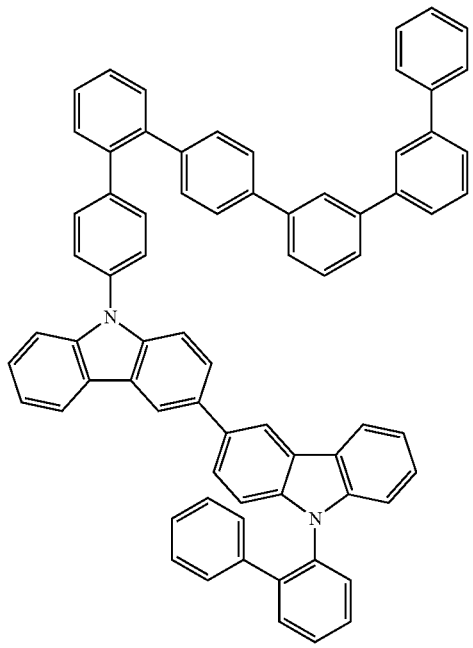

-continued
A136
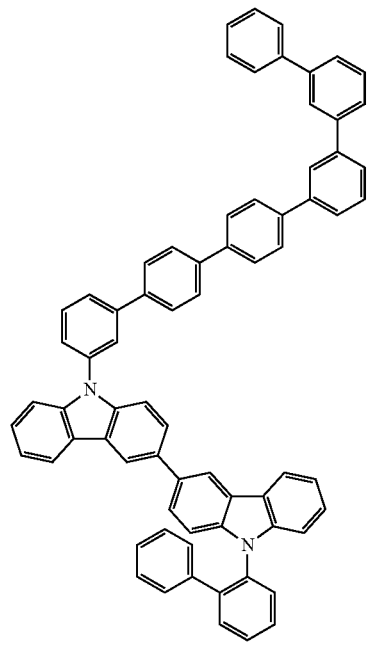
A137
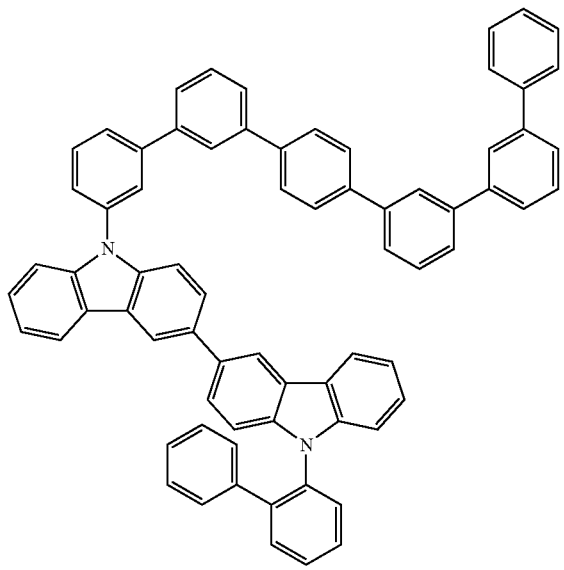
A138
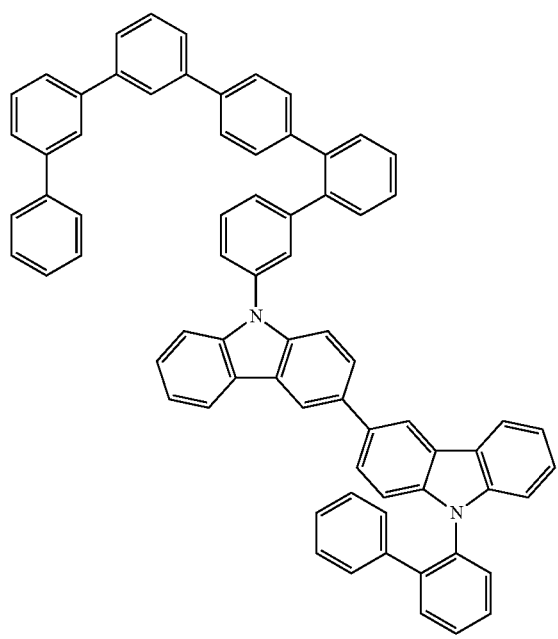
A139
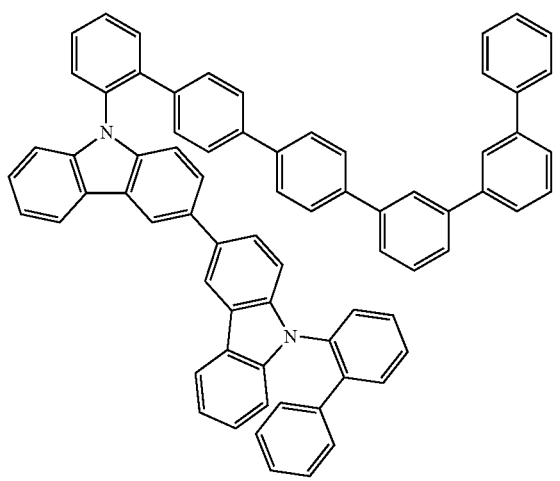

-continued
A140
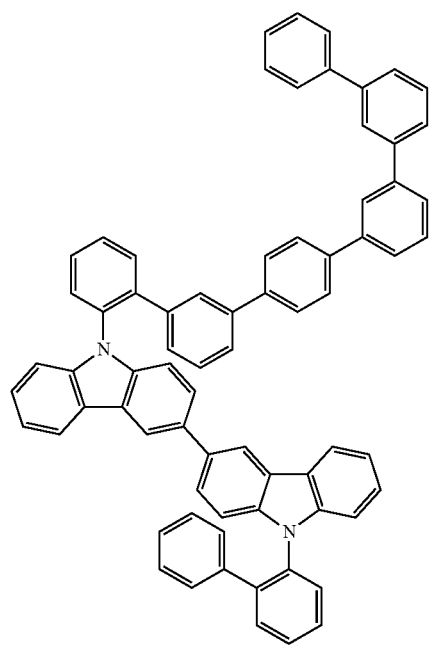
A141
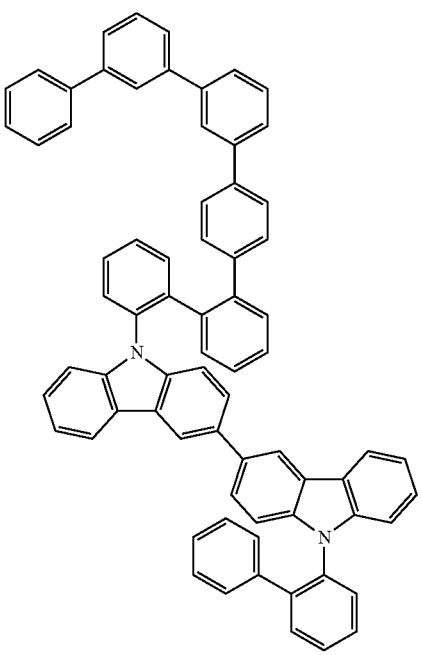
A142
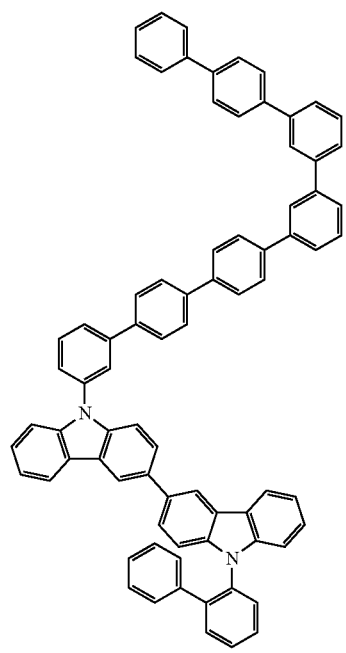
A143

-continued
A144
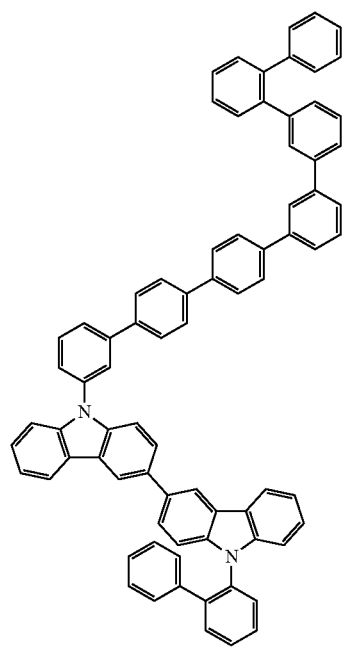
A145
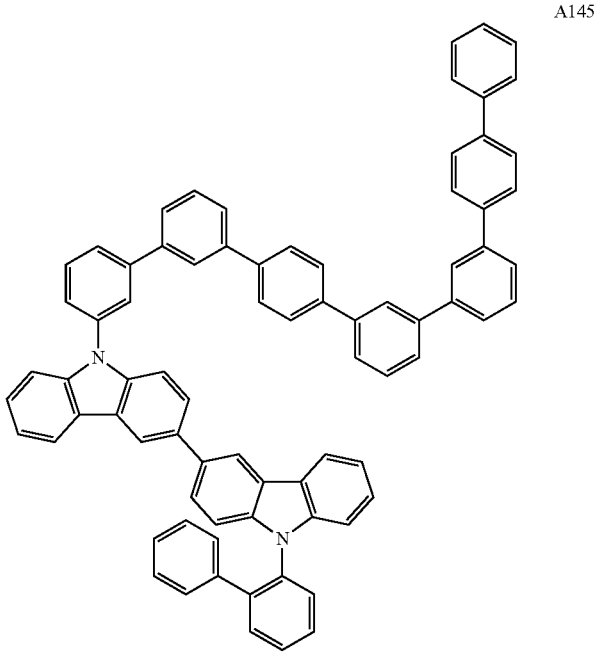
A146
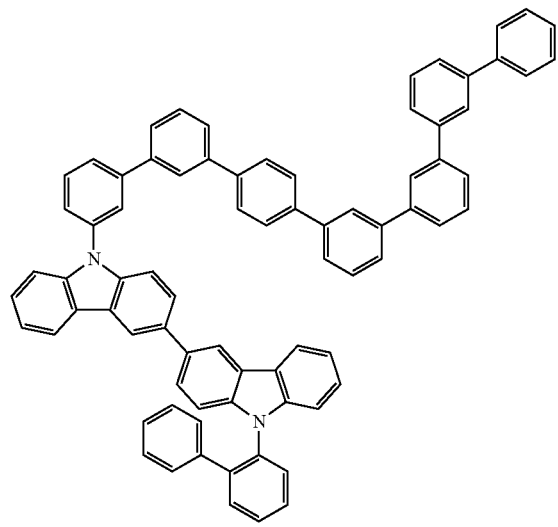
A147
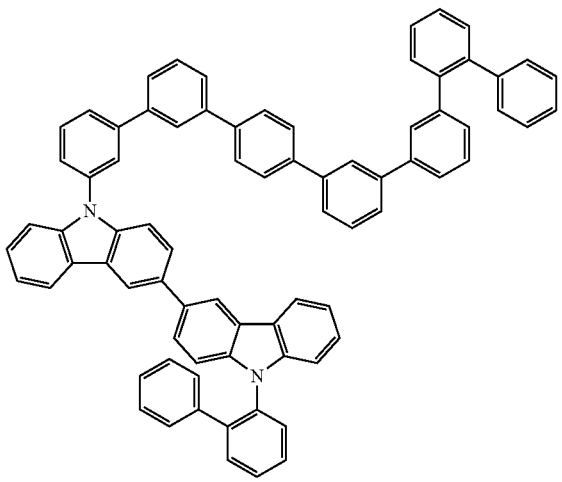

-continued
A148
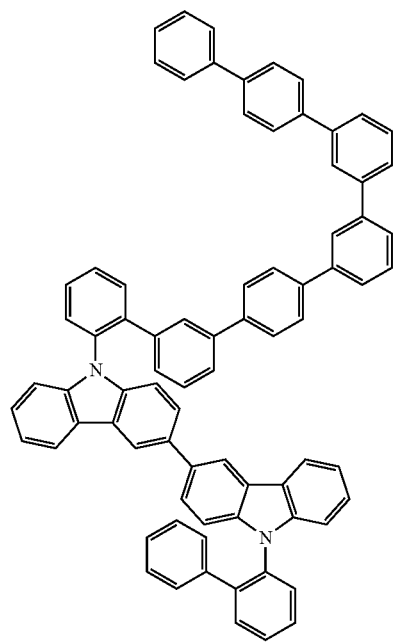
A149
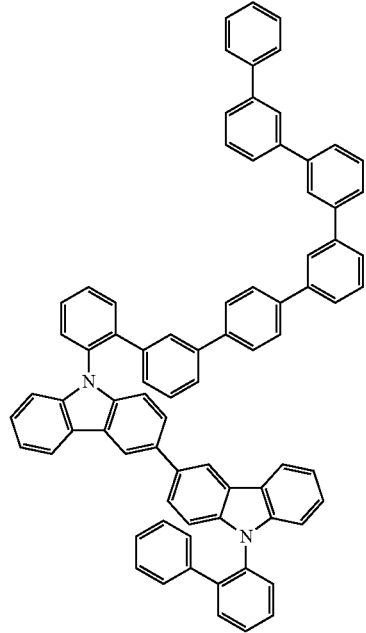
A150
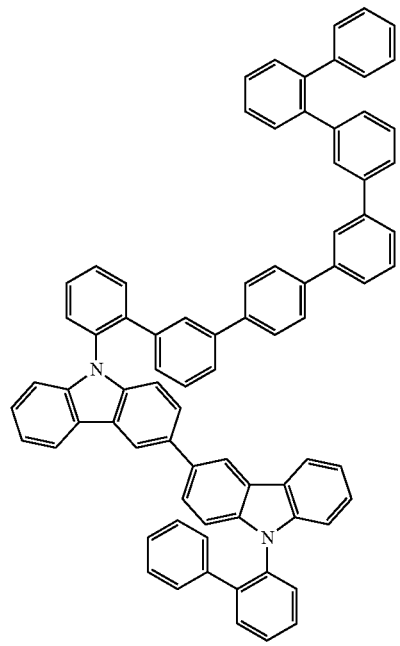
A151
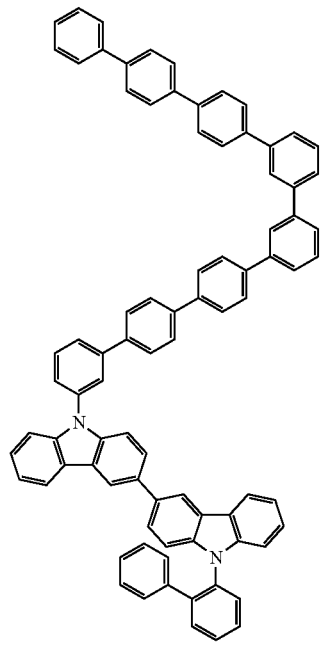

-continued
A152
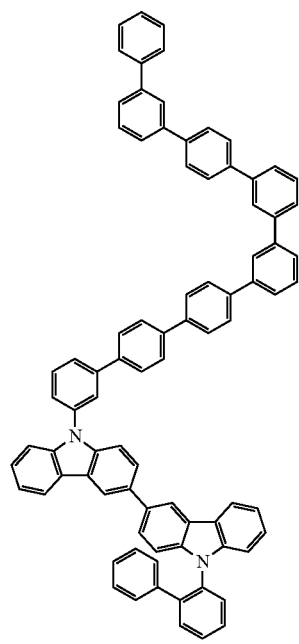
A153
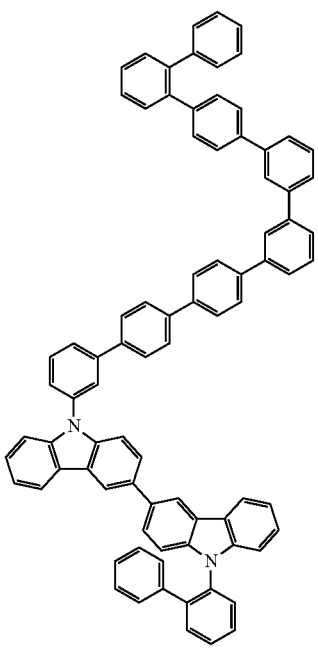
A154
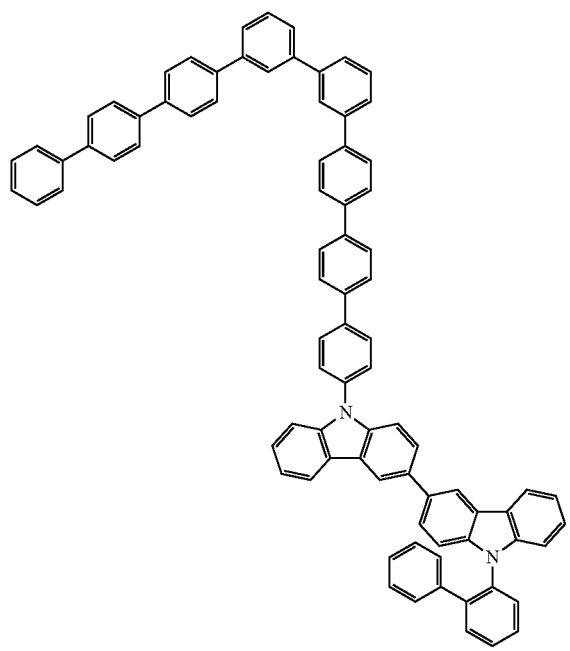

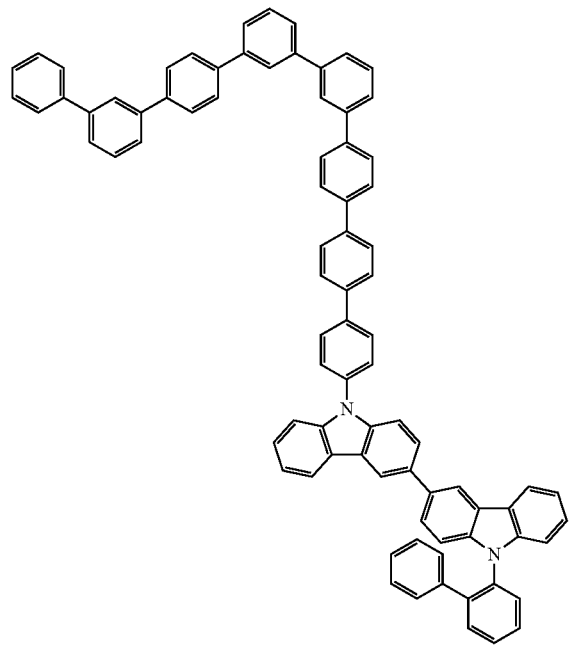
A155
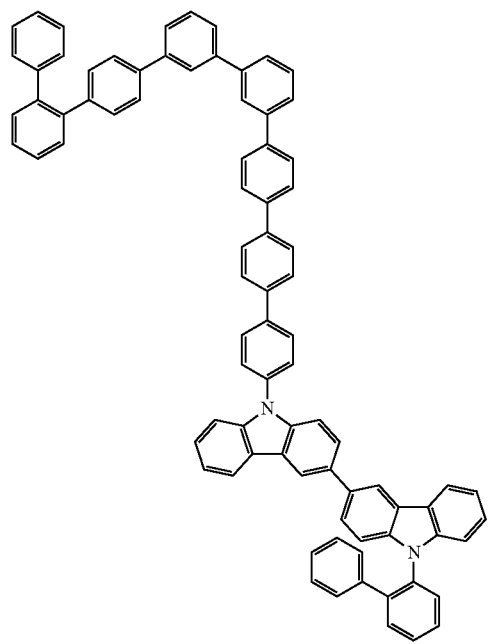
A156
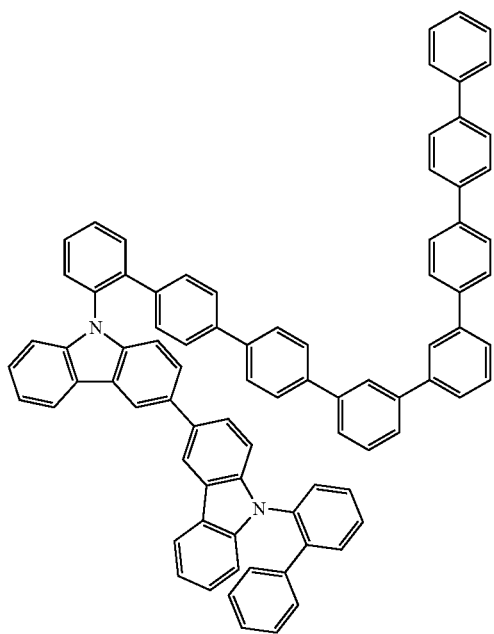
A157

-continued
A158
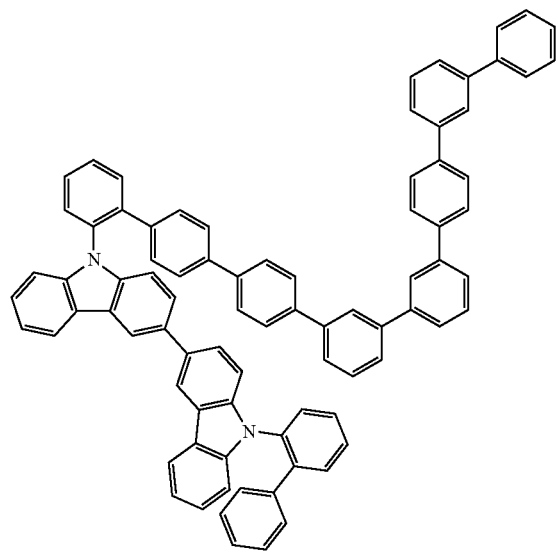
A159
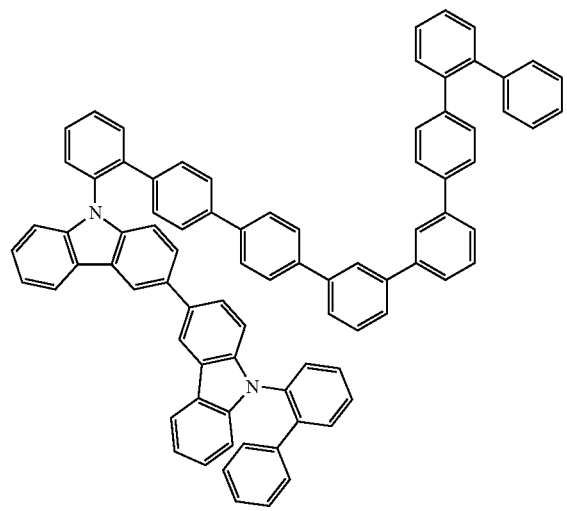
A160
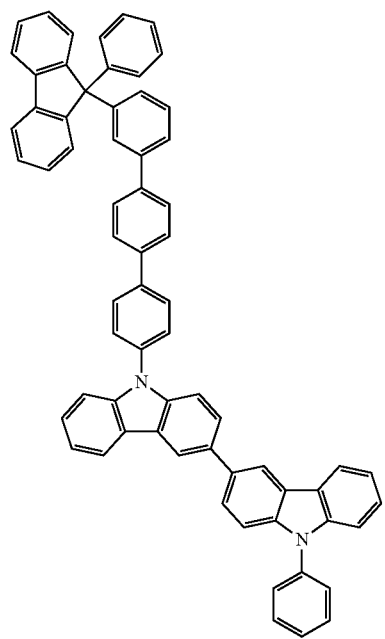
A161
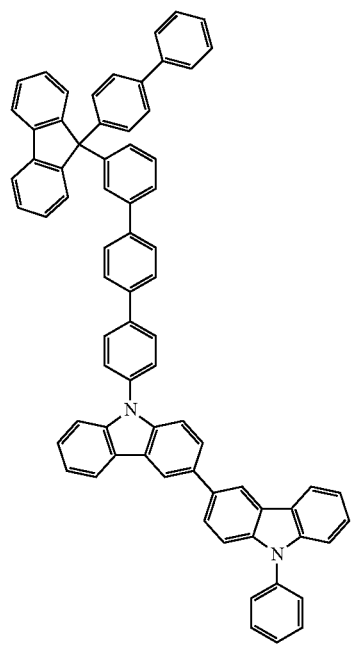

-continued
A162
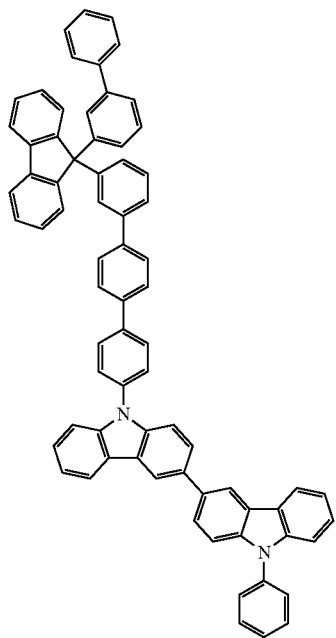
A163
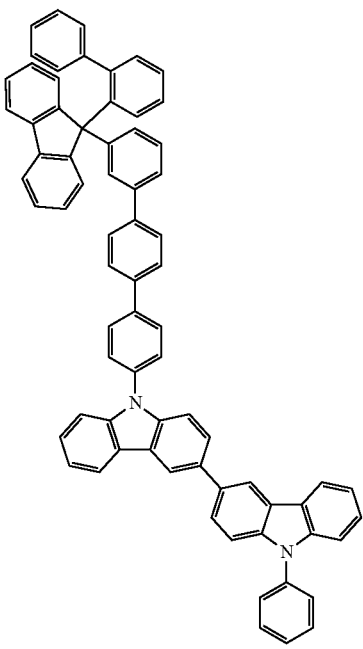
A164
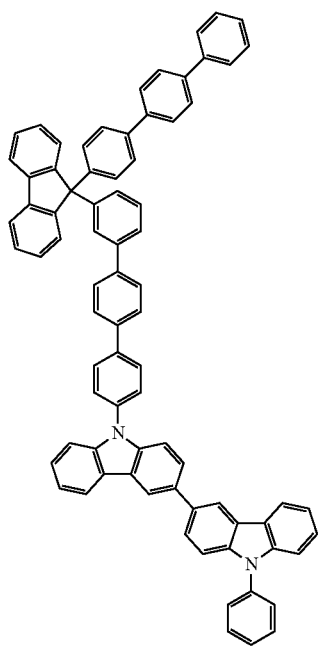
A165
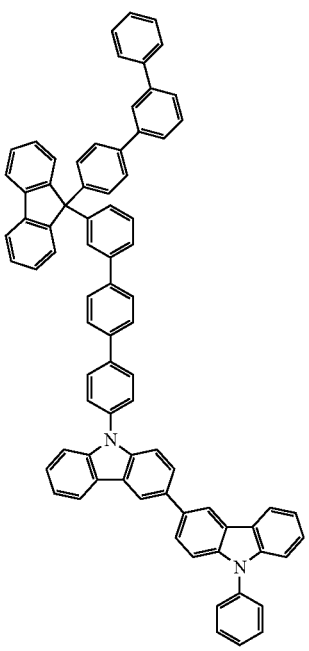

-continued
A166
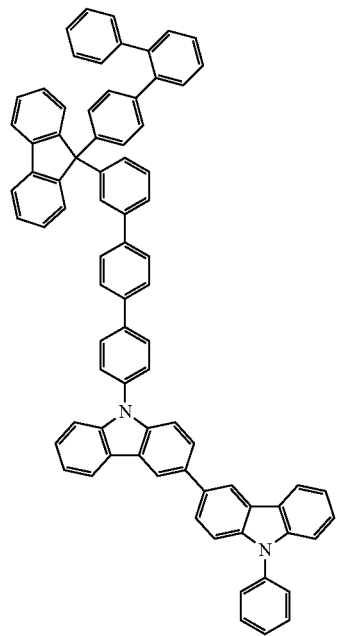
A167
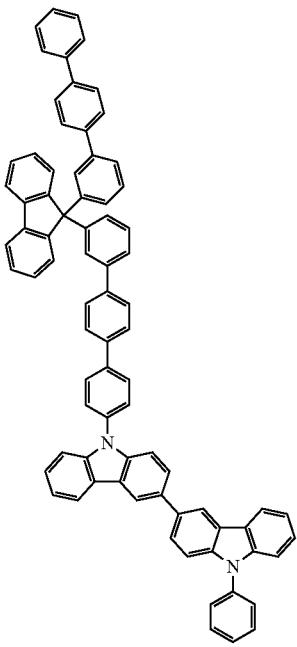
A168
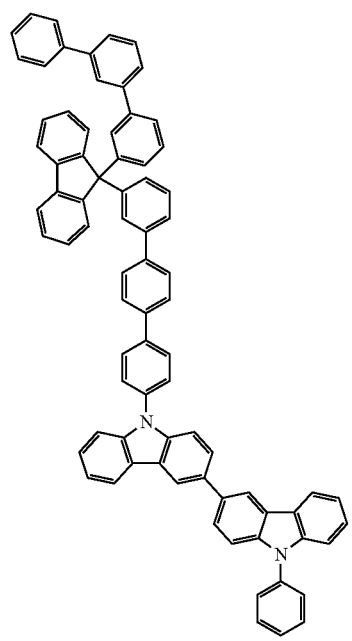
A169
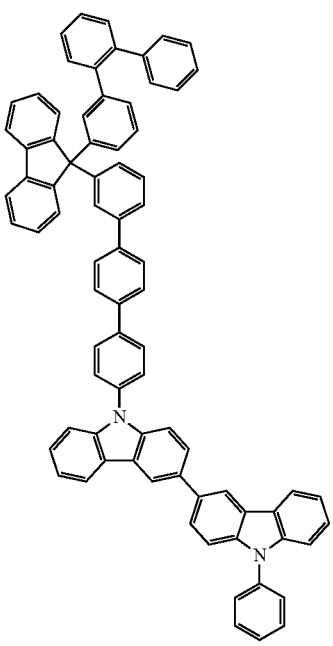

-continued
A170 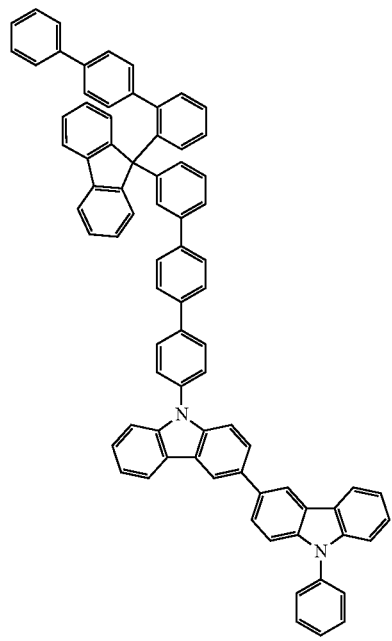
A171 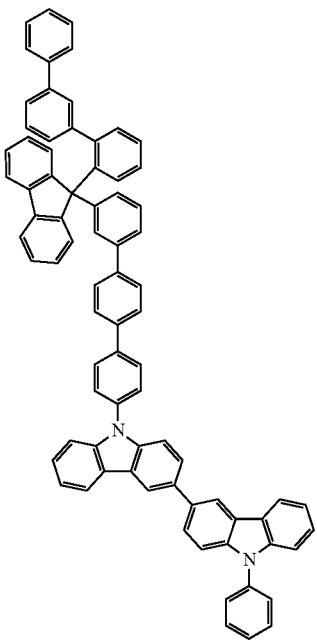
A172 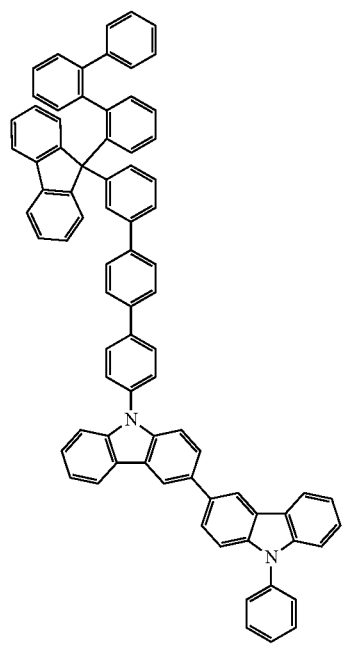
A173 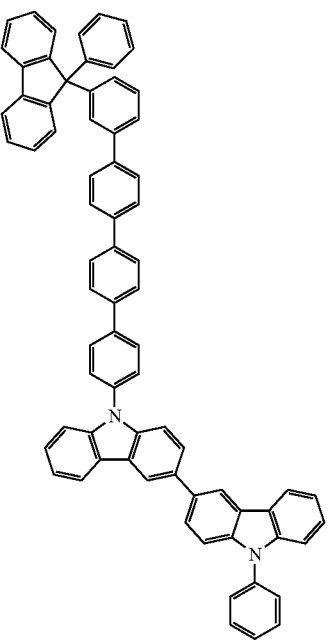

-continued
A174
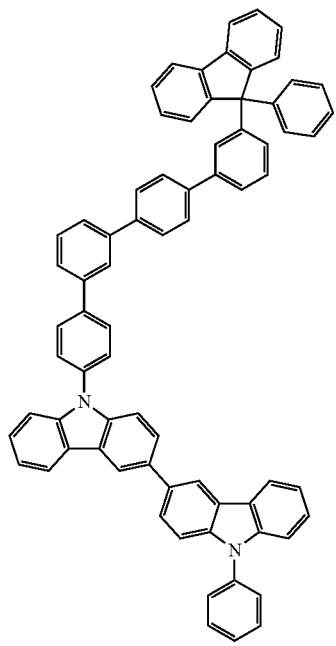
A175
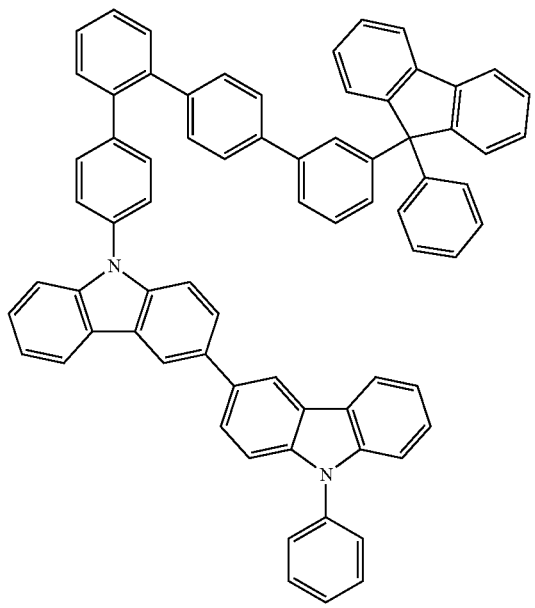
A176
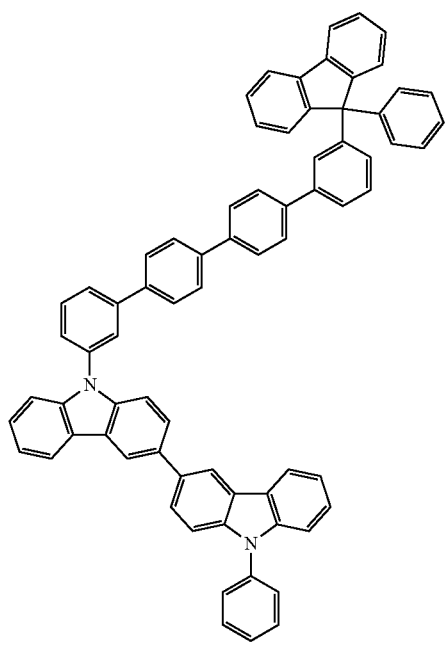
A177
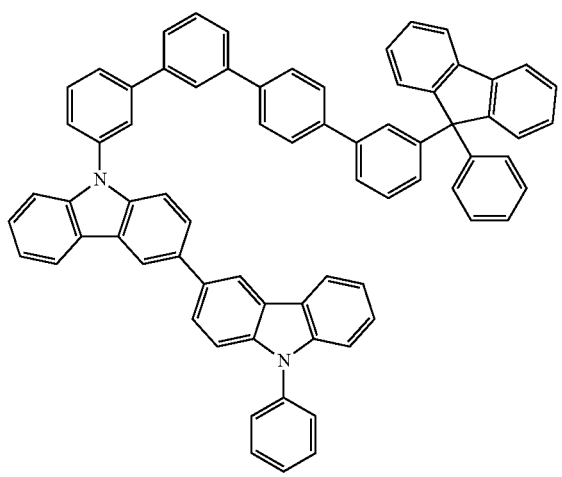

-continued
A178
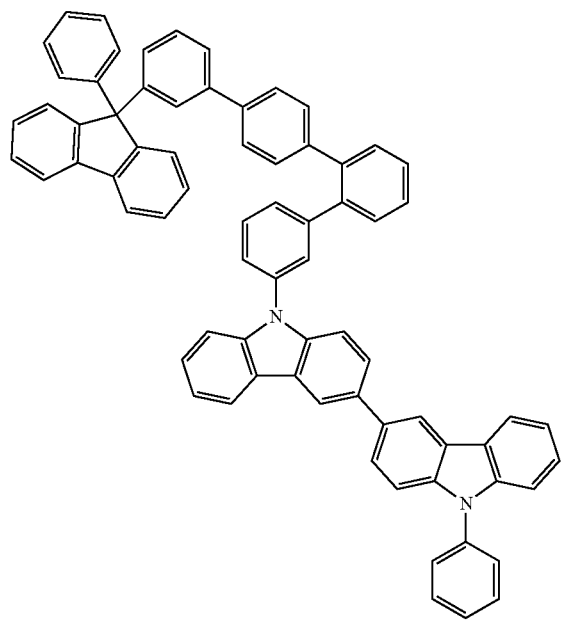
A179
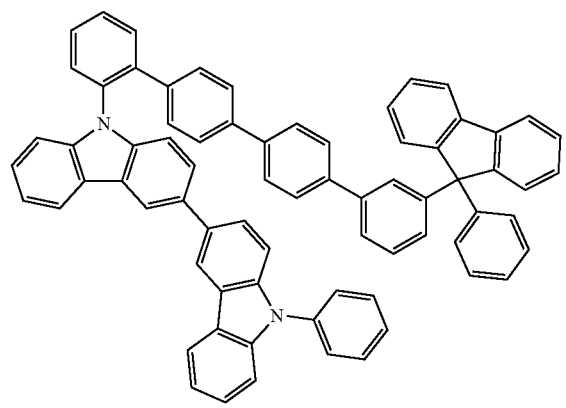
A180
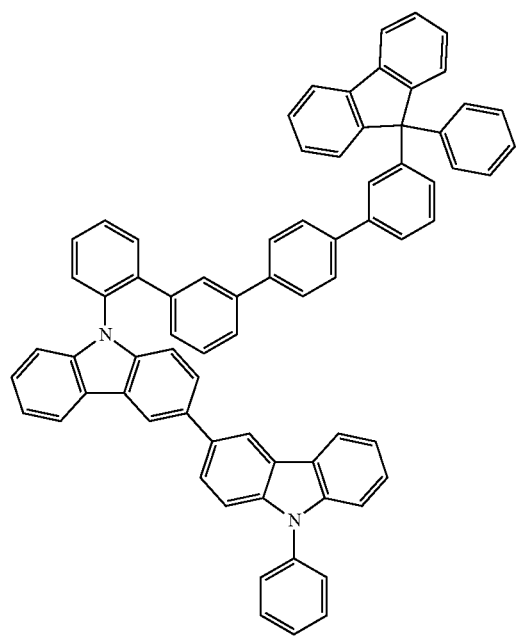
A181
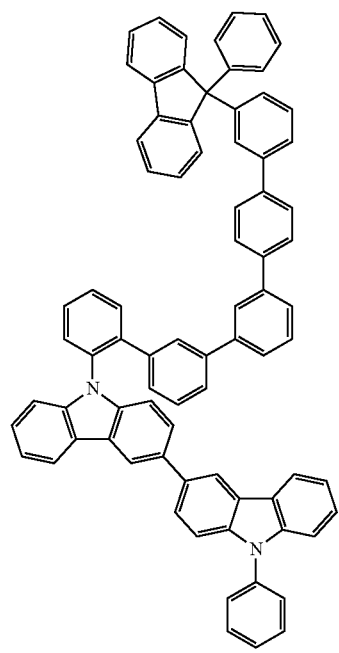

-continued
A182
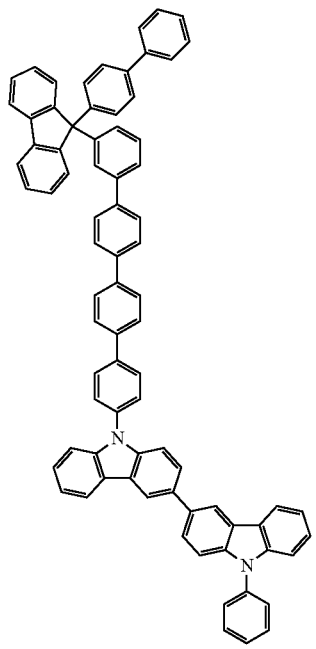
A183
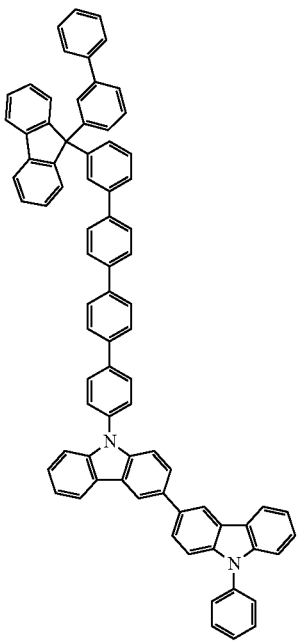
A184
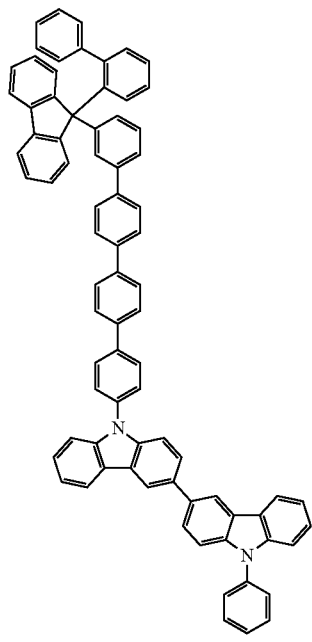
A185
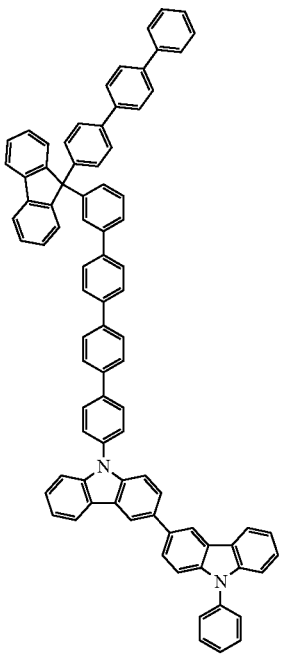

-continued
A186
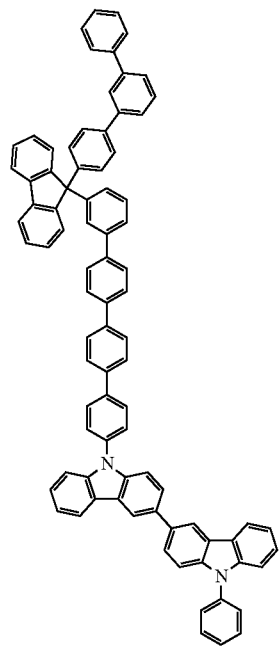
A187
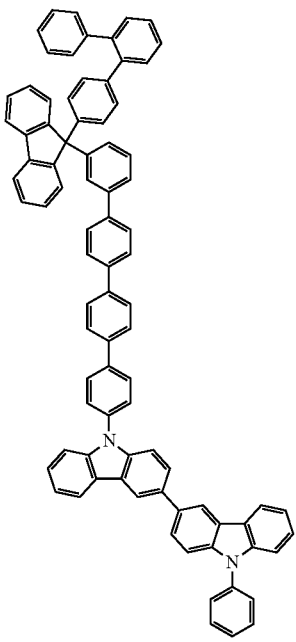
A188
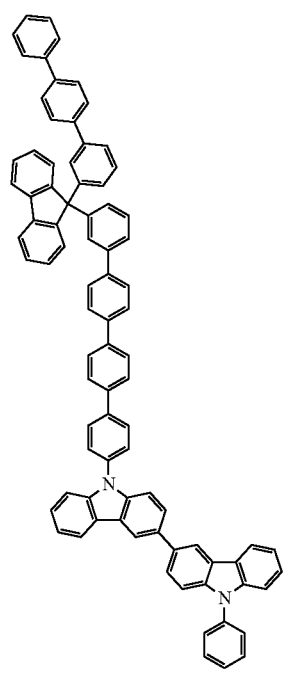
A189
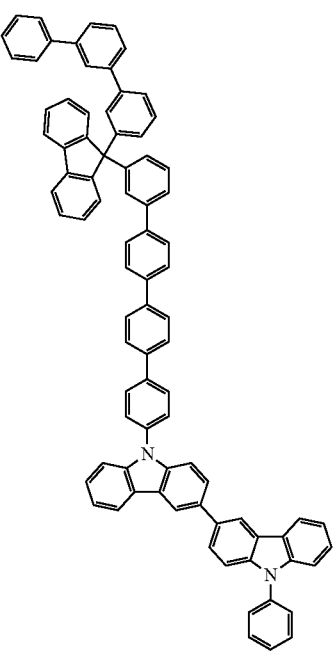

-continued
A190
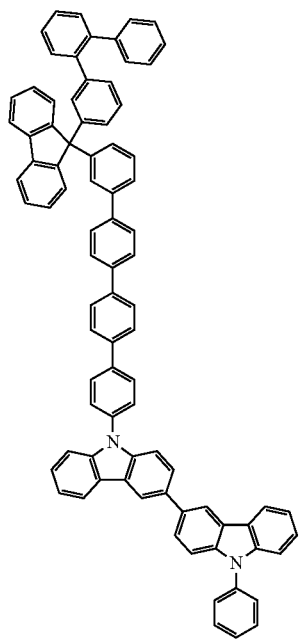
A191
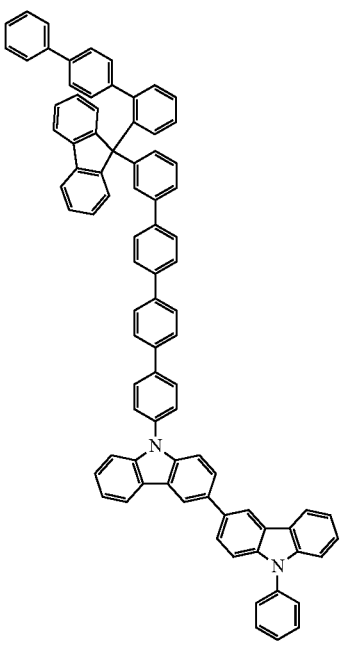
A192
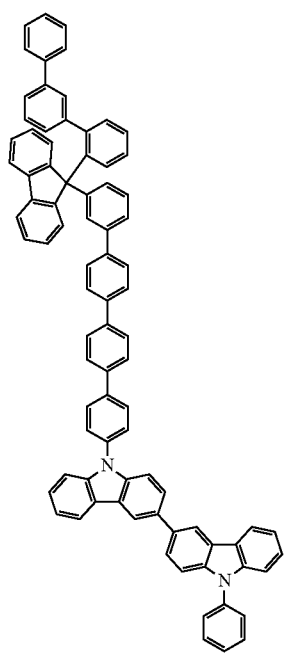
A193
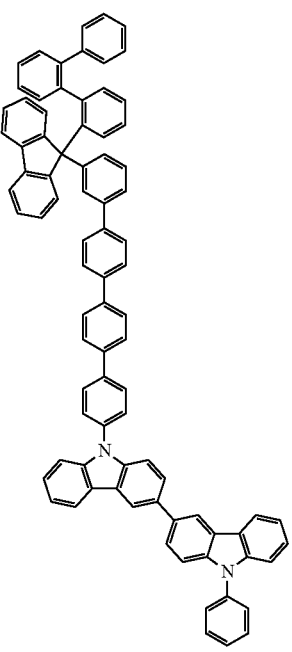

-continued
A194
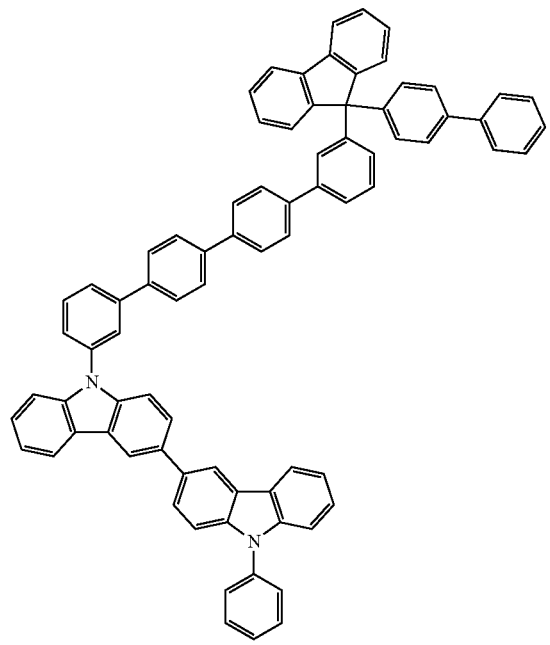
A195
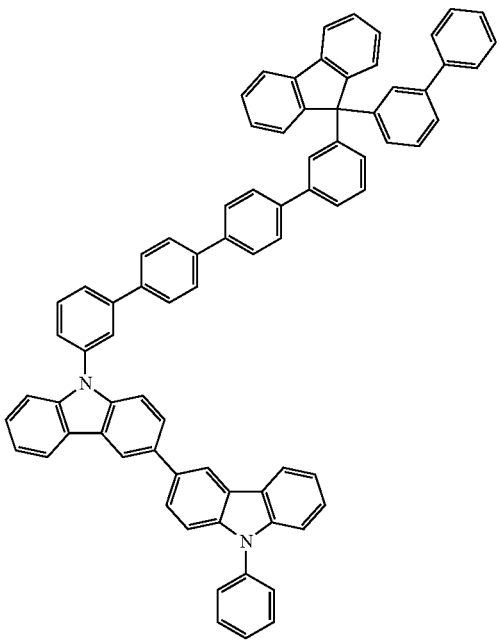
A196
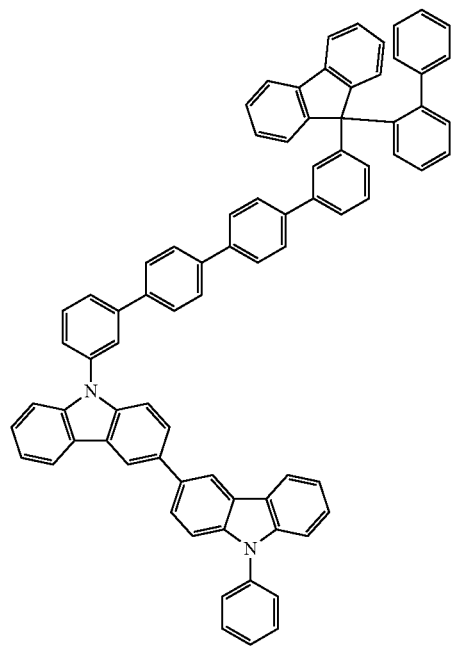

A197
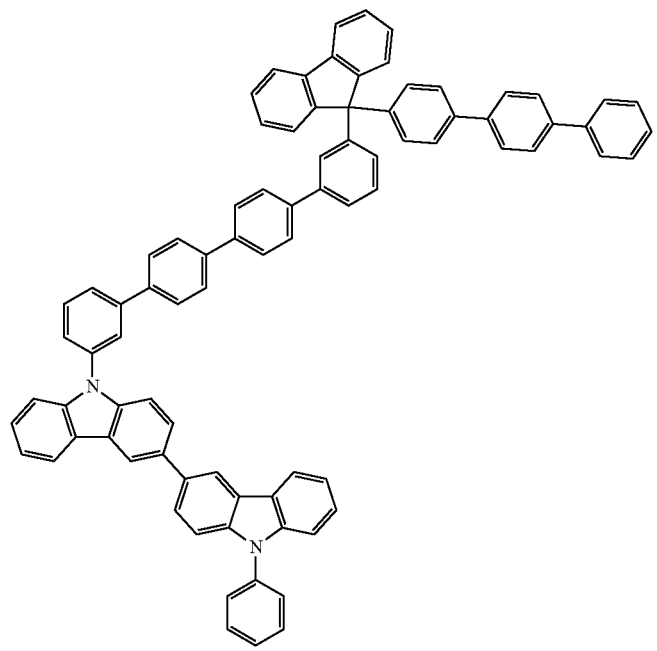
A198
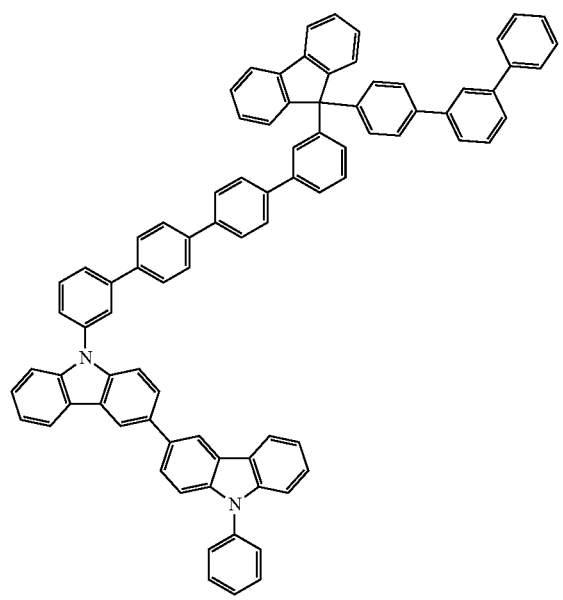
A199
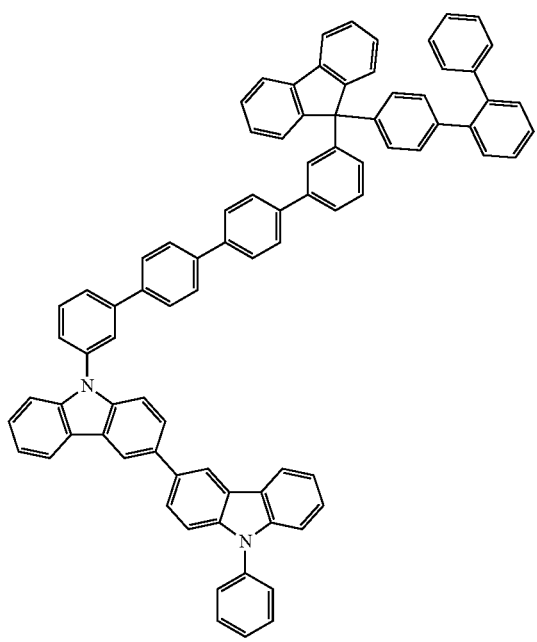

-continued
A200
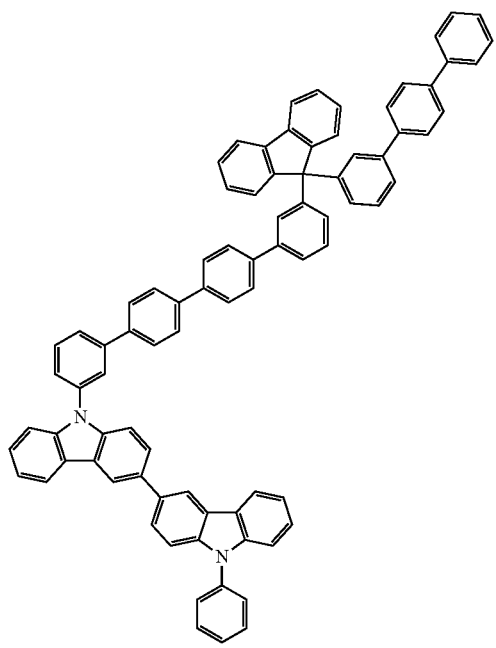
A201
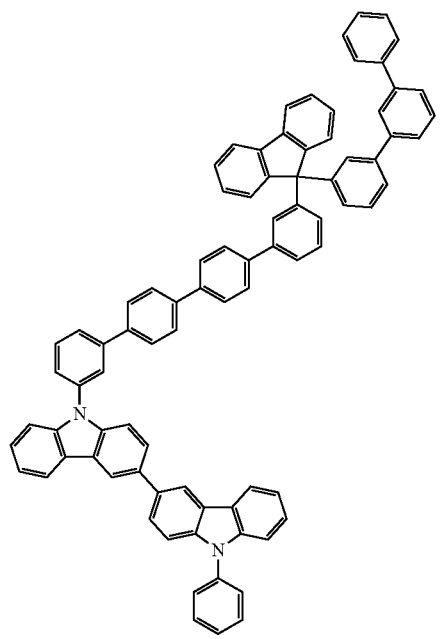
A202
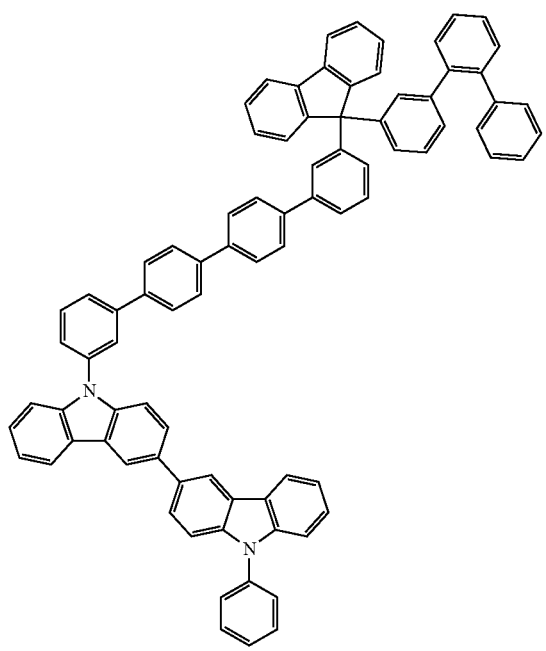
A203
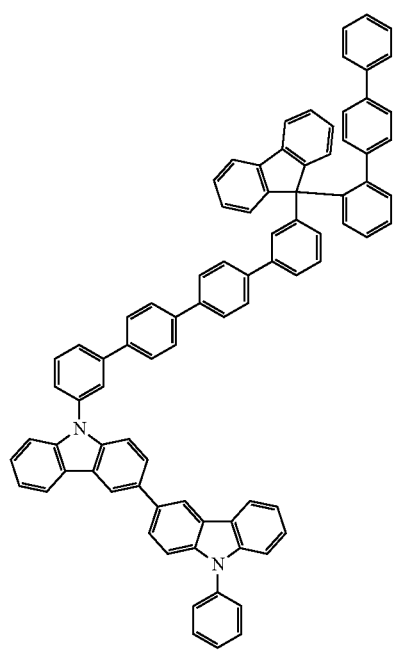

-continued
A204
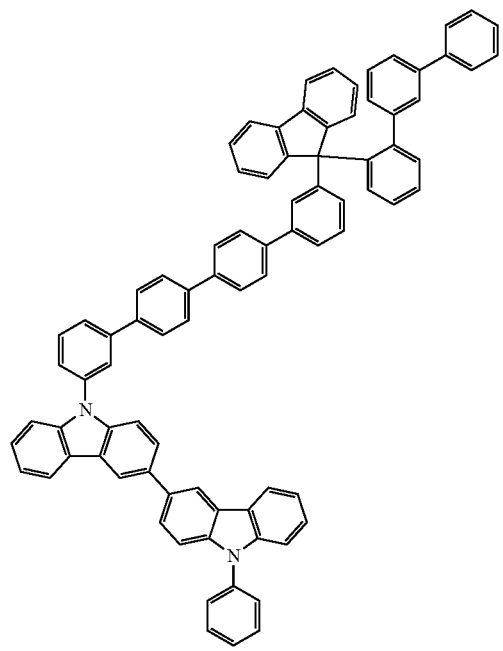
A205
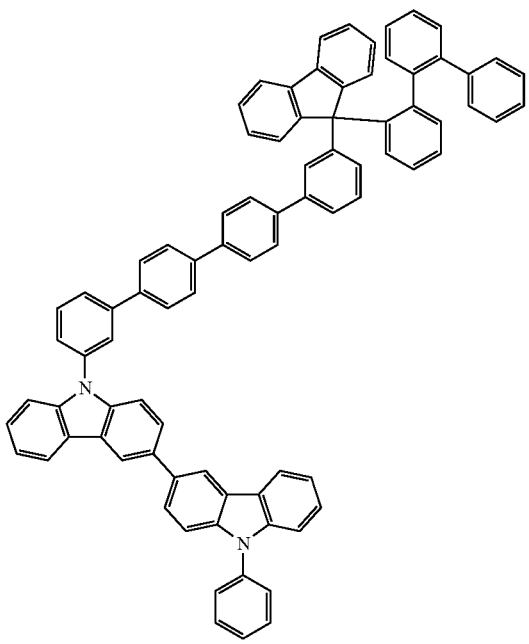
A206
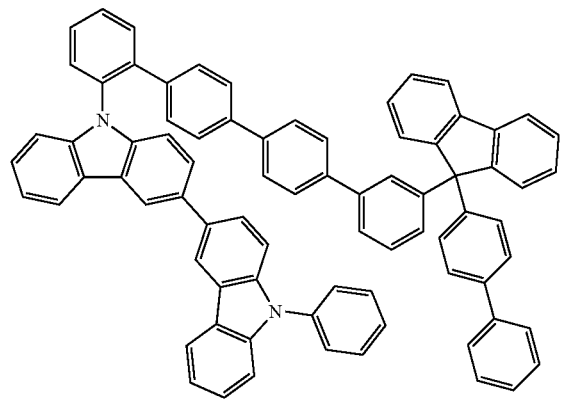
A207
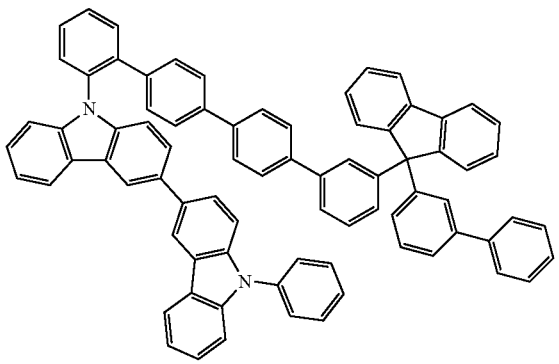
A208
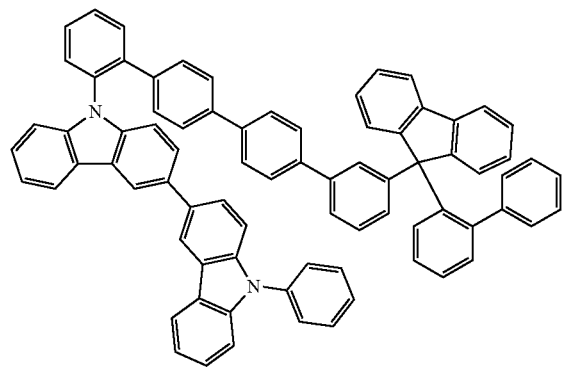
A209
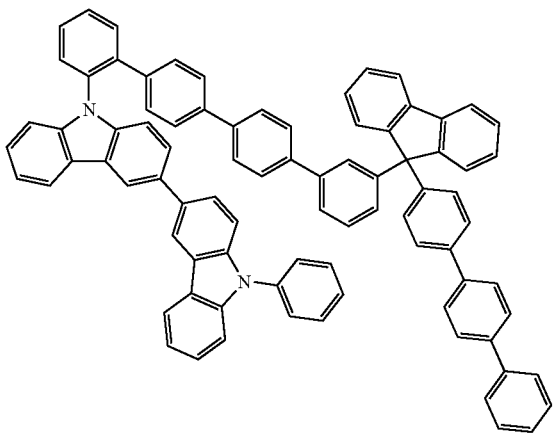

-continued
A210
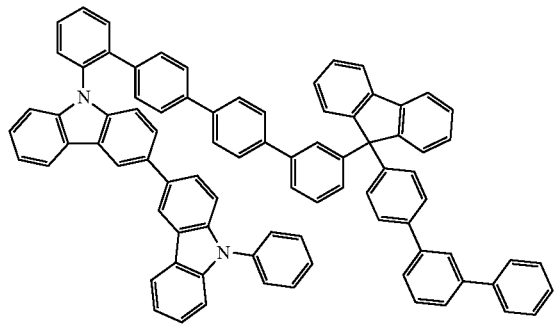
A211
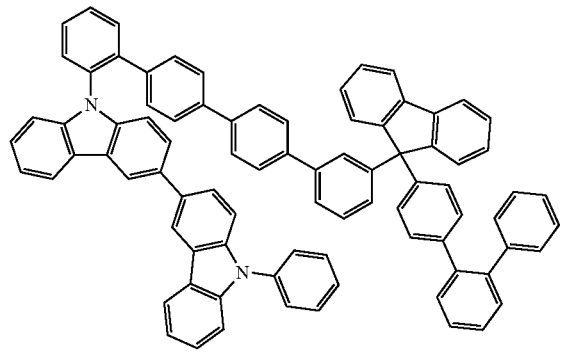
A212
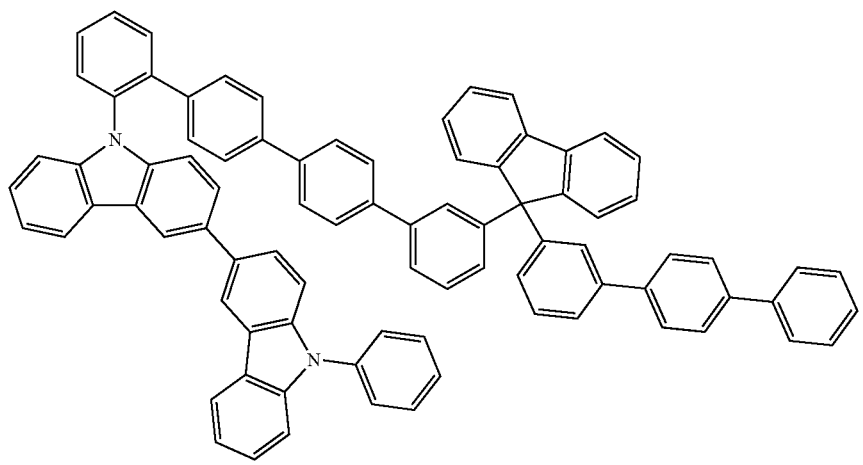
A213
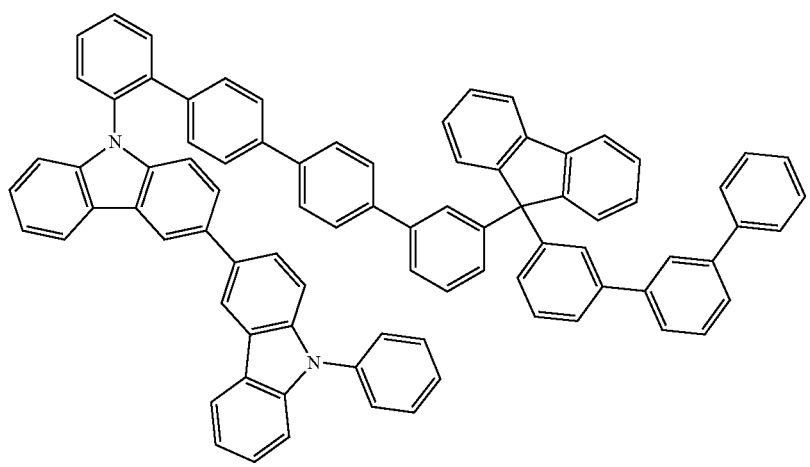

-continued
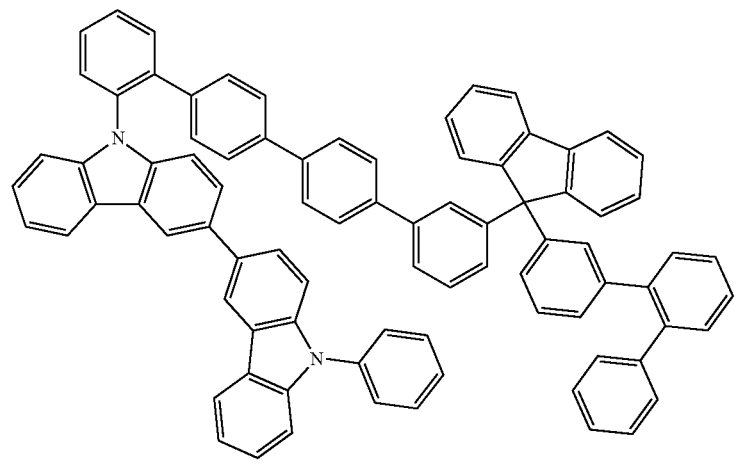
A214
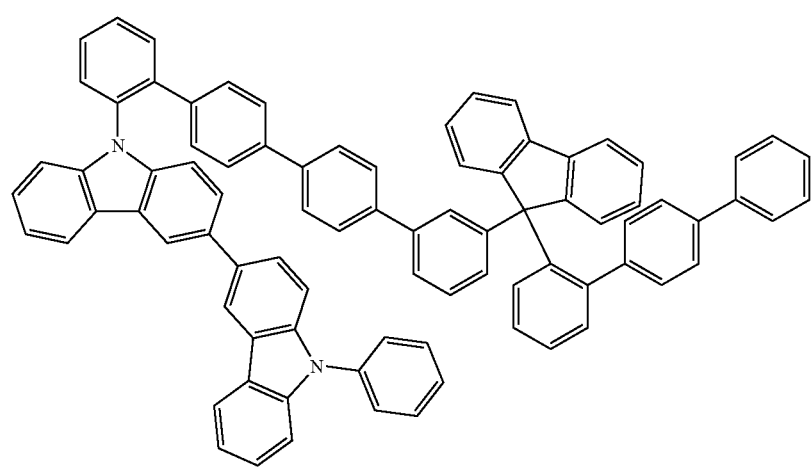
A215
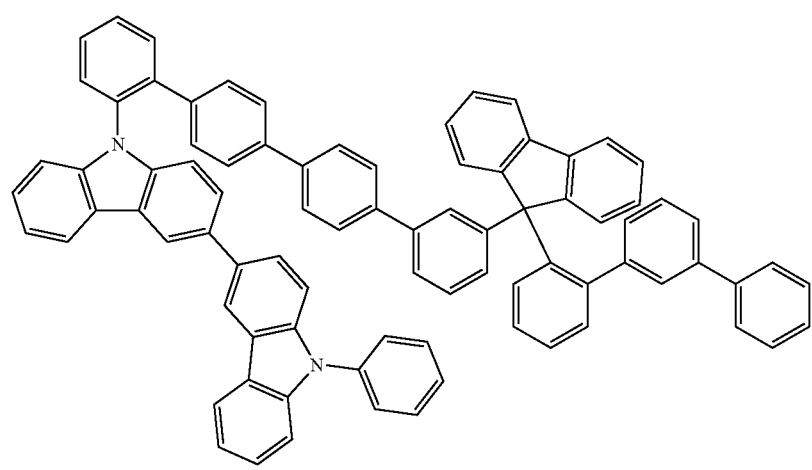
A216

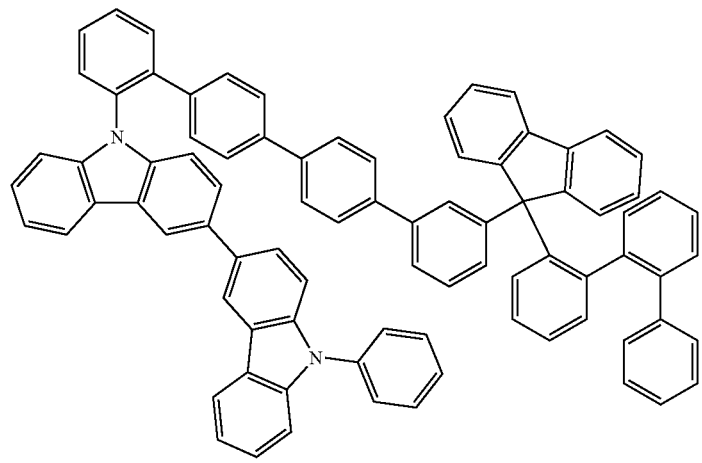
A217
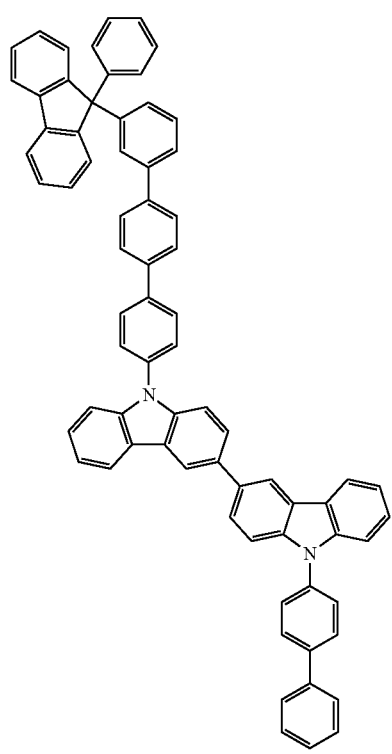
A218
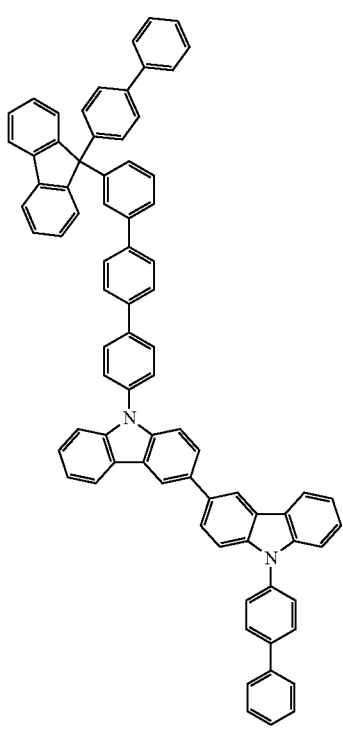
A219

-continued
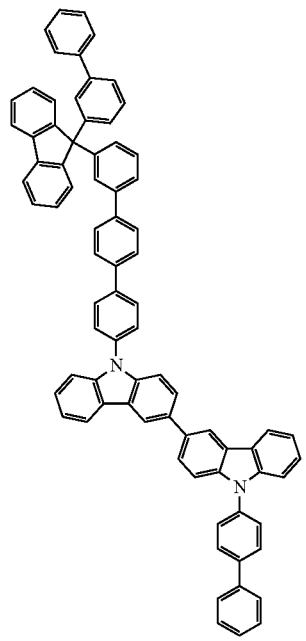
A220
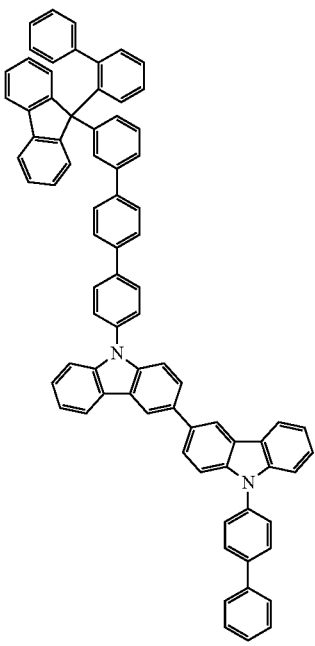
A221
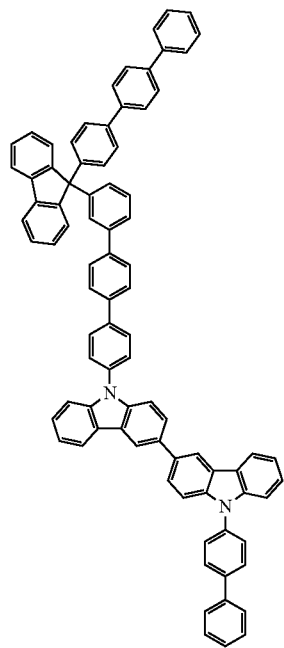
A222
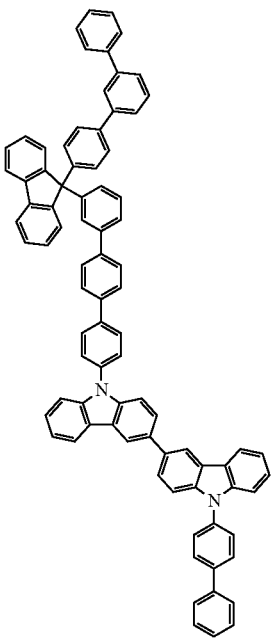
A223

-continued
A224
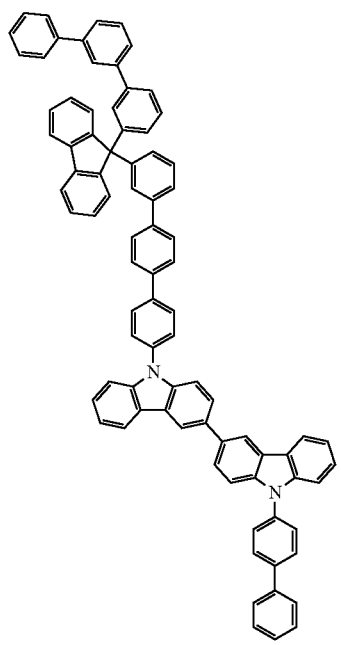
A225
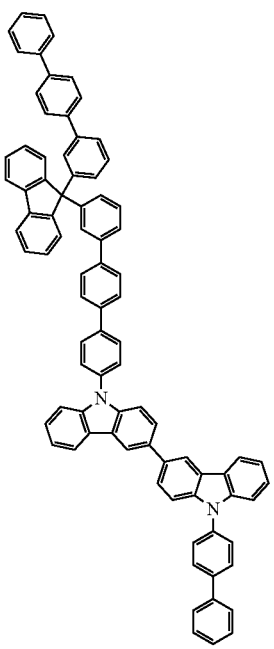
A226
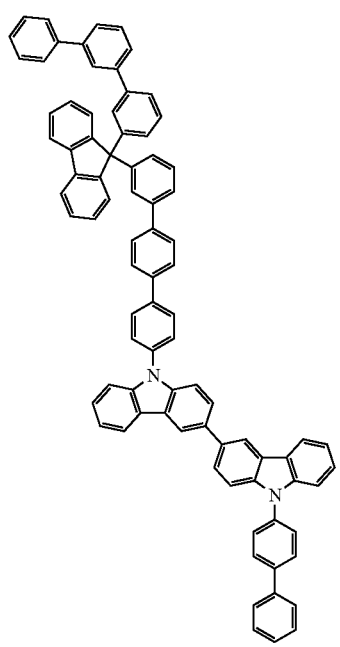
A227
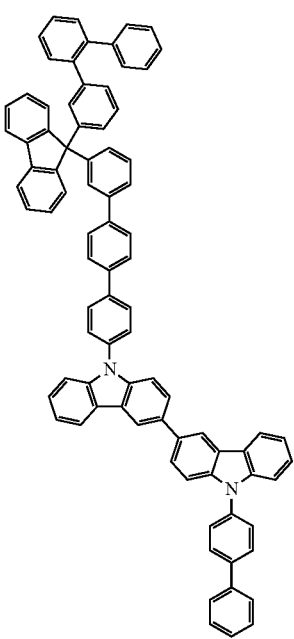

-continued
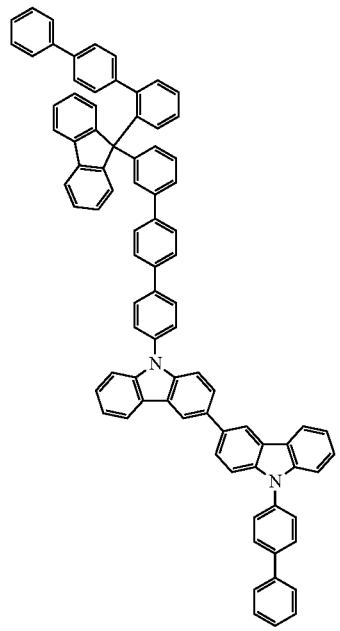
A228
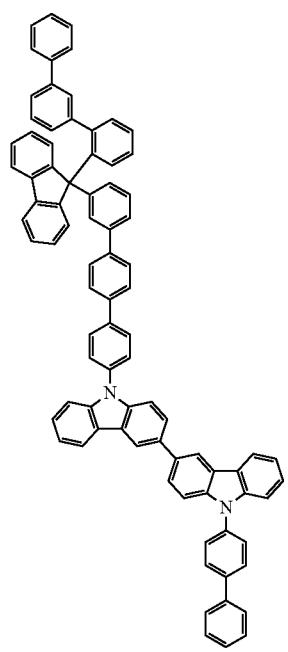
A229
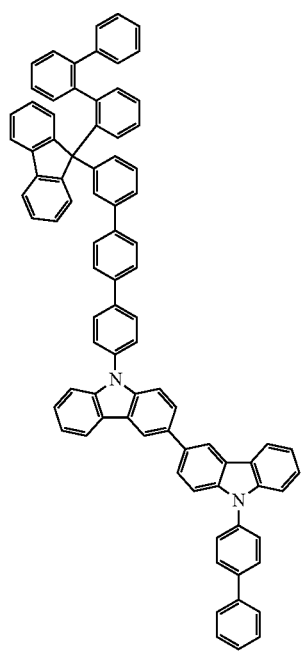
A230

-continued
A231
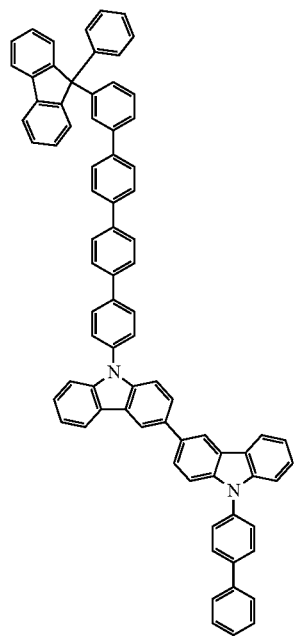
A232
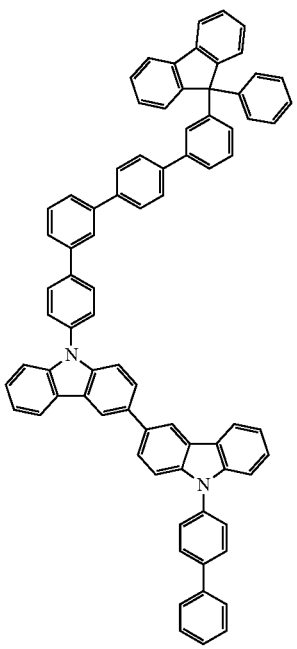
A233
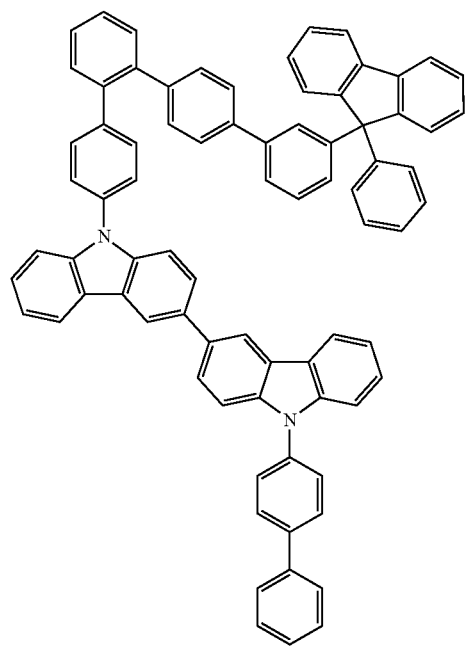
A234
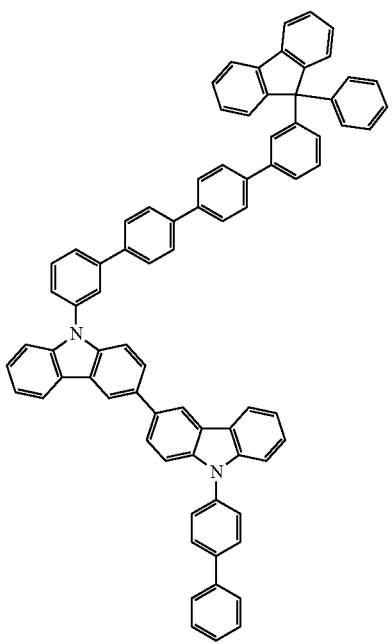

-continued
A235 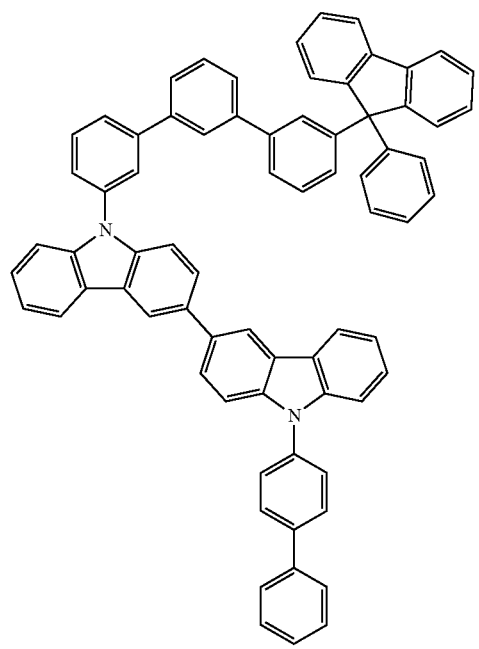
A236 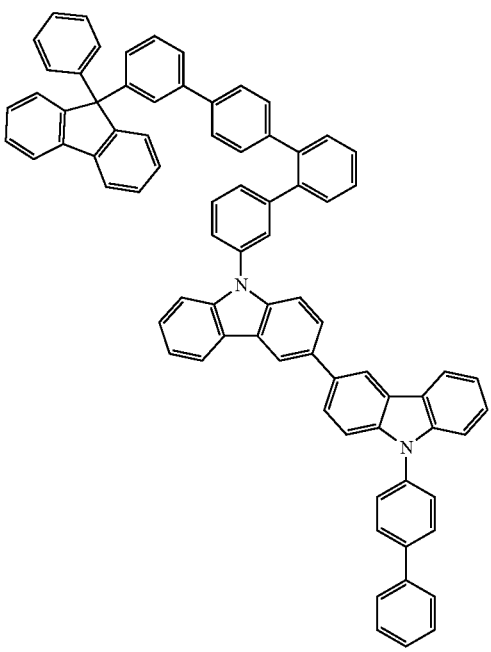
A237 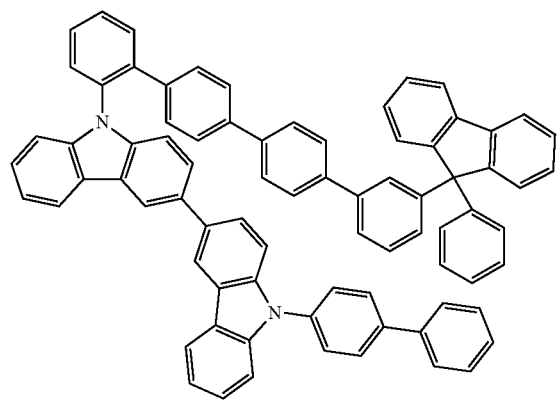
A238 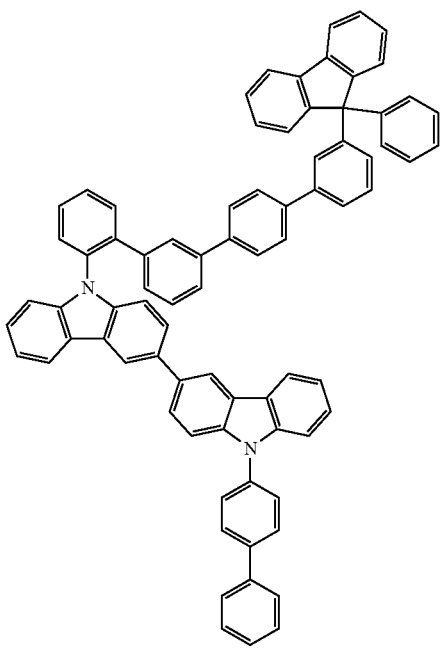

-continued
A239
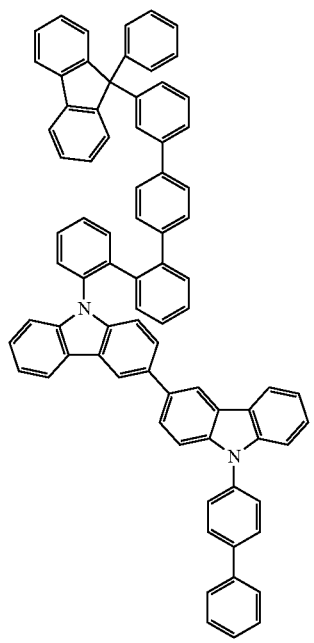
A240
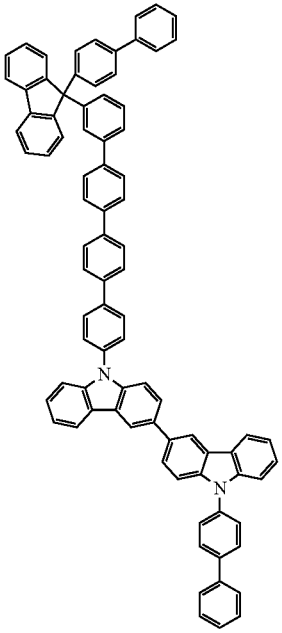
A241
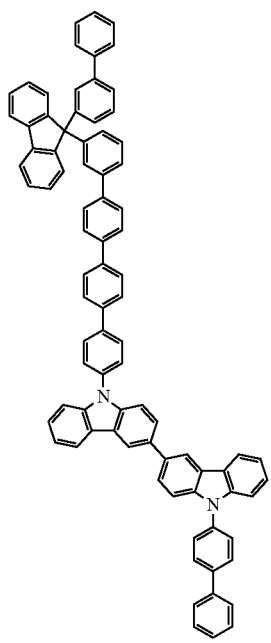
A242
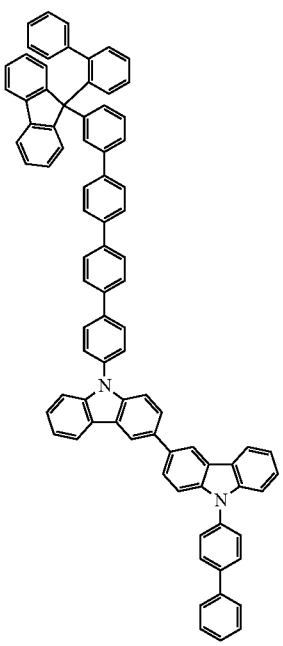

-continued
A243
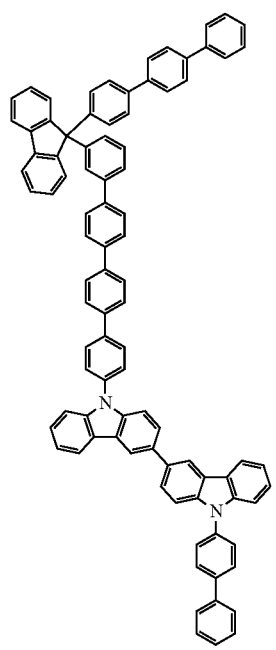
A244
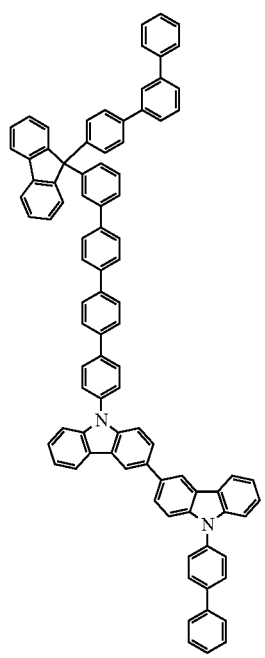
A245
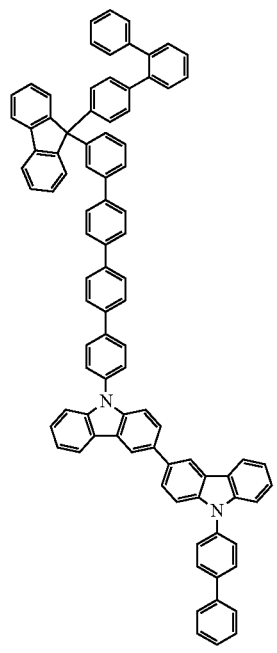
A246
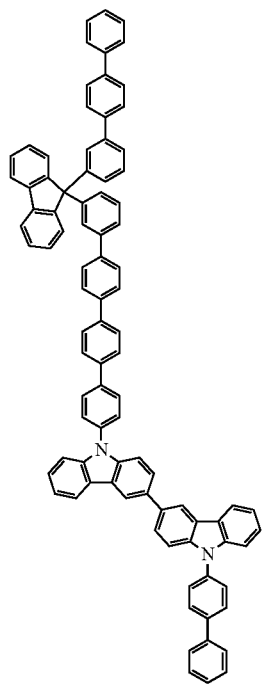

-continued
A247
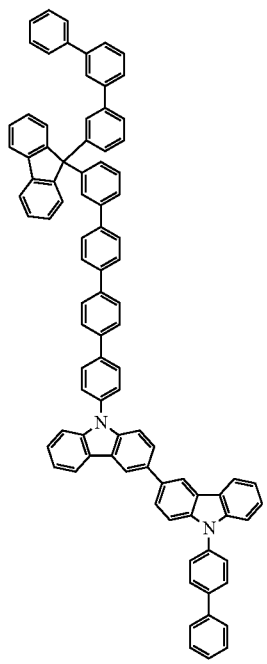
A248
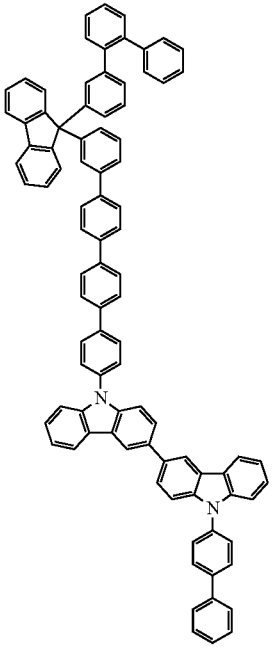
A249
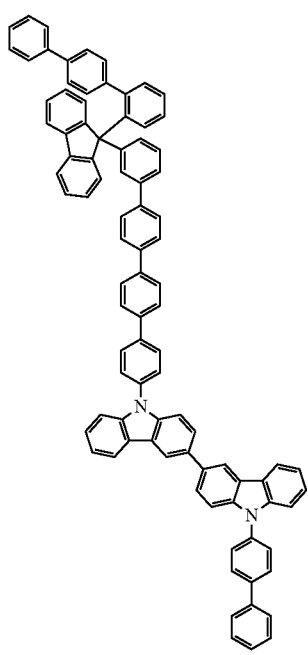
A250
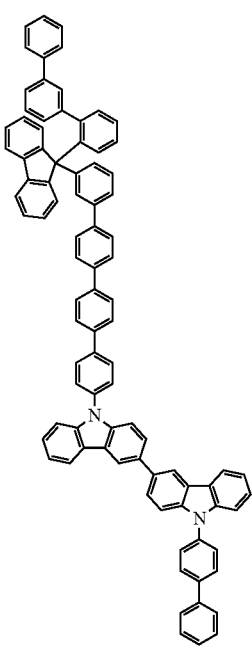

-continued
A251
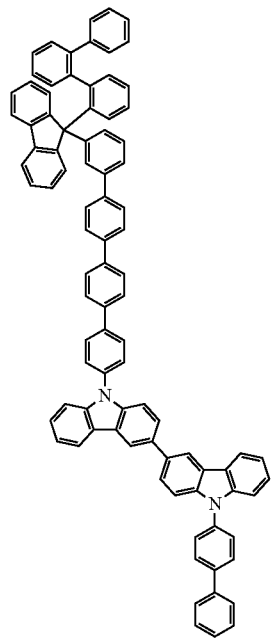
A252
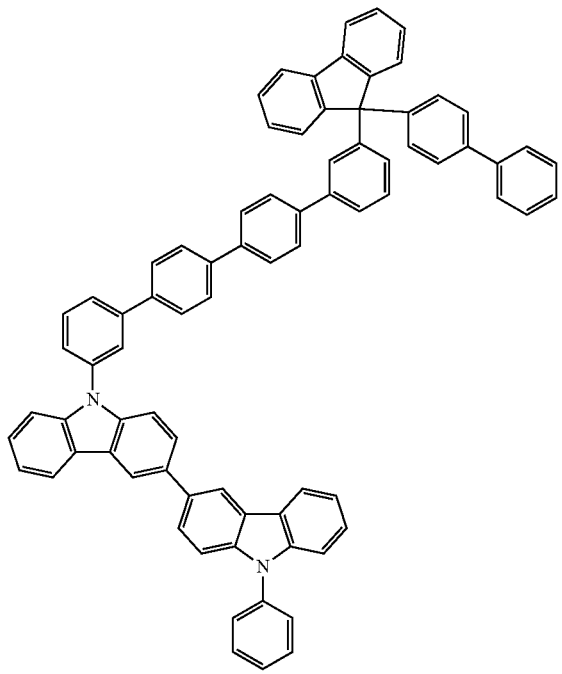
A253
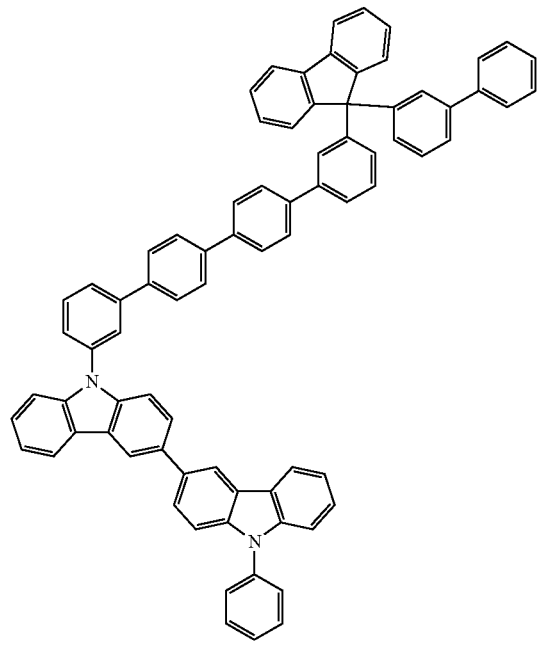
A254
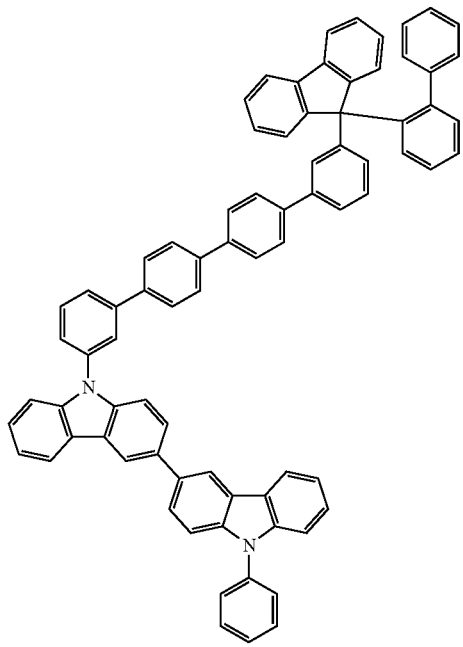

-continued
A255
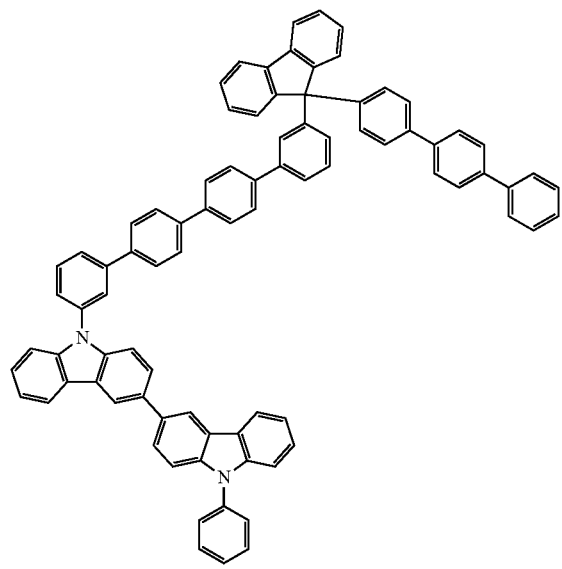
A256
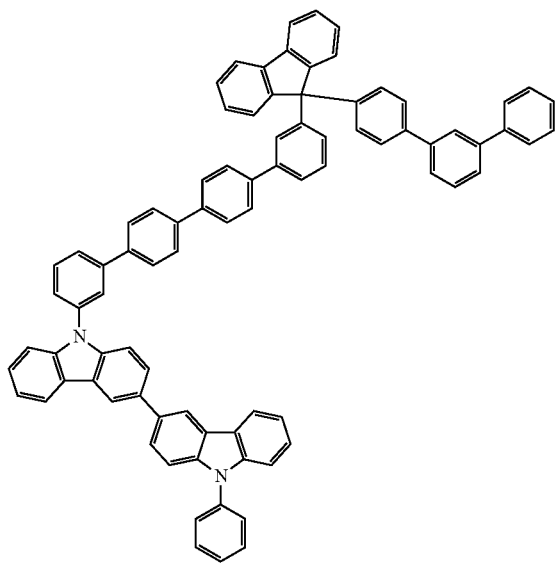
A257
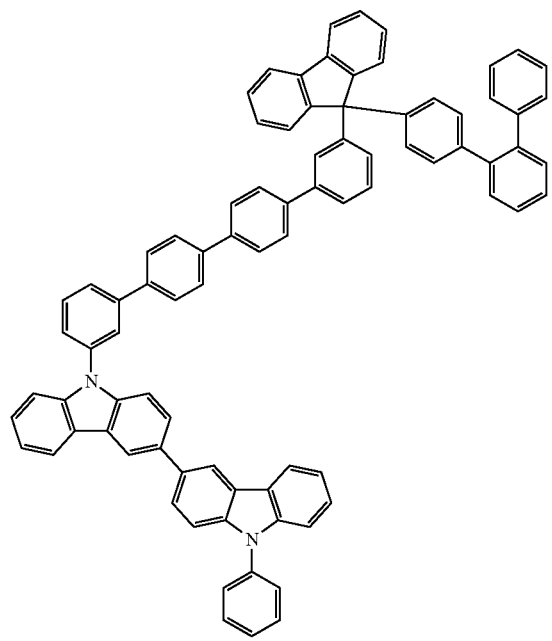

A258
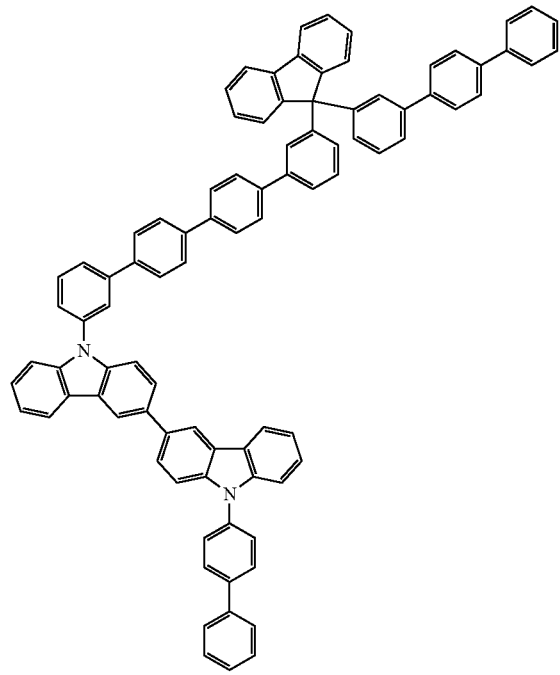
A259
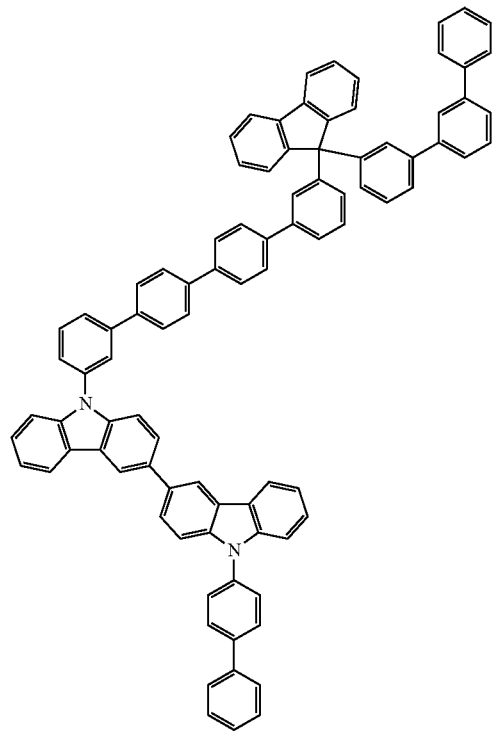
A260
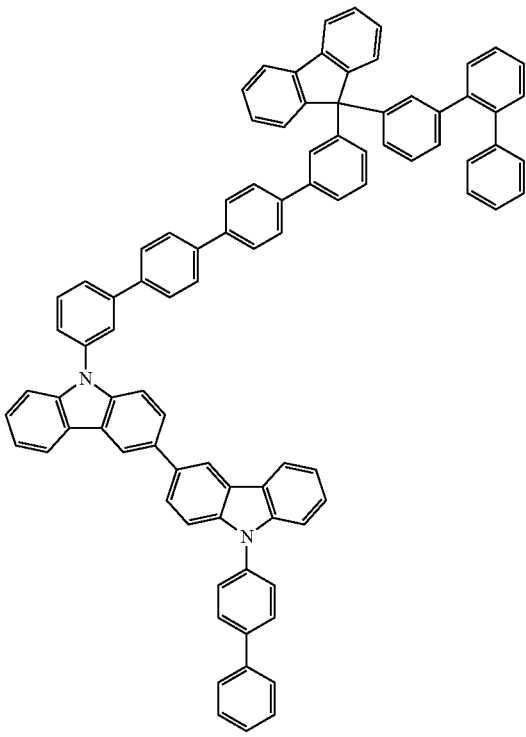

-continued
A261
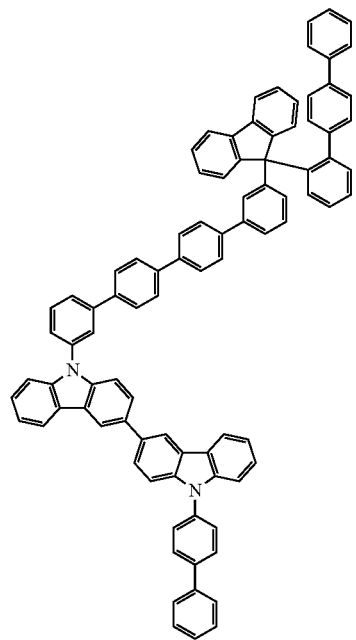
A262
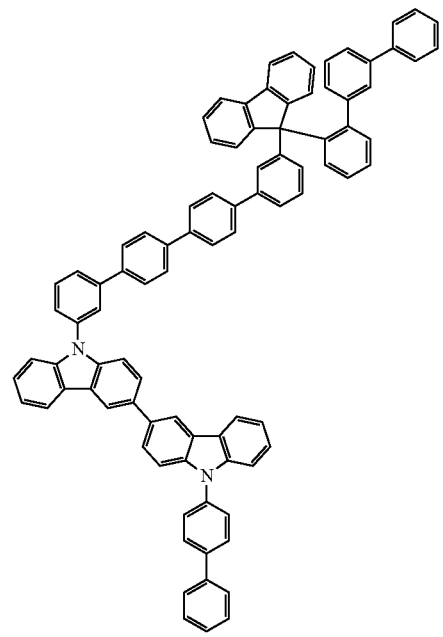
A263
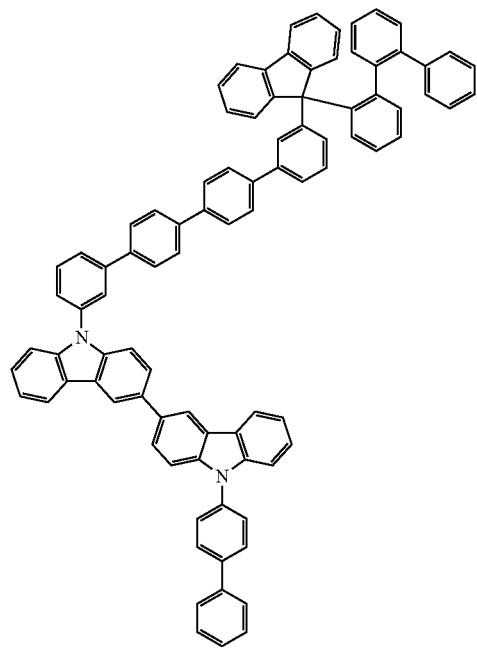
A264
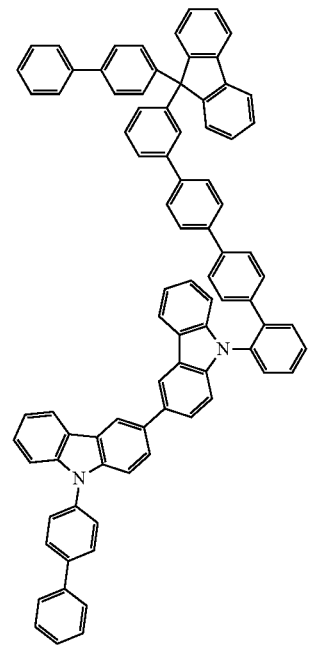

A265
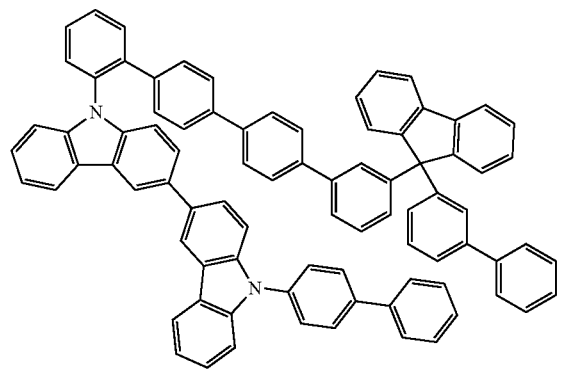
A266
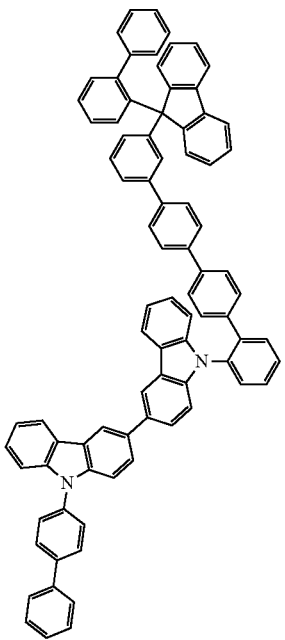
A267
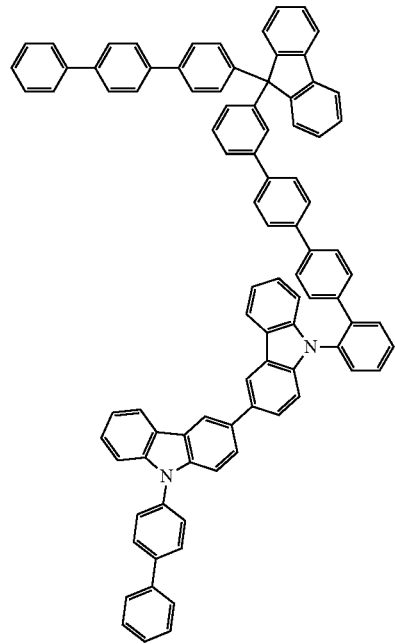
A268
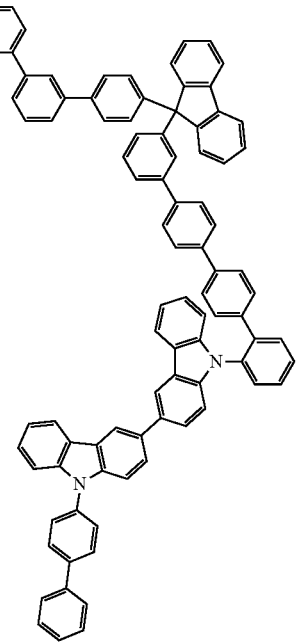

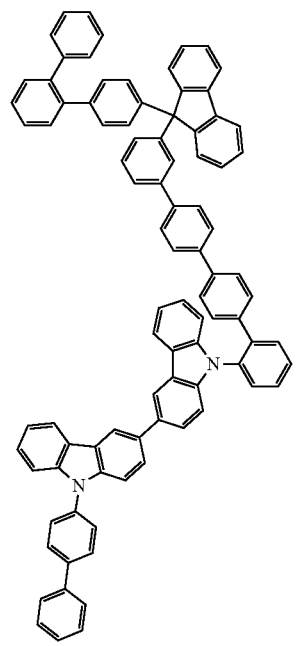
A269
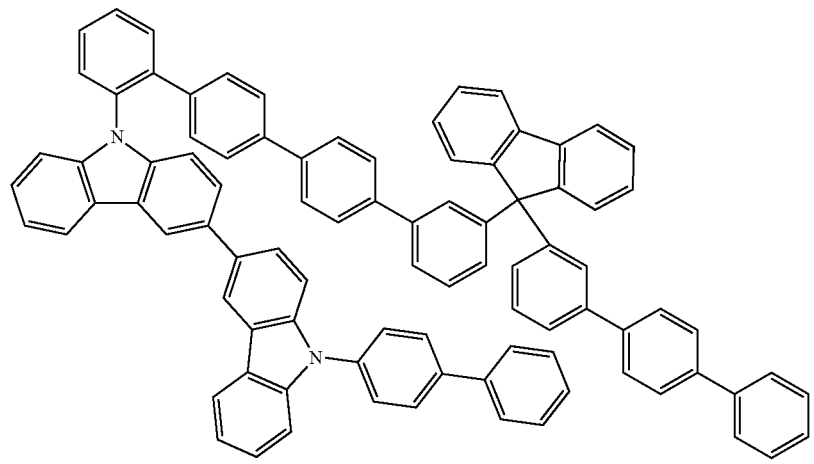
A270
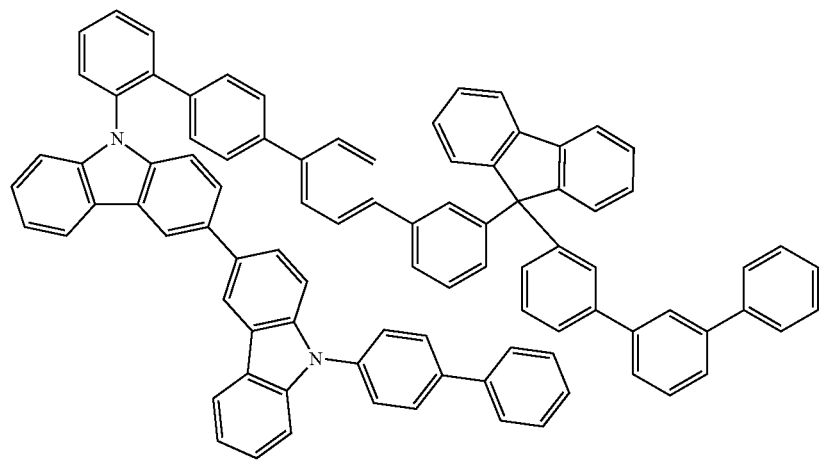
A271

A272
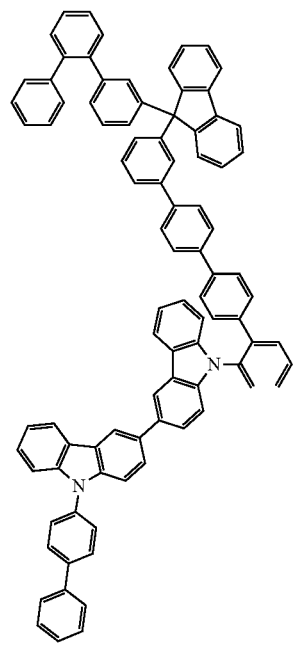
A273
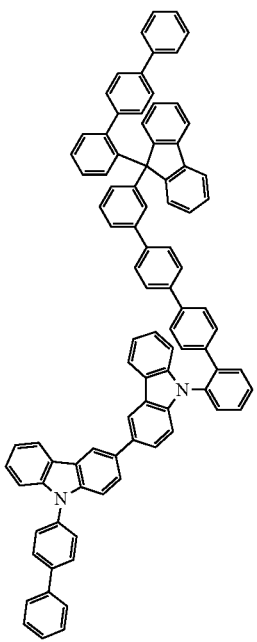
A274
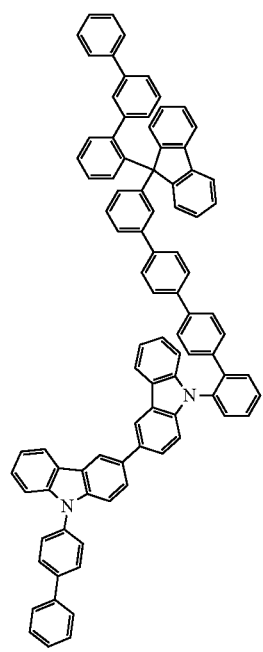
A275
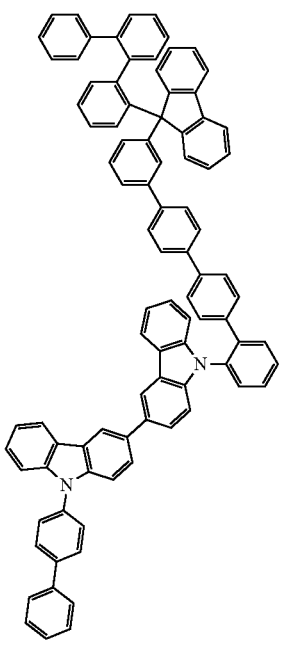

A276
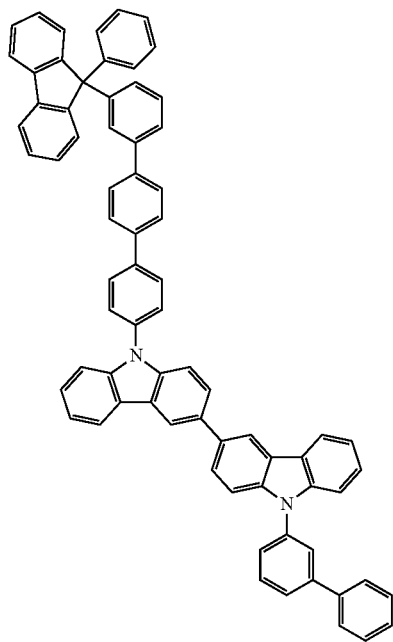
A277
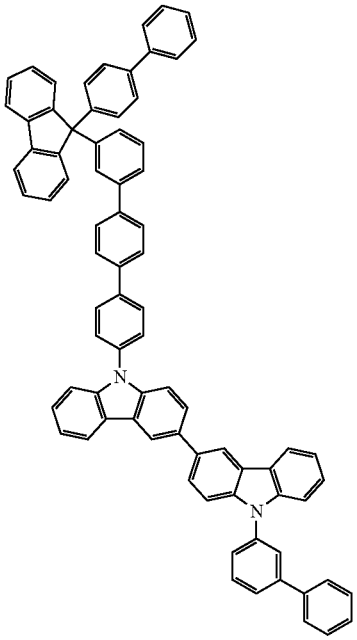
A278
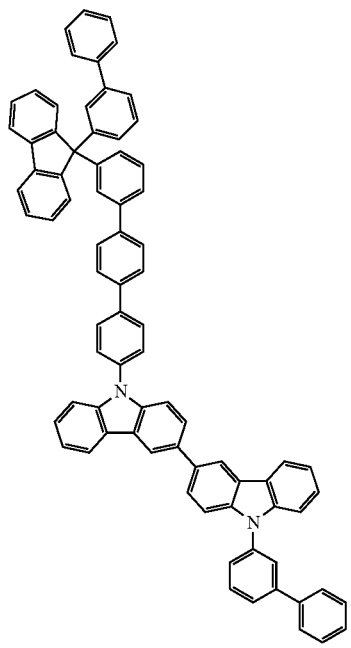
A279
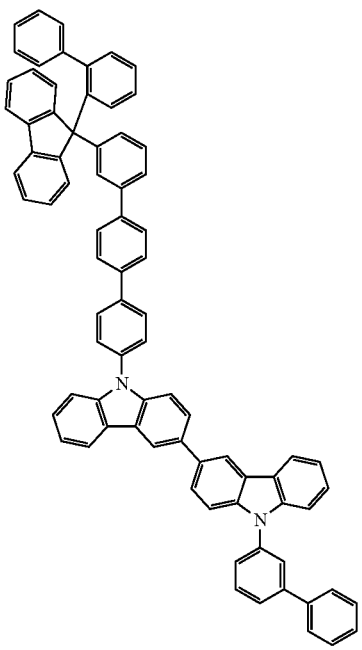

-continued
A280
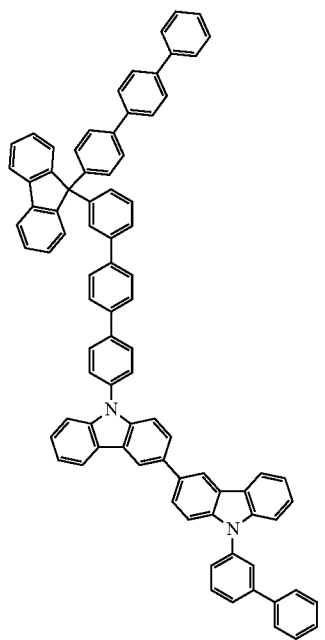
A281
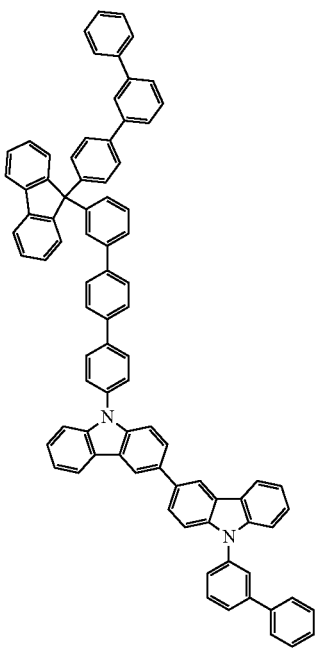
A282
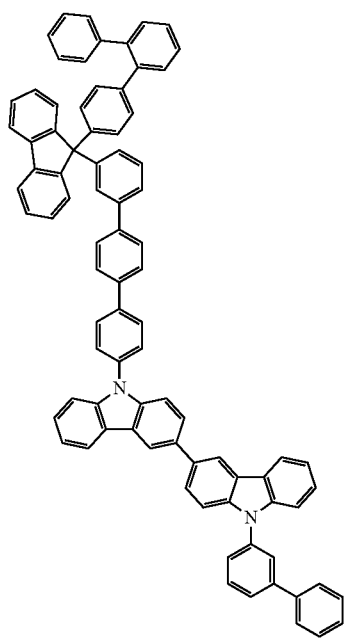
A283
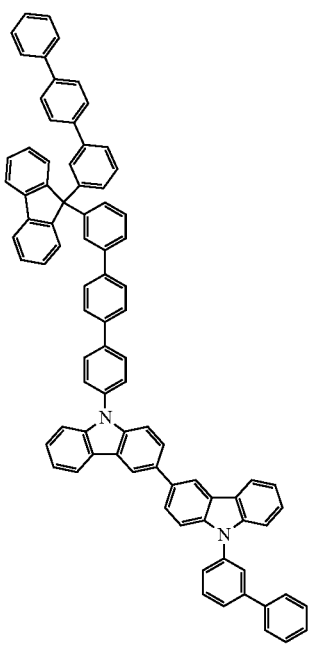

-continued
A284
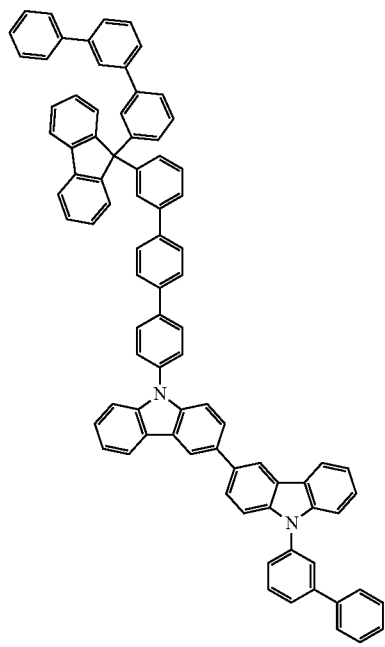
A285
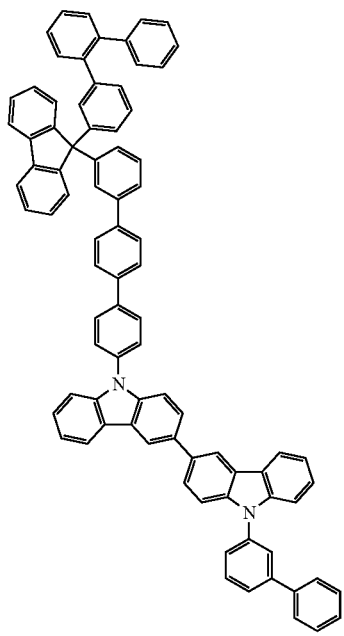
A286
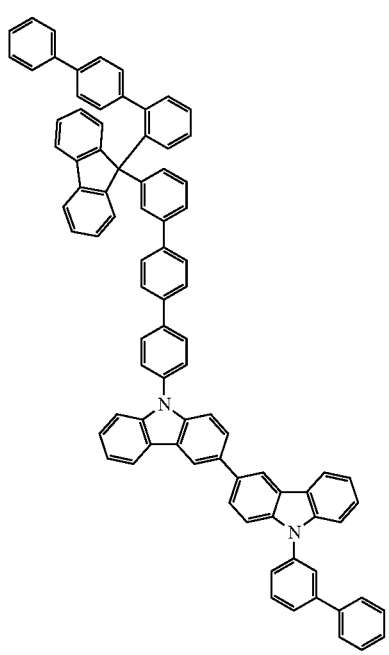
A284
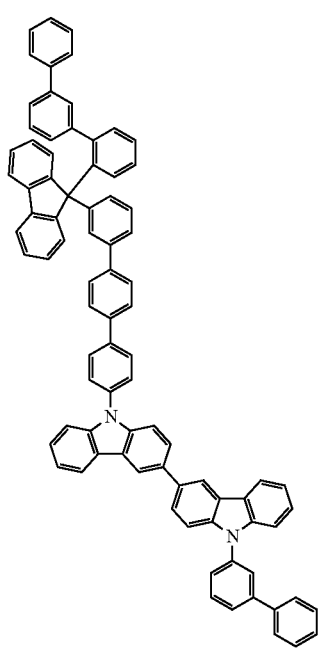

-continued
A288 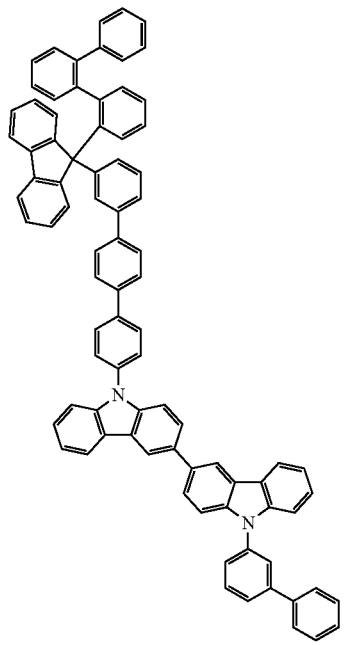
A289 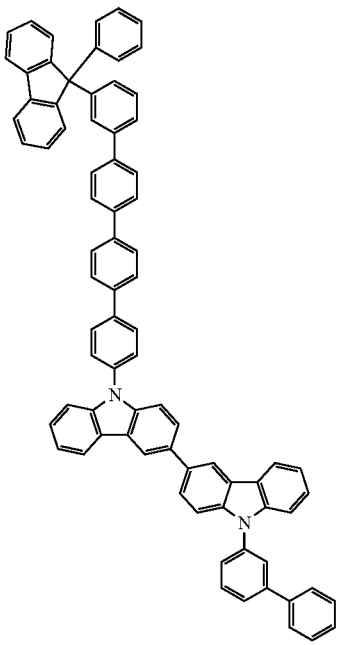
A290 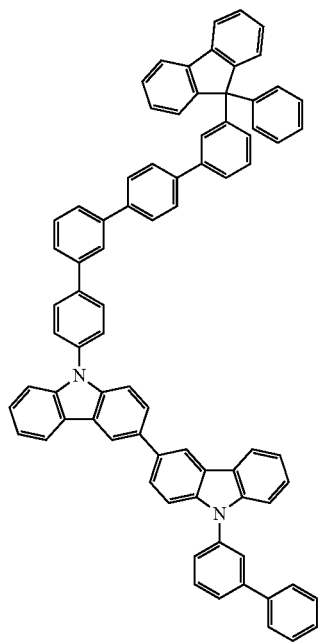
A291 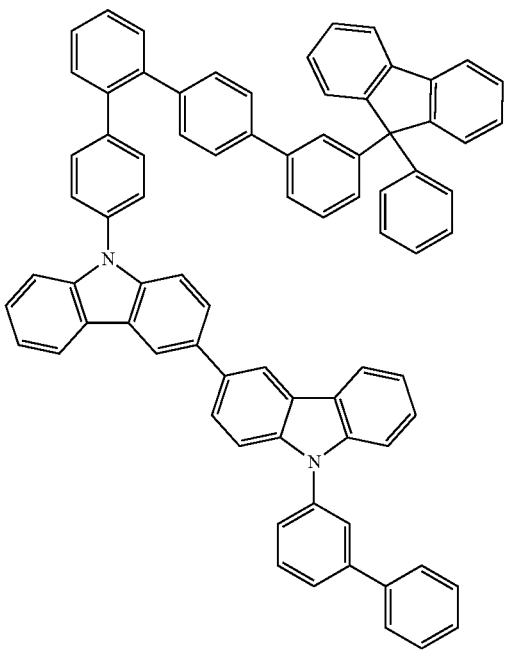

-continued
A292
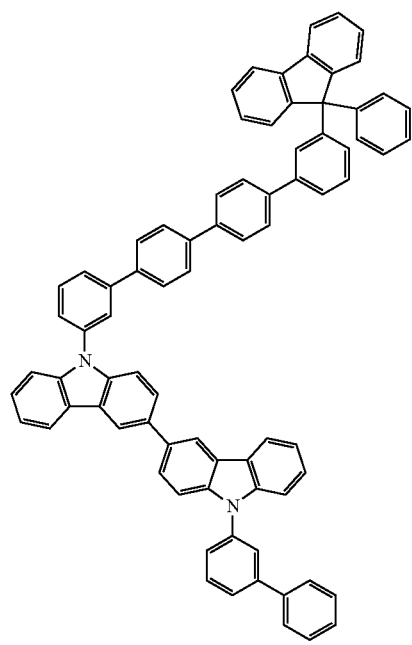
A293
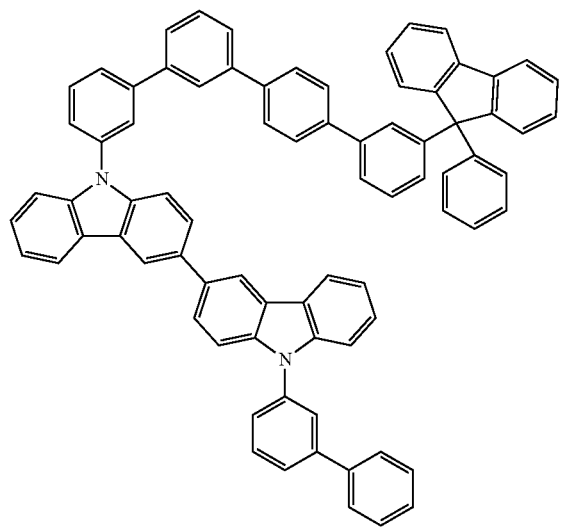
A294
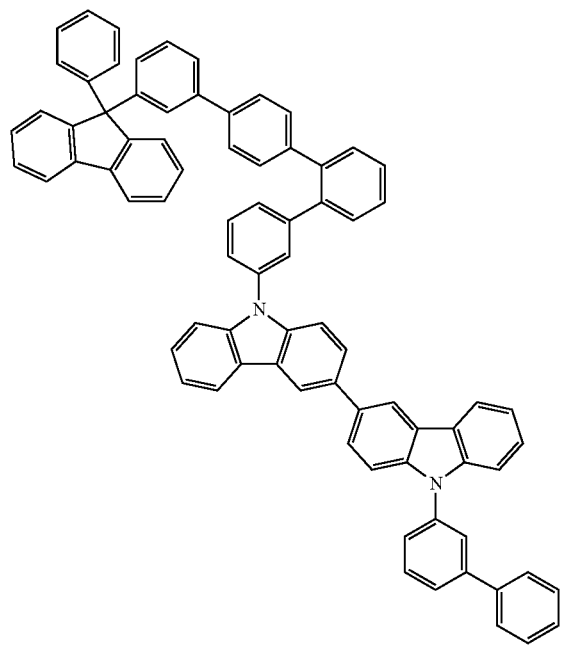
A295
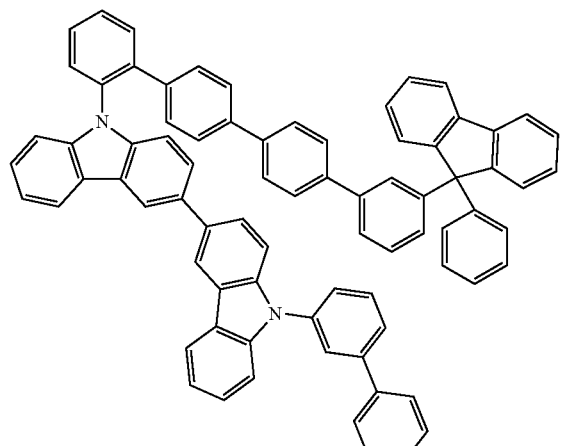

-continued
A296
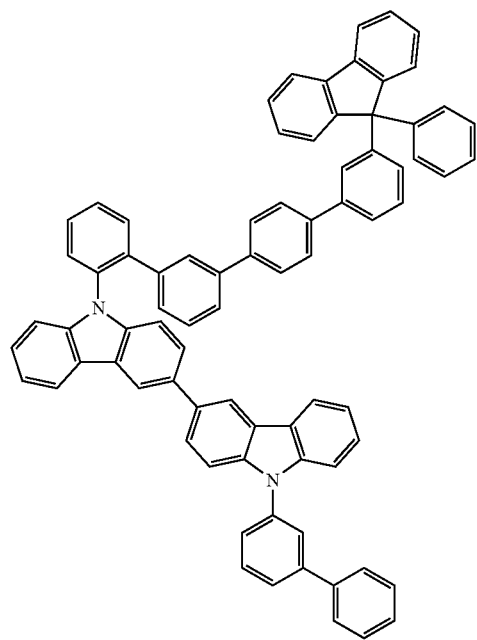
A297
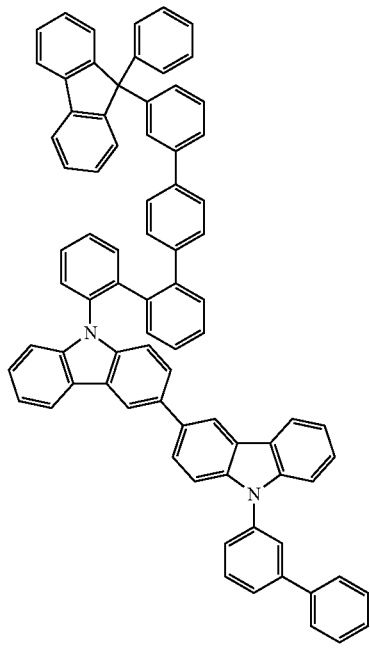
A298
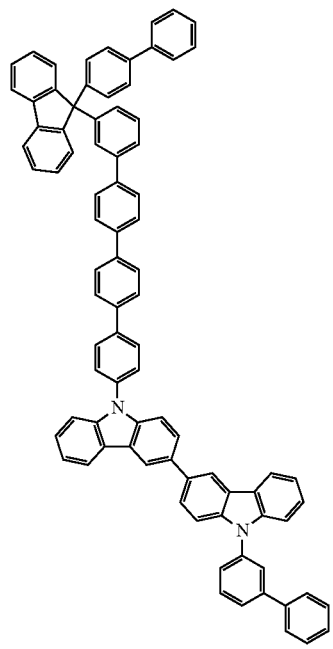
A299
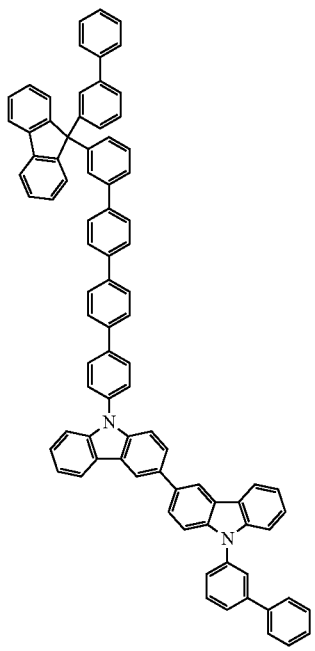

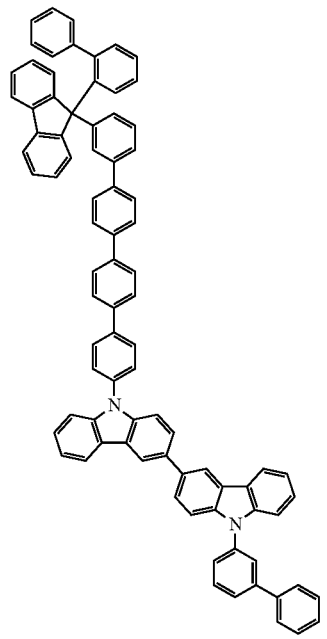
A300

187               188
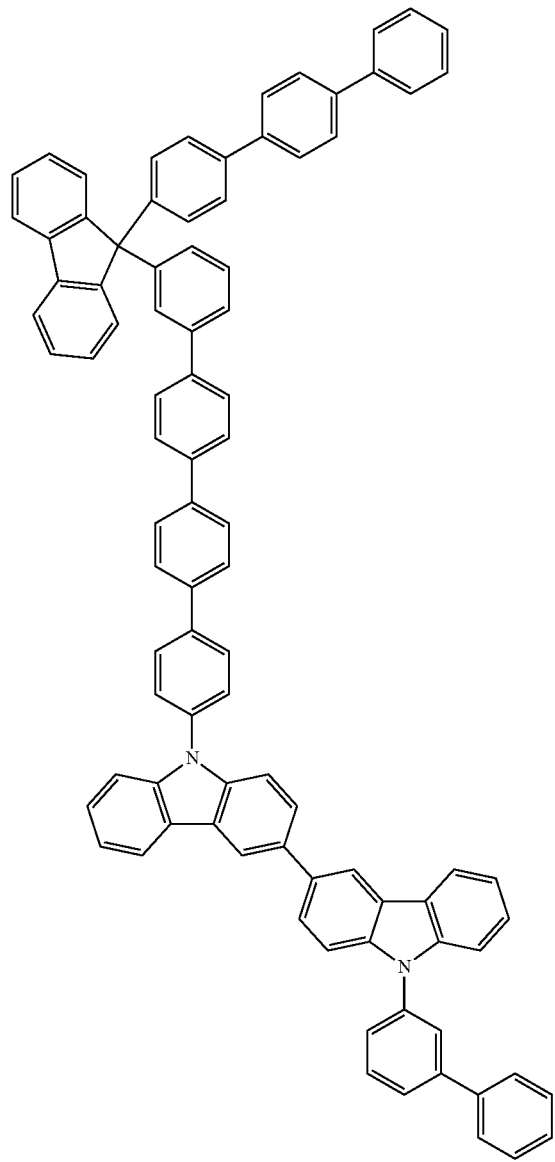 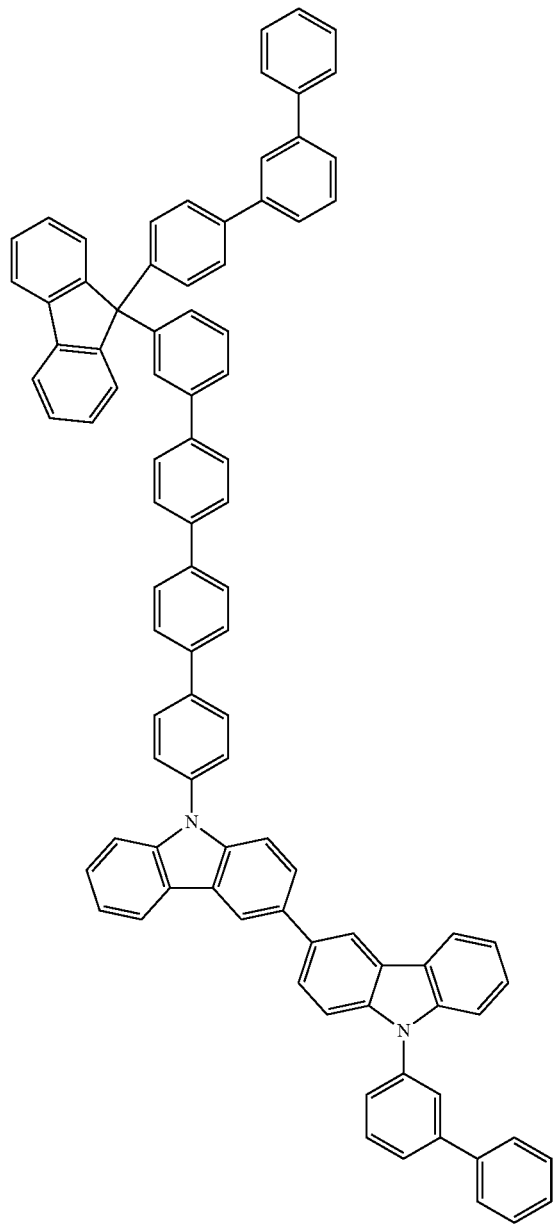
A301                A302

-continued
A303
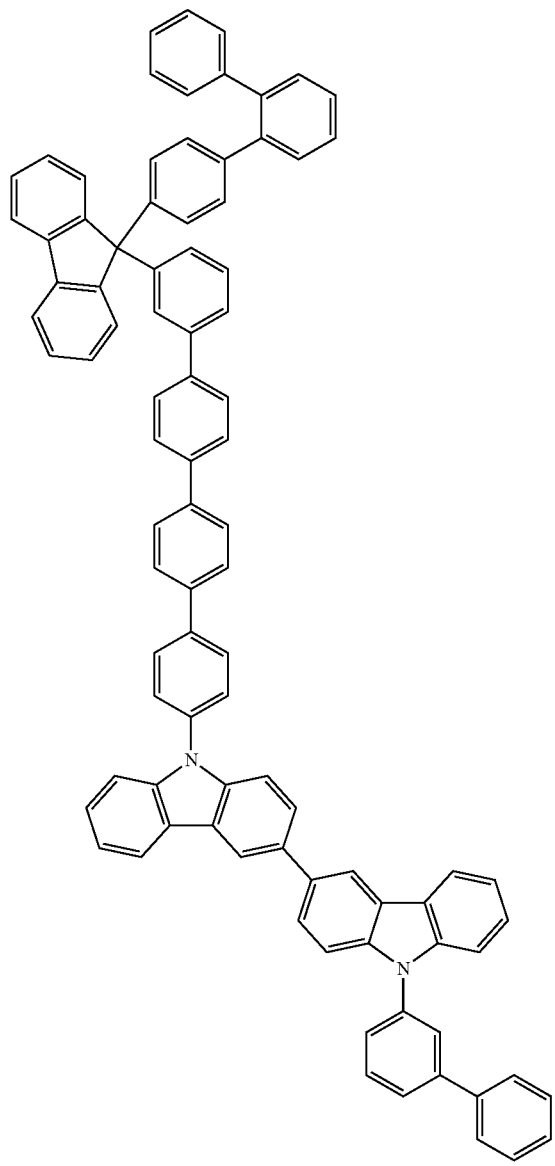
A304
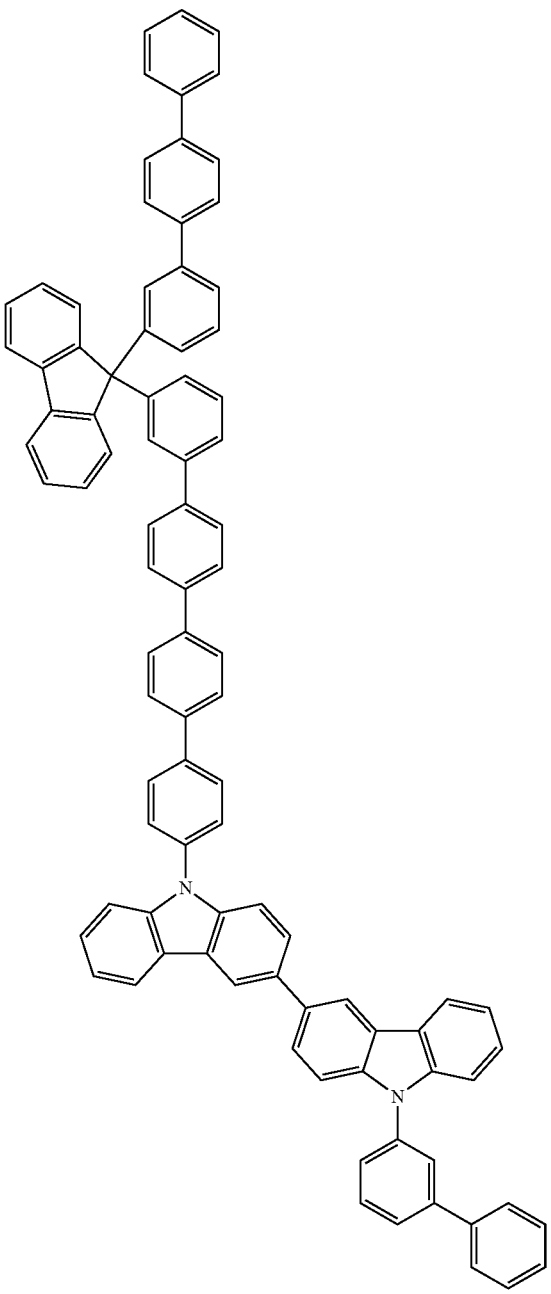

-continued
A305
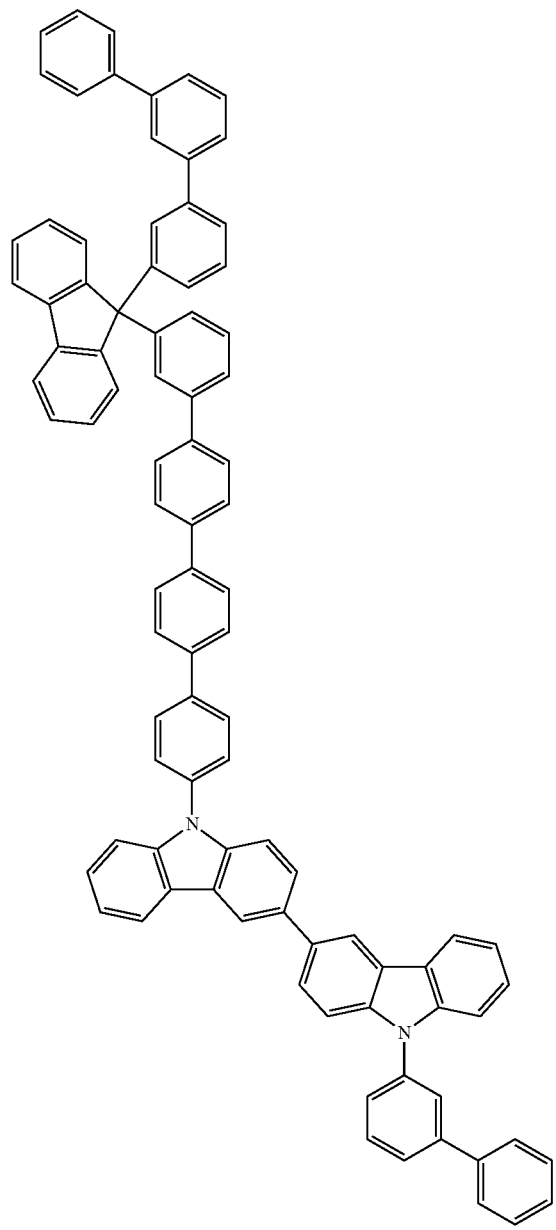
A306
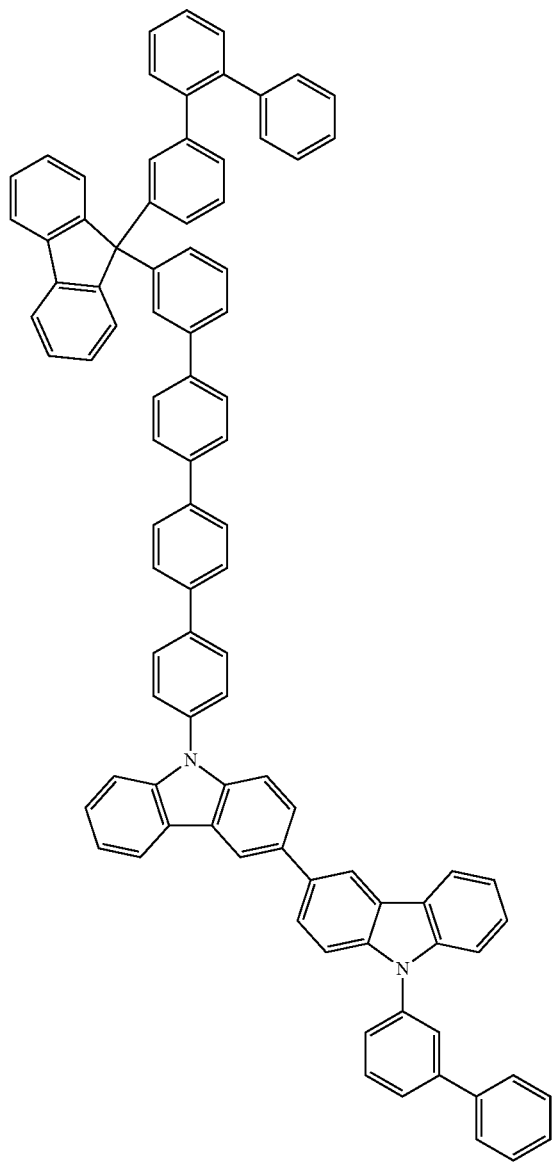

A307
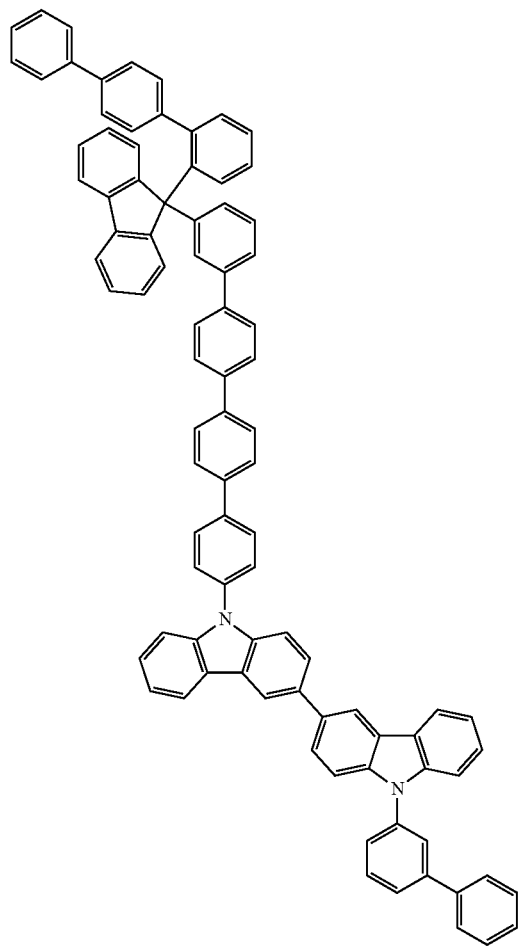
A308
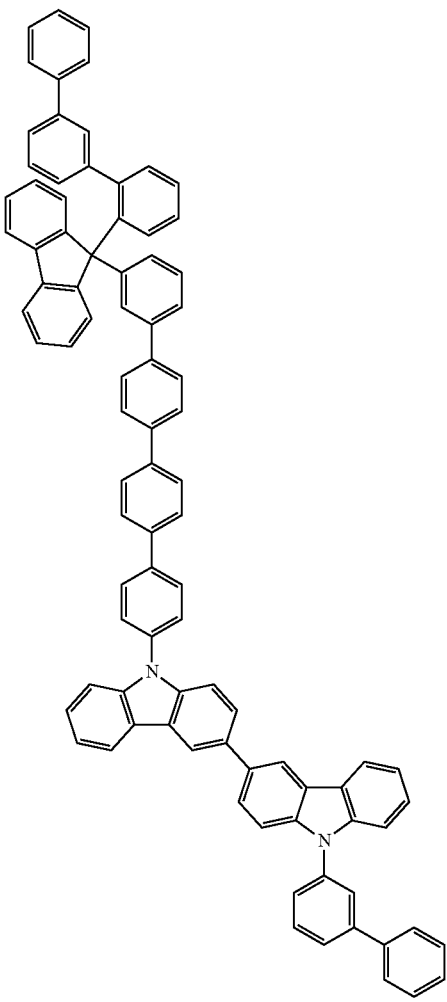

-continued
A309
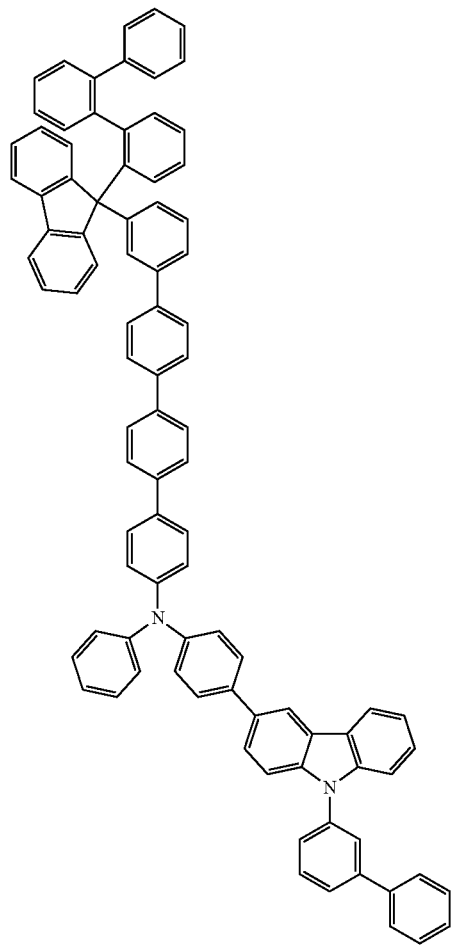
A310
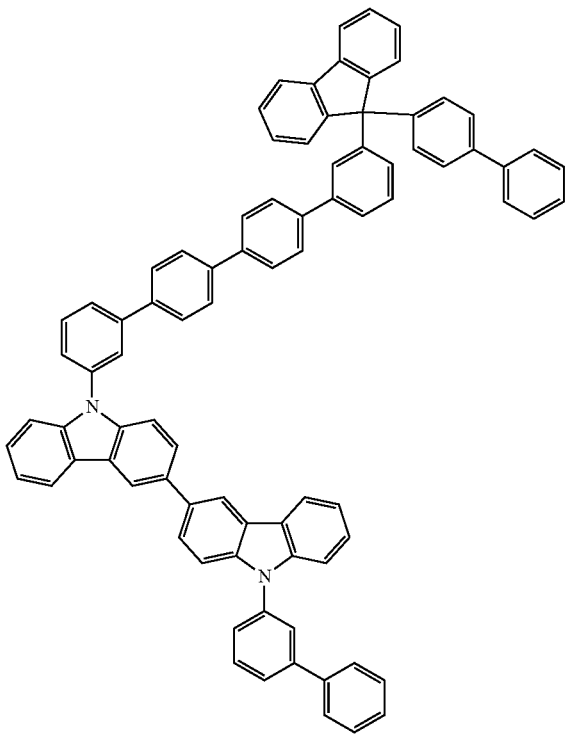

-continued
A311
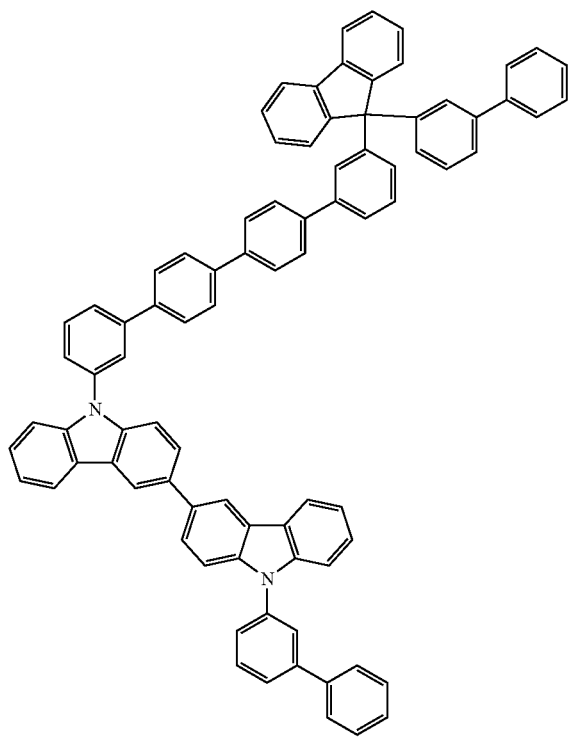
A312
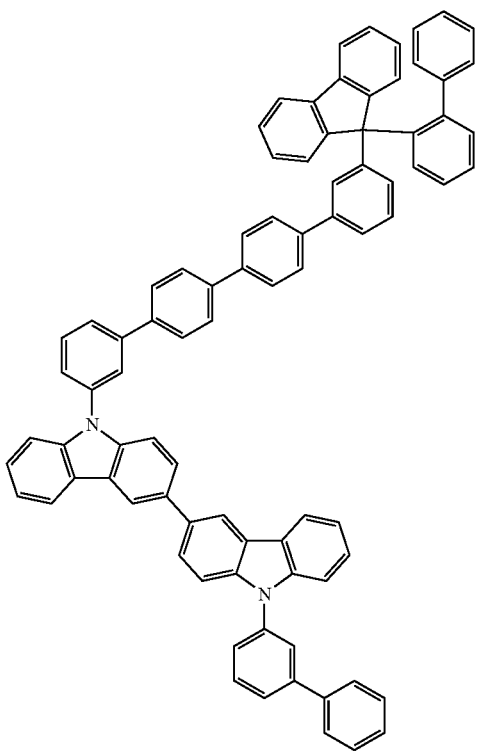
A313
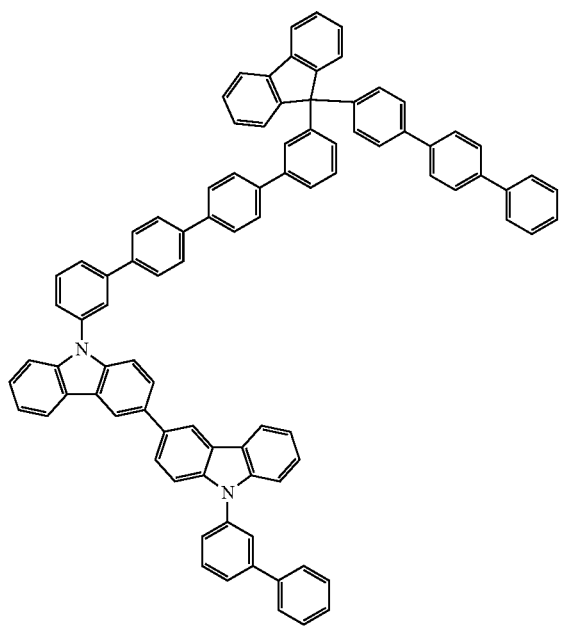
A314
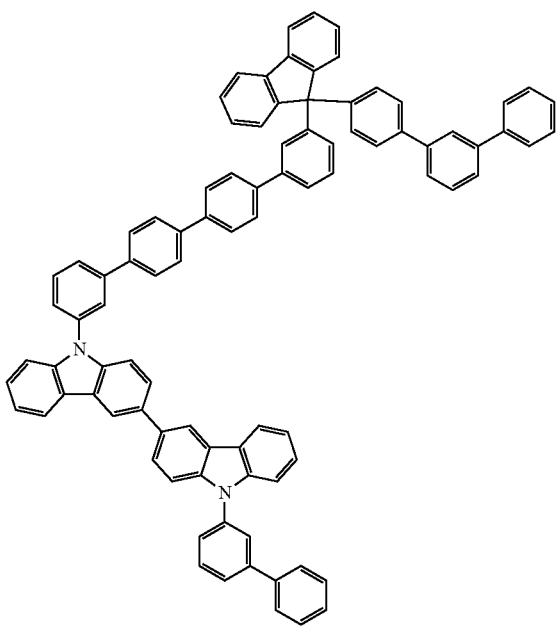

-continued
A315
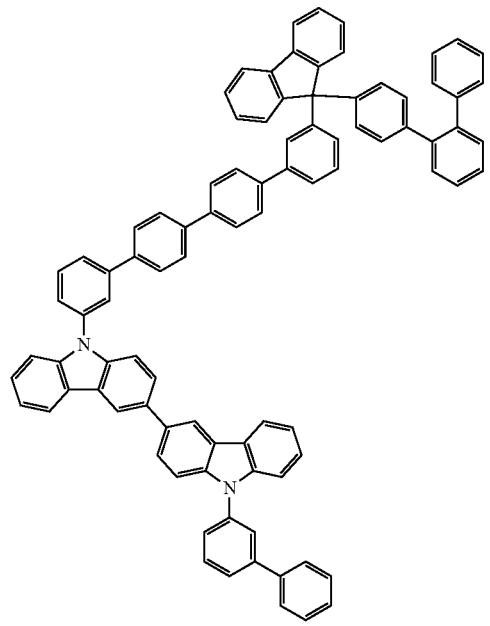
A316
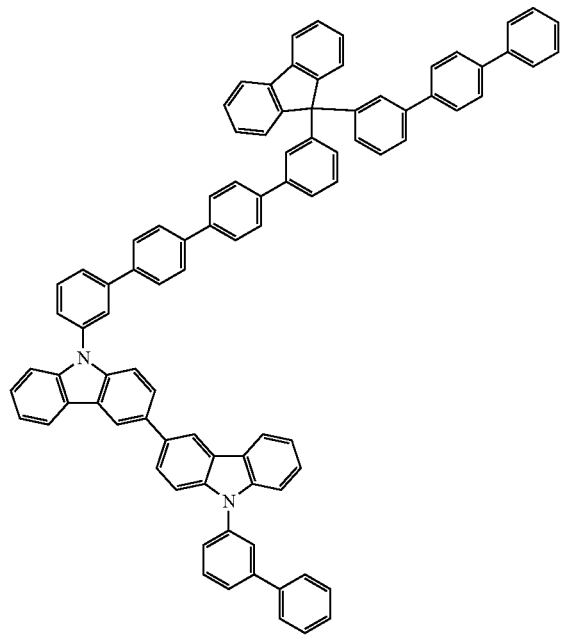
A317
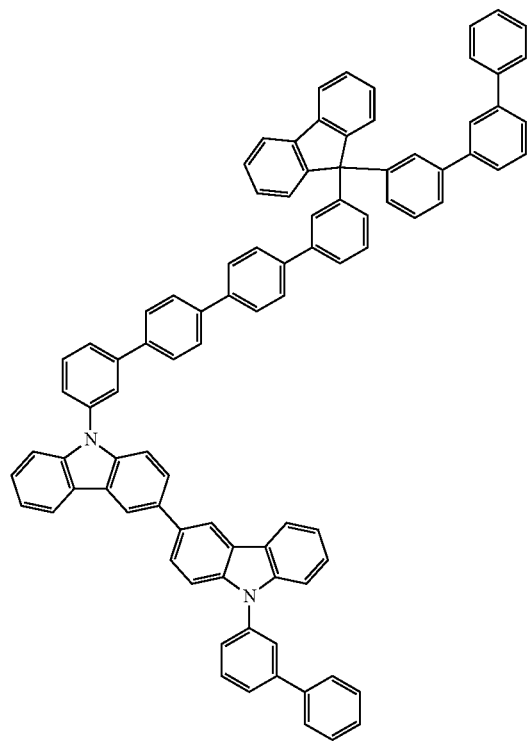
A318
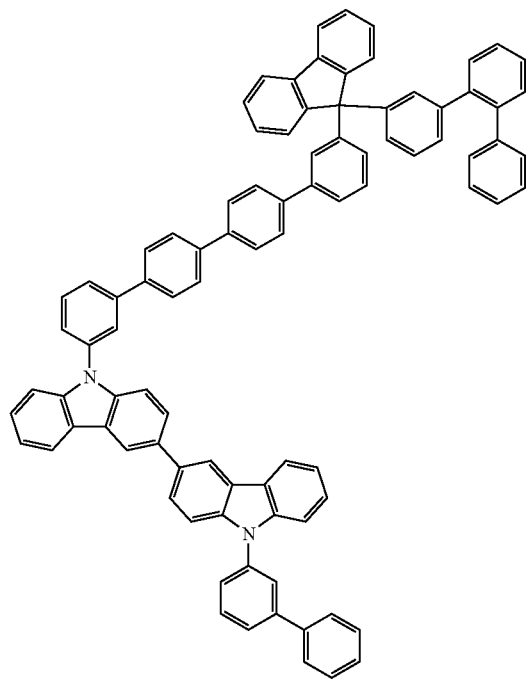

-continued
A319
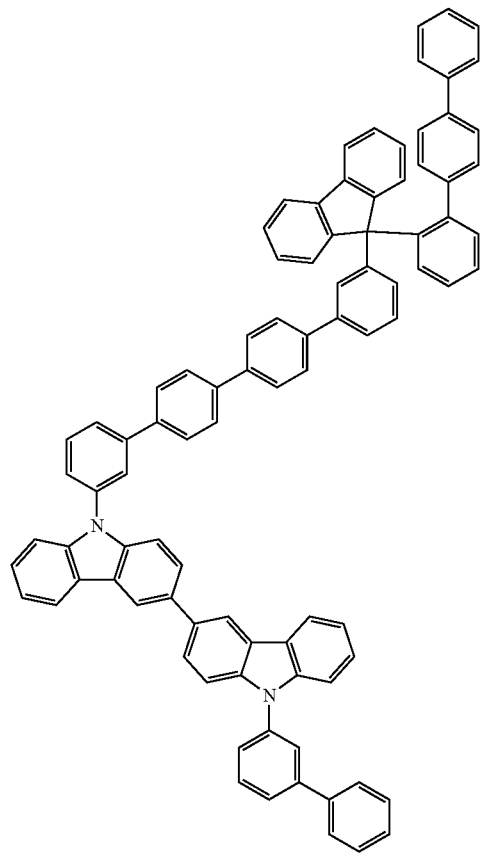
A320
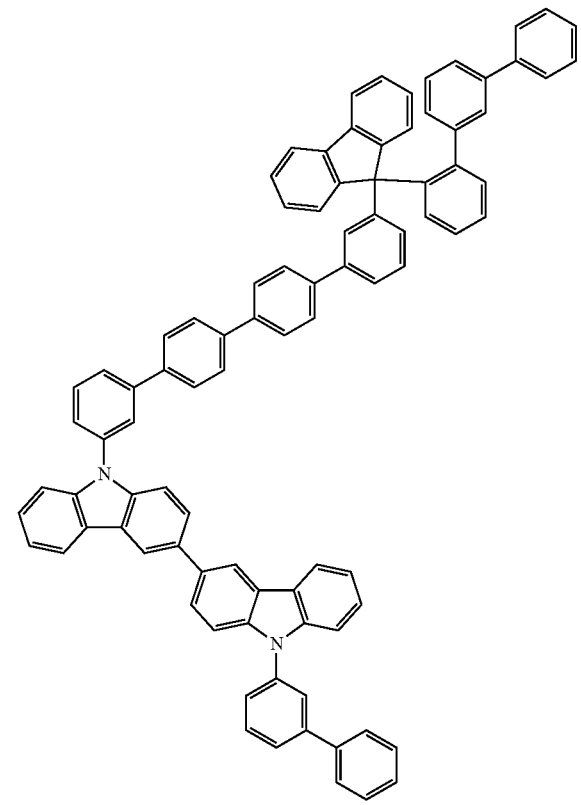
A321
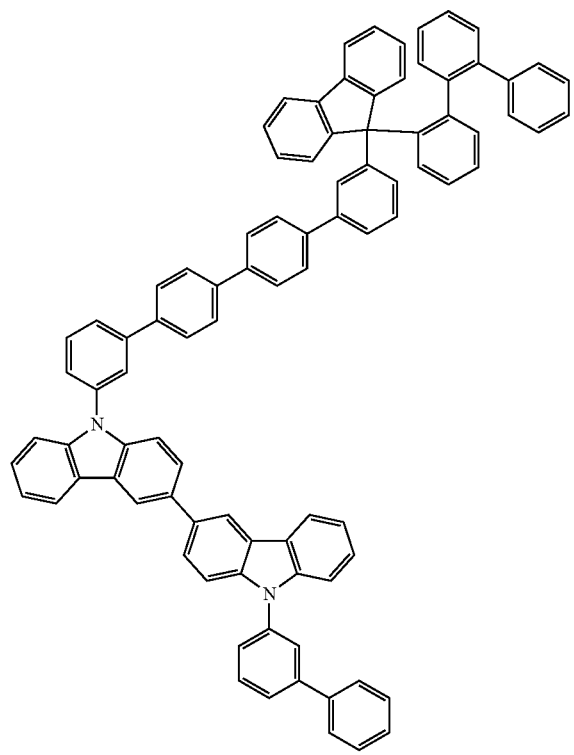
A322
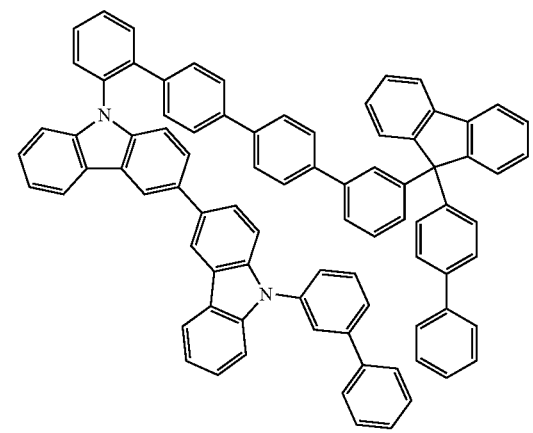

-continued
A323
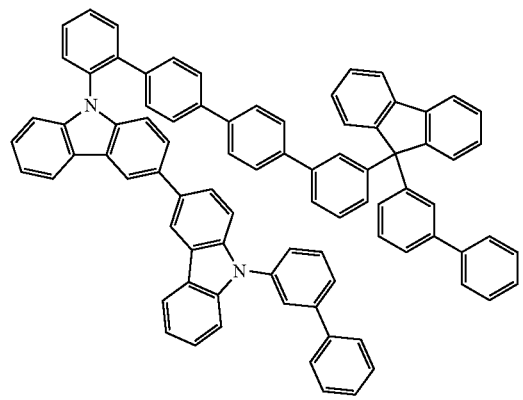
A324
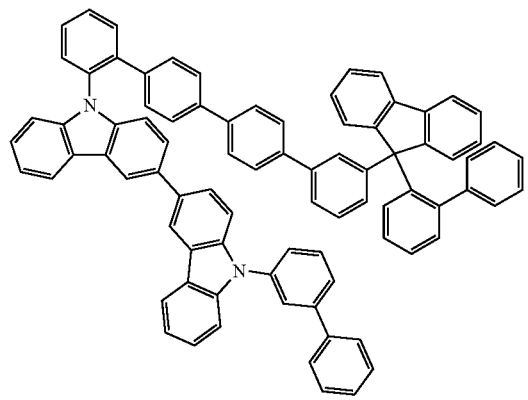
A325
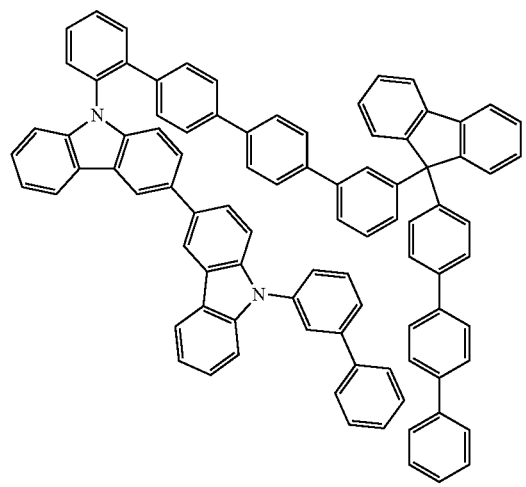
A326
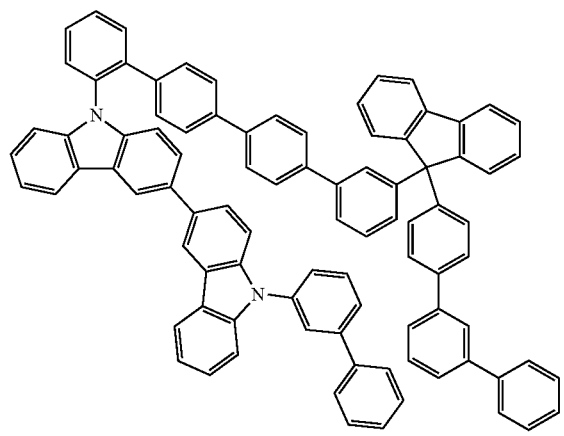
A327
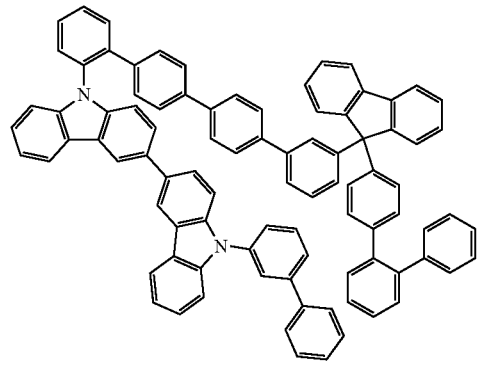
A328
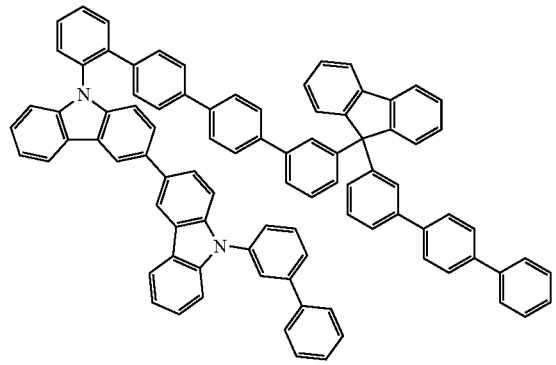

-continued
A329
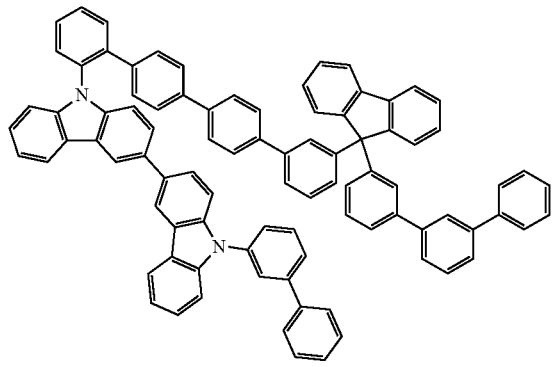
A330
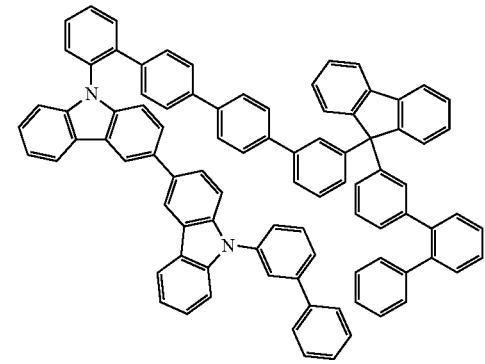
A331
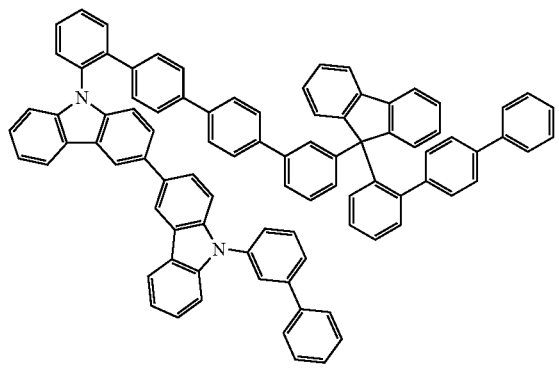
A332
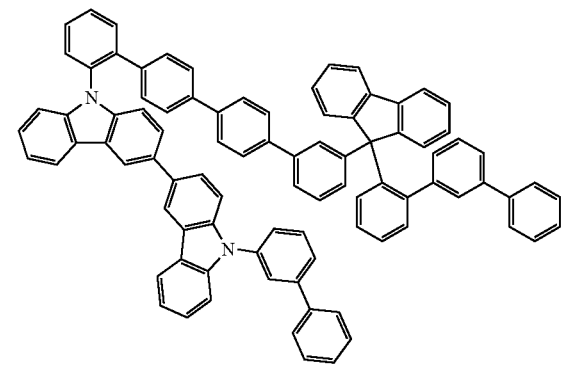
A333
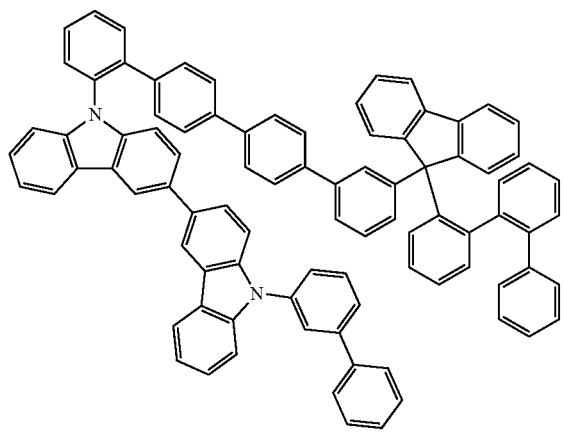
A334
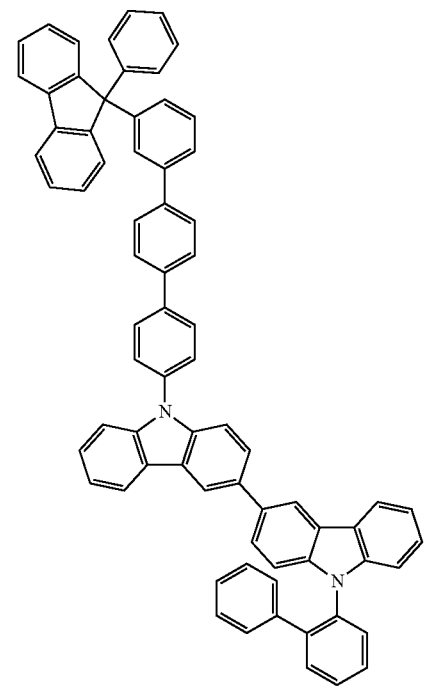

-continued
A335
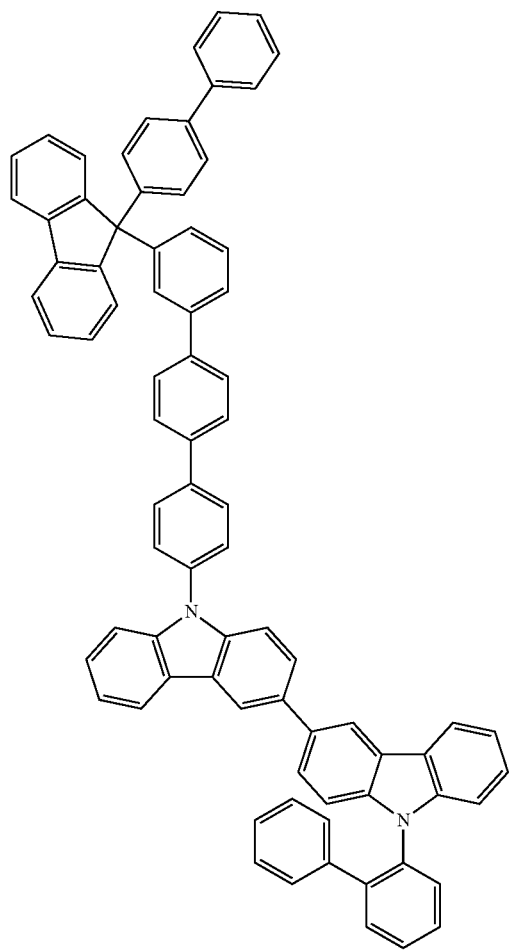
A336
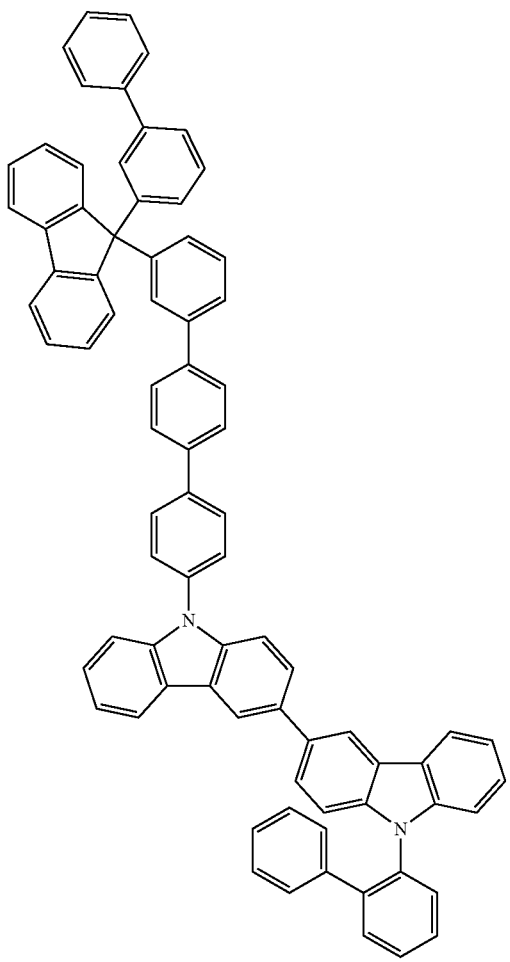

A337
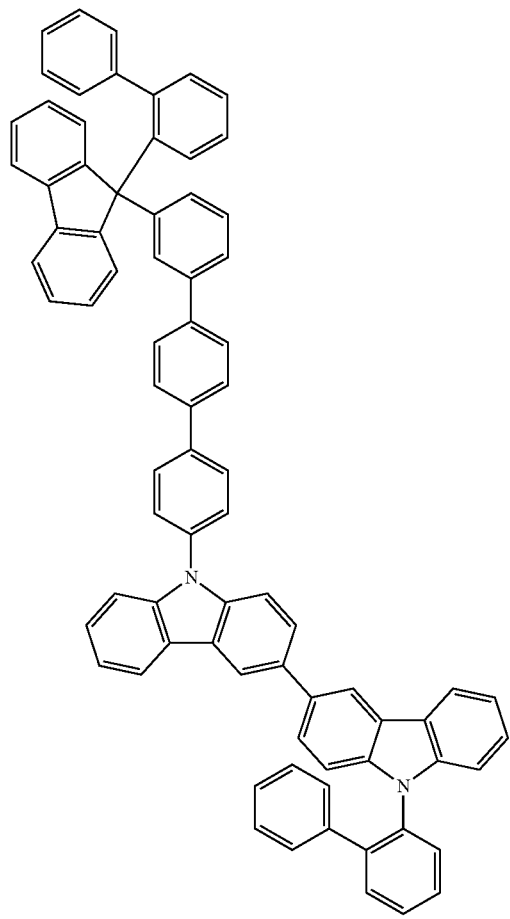
A338
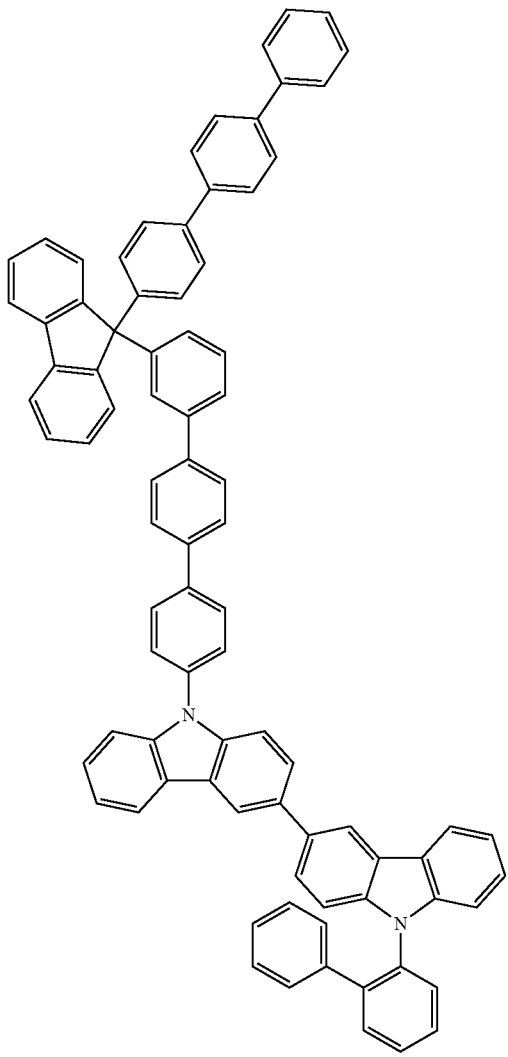

-continued
A339
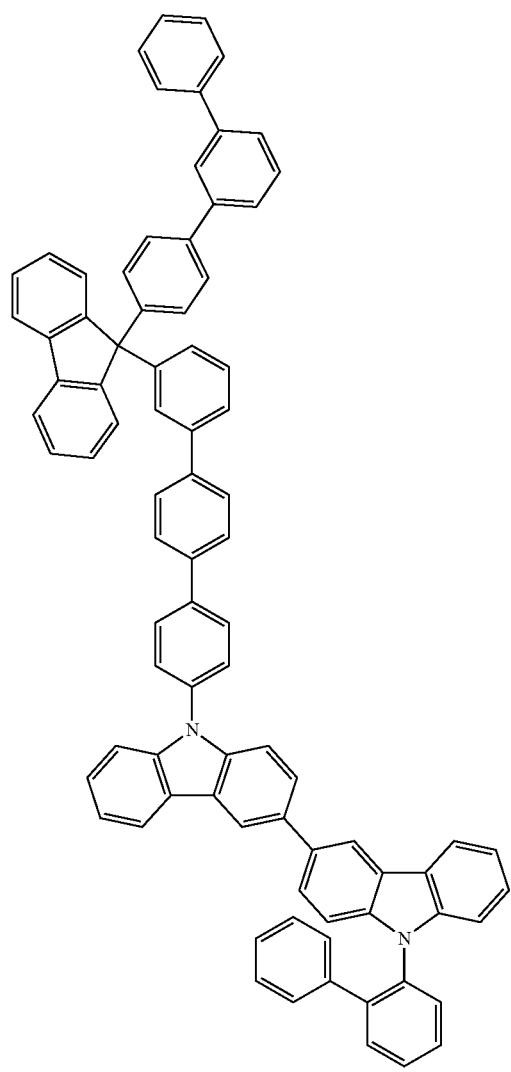
A340
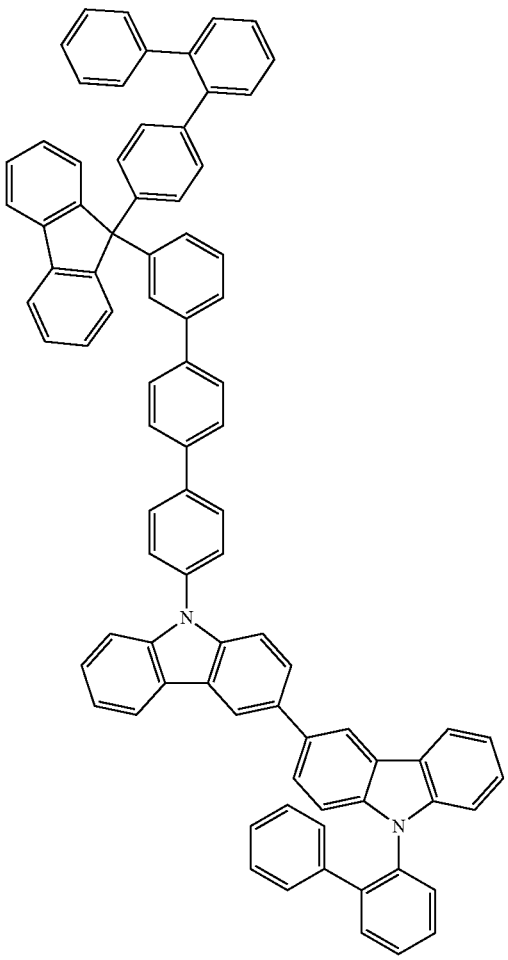

-continued
A341
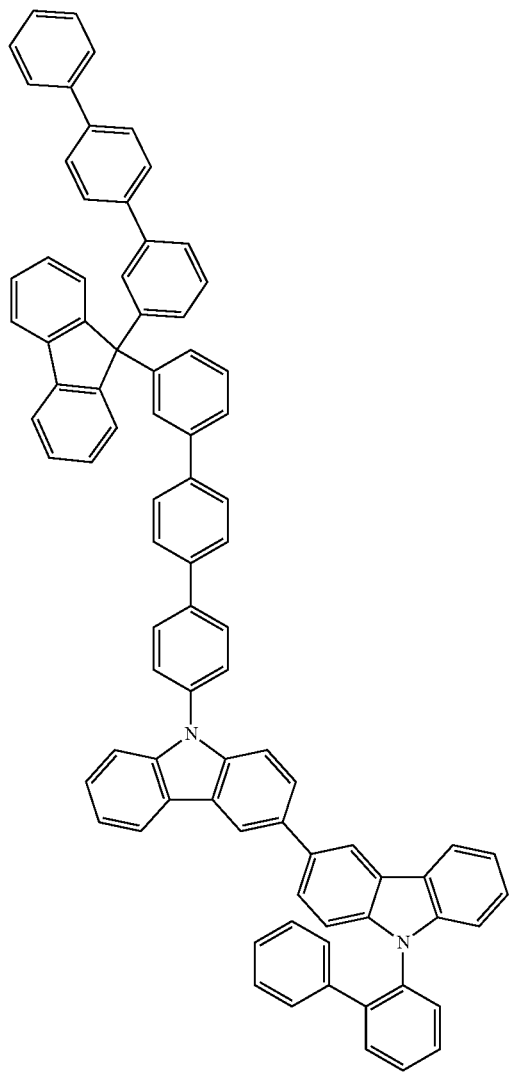
A342
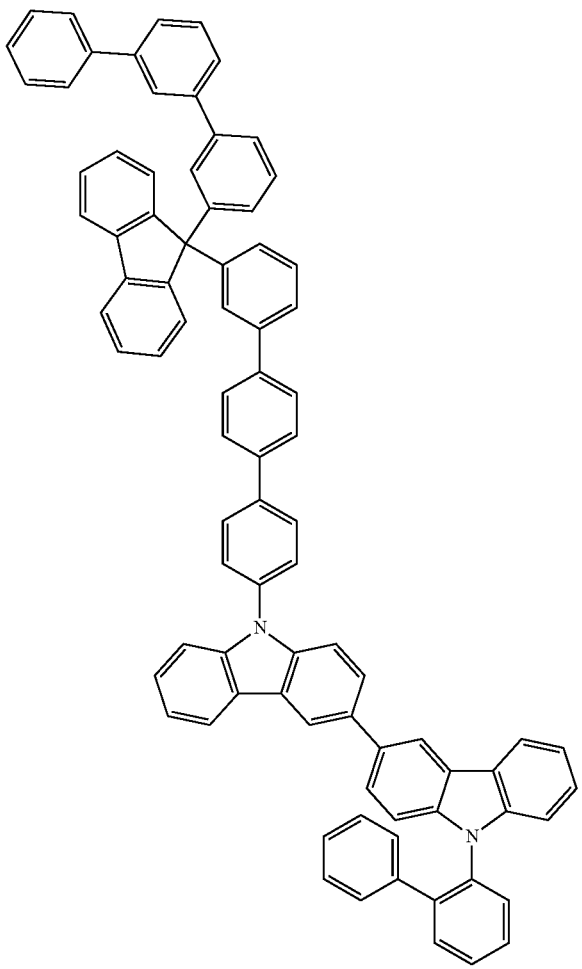

-continued
A343
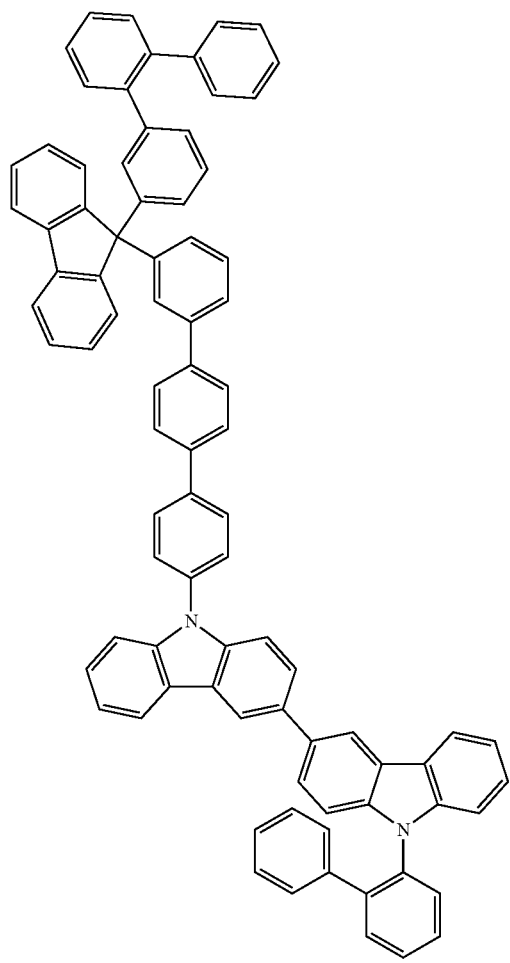
A344
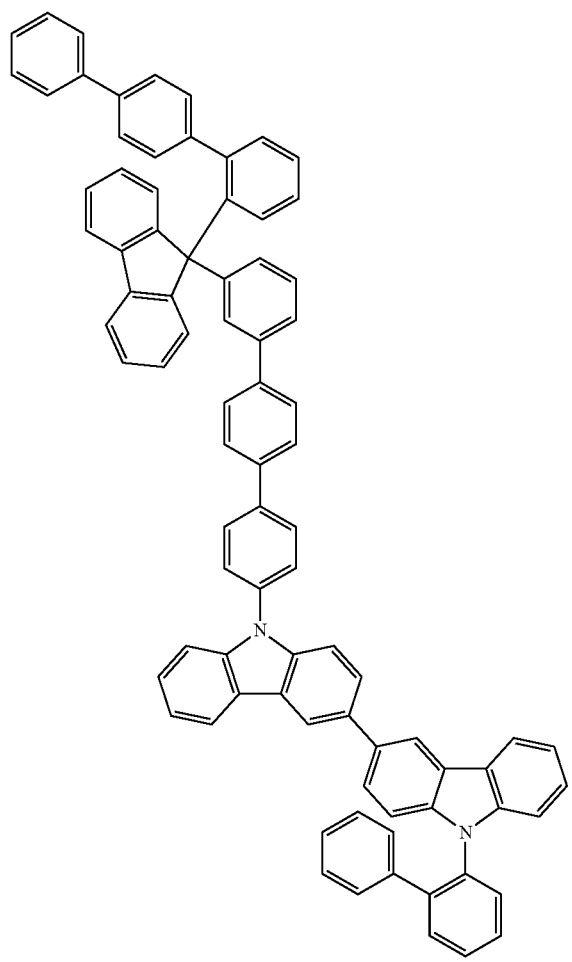

-continued
A345
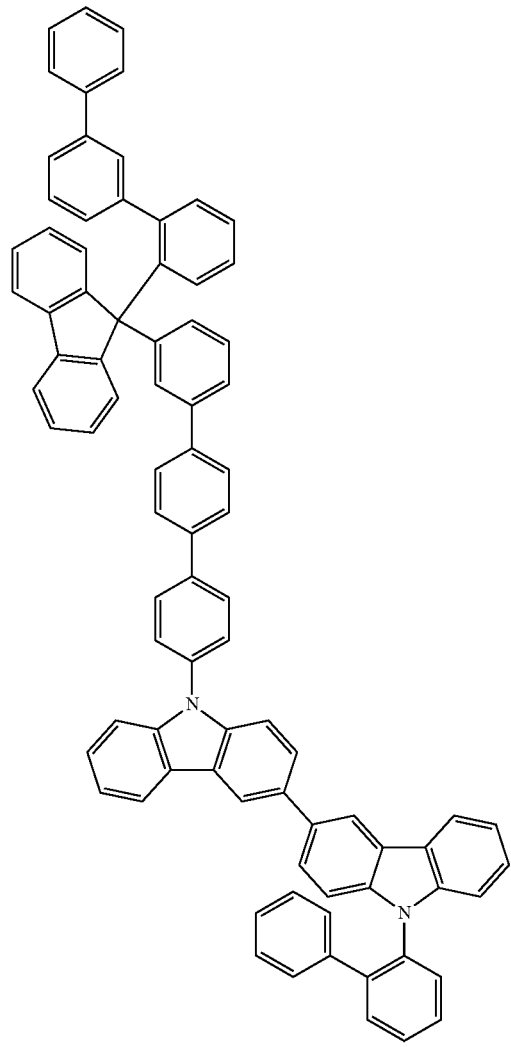
A346
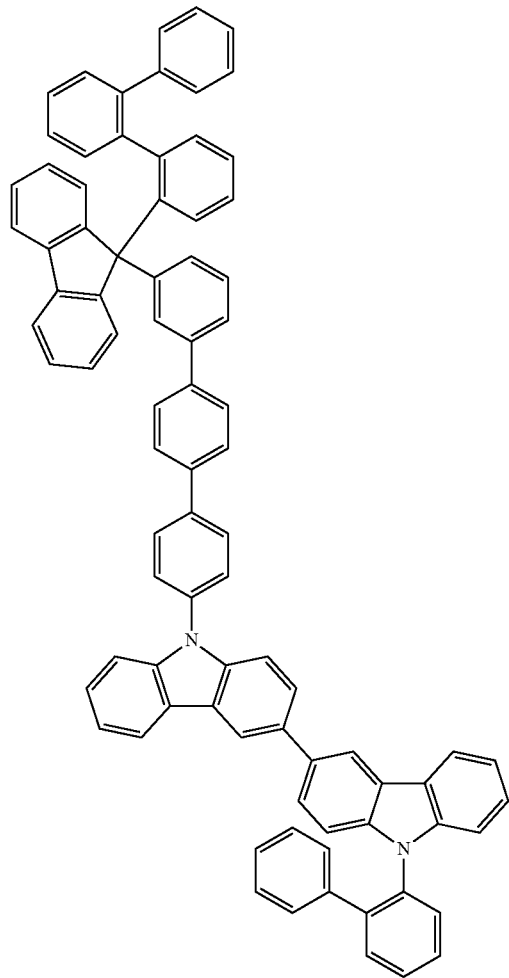

-continued
A347
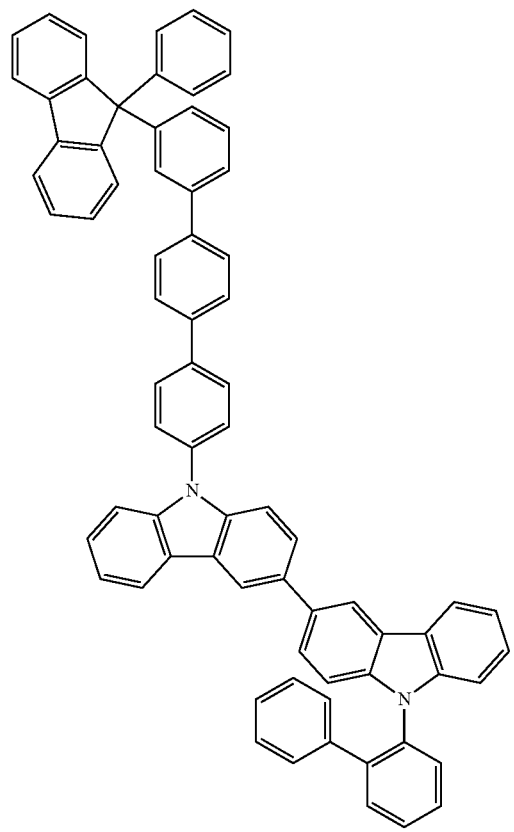
A348
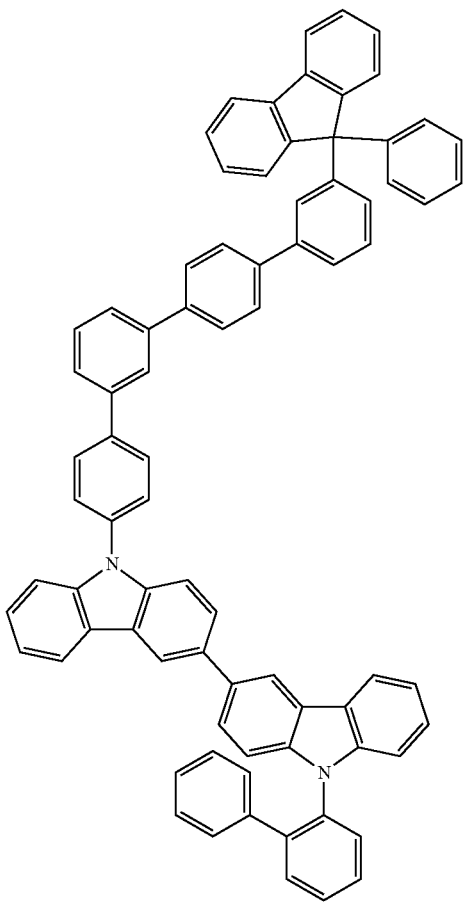

-continued
A349
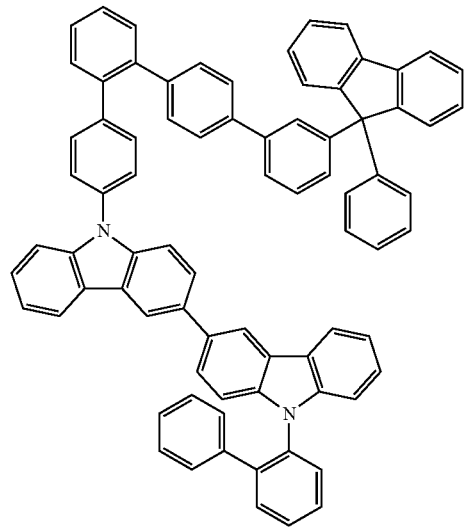
A350
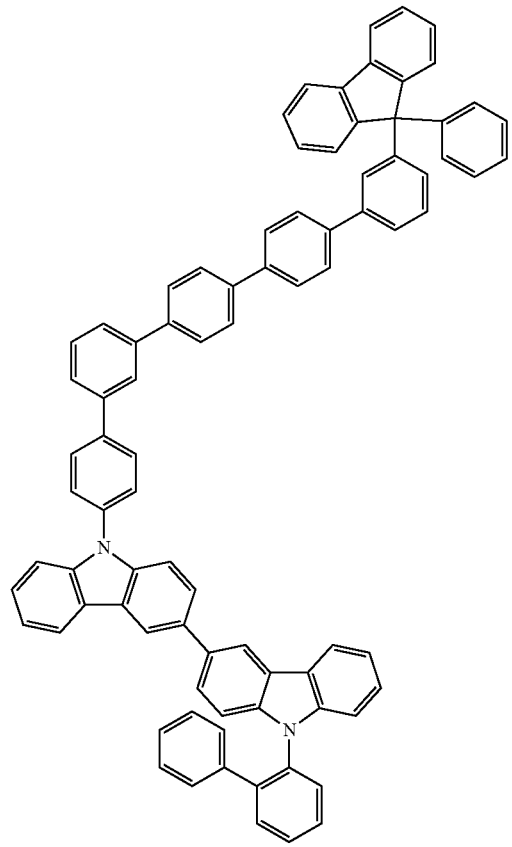
A351
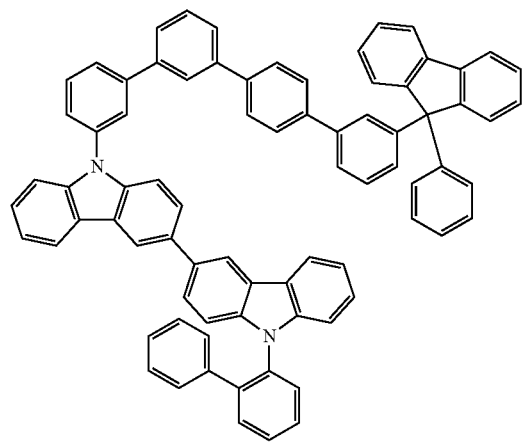
A352
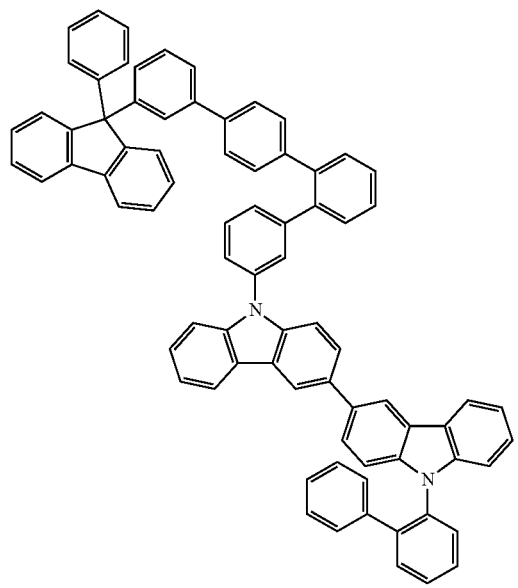

-continued
A353
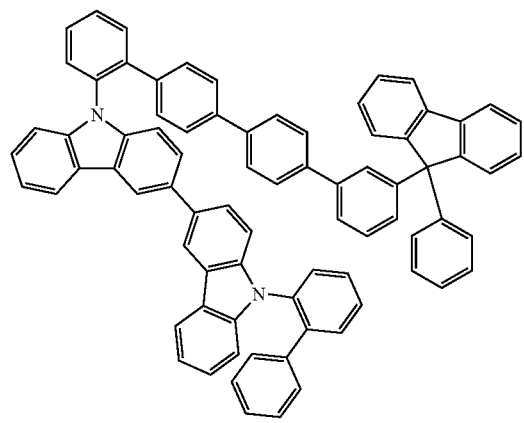
A354
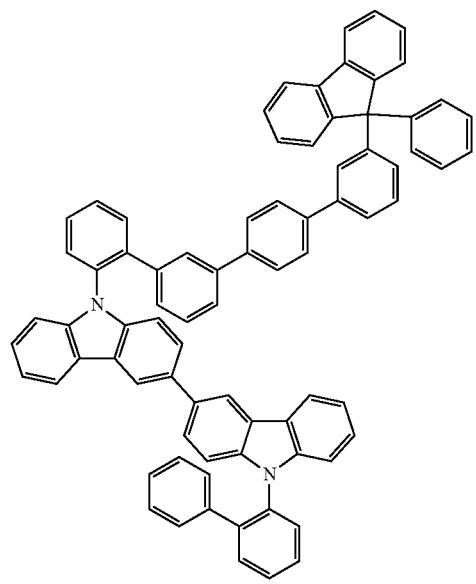
A355
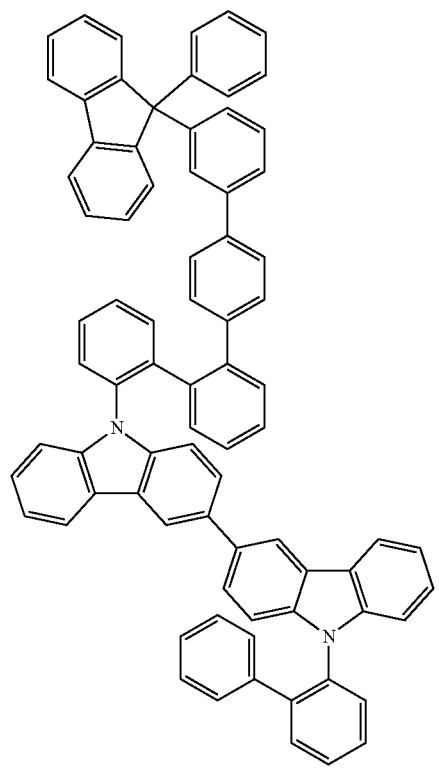
A356
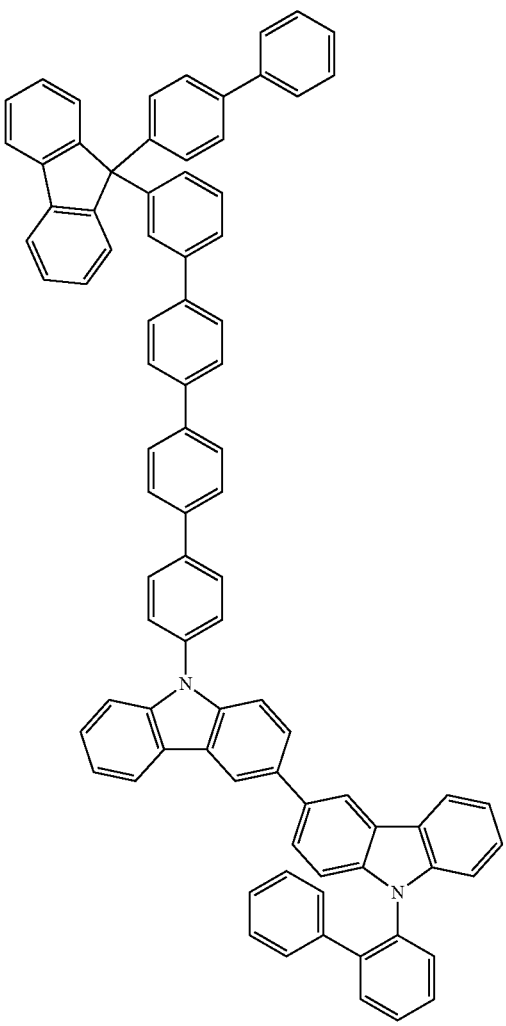

225 226
-continued
A357 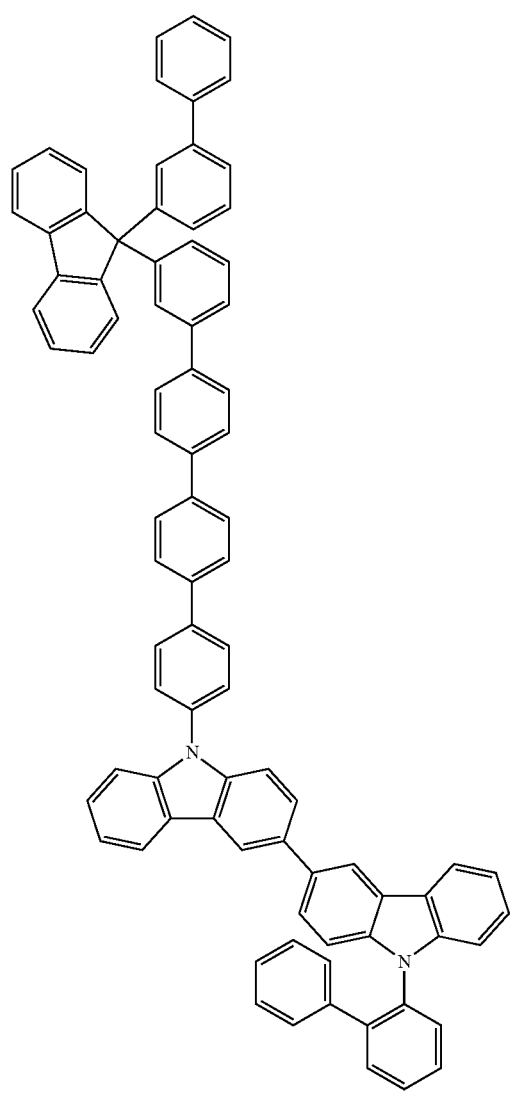
A358 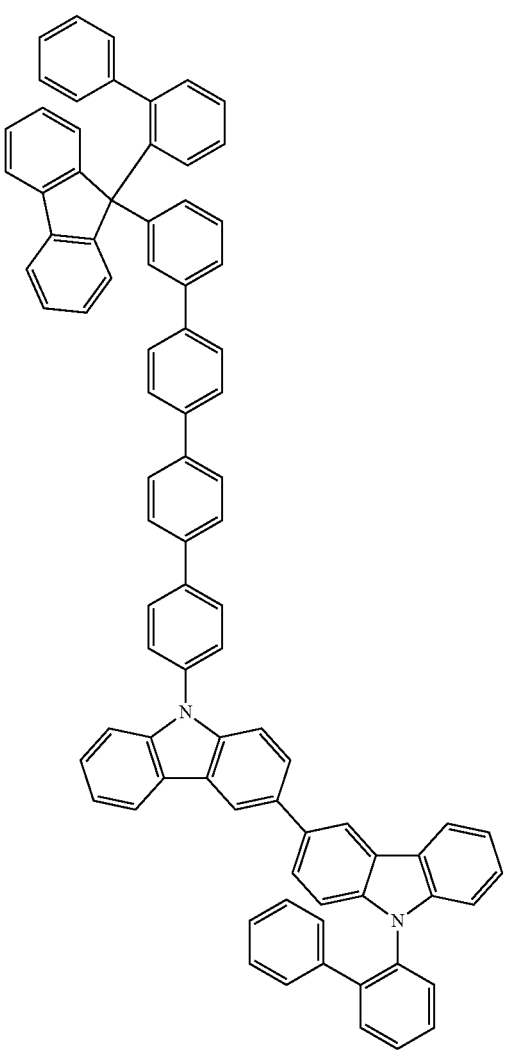

-continued
227
A359
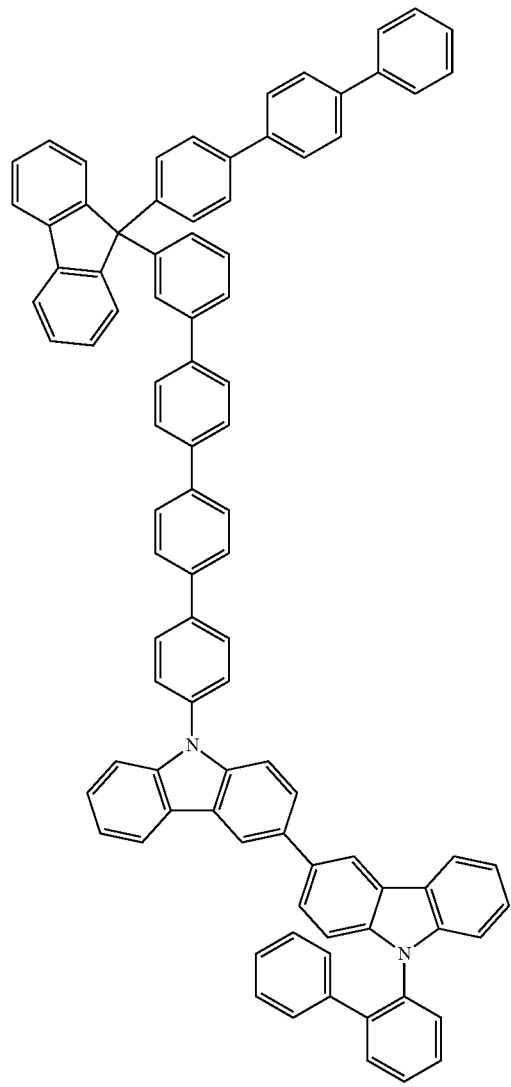
228
A360
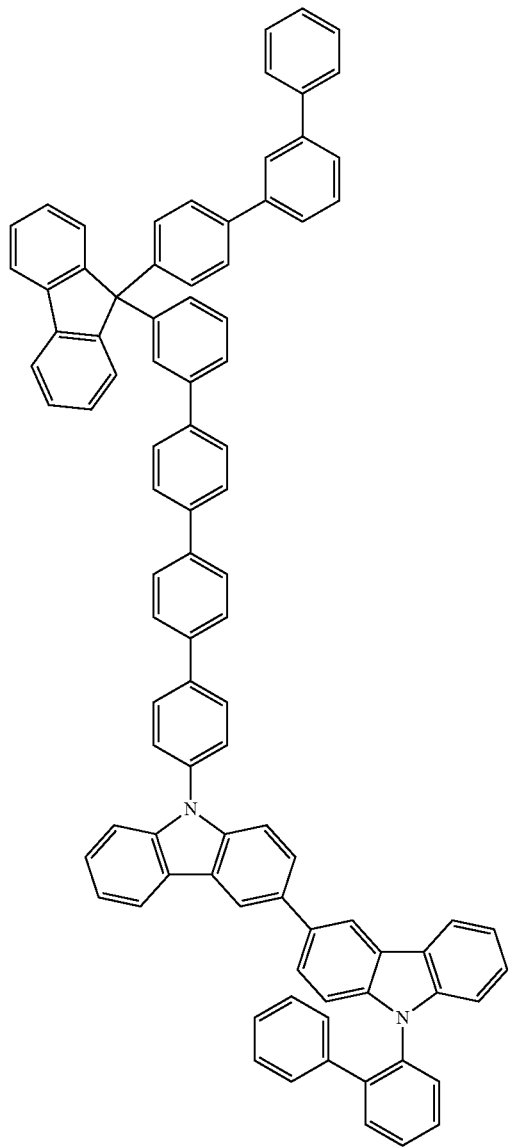

A361
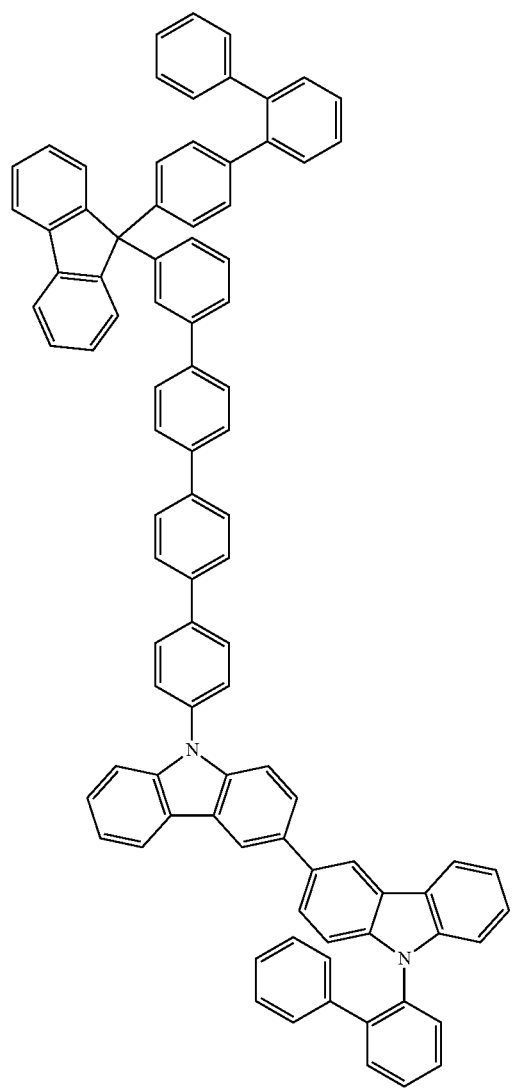
A362
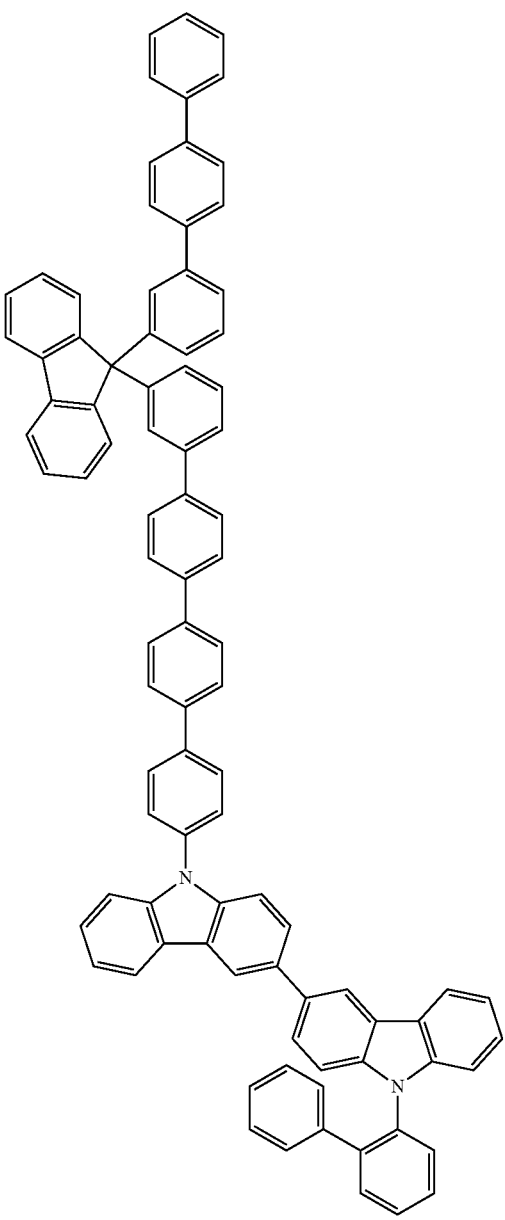

-continued
A363
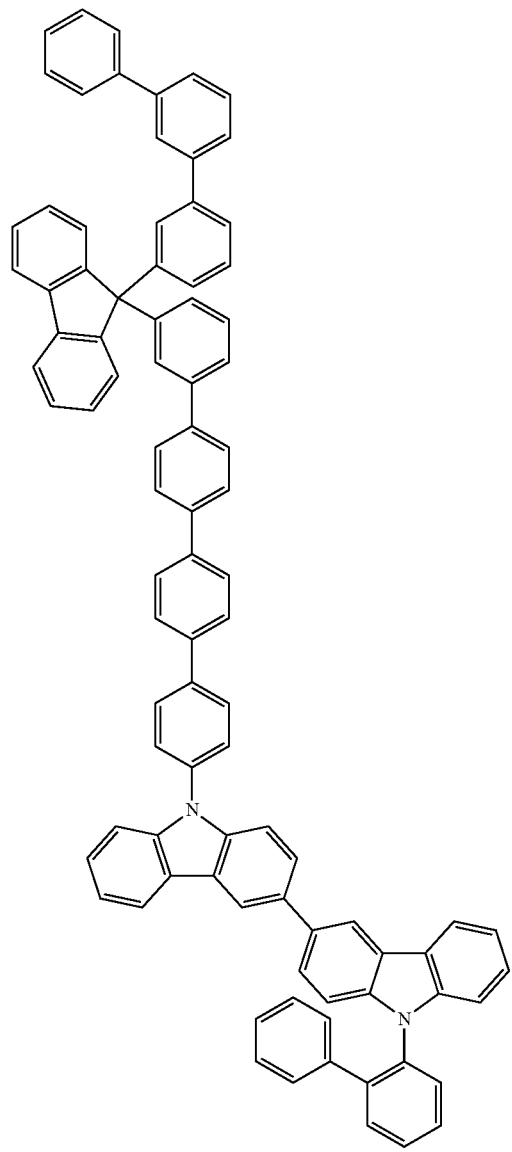
A364
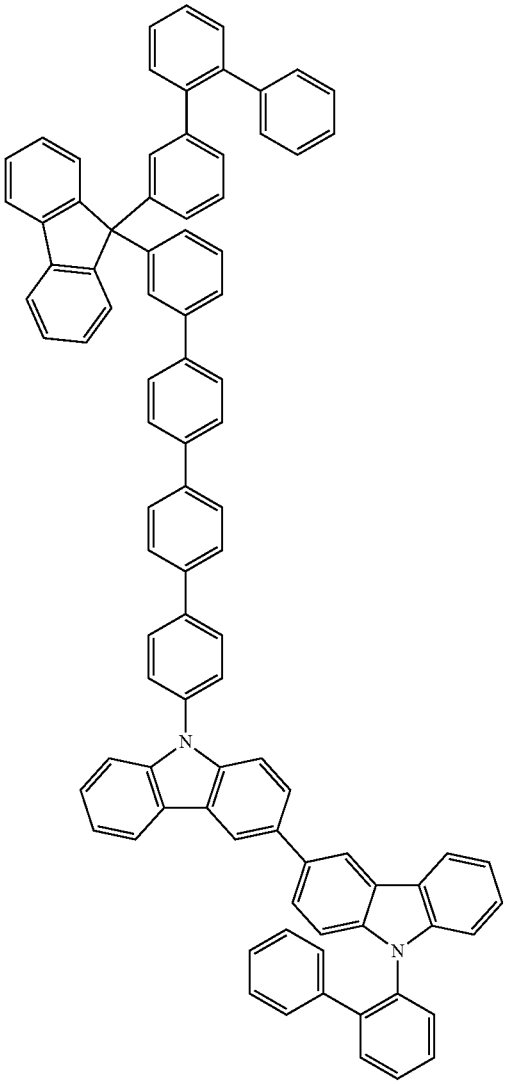

-continued
A365
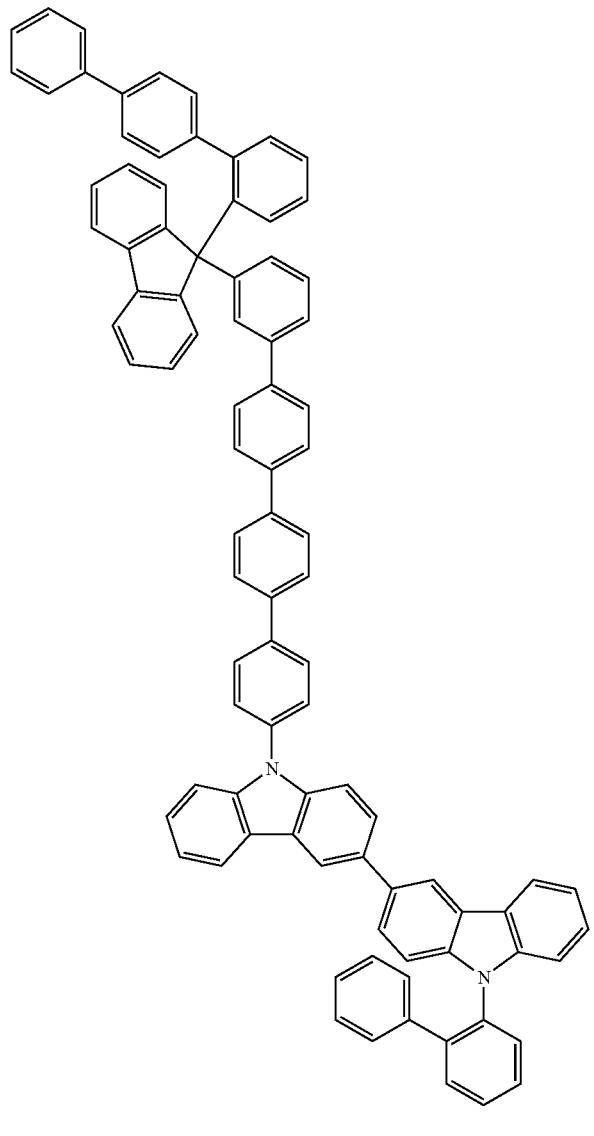
A366
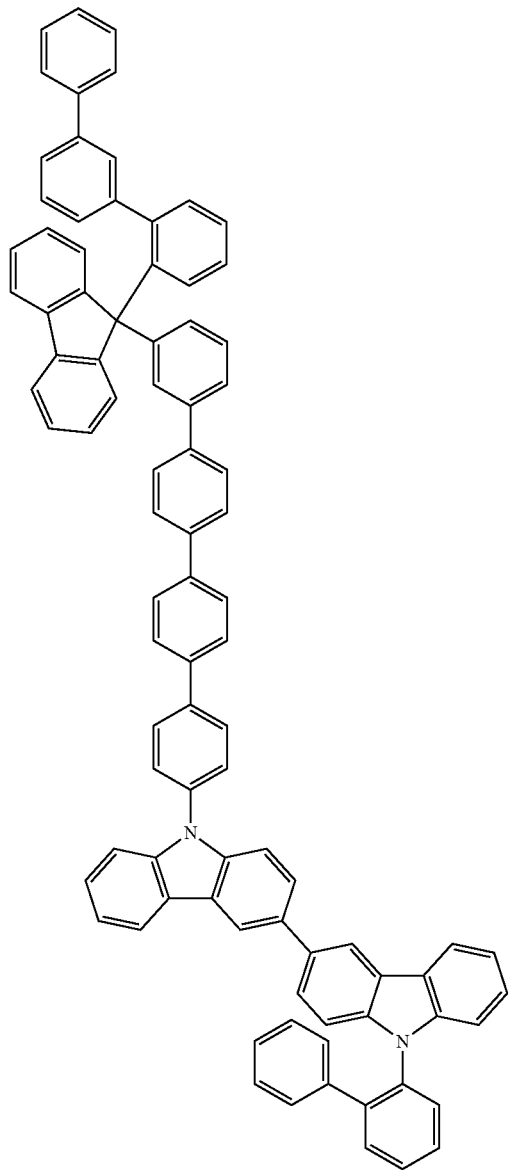

-continued
A367
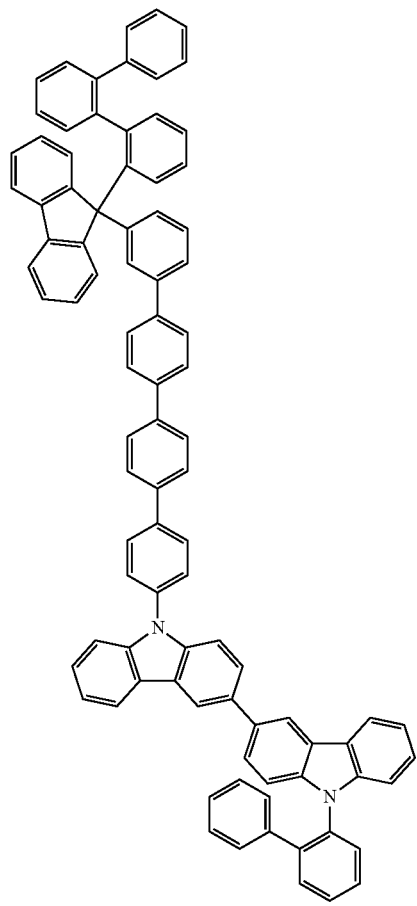
A368
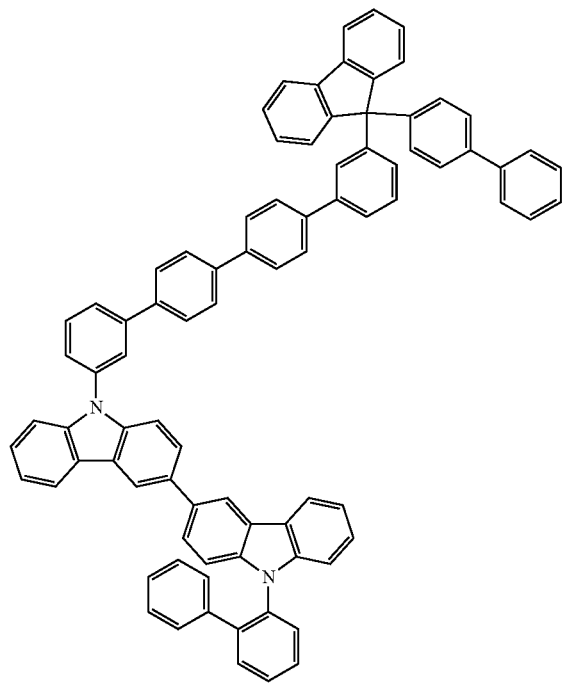
A369
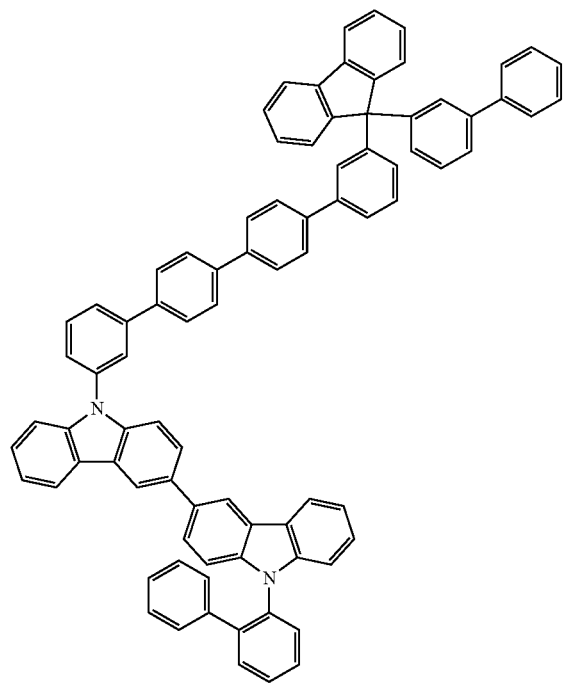
A370
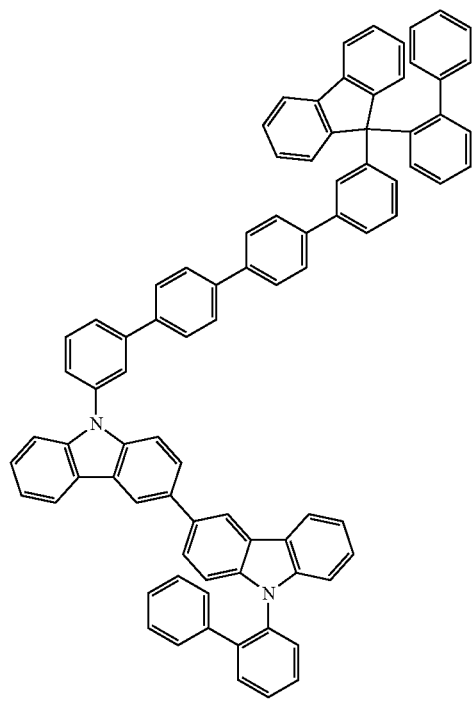

-continued
A371
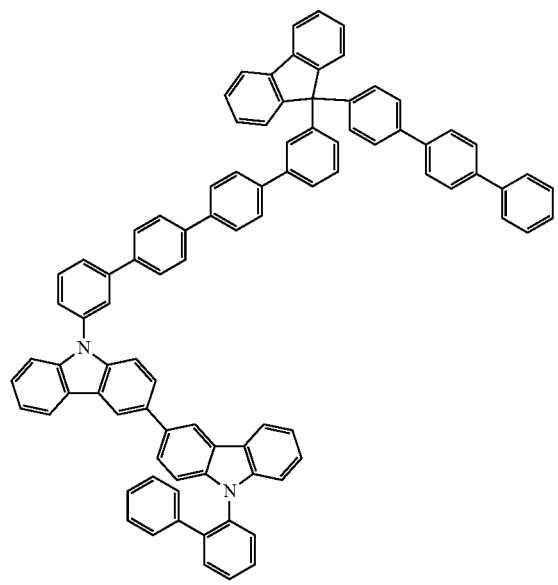
A372
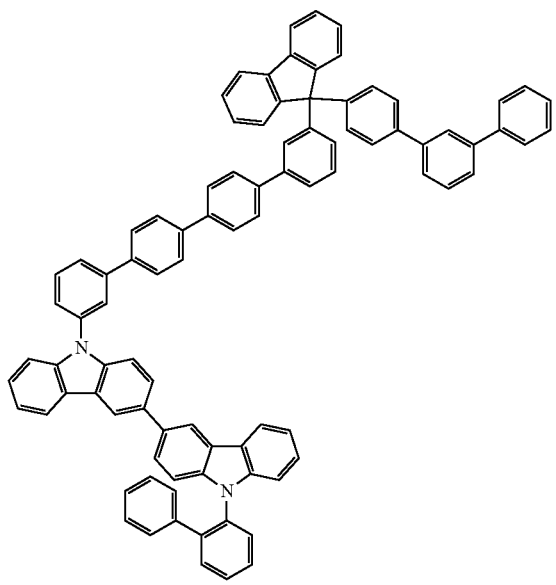
A373
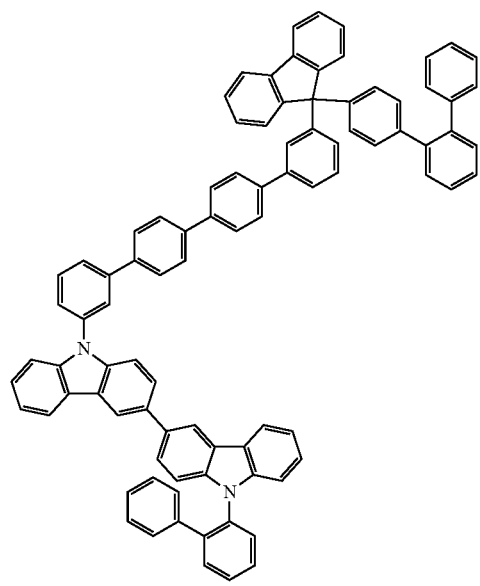
A374
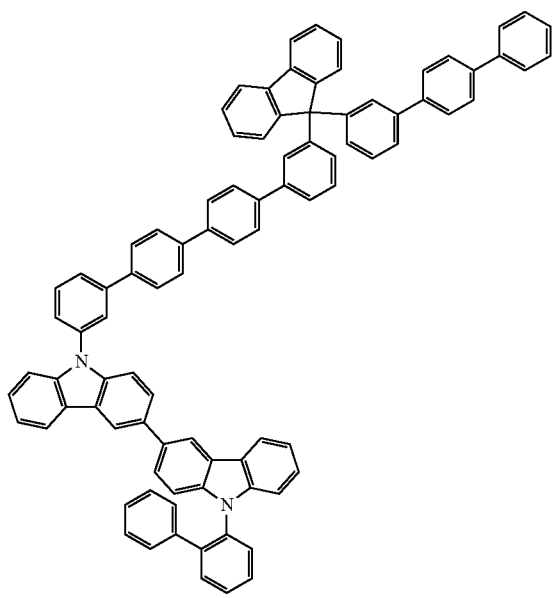

-continued
A375
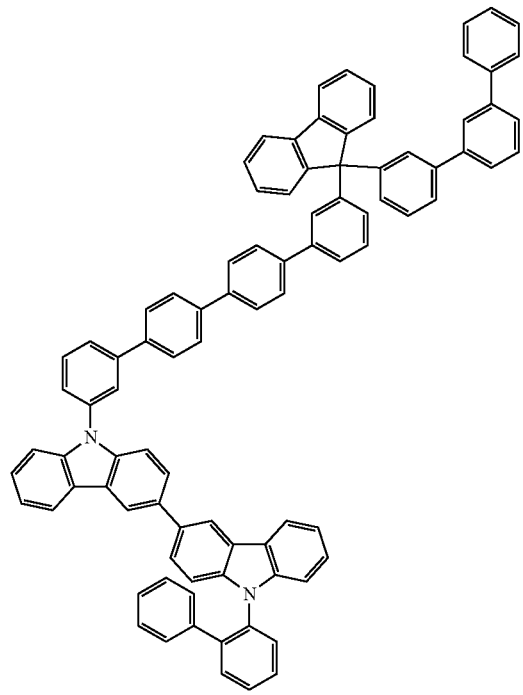
A376
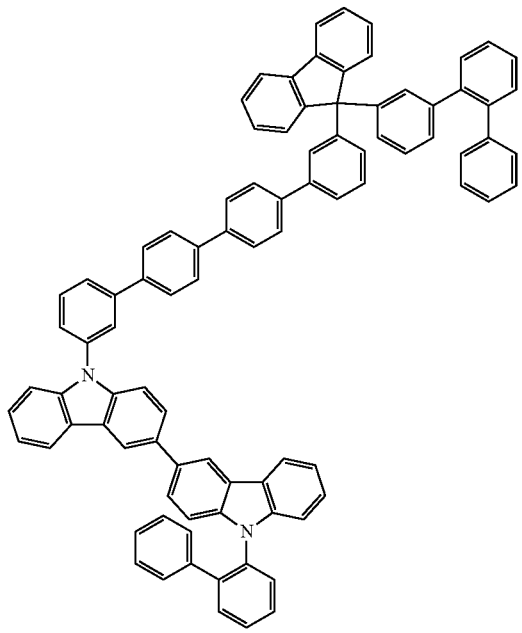
A377
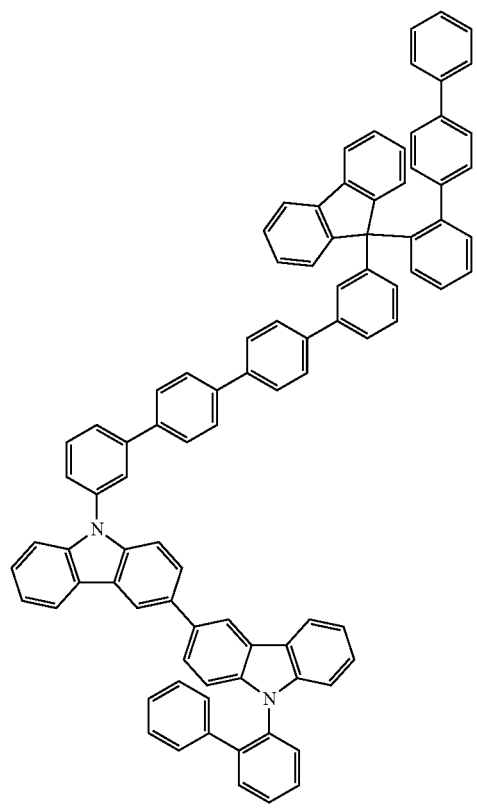
A378
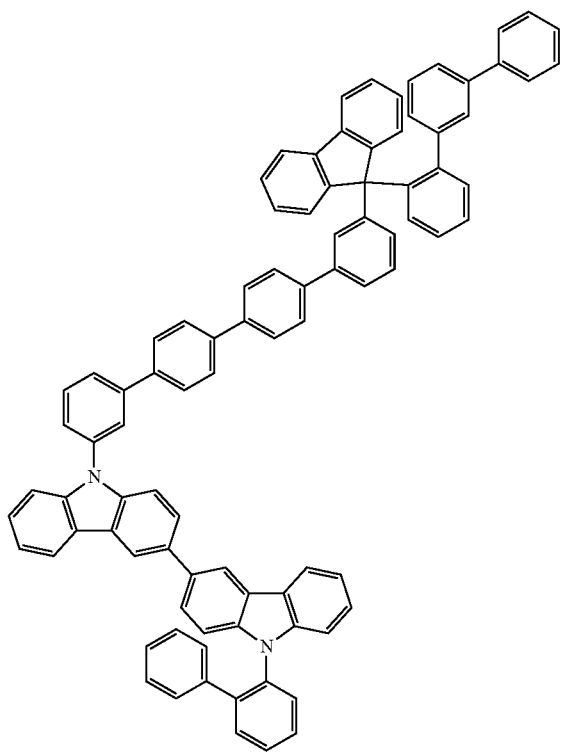

-continued
A379
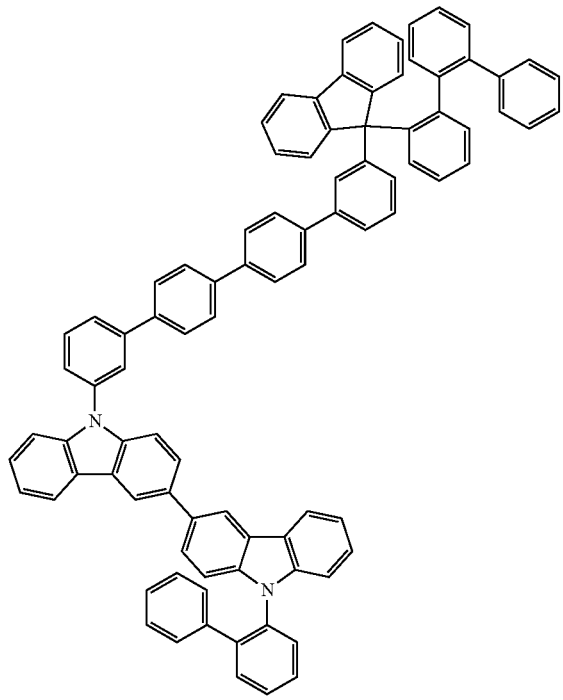
A380
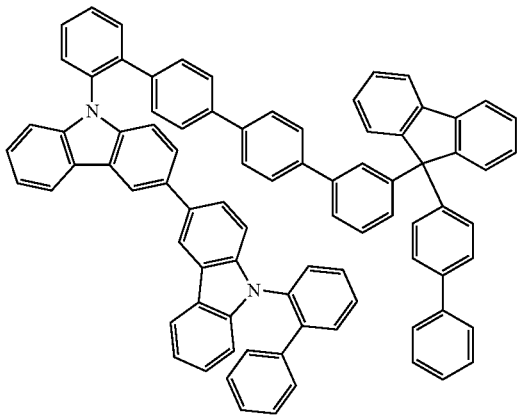
A381
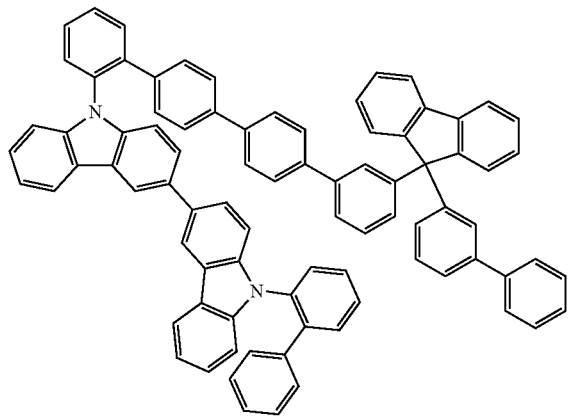
A382
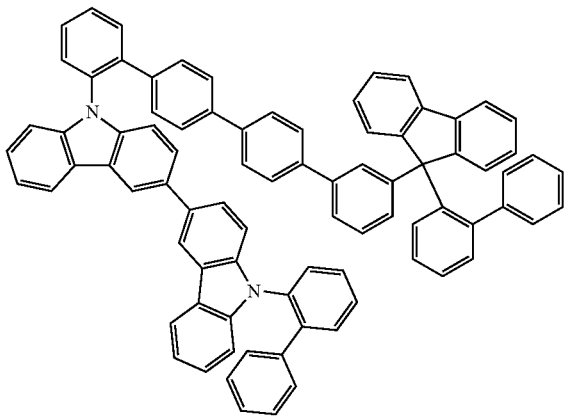
A383
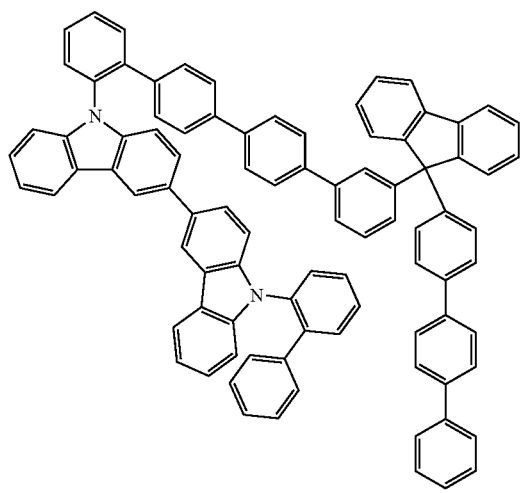
A384
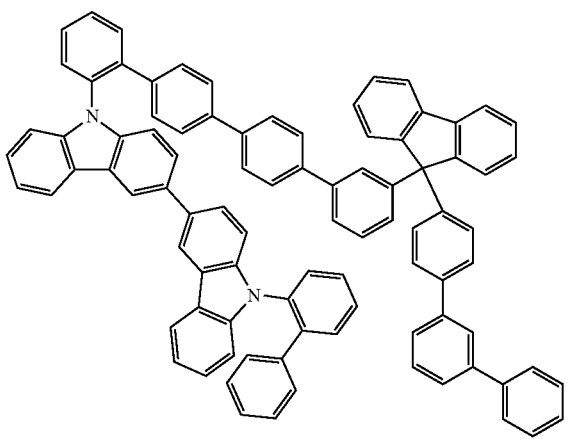

-continued
A385
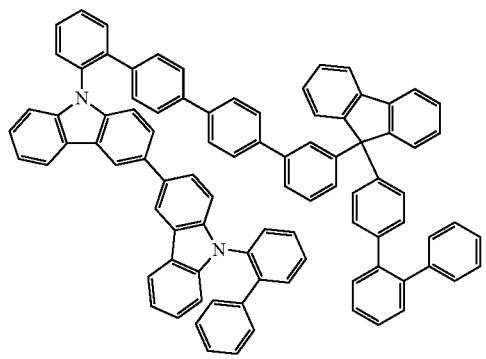
A386
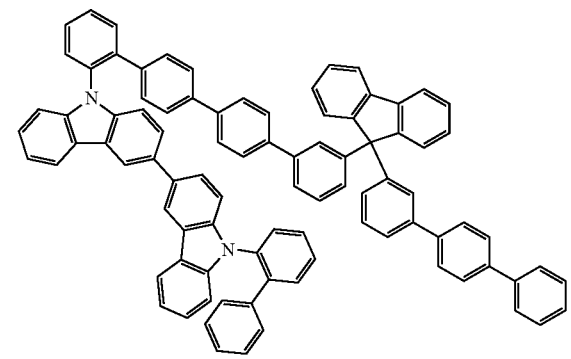
A387
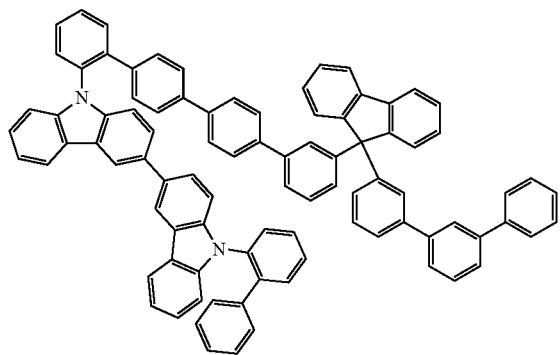
A388
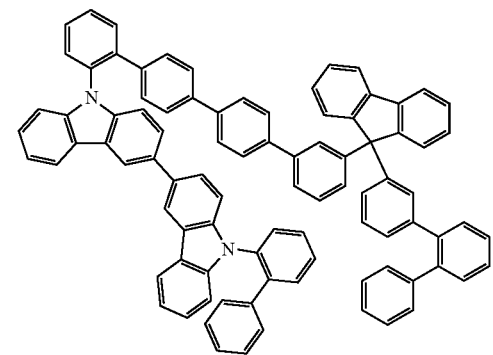
A389
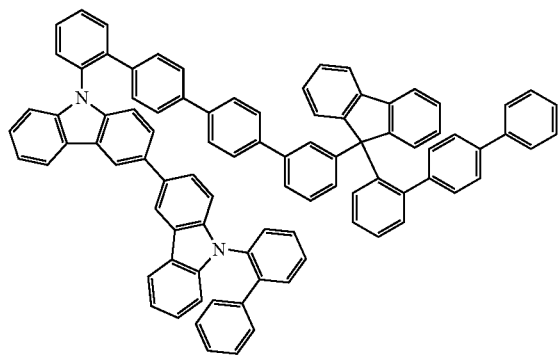
A390
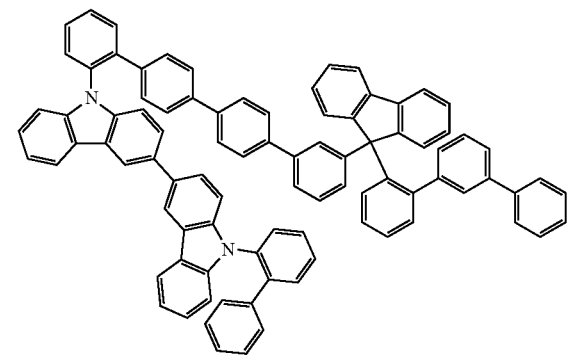

-continued
A391
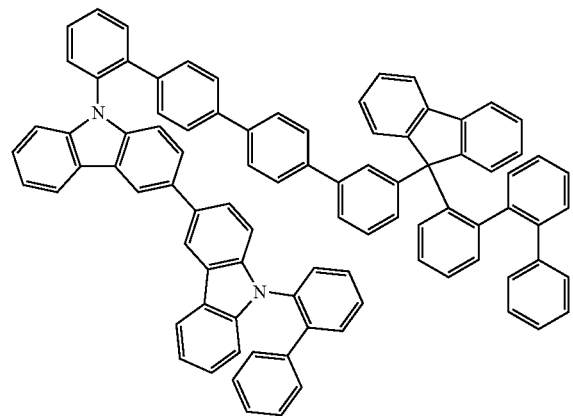
A392
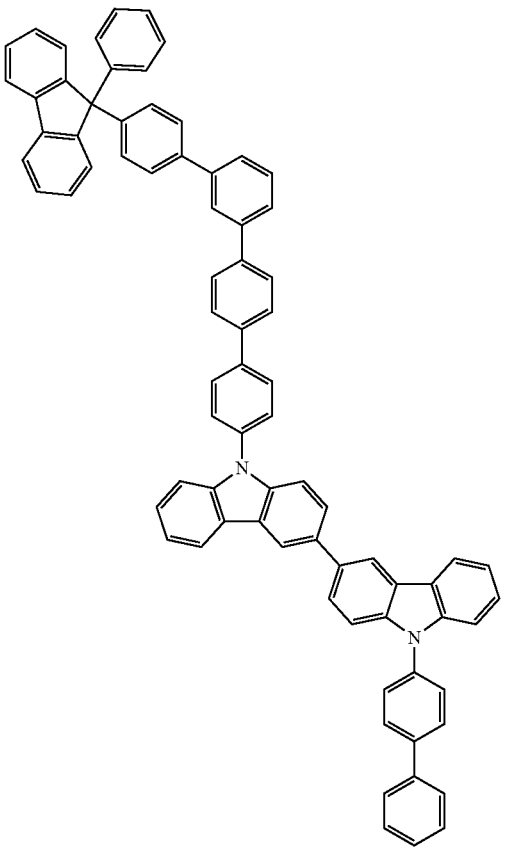

247 248
-continued
A393 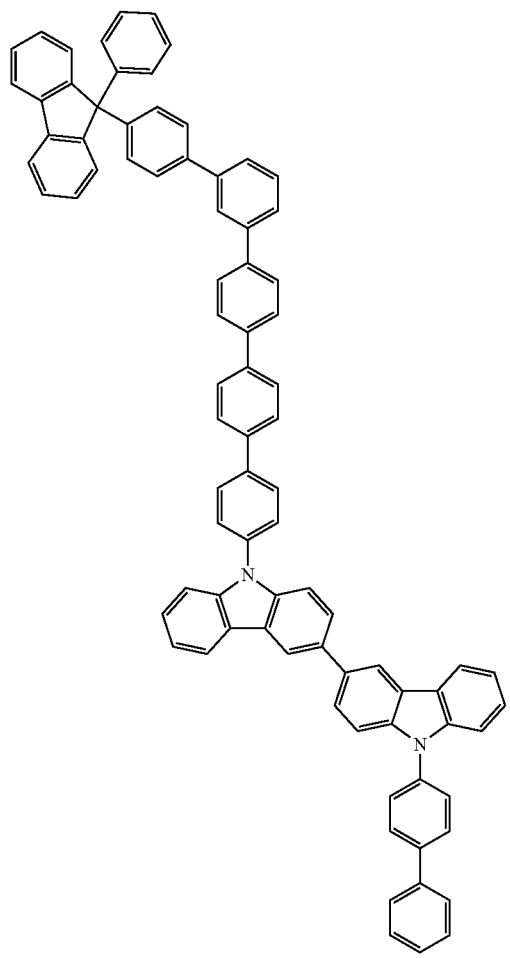
A394 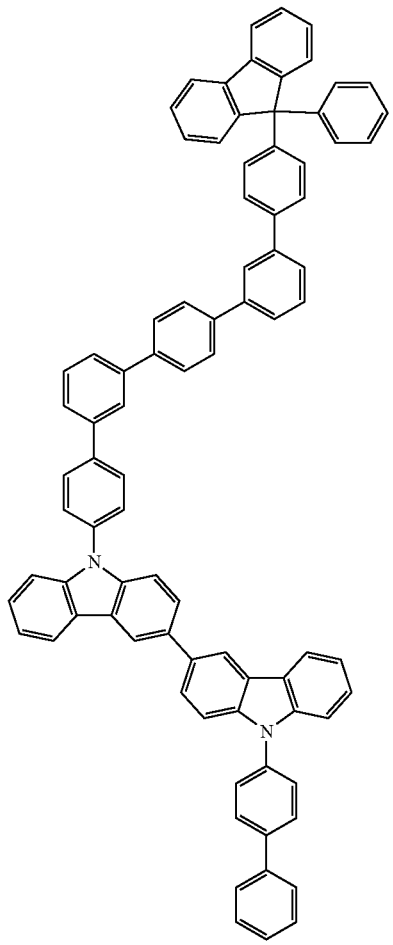

-continued
A395
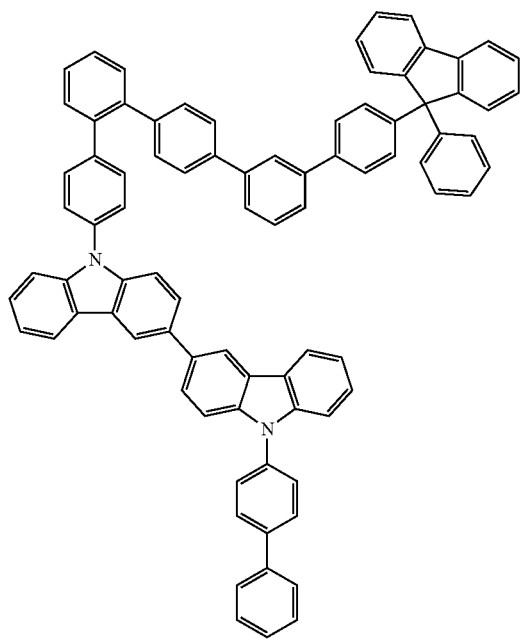
A396
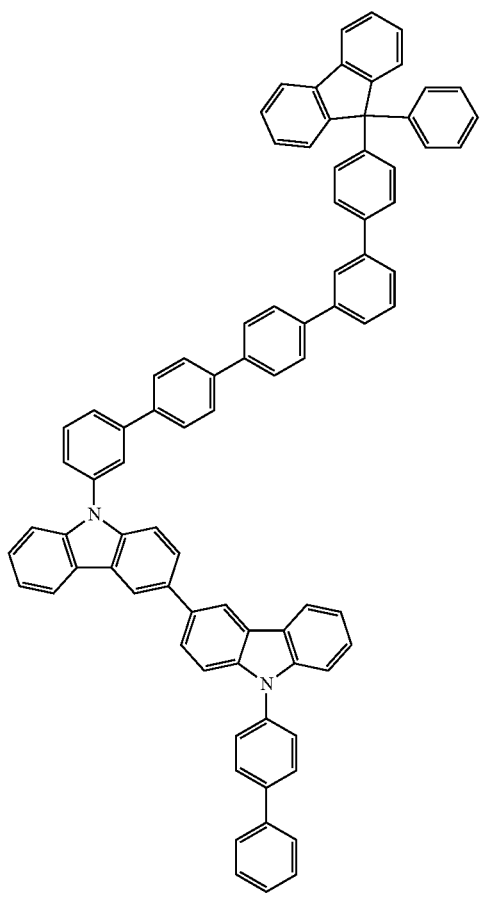
A397
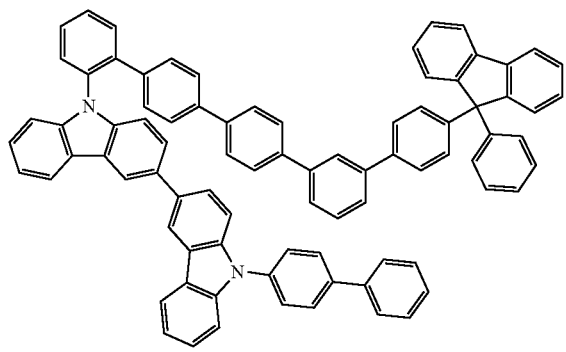
A398
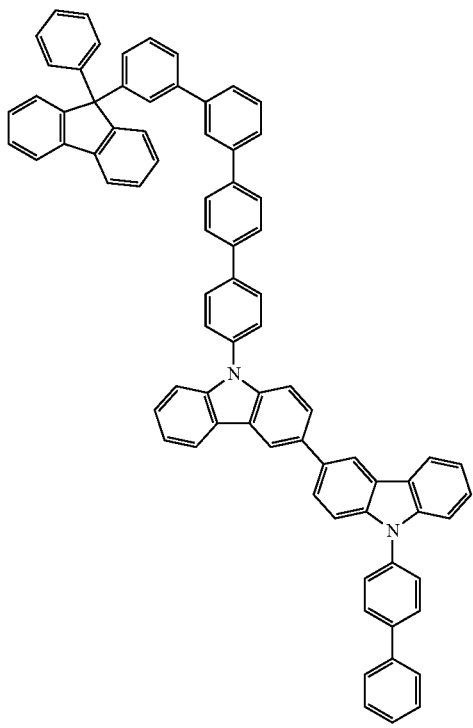

-continued
A399
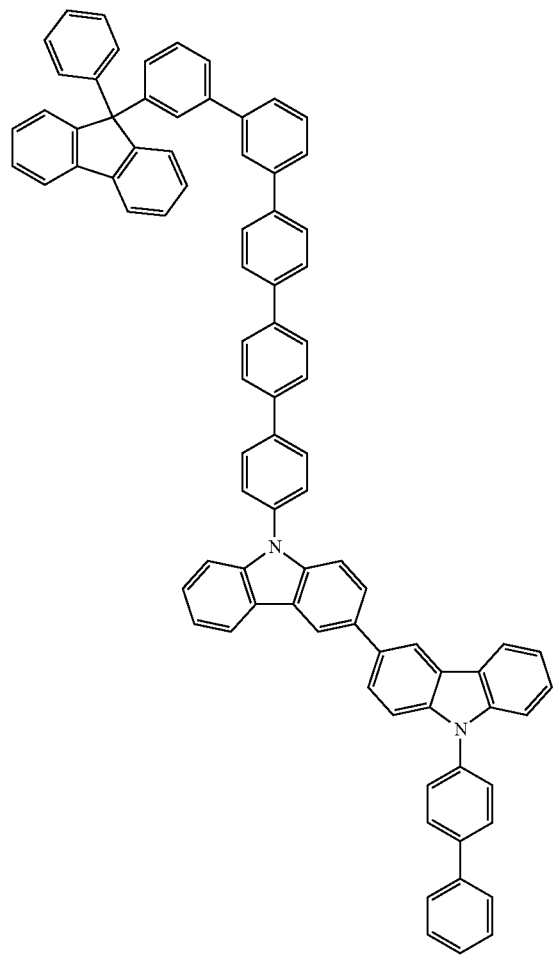
A400
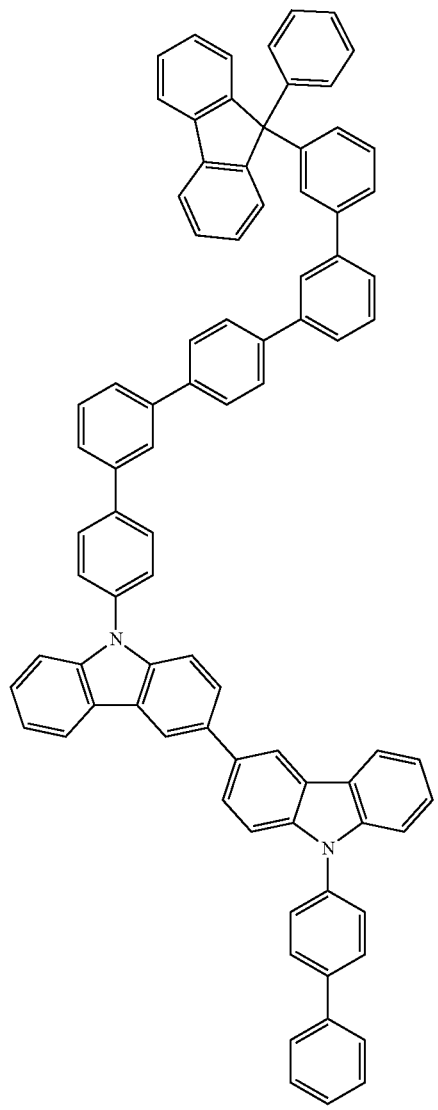

-continued
A401
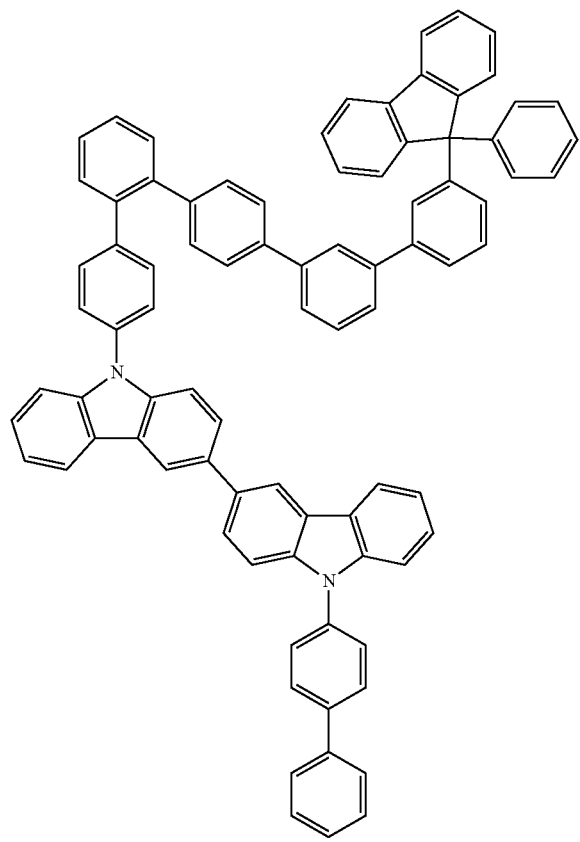
A402
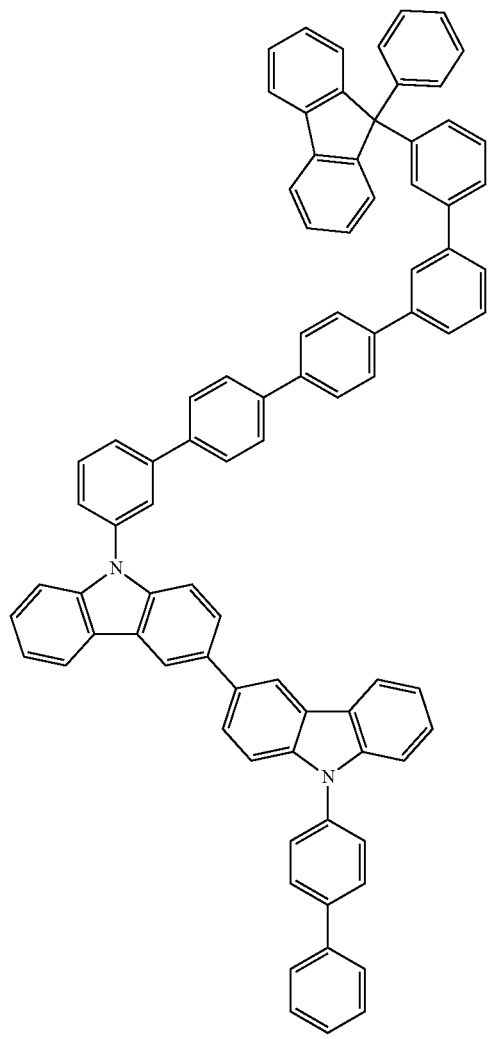

-continued
A403
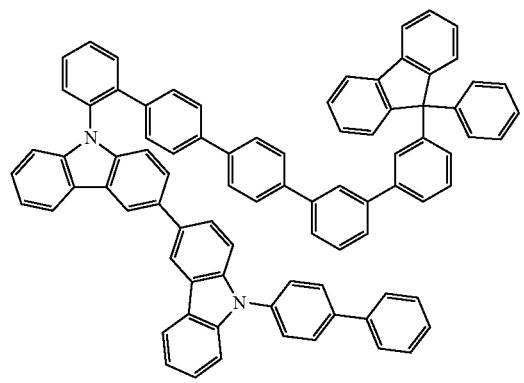
A404
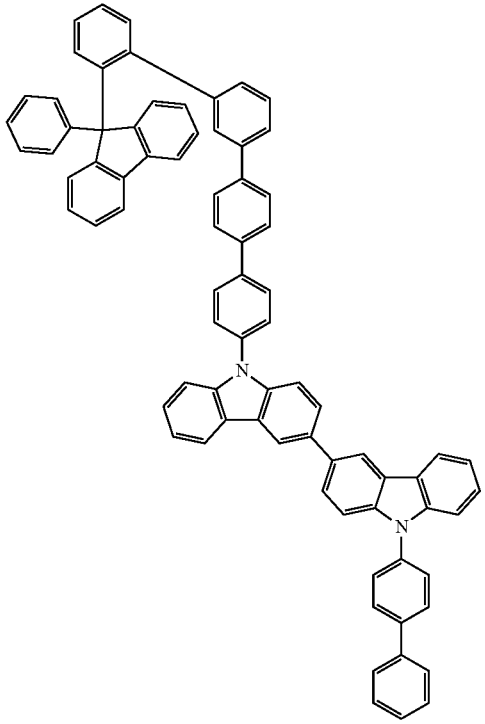

A405
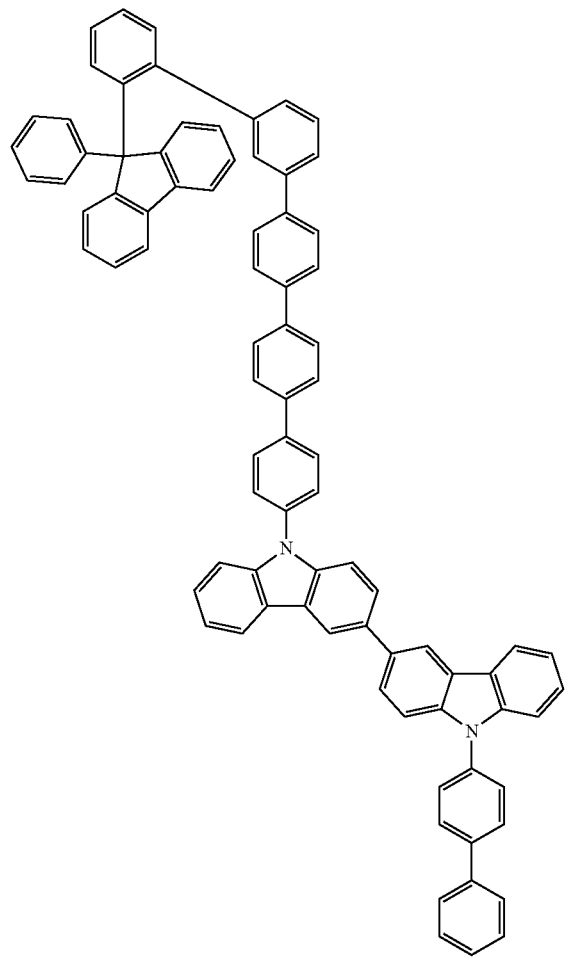
A406
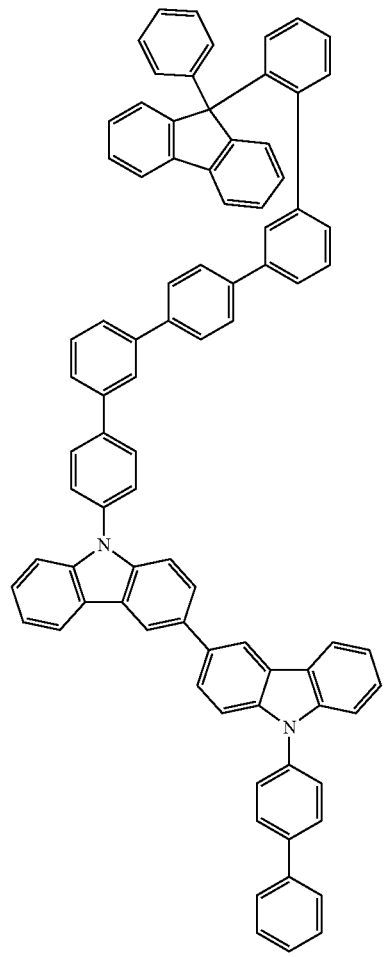

-continued
A407
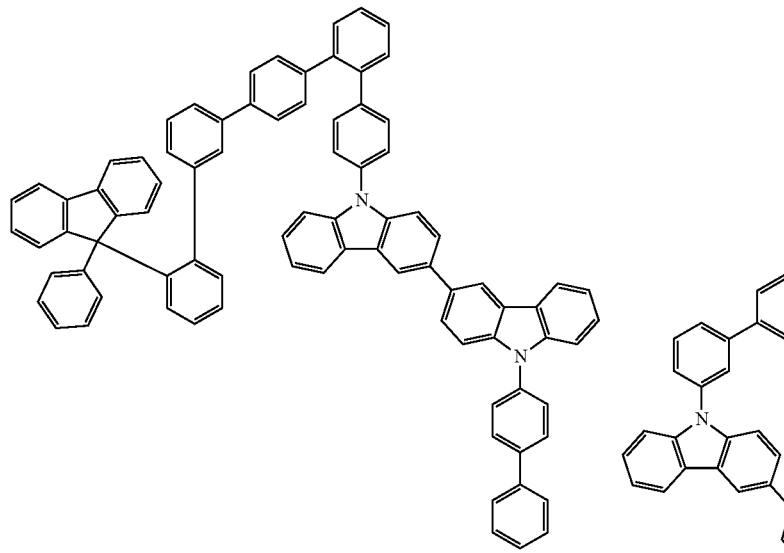
A408
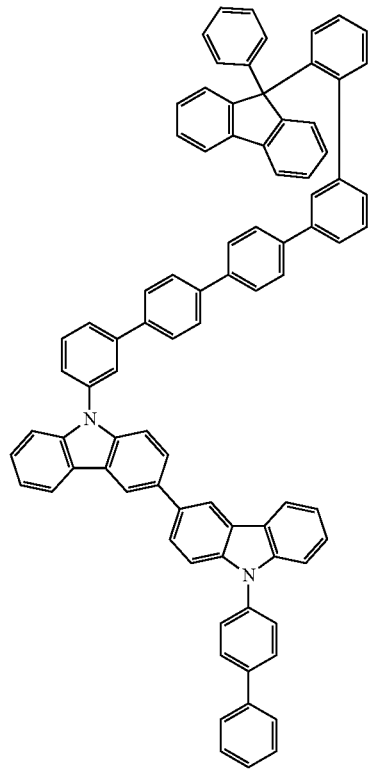
A409
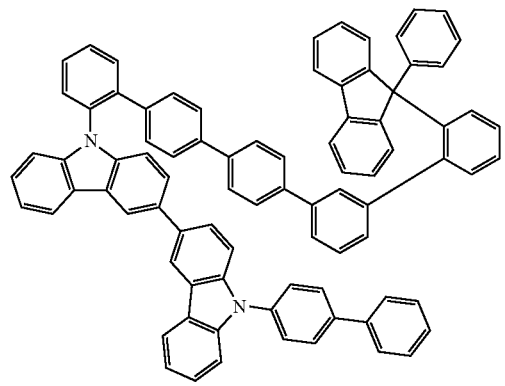
A410
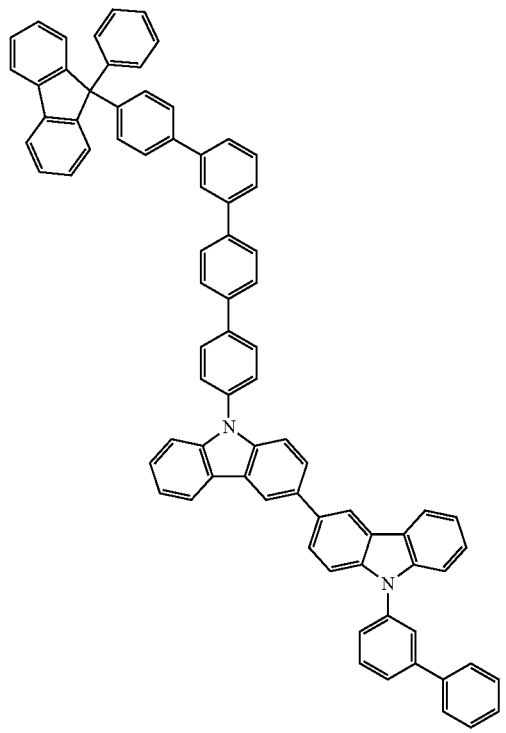

-continued
A411
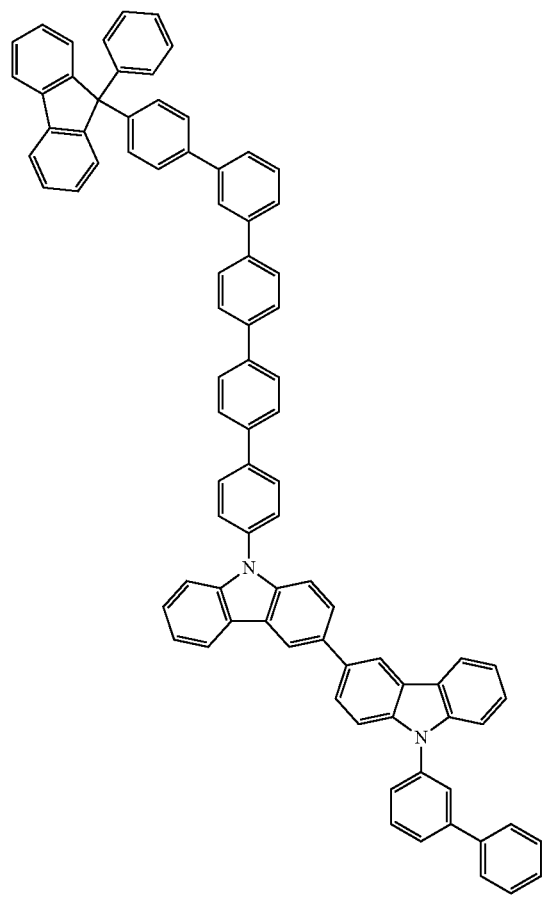
A412
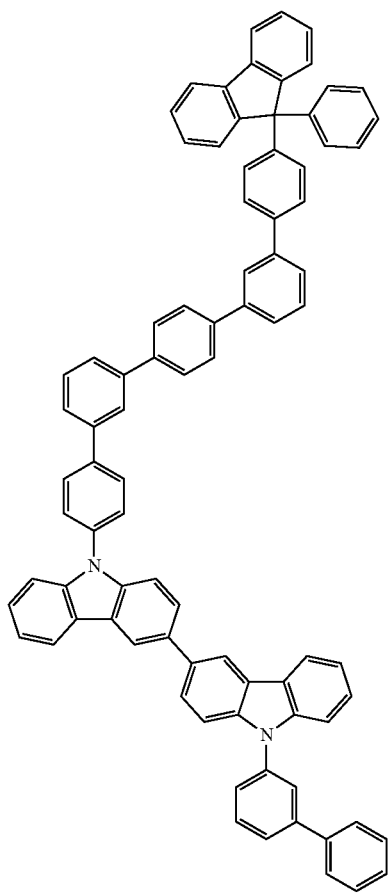
A413
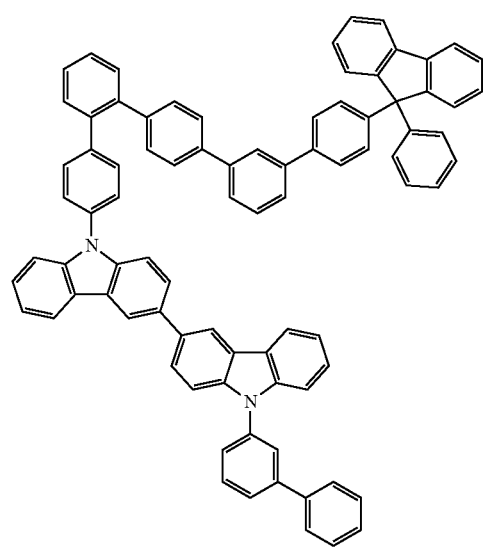
A414
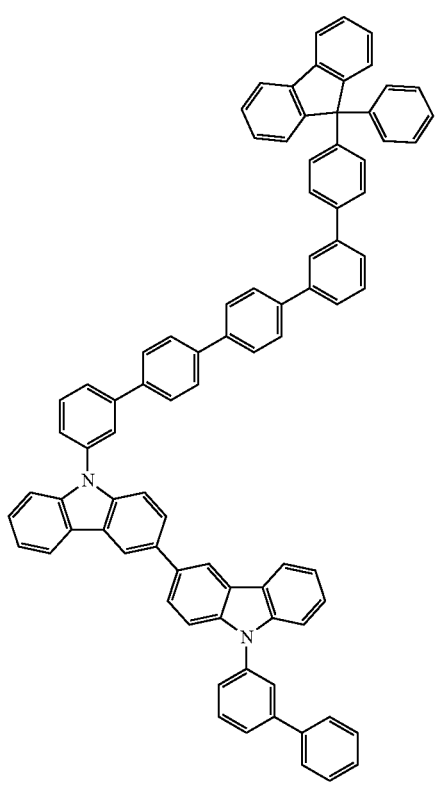

-continued
A415
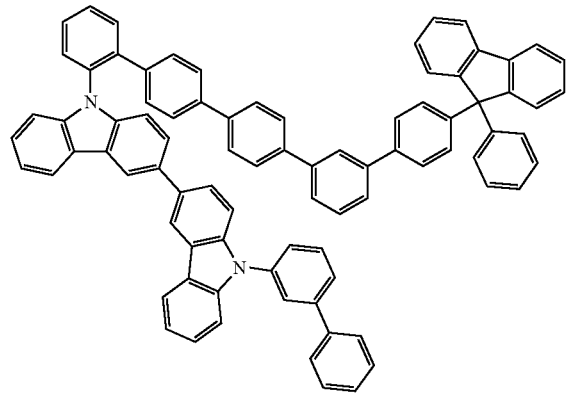
A416
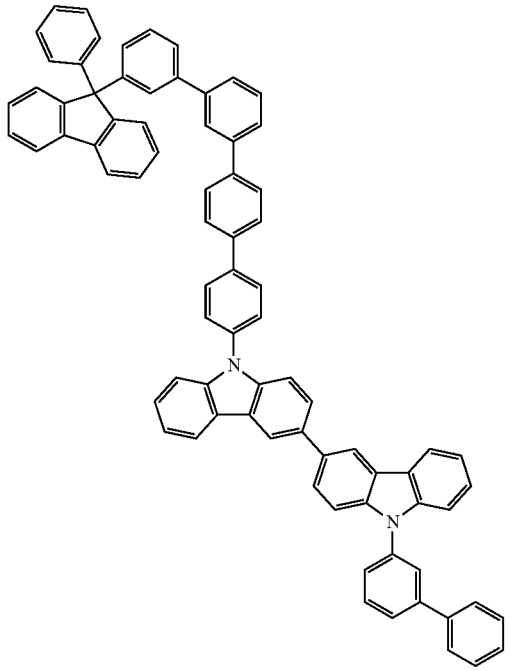
A417
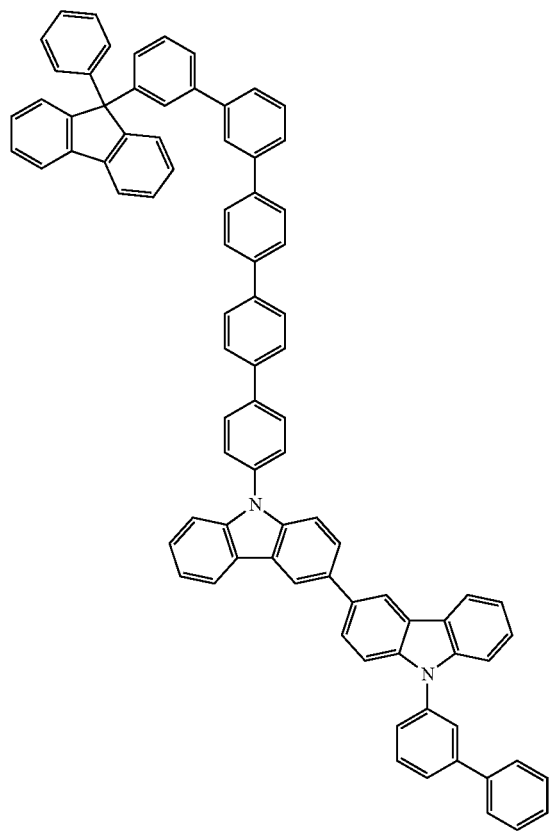
A418
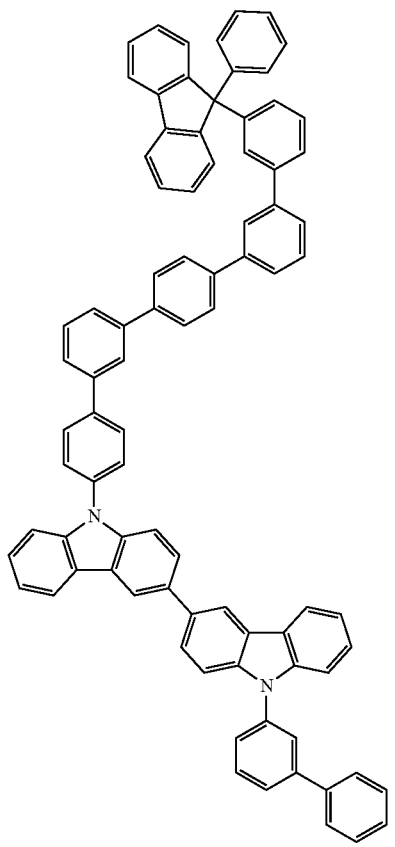

-continued
A419
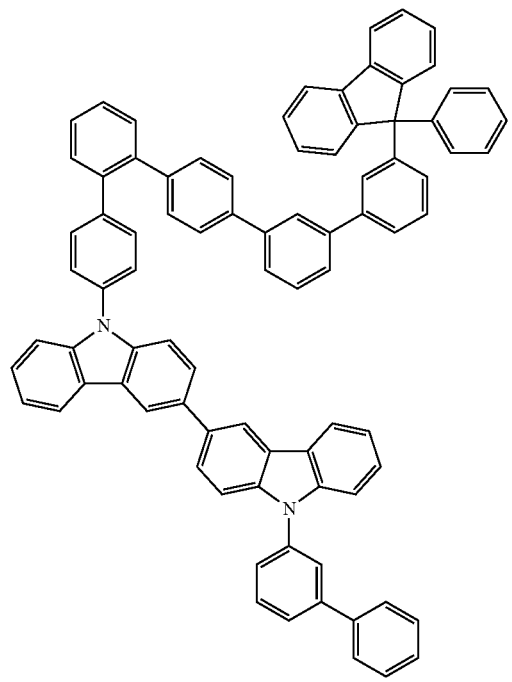
A420
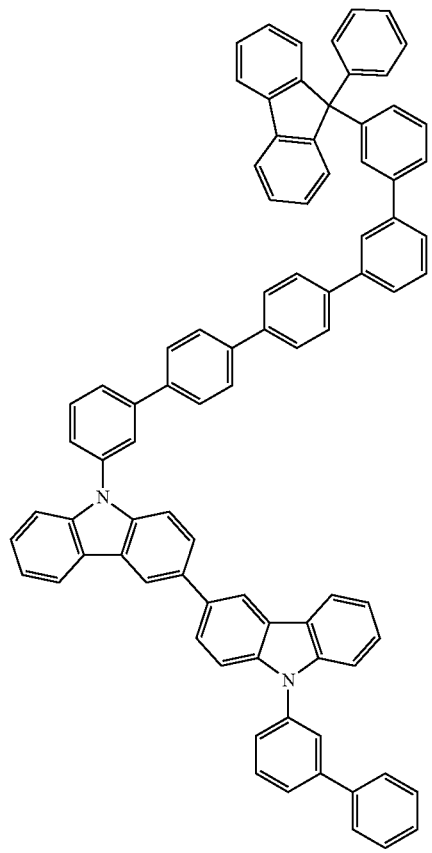
A421
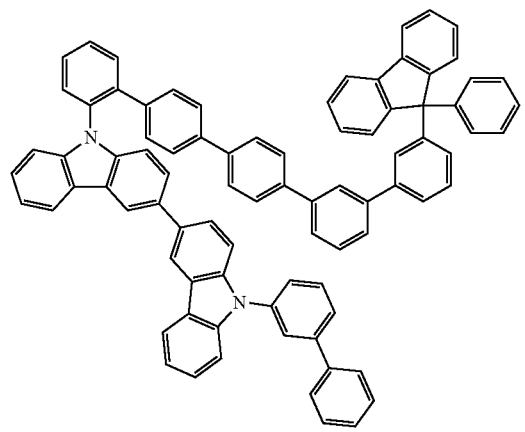
A422
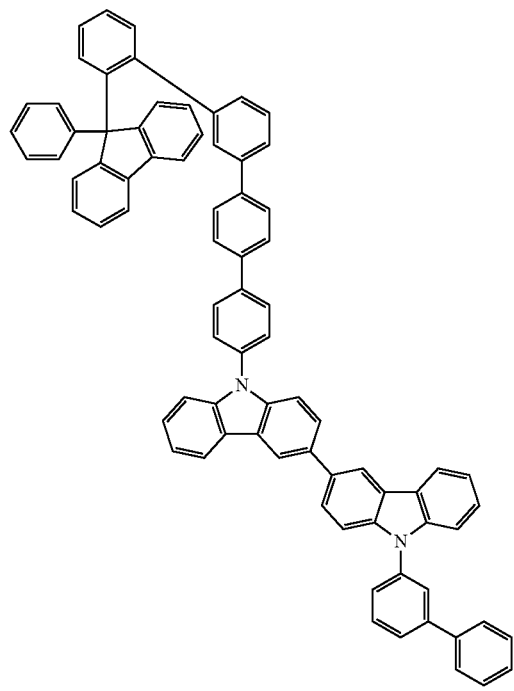

-continued
A423
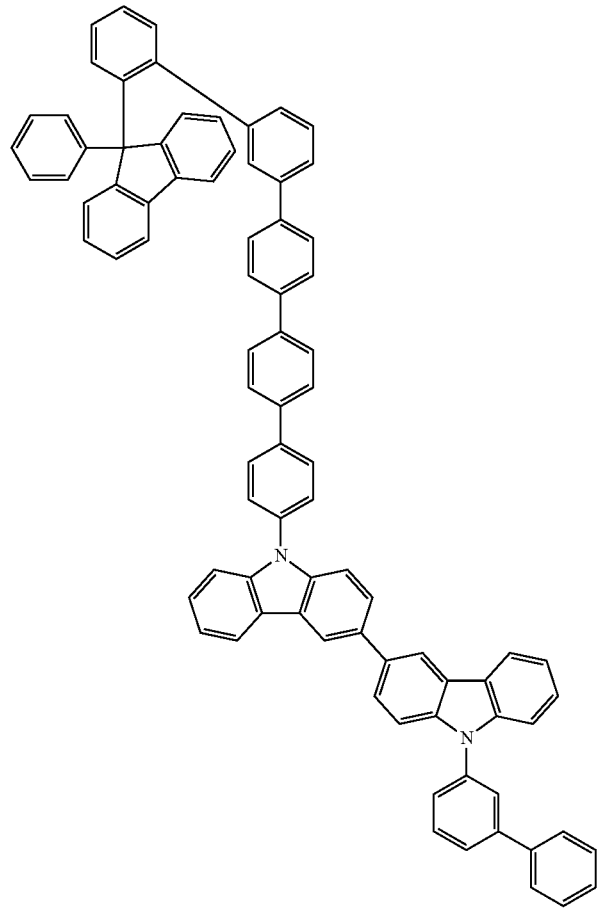
A424
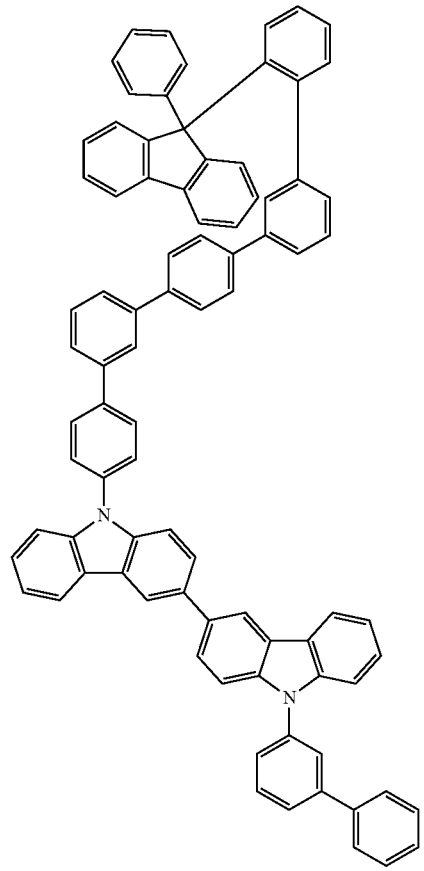
A425
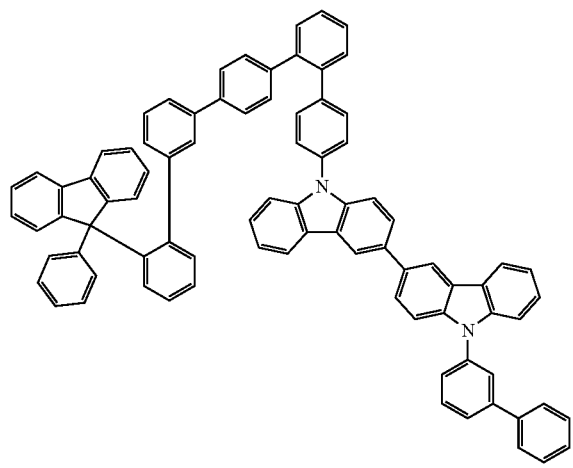
A426
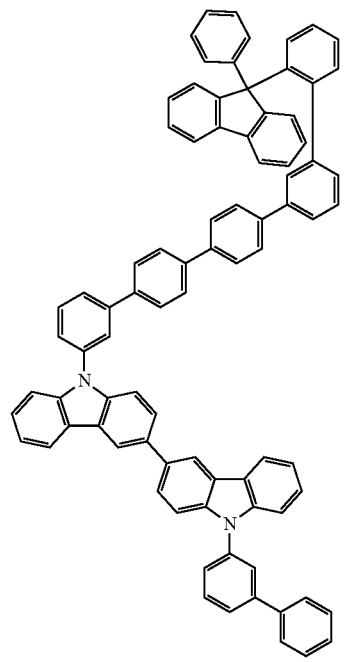

-continued
A427
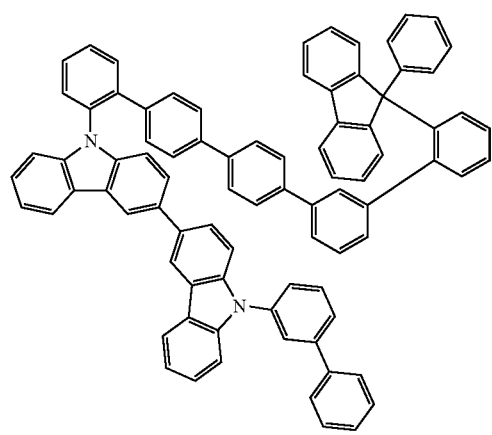
A428
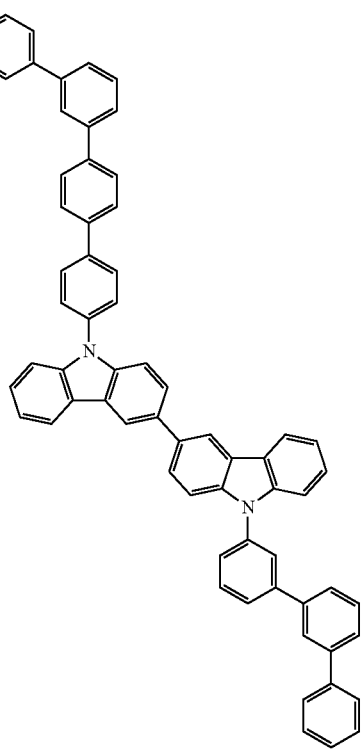
A429
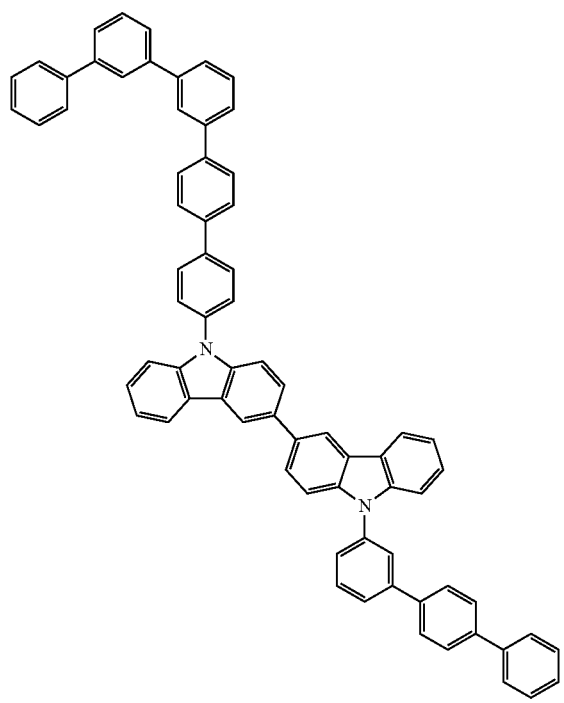
A430
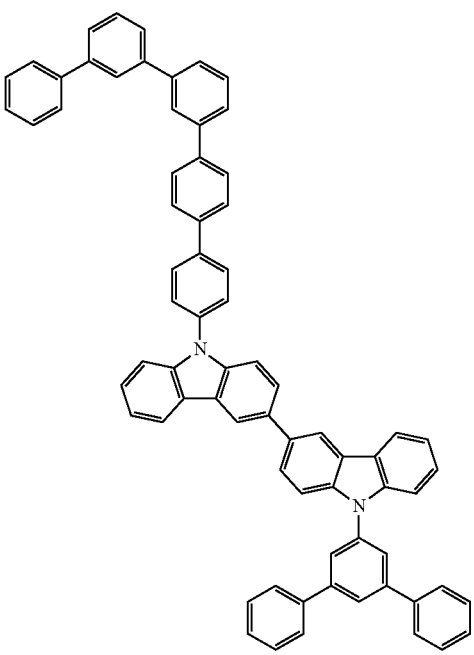

-continued
A431
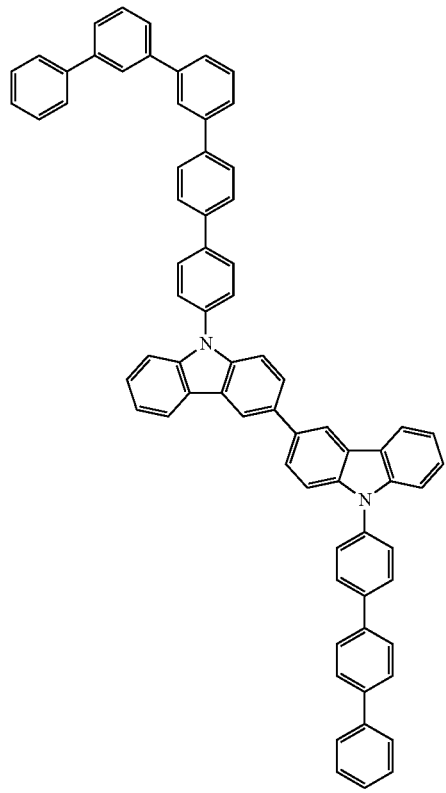
A432
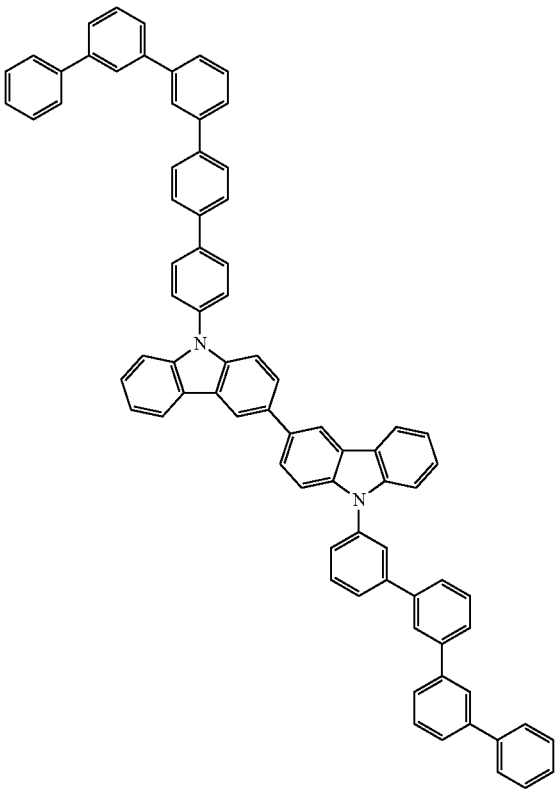
A433
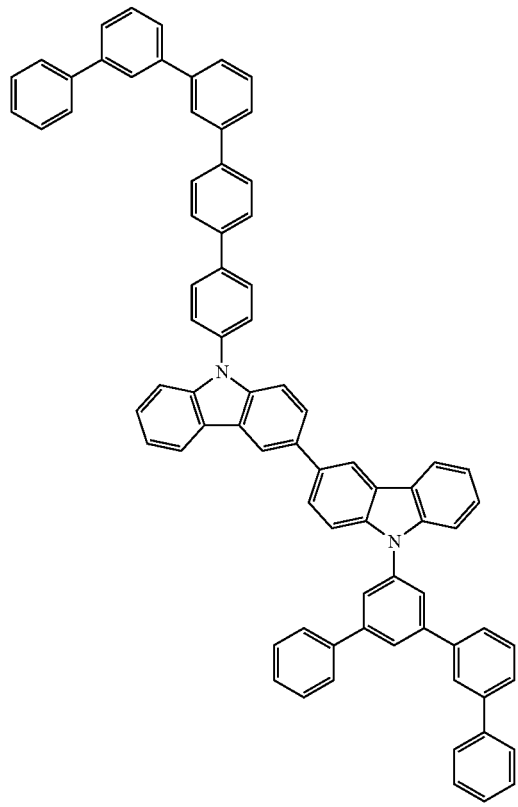
A434
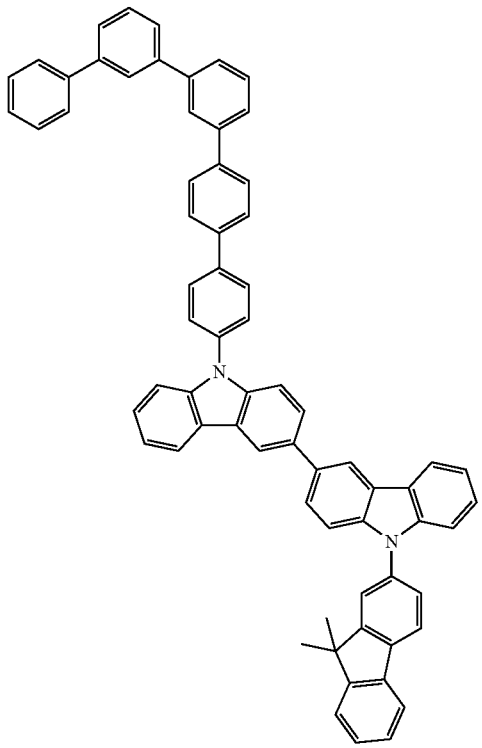

-continued
273
A435
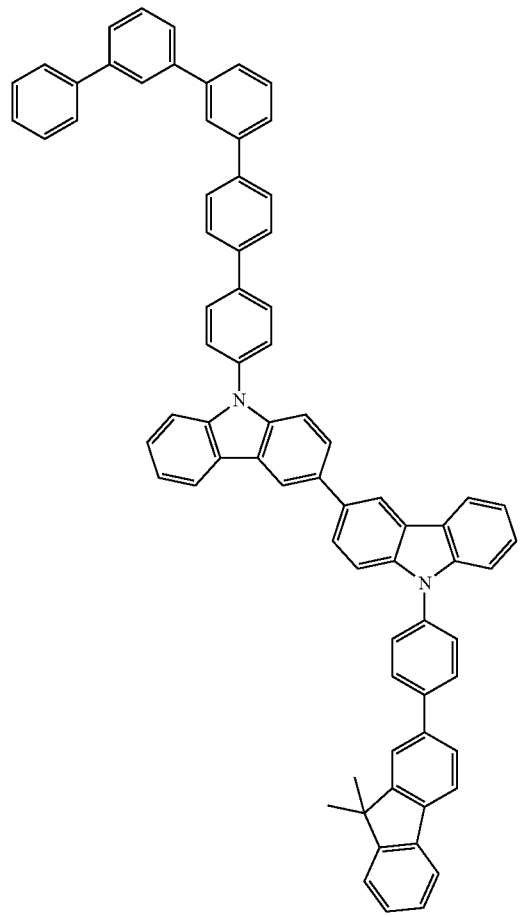
274
A436
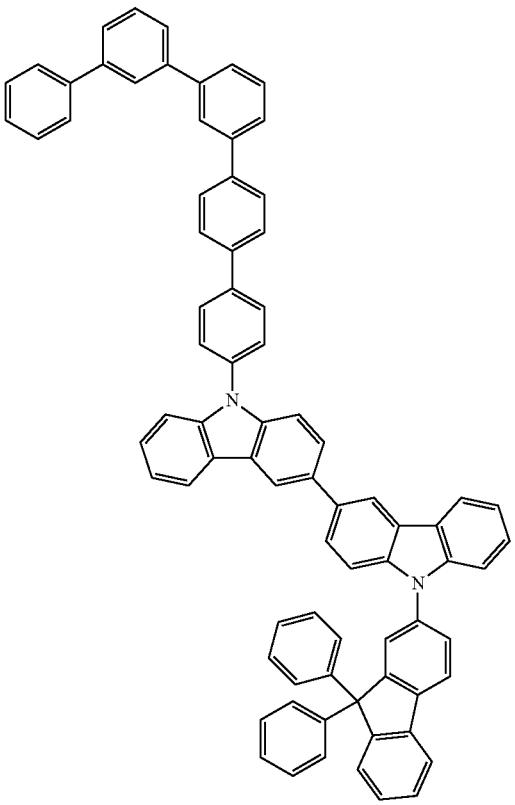

-continued
A437
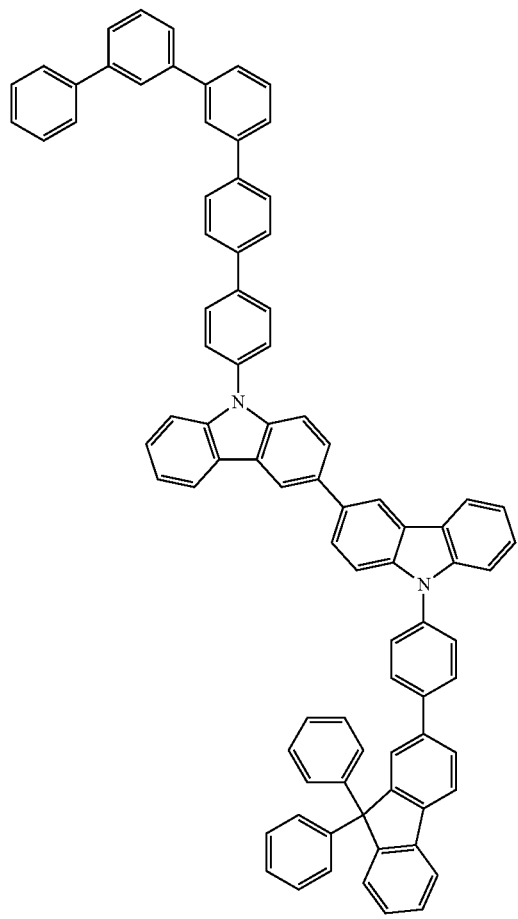
A438
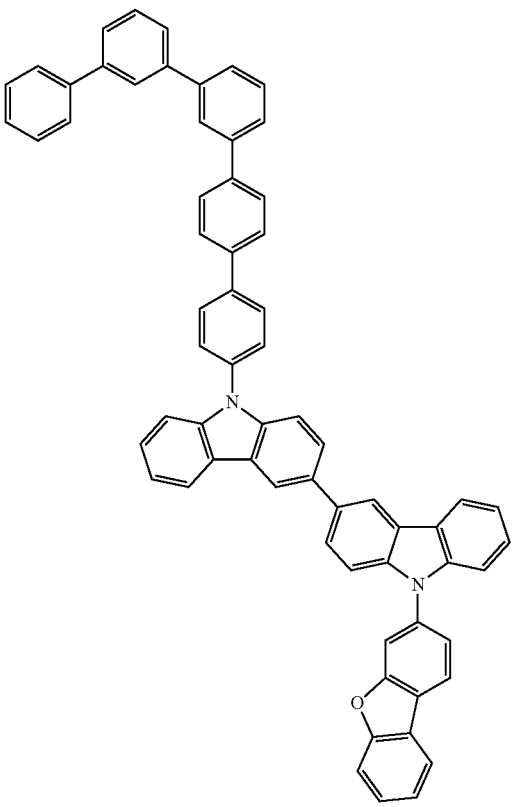

-continued
A439
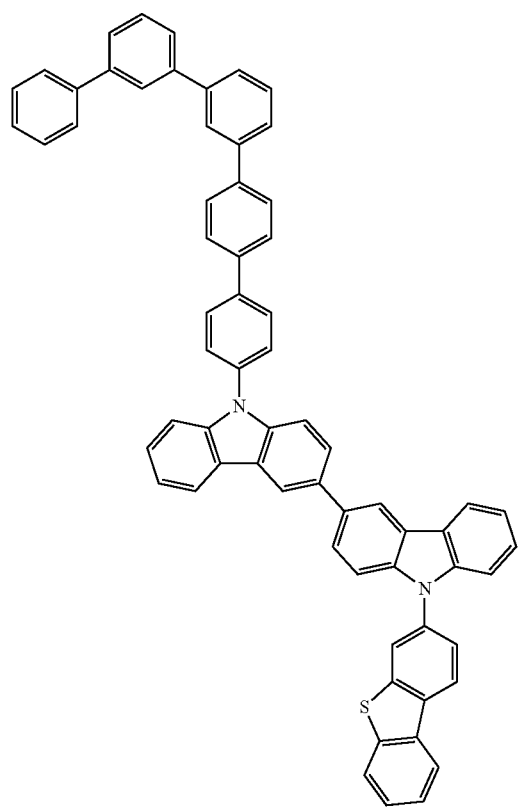
A440
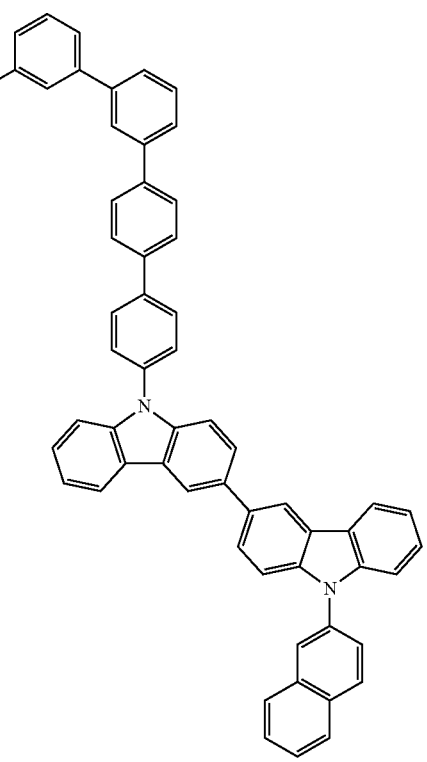
A441
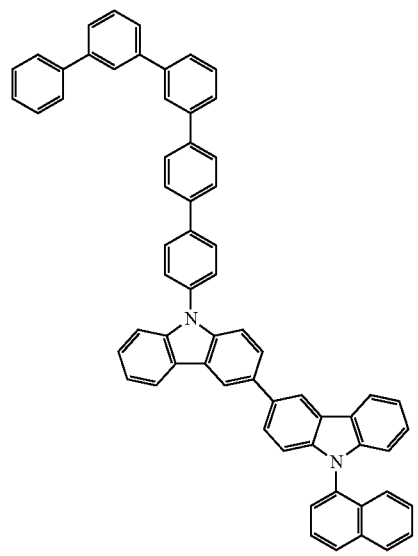
A442
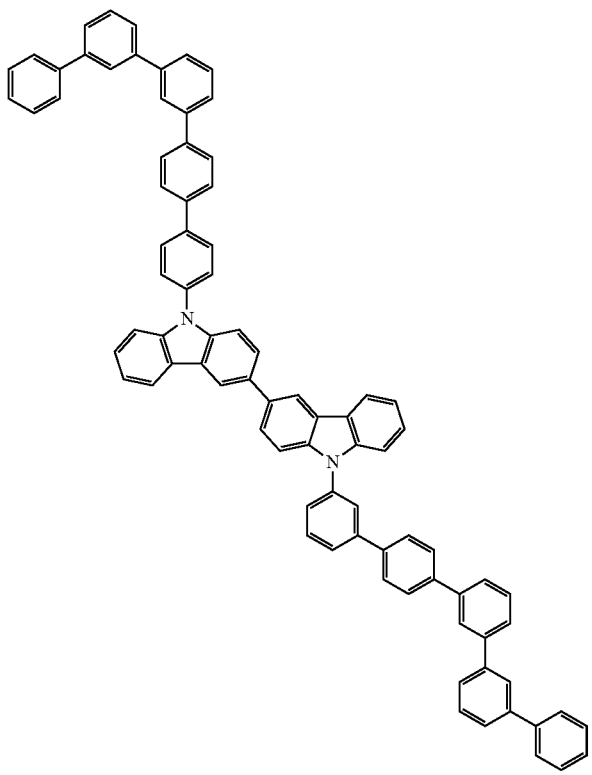

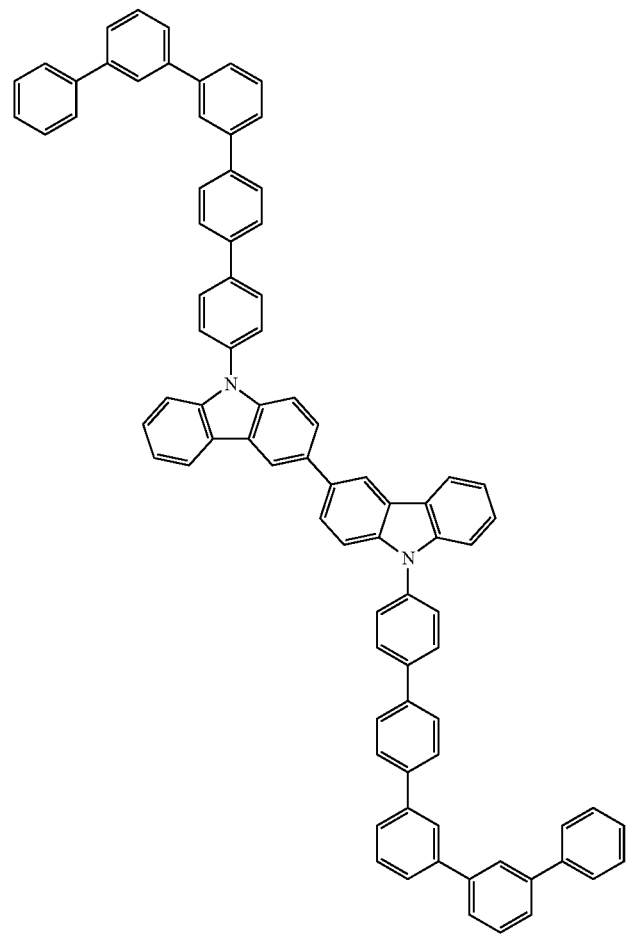
A443

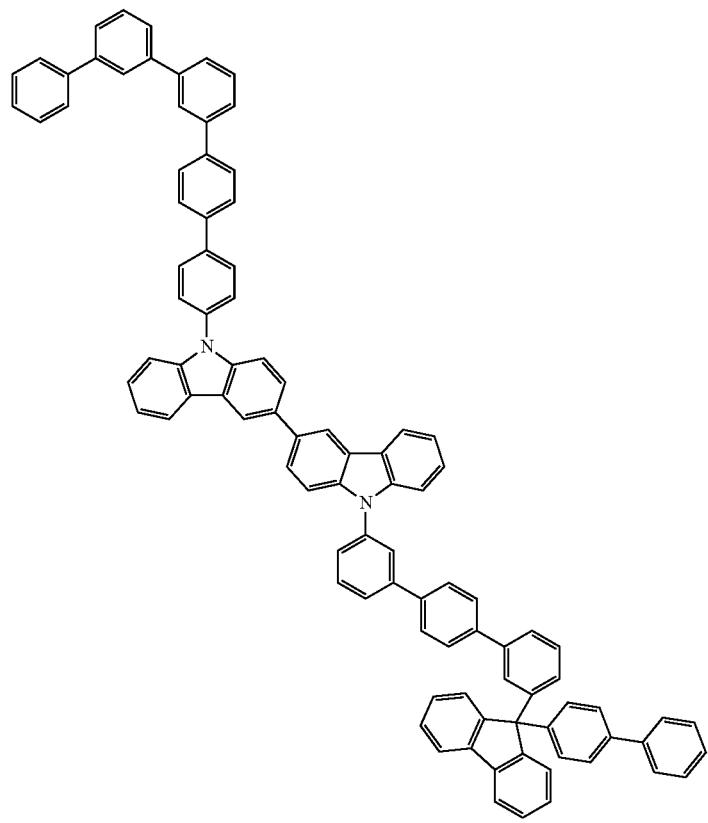
A444

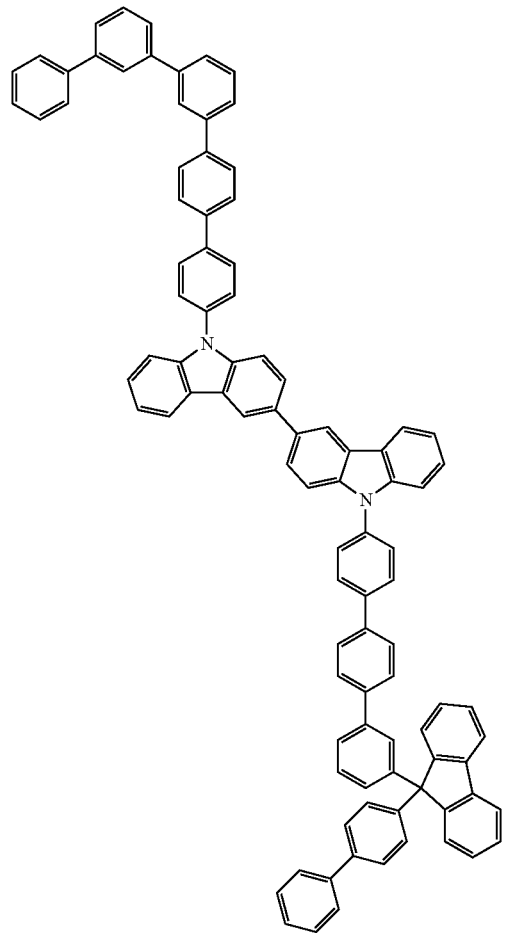
A445
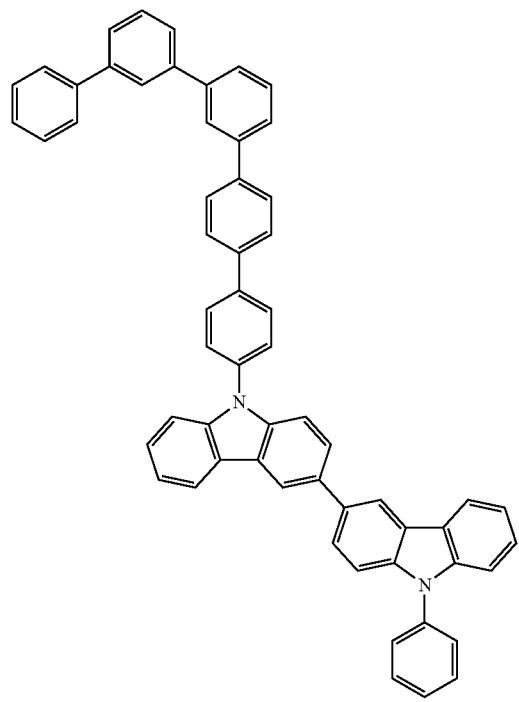
A446
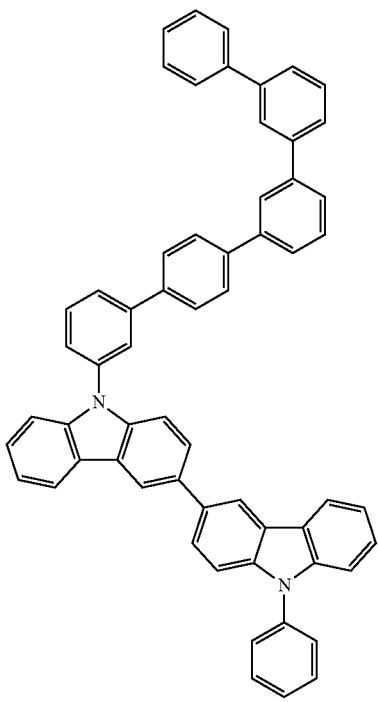
A447

-continued
A448
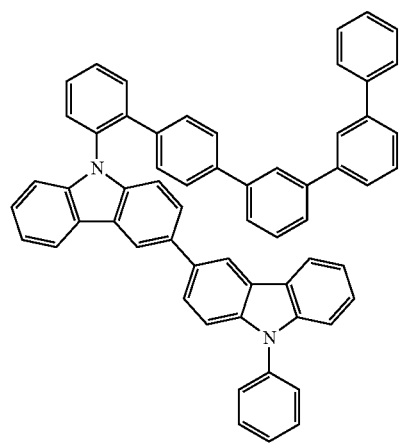
A449
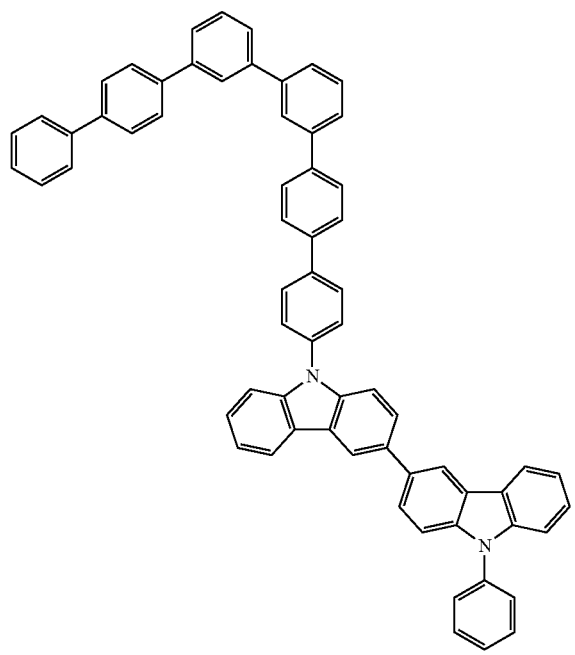
A450
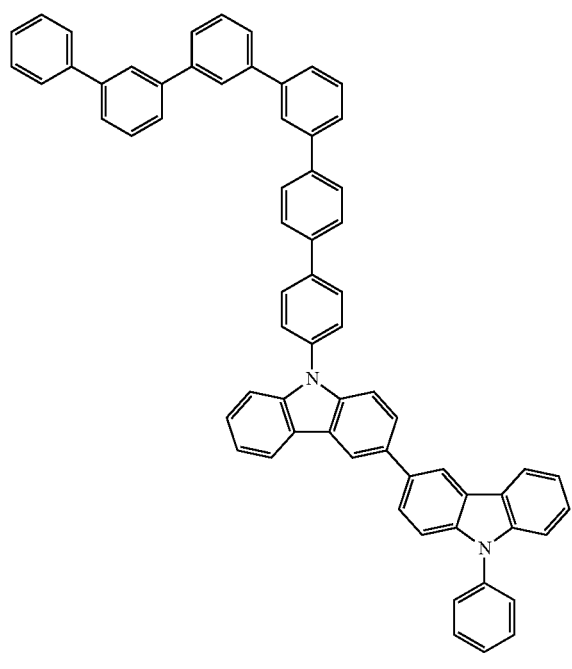
A451
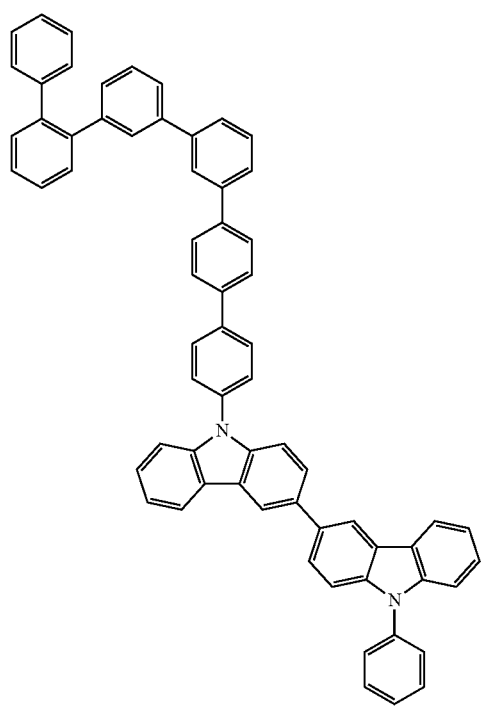

-continued
A452
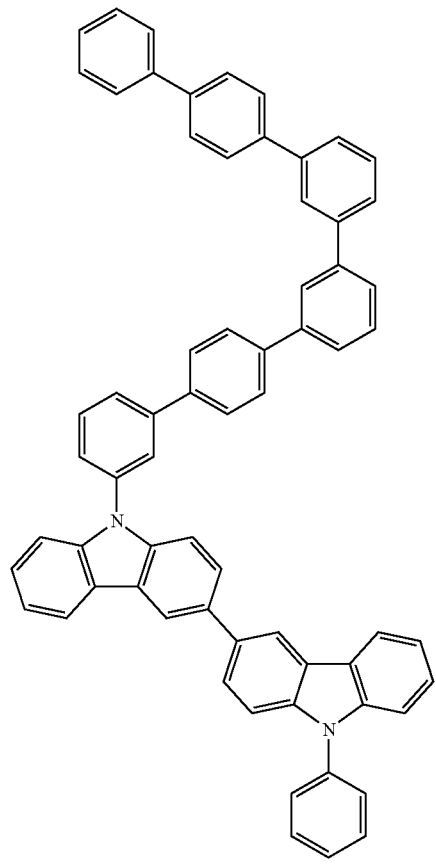
A453
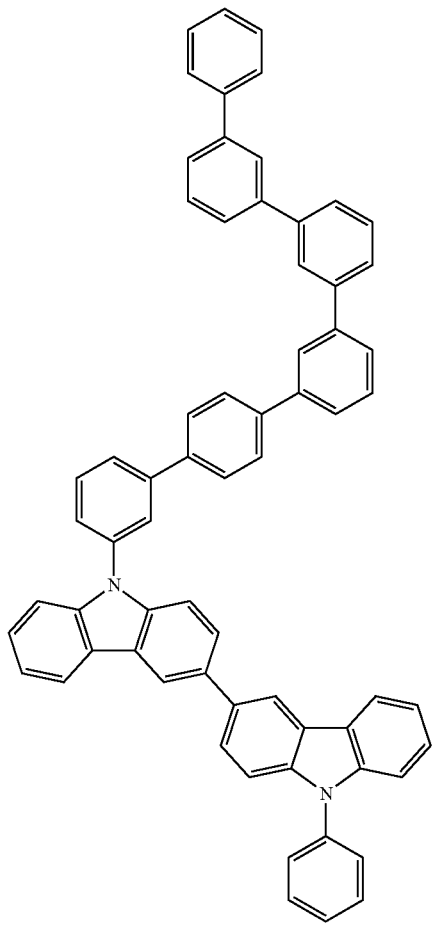

-continued
289  A454
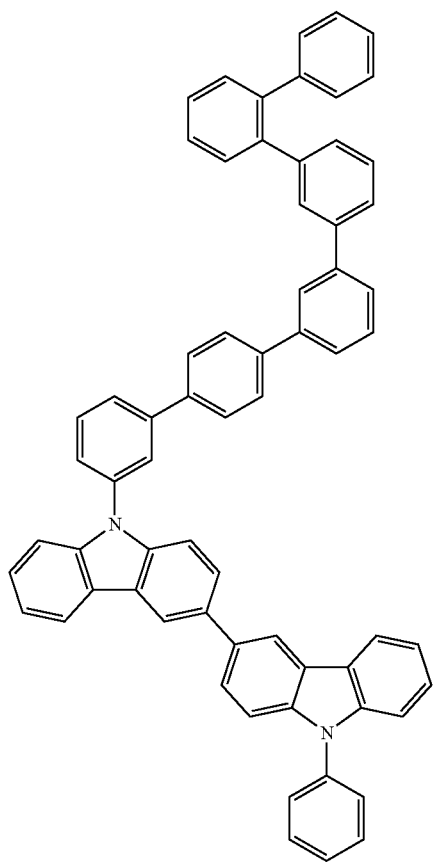
290  A455
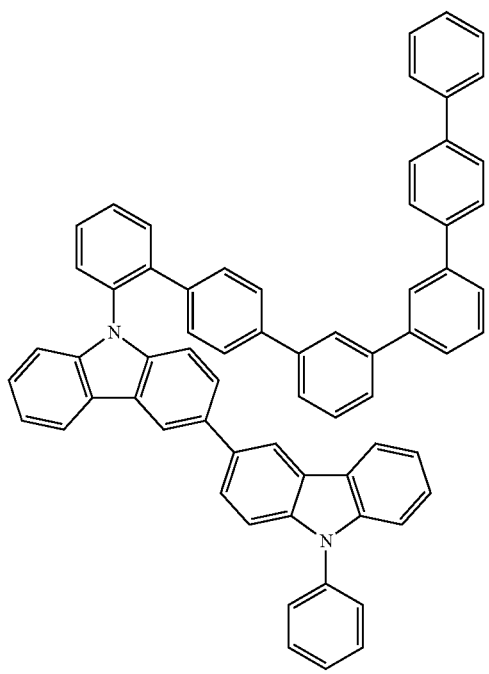
A456
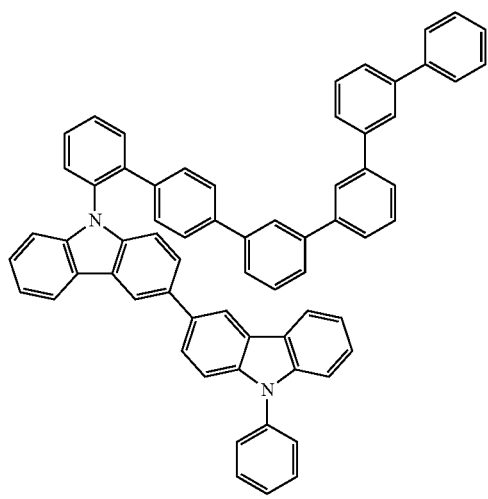
A457
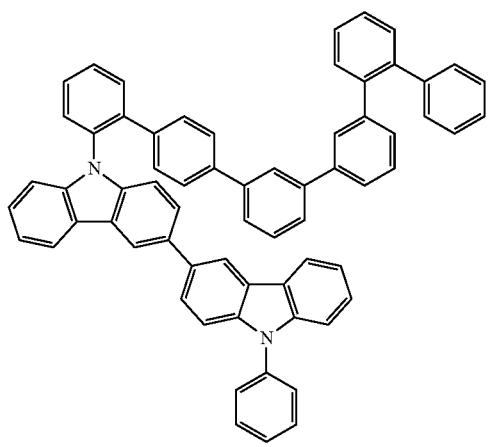

-continued
A458
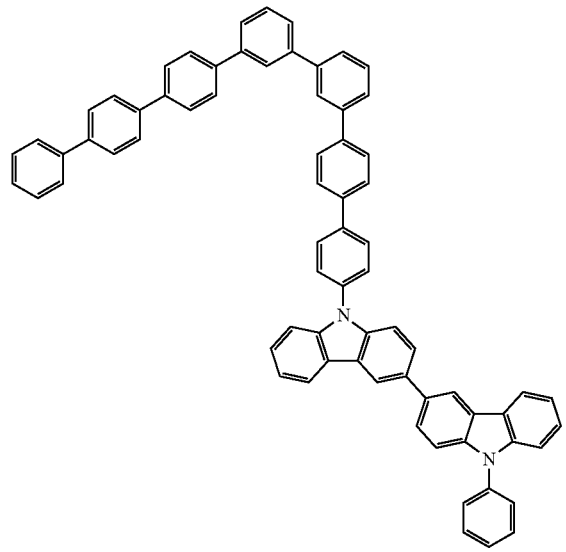
A459
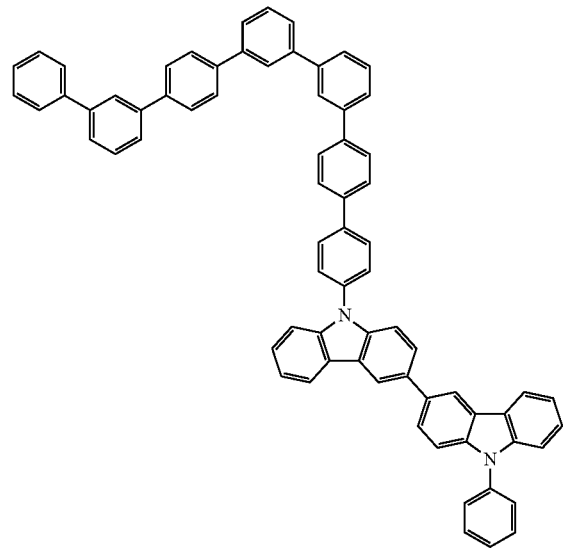
A460
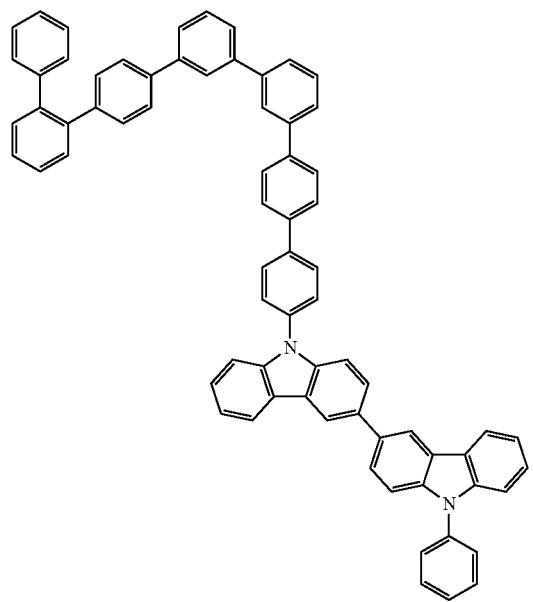
A461
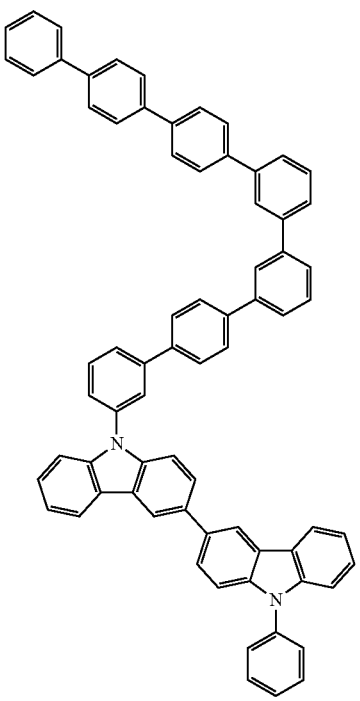

-continued
A462
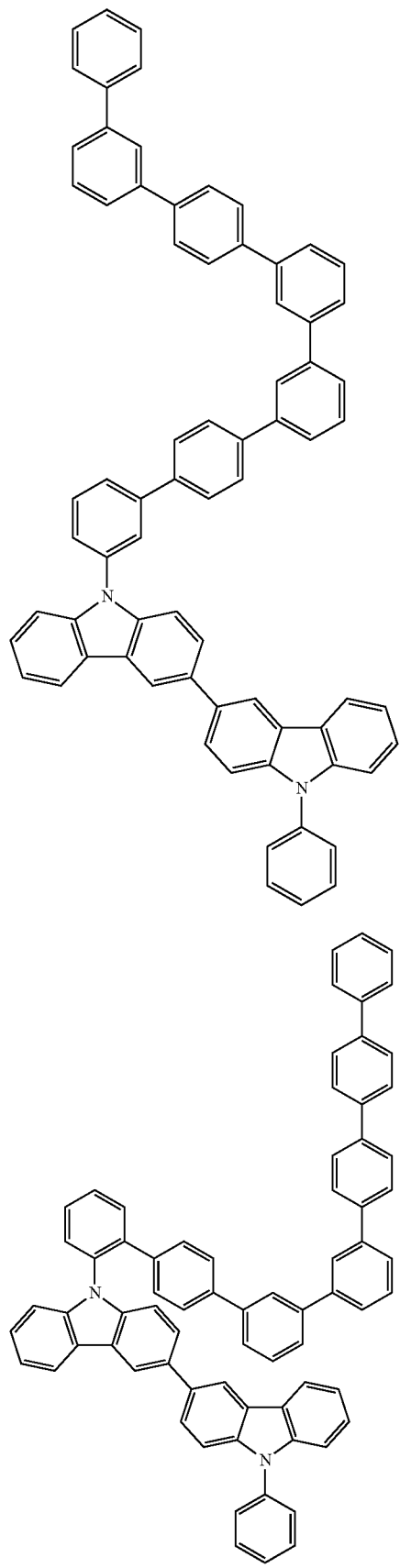
A463
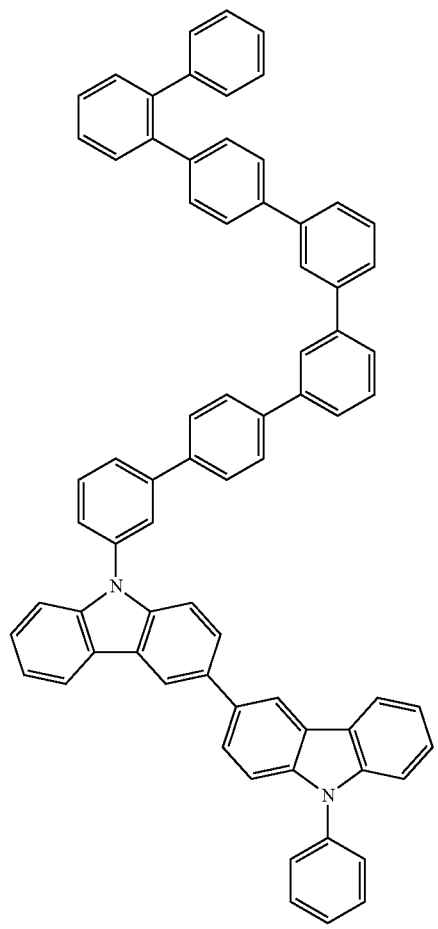
A464
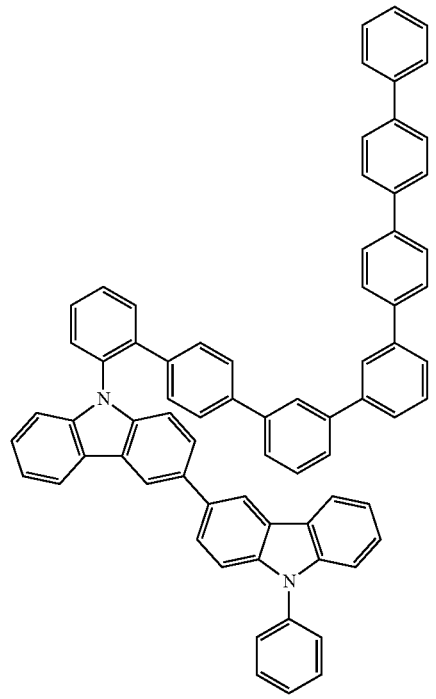
A465
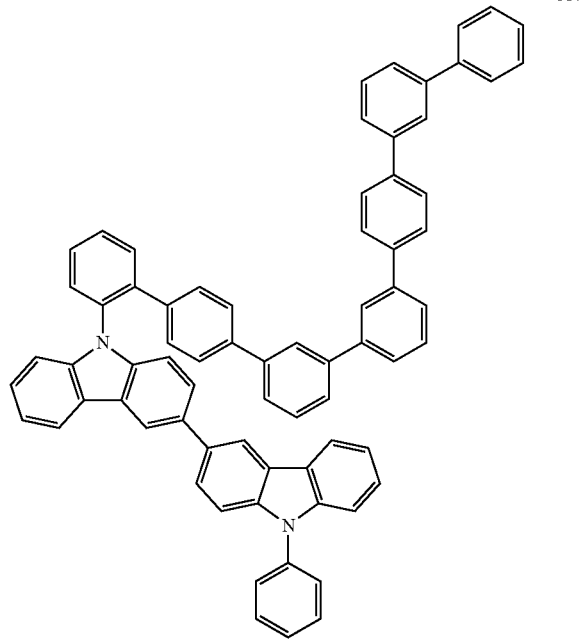

-continued
A466
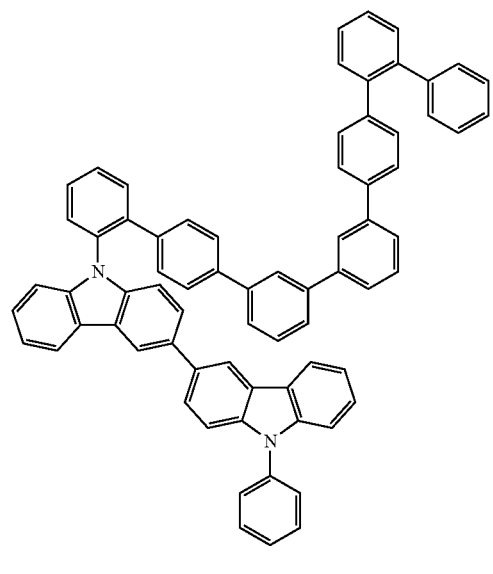
A467
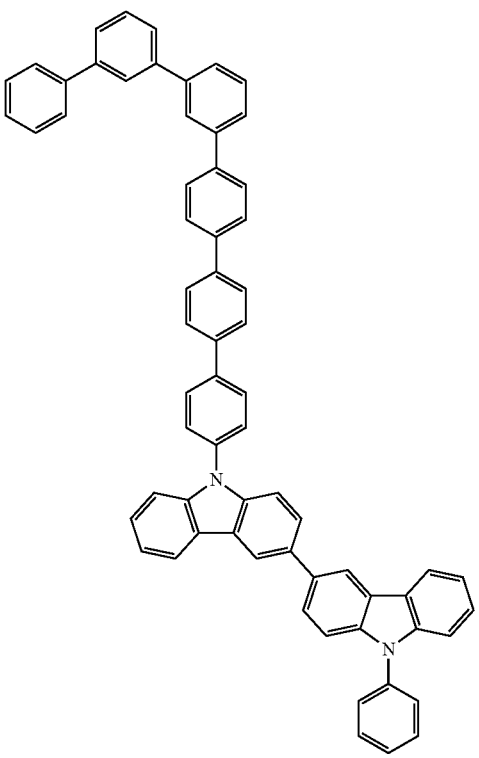
A468
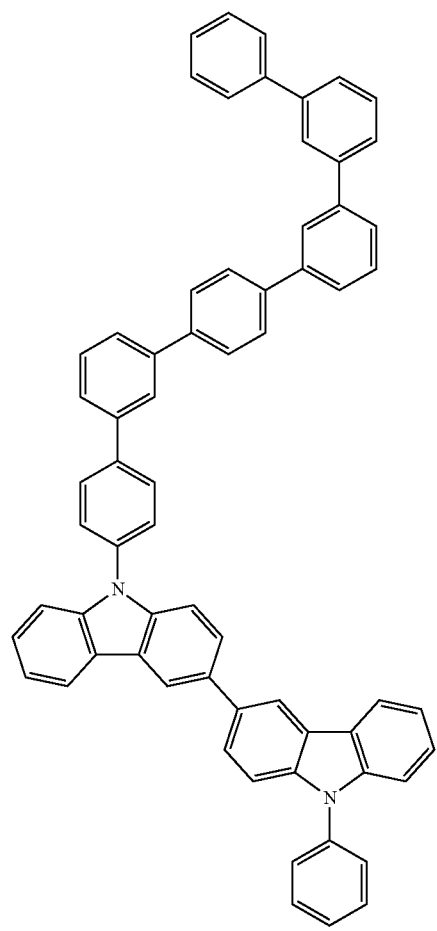
A469
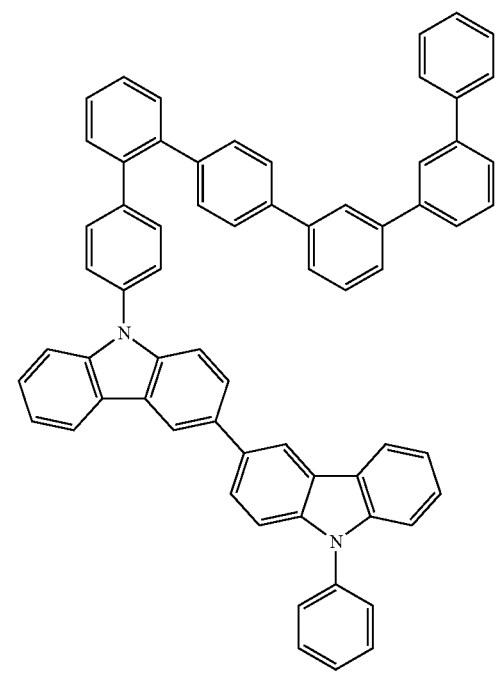

297    298
-continued
A470
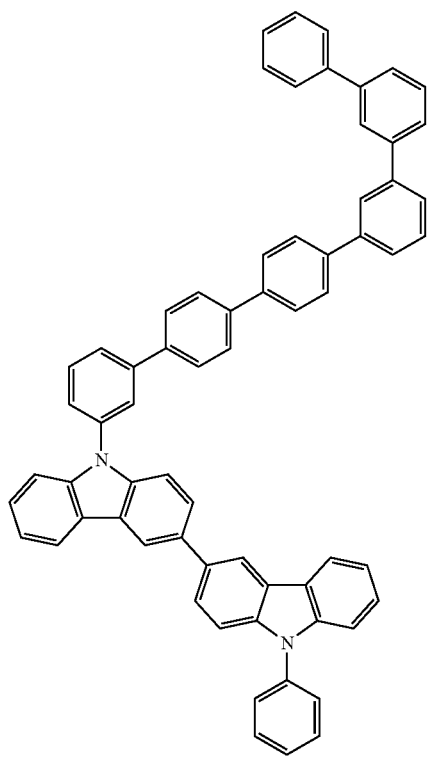
A471
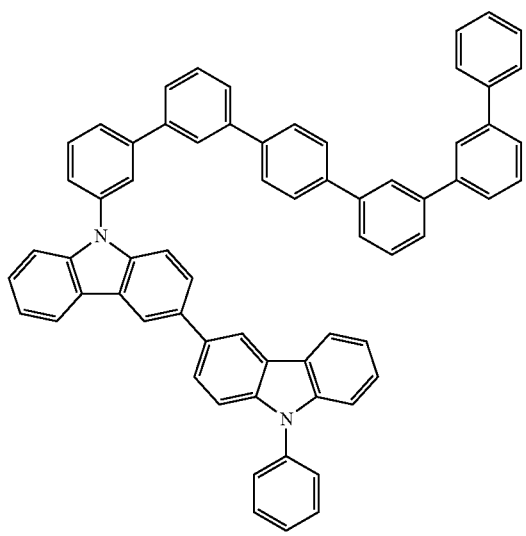
A472
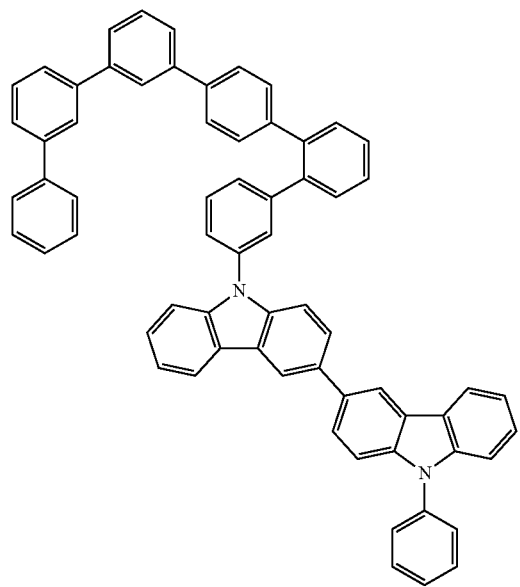
A473
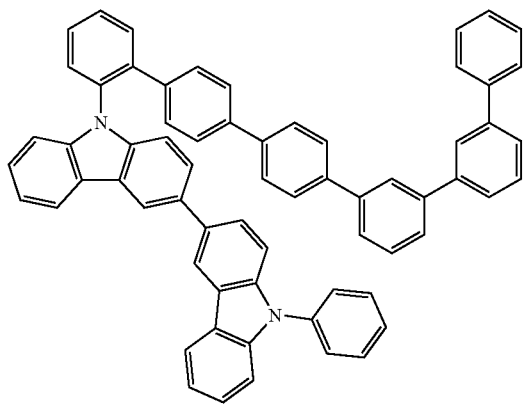

-continued
A474
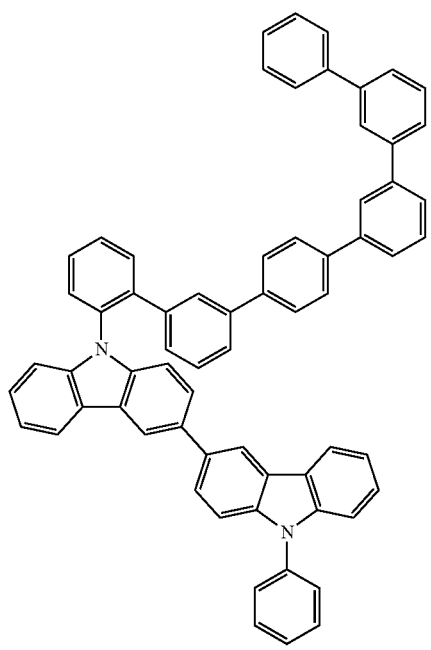
A475
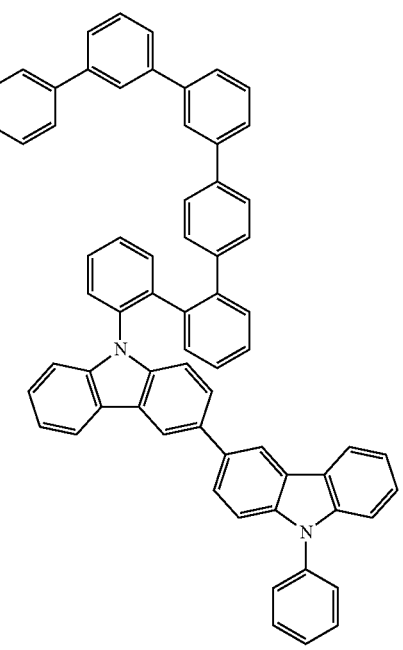
A476
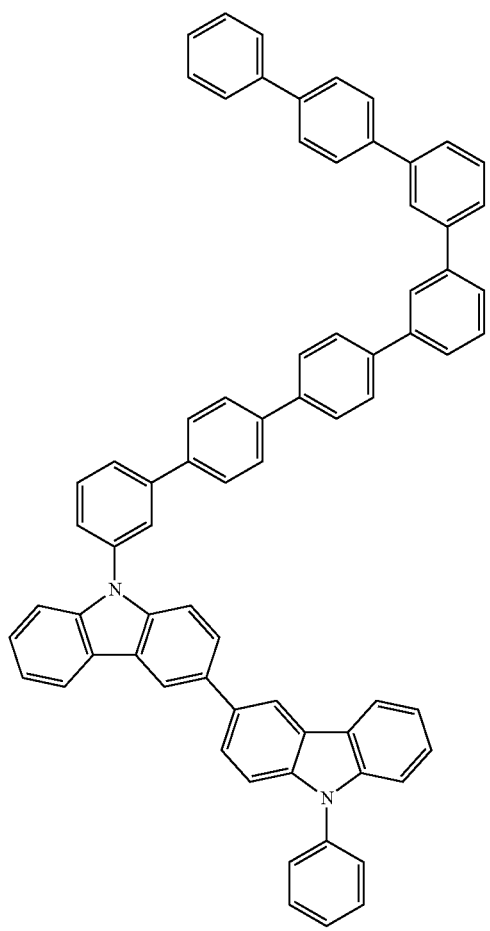
A477
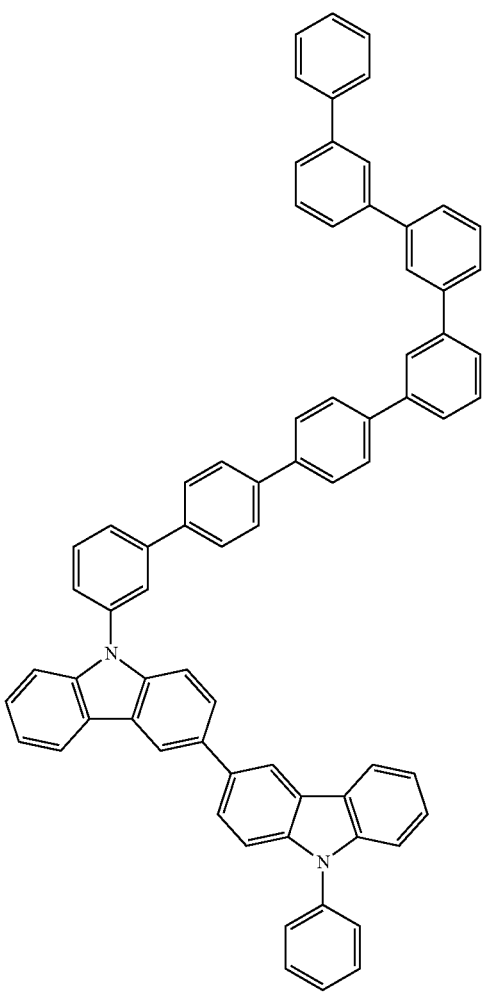

-continued
A478
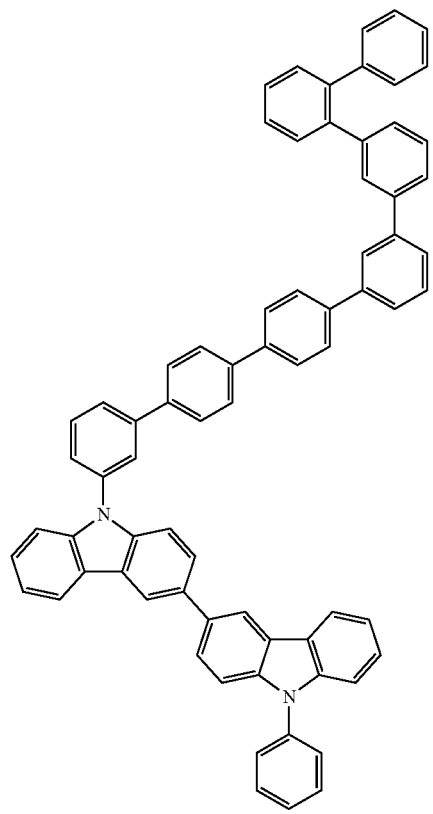
A479
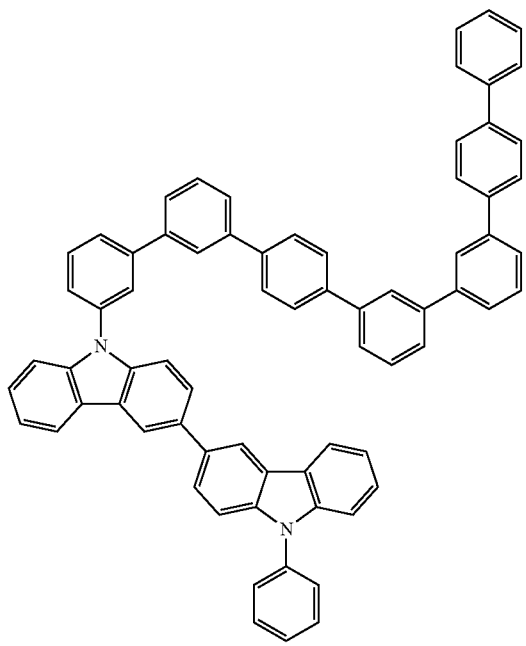
A480
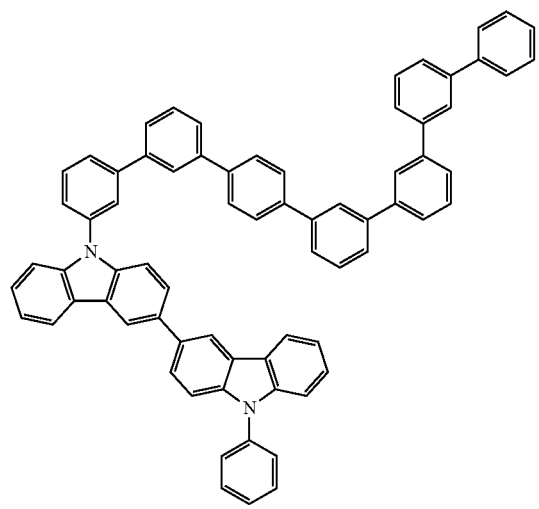
A481
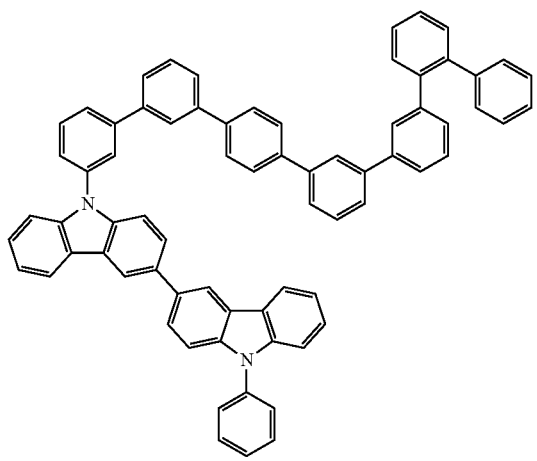

-continued
303 A482
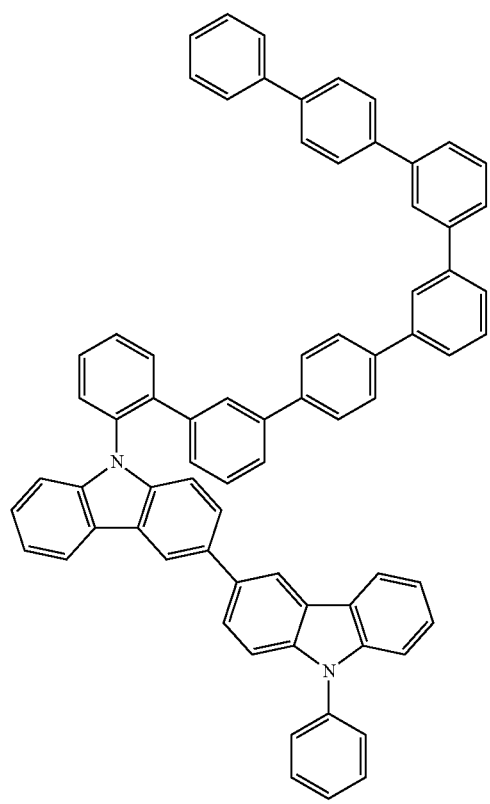
304 A483
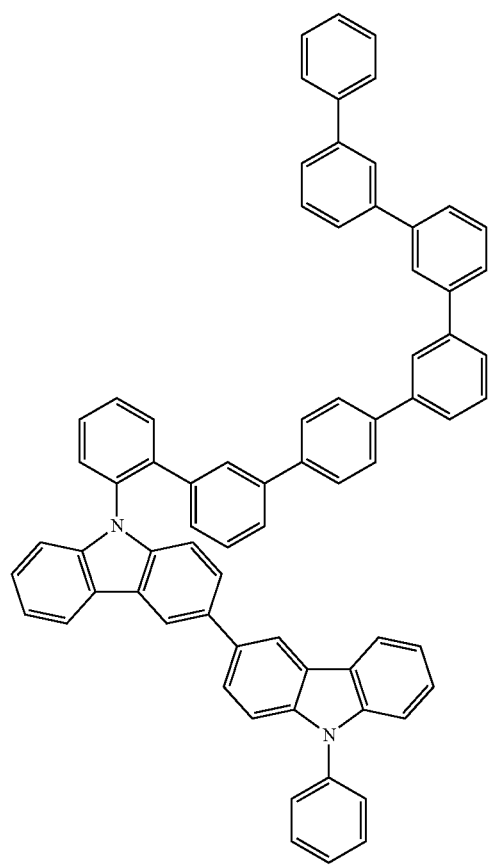

-continued
A484
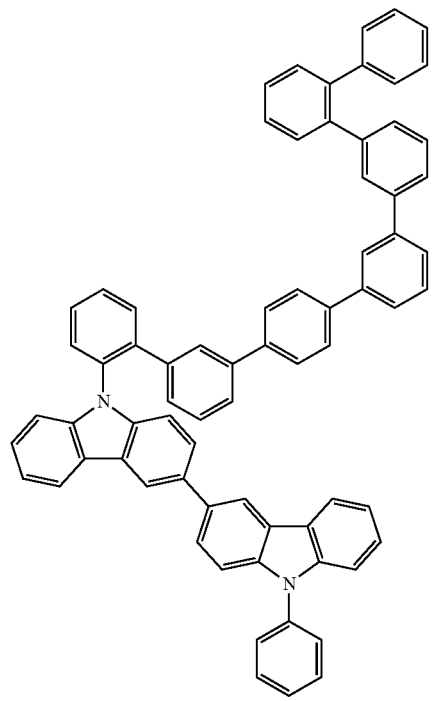
A485
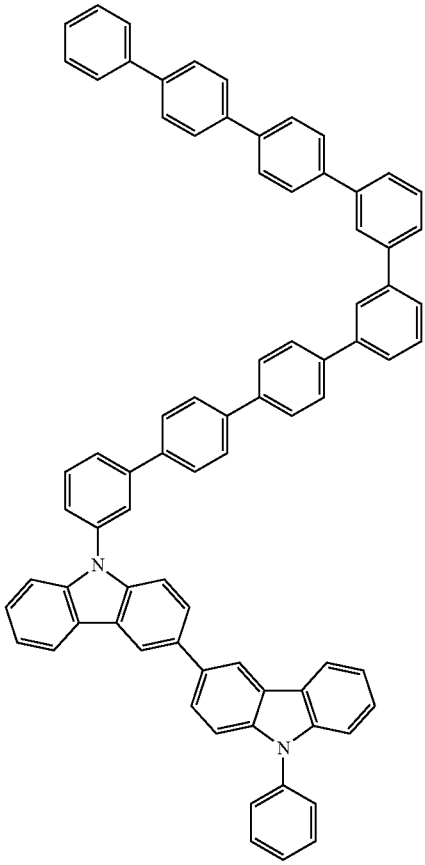

-continued
A486
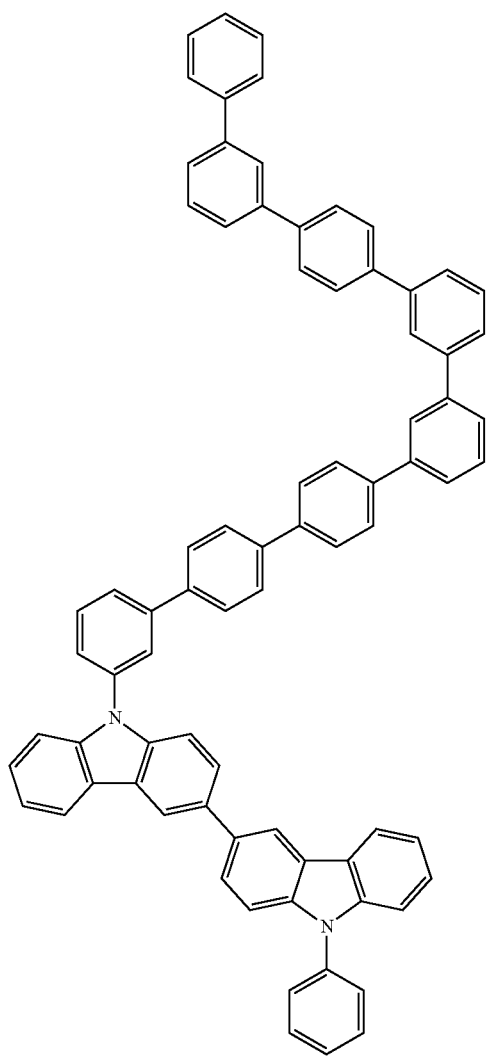
A487
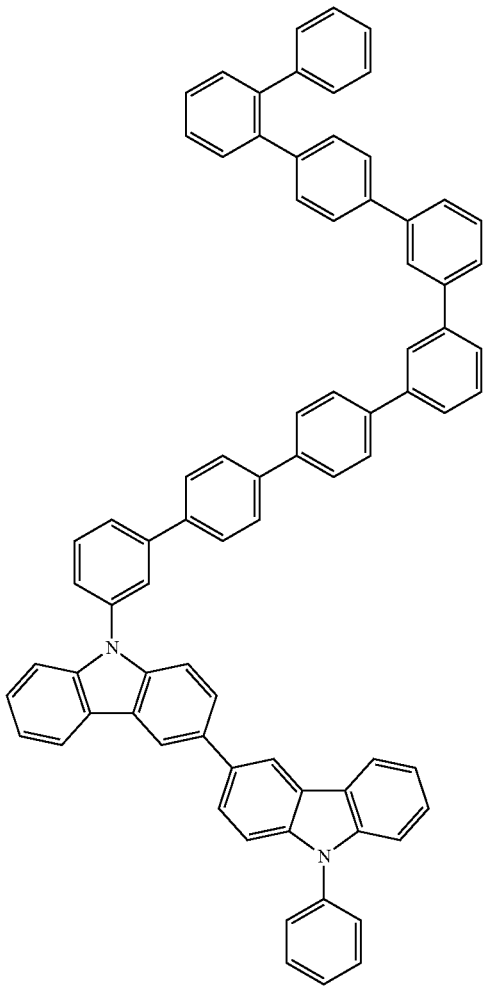

-continued
A488
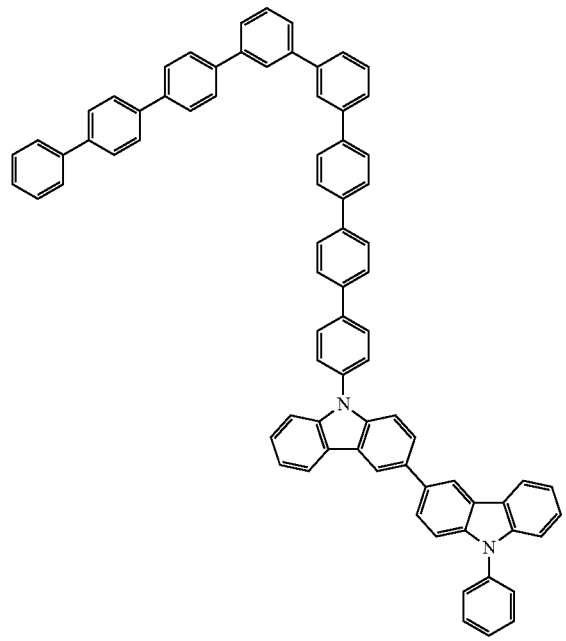
A489
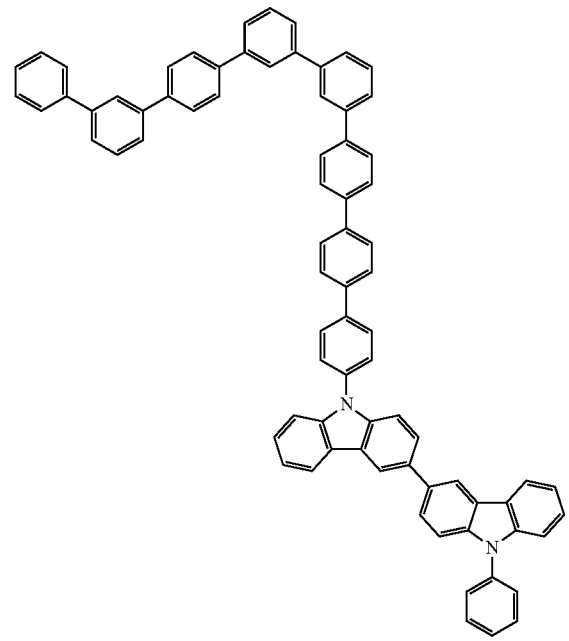
A490
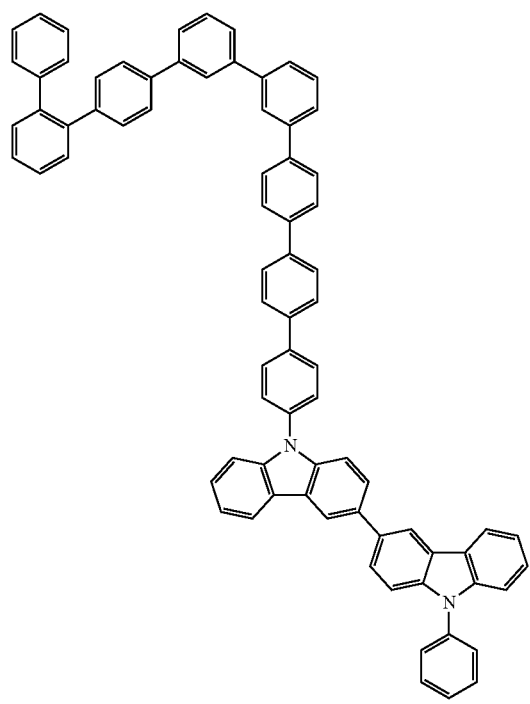
A491
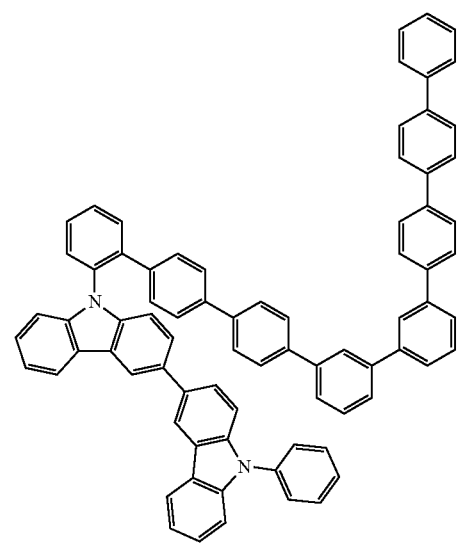

-continued
311
A492
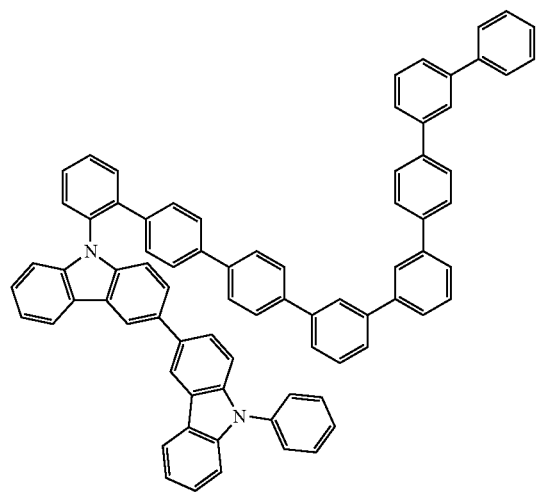
312
A493
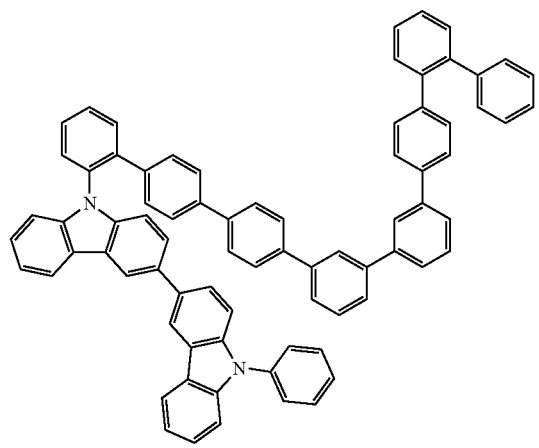
A494
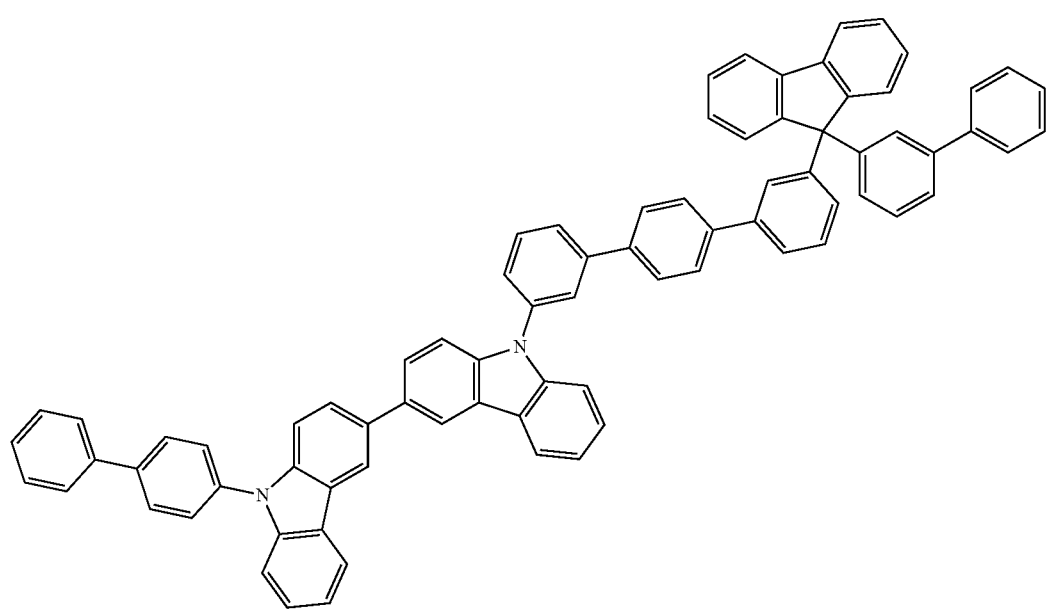

-continued

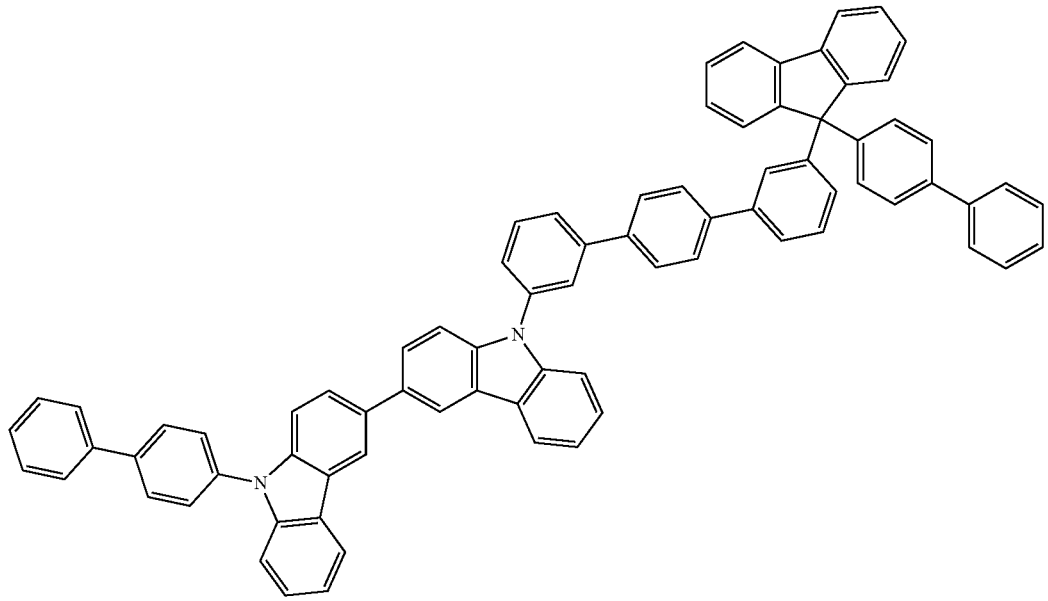

A495

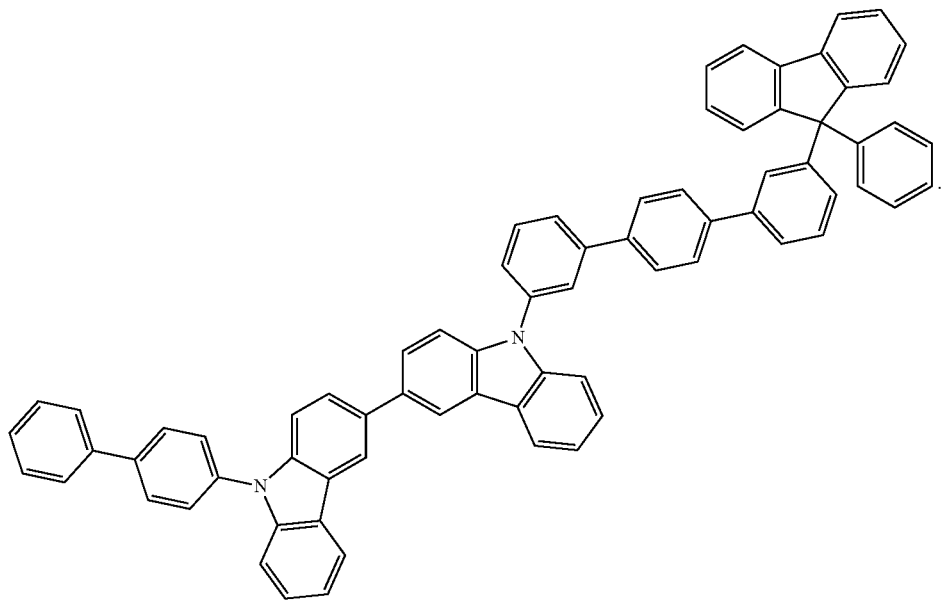

A496

For example, the heterocyclic compound may be of Compounds A1, A17, A276 to A278, and A494 to A496, but embodiments of the present disclosure are not limited thereto.

The heterocyclic compound represented by Formula 1 includes a p-terphenyl (para-terphenyl) moiety, so that the LUMO level thereof is set to a wide band gap (WG)-host level, thereby securing hole mobility.

When the p-terphenyl structure is not included, the LUMO level of the compound is not suitable as a wide band gap-host and a target performance may not be executed.

In addition, the heterocyclic compound represented by Formula 1 includes a group represented by Formula 1A or 1B, and the group represented by Formula 1A or 1B is connected to a neighboring phenyl group at a meta position, and may act as a soluble group.

Specifically, in the heterocyclic compound represented by Formula 1, the group represented by Formula 1A or 1B is connected to the neighboring phenyl group at the meta position, and thus, the number of conformation of a molecule is increased by the rotation of a single bond, resulting in the increase in the solubility according to the law in which entropy is increased.

By introducing the group represented by Formula 1A or 1B, solubility and pot life may be improved.

By including a p-terphenyl (para-terphenyl) moiety, the LUMO level may be set to a wide band gap (WG)-host level, thereby securing hole mobility.

In addition, since the heterocyclic compound represented by Formula 1 includes a p-terphenyl group and two carbazole groups in the core, due to the pi-conjugation effects, the heterocyclic compound includes a LUMO level that is continuously formed from carbazole groups, and the like to a p-terphenyl group, and may have high stability for electron injection and very suitable electron mobility.

The heterocyclic compound represented by Formula 1 may be included in an organic layer between a pair of electrodes of an organic light-emitting device. For example, the heterocyclic compound represented by Formula 1 may be included in an emission layer, and may be suitable as a host.

The heterocyclic compound represented by Formula 1 may provide high luminescent efficiency and light-emission lifespan. The reason for this is considered to be that the heterocyclic compound represented by Formula 1 has a low LUMO level and high solubility as described above.

In addition, the heterocyclic compound represented by Formula 1 is difficult to precipitate in the solution, and the pot life of the solution is long. Thus, even when a wet film-forming method is used, the heterocyclic compound may provide an organic light-emitting device having high luminescent efficiency and light-emission lifespan.

The heterocyclic compound represented by Formula 1 may be synthesized by using a known organic synthetic method. For example, as a method of synthesizing 3,3'-biscarbazole core, there is a method in which a coupling reaction of boronic acid or boronic ester with a halogen or triflate is used by using a palladium catalyst or a copper catalyst. In addition, as a method of introducing a substituent on a nitrogen atom of a carbazole, there is a method in which a coupling reaction between a carbazole derivative and halogen is used by using a palladium catalyst or a copper catalyst. For example, as a method of introducing a substituent, there is a method in which a coupling reaction of boronic acid or boronic ester with a halogen or triflate is used by using a palladium catalyst or a copper catalyst. A synthesis method for the heterocyclic compound represented by Formula 1 would be apparent to those of ordinary skill in the art by referring to the following examples.

Heterocyclic Compound (2)

A heterocyclic compound represented by Formula 2 according to one or more embodiments will be described in detail as follows:

Formula 2

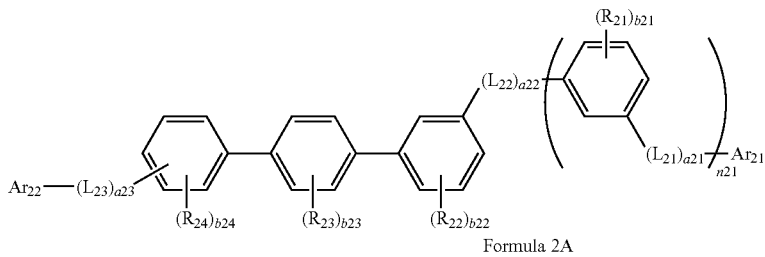

Formula 2A

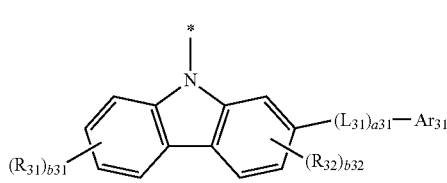

Formula 2B

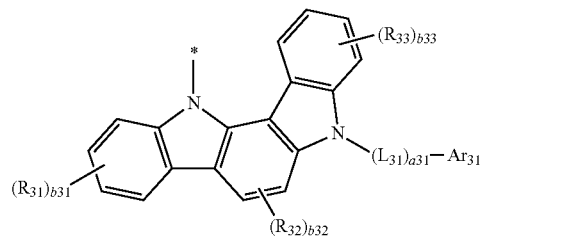

Formula 2C

In Formulae 2 and 2A to 2C, $L_{21}$ to $L_{23}$ and $L_{31}$ may each independently be a single bond, a substituted or unsubstituted $C_5$-$C_{60}$ carbocyclic group, or a substituted or unsubstituted $C_1$-$C_{60}$ heterocyclic group.

However, the $C_1$-$C_{60}$ heterocyclic group of $L_{21}$ to $L_{23}$ and $L_{31}$ is not an azine group.

The term "azine group" as used herein refers to a 6-membered aromatic ring including nitrogen as a ring-forming atom.

For example, $L_{21}$ to $L_{23}$ and $L_{31}$ may each independently be a single bond, a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthylene group, a heptaphene group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiene group, a silole group, a benzofuran group, a benzothiene group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzoisoxazole group, a thiazole group, an isothiazole group, a benzothiazole group, a benzisothiazole group, an imidazopyridine group, an imidazopyrimidine group, an imidazophenanthridine group, a benzimidazophenanthridine group, an azadibenzofuran group, an azacarbazole group, an azadibenzothiene group, a diazadibenzofuran group, a diazacarbazole group, a diazadibenzothiene group, a xanthone group, or a thioxanthone group; or a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthylene group, a heptaphene group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiene group, a silole group, a benzofuran group, a benzothiene group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzoisoxazole group, a thiazole group, an isothiazole group, a benzothiazole group, a benzisothiazole group, an imidazopyridine group, an imidazopyrimidine group, an imidazophenanthridine group, a benzimidazophenanthridine group, an azadibenzofuran group, an azacarbazole group, an azadibenzothiene group, a diazadibenzofuran group, a diazacarbazole group, a diazadibenzothiene group, a xanthone group, or a thioxanthone group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a tnazolyl group, a tetrazolyl group, an indazolyl group, an oxazolyl group, an isoxazolyl group, a benzoxazolyl group, a benzoisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazacarbazolyl group, a diazadibenzothienyl group, a xanthonenyl group, a thioxanthonyl group, or any combination thereof.

For example, $L_{21}$ to $L_{23}$ and $L_{31}$ may each independently be a single bond, a benzene group, a biphenyl group, a terphenyl group, or a tetraphene group; or a benzene group, a biphenyl group, a terphenyl group, or a tetraphene group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a biphenyl group, a terphenyl group, or any combination thereof.

For example, $L_{21}$ to $L_{23}$ and $L_{31}$ may each independently be a single bond or a group represented by Formulae 6-1 to 6-8 below:

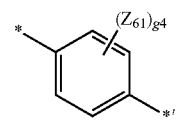

6-1

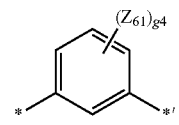

6-2

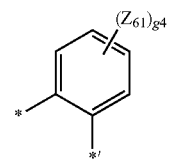

6-3

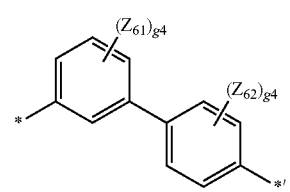

6-4

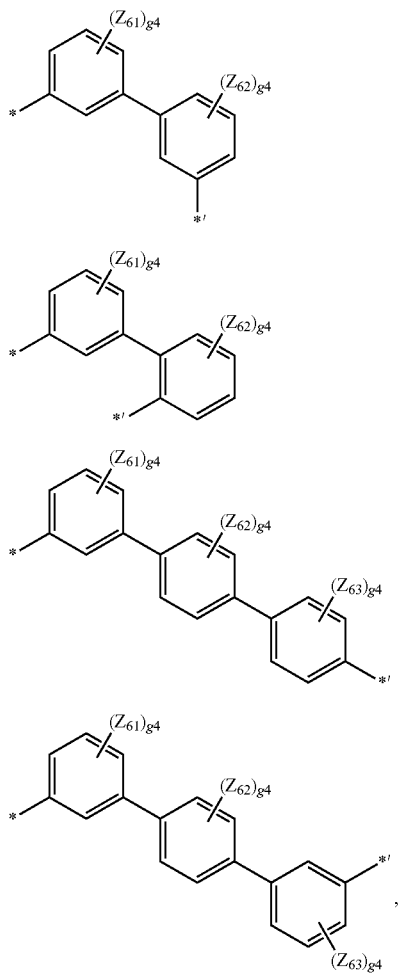

$Z_{61}$ to $Z_{63}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), g4 may be an integer from 0 to 4, $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* and *' each indicate a binding site to a neighboring atom.

For example, $L_{31}$ may be a single bond or a group represented by Formula 6-1, but embodiments of the present disclosure are not limited thereto.

The designations a21 to a23 and a31 in Formulae 2 and 2A to 2C may each independently be an integer from 1 to 5. a21 indicates the number of groups represented by $L_{21}$, and when a21 is 2 or more, $L_{21}$(s) in the number of a21 may be identical to or different from each other, a22 indicates the number of groups represented by $L_{22}$, and when a22 is 2 or more, $L_{22}$(s) in the number of a22 may be identical to or different from each other, a23 indicates the number of groups represented by $L_{23}$, and when a23 is 2 or more, $L_{23}$(s) in the number of a23 may be identical to or different from each other, and a31 indicates the number of groups represented by $L_{31}$, and when a31 is 2 or more, $L_{31}$ in the number of a31 may be identical to or different from each other.

For example, a31 may be 1, but embodiments of the present disclosure are not limited thereto.

In Formulae 2 and 2A to 2C, $Ar_{21}$ and $Ar_{31}$ may each independently be a substituted or unsubstituted $C_5$-$C_{60}$ carbocyclic group, or a substituted or unsubstituted $C_1$-$C_{60}$ heterocyclic group, and $Ar_{22}$ may be groups represented by Formulae 2A to 2C. However, the $C_1$-$C_{60}$ heterocyclic group of $Ar_{21}$ and $Ar_{31}$ is not an azine group.

For example, $Ar_{21}$ and $Ar_{31}$ may each independently be: a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazacarbazolyl group, a diazadibenzothienyl group, a xanthonenyl group, or a thioxanthonyl group; or a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazacarbazolyl group, a diazadibenzothienyl group, a xanthonenyl group, or a thioxanthonyl group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazacarbazolyl group, a diazadibenzothienyl group, a xanthonenyl group, a thioxanthonyl group, or any combination thereof.

For example, $Ar_{21}$ and $Ar_{31}$ may each independently be: a phenyl group, a biphenyl group, a terphenyl group, a tetraphenyl group, a pentaphenyl group, or a carbazolyl group; or a phenyl group, a biphenyl group, a terphenyl group, a tetraphenyl group, a pentaphenyl group, or a carbazolyl group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a biphenyl group, a terphenyl group, or any combination thereof.

For example, $Ar_{31}$ in Formula 2A may be: a carbazolyl group; or a carbazolyl group substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a biphenyl group, a terphenyl group, or any combination thereof.

For example, a moiety represented by

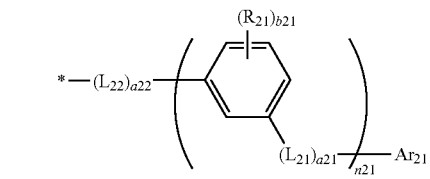

may be a group represented by one of Formulae 7-1 to 7-4 below, but embodiments of the present disclosure are not limited thereto:

7-1
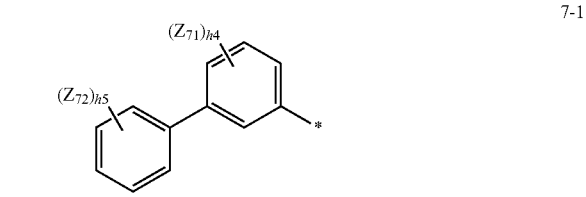

7-2
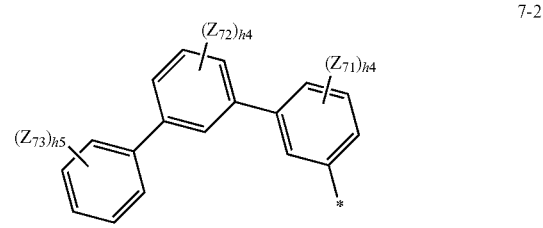

7-3
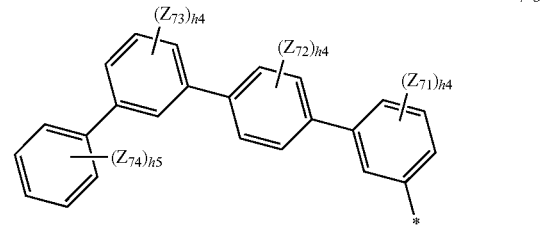

7-4
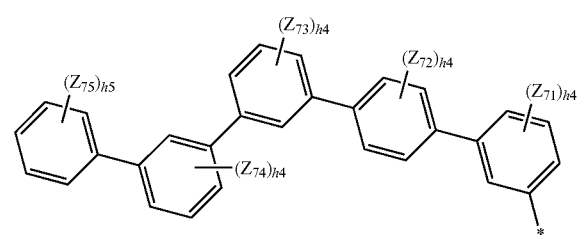

In Formulae 7-1 to 7-4, $Z_{71}$ to $Z_{74}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —Si($Q_{31}$)($Q_{32}$)($Q_{33}$), h4 may be an integer from 0 to 4, h5 may be an integer from 0 to 5, $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* indicates a binding site to a neighboring atom.

For example, a moiety represented by *—(L$_{31}$)$_{a31}$—Ar$_{31}$ in Formulae 2B and 2C may be a group represented by one of Formulae 8-1 to 8-5, but embodiments of the present disclosure are not limited thereto:

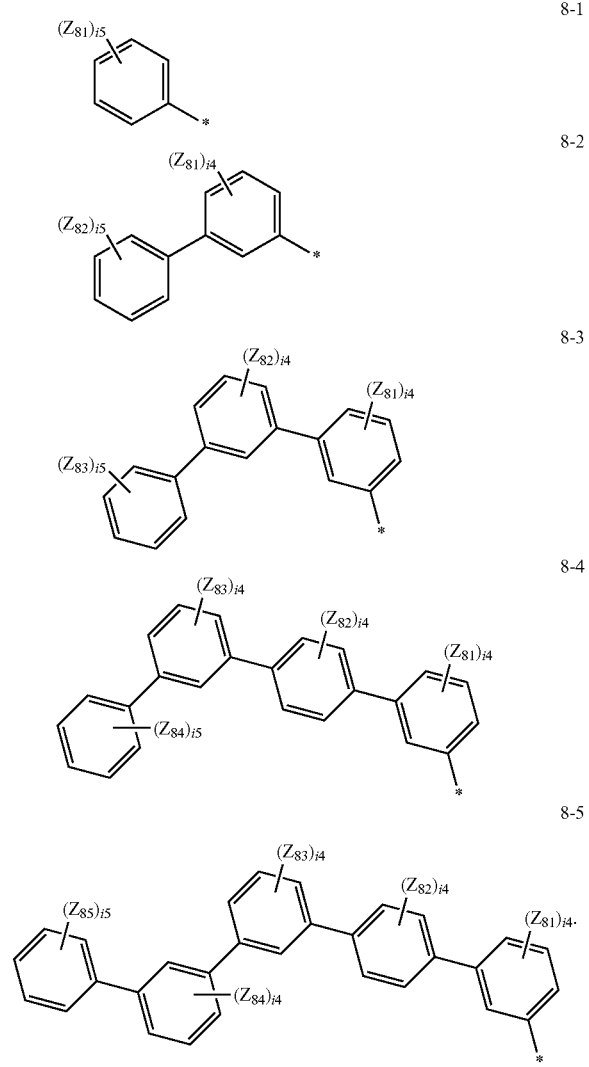

In Formulae 8-1 to 8-5,

Z$_{81}$ to Z$_{83}$ may each independently be hydrogen, deuterium, —F, —Cl, —Br, —I, a hydroxyl group, a cyano group, a C$_1$-C$_{20}$ alkyl group, a C$_1$-C$_{20}$ alkoxy group, a phenyl group, or —Si(Q$_{31}$)(Q$_{32}$)(Q$_{33}$), i4 may be an integer from 0 to 4, i5 may be an integer from 0 to 5, Q$_{31}$ to Q$_{33}$ may each independently be hydrogen, deuterium, a C$_1$-C$_{20}$ alkyl group, a C$_1$-C$_{20}$ alkoxy group, a phenyl group, or a biphenyl group, and

* indicates a binding site to a neighboring atom.

In Formulae 2 and 2A to 2C, R$_{21}$ to R$_{24}$ and R$_{31}$ to R$_{33}$ may each independently be hydrogen, deuterium, —F, —Cl, —Br, —I, a cyano group, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{60}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_7$-C$_{60}$ alkylaryl group, a substituted or unsubstituted C$_7$-C$_{60}$ aryl alkyl group, a substituted or unsubstituted C$_2$-C$_{60}$ arylalkyloxy group, a substituted or unsubstituted C$_7$-C$_{60}$ arylalkylthio group, a substituted or unsubstituted C$_8$-C$_{30}$ arylalkenyl group, a substituted or unsubstituted C$_8$-C$_{30}$ arylalkynyl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted C$_2$-C$_{60}$ alkylheteroaryl group, a substituted or unsubstituted C$_1$-C$_{60}$ heteroaryloxy group, a substituted or unsubstituted C$_1$-C$_{60}$ heteroarylthio group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), or —N(Q$_1$)(Q$_2$), wherein the C$_1$-C$_{60}$ heteroaryl group of R$_{21}$ to R$_{24}$ and R$_{31}$ to R$_{33}$ is not an azine group, b21 to b24 and b31 to b33 may each independently be an integer from 0 to 4, and any two adjacent groups among R$_{21}$(s) in the number of b21, R$_{22}$(s) in the number of b22, R$_{23}$(s) in the number of b23, R$_{24}$(s) in the number of b24, R$_{31}$(s) in the number of b31, R$_{32}$(s) in the number of b32, and R$_{33}$(s) in the number of b33 may optionally be linked to each other to form a substituted or unsubstituted C$_5$-C$_{30}$ carbocyclic group or a substituted or unsubstituted C$_1$-C$_{30}$ heterocyclic group.

For example, R$_{21}$ to R$_{24}$ and R$_{31}$ to R$_{33}$ may each independently be: hydrogen, deuterium, —F, —Cl, —Br, —I, a cyano group, a C$_1$-C$_{20}$ alkyl group, a C$_2$-C$_{20}$ alkenyl group, a C$_2$-C$_{20}$ alkynyl group, and a C$_1$-C$_{20}$ alkoxy group; and a C$_1$-C$_{20}$ alkyl group, a C$_2$-C$_{20}$ alkenyl group, a C$_2$-C$_{20}$ alkynyl group, or a C$_1$-C$_{20}$ alkoxy group, each substituted with at least one deuterium, —F, —Cl, —Br, —I, a cyano group, or any combination thereof.

For example, R$_{21}$ to R$_{24}$ and R$_{31}$ to R$_{33}$ may each be hydrogen.

In Formulae 2 and 2A to 2C, n21 may be an integer from 1 to 5.

For example, n21 may be 1 or 2.

In one or more embodiments, the group represented by Formula 2A may be represented by Formula 2A-1 below:

Formula 2A-1

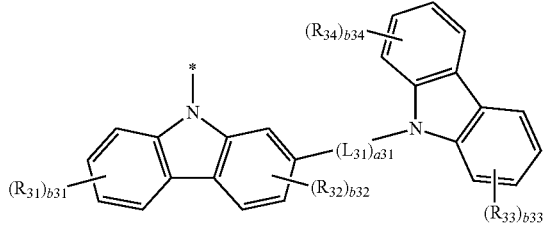

In Formula 2A-1,

L$_{31}$, a31, R$_{31}$ to R$_{33}$, b31 to b33, and * may each be understood by referring to descriptions thereof provided herein.

R$_{34}$ may be understood by referring to descriptions provided in connection with R$_{31}$ to R$_{33}$ as described above. b34 may be an integer from 0 to 4.

In one or more embodiments, the heterocyclic compound represented by Formula 2 may be a compound represented by one of Formulae 2-1 to 2-3 below:

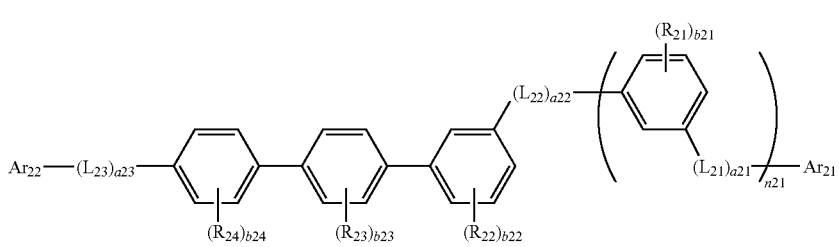

Formula 2-1

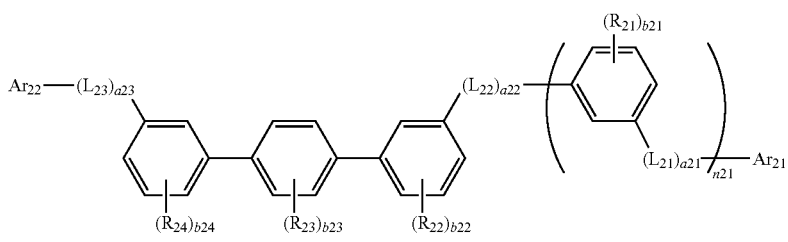

Formula 2-2

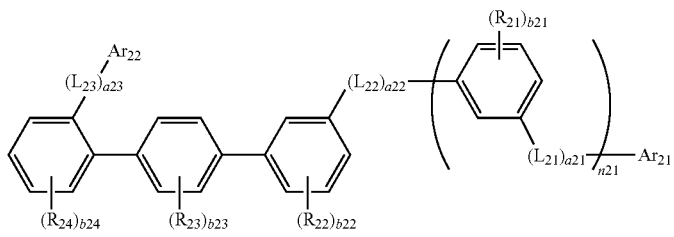

Formula 2-3

In Formulae 2-1 to 2-3, $L_{21}$ to $L_{23}$, a21 to a23, $Ar_{21}$, $Ar_{22}$, $R_{21}$ to $R_{24}$, b21 to b24, and n21 may each be understood by referring to descriptions thereof provided herein.

For example, the heterocyclic compound represented by Formula 2 may include two or more m-phenyl moieties, but embodiments of the present disclosure are not limited thereto.

In one or more embodiments, the heterocyclic compound represented by Formula 2 may satisfy Equation 1 below:

Equation 1

$$|E_{HOMO}-E_{LUMO}|>3.0 \text{ eV}$$

In Equation 1, $E_{HOMO}$ is the value of a highest occupied molecular orbital (HOMO) energy level of the heterocyclic compound, and $E_{LUMO}$ is the value of a lowest unoccupied molecular orbital (LUMO) energy level of the heterocyclic compound.

The value of $|E_{HOMO}-E_{LUMO}|$ is not particularly limited as long as it satisfies Equation 1, and may be, for example, 3.1 eV or more, or, for example, 3.2 eV or more.

For example, the value of $|E_{HOMO}-E_{LUMO}|$ may be 6.0 eV or less.

In one or more embodiments, the heterocyclic compound represented by Formula 2 may satisfy Equation 1-1 below:

Equation 1-1

$$3.0 \text{ eV} \leq |E_{HOMO}-E_{LUMO}| \leq 6.0 \text{ eV}.$$

For example, the glass transition temperature ($T_g$) of the heterocyclic compound represented by Formula 2 may be 140° C. or less. For example, $T_g$ of the heterocyclic compound is not particularly limited, but may be 130° C. or less, and 60° C. or more, e.g., 100° C. or more.

In one or more embodiments, the heterocyclic compound represented by Formula 2 may be Compounds 1 to 23 below, but embodiments of the present disclosure are not limited thereto:

1

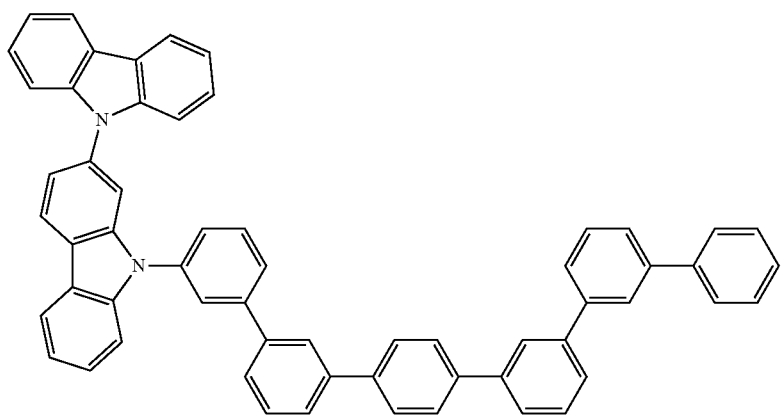

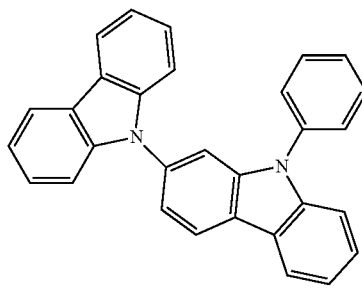
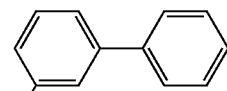
2
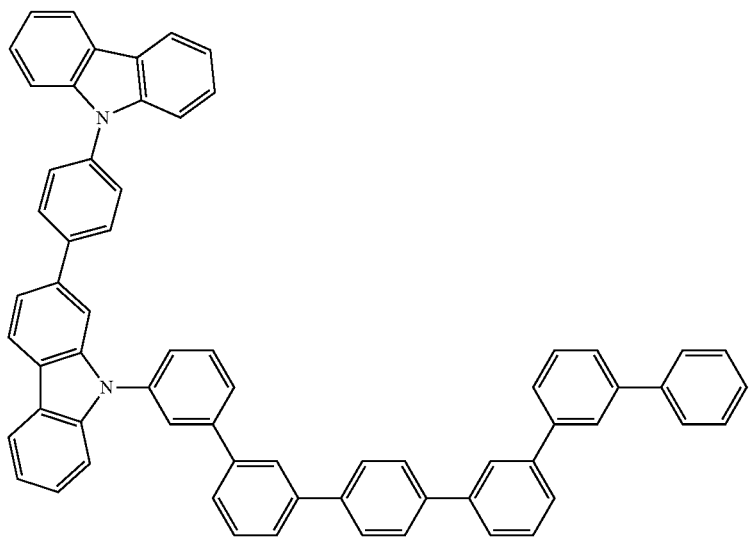
3
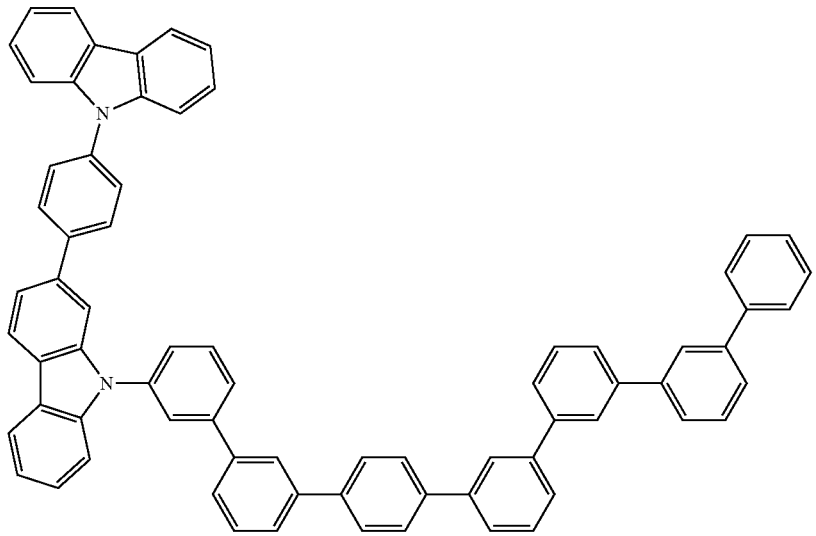
4

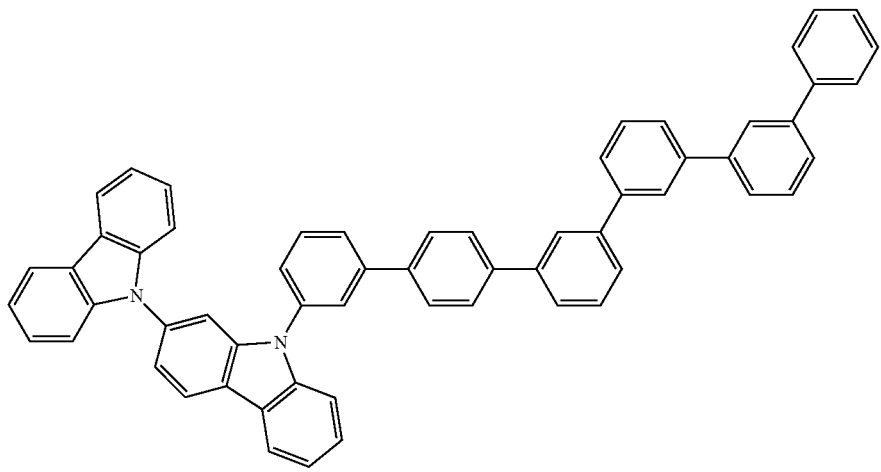
5
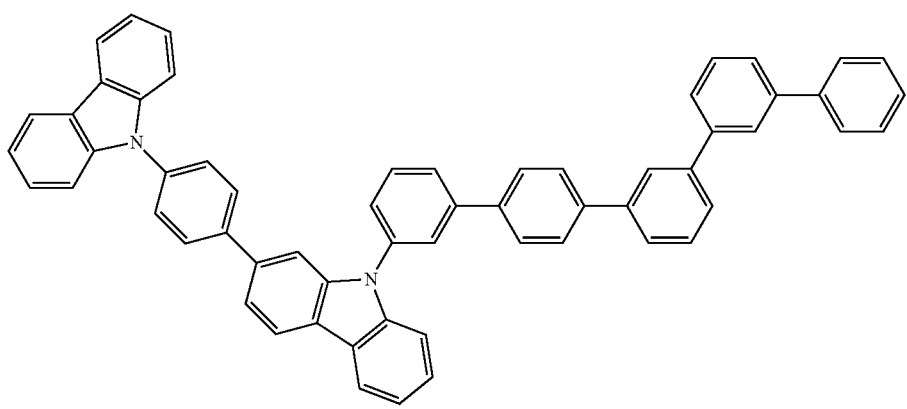
6
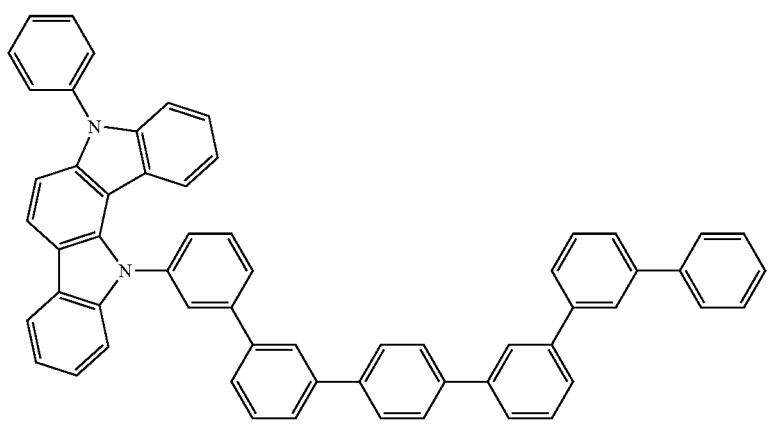
7

8
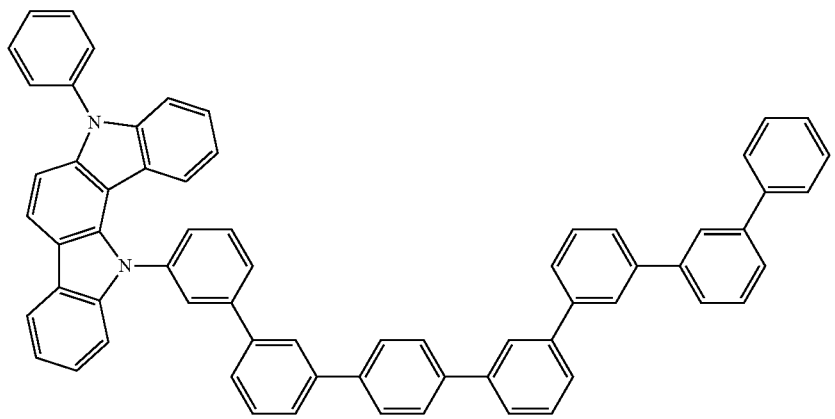
9
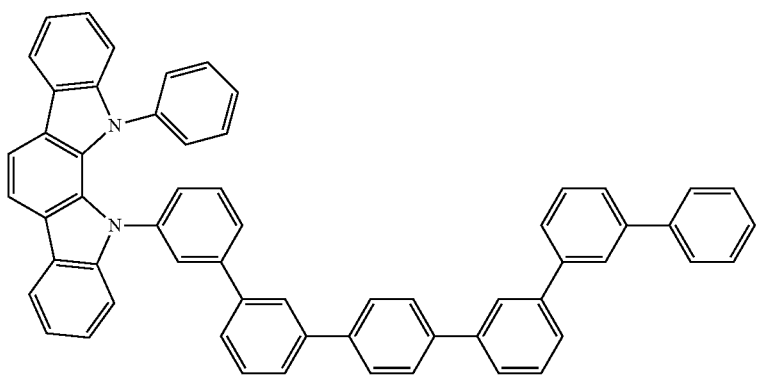
10
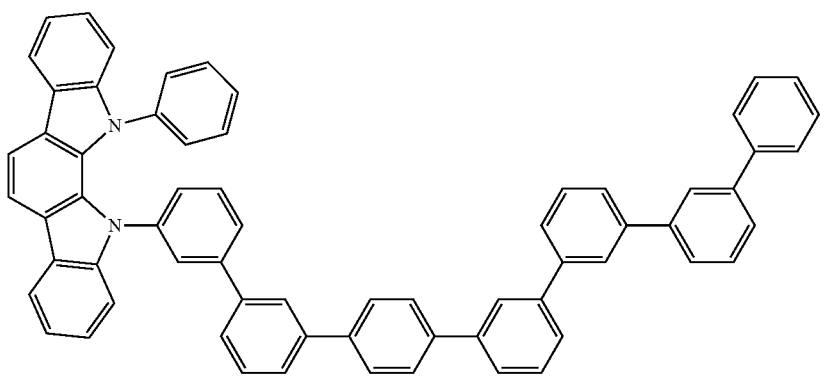

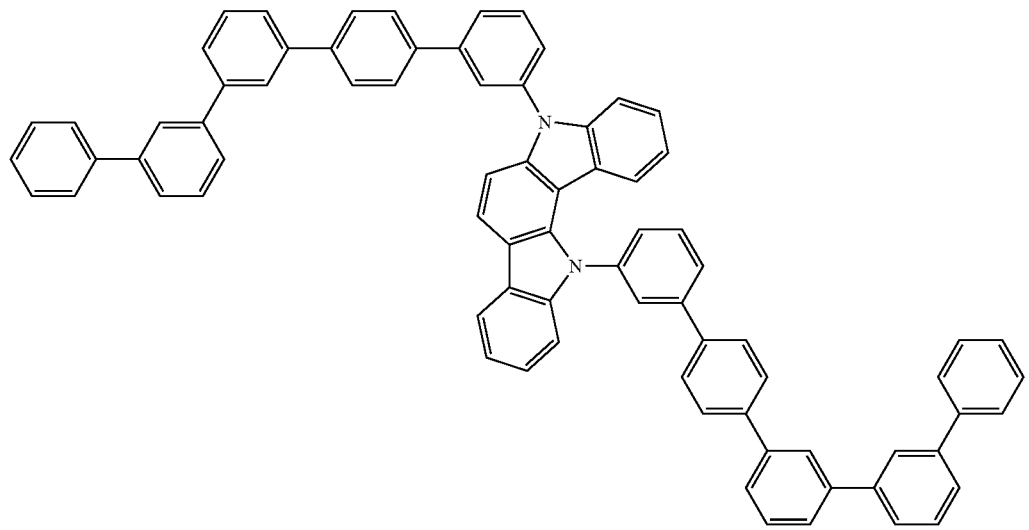
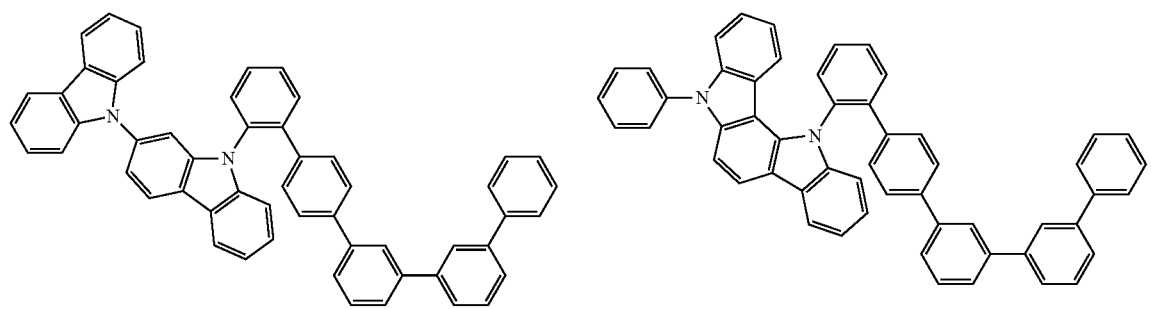
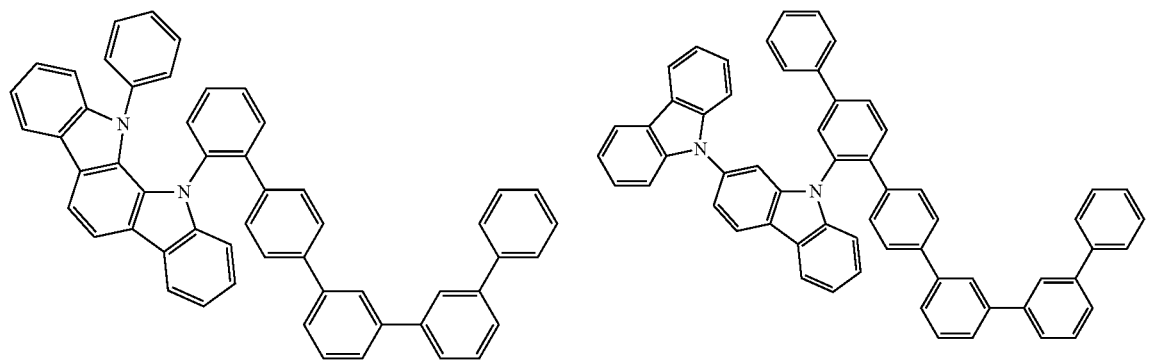
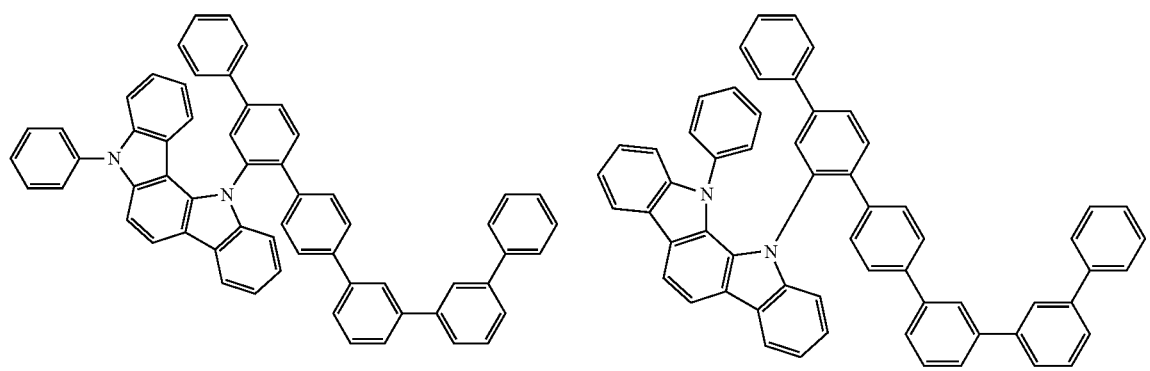

-continued

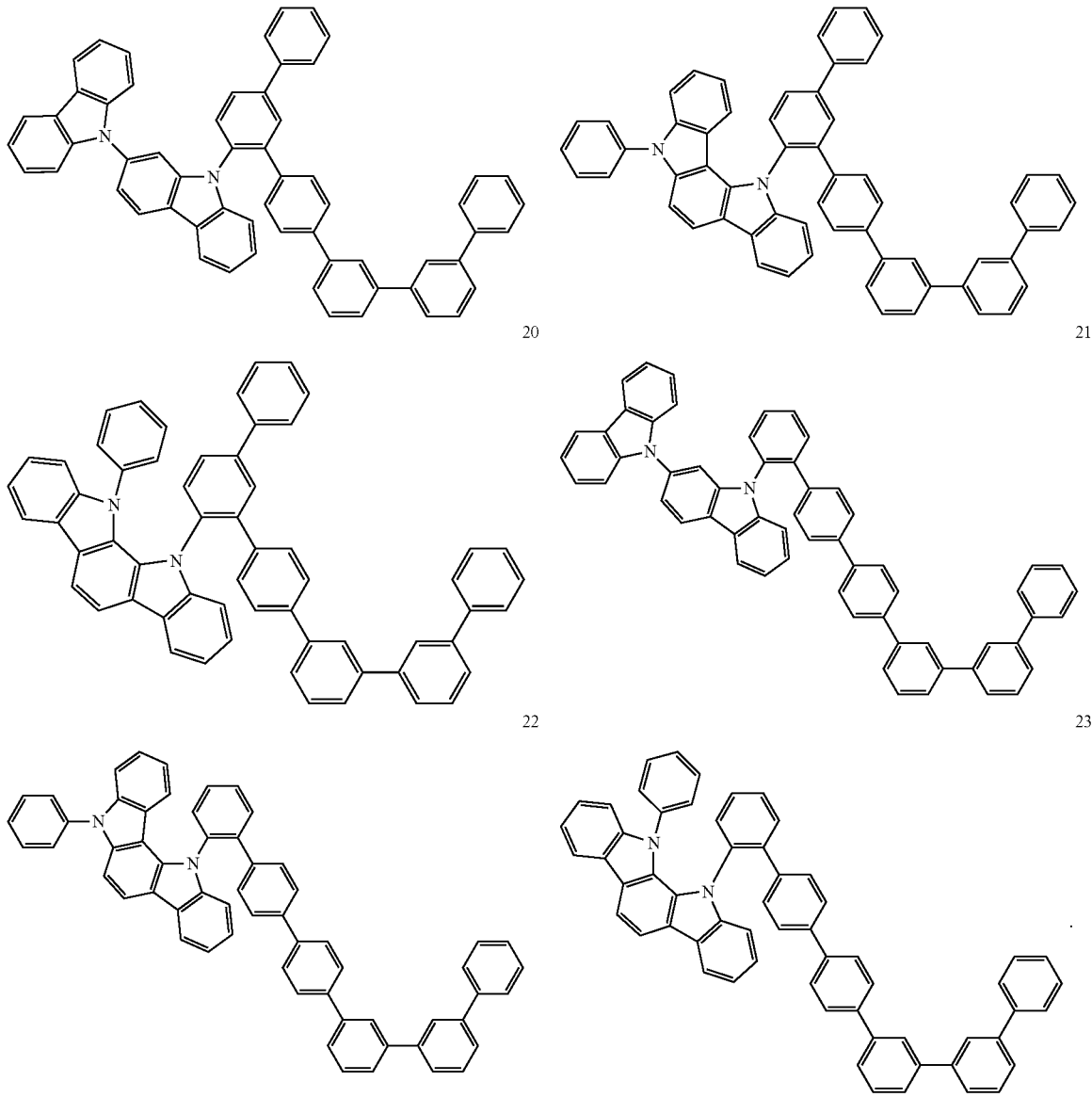

For example, the heterocyclic compound may be one of Compounds 1 and 2, but embodiments of the present disclosure are not limited thereto.

The heterocyclic compound represented by Formula 2 includes a carbazole group having a substituent at the 2-position, an indolocarbazole group, or a p-terphenyl group. The p-terphenyl group has a substituent at both ends, and at least one substituent thereof is present in the meta position of the p-terphenyl group. In addition, the substituent included in the p-terphenyl group has at least one m-phenyl group.

Due to these structures, the number of conformations (the number of conformation patterns) is increased and thus, aggregation of molecules may be minimized. Therefore, the glass transition temperature is lowered and crystallization is less likely to occur. As a result, the heterocyclic compound has high solubility so that is hard to precipitate in a solution, and the pot life of the solution is prolonged.

In addition, due to the relatively low glass transition temperature in the drying process of removing the solvent, it is relatively easy for the compound molecules to thermally move in a film containing the compound. Therefore, voids, through which volatile impurity molecules pass, are likely to occur, and volatile impurity molecules may easily diffuse and be removed. As a result, the luminescent efficiency and light-emission lifespan of organic light-emitting devices are improved.

The heterocyclic compound has, as a highest occupied molecular orbital (HOMO)-polarized moiety, a carbazole group or an indolocarbazole group, and, as a lowest unoccupied molecular orbital (LUMO)-polarized moiety, a p-terphenyl group. Thus, the heterocyclic compound has the balance between the HOMO level and the LUMO level and the balance of the carrier mobility between electrons and holes. As a result, since, with respect to the layer including the heterocyclic compound, a portion in which charges recombine and a portion in which excitons are generated are dispersed, and loads are dispersed, the lifespan of the organic light-emitting device is improved.

The heterocyclic compound represented by Formula 2 may have an energy gap between a HOMO energy level and a LUMO energy level of 3.0 eV or more. Accordingly, the heterocyclic compound may be a wide band-gap material.

In addition, since, in the heterocyclic compound represented by Formula 2, a p-terphenyl group is connected to the phenyl group at the meta position, the number of conformation of the molecule is increased due to the rotation of a single bond, resulting in the increase in the solubility according to the law in which entropy is increased.

The heterocyclic compound represented by Formula 2 may be included in an organic layer between a pair of electrodes of an organic light-emitting device. For example, the heterocyclic compound represented by Formula 2 may be included in an emission layer, and may be suitable as a host.

The heterocyclic compound represented by Formula 2 may provide high luminescent efficiency and light-emission lifespan. The reason for this is considered to be that the heterocyclic compound represented by Formula 2 has a low glass transition temperature, a low LUMO level, and the balance of carrier mobility between electrons and holes.

In addition, the heterocyclic compound represented by Formula 2 is difficult to precipitate in the solution, and the pot life of the solution is long. Thus, even when a wet film-forming method is used, the heterocyclic compound may provide an organic light-emitting device having high luminescent efficiency and light-emission lifespan.

The heterocyclic compound represented by Formula 2 may be synthesized by using a known organic synthetic method. A synthesis method for the heterocyclic compound represented by Formula 2 would be understood by those of ordinary skill in the art by referring to the following examples.

Composition

Hereinafter, a composition according to an embodiment will be described in detail as follows.

The composition may include at least one heterocyclic compound represented by Formula 1 or 2.

The heterocyclic compound may be included in an organic layer between a pair of electrodes of an organic light-emitting device. For example, the heterocyclic compound represented by Formula 1 or 2 may be included in an emission layer, and may be suitable as a host.

The heterocyclic compound represented by Formula 1 may provide high luminescent efficiency and high light-emission lifespan. The reason for this is considered to be that the heterocyclic compound represented by Formula 1 or 2 has a low glass transition temperature, a low LUMO level, and the balance of carrier mobility between electrons and holes.

In addition, the heterocyclic compound is difficult to precipitate in the solution, and the pot life of the solution is long. Thus, even when a wet film-forming method is used, the heterocyclic compound may provide an organic light-emitting device having high luminescent efficiency and light-emission lifespan.

For example, the composition may further include one or more of a first compound containing a carbazole-based moiety or a third compound containing an m-phenyl moiety.

For example, the composition may further include a second compound containing an azine-based moiety.

For example, the composition may further include a luminescent material.

For example, the composition may further include one or more of a first compound including a carbazole-based moiety, a second compound including an azine-based moiety, and a luminescent material.

For example, the amount of the heterocyclic compound in the composition may be from about 5 wt % to about 95 wt %, for example, about 10 wt % to about 90 wt %, for example, about 20 wt % to about 80 wt %, based on the total weight of the composition.

Within these ranges, the solubility of the heterocyclic compound is further improved, and precipitation thereof is less likely to occur in the solution, resulting in a longer pot life of the solution. Further, the luminescent efficiency and light-emission lifespan of organic light-emitting devices are improved.

Hereinafter, the luminescent material, and the first compound to the third compound will be described in detail.

The first compound includes a carbazole-based moiety as described above. That is, the composition according to an embodiment of the present disclosure may contain a carbazole-based moiety to further increase the effect of inhibiting aggregation of molecules, and also to improve the balance of carrier mobility between electrons and holes. Thus, the solubility of the composition is further increased, and precipitation hardly occurs in the solution, and thus, the pot life of the solution may be prolonged. Further, the luminescent efficiency and light-emission lifespan of organic light-emitting devices are improved.

For example, the composition may further include one or more first compound represented by Formula 9 and second compound represented by Formula 10:

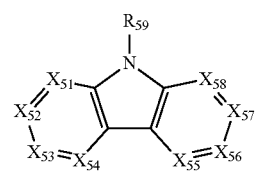

Formula 9

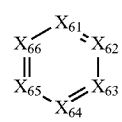

Formula 10

In Formulae 9 and 10, $X_{51}$ may be N or $C(R_{51})$; $X_{52}$ may be N or $C(R_{52})$; $X_{53}$ may be N or $C(R_{53})$; $X_{54}$ may be N or $C(R_{54})$, $X_{55}$ may be N or $C(R_{55})$; $X_{56}$ may be N or $C(R_{56})$; $X_{57}$ may be N or $C(R_{57})$; $X_{58}$ may be N or $C(R_{58})$;

$X_{61}$ may be N or $C(R_{61})$; $X_{62}$ may be N or $C(R_{62})$; $X_{63}$ may be N or $C(R_{63})$; $X_{64}$ may be N or $C(R_{64})$; $X_{65}$ may be N or $C(R_{65})$; and $X_{66}$ may be N or $C(R_{66})$, and at least one of $X_{61}$ to $X_{66}$ may be N;

$R_{51}$ to $R_{58}$ and $R_{61}$ to $R_{66}$ may each independently be hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, $R_{59}$ may be a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, and at least one $R_{61}$ to $R_{66}$ may be a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

For example, any two adjacent groups among $R_{51}$ to $R_{58}$ and $R_{61}$ to $R_{66}$ in Formulae 9 and 10 may optionally be linked to each other to form a ring, but embodiments of the present disclosure are not limited thereto.

The first compound represented by Formula 9 may be, for example, represented by Formula 9-1 below:

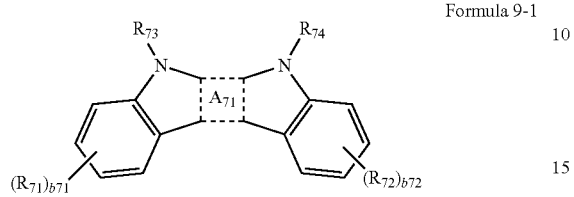

Formula 9-1

In Formula 9-1, ring $A_{71}$ may be a substituted or unsubstituted $C_6$-$C_{60}$ carbocyclic group or a substituted or unsubstituted $C_1$-$C_{60}$ heterocyclic group, $R_{71}$ to $R_{74}$ may each independently be hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, and b71 and b72 may each independently be an integer from 0 to 4.

The first compound represented by Formula 9 may be, for example, represented by Formula 9-2 below:

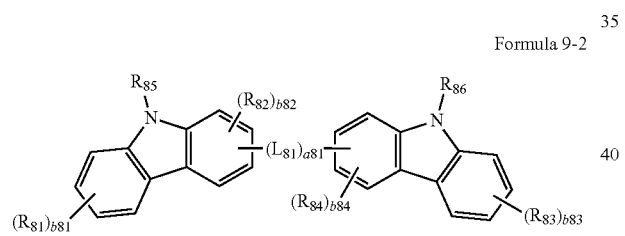

Formula 9-2

In Formula 9-2, $L_{81}$ may be a single bond, a substituted or unsubstituted $C_6$-$C_{60}$ aryl group, a substituted or unsubstituted $C_1$-$C_{60}$ heteroaryl group, a substituted or unsubstituted divalent non-aromatic condensed polycyclic group, or a substituted or unsubstituted divalent non-aromatic condensed heteropolycyclic group, a81 may be an integer from 1 to 5, $R_{81}$ to $R_{86}$ may each independently be hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, b81 and b83 may each independently be an integer from 0 to 4, and b82 and b84 may each independently be an integer from 0 to 4.

For example, the first compound may be a compound represented by Formulae H1-1 to H1-13, H2-1 to H2-34, and H3-1 to H3-3 below:

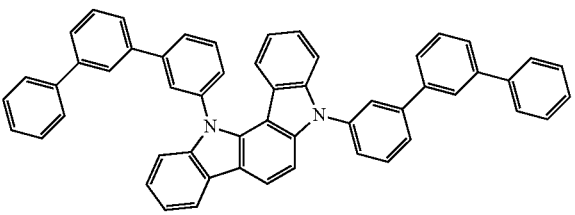

(H1-1)

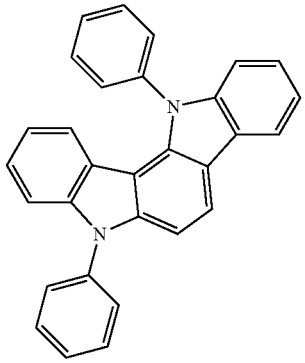

(H1-2)

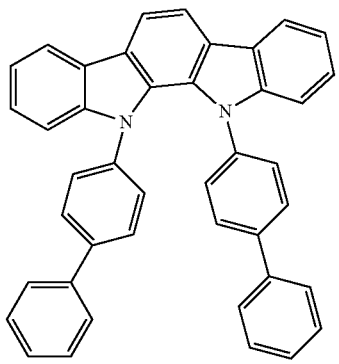

(H1-3)

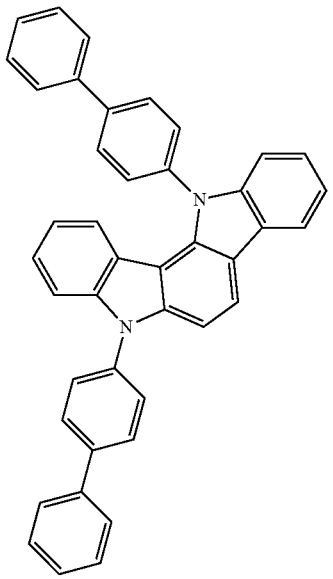

(H1-4)

(H1-5)
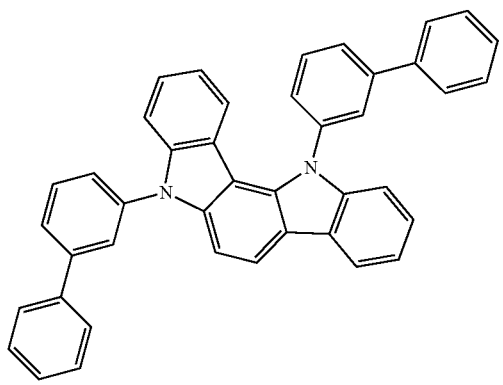
(H1-6)
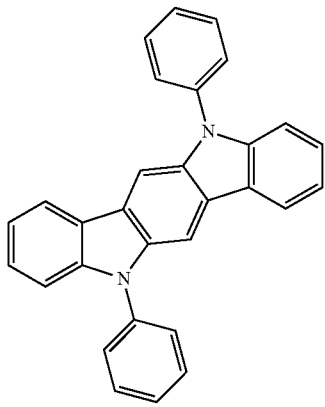
(H1-7)
(H1-8)
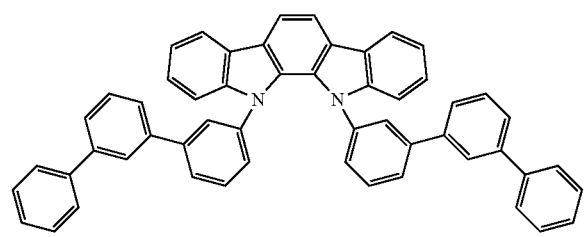
(H1-9)
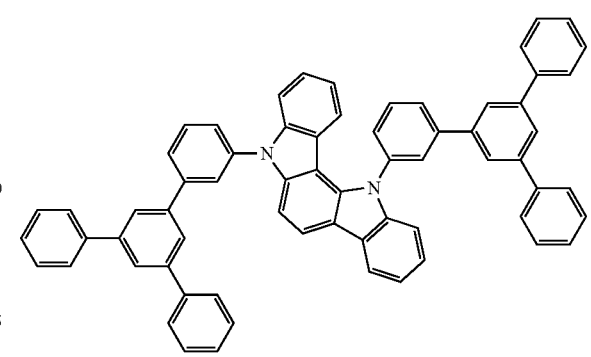
(H1-10)
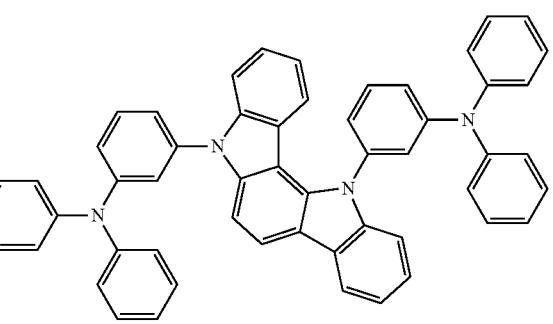
(H1-11)
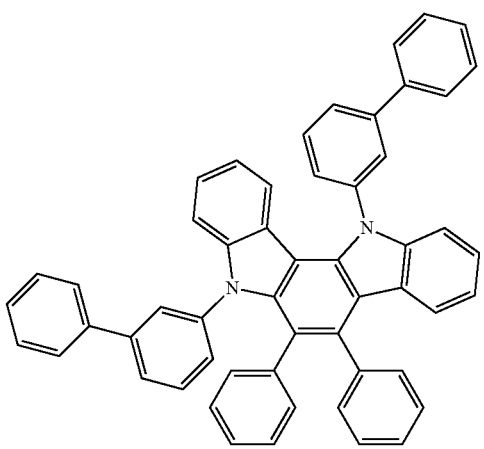

(H1-12)
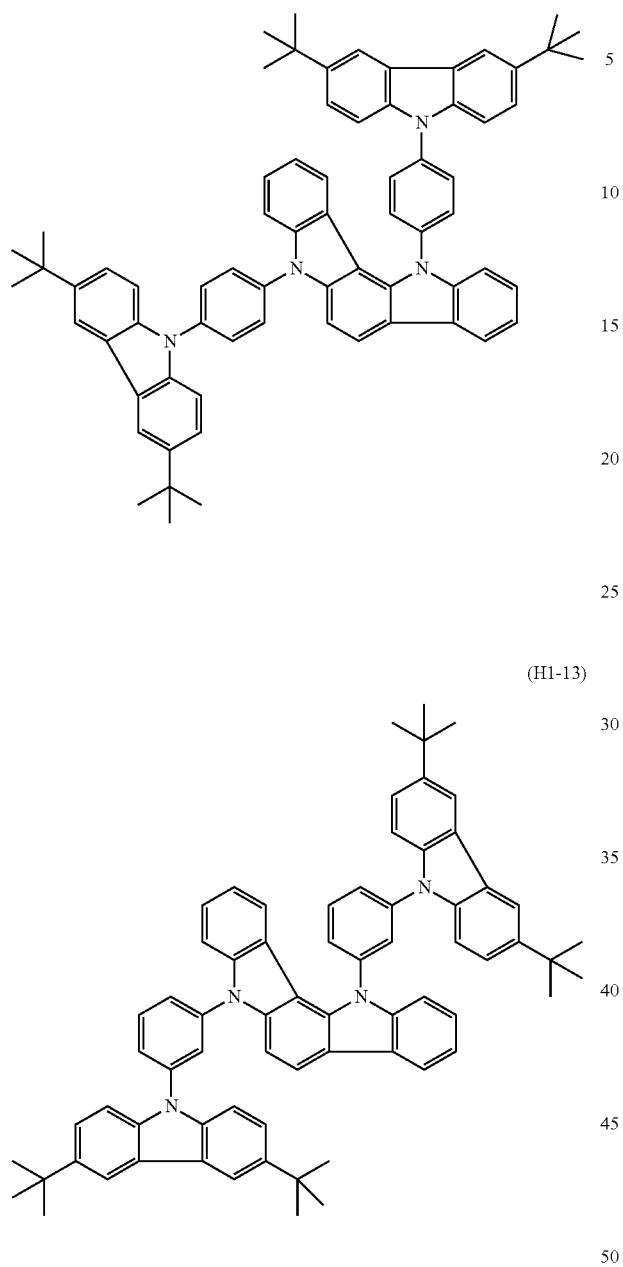
(H1-13)
(H2-2)
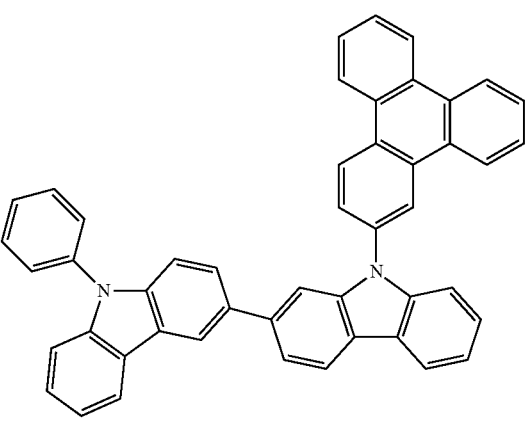
(H2-3)
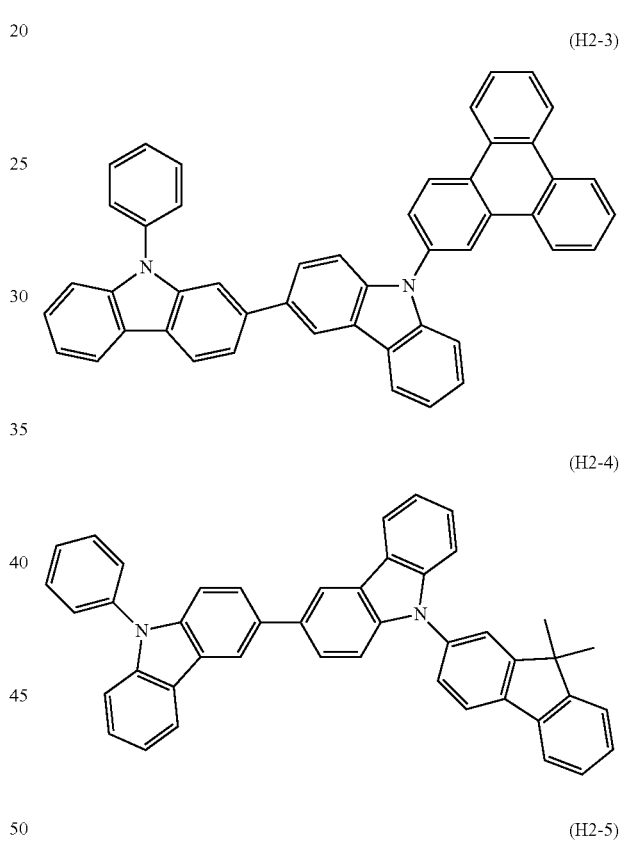
(H2-4)
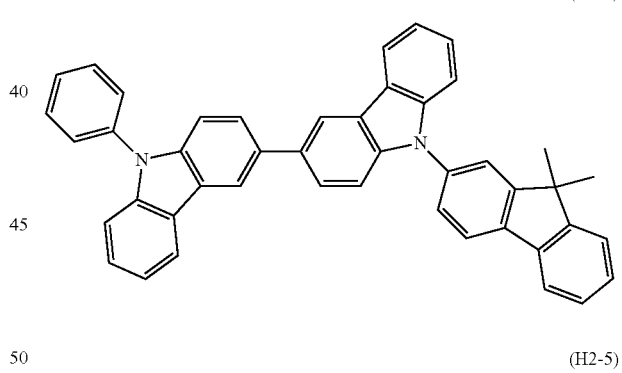
(H2-1)
(H2-5)
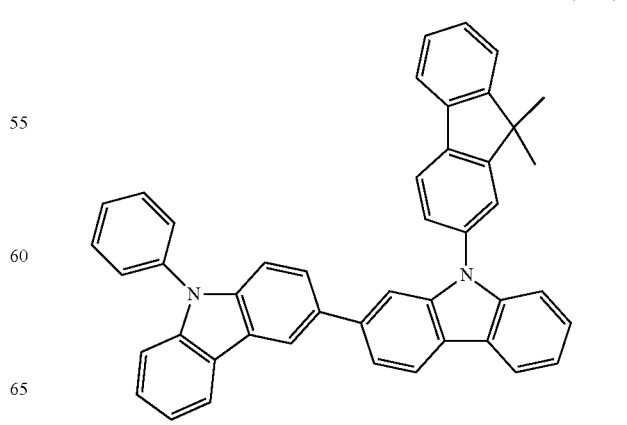

(H2-6)
(H2-7)
(H2-8)
(H2-9)
(H2-10)
(H2-11)
(H2-12)
(H2-13)

-continued
(H2-14)
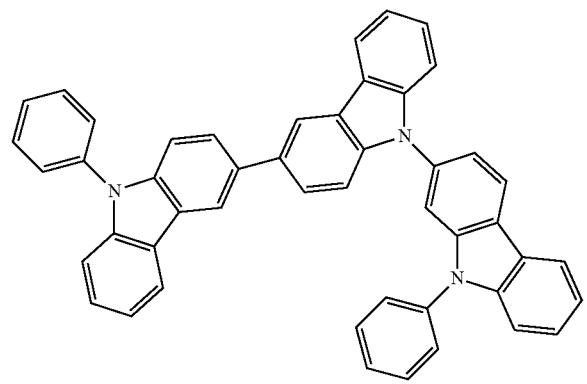
(H2-13)
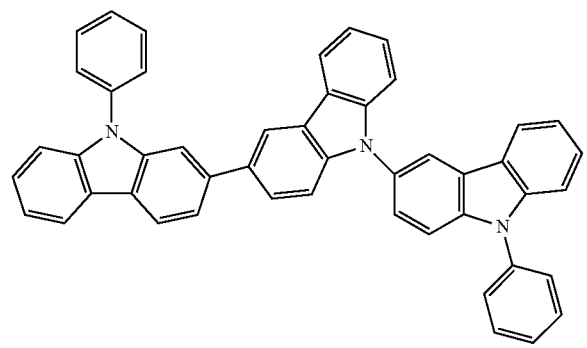
(H2-15)
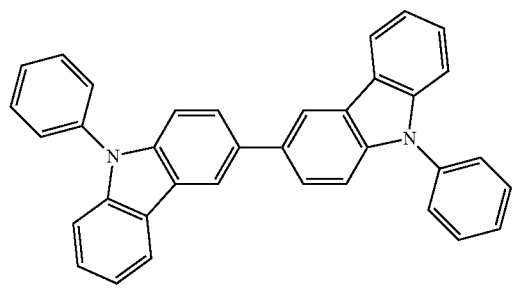
(H2-16)
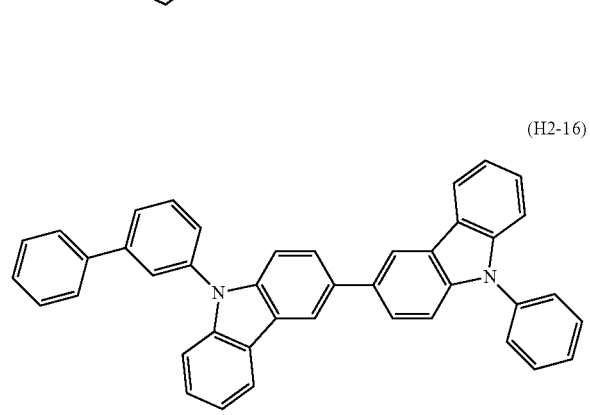
(H2-17)
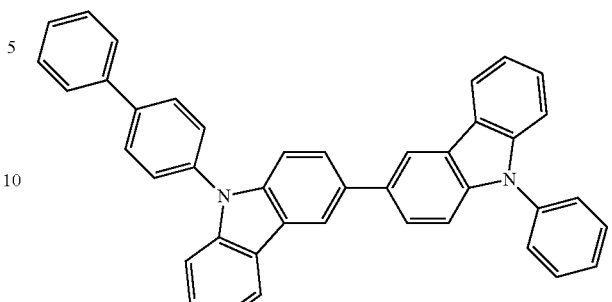
(H2-18)
(H2-19)
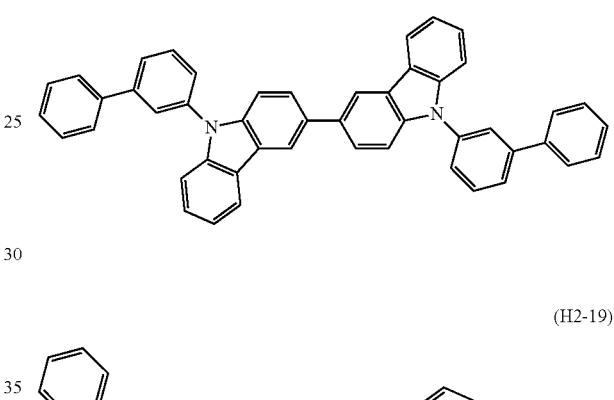
(H2-20)
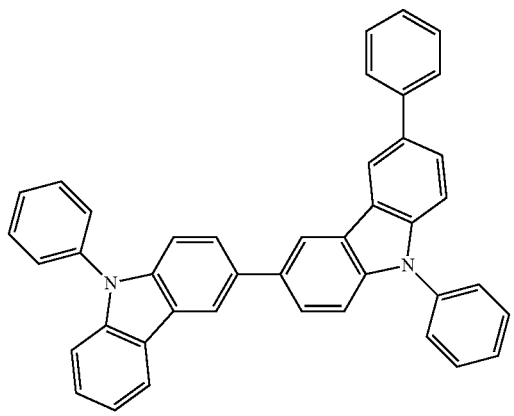

(H2-21)
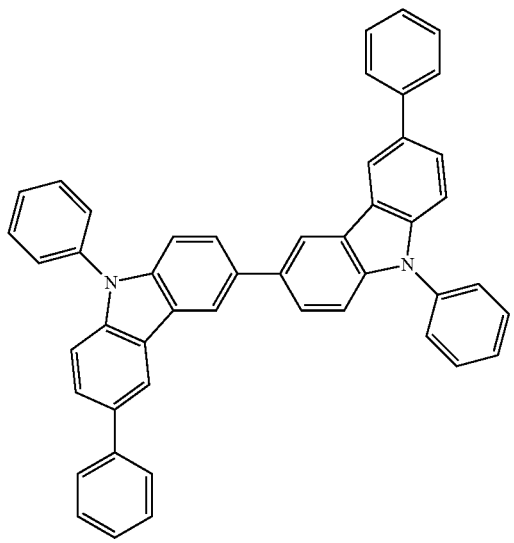
(H2-22)
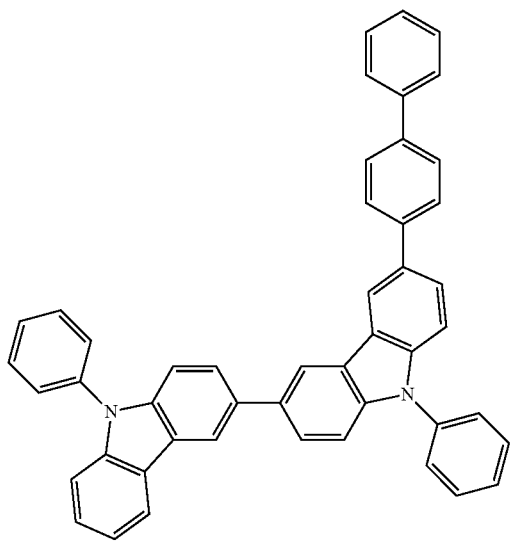
(H2-23)
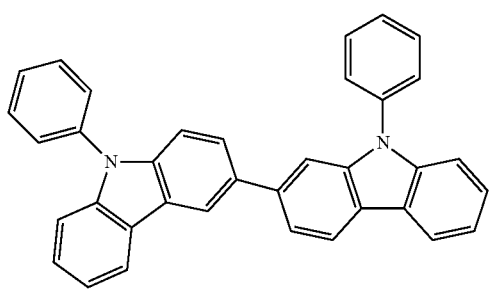
(H2-24)
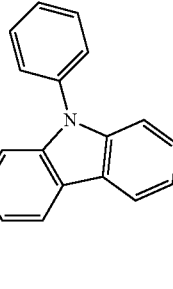
(H2-25)
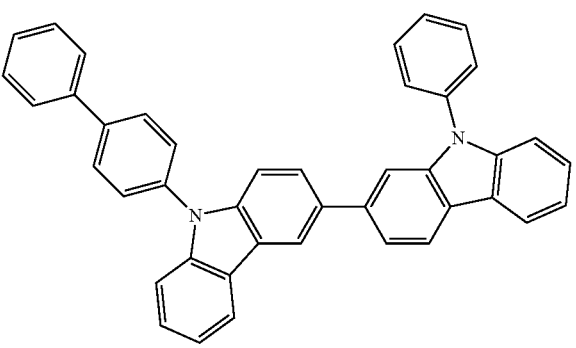
(H2-26)
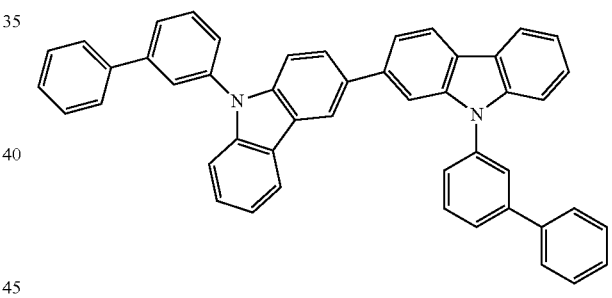
(H2-27)
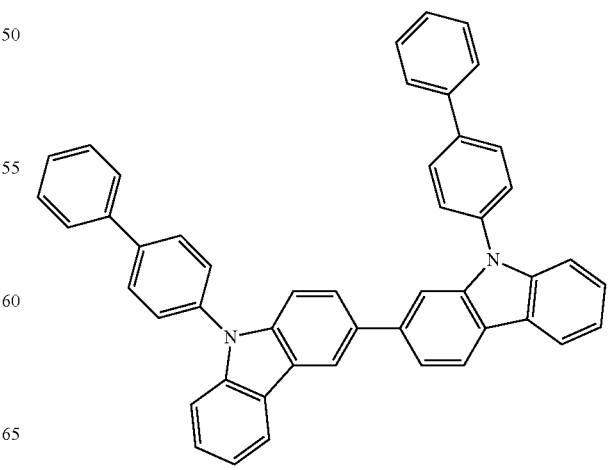

-continued
(H2-28)
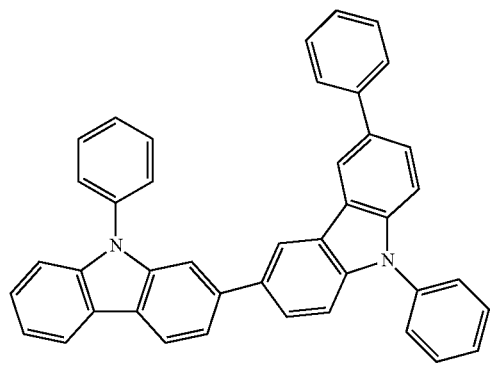
(H2-29)
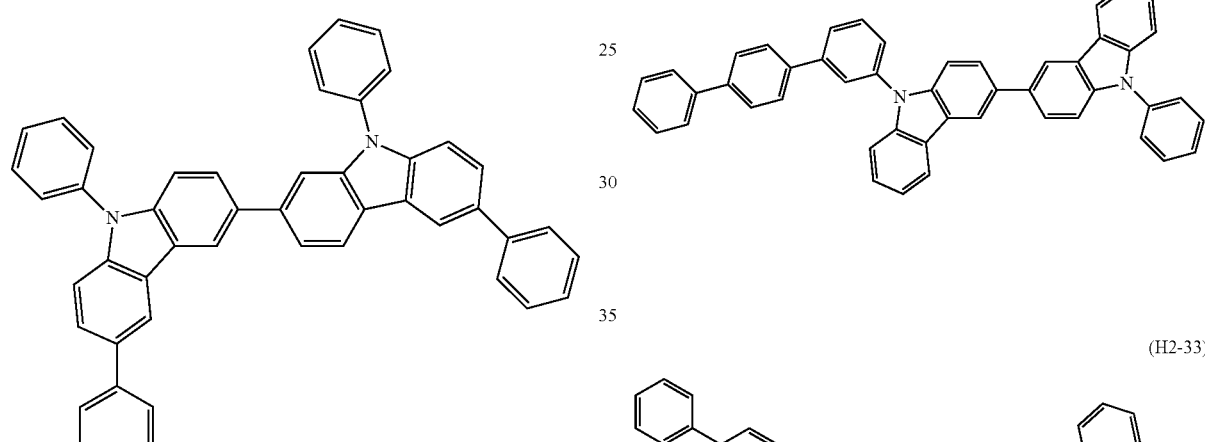
(H2-30)
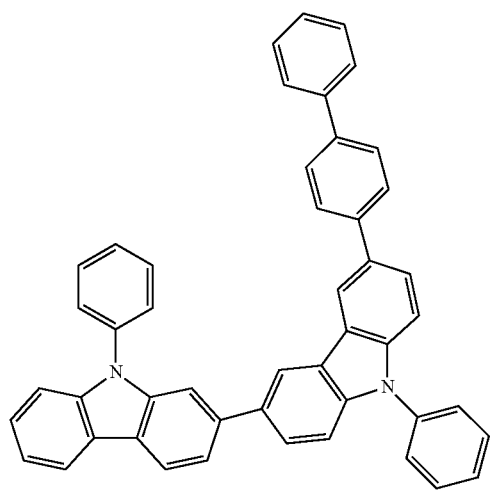
(H2-31)
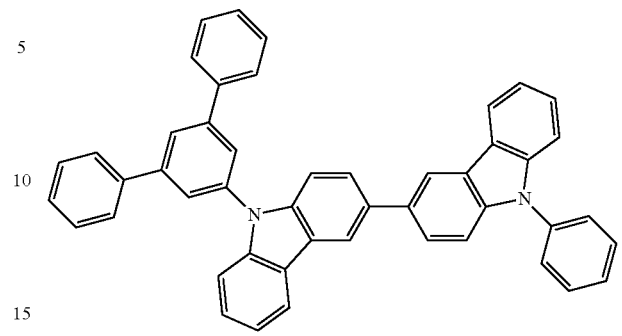
(H2-32)
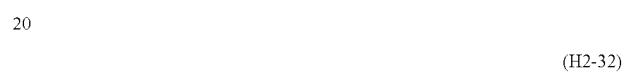
(H2-33)
(H2-34)
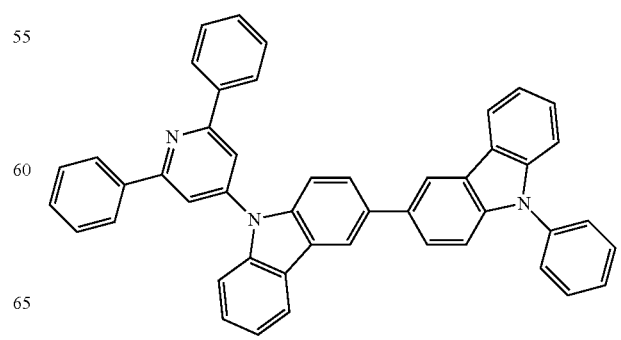

(H2-35)

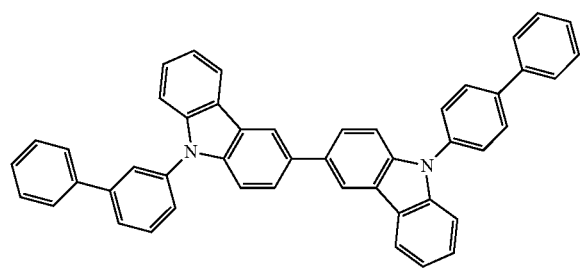

(H3-2)

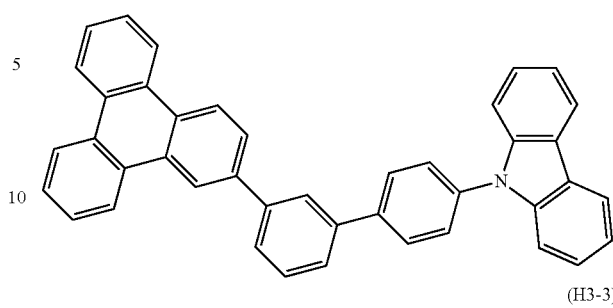

(H3-3)

(H3-1)

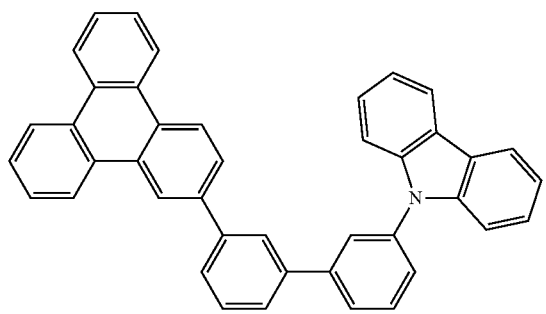

The first compound including a carbazole-based moiety other than the compound represented by Formula 9 is not limited to the above-described example compounds. For example, the first compound may be known carbazole derivatives disclosed in paragraphs to [0104] of US Patent Publication No. US2016/0093808, Japanese Patent Laid-Open Publication No. 2014-509067 and the like, which are herein incorporated by reference. The carbazole derivatives described in these references may also be used as a ground for corrections herein.

For example, the second compound may be compounds represented by Formulae Az1 to Az38 below:

Az1

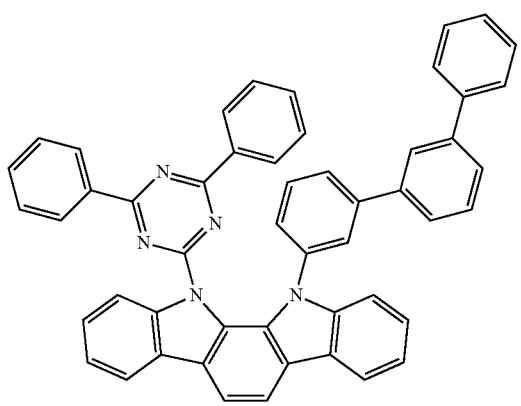

Az2

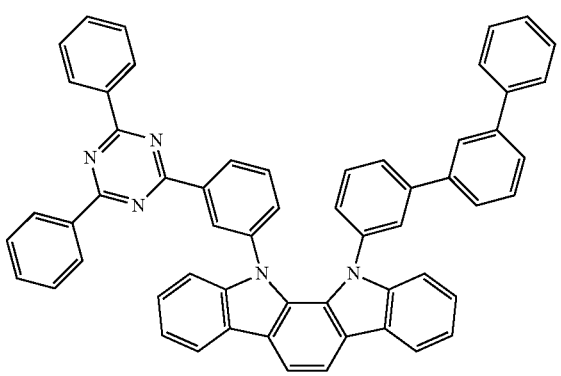

-continued
Az3
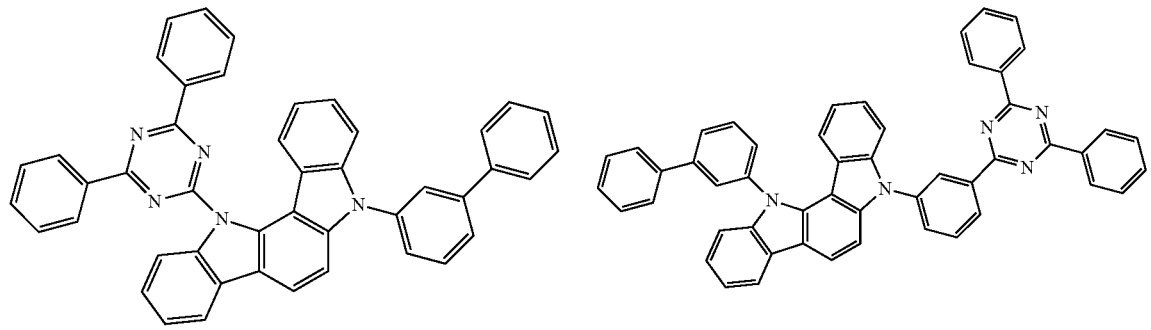
Az4
Az5
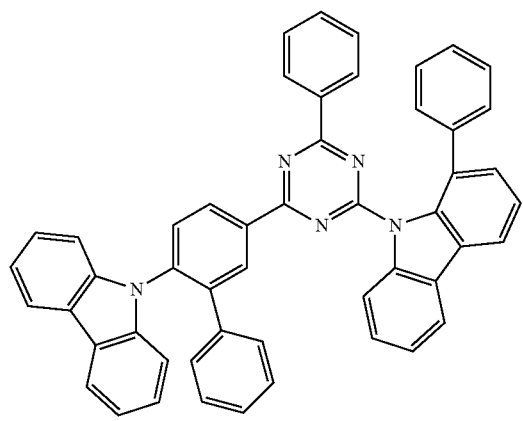
Az6
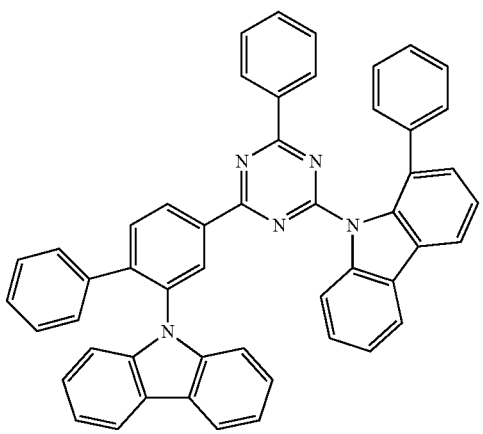
Az7
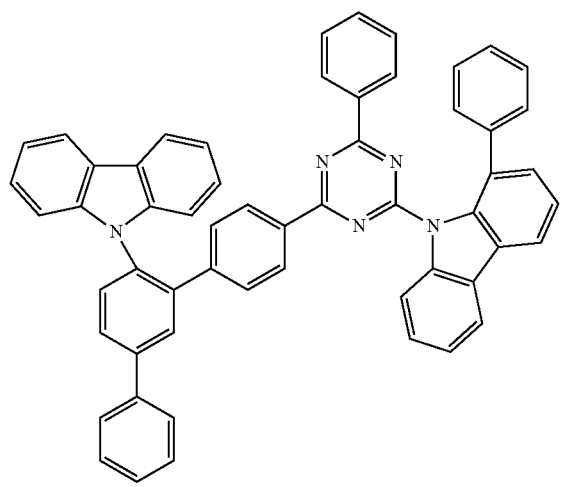
Az8
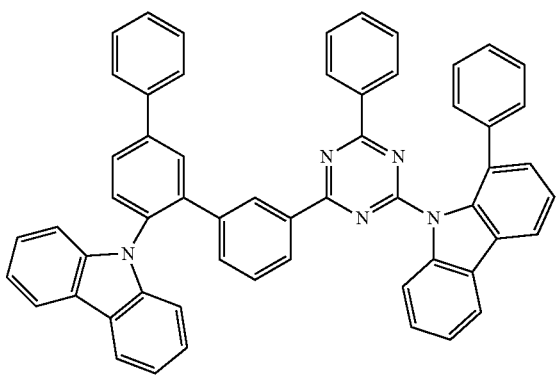

-continued
Az9
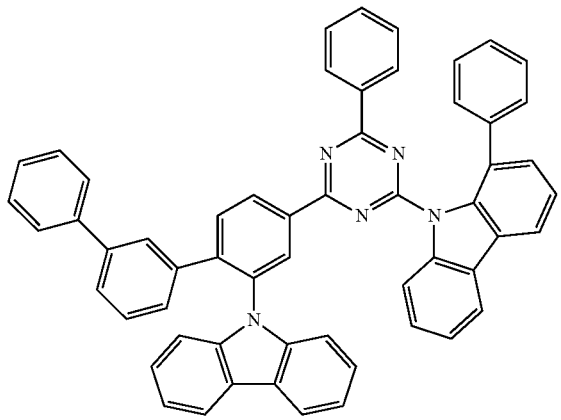
Az10
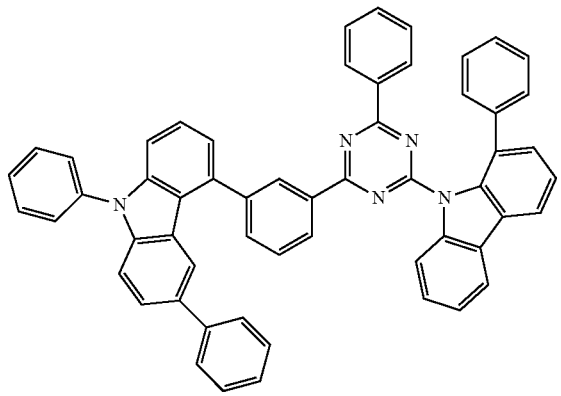
Az11
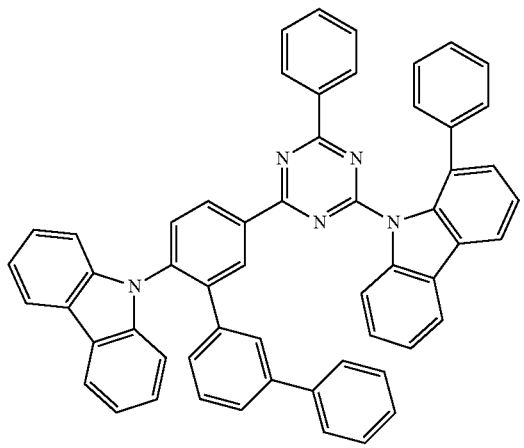
Az12
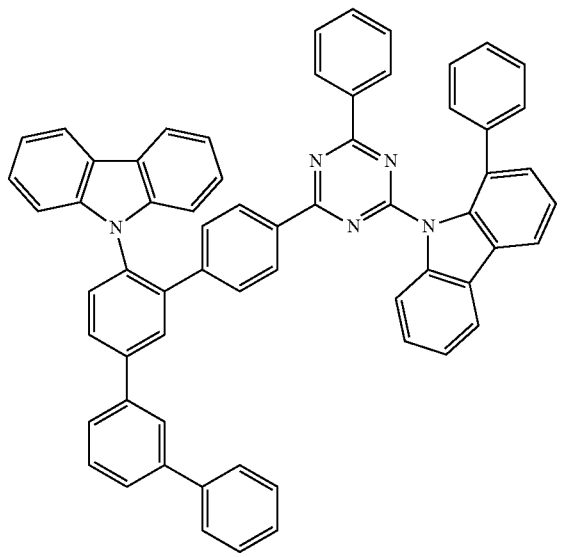
Az13
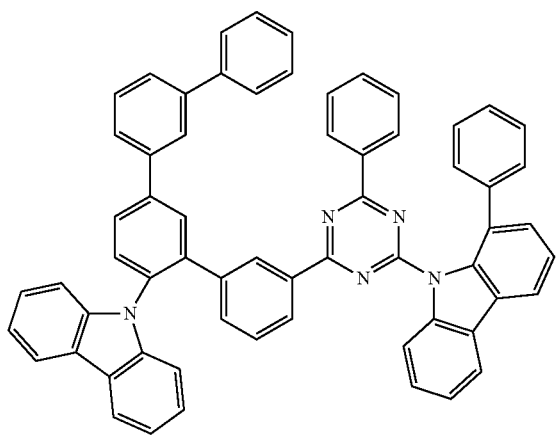
Az14
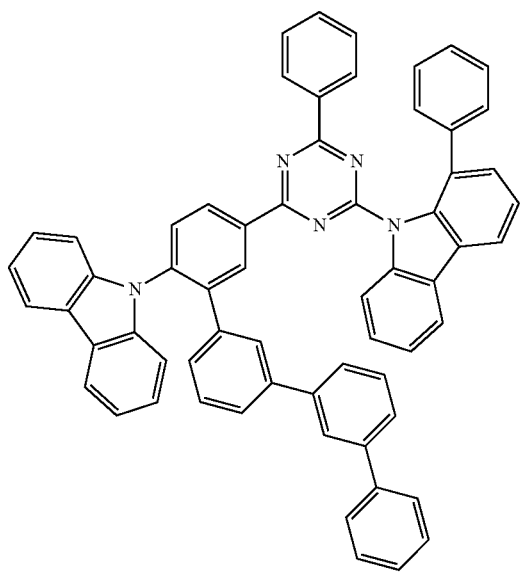

-continued
Az15
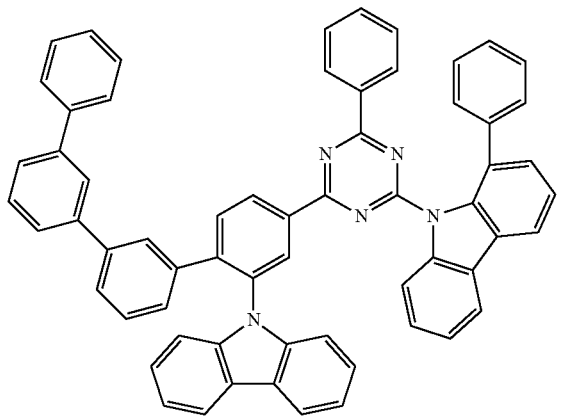
Az16
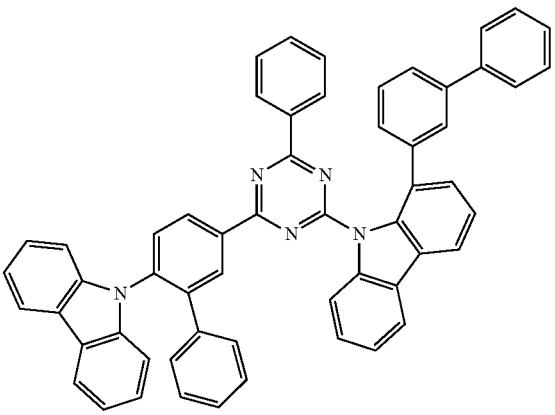
Az17
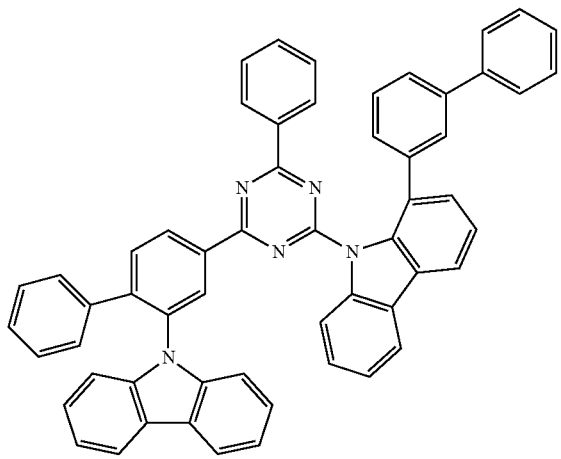
Az18
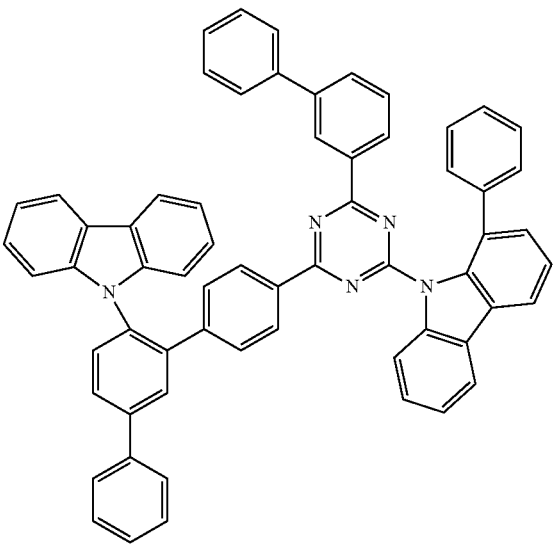
Az19
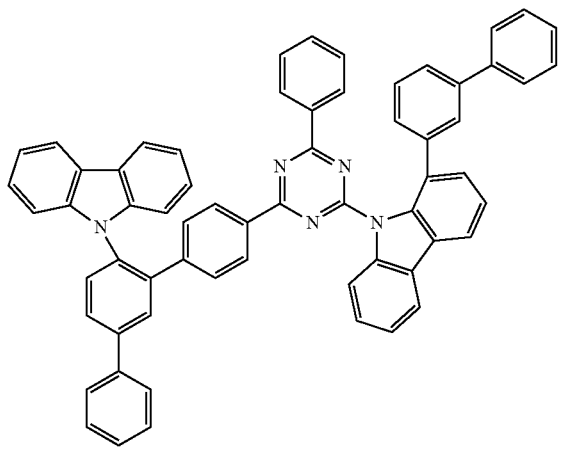
Az20
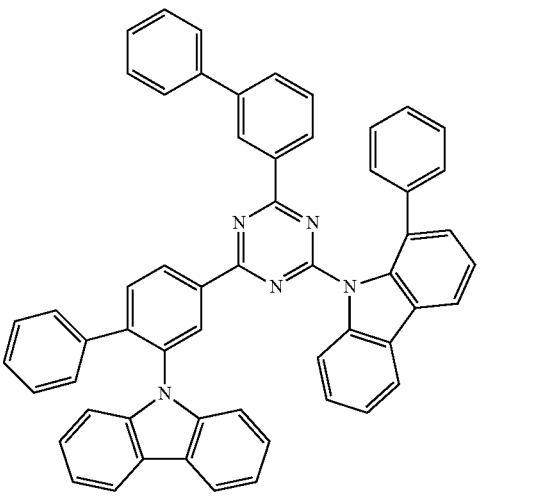

-continued
| Az21 | Az22 |
|---|---|
| 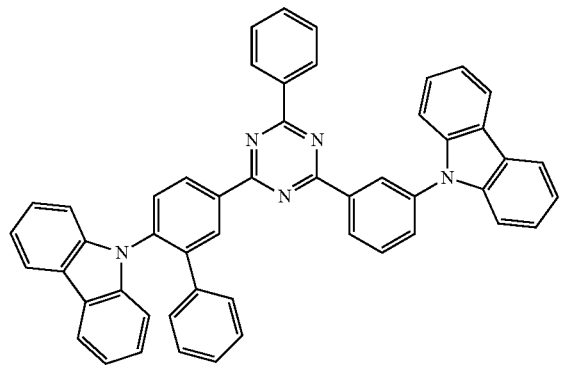 | 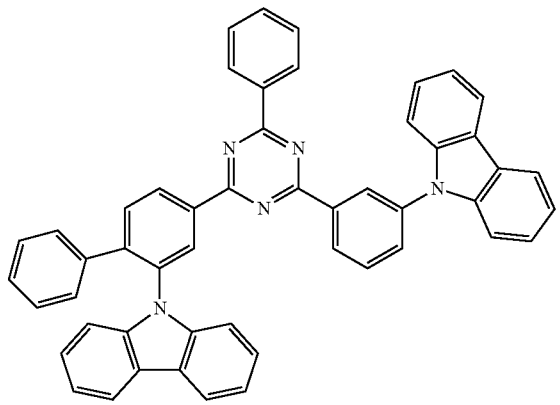 |
| Az23 | Az24 |
| 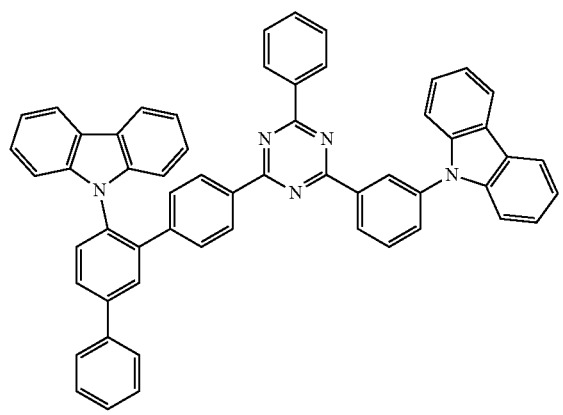 | 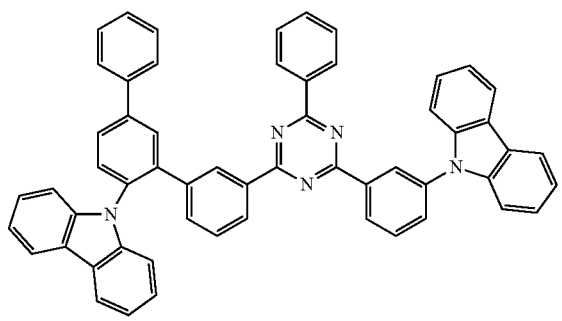 |
| Az25 | Az26 |
| 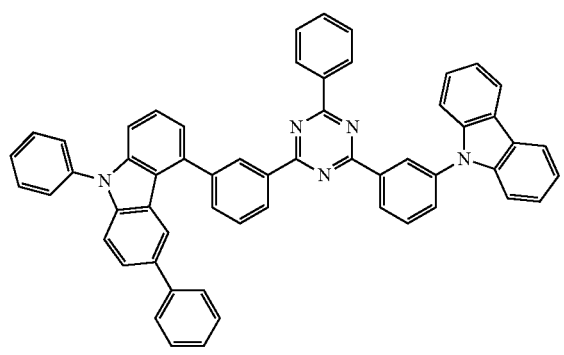 | 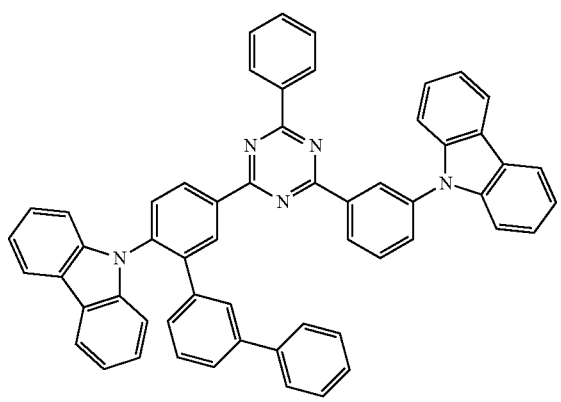 |

-continued
Az27
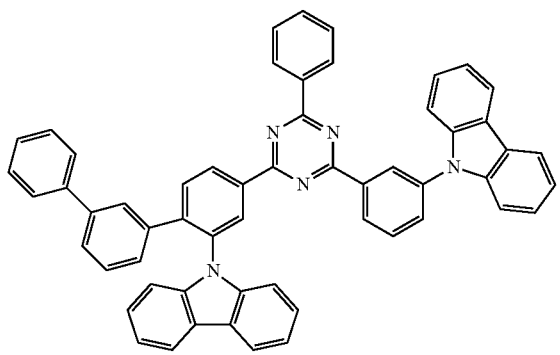
Az28
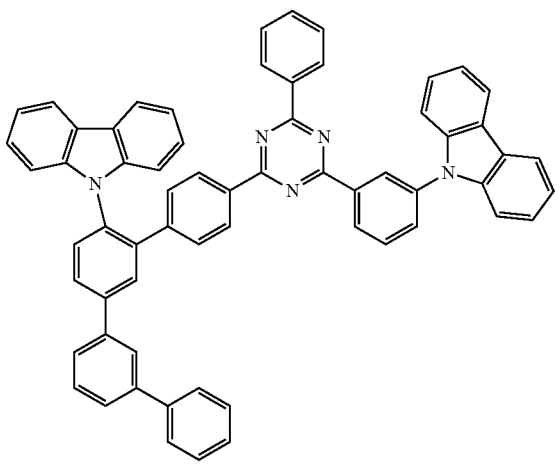
Az29
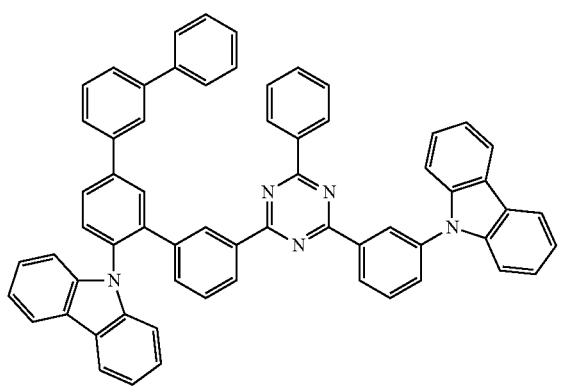
Az30
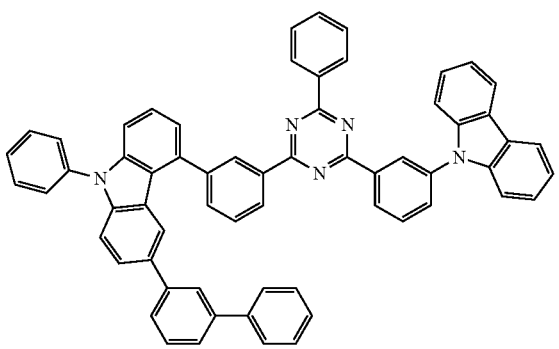
Az31
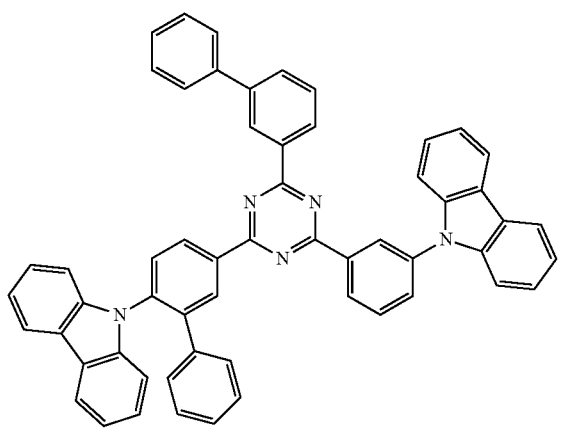
Az32
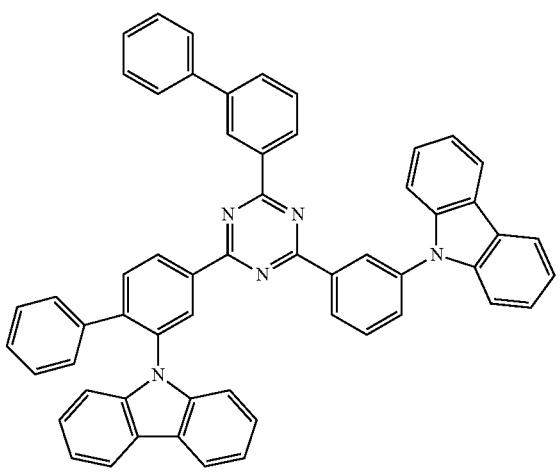

-continued
Az33
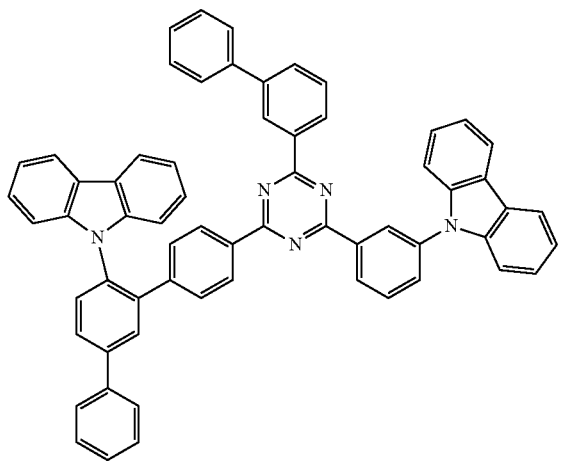
Az34
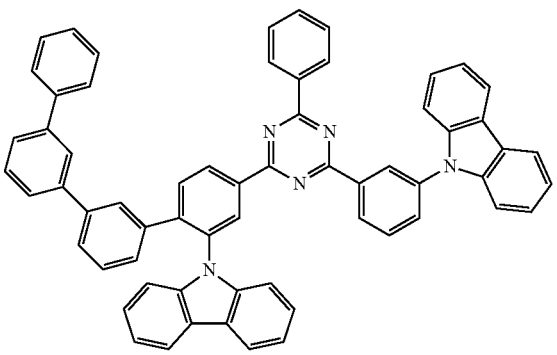
Az35
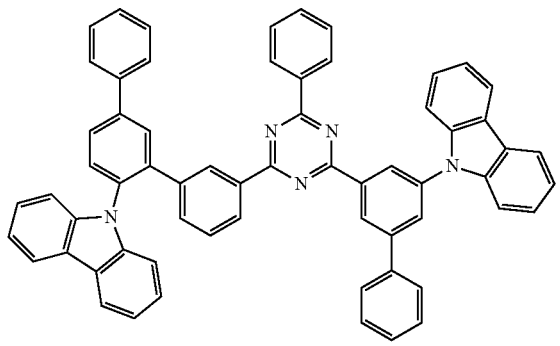
Az36
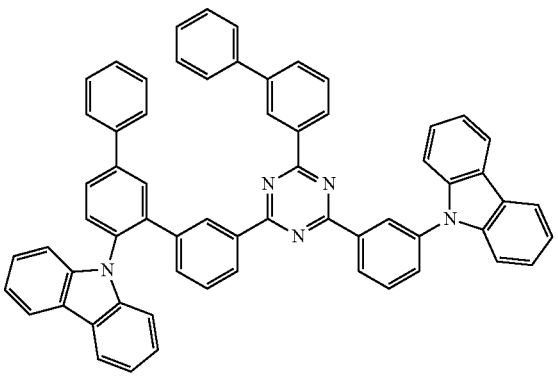
Az37
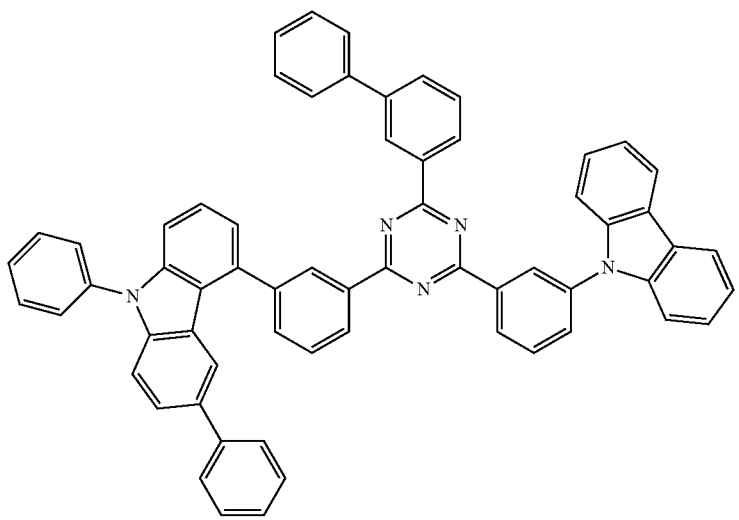

-continued

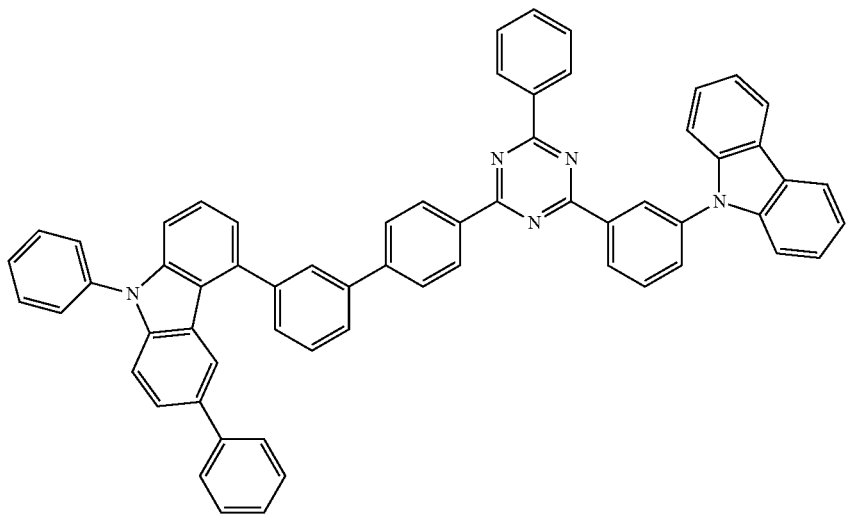

Az38

The first compound may have the lowest HOMO level, except for the luminescent material (dopant) among the compounds contained in the composition. Therefore, the first compound has a high hole injection capability and/or a high hole transport capability.

Accordingly, by adjusting the ratio of the first compound in the composition, the hole injection capability and/or hole transport capability of the composition may be controllable. Thus, the amount of holes in an emission layer of an organic light-emitting device including the composition and a hole density profile in the thickness direction of the emission layer may be easily controlled.

When the composition further includes the first compound, the difference (ΔHOMO) (hole trap depth) between the HOMO level ($HOMO_0$) of the heterocyclic compound represented by Formula 1 or 2 and the HOMO level ($HOMO_{Cz}$) of the first compound may be obtained from Equation 1. Herein, $HOMO_0$ and $HOMO_{Cz}$ are both negative.

Equation 1

$$\Delta HOMO = HOMO_{Cz} - HOMO_0$$

ΔHOMO may be, for example, about 0.05 eV to about 1.0 eV, for example, about 0.10 eV to about 0.8 eV, or, for example, about 0.15 eV to about 0.7 eV.

For example, the third compound is represented by Formula 11:

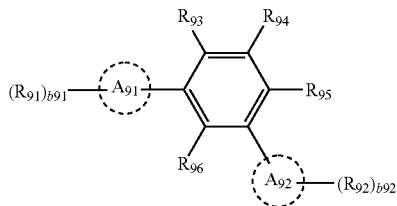

Formula 11

In Formula 11, $A_{91}$ and $A_{92}$ are each independently selected from a substituted or unsubstituted $C_5$-$C_{60}$ carbocyclic group, or a substituted or unsubstituted nitrogen-free $C_1$-$C_{60}$ heterocyclic group, $R_{91}$ to $R_{96}$ may each independently be selected from hydrogen, deuterium, halogen, a substituted or unsubstituted $C_1$-$C_{60}$ alkyl group, a substituted or unsubstituted $C_3$-$C_{60}$ cycloalkyl group, a substituted or unsubstituted $C_1$-$C_{60}$ heteroalkyl group, a substituted or unsubstituted $C_6$-$C_{60}$ aryl alkyl group, a substituted or unsubstituted $C_1$-$C_{60}$ alkoxy group, a substituted or unsubstituted $C_6$-$C_{60}$ aryloxy group, an amino group, a silyl group, a substituted or unsubstituted $C_2$-$C_{60}$ alkenyl group, a substituted or unsubstituted $C_3$-$C_{60}$ cycloalkenyl group, a substituted or unsubstituted $C_2$-$C_{60}$ heteroalkenyl group, a substituted or unsubstituted $C_2$-$C_{60}$ alkynyl group, a substituted or unsubstituted $C_6$-$C_{60}$ aryl group, a substituted or unsubstituted $C_1$-$C_{60}$ heteroaryl group, an acyl group, a carbonyl group, a carboxylic acid group, an ester group, a nitrite group, an isonitrile group, a sulfonyl group, a sulfinyl group, a phosphine group, and any combination thereof, b91 and b92 may each independently selected be an integer from 0 to 20.

For example, the third compound may be selected from a compound represented by Formulae H3-1 to H3-3 above and WG-1 below:

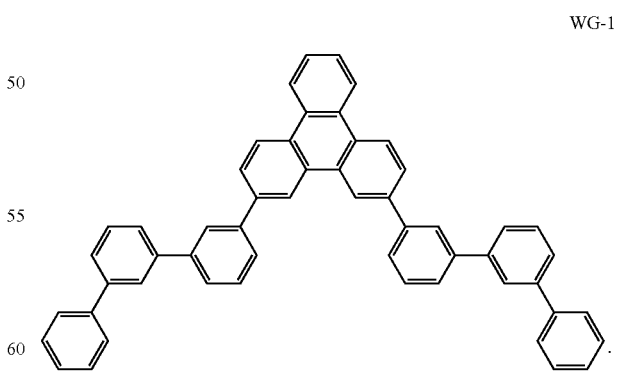

WG-1

FIG. 1 shows a diagram illustrating an exemplary energy level relationship between the heterocyclic compound represented by Formula 1 or 2 and the first compound including a carbazole group in the composition according to an embodiment; Referring to FIG. 1, it can be seen the preferred relationship between $HOMO_0$ and $HOMO_{Cz}$. Within this range, the luminescent efficiency and light-emission lifespan of the organic light-emitting device are further improved.

The second compound has the deepest LUMO level among the compounds contained in the composition. Therefore, the second compound has a high electron injection capability and/or a high electron transport capability.

Accordingly, by adjusting the ratio of the second compound in the composition, the electron injection capability and/or electron transport capability of the composition may be controllable. Thus, the amount of electrons in an emission layer of an organic light-emitting device including the composition and an electron density profile in the thickness direction of the emission layer may be easily controlled.

When the composition further includes the second compound, the difference ($\Delta$LUMO) (electron trap depth) between the LUMO level ($LUMO_0$) of the heterocyclic compound represented by Formula 1 or 2 and the LUMO level ($LUMO_{Azine}$) of the second compound may obtained from Equation 2. Herein, $LUMO_0$ and $LUMO_{Azine}$ are both negative.

Equation 2

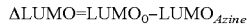

$\Delta LUMO = LUMO_0 - LUMO_{Azine}$ $\Delta$LUMO may be, for example, about 0.05 eV to about 1.0 eV, for example, about 0.05 eV to about 0.5 eV, or, for example, about 0.05 eV to about 0.3 eV.

Figure 2:
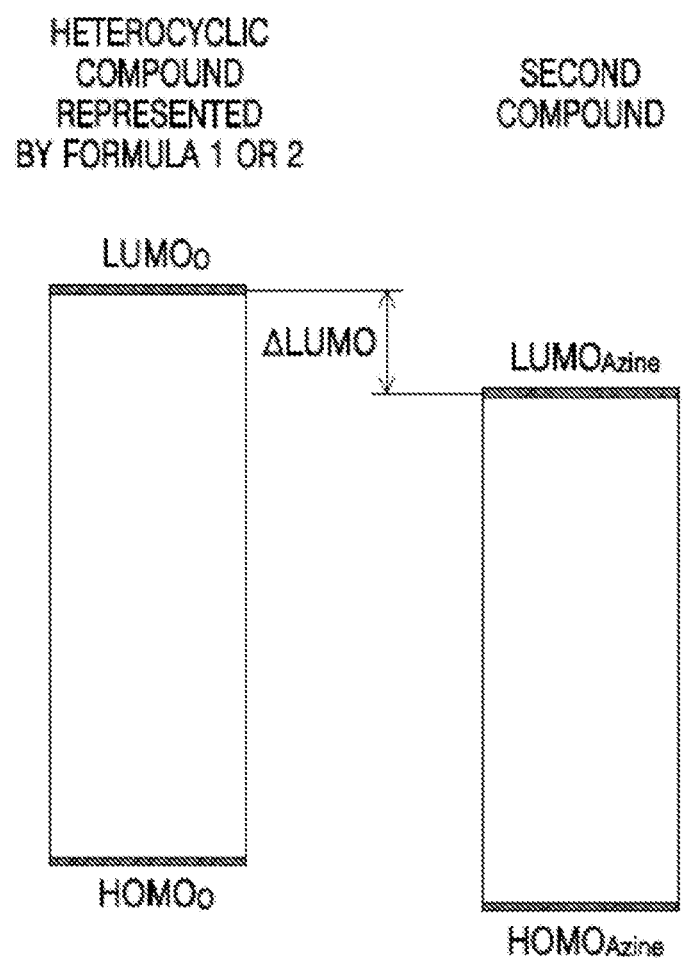
FIG. 2 shows a diagram illustrating an exemplary energy level relationship between a heterocyclic compound represented by Formula 1 or 2 and a second compound including an azine group in a composition according to an embodiment.

FIG. 2 shows a diagram illustrating an exemplary energy level relationship between the heterocyclic compound represented by Formula 1 or 2 and the second compound including an azine group in the composition according to an embodiment. Referring to FIG. 2, it can be seen the preferred relationship between $LUMO_0$ and $LUMO_{Azine}$. Within this range, the luminescent efficiency and light-emission lifespan of the organic light-emitting device are further improved.

When the composition includes the heterocyclic compound and the first compound, the composition may be excellent in terms of the hole injection capability and/or the hole transport capability, and the composition may be used in a hole injection layer, hole transport layer and/or emission layer of an organic light-emitting device.

When the composition includes the heterocyclic compound and the second compound, the composition may be excellent in terms of the electron injection capability and/or the electron transport capability, and the composition may be used in an electron injection layer, electron transport layer and/or emission layer of an organic light-emitting device.

When the composition includes the heterocyclic compound, the first compound, and the second compound, the composition may be excellent in terms of the hole injection capability, the hole transport capability, the electron injection capability and/or the electron transport capability, and the composition may be used in a hole injection layer, hole transport layer, electron injection layer, electron transport layer and/or emission layer of an organic light-emitting device.

In one or more embodiments, the composition may include the first compound and the second compound, but embodiments of the present disclosure are not limited. When the composition includes the first compound and the second compound together, the control of the hole and the control of the electron may be performed independently. Therefore, a high level of process convenience may be provided in the process of optimizing the performance of the organic light-emitting device using such a composition.

The heterocyclic compound represented by Formula 2 in the composition may be a wide band gap host. Due to the heterocyclic compound represented by Formula 2, the luminescent efficiency and light-emission lifespan of the organic light-emitting device may be further improved.

The composition may further include a luminescent material.

The luminescent material is not particularly limited as long as it has a luminescent function, and may be a fluorescent dopant, a phosphorescent dopant, a quantum dot, or the like.

The fluorescent dopant may be a compound capable of emitting light from a singlet exciton, and examples thereof include a perylene and a derivative thereof, a rubrene and a derivative thereof, a coumarin and a derivative thereof, and a 4-dicyanomethylene-2-(p-dimethylaminostyryl)-6-methyl-4H-pyran (DCM) and a derivative thereof, but embodiments of the present disclosure are not limited thereto.

The phosphorescent dopant may be a compound capable of emitting light from a triplet exciton, and may be an organometallic compound. For example, phosphorescent dopant may be an iridium complex, such as bis[2-(4,6-difluorophenyl)pyridinate]picolinate iridium (III) (Flrpic), bis(1-phenylisoquinoline)(acetylacetonate) iridium (III) (Ir(piq)$_2$(acac)), tris(2-phenylpyridine) iridium (III) (Ir(ppy)$_3$), tris(2-(3-p-xylyl)phenyl)pyridine iridium (III) (dopant), or the like, an osmium complex, or a platinum complex, but embodiments of the present disclosure are not limited thereto.

For example, the phosphorescent dopant may be a phosphorescent platinum group metallic complex. The platinum group metal is referred as a generic term of ruthenium (Ru), rhodium (Rh), palladium (Pd), osmium (Os), iridium (Ir), and platinum (Pt). In particular, a phosphorescent iridium (Ir) complex and a phosphorescent platinum (Pt) complex are more preferable.

For example, the phosphorescent dopant may include one or more ligands groups represented by Formulae L1 to L17 below:

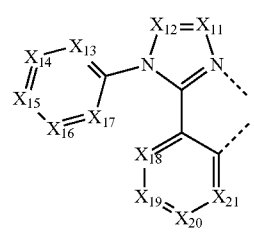

L1

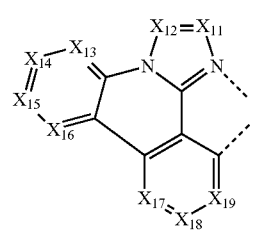

L2

-continued
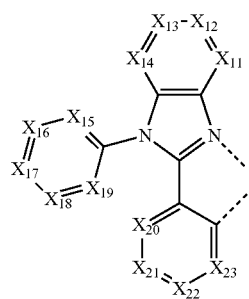 L3
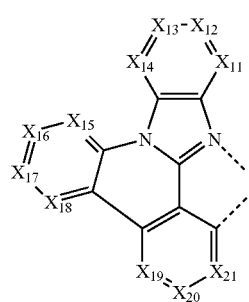 L4
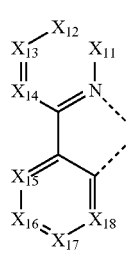 L5
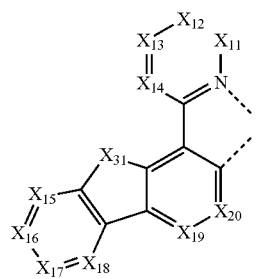 L6
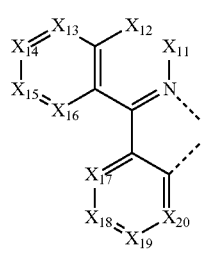 L7
-continued
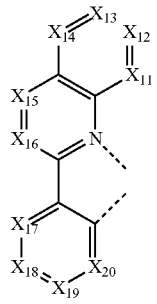 L8
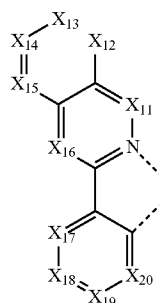 L9
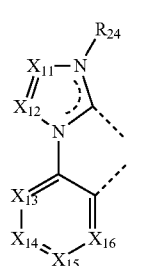 L10
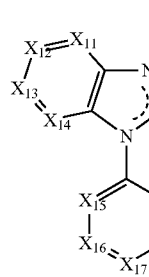 L11
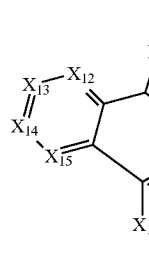 L12
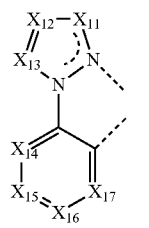 L13

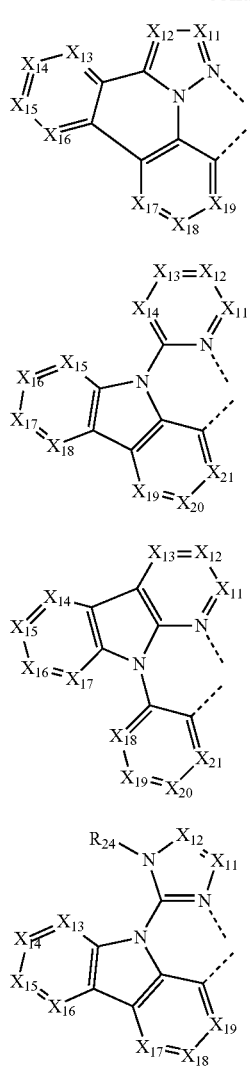

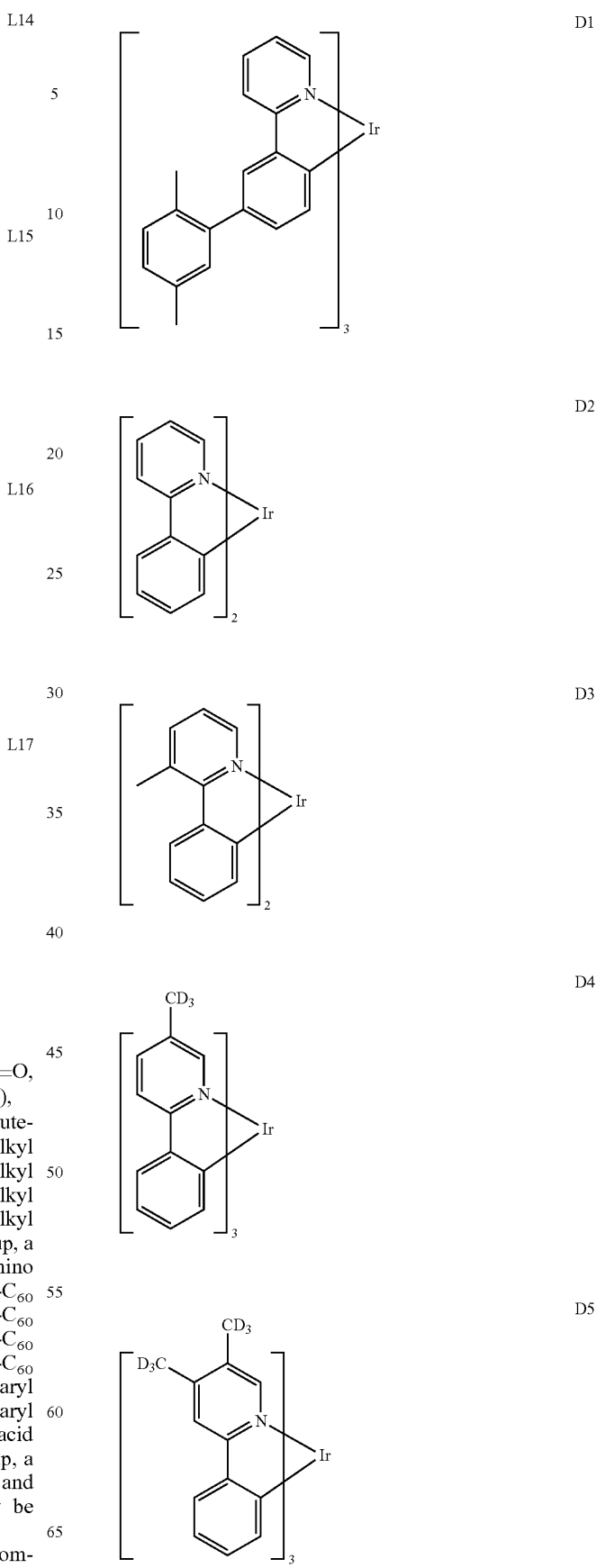

In Formulae L1 to L17, $X_{11}$ to $X_{23}$ may each independently be $C(R_{21})$ or N, $X_{31}$ may be $B(R_{22})$, $N(R_{22})$, $P(R_{22})$, O, S, Se, C=O, S=O, $SO_2$, $C(R_{22})(R_{23})$, $Si(R_{22})(R_{23})$, or $Ge(R_{22})(R_{23})$, $R_{21}$ to $R_{24}$ may each independently be hydrogen, deuterium, halogen, a substituted or unsubstituted $C_1$-$C_{60}$ alkyl group, a substituted or unsubstituted $C_3$-$C_{60}$ cycloalkyl group, a substituted or unsubstituted $C_1$-$C_{60}$ heteroalkyl group, a substituted or unsubstituted $C_7$-$C_{60}$ aryl alkyl group, a substituted or unsubstituted $C_1$-$C_{60}$ alkoxy group, a substituted or unsubstituted $C_6$-$C_{60}$ aryloxy group, an amino group, a silyl group, a substituted or unsubstituted $C_2$-$C_{60}$ alkenyl group, a substituted or unsubstituted $C_3$-$C_{60}$ cycloalkenyl group, a substituted or unsubstituted $C_2$-$C_{60}$ heteroalkenyl group, a substituted or unsubstituted $C_2$-$C_{60}$ alkynyl group, a substituted or unsubstituted $C_6$-$C_{60}$ aryl group, a substituted or unsubstituted $C_1$-$C_{60}$ heteroaryl group, an acyl group, a carbonyl group, a carboxylic acid group, an ester group, a nitrite group, an isonitrile group, a sulfonyl group, a sulfinyl group, or a phosphine group, and any two adjacent groups among $R_{21}$ to $R_{24}$ may be condensed or combined to each other to form a ring.

For example, the phosphorescent dopant may be of Compounds D1 to D143 below:

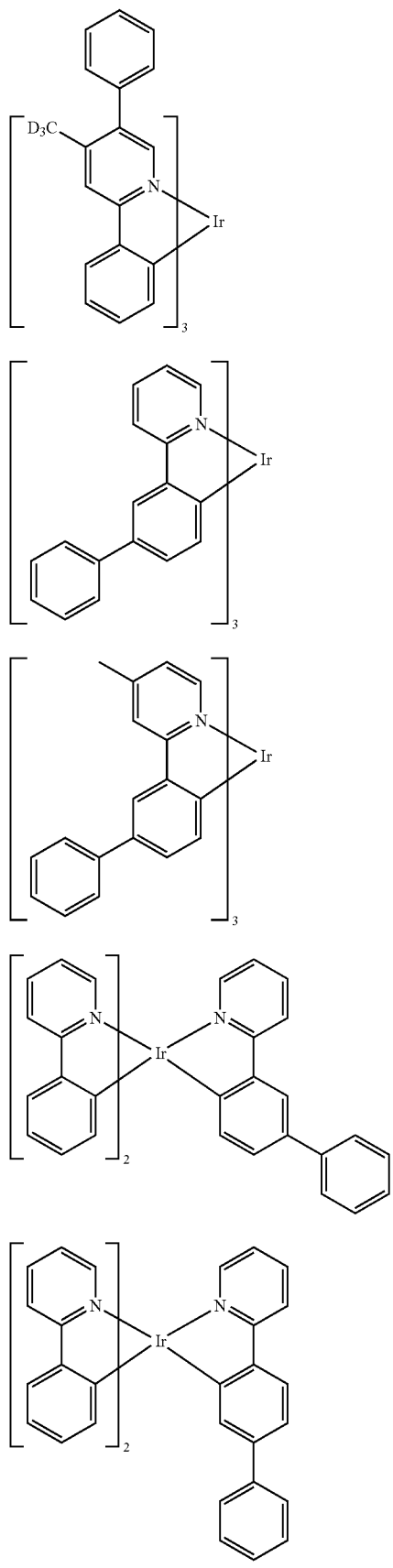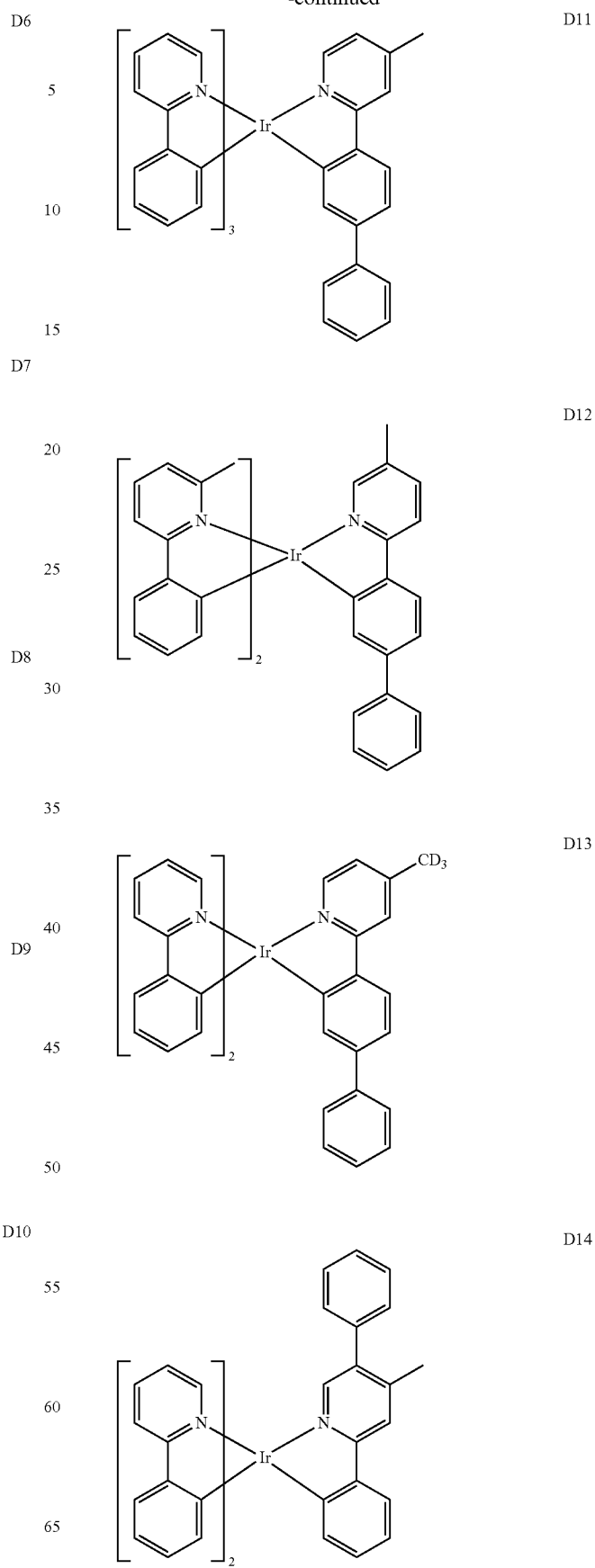

D15 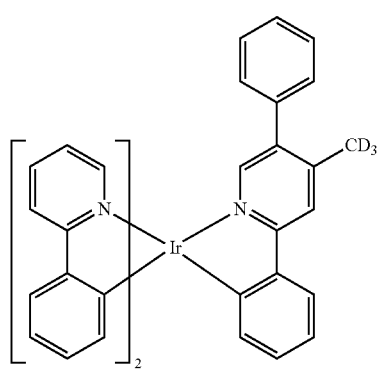
D16 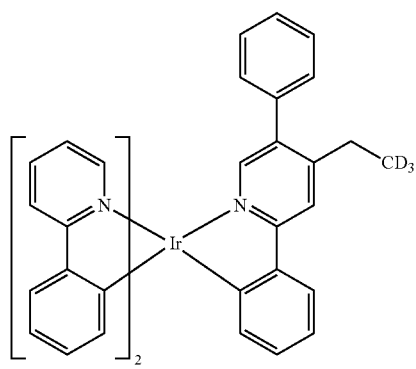
D17 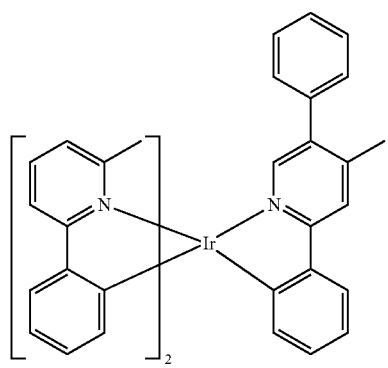
D18 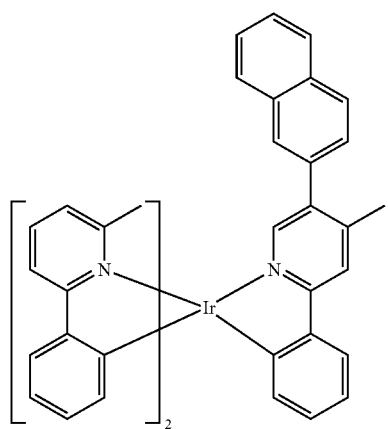
D19 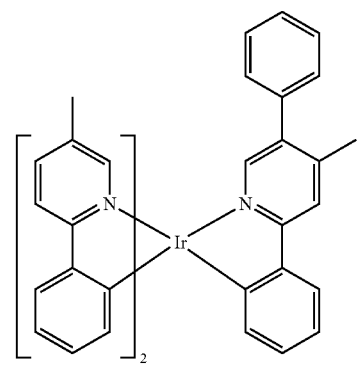
D20 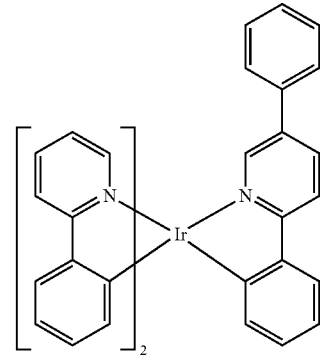
D21 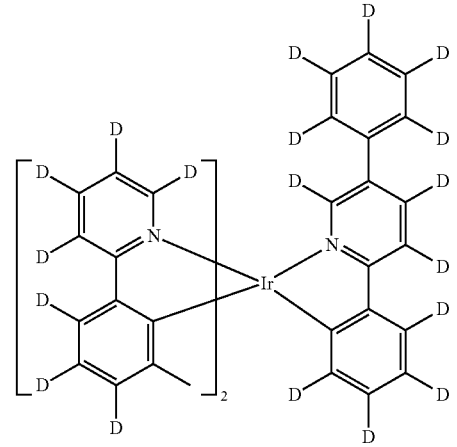
D22 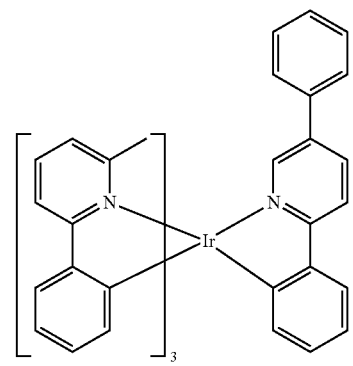

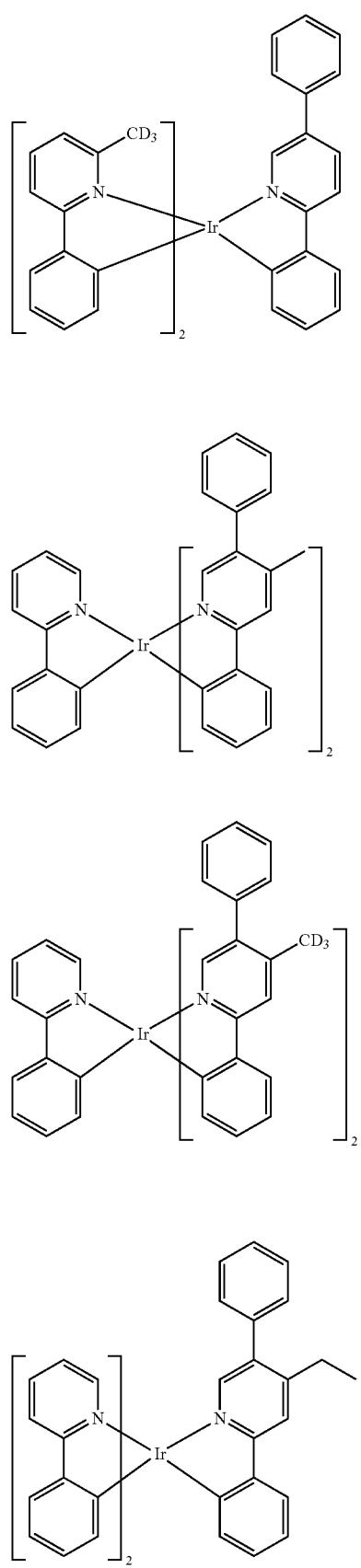
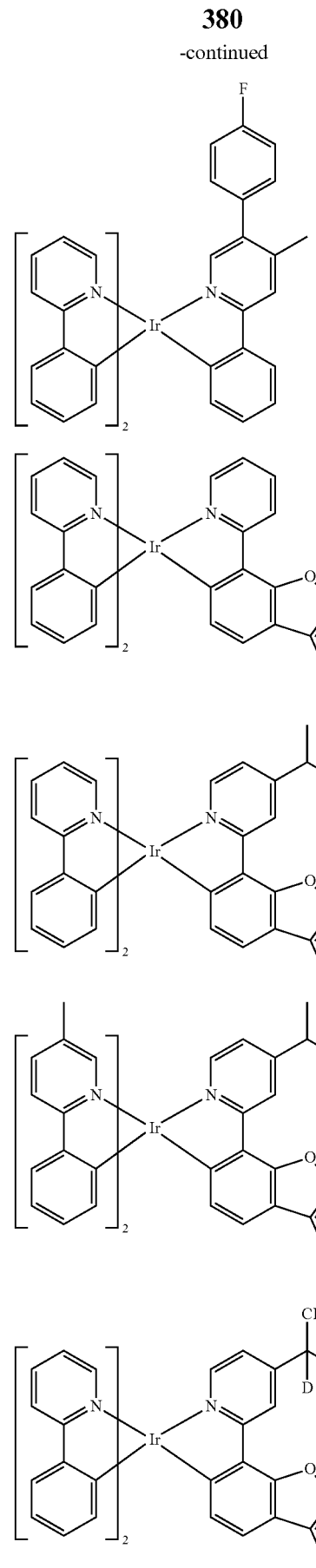

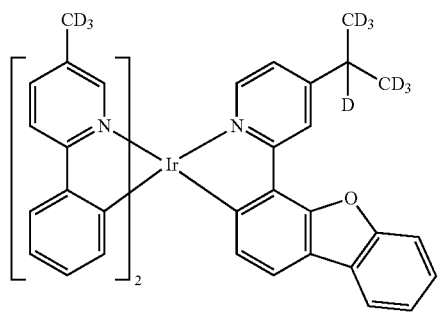
D32
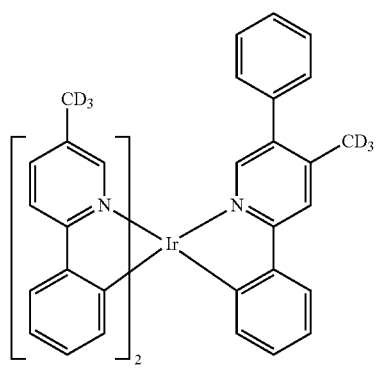
D33
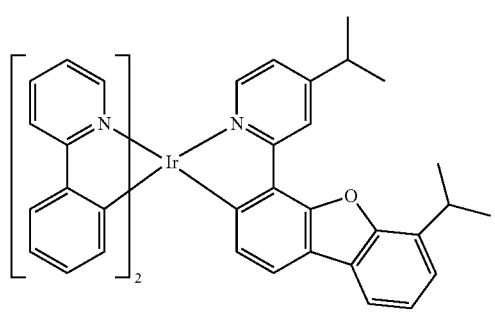
D34
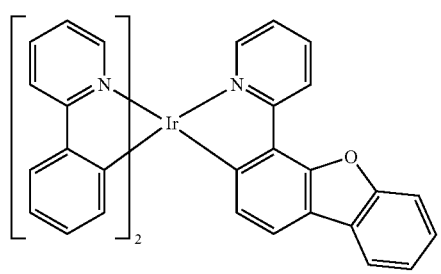
D35
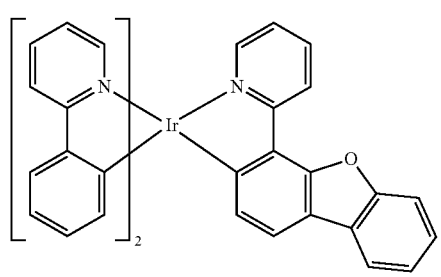
D36
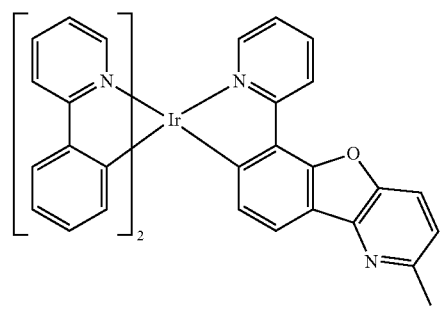
D37
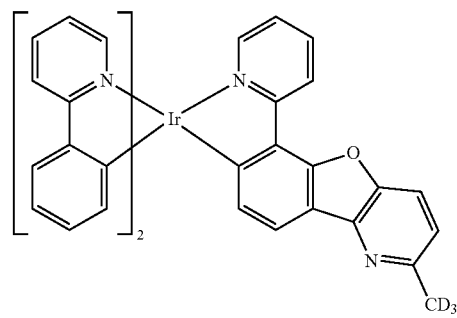
D38
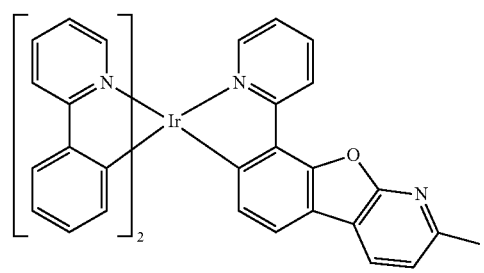
D39
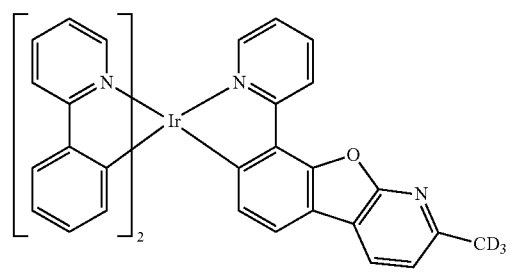
D40
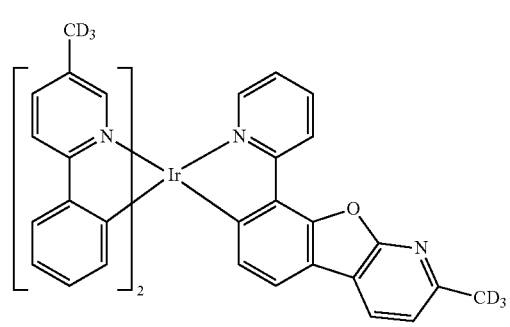
D41

-continued
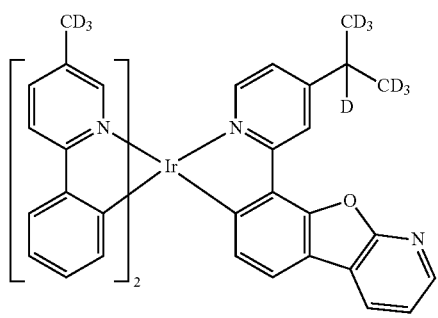
D42
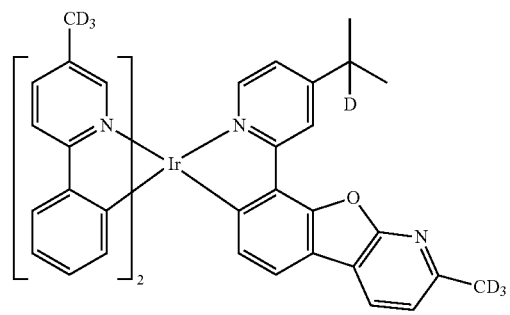
D46
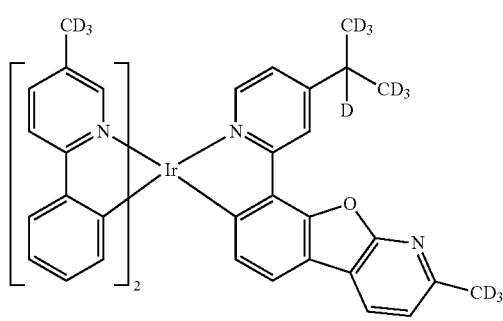
D43
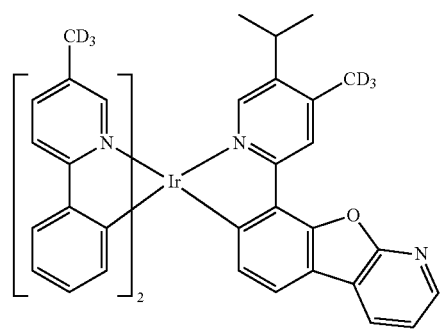
D47
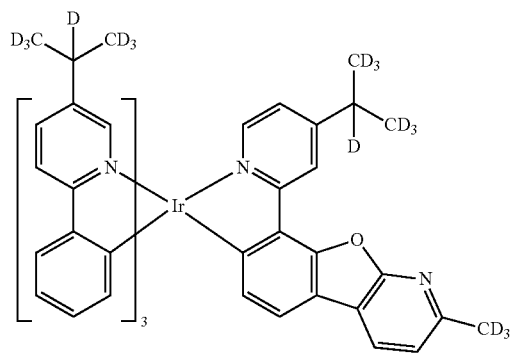
D44
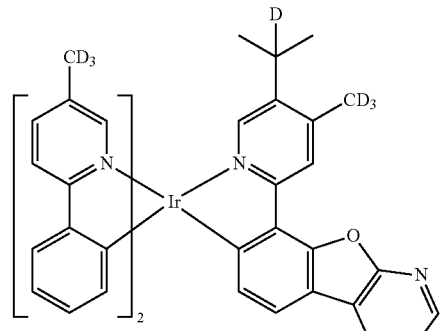
D48
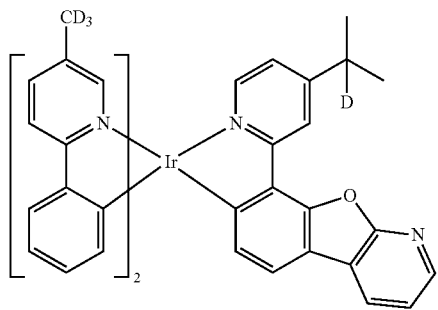
D45
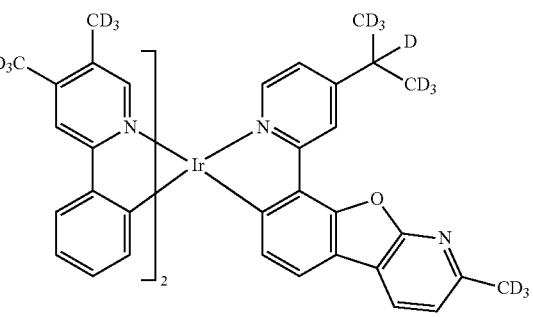
D49

D50 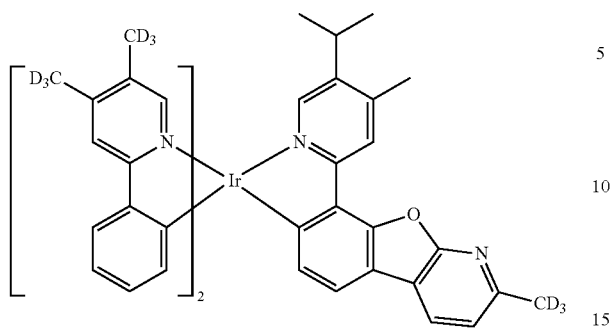
D54 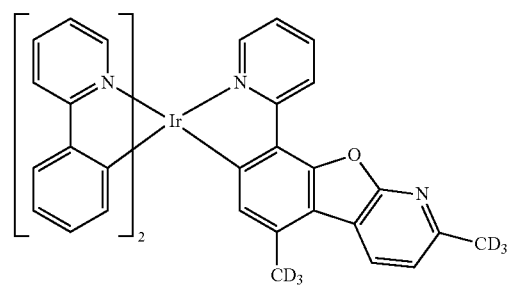
D51 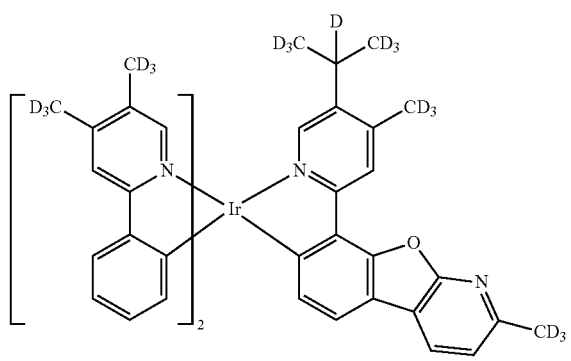
D55 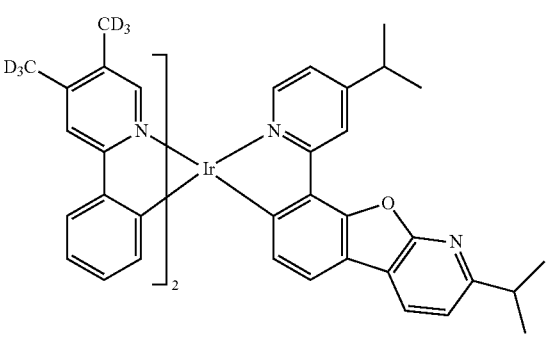
D52 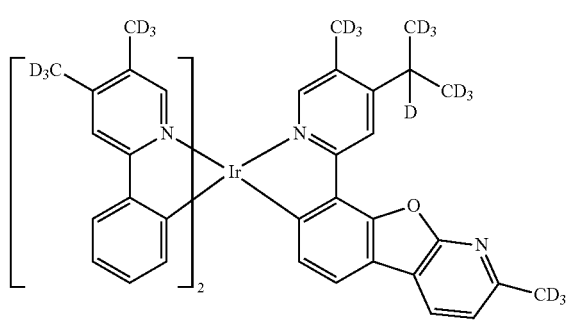
D56 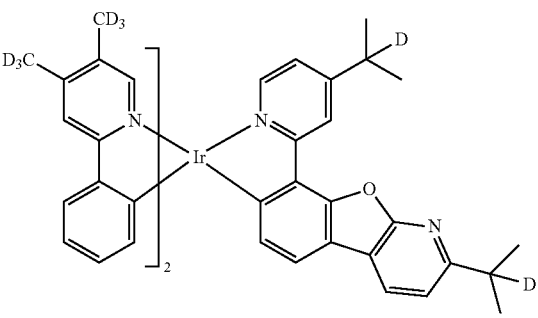
D53 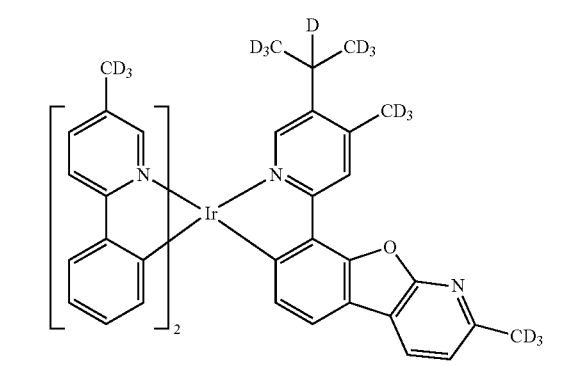
D57 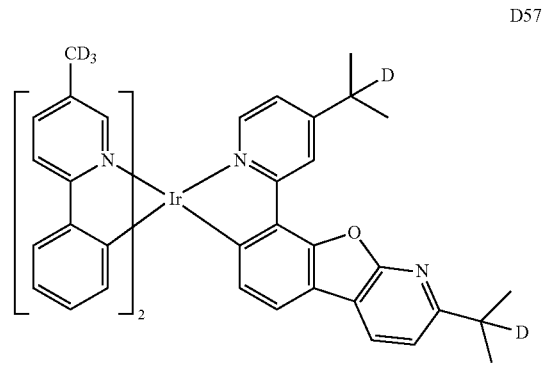

D58
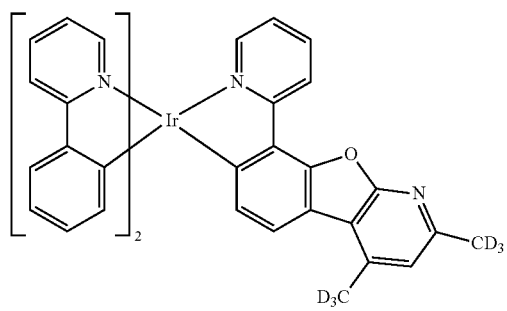
D59
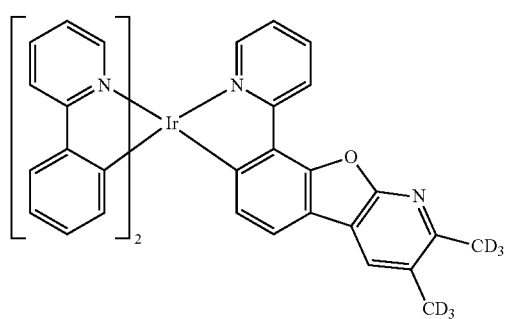
D60
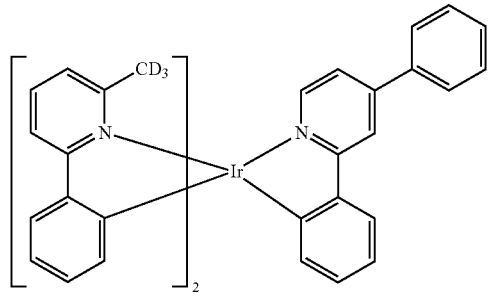
D61
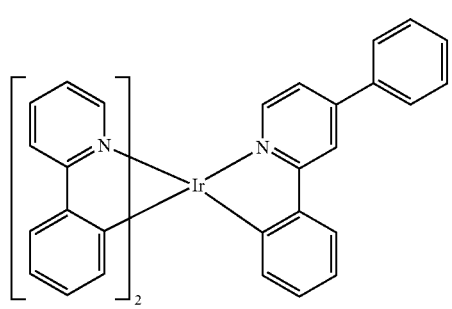
D62
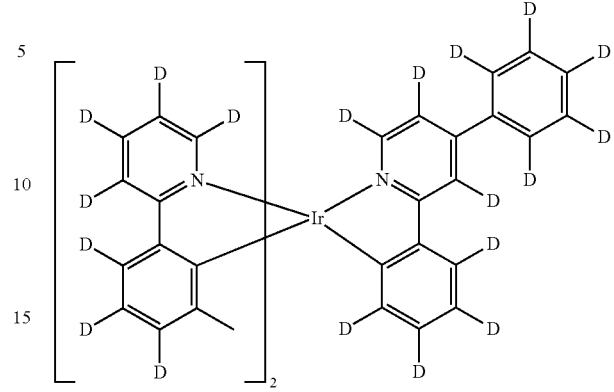
D63
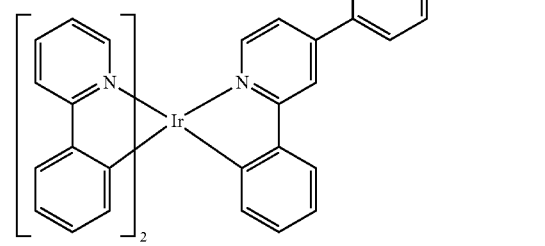
D64
D65
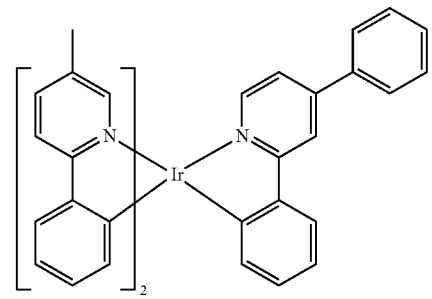
D66
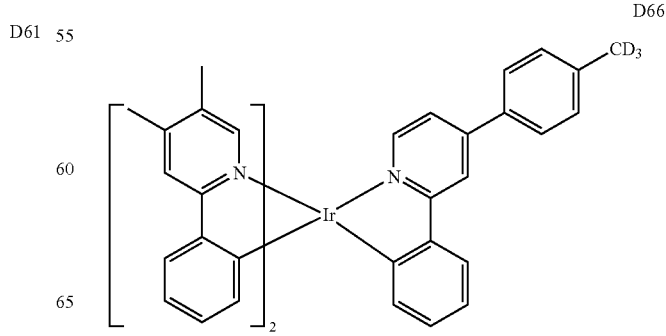

D67
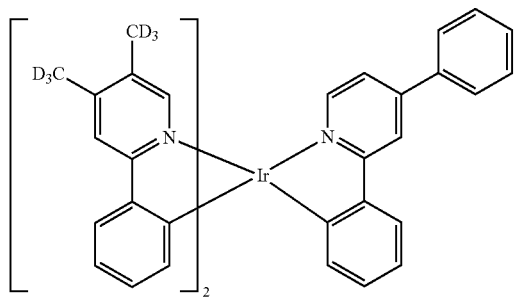
D68
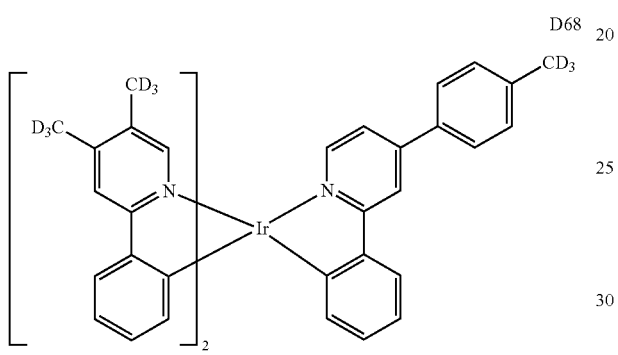
D69
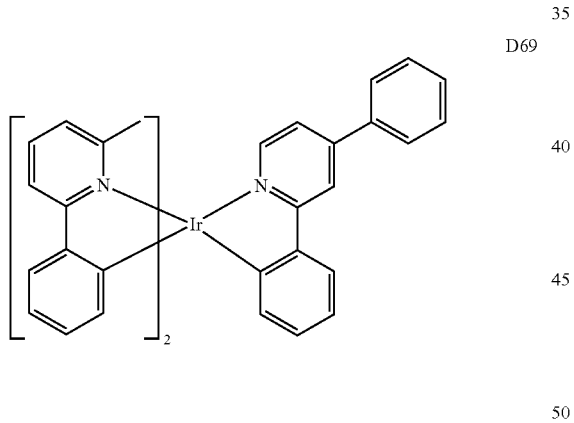
D70
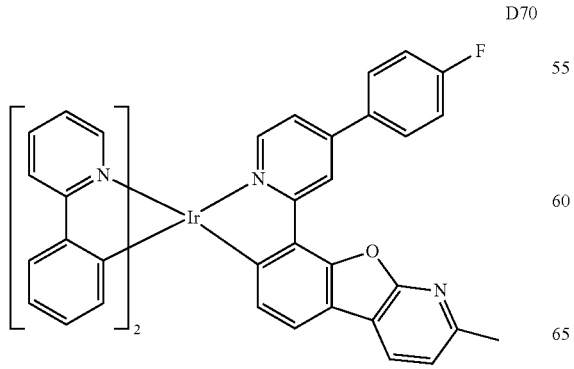
D71
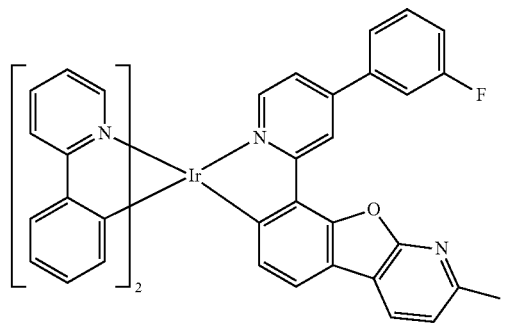
D72
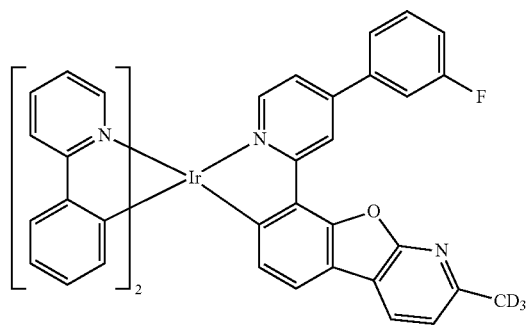
D73
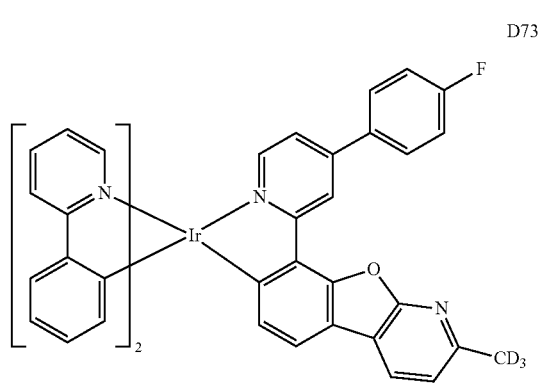
D74
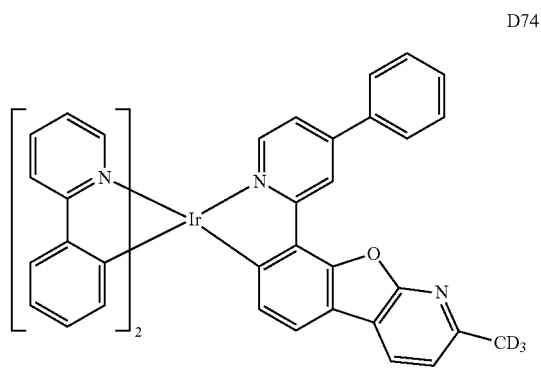

D75
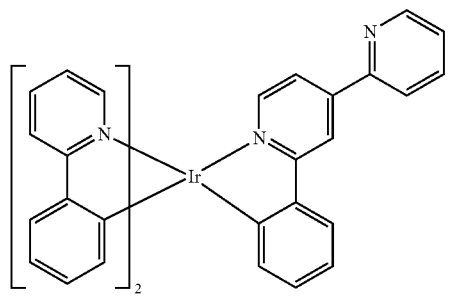
D76
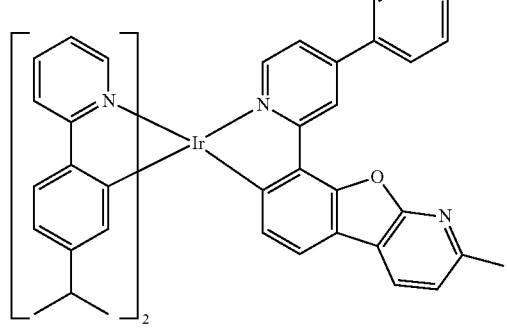
D77
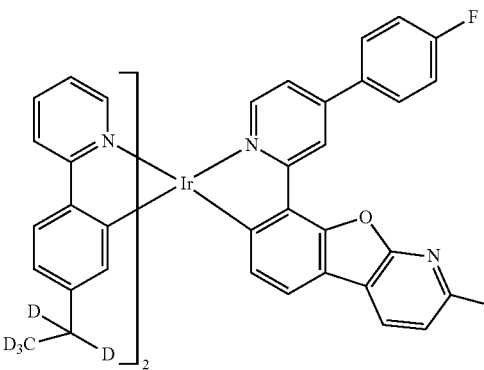
D78
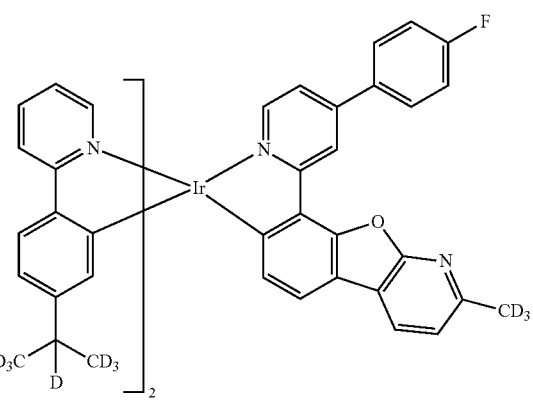
D79
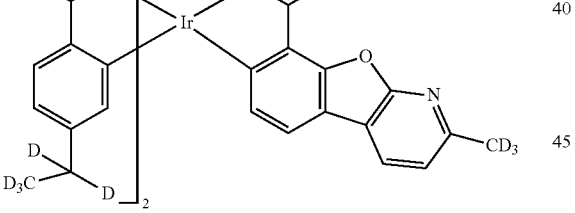
D80
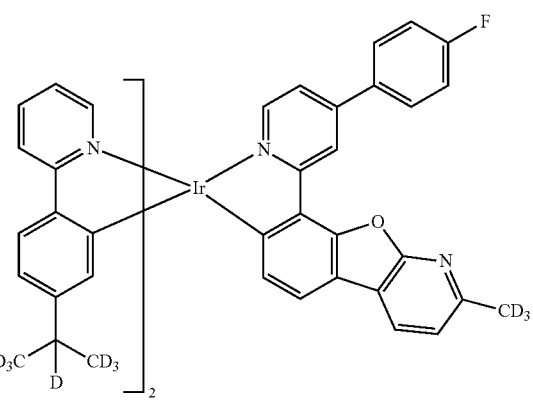
D81
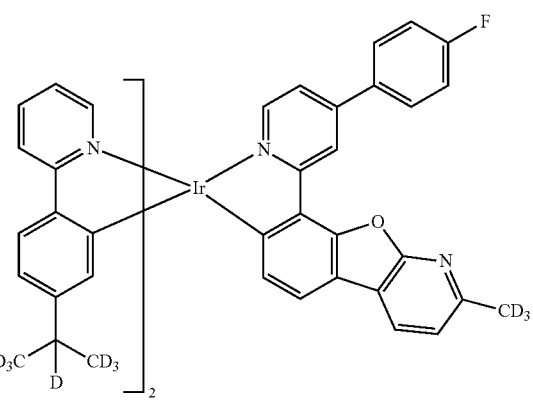
D82
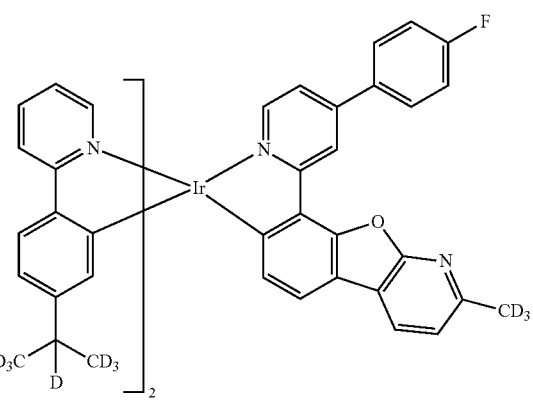

-continued
D83
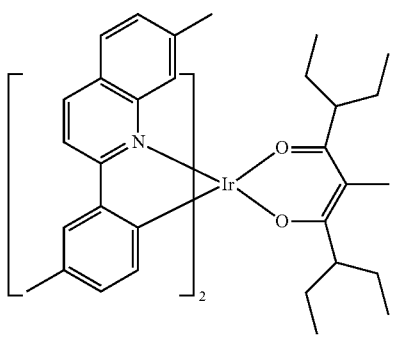
D84
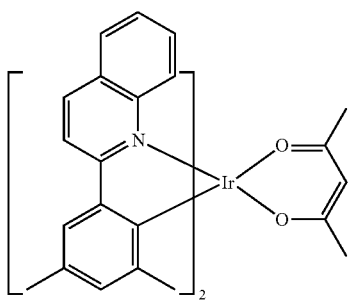
D85
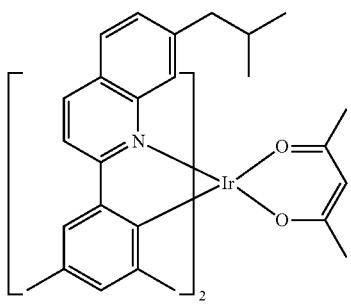
D86
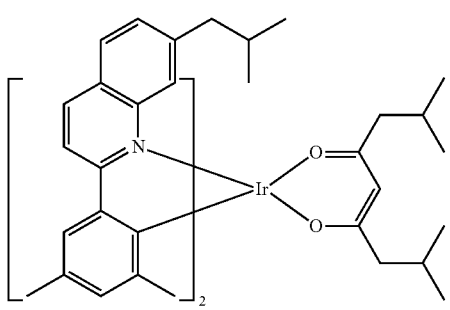
D87
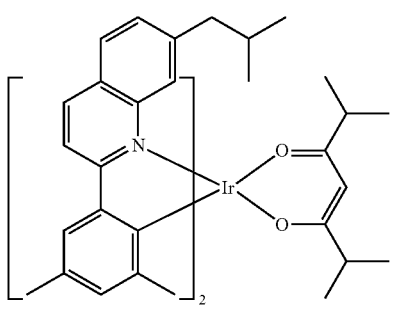
-continued
D88
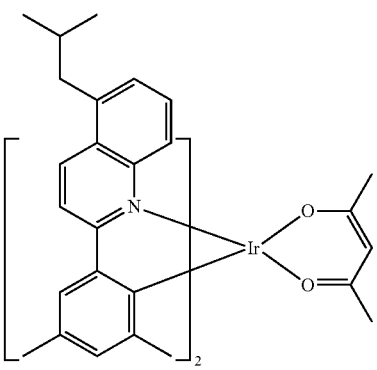
D89
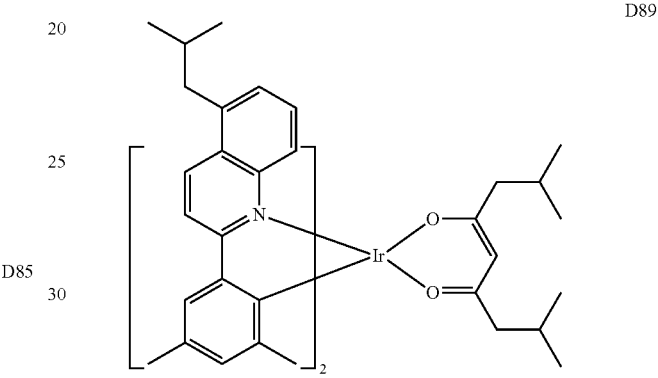
D90
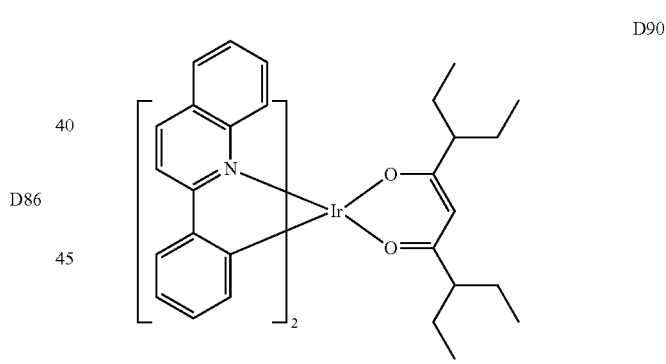
D91
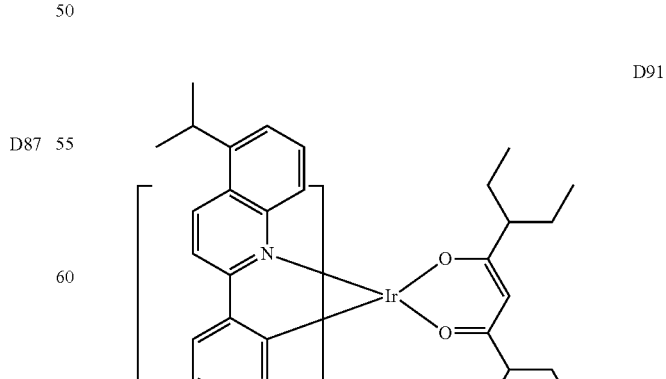
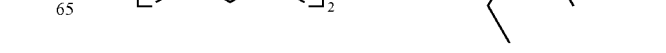

D92 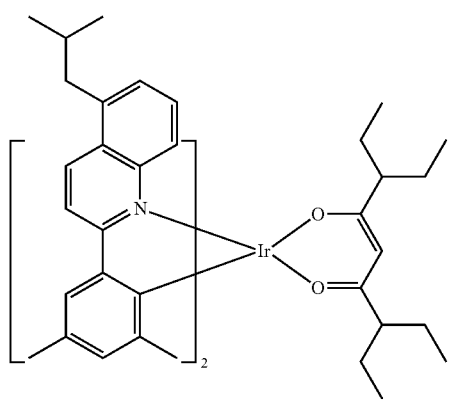
D93 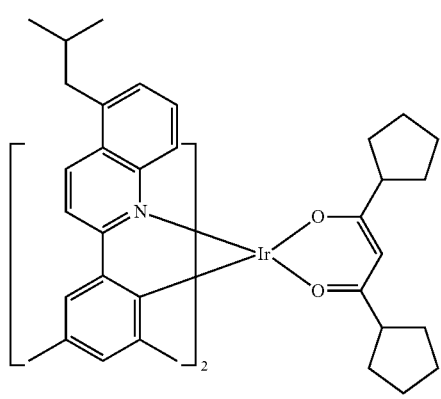
D94 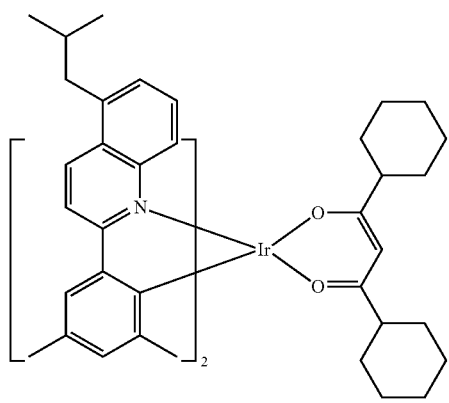
D95 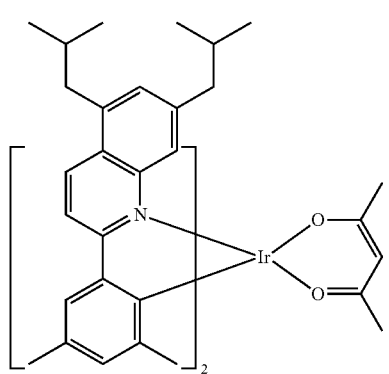
D96 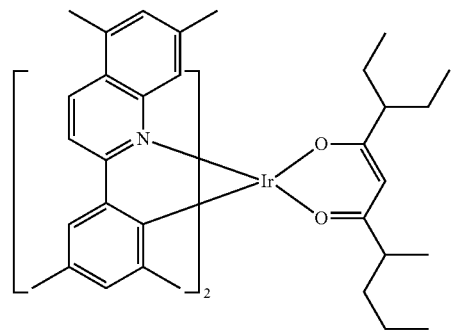
D97 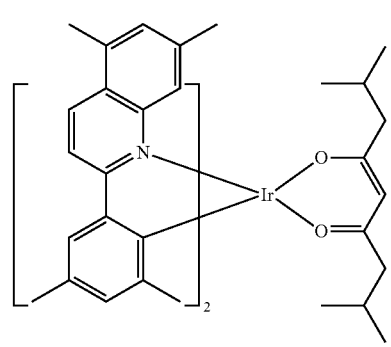
D98 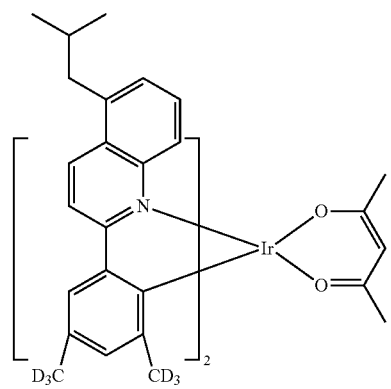
D99 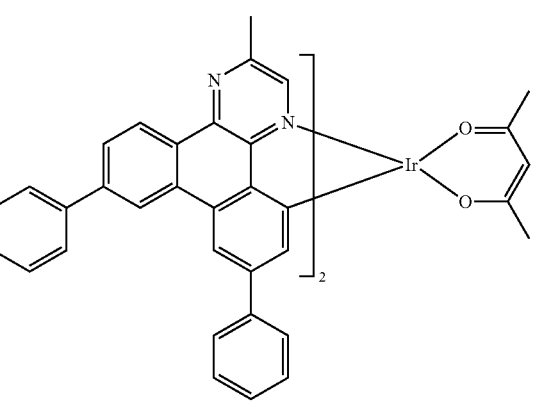

D100 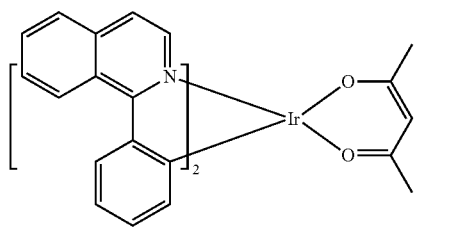
D101 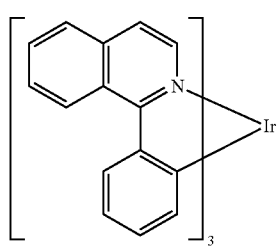
D102 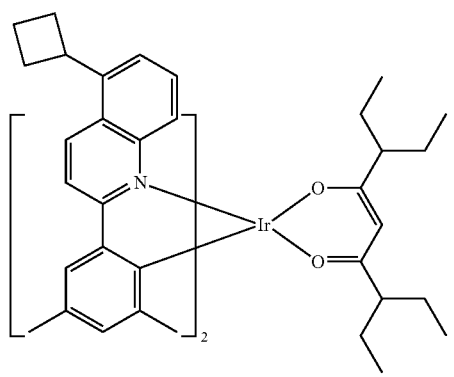
D105 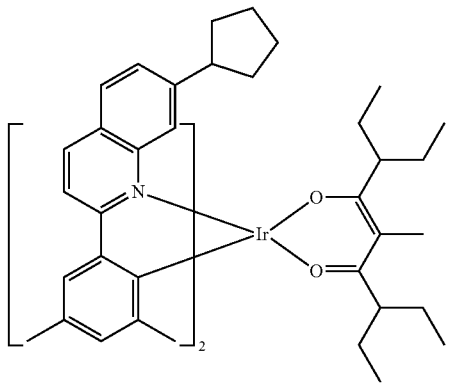
D106 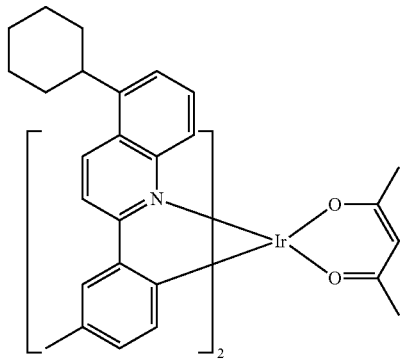
D107 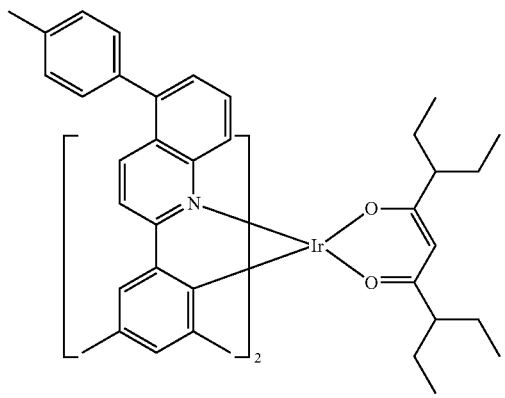
D108 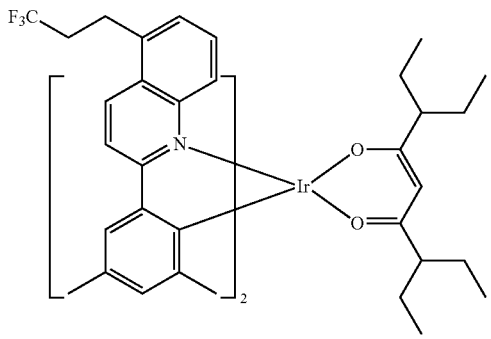

D109 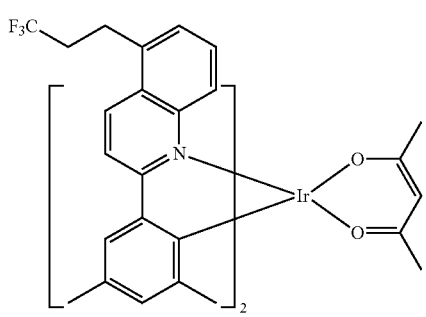
D113 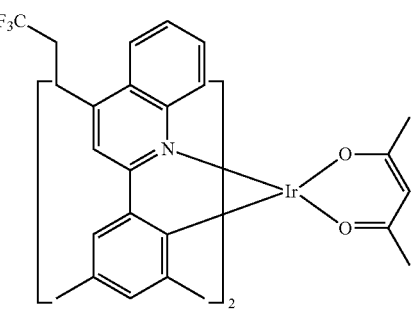
D110 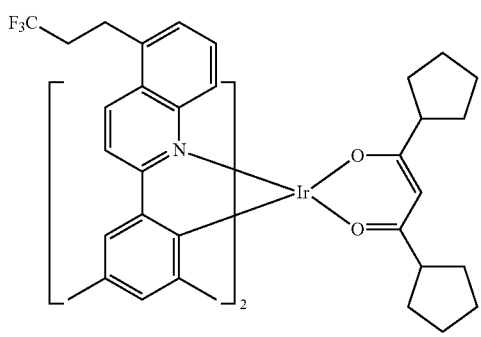
D114 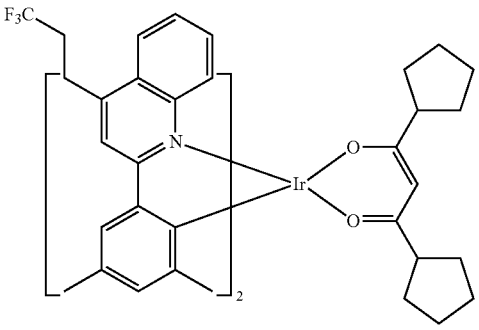
D111 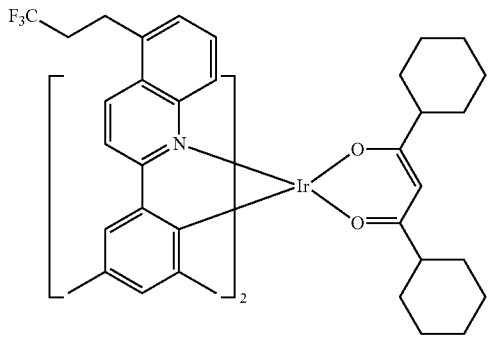
D115 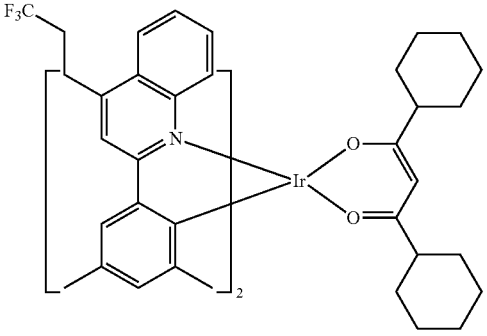
D112 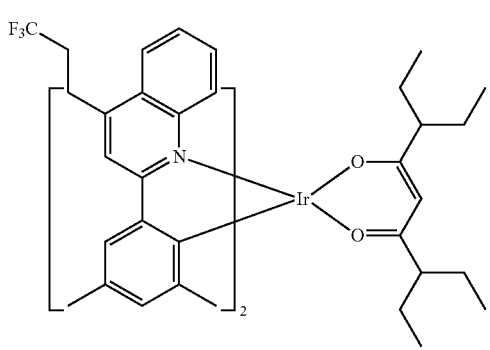
D116 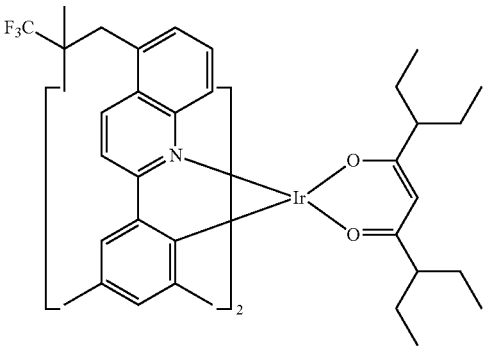

D117
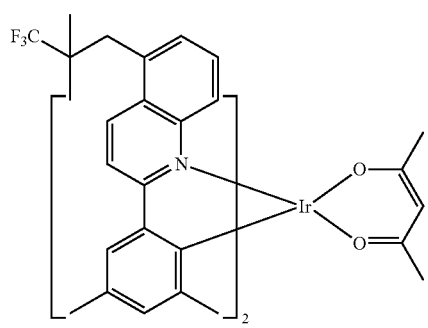
D118
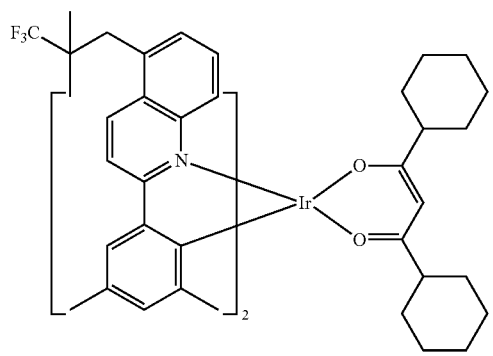
D119
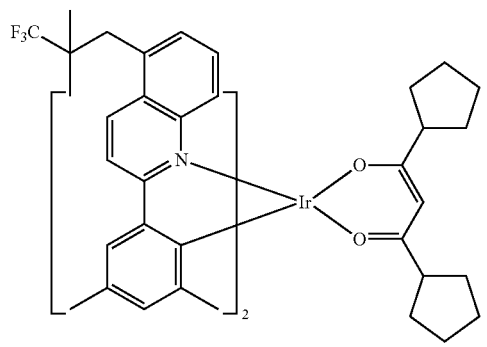
D120
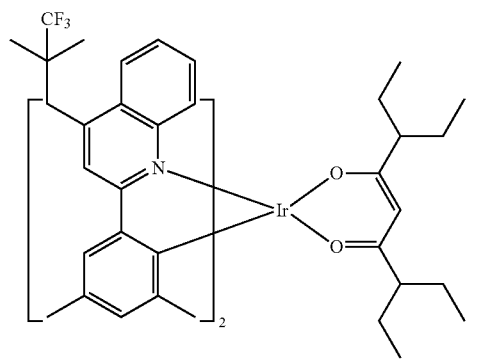
D121
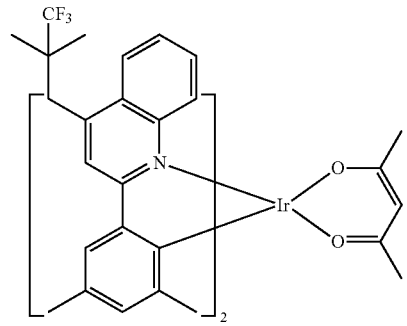
D122
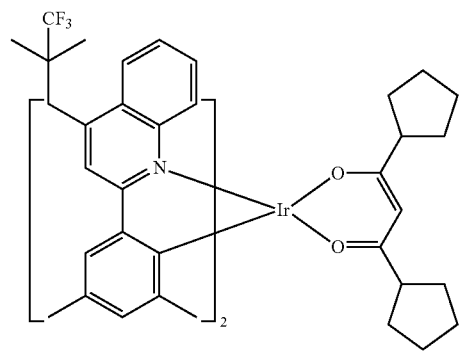
D123
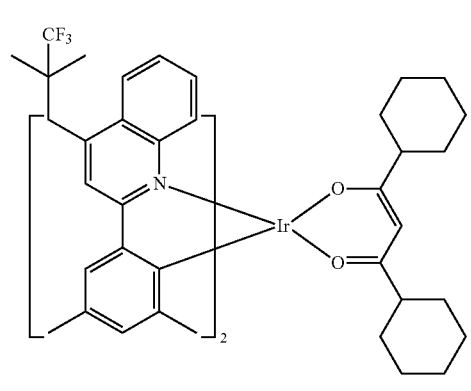
D124
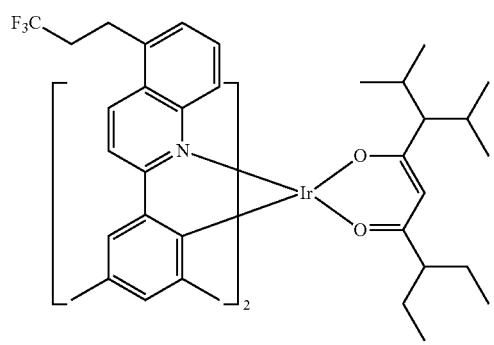

D125
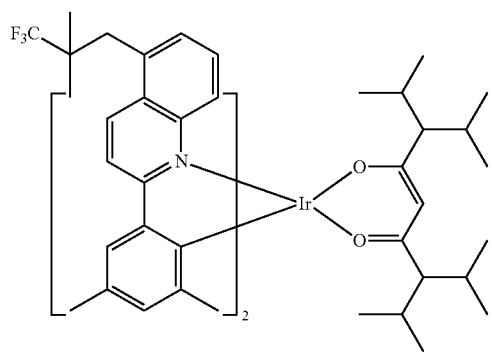
D126
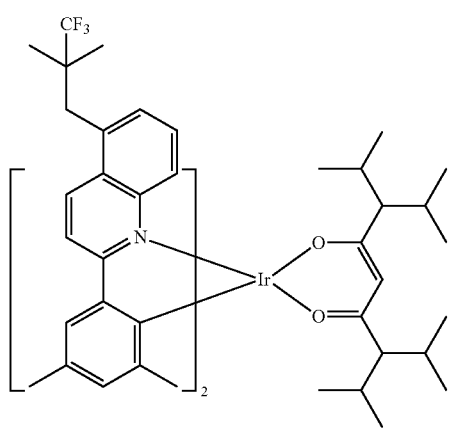
D127
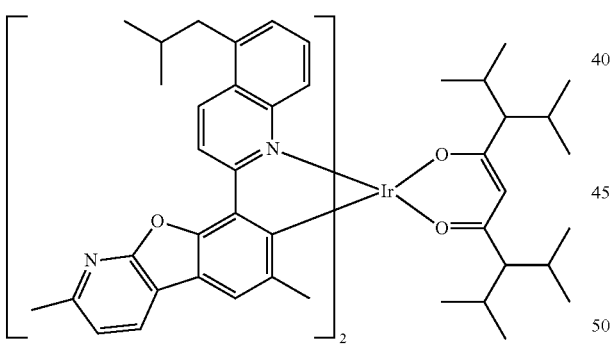
D128
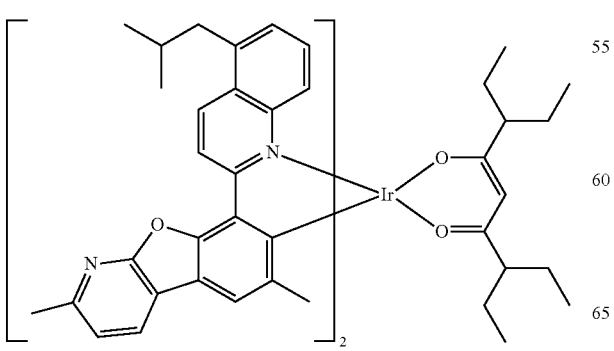
D129
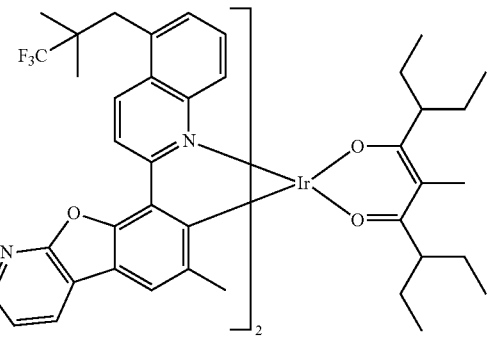
D130
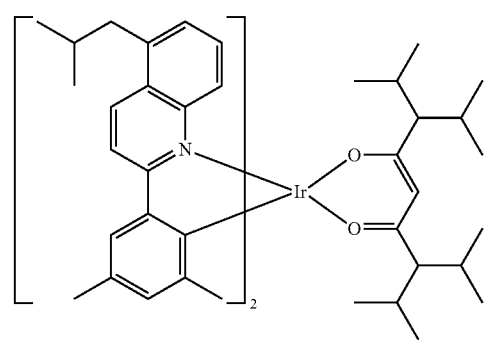
D131
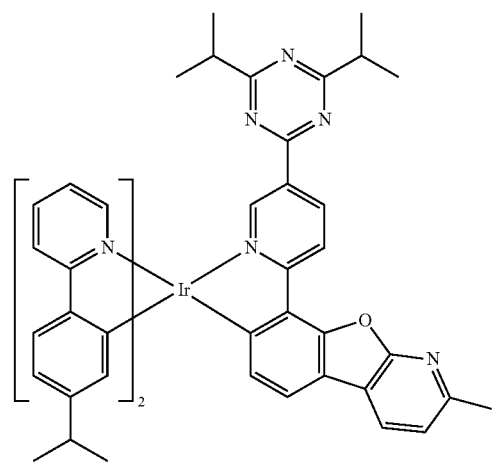
D132
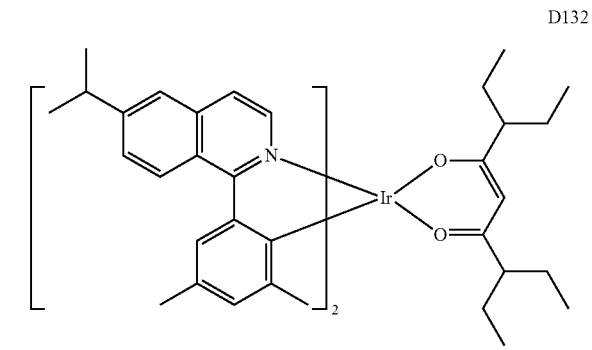

-continued
D133
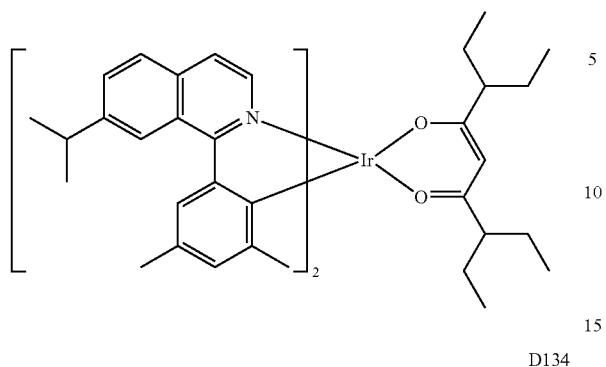
D134
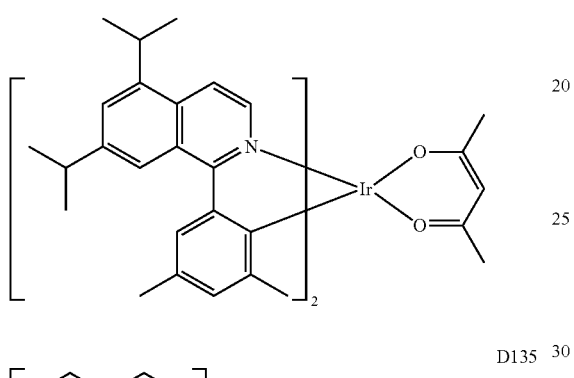
D135
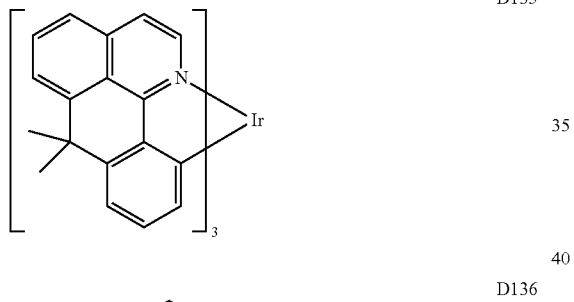
D136
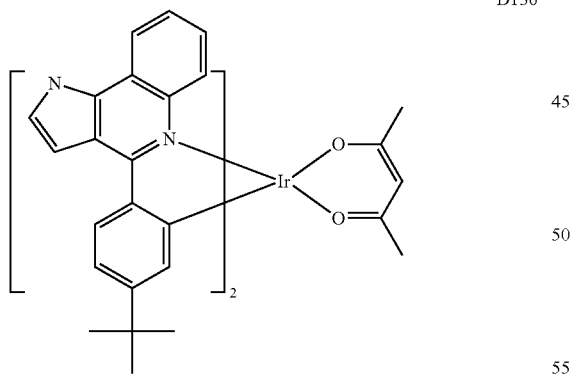
D137
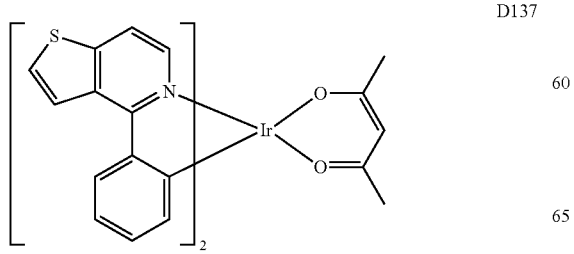
-continued
D138
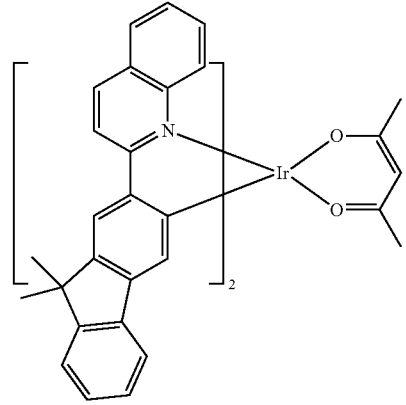
D139
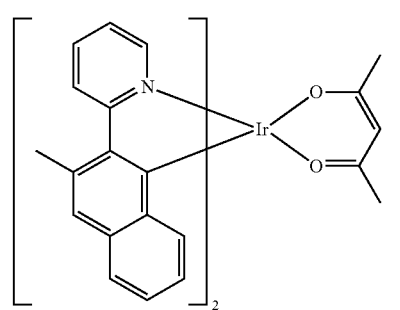
D140
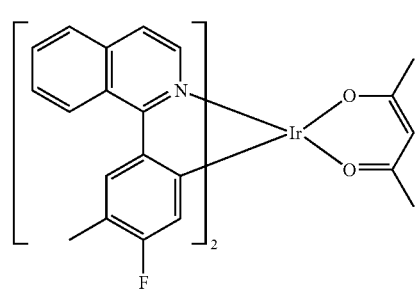
D141
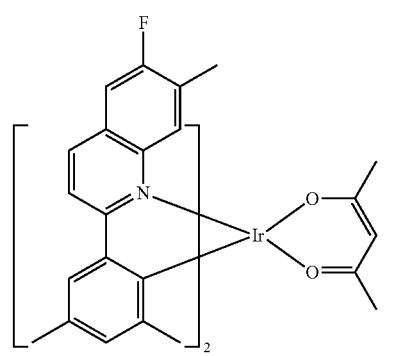
D142
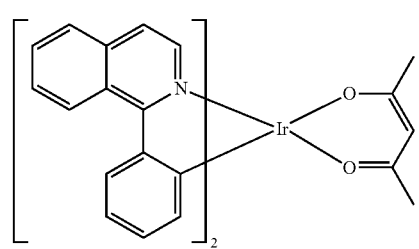

-continued

D143

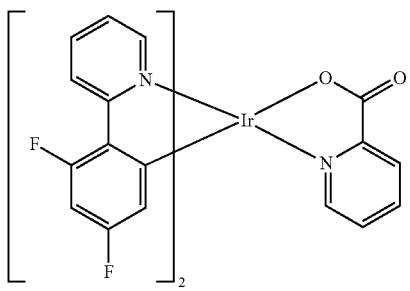

The phosphorescent dopant, is not limited to the above-described example compound, and may be any known phosphorescent platinum group metal complexes described in, for example, paragraphs [0105] to [0113] of US Patent Publication No. 2016/0093808, Japanese Patent Application Publication No. 2014-509067, herein incorporated by reference. The phosphorescent platinum group metal complexes described in these references may also be used as a ground for corrections herein.

The quantum dot may be a nanoparticle of a II-VI group semiconductor compound, a III-V group semiconductor compound, or a IV-VI group semiconductor compound. For example, the quantum dot may be CdO, CdS, CdSe, CdTe, ZnO, ZnS, ZnSe, ZnTe, HgS, HgSe, HgTe, MgSe, MgS CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, GaN, GaP, GaAs, AlN, AlP, AlAs, InN, InP, InAs, InSb, GaNP, GaNAs, GaNSb, GaPAs, GaPSb, AlNP, AlNAs, AlNSb, AlPAs, AlPSb, InNP, InNAs, InPAs, InPSb, GaAlNP, SnS, SnSe, SnTe, PbS, PbSe, PbTe, SnSeS, SnSeTe, SnSTe, PbSeS, PbSeTe, PbSTe, SnPbS, SnPbSe, SnPbTe, or the like, but embodiments of the present disclosure are not limited thereto. In addition, a particle diameter of the quantum dot is not particularly limited, but may be, for example, in a range of about 1 nm to about 20 nm. The quantum dot may have a single-core structure or a core-shell structure.

The amount of luminescent material in the composition may be, based on 100 parts by weight of the heterocyclic compound represented by Formula 1 or Formula 2 functioning as a host material, from about 0.5 parts by weight to about 50 parts by weight, for example, from about 1 part by weight to about 30 parts by weight, or, for example, about 2 parts by weight to about 25 parts by weight.

The amount of luminescent material in the composition may be, based on 100 parts by weight of the total weight of the heterocyclic compound represented by Formula 1 or Formula 2 functioning as a host material, the first compound, and the second compound, from about 0.5 parts by weight to about 50 parts by weight, for example, from about 1 part by weight to about 30 parts by weight, or, for example, about 2 parts by weight to about 25 parts by weight.

Within these ranges, the solubility of the composition is further increased, and precipitation hardly occurs in the solution, and thus, the pot life of the solution may be prolonged. Further, the luminescent efficiency and light-emission lifespan of organic light-emitting devices are improved.

For example, the composition may include the heterocyclic compound, the first compound, the second compound, and the luminescent material (e.g., phosphorescent dopant).

Figure 3:
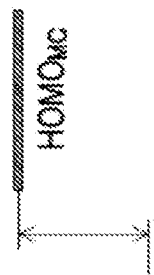
FIG. 3 shows a diagram illustrating an exemplary energy level relationship among a heterocyclic compound represented by Formula 1 or 2, a second compound including an azine group, and a phosphorescent platinum group metal complex in a composition according to an embodiment.
Figure 3:
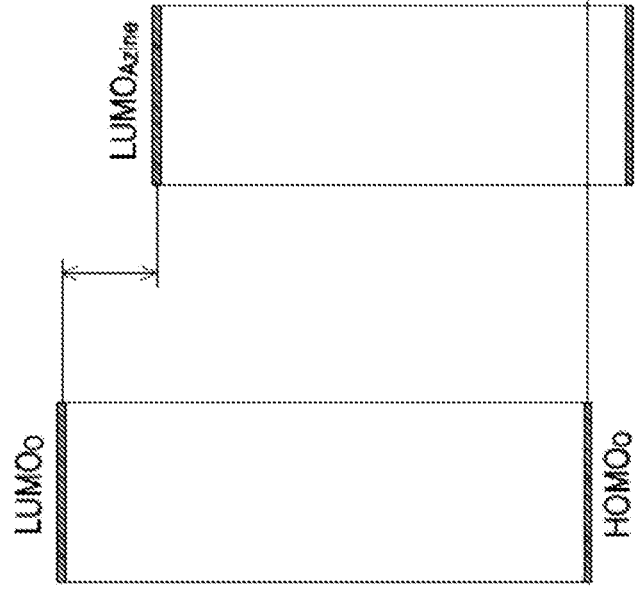
Figure 3:
Figure 4:
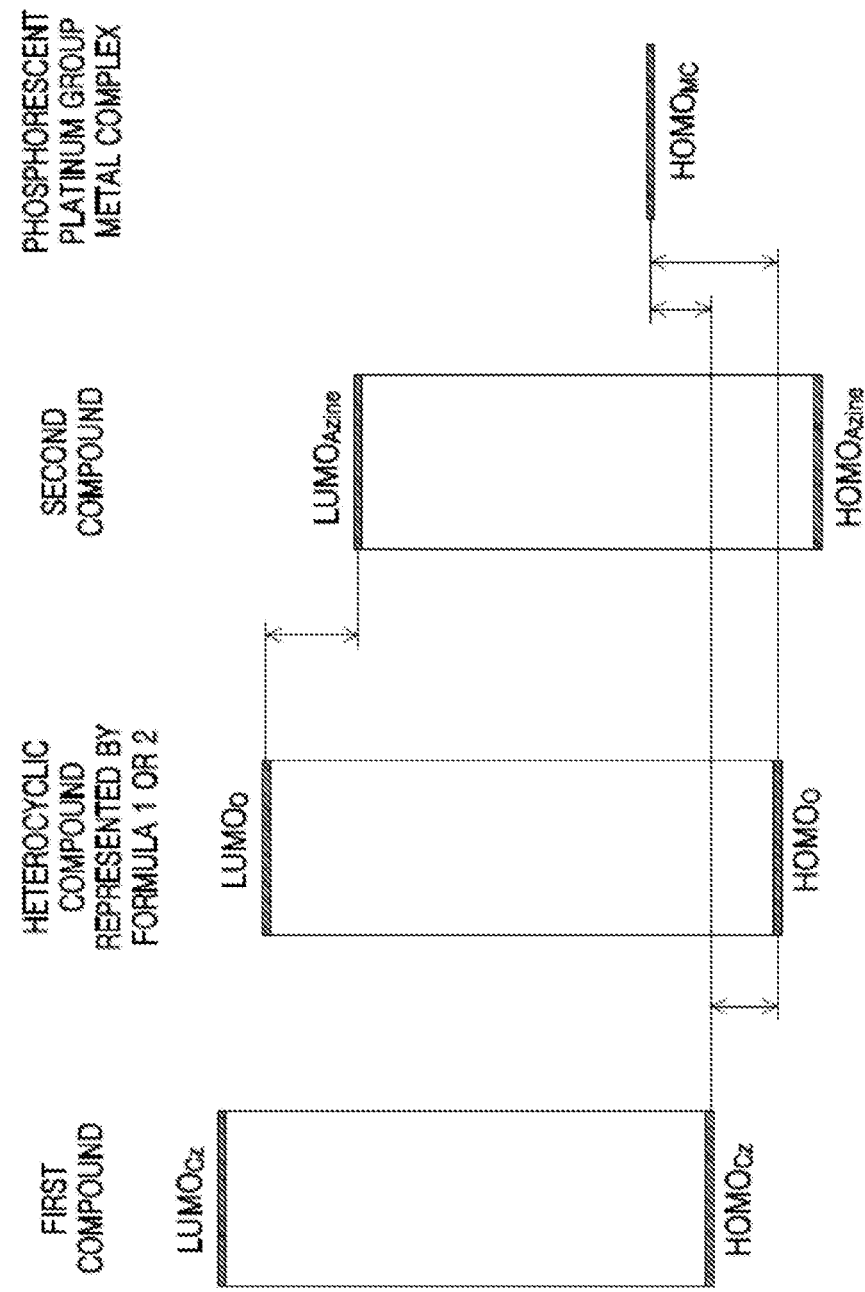
FIG. 4 shows a diagram illustrating an exemplary energy level relationship among a heterocyclic compound represented by Formula 1 or 2, a first compound including a carbazole group, a second compound including an azine group, and a phosphorescent platinum group metal complex in a composition according to an embodiment.

FIG. 3 shows a diagram illustrating an exemplary energy level relationship among the heterocyclic compound represented by Formula 1 or 2, the second compound including an azine group, and the phosphorescent platinum group metal complex in the composition according to an embodiment, and FIG. 4 shows a diagram illustrating an exemplary energy level relationship among the heterocyclic compound represented by Formula 1 or 2, the first compound including a carbazole group, the second compound including an azine group, and the phosphorescent platinum group metal complex in the composition according to an embodiment.

As shown in FIG. 3, the LUMO ($LUMO_0$) of the heterocyclic compound represented by Formula 1 or Formula 2 is shallower than the LUMO ($LUMO_{Azine}$) of the second compound. In addition, the HOMO ($HOMO_0$) of the heterocyclic compound represented by Formula 1 or 2 is deeper than the HOMO ($HOMO_{Cz}$) of the first compound. In addition, the hole mobility of the heterocyclic compound represented by Formula 1 or 2 is lower than that of the first compound.

Referring to FIG. 4, the $LUMO_0$ is shallower than the $LUMO_{Azine}$. The $HOMO_0$ is deeper than the $HOMO_{Cz}$. In addition, the hole mobility of the heterocyclic compound represented by Formula 1 or 2 is lower than that of the first compound.

Therefore, when the composition including the heterocyclic compound represented by Formula 1 or Formula 2, a hole transport host material such as a first compound, an electron transport host material such as a second compound, and the phosphorescent luminescent metal complex of platinum group is included in the emission layer, the following mechanism would occur.

First, electrons are trapped in the deepest $LUMO_{azine}$ in an organic layer including the composition. However, the trapped electrons are detrapped in $LUMO_0$ and continue to move. Therefore, in the organic layer, electrons move by the repetition of the trapping and the detrapping, and the electron mobility decreases. This is the same as the embodiment illustrated in FIG. 3.

Meanwhile, holes are trapped in the HOMO ($HOMO_{MC}$) of phosphorescent luminescent metal complexes. The trapped holes are then detrapped in the $HOMO_{Cz}$ to resume their movement. In addition, the heterocyclic compound represented by Formula 1 or 2 is present in the organic layer at a certain ratio.

The composition may further include a solvent.

For example, the solvent may have a boiling point of 100° C. or higher and 350° C. or lower at 101.3 kPa (1 atm).

The amount of the solvent in the composition is not particularly limited. For example, the concentration of the heterocyclic compound in the composition may be 0.1 wt % or more and 10 wt % or less, for example, 0.5 wt % or more and 5 wt % or less. When the concentration of the heterocyclic compound is within the above range, it is preferable in terms of solubility, and precipitation is unlikely to occur in the solution, and the pot life of the solution is improved.

The solvent is not particularly limited, so long as it is capable of dissolving the heterocyclic compound represented by Formula 1 or 2 Preferably, the solvent is capable of further dissolving the first compound represented by Formula 9 and/or the second compound represented by Formula 10. For example, the solvent may be toluene, xylene, N,N-dimethyl formamide, dimethylsulfoxide, hexamethylphosphoric acid triamide, phenylcyclohexane, tetrahydronaphthalene, ethylbenzene, diethylbenzene, mesitylene, propylbenzene, cyclohexylbenzene, dimethoxybenzene, anisole, ethoxytoluene, phenoxytoluene, isopropylbiphenyl, dimethylanisole, phenyl acetate, phenyl propionate, methyl benzoate, ethyl benzoate, or the like, but embodiments of the present disclosure are not limited thereto.

Thus, the composition may be used as a material for a light-emitting device (for example, an organic light-emitting device, a quantum dot light-emitting device, etc.). Specifically, the composition may be used in an emission layer, a charge injection layer, and/or a charge transport layer of a light-emitting device. In one or more embodiments, the composition may be used in an emission layer of a light-emitting device. In one or more embodiments, the composition may be used when a light-emitting device is manufactured by using a solution coating method, wherein the current efficiency and light-emission lifespan of the light-emitting device may be maintained or improved.

Organic Light-Emitting Device

Figure 5:
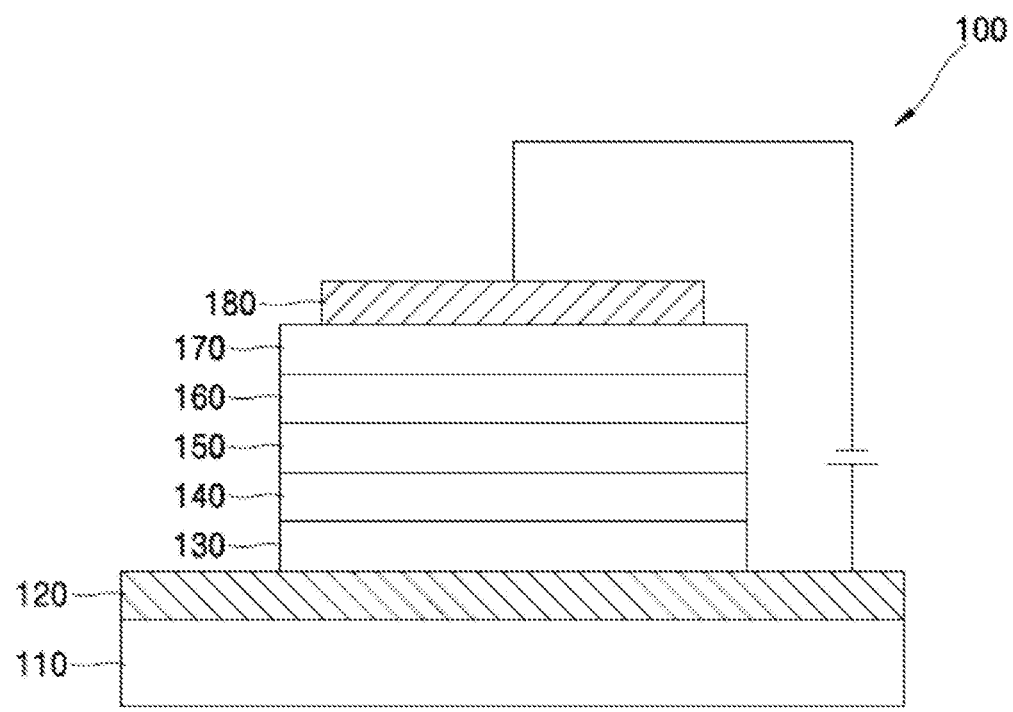
FIG. 5 is a schematic cross-sectional view of an organic light-emitting device according to an embodiment.

Hereinafter, an organic light-emitting device according to an embodiment will be described in detail with reference to FIG. 5. FIG. 5 is a schematic cross-sectional view of an organic light-emitting device according to an embodiment.

An organic light-emitting device 100 according to an embodiment includes a substrate 110, a first electrode 120 disposed on the substrate 110, a hole injection layer 130 disposed on the first electrode 120, a hole transport layer 140 disposed on the hole injection layer 130, an emission layer 150 disposed on the hole transport layer 140, an electron transport layer 160 disposed on the emission layer 150, an electron injection layer 170 disposed on the electron transport layer 160, and a second electrode 180 disposed on the electron injection layer 170.

The heterocyclic compound represented by Formula 1 or 2 may be included in, for example, at least one of organic layers (e.g., at least one selected from the hole injection layer 130, the hole transport layer 140, the emission layer 150, the electron transport layer 160, and the electron injection layer 170) disposed between the first electrode 120 and the second electrode 180. In detail, the heterocyclic compound represented by Formula 1 or 2 may be included as a host in the emission layer 150. For example, the heterocyclic compound represented by Formula 1 or 2 may be included in other organic layers in addition to the emission layer 150. For example, the heterocyclic compound represented by Formula 1 or 2 may be included as a charge transport material in the hole injection layer 130 and/or the hole transport layer 140.

The term "organic layer" as used herein refers to a single layer and/or a plurality of layers between the first electrode and the second electrode of the organic light-emitting device. The "organic layer" may include, in addition to an organic compound, an organometallic compound including metal.

The expression "(an organic layer) includes at least one heterocyclic compound" as used herein may include a case in which "(an organic layer) includes identical compounds represented by Formula 1" and a case in which "(an organic layer) includes two or more different heterocyclic compounds represented by Formula 1."

For example, the organic layer may include, as the heterocyclic compound, only Compound 1. Here, Compound 1 may exist only in the emission layer of the organic light-emitting device. In one or more embodiments, the organic layer may include, as the heterocyclic compound, Compound 1 and Compound 2. In this regard, Compound 1 and Compound 2 may exist in an identical layer (for example, Compound 1 and Compound 2 all may exist in an emission layer).

The substrate 110 may be any substrate that is used in an organic light-emitting device according to the related art. For example, the substrate 110 may be a glass substrate, a silicon substrate, or a transparent plastic substrate, each having excellent mechanical strength, thermal stability, surface smoothness, ease of handling, and water resistance, but embodiments of the present disclosure are not limited thereto.

The first electrode 120 may be formed on the substrate 110. The first electrode 120 may be, for example, an anode, and may include a material with a high work function to facilitate hole injection, such as an alloy or a conductive compound. The first electrode 120 may be a reflective electrode, a semi-reflective electrode, or a transmissive electrode. The first electrode 120 may have a single-layered structure or a multi-layered structure including two or more layers. For example, the first electrode 120 may be a transparent electrode formed of indium tin oxide (ITO), indium zinc oxide (IZO), tin oxide ($SnO_2$), or zinc oxide (ZnO), which has excellent transparency and conductivity. On the transparent first electrode 120, magnesium (Mg), aluminum (Al), aluminum-lithium (Al—Li), calcium (Ca), magnesium-indium (Mg—In), or magnesium-silver (Mg—Ag) may be disposed, so as to form a reflective electrode. In one or more embodiments, the first electrode 120 may have a three-layered structure of ITO/Ag/ITO, but embodiments of the present disclosure are not limited thereto.

The hole transport region may be disposed on the first electrode 120.

The hole transport region may include at least one a hole injection layer 130, a hole transport layer 140, an electron blocking layer (not shown), and a buffer layer (not shown).

The hole transport region may include only either a hole injection layer or a hole transport layer 140. In one or more embodiments, the hole transport region may have a hole injection layer/hole transport layer structure or a hole injection layer/hole transport layer/electron blocking layer structure, wherein for each structure, constituting layers are sequentially stacked from the first electrode 120 in the stated order.

The hole injection layer 130 may include, for example, at least one poly(ether ketone)-containing triphenylamine (TPAPEK), 4-isopropyl-4'-methyldiphenyliodonium tetrakis(pentafluorophenyl) borate (PPBI), N,N'-diphenyl-N,N'-bis-[4-(phenyl-m-tolyl-amino)-phenyl]-biphenyl-4,4'-diamine (DNTPD), copper phthalocyanine, 4,4',4"-tris(3-methylphenylphenylamino triphenylamine (m-MTDATA), N,N'-di(1-naphthyl)-N,N'-diphenylbenzidine (NPB), 4,4',4"-tris(diphenylamino) triphenylamine (TDATA), 4,4',4"-tris(N,N-2-naphthylphenylamino) triphenylamine (2-TNATA), polyaniline/dodecylbenzenesulphonic acid (PANI/DBSA), poly(3,4-ethylenedioxythiophene)/poly(4-styrenesulfonate) (PE DOT/PSS), polyaniline/10-camphorsulfonic acid (PANI/CSA), polyaniline/poly(4-styrenesulfonate) (PANI/PSS), or any combination thereof.

The hole injection layer 130 may be formed to a thickness in a range of about 10 nm to about 1,000 nm, for example, about 10 nm to about 100 nm.

The hole transport layer 140 may include, for example, at least one a carbazole derivative, such as 1,1-bis[(di-4-tolylamino)phenyl]cyclohexane (TAPC), N-phenylcarbazole, and polyvinylcarbazole, N,N'-bis(3-methylphenyl)-N,N'-diphenyl-[1,1-biphenyl]-4,4'-diamine (TPD), 4,4',4"-tris (N-carbazolyl) triphenylamine (TCTA), N,N'-di(1-naphthyl)-N,N'-diphenylbenzidine (NPB), poly(9,9-dioctyl-fluorene-co-N-(4-butylphenyl)-diphenylamine (TFB), or any combination thereof.

The hole transport layer 140 may be formed to a thickness in a range of about 10 nm to about 1,000 nm, for example, about 10 nm to about 150 nm.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be a quinone derivative, a metal oxide, a cyano group-containing compound, or any combination thereof, but embodiments of the present disclosure are not limited thereto. Non-limiting examples of the p-dopant are a quinone derivative, such as tetracyanoquinodimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or HT-D2 below, but are not limited thereto:

HT-D1

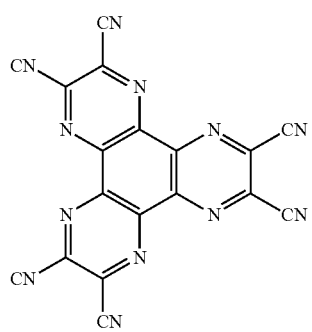

F4-TCNQ

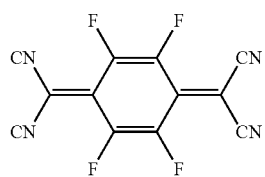

HT-D2

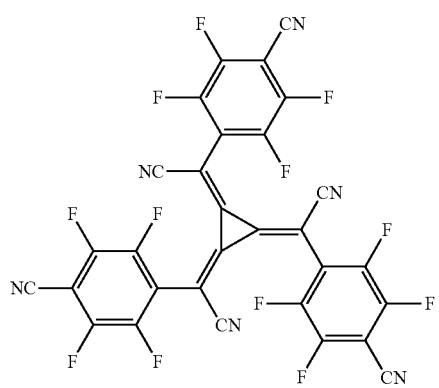

Meanwhile, when the hole transport region includes a buffer layer, a material for forming the buffer layer may be materials for forming the hole transport region described above and materials for a host to be explained later. However, the material for forming the buffer layer is not limited thereto.

In addition, when the hole transport region includes an electron blocking layer, a material for forming the electron blocking layer may be a material for forming the hole transport region described above or a material for a host to be explained later. However, the material for forming the electron blocking layer is not limited thereto. For example, when the hole transport region includes an electron blocking layer, a material for the electron blocking layer may be mCP.

The emission layer 150 is formed on the hole transport region. The emission layer 150 emits light by fluorescence or phosphorescence. The emission layer 150 may include a host and/or a dopant, and the dopant may include the heterocyclic compound represented by Formula 1 or 2. In addition, for use as the host and the dopant in the emission layer 150, any known material may be used.

For example, the host may include (tris(8-quinolinato) aluminium (Alq$_3$), 4,4'-bis(carbazol-9-yl)biphenyl (CBP), poly(N-vinylcarbazole) (PVK), 9,10-di(naphthalene)anthracene (ADN), 4,4',4"-tris(N-carbazolyl)triphenylamine (TCTA), 1,3,5-tris(N-phenyl-benzimidazol-2-yl)benzene (TPBi) 3-tert-butyl-9,10-di(naphth-2-yl)anthracene (TBADN), distyrylarylene (DSA), 4,4'-bis(9-carbazolyl)-2,2'-dimethyl-bipheny (dmCBP), or the like, but embodiments of the present disclosure are not limited thereto.

In one or more embodiments, the host may further include one of the first compound and the second compound, but embodiments of the present disclosure are not limited thereto.

For example, the dopant may include a perylene or a derivative thereof, a rubrene or a derivative thereof, a coumarin or a derivative thereof, a DCM or a derivative thereof, an iridium complex, such as Flrpic, Ir(piq)$_2$(acac), Ir(ppy)$_3$, or tris(2-(3-p-xylyl)phenylpyridine) iridium (III) (dopant), or the like, an osmium complex, or a platinum complex, but embodiments of the present disclosure are not limited thereto.

When the emission layer includes the host and the dopant, an amount of the dopant may be in a range of about 0.01 parts by weight to about 15 parts by weight based on 100 parts by weight of the host, but embodiments of the present disclosure are not limited thereto.

The emission layer 150 may be formed to a thickness in a range of about 10 nm to about 60 nm.

When the organic light-emitting device is a full-color organic light-emitting device, the emission layer may be patterned into a red emission layer, a green emission layer, or a blue emission layer. In one or more embodiments, due to a stacked structure including a red emission layer, a green emission layer, and/or a blue emission layer, the emission layer may emit white light.

The electron transport region may be formed on the emission layer 150.

The electron transport region may include at least one a hole blocking layer (not shown), an electron transport layer 160, an electron injection layer 170, or any combination thereof.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

For example, to prevent diffusion of excitons or holes into the electron transport layer 160, the organic light-emitting device 100 may further include a hole blocking layer between the electron transport layer 160 and the emission layer 150. The hole blocking layer may include, for example, at least one an oxadiazole derivative, a triazole derivative, BCP, Bphen, BAlq, Compound HB1 below, or any combination thereof, but embodiments of the present disclosure are not limited thereto:

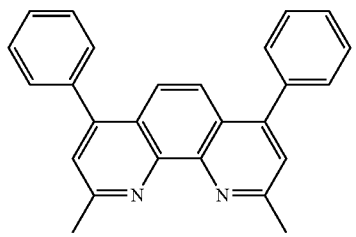

BCP

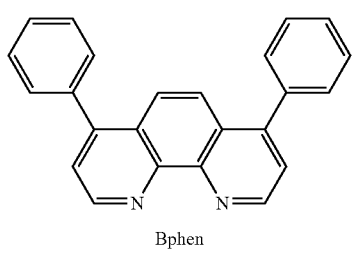

Bphen

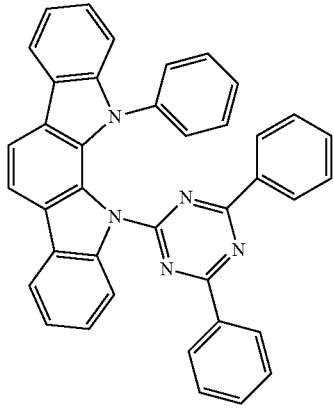

HB1

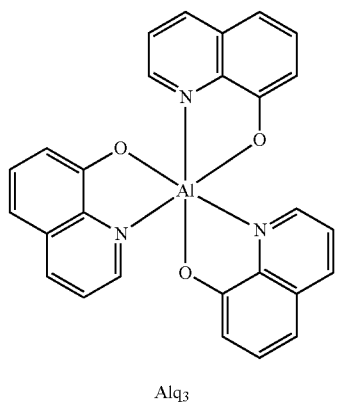

Alq₃

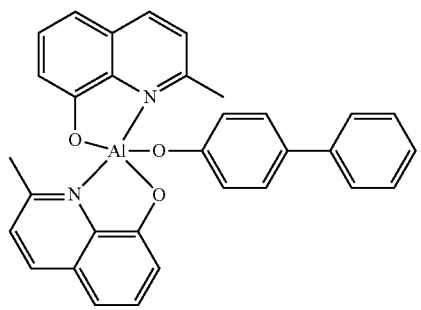

BAlq

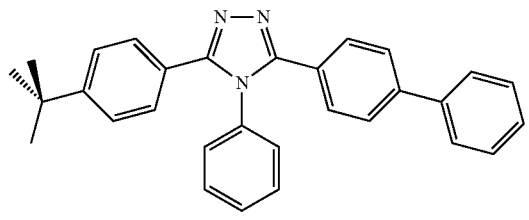

TAZ

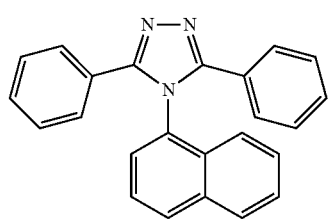

NTAZ

A thickness of the hole blocking layer may be in a range of about 20 nm to about 1,000 nm, for example, about 30 nm to about 300 nm. When the thickness of the hole blocking layer is within these ranges, the hole blocking layer may have excellent hole blocking characteristics without a substantial increase in driving voltage.

The electron transport layer 160 may include: a pyridine ring-containing compound, such as tris(8-quinolinato)aluminium (Alq₃), BAlq, and 1,3,5-tri[(3-pyridyl)-phen-3-yl] benzene); a triazine ring-containing compound, such as 2,4,6-tris(3'-(pyridin-3-yl)biphenyl-3-yl)-1,3,5-triazine; an imidazole ring-containing compound, such as 2-(4-(N-phenylbenzimidazolyl-1-yl-phenyl)-9,10-dinaphthylanthracene; a triazole ring-containing compound, such as TAZ and NTAZ; 11,3,5-tris(N-phenyl-benzimidazol-2-yl)benzene (TPBi); BCP; Bphen; or the like:

In one or more embodiments, the electron transport layer 160 may include a commercial product, such as KLET-01, KLET-02, KLET-03, KLET-10, and KLET-M1 (hereinbefore, available from Chemipro Kasei Inc.).

Also, the electron transport layer 160 may further include, in addition to the materials described above, a metal-containing material.

The metal-containing material may include a Li complex. The Li complex may include, for example, Compound ET-D1 (lithium quinolate, LiQ), ET-D2, or a combination thereof:

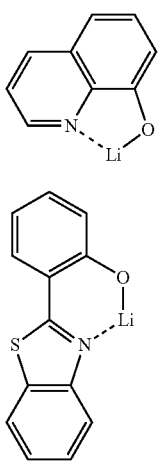

ET-D1

ET-D2

The electron injection layer 160 may be, for example, formed to a thickness in a range of about 15 nm to about 50 nm.

The electron injection layer 170 may be formed on the electron transport layer 160.

The electron injection layer 170 may include, for example, a lithium compound, such as (8-hydroxyquinolinato)lithium (Liq) and lithium fluoride (LiF), sodium chloride (NaCl), cesium fluoride (CsF), lithium oxide ($Li_2O$), or barium oxide (BaO).

The electron injection layer 170 may be formed to a thickness in a range of about 0.3 nm to about 9 nm.

The second electrode 180 may be formed on the electron injection layer 170. The second electrode 180 may be, specifically, a cathode, and may be formed of a material metal, an alloy, an electrically conductive compound, and a combination thereof, which have a relatively low work function. For example, second electrode 180 may be a reflective electrode formed of metal, such as lithium (Li), magnesium (Mg), aluminum (Al), and calcium (Ca), or an alloy, such as aluminum-lithium (Al—Li), magnesium-indium (Mg—In), and magnesium-silver (Mg—Ag). In one or more embodiments, the second electrode 180 may be a transparent electrode having a thickness of 20 nm or less and formed of metal or in a transparent conductive film, such as an alloy thin film, indium tin oxide ($In_2O_3$—$SnO_2$), and indium zinc oxide ($In_2O_3$—ZnO).

In one or more embodiments, the laminated structure of the organic light-emitting device 100 according to an embodiment is not limited to the above-described example. In one or more embodiments, the organic light-emitting device 100 may have other laminated structures. For example, the organic light-emitting device 100 may not include one or more of the hole injection layer 130, the hole transport layer 140, the electron transport layer 160, and the electron injection layer 170, or may include other layers. In one or more embodiments, layers which constitute the organic light-emitting device 100 may each include a single layer or a multiple layers.

The manufacturing method of each layer of the organic light-emitting device 100 according to an embodiment is not particularly limited, and may be manufactured by various methods such as a vacuum deposition method, a solution coating method, an LB method, or the like.

The solution coating method may include a spin coat method, a casting method, a micro gravure coat method, a gravure coat method, a bar coat method, a roll coat method, a wire bar coat method, a dip coat method, a spry coat method, a screen printing method, a flexographic method, a offset printing method, an ink jet printing method, or the like.

The solvent used for the solution coating method may include toluene, xylene, diethyl ether, chloroform, ethyl acetate, dichloromethane, tetrahydrofuran, acetone, acetonitrile, N,N-dimethylformamide, dimethylsulfoxide, anisole, hexamethyl phosphate triamide, 1,2-dichloro ethane, 1,1,2-trichloroethane, chlorobenzene, o-dichlorobenzene, dioxane, cyclohexane, n-pentane, n-hexane, n-heptane, n-octane, n-nonane, n-decane, methyl ethyl ketone, cyclohexanone, butyl acetate, ethyl cellosolve acetate, ethylene glycol, ethylene glycol mono butyl ether, ethylene glycol mono ethyl ether, ethylene glycol mono methyl ether, dimethoxyethane, propylene glycol, diethoxy methane, triethylene glycol mono ethyl ether, glycerin, 1,2-hexanediol, methanol, ethanol, propanol, isopropanol, cyclohexanol, N-methyl-2-pyrrolidone, or the like, or any combination thereof, and may be any material that can dissolve a material for forming each layer.

The concentration of the composition used in the solution coating method may be, in consideration of coating properties, from about 0.1 wt % or more to about 10 wt % or less, for example, about 0.5 wt % or more to about 5 wt % or less, but embodiments are not limited thereto.

The conditions for the vacuum deposition method depends on the compound used, the structure and thermal properties of the target layer. For example, the deposition temperature may be from about 100° C. to about 500° C., the vacuum pressure may be from about $10^{-8}$ torr to about $10^{-3}$ torr, the deposition rate may be from about 0.01 Å/sec to 100 Å/sec.

In one or more embodiments, the first electrode 120 may be an anode, and the second electrode 180 may be a cathode.

For example, the first electrode 120 may be an anode, the second electrode 180 may be a cathode, and the emission layer 150 disposed between the first electrode 120 and the second electrode 180 may include an organic layer. The organic layer may further include a hole transport region between the first electrode 120 and the emission layer 150 and an electron transport region between the emission layer 150 and the second electrode 180. The hole transport region may include at least one layer the hole injection layer 130, the hole transport layer 140, the buffer layer, and the electron blocking layer, and the electron transport region may include at least one layer the hole blocking layer, the electron transport layer 160, and the electron injection layer 170.

In one or more embodiments, the first electrode 120 may be a cathode, and the second electrode 180 may be an anode.

Hereinbefore, the organic light-emitting device has been described with reference to FIG. 5, but embodiments of the present disclosure are not limited thereto.

Description of Substituents

The expression "X and Y may each independently be" as used herein refers to a case where X and Y may be identical to each other, or a case where X and Y may be different from each other.

The term "substituted" as used herein refers to a case where hydrogen of a substituent such as $R_{11}$ may be further substituted with other substituents.

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, an neopentyl group, a 1,2-dimethylpropyl group, an n-hexyl group, an isohexyl group, a 1,3-dimethylbutyl group, a 1-isopropylpropyl group, a 1,2-dimethylbutyl group, an n-heptyl group, a 1,4-dimethylpentyl group, a 3-ethylpentyl group, a 2-methyl-1-isopropylpropyl group, a 1-ethyl-3-methylbutyl group, an n-octyl group, a 2-ethylhexyl group, a 3-methyl-1-isopropylbutyl group, a 2-methyl-1-isopropyl group, a 1-tert-butyl-2-methylpropyl group, an n-nonyl group, a 3,5,5-trimethyldecyl group, an n-decyl group, an isodecyl group, an n-undecyl group, a 1-methyldecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group), an n-heneicosyl group, an n-docosyl group, an n-tricosyl group, and an n-tetracosyl group.

The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, a propoxy group, an isopropoxy group, an n-butoxy group, an isobutoxy group, a sec-butoxy group, a tert-butoxy group, an n-pentoxy group, an isopentoxy group, a tert-pentoxy group, an neopentoxy group, an n-hexyloxy group, an isohexyloxy group, a heptyloxy group, an octyloxy group, nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a 2-ethylhexyloxy group, and a 3-ethylpentyloxy group.

The term "$C_1$-$C_{60}$ alkylthio group" as used herein refers to a monovalent group represented by —$SA_{102}$ (wherein $A_{102}$ is the $C_1$-$C_{60}$ alkyl group).

The term "$C_3$-$C_{10}$ cycloalkyl group" as used herein refers to a monovalent saturated hydrocarbon monocyclic group having 3 to 10 carbon atoms involved in the ring formation, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_6$-$C_{60}$ aryl group" as used herein refers to a monovalent group having a carbocyclic aromatic system having 6 to 60 carbon atoms involved in the ring formation (that is, when substituted with a substituent, the atom not included in the substituent is not counted as the carbon involved in the ring formation), and the term "$C_6$-$C_{60}$ arylene group" as used herein refers to a divalent group having a carbocyclic aromatic system having 6 to 30 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{30}$ aryl group and the $C_6$-$C_{30}$ arylene group each include two or more rings, the rings may be fused to each other.

The term "$C_6$-$C_{60}$ aryloxy group" as used herein refers to a group represented by —$OA_{103}$ (wherein $A_{103}$ is the $C_6$-$C_{60}$ aryl group). Examples thereof include a 1-naphthyloxy group, a 2-naphthyloxy group, and a 2-azulenyloxy group.

The term "$C_6$-$C_{60}$ arylthio group" as used herein refers to a monovalent group represented by —$SA_{104}$ (wherein $A_{104}$ is the $C_6$-$C_{60}$ aryl group).

The term "$C_1$-$C_{60}$ heteroaryl group" as used herein refers to a monovalent group having a heterocyclic aromatic system that has at least one heteroatom N, O, Si, P, Se, Ge, B, S, or any combination thereof as a ring-forming atom, and 1 to 60 carbon atoms. The term "$C_1$-$C_{30}$ heteroarylene group" as used herein refers to a divalent group having a heterocyclic aromatic system that has at least one N, O, Si, P, Se, Ge, B, S, or any combination thereof, as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a tnazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other.

The term "$C_1$-$C_{60}$ heteroaryloxy group" as used herein refers to a group represented by —$OA_{105}$ (wherein $A_{105}$ is the $C_1$-$C_{60}$ heteroaryl group). Examples thereof include a 2-furanyloxy group, a 2-thienyloxy group, a 2-indolyloxy group, a 3-indolyloxy group, a 2-benzofuriloxy group, and a 2-benzothienyloxy group.

The term "$C_1$-$C_{60}$ heteroarylthio group" as used herein refers to a group represented by —$SA_{106}$ (wherein $A_{106}$ is the $C_1$-$C_{60}$ heteroaryl group).

The term "$C_7$-$C_{60}$ alkylaryl group" as used herein refers to a monovalent group in which an arylene group is substituted with an alkyl group and the sum of the carbon atoms constituting the alkyl group and the aryl group is 7 to 60. An example of the $C_7$-$C_{60}$ alkylaryl group is the toluyl group (i.e., —Ph—$CH_3$).

The term "$C_7$-$C_{60}$ arylalkyl group" as used herein refers to a monovalent group in which an alkylene group is substituted with an aryl group and the sum of the carbon atoms constituting the alkyl group and the aryl group is 7 to 60. Examples of the $C_7$-$C_{60}$ arylalkyl group include a benzyl group, a phenylethyl group, a phenylpropyl group, and a naphthylmethyl group.

The term "$C_6$-$C_{60}$ arylalkyloxy group" as used herein refers to a group represented by —$OA_{105}$ (wherein $A_{105}$ is the $C_7$-$C_{60}$ arylalkyl group).

The term "$C_7$-$C_{60}$ arylalkylthio group" as used herein refers to a group represented by —$SA_{106}$ (wherein $A_{106}$ is the $C_7$-$C_{60}$ arylalkyl group).

The term "$C_8$-$C_{30}$ arylalkenyl group" as used herein refers to a monovalent group in which an alkenylene group is substituted with an aryl group and the sum of the carbon atoms constituting the alkenyl group and the aryl group is 8 to 30.

The term "$C_8$-$C_{30}$ arylalkynyl group" as used herein refers to a monovalent group in which an alkynylene group is substituted with an aryl group and the sum of the carbon atoms constituting the alkynyl group and the aryl group is 8 to 30.

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom selected from N, O, P, Si, Se, Ge, B, S, or any combination thereof, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{30}$ carbocyclic group" as used herein refers to a saturated or unsaturated cyclic group having, as a ring-forming atom, 5 to 30 carbon atoms only. The term "$C_5$-$C_{30}$ carbocyclic group" as used herein refers to a monocyclic group or a polycyclic group, and, according to its chemical structure, a monovalent, divalent, trivalent, tetravalent, pentavalent, or hexavalent group.

The term "$C_1$-$C_{30}$ heterocyclic group" as used herein refers to a saturated or unsaturated cyclic group having, as a ring-forming atom, at least one N, O, P, Si, Se, Ge, B, S, or any combination thereof, other than 1 to 30 carbon atoms. The term "$C_1$-$C_{30}$ heterocyclic group" as used herein refers to a monocyclic group or a polycyclic group, and, according to its chemical structure, a monovalent, divalent, trivalent, tetravalent, pentavalent, or hexavalent group.

In the present specification, at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_7$-$C_{60}$ alkylaryl group, the substituted $C_7$-$C_{60}$ arylalkyl group, the substituted $C_7$-$C_{60}$ arylalkyloxy group, the substituted $C_7$-$C_{60}$ arylalkylthio group, the substituted $C_8$-$C_{30}$ arylalkenyl group, the substituted $C_8$-$C_{30}$ arylalkynyl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), —P(=O)($Q_{18}$)($Q_{19}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), —P(=O)($Q_{28}$)($Q_{29}$), or any combination thereof; or
—N($Q_{31}$)($Q_{32}$), —Si($Q_{33}$)($Q_{34}$)($Q_{35}$), —B($Q_{36}$)($Q_{37}$), or —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one $C_1$-$C_{60}$ alkyl group, $C_6$-$C_{60}$ aryl group, or any combination thereof, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group.

Others

The wording "A to B" used herein refers to a range from A to B, wherein A and B are inclusive.

Although one or more embodiments of the present disclosure has been described above with reference to the accompanying drawings, the present disclosure is not limited to the embodiments. It will be apparent to those skilled in the art that various changes or modifications can be made within the scope of the technical idea described in the claims. It is understood that such various changes and modifications also fall within the technical scope of the present disclosure.

Hereinafter, with reference to Examples and Comparative Examples, a heterocyclic compound represented by Formula 1 or 2 and an organic light-emitting device including the same will be described in detail. Examples to be described below are presented as examples only, and the heterocyclic compound and organic light-emitting device according to an example of the present invention are not limited to the examples to be described later.

The wording "'B' was used instead of 'A'" used in describing Synthesis Examples means that a molar equivalent of 'B' was identical to a molar equivalent of 'A'.

The unit "%" is based on a weight unless described otherwise.

EXAMPLES

Synthesis Example A1: Synthesis of Compound A17

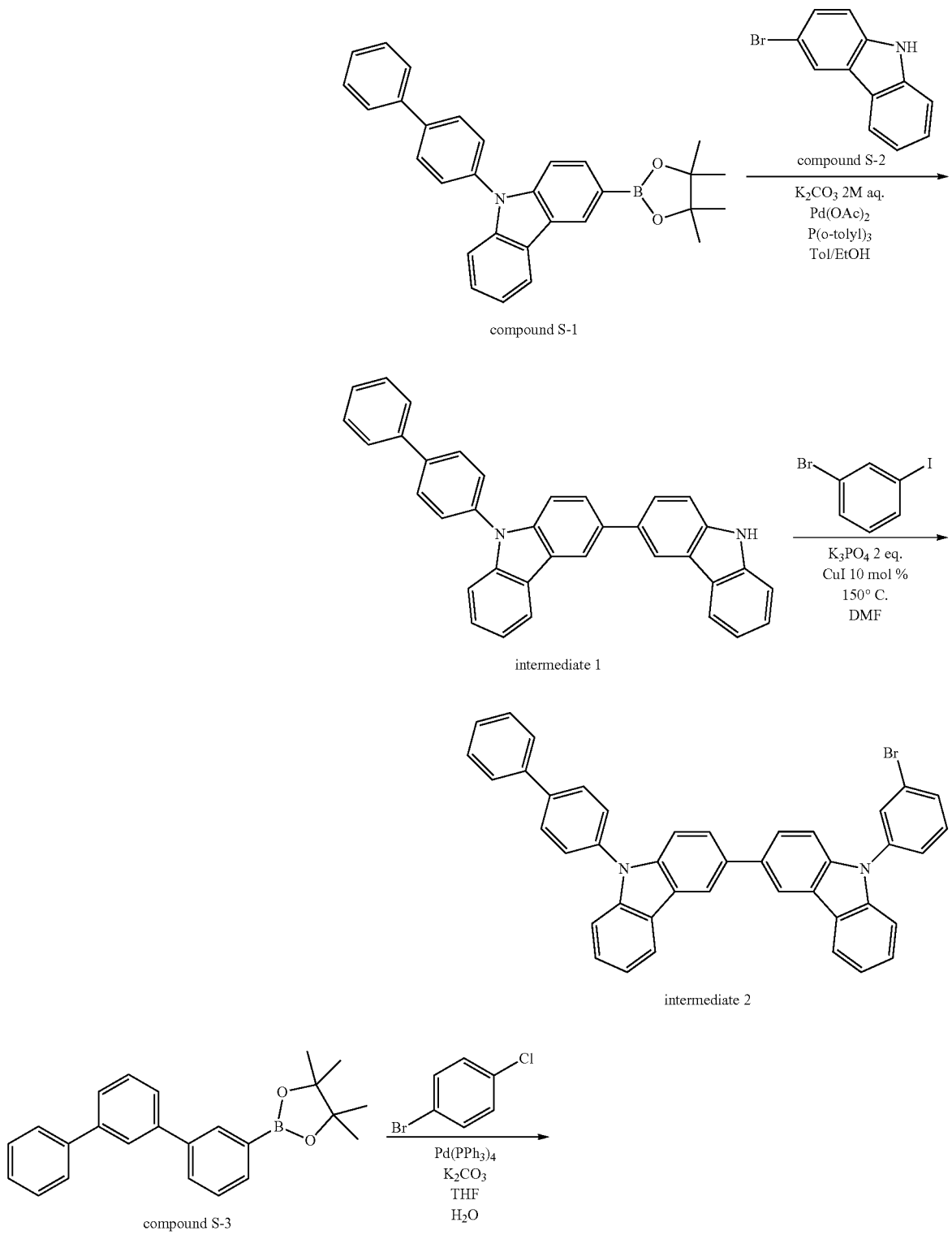

423 424
-continued
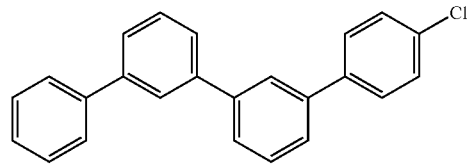
intermediate 3
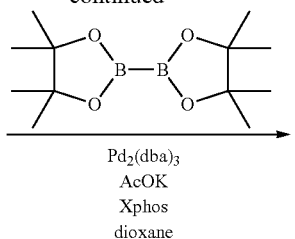
Pd₂(dba)₃
AcOK
Xphos
dioxane
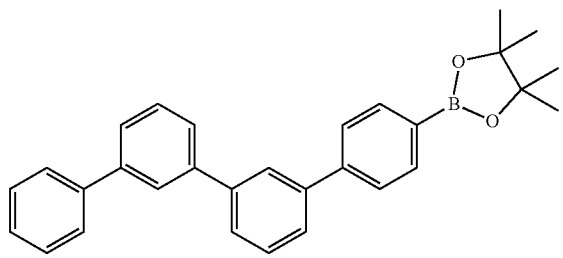
intermediate 4
intermediate 4
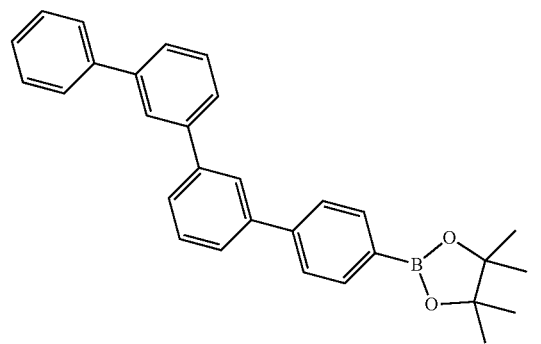
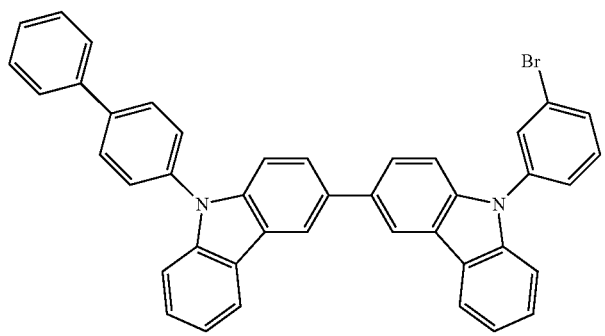
intermediate 2
Pd(OAc)₂ 3 mol %
P(o-tolyl)₃ 4.5 mol %
K₂CO₃ 2M aq. 2.0 eq.
toluene/EtOH = 0.2M(2:1)
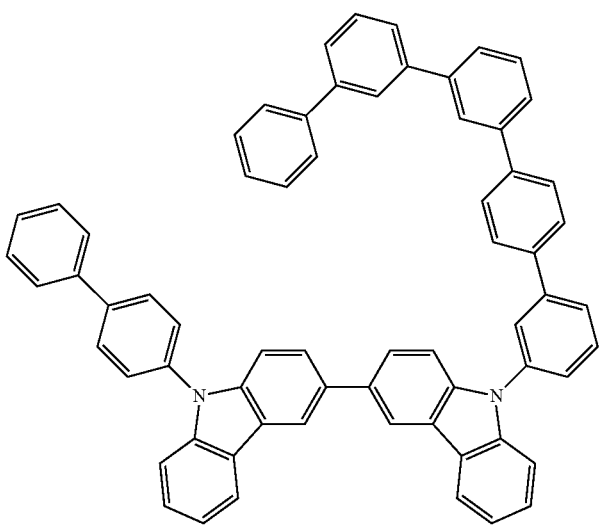
A17

Synthesis of Intermediate 1

Compound S-1 (1 equivalent, 224.5 mmol, 100 g), Compound S-2 (1.1 equivalent, 247.0 mmol, 60.8 g), toluene (740 mL), and ethanol (370 mL) were added to a three-neck flask and stirred. Then, a 2M aqueous potassium carbonate solution (62.1 g of $K_2CO_3$, 225 mL of water) was added and stirred. Then, palladium (II) acetate (Pd(OAc)$_2$, 3 mol %, 6.74 mmol, 1.51 g) and tri(o-tolyl) phosphine (P(o-tolyl)$_3$, 4.5 mol %, 10.1 mmol, 2.01 g) were added and stirred at 90° C. for 3 hours under an inert atmosphere. After the temperature was lowered to room temperature (25° C. or lower), water (500 mL or less) was added and stirred, and then the solid was filtered off. The solid isolated by filtering was washed with methanol and dissolved in tetrahydrofuran (THF, 1 L or less), and 100 g of activated carbon was added thereto, followed by heating at 60° C. for 2 hours. The solution was then filtered through Celite, the filtrate was concentrated, and the concentrated solid was dispersed in methanol and isolated by filtering. The obtained solid was suspended in toluene (about 1 g/15 mL), heated at 120° C. for 2 hours, and then cooled to room temperature. The solid was isolated by filtering and dried under vaccum at 50° C. for 12 hours to obtain Intermediate 1 (yield of 80%).

Subsequently, Intermediate 2 was synthesized according to the following method.

Synthesis of Intermediate 2

Intermediate 1 (187.5 mmol, 90.86 g), 1-bromo-3-iodo benzene (1.1 e. q., 206.2 mmol, 58.35 g), and tripotassium phosphate ($K_3PO_4$ 2.0 e.q., 375 mmol, 79.60 g), N,N-dimethylforamide (DMF, 187.5 mL) were added to a three-neck flask and stirred under an inert atmosphere. Copper (I) iodide (CuI 0.1 eq, 18.75 mmol, 3.57 g) was then added and stirred at 150° C. for 5 hours. After cooling to room temperature, the filtrate obtained by dilution with toluene (500 mL or less) and celite filtration was concentrated. The result was purified by silica gel column chromatography and the obtained faction was concentrated. The solid was dispersed in methanol and isolated by filtration, and dried in a vacuum condition at 50° C. for 12 hours to obtain Intermediate 2 (yield of 70%).

Synthesis of Intermediate 3

Compound S-3 (1 e.q., 140.3 mmol, 50 g) and 1-bromo-4-chlorobenzene (1.2 e.q., 168.4 mmol, 32.2 g) and THF (600 mL) were added to a three neck-flask and stirred. Then, 2M aqueous potassium carbonate solution (58.2 g of $K_2CO_3$, 210.5 mL of water) was added thereto and stirred. Thereafter, tetrakis(triphenylphosphine) palladium (0) (2 mol %, 2.81 mmol, 3.24 g) was added thereto, and the mixture was stirred at 70° C. for 3 hours under an inert atmosphere. After completion of the reaction, the mixture was extracted using toluene and water, and the solvent of the organic layer was distilled off. This was purified by column chromatography to give Intermediate 3 (yield of 85%).

Synthesis of Intermediate 4

Intermediate 3 (1 e.q., 140.3 mmol, 50 g), bis(pinacolato) diboron (1.2 e.q., 168.4 mmol, 32.2 g), aqueous potassium acetate solution ($CH_3COOK$ 58.2 g, 210.5 mL of water), and dioxane were added to a three neck-flask and stirred. Then, tris(dibenzylidene acetone)dipaladium (0) (Pd$_2$(dba)$_3$, 2 mol %, 2.81 mmol, 3.24 g) and 2-dicyclohexylphosphino-2',4',6'-triisopropylbiphenyl (Xphos) were stirred at 100° C. for 3 hours in an inert atmosphere. After the reaction was completed, the reaction mixture was allowed to cool to room temperature and impurities were filtered therefrom using Celite (registered trade mark). After the solvent was subjected to a distillation process, precipitation was performed thereon using toluene and hexane to obtain Intermediate 4 (yield of 88%).

Synthesis of Compound A17

Intermediate 2 (1 e.q., 9.38 mmol, 6.0 g), Intermediate 4 (1 e.q., 9.38 mmol, 4.1 g), toluene (30 mL), and ethanol (15 mL) were added to a three neck-flask and stirred. Then, 2M aqueous potassium carbonate solution (2.6 g of $K_2CO_3$, 9.4 mL of water) was added and stirred. Then, palladium (II) acetate (Pd(OAc)$_2$, 3 mol %, 0.28 mmol, 0.063 g) and tri(o-tolyl) phosphine (P(o-tolyl)$_3$, 4.5 mol %, 0.42 mmol, 0.128 g) were stirred in an inert atmosphere at 90° C. for 3 hours. After completion of the reaction, the mixture was extracted using toluene and water, and the solvent of the organic layer was distilled off. The result was purified by column chromatography to obtain Compound A17 (yield of 55%).

Synthesis Example A2: Synthesis of Compound A1

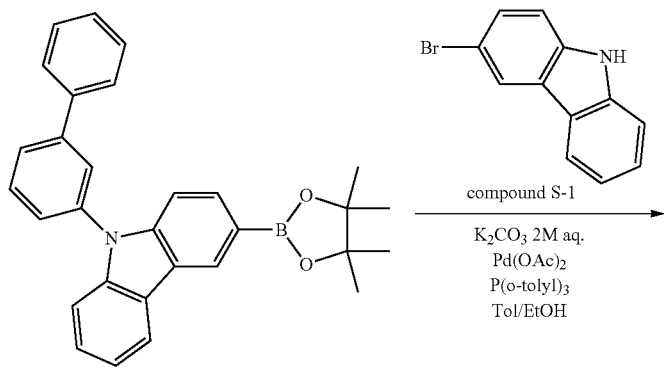

compound S-4

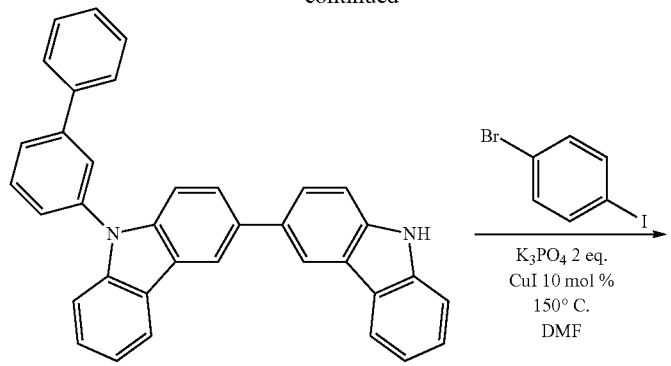

intermediate 5

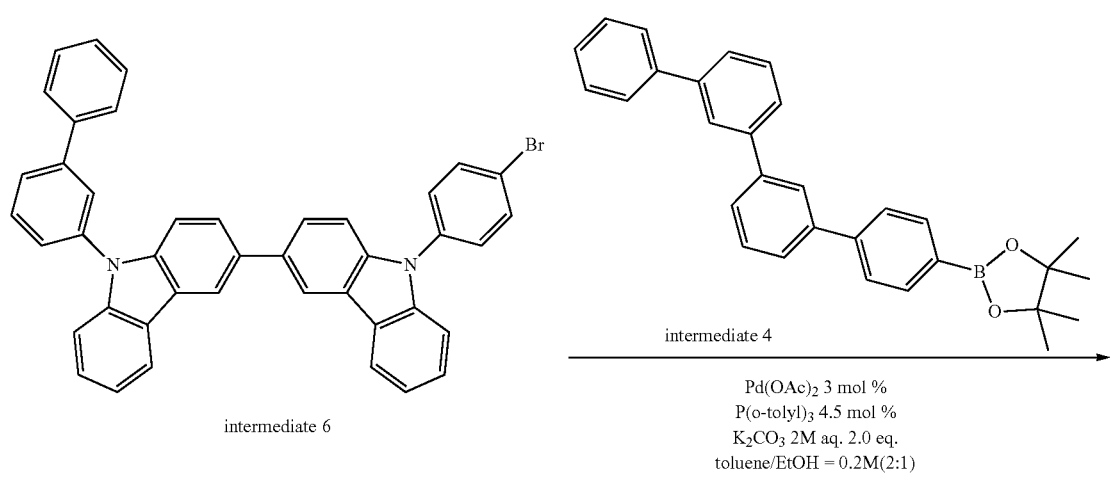

intermediate 6    intermediate 4

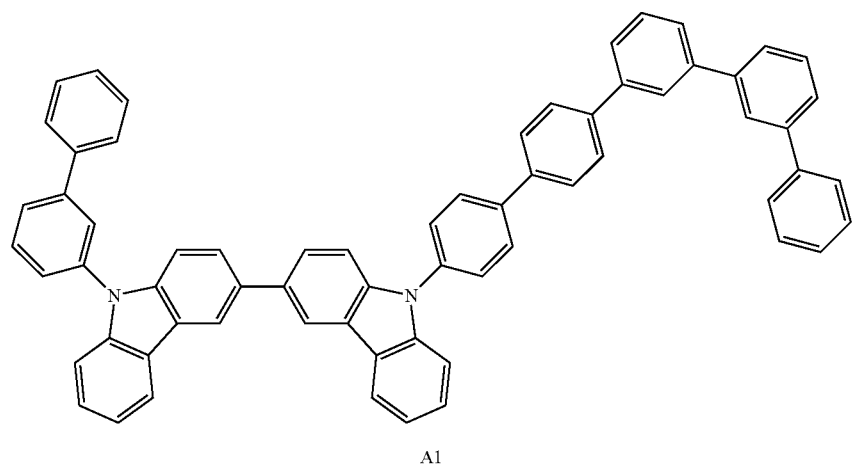

A1

Synthesis of Intermediate 5

Intermediate 5 was synthesized in the same manner as used to synthesize Intermediate 1, except that Compound S-4 was used instead of Compound S-1 (yield of 80%).

Synthesis of Intermediate 6

Intermediate 6 was synthesized in the same manner as used to synthesize Intermediate 2, except that Intermediate 5 was used instead of intermediate 1 and, 1-bromo-4- iodobenzene was used instead of 1-bromo-3-iodobenzene (yield of 75%).
Synthesis of Compound A1
Compound A1 was synthesized in the same manner as used to synthesize Compound A17, except that Intermediate 6 was used instead of Intermediate 2 (yield of 53%).
Synthesis Example A3: Synthesis of Compound A278
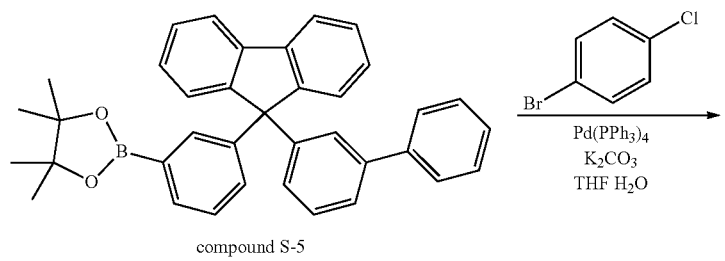
compound S-5
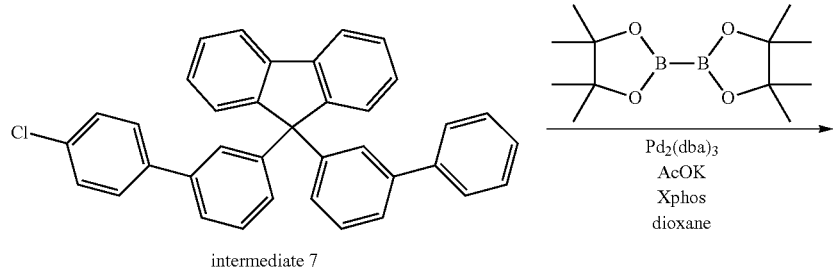
intermediate 7
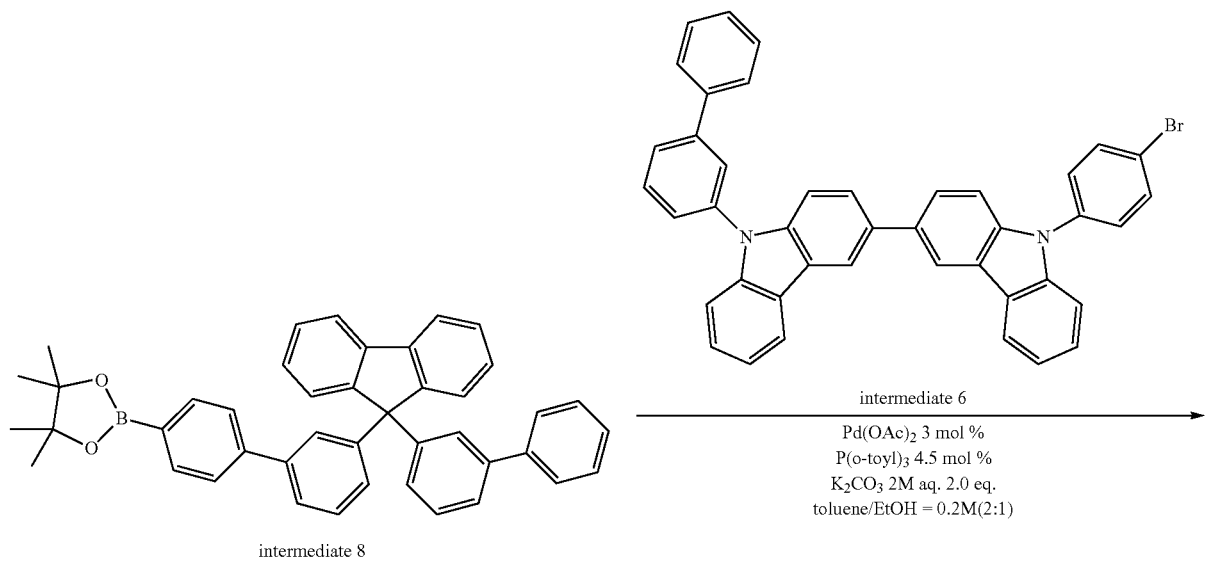
intermediate 8

-continued

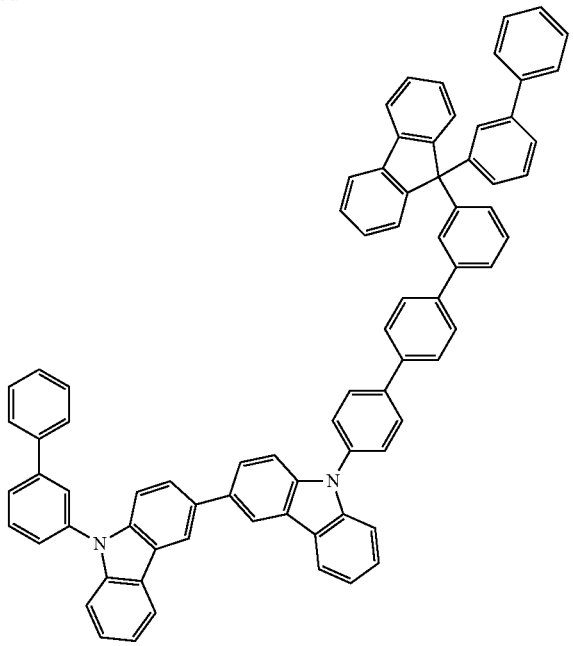

A278

Synthesis of Intermediate 7

Intermediate 7 was synthesized in the same manner as used to synthesize Intermediate 3, except that Compound S-5 was used instead of Compound S-3 (yield of 79%).

Synthesis of Intermediate 8

Intermediate 8 was synthesized in the same manner as used to synthesize Intermediate 4, except that Intermediate 7 was used instead of Intermediate 3 (yield of 70%).

Synthesis of Compound A278

Compound A278 was synthesized in the same manner as used to synthesize Compound A1, except that Intermediate 8 was used instead of Intermediate 4 (yield of 51%).

Synthesis Example A4: Synthesis of Compound A277

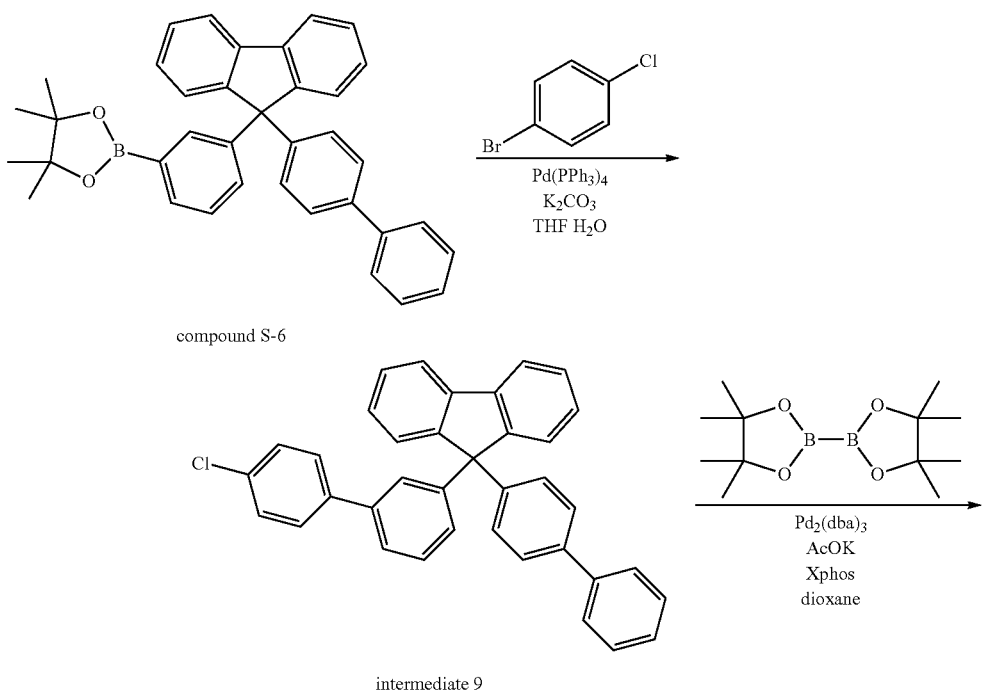

-continued

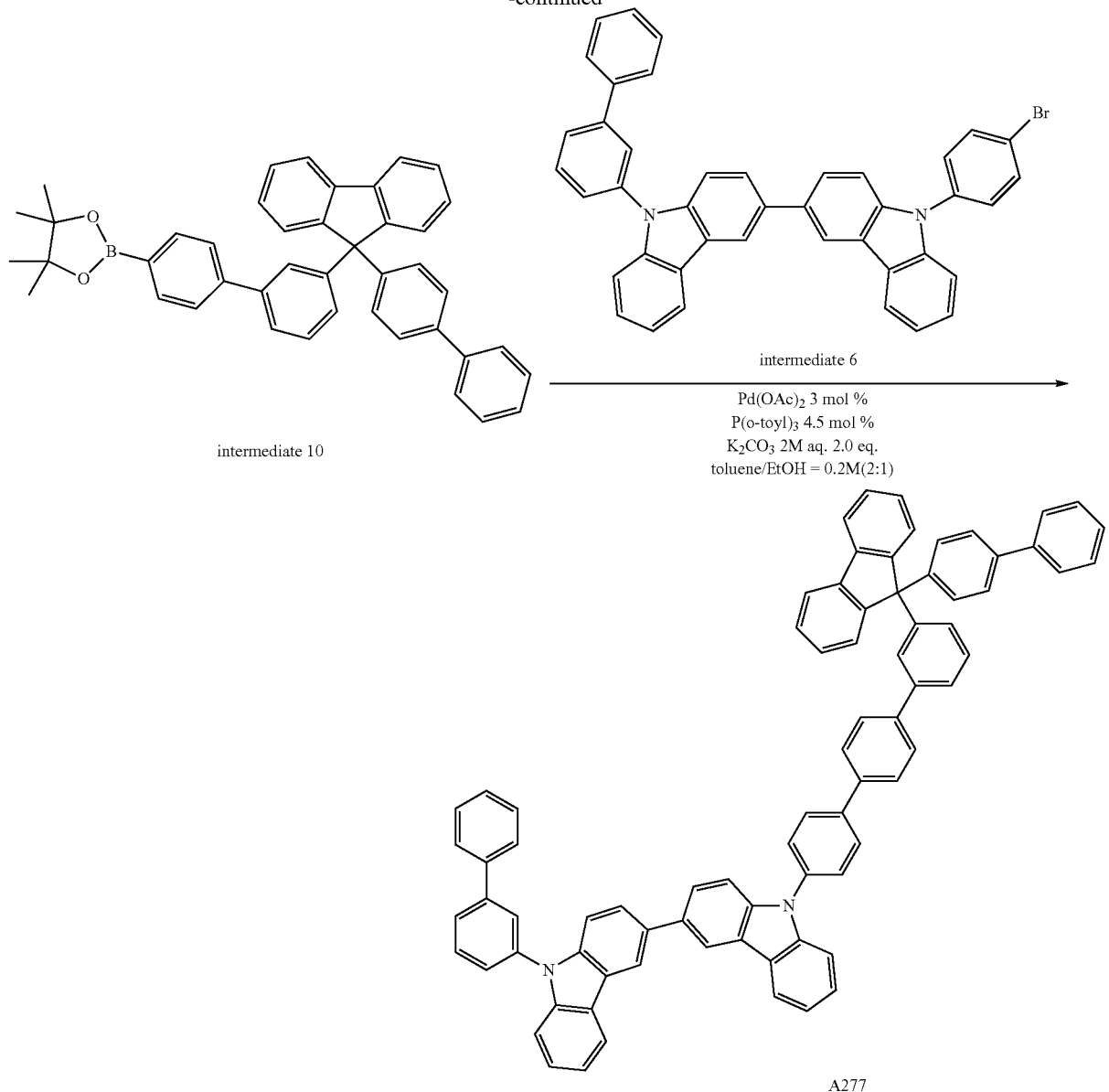

Synthesis of Intermediate 9

Intermediate 9 was synthesized in the same manner as used to synthesize Intermediate 3, except that Compound S-6 was used instead of Compound S-3 (yield of 83%).

Synthesis of Intermediate 10

Intermediate 10 was synthesized in the same manner as used to synthesize Intermediate 4, except that Intermediate 9 was used instead of Intermediate 3 (yield of 77%).

Synthesis of Compound A277

Compound A277 was synthesized in the same manner as used to synthesize Compound A1, except that Intermediate 10 was used instead of Intermediate 4 (yield of 50%).

Synthesis Example A5: Synthesis of Compound A494
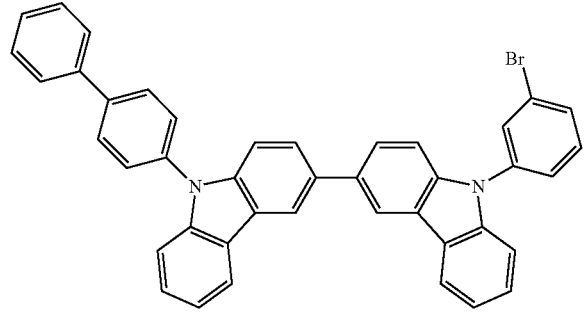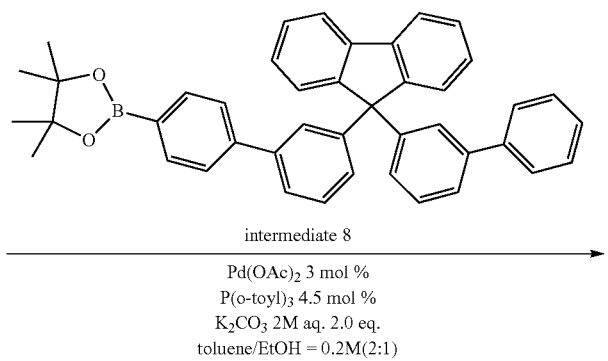
intermediate 2
intermediate 8
Pd(OAc)$_2$ 3 mol %
P(o-toyl)$_3$ 4.5 mol %
K$_2$CO$_3$ 2M aq. 2.0 eq.
toluene/EtOH = 0.2M(2:1)
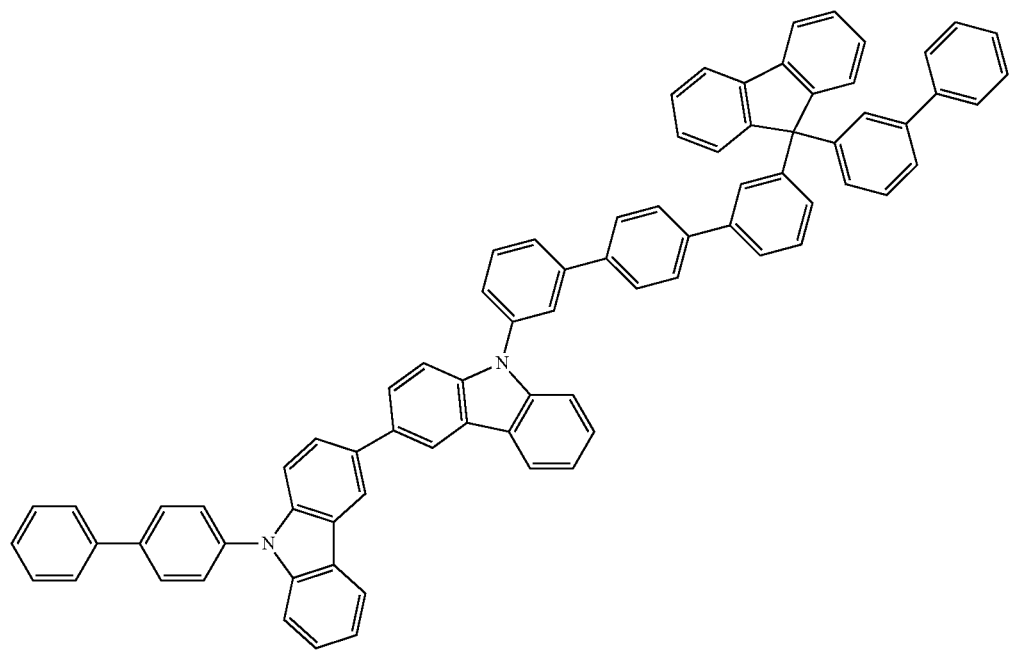
A494
Synthesis of Compound A494
Compound A494 was synthesized in the same manner as used to synthesize Compound A17, except that Intermediate 8 was used instead of Intermediate 4 (yield of 59%).

Synthesis Example A6: Synthesis of Compound A495
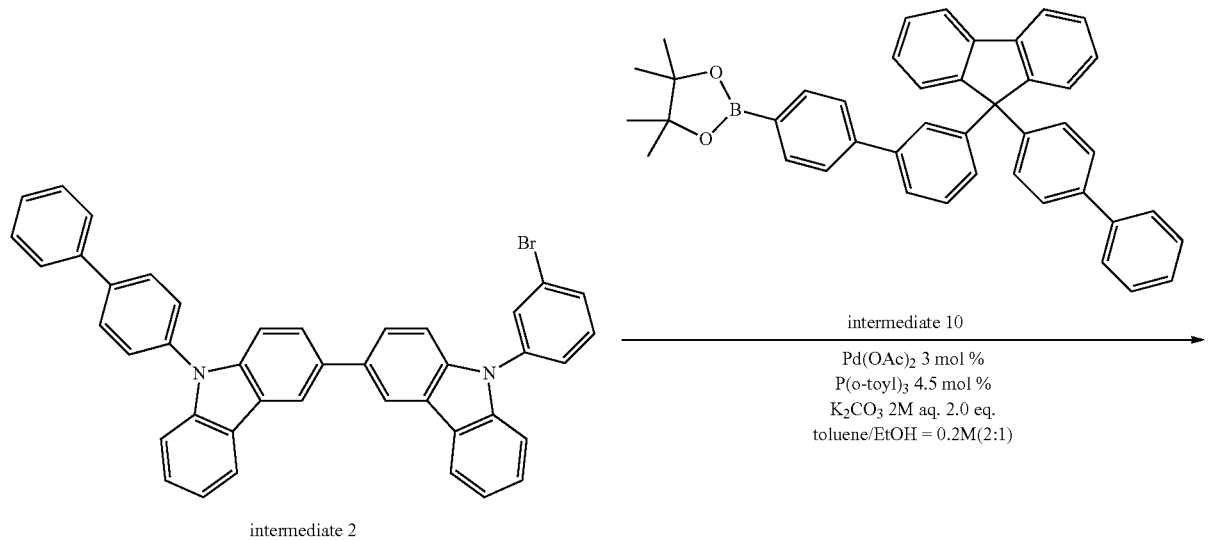
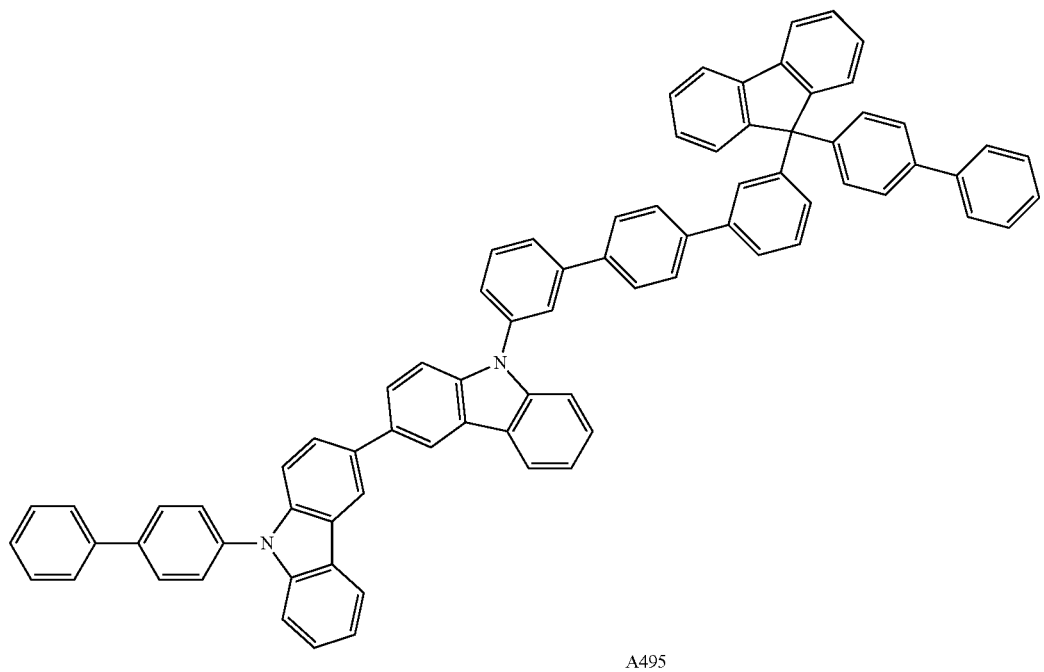
Synthesis of Compound A495
Compound A495 was synthesized in the same manner as used to synthesize Compound A17, except that Intermediate 10 was used instead of Intermediate 4 (yield of 49%).

Synthesis Example A7: Synthesis of Compound A276
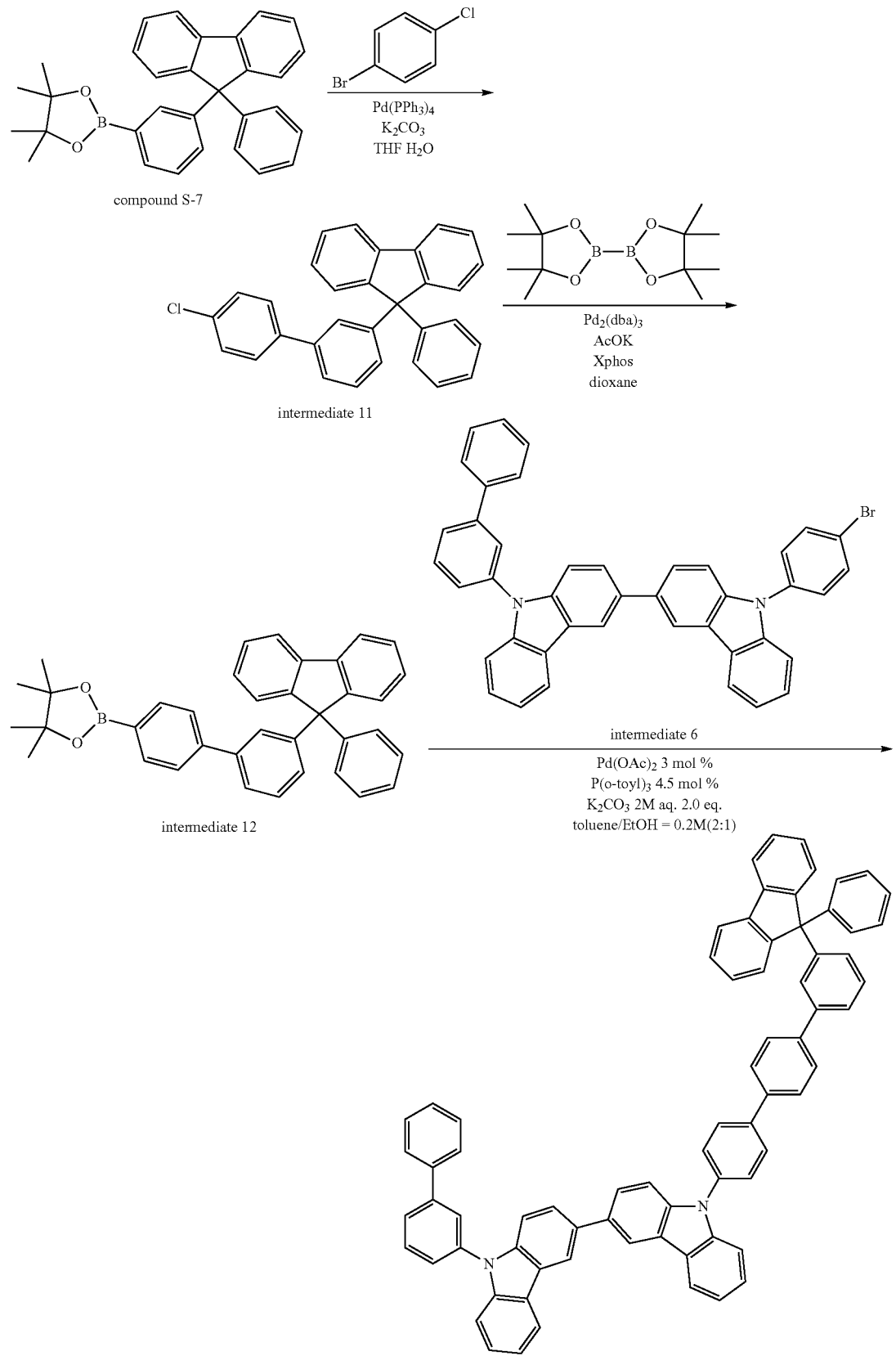

Synthesis of Intermediate 11

Intermediate 11 was synthesized in the same manner as used to synthesize Intermediate 3, except that Compound S-7 was used instead of Compound S-3 (yield of 84%).

Synthesis of Intermediate 12

Intermediate 12 was synthesized in the same manner as used to synthesize Intermediate 4, except that Intermediate 11 was used instead of Intermediate 3 (yield of 76%).

Synthesis of Compound A276

Compound A276 was synthesized in the same manner as used to synthesize Compound A1, except that Intermediate 12 was used instead of Intermediate 4 (yield of 50%).

Synthesis Example A8: Synthesis of Compound A496

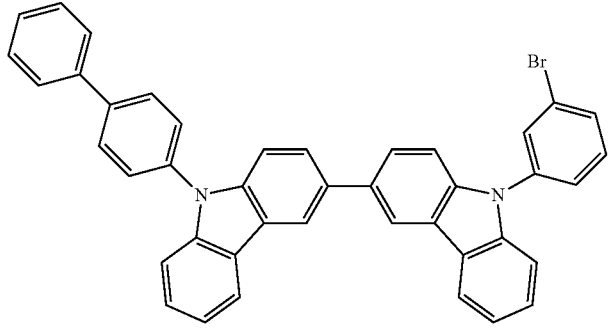

intermediate 2

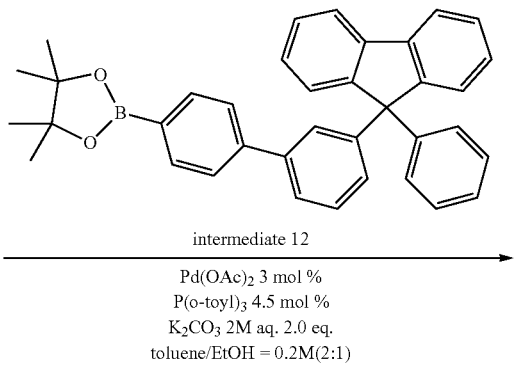

intermediate 12

Pd(OAc)₂ 3 mol %
P(o-toyl)₃ 4.5 mol %
K₂CO₃ 2M aq. 2.0 eq.
toluene/EtOH = 0.2M(2:1)

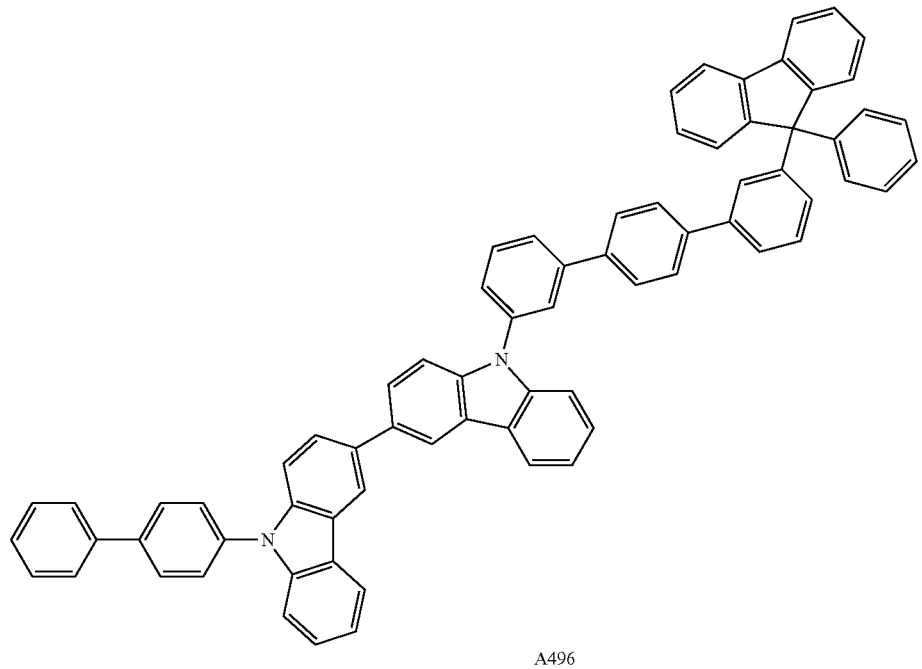

A496

Synthesis of Compound A496

Compound A496 was synthesized in the same manner as used to synthesize Compound A17, except that Intermediate 12 was used instead of Intermediate 4 (yield of 52%).

Comparative Synthesis Example A: Synthesis of Comparative Compound C1

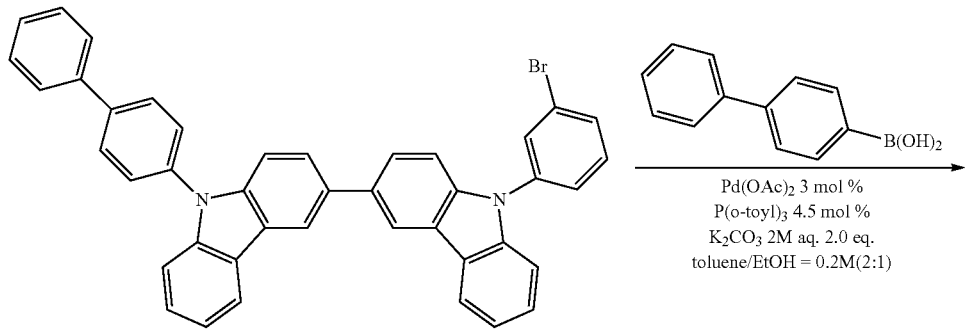

intermediate 2

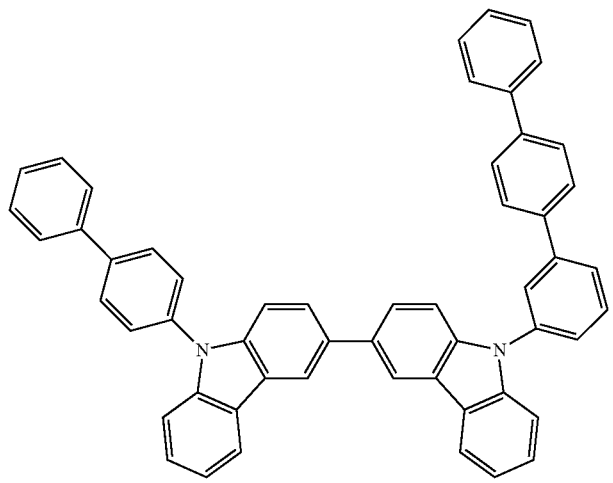

C1

Comparative Compound C1 was synthesized in the same manner as used to synthesize Compound A17, except that 4-biphenylboronic acid was used instead of Intermediate 4 (yield of 53%).

Comparative Synthesis Example B

The following compound C2 was prepared as a compound of Comparative Synthesis Example B.

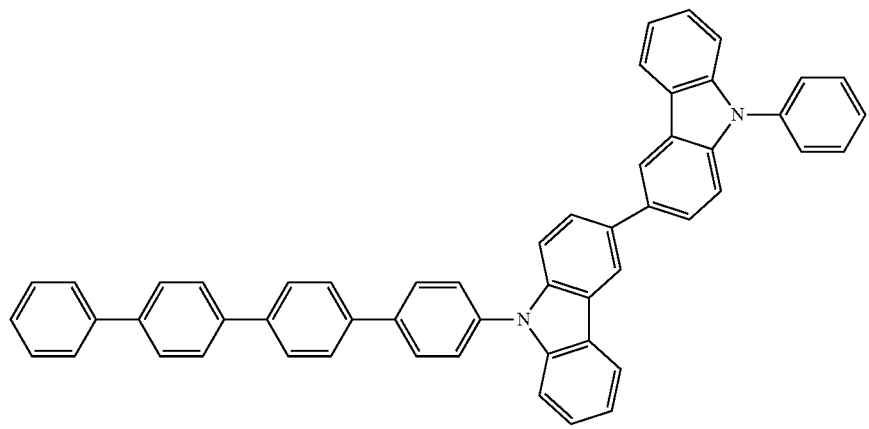

Comparative Synthesis Example C The following compound C3 was prepared as a compound of Comparative Synthesis Example C.

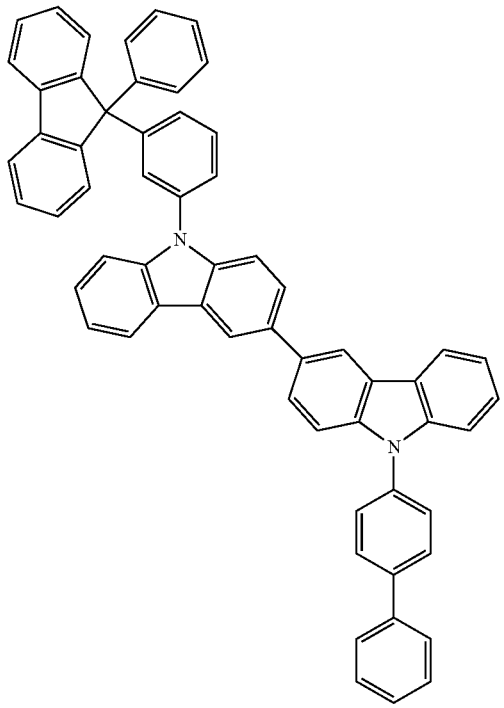

C3

Evaluation of Compounds

Measurements of HOMO Level and LUMO Level
Measurements of HOMO Level

The compounds synthesized in Synthesis Examples A1 to A8 and Comparative Synthesis Example A and the compounds of Comparative Compounds C2 and C3 were each dissolved in xylene to prepare coating solutions having a concentration of 1 wt %. Using the coating solutions, films were formed by using a spin coat method on a UV-treated ITO glass substrate at 2000 rpm, and then, the films were dried at 150° C. on a hotplate for 30 minutes, thereby obtaining samples for a measurement. The HOMO levels of the samples were measured using a photoelectron spectrometer AC-3 (manufactured by Riken Keiki Co., Ltd.) in the atmosphere. In this regard, for each sample, the intersection of the first tangential line was calculated from the measurement results, and was set as a HOMO level. The HOMO levels are usually negative.

Measurements of LUMO Levels

The compounds synthesized in Synthesis Examples A1 to A8 and Comparative Synthesis Example A and the compounds of Comparative Synthesis Examples B and C were each dissolved in toluene to prepare coating solutions having a concentration of 3.2 wt %. Using the coating solutions, films were formed by using a spin coat method on a UV-treated ITO glass substrate at 1600 rpm, and then, the films were dried at 250° C. on a hotplate for 60 minutes, thereby obtaining samples for a measurement. The thickness of each sample was about 70 nm. The obtained samples were cooled to 77 K (−196° C.) and the photoluminescence (PL) spectrum thereof was measured. For each sample, the LUMO level [eV] was computed using the peak value of the shortest wavelength side of a PL spectrum.

The results are shown in Table 1 below.

Solubility 4 parts by weight of each of the compounds synthesized according to Synthesis Examples A1 to A8 and Comparative Synthesis Example A and the compounds of Comparative Synthesis Examples B and C were added to 96 parts by weight of methyl benzoate and heated at 150° C. Solubility thereof was visually determined as follows. The results are shown in Table 1 below.

The symbol "○" represents that the compound dissolved, with no residue.

The symbol "Δ" represents that the compound partially dissolved.

The symbol "X" represents that the compound did not dissolve.

Evaluation of Pot Life of Solution 10 parts by weight of each of the compounds synthesized according to Synthesis Examples A1 to A8 and Comparative Synthesis Example A and the compounds of Comparative Synthesis Examples B and C were added to 90 parts by weight of methyl benzoate and dissolved by heating at 150° C., and then, the solutions were cooled to room temperature. The time period from when the temperature reached room temperature to when the solid started to precipitate, which can be identified with the naked eye, was evaluated ("pot life") for each compound. The results are shown in Table 1 below.

TABLE 1

| Compound | | HOMO (eV) | LUMO (eV) | Solubility | pot life |
|---|---|---|---|---|---|
| Synthesis Example A1 | A17 | −5.7 | −2.5 | ○ | 1 month or more |
| Synthesis Example A2 | A1 | −5.7 | −2.5 | ○ | 1 month or more |
| Synthesis Example A3 | A278 | −5.7 | −2.5 | ○ | 1 month or more |
| Synthesis Example A4 | A277 | −5.7 | −2.5 | ○ | 1 month or more |
| Synthesis Example A5 | A494 | −5.7 | −2.5 | ○ | 1 month or more |
| Synthesis Example A6 | A495 | −5.7 | −2.5 | ○ | 1 month or more |
| Synthesis Example A7 | A276 | −5.7 | −2.5 | ○ | 1 month or more |
| Synthesis Example A8 | A496 | −5.7 | −2.5 | ○ | 1 month or more |
| Comparative Synthesis Example A | C1 | −5.7 | −2.5 | Δ | Less than 5 hours |
| Comparative Synthesis Example B | C2 | −5.7 | −2.5 | x | Less than 1 hour |
| Comparative Synthesis Example C | C3 | −5.5 | −2.2 | ○ | 1 month or more |

It can be seen from the results of Table 1 that the LUMO of each of the compounds according to Synthesis Example A1 to A8 is deep and the compounds also have excellent solubility with respect to a solvent. Meanwhile, Compound C1 in which *—(L$_2$)$_{a2}$—Ar$_2$ is a hydrogen atom in Formula 1 did not have sufficient solubility with respect to a solvent. It can be seen that the solutions of each of the compounds according to Synthesis Examples A1 to A8 have a long pot life and are suitable for manufacturing an organic light-emitting device (coated type) by using a wet type method.

In the case of Compounds C1 and C2, it can be seen that their pot lives are short due to the low solubility with respect to a solvent as described above.

Compounds A17 and A277 were selected from Table 1, and corresponding devices were evaluated.

Materials for Device

The materials used for fabricating the device are as follows.

Synthesis of Polymer P-1

P-1

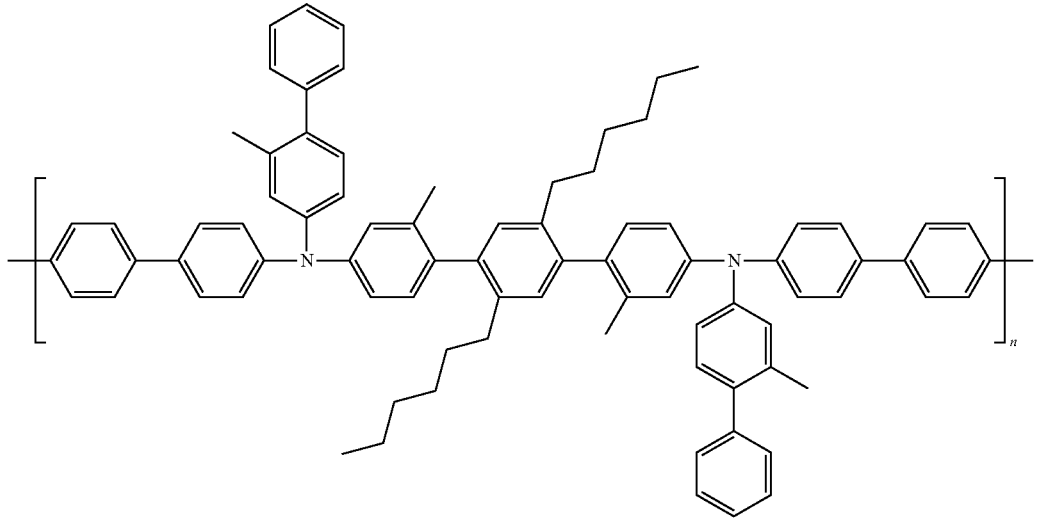

The same polymer as Compound T described in WO2011/159872 was synthesized according to the synthesis method described in that document incorporated herein by reference. The obtained polymer was called P-1. The number average molecular weight of the polymer P-1 was 141000 g/mol, and the weight average molecular weight thereof was 511000 g/mol.

Synthesis of Compound FA-14

FA-14

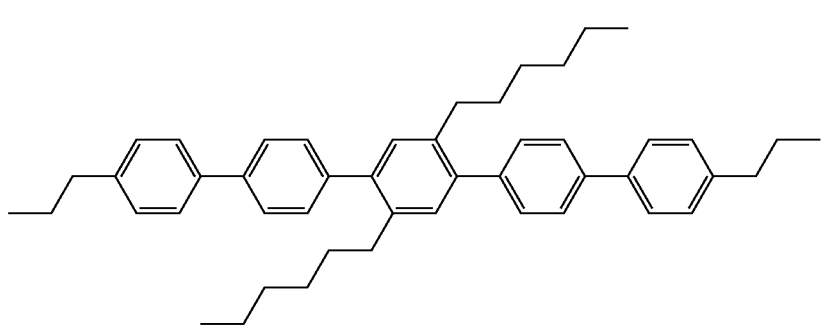

FA-14, described in US Patent Publication No. 2016/0315259, was synthesized according to the synthetic method described in that document, incorporated herein by reference.

Synthesis of Compound ET-1

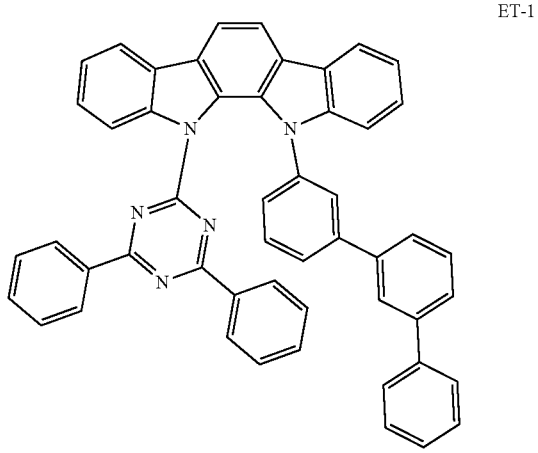

ET-1

Compound ET-1 compound described in WO 2016/033167 was synthesized according to the synthesis method described in that document incorporated herein by reference.

Synthesis of Compound WG-1

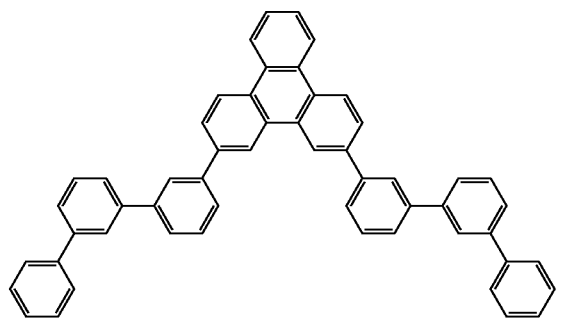

WG-1

Compound H2-4 described in WO 2016/033167 was synthesized according to the synthesis method described in that document, incorporated herein by reference.

Manufacturing of Organic Light-Emitting Device
Manufacturing of Organic Light-Emitting Device A1

An ITO glass substrate was prepared on which indium tin oxide (ITO), as a first electrode (anode), having a thickness of 150 nm was deposited in a stripe form. Poly(3,4-ethylene dioxythiophene)/poly(4-styrene sulfonate) (PEDOT/PSS) (the product of Sigma-Aldrich) was coated on the glass substrate to form a hole injection layer having a dry-film thickness of 15 nm by using a spin coat method.

80 parts by weight of polymer P-1 synthesized as described above and 20 parts by weight of Compound FA-14 were dissolved in the anisole (solvent), to prepare a coating solution for forming a hole transport layer. On the hole injection layer formed above, the coating solution for forming the hole transport layer was applied by using a spin coat method, and heated at 250° C. for 1 hour to form a hole transport layer having a thickness (dry-film thickness) of 125 nm.

Compounds A17, ET-1, and WG-1 (a mixed weight ratio of 3:7:4.5) synthesized as described above and tris(2-(3-p-xylyl)phenylpyridine)iridium (III), which is a dopant, were dissolved in methyl benzoate to prepare a coating solution for an emission layer in which the solid content was 4 wt %. In preparing the coating solution for the emission layer, the doping amount of the dopant was adjusted to be 10 wt % based on the total weight of the emission layer. On the hole transport layer formed above, the coating solution for forming the emission layer was applied by using a spin coat method, and heated at 240° C. for 30 minutes to form an emission layer having a thickness (dry-film thickness) of 55 nm.

(8-quinolinolato)lithium (Liq) and KLET-03 (the product of Chemipro Kasei Inc.) were co-deposited at a weight ratio of 1:1 on the emission layer in a vacuum deposition apparatus to form an electron transport layer having a thickness of 20 nm.

Lithium fluoride (LiF) was deposited on the formed electron transport layer by a vacuum deposition apparatus to form an electron injection layer having a thickness of 3.5 nm.

Aluminum (Al) was deposited on the formed electron injection layer by a vacuum deposition apparatus, thereby forming a second electrode (cathode) having a thickness of 100 nm.

Then, in a glove box in the nitrogen atmosphere having 1 ppm or less of water concentration and 1 ppm or less of oxygen concentration, a sealing process was performed using a glass sealing tube With a desiccant and a ultraviolet curable resin, thereby obtaining organic light-emitting device A1.

Manufacturing of Organic Light-Emitting Device A2

Organic light-emitting device A2 was manufactured in the same manner as used to prepare the organic light-emitting device A1, except that, in preparing a coating solution for an emission layer, Compound A277 was used instead of Compound A17.

Evaluation of Organic Light-Emitting Devices
Current Efficiency, Light-Emission Lifespan Voltage was applied to Organic light-emitting devices A1 and A2 by using a direct current (DC) constant voltage power supply (KEYENCE source meter). While the light emission of the organic light emitting device was measured by a luminance measuring device (the product of Topcom, SR-3), the current was gradually increased and when the luminance was 6000 cd/m$^2$, the organic light-emitting device was left while the current was kept constant.

Here, the current value per unit area (current density) of the organic light-emitting device was measured, and the luminance (cd/m$^2$) was divided by the current density (A/m$^2$) to calculate the current efficiency (cd/A). In addition, the time during which the luminance value measured by using the luminance measuring device was gradually changed (decreased) and reached to 95% of the initial luminance, was set to "LT95 light-emission lifespan (time)." In addition, the current efficiency represents the efficiency (conversion efficiency) for converting the current into light emission energy, and the higher the current efficiency, the higher the performance of the organic light emitting device.

The results are shown in Table 2 below.

TABLE 2

|  | Compound | Current efficiency | L195 light-emission lifespan (hours) |
|---|---|---|---|
| Organic light-emitting device A1 | A17 | 55.0 | 52.5 |
| Organic light-emitting device A2 | A277 | 57.2 | 37.1 |
| Comparative Example Device C1 | C1 | Not measurable | Not measurable |
| Comparative Example Device C2 | C2 | Not measurable | Not measurable |
| Comparative Example Device C3 | C3 | 55.1 | 31.7 |

From the results of Table 2, it can be seen that the organic light-emitting devices A1 and A2 prepared using Compounds A17 and A277, respectively, according to the present disclosure show excellent current efficiency and light-emission lifespan. On the other hand, Comparative example devices C1 and C2 could not be manufactured by using Compounds C1 and C2 which have short solution pot life, and thus, the current efficiency and light-emission lifespan thereof could not be measured.

In addition, Comparative example device C3 using Compound C3 having a long solution pot life did not have a long light-emission lifespan.

Manufacturing of Organic Light-Emitting Device A3

An ITO glass substrate was prepared on which indium tin oxide (ITO), as a first electrode (anode), having a thickness of 150 nm was deposited in a stripe form. Poly(3,4-ethylene dioxythiophene)/poly(4-styrene sulfonate) (PEDOT/PSS) (the product of Sigma-Aldrich) was coated on the glass substrate to form a hole injection layer having a dry-film thickness of 15 nm by using a spin coat method.

80 parts by weight of polymer P-1 synthesized as described above and 20 parts by weight of Compound FA-14 were dissolved in the anisole (solvent) to prepare a coating solution for forming a hole transport layer. On the hole injection layer formed above, the coating solution for forming the hole transport layer was applied by using a spin coat method, and heated at 250° C. for 1 hour to form a hole transport layer having a thickness (dry-film thickness) of 125 nm.

Compounds A17, ET-1, and HT-1 (a mixed weight ratio of 3:7:3) synthesized as described above and tris(2-(3-p-xylyl) phenylpyridine)iridium (III), which is a dopant, were dissolved in methyl benzoate to prepare a coating solution for an emission layer in which the solid content was 4 wt %. In preparing the coating solution for the emission layer, the doping amount of the dopant was adjusted to be 10 wt % based on the total weight of the emission layer. On the hole transport layer formed above, the coating solution for forming the emission layer was applied by using a spin coat method, and heated at 240° C. for 30 minutes to form an emission layer having a thickness (dry-film thickness) of 55 nm.

(8-quinolinolato)lithium (Liq) and KLET-03 (the product of Chemipro Kasei Inc.) were co-deposited at a weight ratio of 1:1 on the emission layer in a vacuum deposition apparatus to form an electron transport layer having a thickness of 20 nm.

Lithium fluoride (LiF) was deposited on the formed electron transport layer by a vacuum deposition apparatus to form an electron injection layer having a thickness of 3.5 nm.

Aluminum (Al) was deposited on the formed electron injection layer by a vacuum deposition apparatus, thereby forming a second electrode (cathode) having a thickness of 100 nm.

Then, in a glove box in the nitrogen atmosphere having 1 ppm or less of water concentration and 1 ppm or less of oxygen concentration, a sealing process was performed using a glass sealing tube with a desiccant and a ultraviolet curable resin, thereby obtaining Organic light-emitting device A3.

Manufacturing of Organic Light-Emitting Device A4

Organic light-emitting device A4 was manufactured in the same manner as used to prepare Organic light-emitting device A3, except that, in preparing a coating solution for an emission layer, Compound A277 was used instead of Compound A17.

Manufacturing of Organic Light-Emitting Device C4

Organic light-emitting device A4 was manufactured in the same manner as used to prepare Organic light-emitting device A3, except that, in preparing a coating solution for an emission layer, Compound HT-1 was used instead of Compound A17.

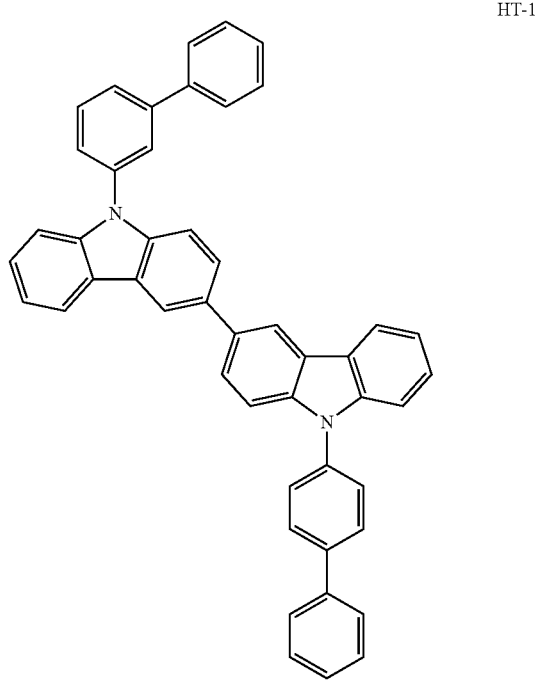 [SMILES: c1ccc(-c2ccc(-n3c4ccccc4c4cc(-c5ccc6c(c5)c5ccccc5n6-c5cccc(-c6ccccc6)c5)ccc43)cc2)cc1]

HT-1

Evaluation of Organic Light-Emitting Devices

Current Efficiency, Light-Emission Lifespan

Voltage was applied to Organic light-emitting devices A3, A4 and C4 by using a direct current (DC) constant voltage power supply (KEYENCE source meter). While the light emission of the organic light emitting device was measured by a luminance measuring device (the product of Topcom, SR-3), the current was gradually increased and when the luminance was 6000 cd/m², the organic light-emitting device was left while the current was kept constant.

Here, the current value per unit area (current density) of the organic light-emitting device was measured, and the luminance (cd/m²) was divided by the current density (A/m²) to calculate the current efficiency (cd/A). In addition, the time during which the luminance value measured by using the luminance measuring device was gradually changed (decreased) and reached to 95% of the initial luminance, was set to "LT95 light-emission lifespan (time)." In addition, the current efficiency represents the efficiency (conversion efficiency) for converting the current into light emission energy, and the higher the current efficiency, the higher the performance of the organic light emitting device.

The results are shown in Table 3 below.

TABLE 3

| | Compound | Current efficiency | L195 luminescence lifespan (hours) |
|---|---|---|---|
| Organic light-emitting device A3 | A17 | 52.6 | 72.6 |
| Organic light-emitting device A4 | A277 | 54.9 | 47.0 |
| Comparative Example Device C4 | HT-1 | 51.4 | 34.4 |

Synthesis Example 1: Synthesis of Compound 1

Synthesis of Intermediate 1a

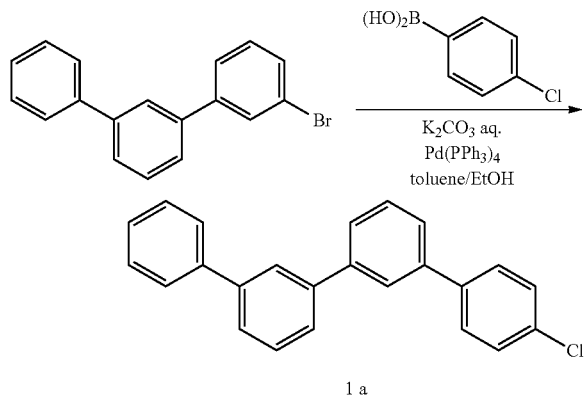

1a 3-bromo-1,1':3',1''-terphenyl (1 mol, 309.2 g), 4-chlorophenyl borate (1.05 e.q., 1.05 mol, 164.2 g), toluene (2L), and ethanol (200 ml) were added to a three neck-flask under a nitrogen atmosphere and dissolved by stirring. Then, a potassium carbonate ($K_2CO_3$) 2M aqueous solution (1.5 e.q., 750 ml) was added thereto. Then, tetrakis(triphenylphosphine) palladium(0) ($Pd(PPh_3)_4$) (3 mol %, 30 mmol, 34.7 g) was added thereto and stirred at 70 for 12 hours. The temperature was decreased to room temperature, and a filtration process was performed thereon using CELITE, followed by washing twice with pure water. The obtained product was dried using anhydrous magnesium sulfate and filtered through a pad of silica gel. The filtrate was concentrated under vacuum to remove the solvent to obtain the crude product.

Then, the obtained product was recrystallized three times by using toluene and hexane (the ratio of toluene to hexane was 2 ml:10 ml/1 g) and vacuum-dried (50° C., 12 hours) to obtain the target product (Intermediate 1a) of a white solid. The amount of Intermediate 1a was 153.7 g, and the yield thereof was 45%.

Synthesis of Intermediate 1b

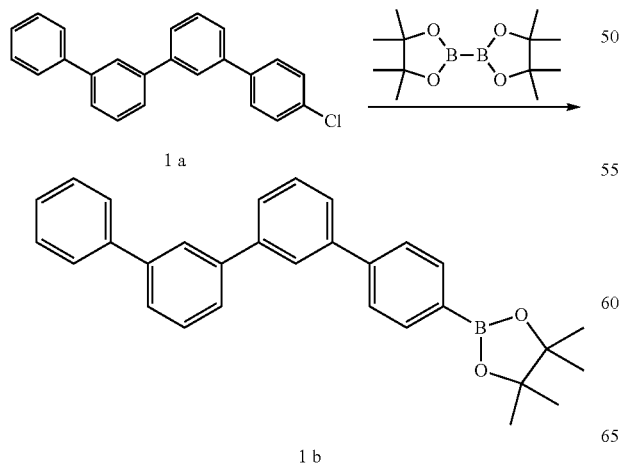

1b

Intermediate 1a (129 mmol, 44.0 g), bis(pinacolato)diboron (1.05 e.q., 142 mmol, 36.1 g), potassium acetate (2 e.q., 258 mmol, 25.3 g), and 1,4-dioxane (258 ml) were added to a three neck-flask in the nitrogen atmosphere and then dispersed by stirring.

Then, palladium acetate (2 mol %, 2.58 mmol, 579 mg) and X-Phos (2-dicyclohexylphosphino-2',4',6'-triisopropylbiphenyl) (4 mol %, 5.16 mmol, 2.46 g) were added thereto and stirred at 80° C. for 10 hours.

After the temperature was decreased to room temperature, the mixture was diluted with toluene (300 ml), filtered using CELITE, and washed three times with pure water. The obtained product was dried using anhydrous magnesium sulfate and filtered through a pad of silica gel. The filtrate was concentrated under vacuum to remove the solvent to obtain the crude product.

The resultant product was recrystallized in hexane (10 ml/1 g), and dried in a vacuum condition (50° C., 12 hours) to obtain the target product (Intermediate 1b) of a white solid. The amount of Intermediate 1b was 43.9 g, and the yield thereof was 79%.

Synthesis of Intermediate 1c

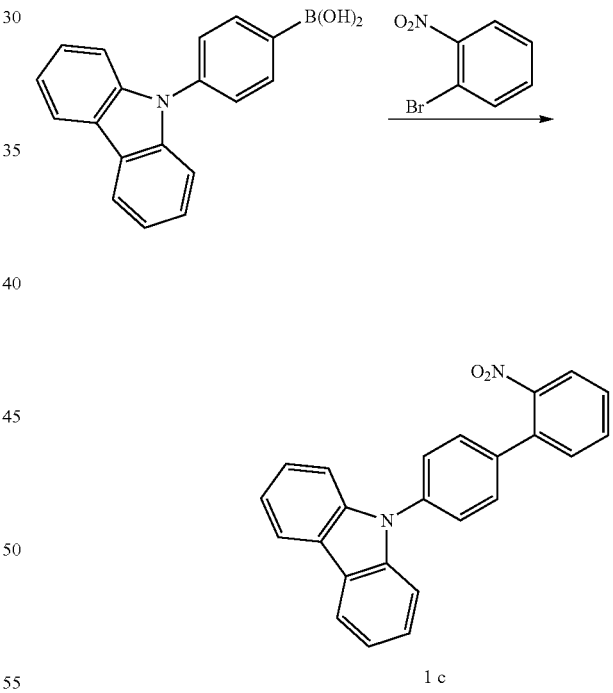

1c (4-(9H-carbazol-9-yl)phenyl)boronic acid (210 mmol, 60.3 g), 1-bromo-2-nitrobenzene (1.0 e.q., 200 mmol, 40.4 g), toluene (800 ml), and ethanol (200 ml) were added to a three neck-flask under a nitrogen atmosphere, and dissolved by stirring. Then, a potassium carbonate ($K_2CO_3$) 2M aqueous solution (1.5 e.q., 150 ml) was added thereto. Thereafter, $Pd(PPh_3)_4$ (3 mol %, 6 mmol, 6.93 g) was added thereto, and the mixture was stirred at 70° C. for 6 hours. After the temperature was decreased to room temperature, the mixture was diluted with toluene (1 L), filtered using CELITE, and washed three times with pure water. The obtained product was dried using anhydrous magnesium sulfate and filtered through a pad of silica gel. The filtrate was concentrated under vacuum to remove the solvent to obtain the crude product. The resultant product was recrystallized twice using toluene and ethanol (a ratio of toluene and ethanol was 3 ml:7 ml/1 g) to obtain the target product (Intermediate 1c) of a pale yellow solid. The amount of Intermediate 1c was 64.1 g, and the yield thereof was 88%.

Synthesis of Intermediate 1d

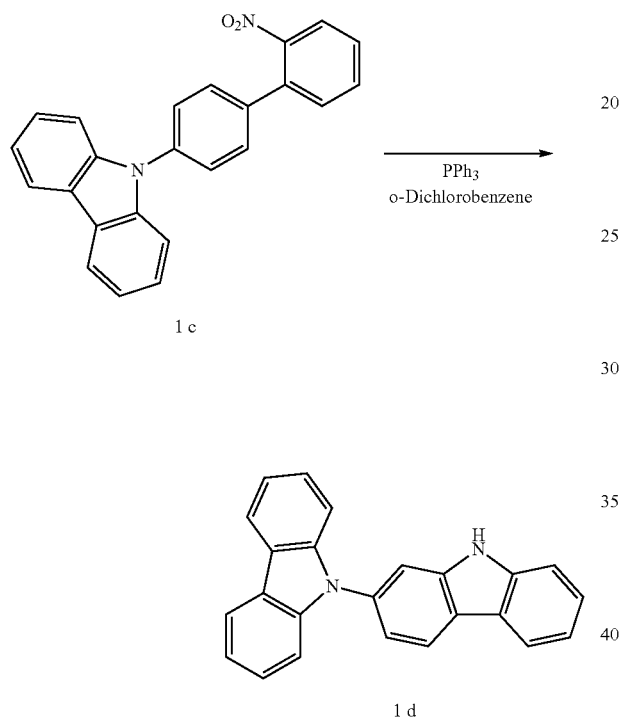

Intermediate 1c (175 mmol, 63.8 g), triphenylphosphine (3.0 e.q., 525 mmol, 137.7 g), and o-dichlorobenzene (525 ml) were added to a three neck-flask in the nitrogen atmosphere, and then, dispersed by stirring. Thereafter, the mixture was stirred at 150° C. for 10 hours. After the temperature was decreased to room temperature, the resultant mixture was diluted with methanol (2 L) and precipitated solid was obtained therefrom. Ultrasonic irradiation was then performed thereon for 30 minutes. The precipitated solid was collected by filtration, and then dried in a vacuum condition (50° C., 20 hours).

The obtained product was dissolved in tetrahydrofuran and then subjected to a silica gel short column chromatography to remove origin impurities therefrom. Also, a concentration process was performed thereon by adsorption-removing the colored impurities by using activated carbon. Then, the resultant product was recrystallized in toluene to obtain a pale yellow solid (Intermediate 1d). The amount of Intermediate 1d was 27.3 g, and the yield thereof was 47%.

Synthesis of Intermediate 1e

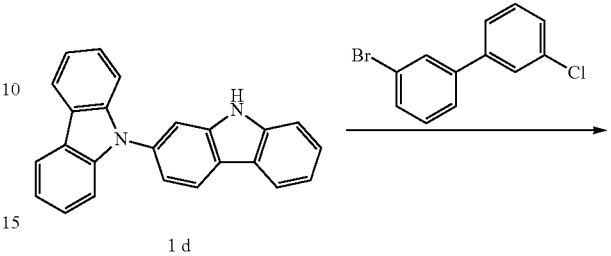

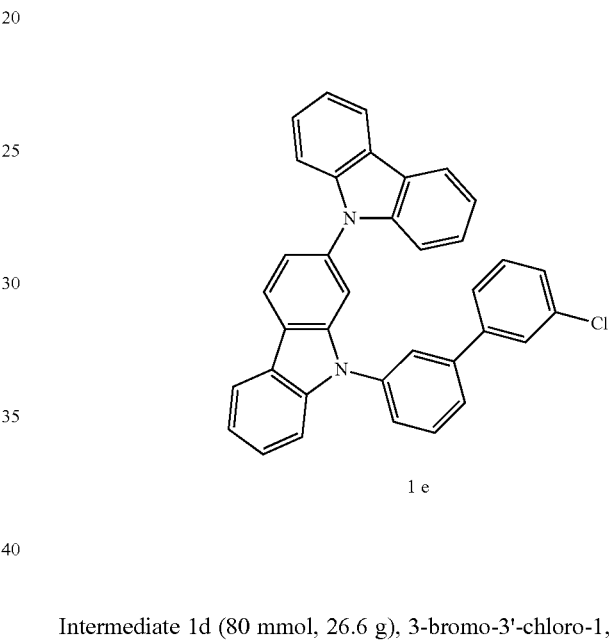

Intermediate 1d (80 mmol, 26.6 g), 3-bromo-3'-chloro-1,1'-biphenyl (1.2 e.q., 96 mmol, 25.7 g), xylene (320 ml), and sodium tert-butoxide (2 e.q., 160 mmol, 15.4 g) were added to a three neck-flask under a nitrogen atmosphere, and then, dissolved by stirring. Then, tris(dibenzylidene acetone)dipalladium(0) ($Pd_2(dba)_3$) (2 mol %, 1.6 mmol, 1.47 g) and tri-tert-butylphosphonium tetrafluoroborate (8 mol %, 6.4 mmol, 1.86 g) were added thereto and stirred at 130° C. for 6 hours. After the temperature was decreased to room temperature, a filtration process was performed thereon using CELITE. The filtrate was filtered through a pad of silica gel. The filtrate was concentrated under vacuum to remove the solvent to obtain the crude product.

The obtained product was purified by silica gel column chromatography (mobile phase included toluene and hexane at a ratio of 4:6). In addition, the purification product was recrystallization with ethyl acetate and hexane (the ratio of ethyl acetate and hexane was 4 ml:6 ml/1 g) to obtain a white solid (Intermediate 1e). The amount of intermediate 1e was 24.5 g, and the yield thereof was 59%.

Synthesis of Compound 1

Synthesis of Intermediate 1e

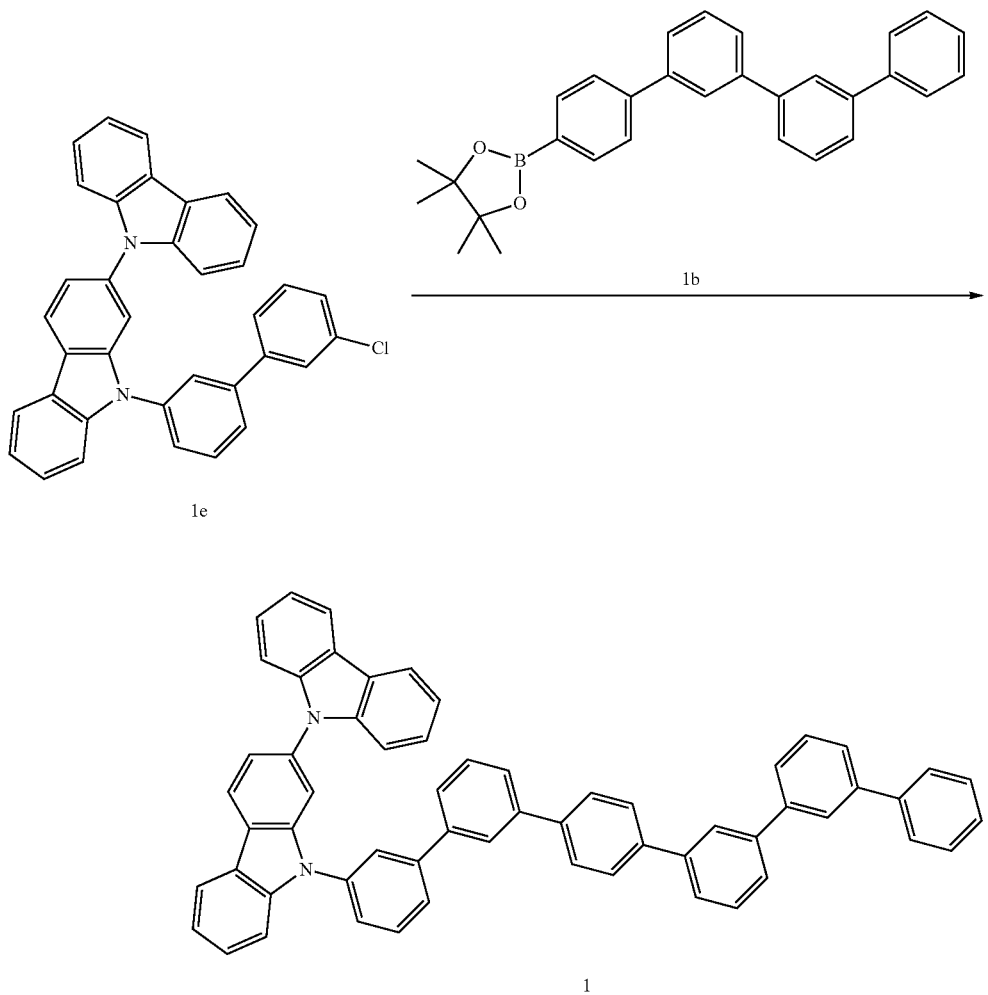

Intermediate 1e (15 mmol, 7.79 g), Intermediate 1b (16.5 mmol, 7.13 g), toluene (150 ml), and ethanol (15 ml) were added to a three neck-flask in the nitrogen atmosphere and then dissolved by stirring. Then, a potassium carbonate ($K_2CO_3$) 2M aqueous solution (1.5 e.q., 11.3 ml) was added thereto. Then, palladium acetate (3 mol %, 0.45 mmol, 101 mg) and 2-dicyclohexylphosphino-2',6'-dimethoxybiphenyl (S-Phos) (4.5 mol %, 0.68 mmol, 279 mg) were added thereto and stirred at 80° C. for 8 hours. After the temperature was decreased to room temperature, the mixture was diluted with toluene (200 ml), filtered using CELITE, and washed twice with pure water. The obtained product was dried using anhydrous magnesium sulfate and filtered through a pad of silica gel. The filtrate was concentrated under vacuum to remove the solvent to obtain the crude product. The obtained product was purified by silica gel column chromatography (the mobile phase included toluene and hexane at a ratio of 5:5), and dispersion-washed with ethyl acetate to obtain a white solid (Compound 1). The amount of Compound 1 was 8.40 g and the yield thereof was 71%.

Synthesis Example 2: Synthesis of Compound 2

Synthesis of Intermediate 2a

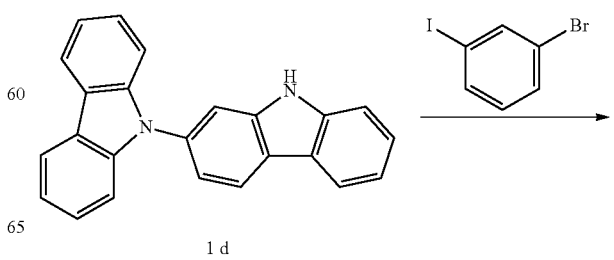

-continued

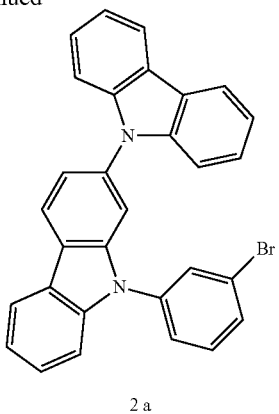

2a

Intermediate 1d (50 mmol, 16.6 g), 3-bromo iodo benzene (5.0 e.q., 250 mmol, 70.7 g), potassium carbonate (2 e.q., 100 mmol, 13.8 g) and cuprous iodide (CuI) (5 mol %, 2.5 mmol, 476 mg) were added to a three neck-flask in the nitrogen atmosphere and dispersed by stirring. Thereafter, the mixture was stirred at 180° C. for 10 hours. After the temperature was decreased to room temperature, the mixture was diluted with toluene (500 ml), and filtered using CELITE. The filtrate was filtered through a pad of silica gel. The filtrate was concentrated under vacuum to remove the solvent to obtain the crude product.

The obtained product was purified by silica gel column chromatography (mobile phase was toluene and hexane at a ratio of 4:6). In addition, the purification product was recrystallization with ethyl acetate and hexane (the ratio of ethyl acetate and hexane was 4 ml:6 ml/1 g) to obtain a white solid (Intermediate 2a). The amount of intermediate 2a was 18.8 g, and the yield thereof was 77%.

Synthesis of Compound 2

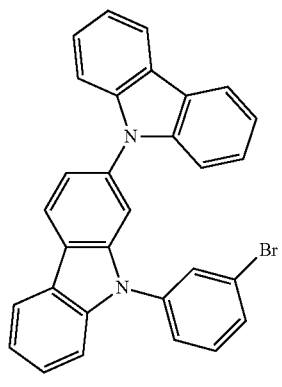

2a

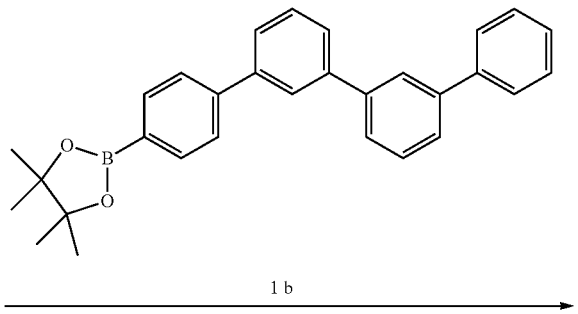

1b

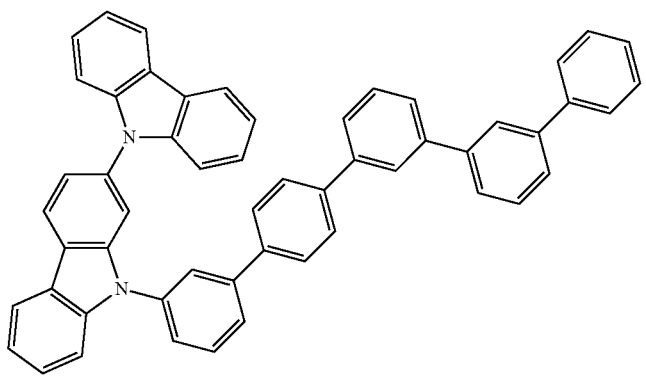

2

Intermediate 2a (15 mmol, 7.31 g), Intermediate 1b (16.5 mmol, 7.13 g), toluene (150 ml), and ethanol (15 ml) were added to a three neck-flask in the nitrogen atmosphere and then dissolved by stirring. Then, a potassium carbonate ($K_2CO_3$) 2M aqueous solution (1.5 e.q., 11.3 ml) was added thereto. Then, palladium acetate (3 mol %, 0.45 mmol, 101 mg) and o-tolyl phosphine (4.5 mol %, 0.68 mmol, 207 mg) were added thereto and stirred at 80° C. for 8 hours. After the temperature was decreased to room temperature, the mixture was diluted with toluene (200 ml), filtered using CELITE, and washed twice with pure water. The obtained product was dried using anhydrous magnesium sulfate and concentrated by filtration through a pad of silica gel.

The obtained product was purified by silica gel column chromatography (mobile phase included toluene and hexane at a ratio of 5:5). Furthermore, dispersion-washing with ethyl acetate was carried out to obtain a white solid (Compound 2). The amount of Compound 2 was 8.13 g, and the yield thereof was 76%.

Compounds 1 and 2 obtained above, and Comparative Compounds C-1 and Cz3 described below were prepared as solid samples.

Comparative Compound C-1

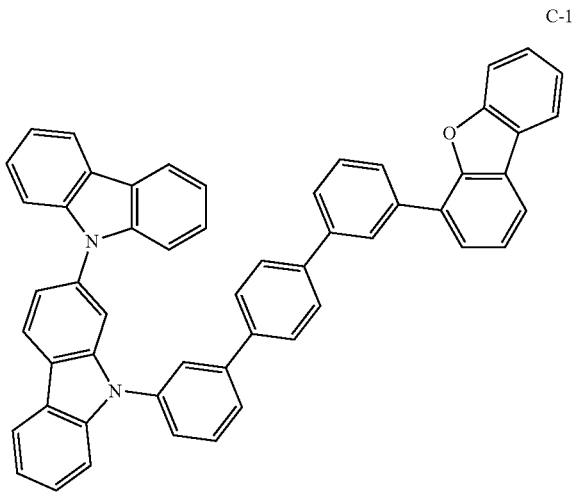

C-1

Comparative Compound Cz3

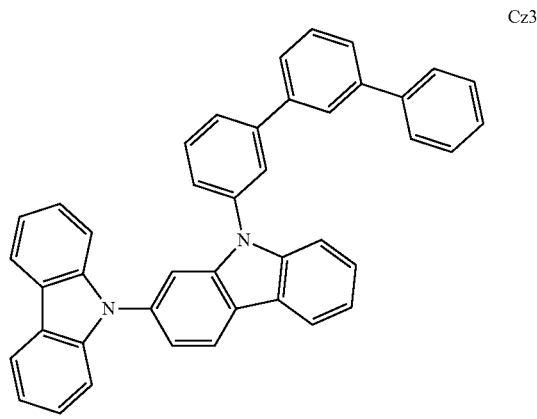

Cz3

Solubility Evaluation 50 mg of a solid sample was placed in a colorless sample bottle, 500 mg of methyl benzoate was added as a solvent, and ultrasonic irradiation was performed for 20 minutes at room temperature to visually identify whether the solid sample remained. And when there was a residual solid sample, the solvent was added little by little, and the ultrasonic irradiation was repeated until the solid sample was completely dissolved, and the solubility was calculated by using the amount of the solvent that was required to dissolve the solid sample. The results are shown in Table 4 below.

Evaluation of Pot Life of Solution 50 mg of a solid sample was placed in a colorless sample bottle, 1.0 g of methyl benzoate was added as a solvent, and was completely dissolved by heating at 150° C., thereby producing 5 wt % of the solution. Thereafter, the solution was cooled to room temperature, and the time from when the temperature reaches room temperature to when the precipitation solid, such as crystals, started to be visually identified, was defined as the pot life. In other words, the longer the pot life, crystallization less occurs. The measurement results are shown in Table 4 below.

TABLE 4

| Compound | Solubility in methyl benzoate at room temperature (wt %) | Pot life of 5 wt % of methyl benzoate solution (hour) |
| --- | --- | --- |
| Compound 1 | 10 | 300 |
| Compound 2 | 8 | 300 |
| Comparative Compound C-1 | 0.5 | 4 |
| Comparative Compound C-3 | 2 | 1 |
| Comparative Compound C-2 | 0.1 | Pot life could not be evaluated |
| Comparative Compound C-3 | 10 | 300 |

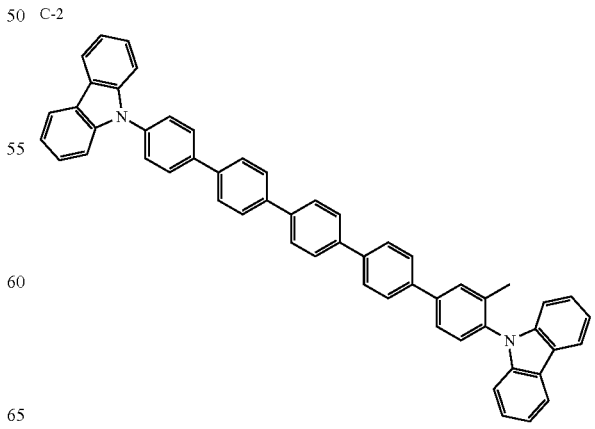

C-2

V-22

TABLE 4-continued

| Compound | Solubility in methyl benzoate at room temperature (wt %) | Pot life of 5 wt % of methyl benzoate solution (hour) |
|---|---|---|
| C-3 | | 5 |

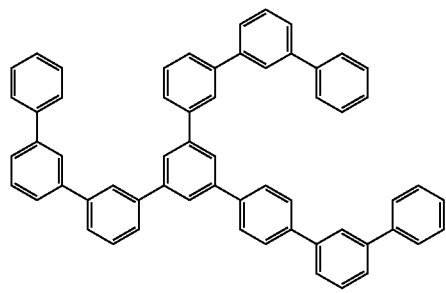

Measurements of HOMO Values and LUMO Values

Compounds 1 and 2 obtained above, and Comparative Compounds C-1 and Cz3 described above were prepared as solid samples. Then, HOMO and LUMO values were measured as follows.

1. Fabrication of Measurement Samples (1) A sample solution was prepared such that the amount of a solid sample was 4 parts by weight with respect to 100 parts by weight of methyl benzoate as a solvent.

(2) The sample solution prepared in the above 1.(1) was coated on each of an ITO substrate and a quartz substrate by using a spin coating method to form a coating film having a dry-film thickness of 50 nm. The obtained coating film was heated at 120° C. for 1 hour under a vacuum pressure of $10^{-1}$ Pa or less, and then cooled to room temperature under a vacuum pressure of $10^{-1}$ Pa or less to form a thin film layer (thin film sample).

2. Measurement of HOMO Values

With respect to the thin-film sample on the ITO substrate manufactured in 1.(2), HOMO values were measured by using a photoelectron spectrometer AC-3 (manufactured by Riken Keiki Co., Ltd.) in the atmosphere.

3. Measurement of LUMO Values

With respect to the thin-film sample on the quartz substrate manufactured in 1.(2), the energy gap value ($E_g$) was measured from the absorption edge of the ultraviolet visible absorption spectrum measured by using a spectrophotometer U-3900 (manufactured by Hitachi Hi-Tech Science), and the LUMO value was calculated according to Equation 3.

Equation 3

$$LUMO = HOMO - E_g$$

The calculation results are shown in Table 5 below.

Measurement of Glass Transition Temperature ($T_g$)

Compounds 1 and 2, and Comparative Compounds C-1 and Cz3 were prepared as solid samples. Moreover, the azine ring derivative Az1, the phosphorescent platinum group metal complex TEG, and the Comparative Compound Cz2 to Cz3 which were used for manufacture of an organic light-emitting device to be described later were prepared as solid samples.

Next, the process of scanning measurement using about 5 mg of solid samples was repeated 3 times using the differential scanning calorimeter DSC6220 (made by Seiko Corporation). Here, the conditions for measurements included the temperature increase rate of 10° C./min in the temperature range of −50 t to 300° C., and the temperature decrease rate of −50° C./min in the temperature range of 300° C. to −50° C. The glass transition temperature ($T_g$) was measured from the second and subsequent scanning calorie curve. The measurement results are shown in Table 5 below.

TABLE 5

| Compound | HOMO (eV) | LUMO (eV) | $T_g$(° C.) |
|---|---|---|---|
| Compound 1 | −6.0 | −2.7 | 114 |
| Compound 2 | −6.0 | −2.8 | 112 |
| Az1 | −5.9 | −3.0 | 125 |
| TEG | −5.4 | −2.9 | — (Not measurable) |
| Comparative Compound Cz1 | −5.6 | −2.3 | 115 |
| Comparative Compound Cz2 | −5.8 | −2.6 | 108 |
| Comparative Compound Cz3 | −6.0 | −3.0 | 95 |
| Comparative Compound C-1 | −6.0 | −2.8 | 149 |
| Comparative Compound C-2 | −6.2 | −3.0 | 108 |
| Comparative Compound C-3 | −6.4 | −2.7 | 121 |

Manufacturing of Organic Light-Emitting Devices

Example 1

First, a glass substrate on which a stripe-shaped indium tin oxide (ITO) was deposited as a first electrode (anode) was prepared. Poly(3,4-ethylene dioxythiophene)/poly(4-styrenesulfonate) (PEDOT/PSS) (manufactured by Sigma-Aldrich)) was applied on the glass substrate by a spin coat method to form a hole injection layer having a dry-film thickness of 30 nm.

Then, prepared was a coating solution for a hole transport layer, the coating solution including the solvent anisole, 3 parts by weight of a hole transporting polymer (HTP1) (weight average molecular weight Mw=400,000, PDI (Mw/Mn)=2.7) having a repeating unit represented by the following formula with respect to 100 parts by weight of the solvent, and 0.6 parts by weight of low molecular weight compound AD1 with respect to 100 parts by weight of the solvent. Subsequently, the obtained coating solution for a hole transport layer was applied by using a spin coat method to form a coating film having a dry-film thickness of 125 nm. The obtained coating film was heated at 120° C. for 1 hour under a vacuum pressure of $10^{-1}$ Pa or less, and then cooled to room temperature under a vacuum pressure of $10^{-1}$ Pa or less to form a hole transport layer.

465 466

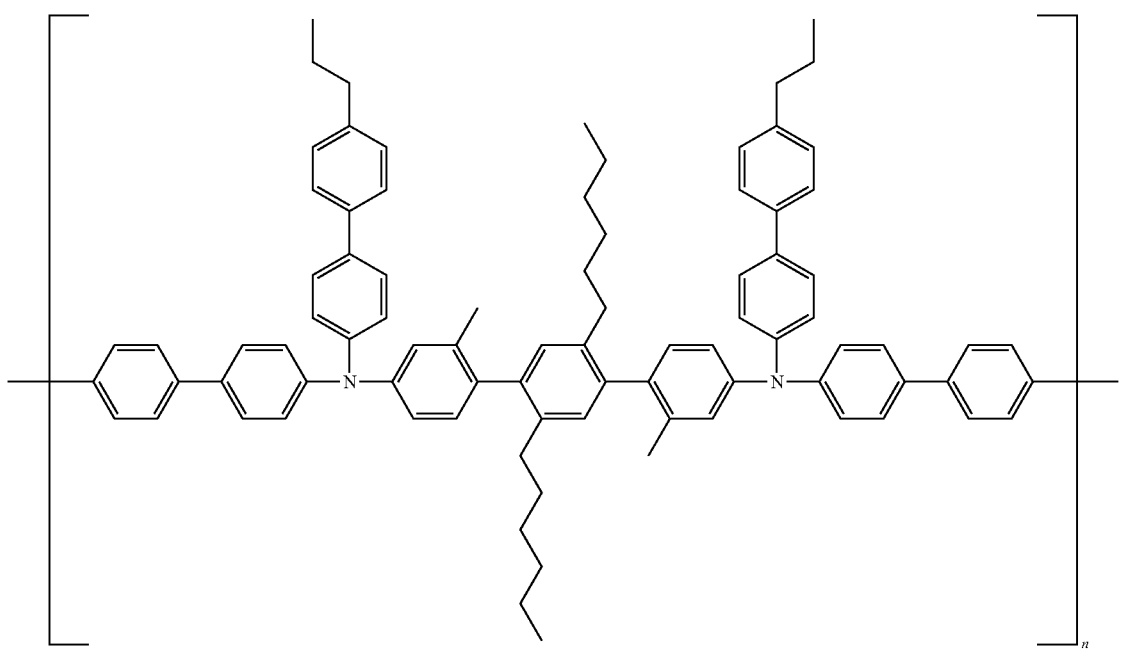

HTP1

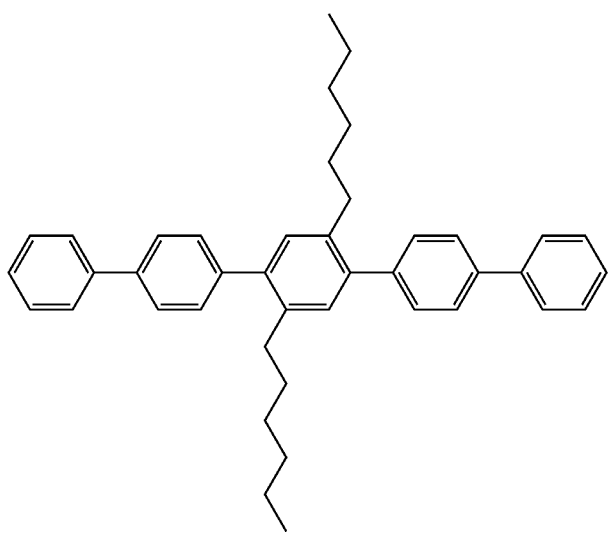

AD1

Subsequently, the ink for an emission layer which is a liquid composition was applied on the hole transport layer to form an emission layer having a dry-film thickness of 50 nm thereon, wherein the ink was a methyl benzoate solution which was a composition including Compound 1 and Compound Az1, which are host materials, and Compound TEG (D1, tris(2-(3-p-xylyl)phenylpyridine)iridium), which is a dopant material.

The ink for an emission layer was prepared to include, with respect to 100 parts by weight of the methyl benzoate, 2.64 parts by weight of Compound 1, 1.32 parts by weight of Az1, and 0.4 parts by weight of TEG.

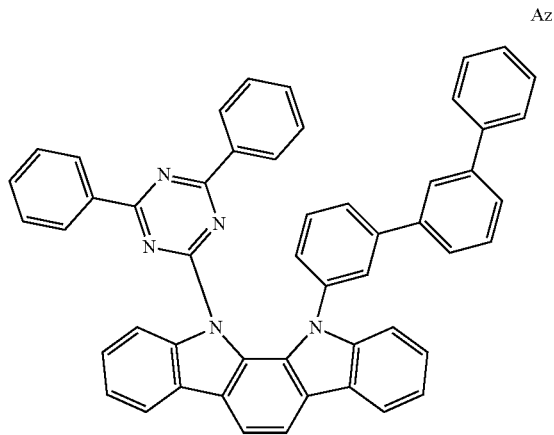

Az1

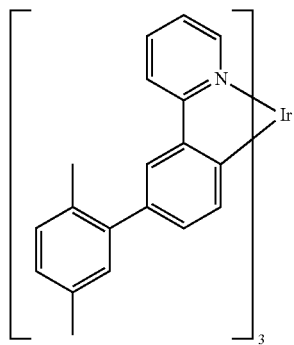

TEG

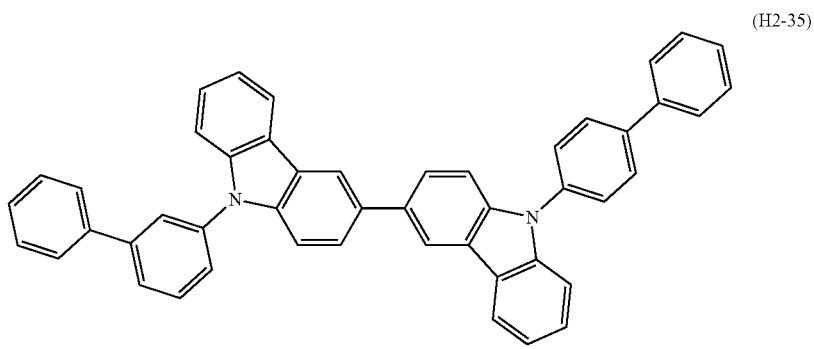

Cz1 (H2-35)

Then, (8-quinolinolato)lithium (Liq) and KLET-03 (the product of Chemipro Kasei Inc.) were co-deposited at a weight ratio of 2:8 on the emission layer in a vacuum deposition apparatus to form an electron transport layer having a thickness of 30 nm.

Lithium fluoride (LiF) was deposited on the electron transport layer by a vacuum deposition apparatus to form an electron injection layer having a thickness of 1 nm.

Also, aluminum (Al) was deposited on the electron injection layer by a vacuum deposition apparatus, thereby forming a second electrode (cathode) having a thickness of 100 nm.

Then, in a glove box in the nitrogen atmosphere having 1 ppm or less of water concentration and 1 ppm or less of oxygen concentration, a sealing process was performed using a glass sealing tube with a desiccant and a ultraviolet curable resin, thereby obtaining an organic light-emitting device.

Example 2

An organic light-emitting device was manufactured in the same manner as in Example 1, except that, as the host material, Compound 2 was used instead of Compound 1.

Example 3

An organic light-emitting device was manufactured in the same manner as in Example 1, except that the ink composition for the emission layer was changed as follows.

The ink for an emission layer was prepared such that, with respect to 100 parts by weight of methyl benzoate, the solid content contained 1.33 parts by weight of Compound 1, 1.33 parts by weight of Compound Cz1 (H2-35), 1.33 parts by weight of Compound Az1, and 0.4 parts by weight of Compound TEG.

Example 4

An organic light-emitting device was manufactured in the same manner as in Example 3, except that, as the host material, Compound 2 was used instead of Compound 1.

Comparative Example 1

An organic light-emitting device was manufactured in the same manner as in Example 1, except that the ink composition for the emission layer was changed as follows.

The ink for an emission layer was prepared including, with respect to 100 parts by weight of methyl benzoate, 2.64 parts by weight of Compound Cz1, 1.32 parts by weight of Compound Az1, and 0.4 parts by weight of Compound TEG.

Comparative Example 2

An organic light-emitting device was manufactured in the same manner as Comparative Example 1 except that, as the host material, Compound Cz2 was used instead of Compound Cz1.

Cz2

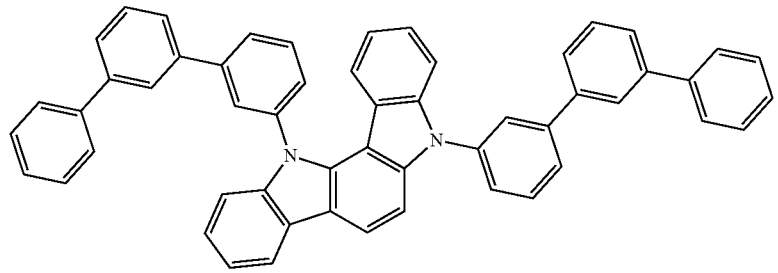

Comparative Example 3

An organic light-emitting device was manufactured in the same manner as Comparative Example 1, except that, as the host material, Compound Cz3 was used instead of Compound Cz1.

Comparative Examples 4 to 6

An organic light-emitting device was manufactured in the same manner as Comparative Example 1, except that, as the host material, Comparative Compounds C-1, C-2 and C-3 were used instead of Compound Cz1, respectively.

Evaluation of Organic Light-Emitting Devices

According to the following method, driving voltage, current efficiency and light-emission lifespan (durability) were evaluated.

Using a DC constant voltage power supply (KEYENCE source meter), while the voltage applied to an organic light-emitting device was continuously changed from 0 V to 20 V, the organic light-emitting device was powered to emit light and the luminance thereof was measured by using a luminance measurement apparatus (SR-3 made by Topcom).

Here, the current value per unit area (current density) of the organic light-emitting device was measured, and the luminance ($cd/m^2$) was divided by the current density ($A/m^2$) to calculate the current efficiency (cd/A). In addition, the current efficiency represents the efficiency (conversion efficiency) for converting the current into light emission energy, and the higher the current efficiency, the higher the performance of the organic light emitting device.

In addition, the light-emission lifespan (durability) was represented as "LT80 (h)," which is the time taken for the luminance to decreased to be 80% of the initial luminance during the continuous operation at the current of 6,000 $cd/m^2$.

The evaluation results are shown in Table 6 below. In Table 6, the current efficiency is expressed as a relative value with respect to the current efficiency of the organic light-emitting device of Comparative Example 1, wherein the current efficiency of the organic light-emitting device of Comparative Example 1 was set to 100. In addition, the light-emission lifespan (durability) is expressed as a relative value with respect to the device lifespan (LT80 (h)) of the organic light-emitting device of Comparative Example 1, wherein the device lifespan (LT80 (h)) of the organic light-emitting device of Comparative Example 1 was set to 100.

TABLE 6

|  | Composition of emission layer | Driving voltage (V) @1,000 (cd/m$^2$) | Current efficiency (Relative value) @1,000 (cd/m$^2$) | Light-emission lifespan (Relative value) @6,000 (cd/m$^2$) |
|---|---|---|---|---|
| Example 1 | Compound 1:Az1:TEG (66:33:10) | 6.4 | 139 | 340 |
| Example 2 | Compound 2:Az1:TEG (66:33:10) | 6.3 | 142 | 330 |
| Example 3 | Compound 1:Cz1:Az1:TEG (33:33:33:10) | 5.7 | 146 | 250 |
| Example 4 | Compound 2:Cz1:Az1:TEG (33:33:33:10) | 5.7 | 140 | 265 |
| Comparative Example 1 | Cz1:Az1:TEG (66:33:10) | 5.5 | 100 | 100 |
| Comparative Example 2 | Cz2:Az1:TEG (66:33:10) | 7.5 | 98 | 45 |
| Comparative Example 3 | Cz3:Az1:TEG (66:33:10) | 6.2 | 111 | 170 |
| Comparative Example 4 | C-1:Az1:TEG (66:33:10) | 6.2 | 91 | 180 |
| Comparative Example 5 | C-2:Az1:TEG (66:33:10) | Due to low solubility, a device could not be manufactured | | |
| Comparative Example 6 | C-3:Az1:TEG (66:33:10) | 8.3 | 122 | 30 |

From the results in Table 6, it can be seen that Examples 1 to 4 using a heterocyclic compound represented by Formula 2 as a host together with an azine ring derivative Az1 showed higher luminescent efficiency and longer light-emission lifespan than Comparative Examples 1 to 4 using a carbazole derivative, which is a commonly used hole transport host material.

In addition, in the case of Comparative Example 5 using C-2 including a p-phenyl moiety instead of an m-phenyl moiety, it was difficult to manufacture a light-emitting device due to the low solubility of C-2, and in the case of Comparative Example 6 using C-3 that does not include carbazole or an indolocarbazole-based moiety, a corresponding device was able to be manufactured, but the characteristics of the driving voltage, current efficiency and light-emission lifespan thereof were inferior to those of Examples.

In addition, by including the compound represented by Formula 2 and the compound containing a carbazole-based moiety (Examples 3 and 4), the driving voltage as well as the luminescent efficiency were improved and the driving voltage was significantly lowered and the power consumption was decreased.

As mentioned above, although the synthesis examples and the examples were described with respect to the present disclosure, the present disclosure is not limited to a specific example, and may be various modified within within the scope of the disclosure as described in the claims.

The heterocyclic compound of the present invention may have a low glass transition temperature and thus have high solubility, thereby increasing the pot life of the solution including the heterocyclic compound, and thus may be suitable for use in a solution coating method.

Specifically, an organic light-emitting device including the heterocyclic compound may have high luminescent efficiency and a long lifespan.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:
1. A heterocyclic compound represented by Formula 1:

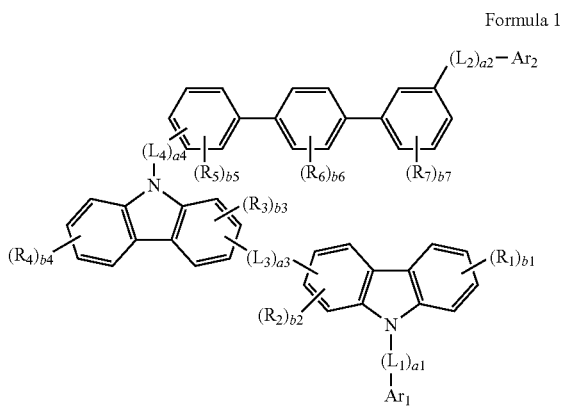

Formula 1

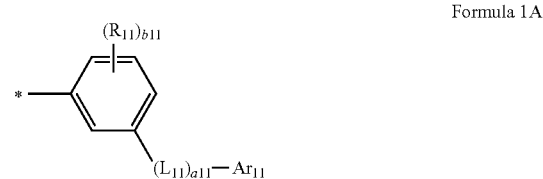

Formula 1A

-continued

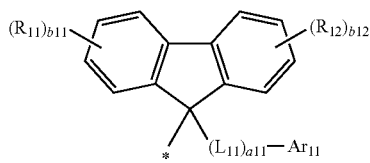

Formula 1B wherein, in Formulae 1, 1A, and 1B,
$L_1$ to $L_4$ and $L_{11}$ may each independently be a single bond, a substituted or unsubstituted $C_5$-$C_{60}$ carbocyclic group, or a substituted or unsubstituted nitrogen-free $C_1$-$C_{60}$ heterocyclic group,
a1 to a4 and a11 may each independently be an integer from 1 to 5,
$Ar_1$ and $Ar_{11}$ may each independently be a substituted or unsubstituted $C_5$-$C_{60}$ carbocyclic group, or a substituted or unsubstituted nitrogen-free $C_1$-$C_{60}$ heterocyclic group,
$Ar_2$ is a group represented by Formula 1A or Formula 1B,
$R_1$ to $R_7$ and $R_{11}$ to $R_{12}$ may each independently be hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ nitrogen-free heterocycloalkyl group, a substituted or unsubstituted $C_3$-$C_{10}$ cycloalkenyl group, a substituted or unsubstituted $C_1$-$C_{10}$ nitrogen-free heterocycloalkenyl group, a substituted or unsubstituted $C_6$-$C_{60}$ aryl group, a substituted or unsubstituted $C_7$-$C_{60}$ alkylaryl group, a substituted or unsubstituted $C_7$-$C_{60}$ aryl alkyl group, a substituted or unsubstituted $C_7$-$C_{60}$ arylalkyloxy group, a substituted or unsubstituted $C_7$-$C_{60}$ arylalkylthio group, a substituted or unsubstituted $C_8$-$C_{30}$ arylalkenyl group, a substituted or unsubstituted $C_8$-$C_{30}$ arylalkynyl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ aryl alkyl group, a substituted or unsubstituted $C_7$-$C_{60}$ arylalkyloxy group, a substituted or unsubstituted $C_7$-$C_{60}$ arylalkylthio group, a substituted or unsubstituted $C_8$-$C_{30}$ arylalkenyl group, a substituted or unsubstituted $C_8$-$C_{30}$ arylalkynyl group, a substituted or unsubstituted nitrogen-free $C_1$-$C_{60}$ heteroaryl group, a substituted or unsubstituted nitrogen-free $C_2$-$C_{60}$ alkylheteroaryl group, a substituted or unsubstituted nitrogen-free $C_1$-$C_{60}$ heteroaryloxy group, a substituted or unsubstituted nitrogen-free $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), or —N($Q_1$)($Q_2$),
b2 and b3 are each independently an integer from 0 to 3,
b1, b4 to b7, and b11 to b12 are each independently an integer from 0 to 4,
two adjacent $R_1$(s) in the number of b1, $R_2$(s) in the number of b2, $R_3$(s) in the number of b3, $R_4$(s) in the number of b4, $R_5$(s) in the number of b5, $R_6$(s) in the number of b6, $R_7$(s) in the number of b7, $R_{11}$(s) in the number of b11, and $R_{12}$(s) in the number of b12 are optionally linked to each other to form a substituted or unsubstituted $C_5$-$C_{30}$ carbocyclic group or a substituted or unsubstituted $C_1$-$C_{30}$ heterocyclic group,
at least one substituent of the substituted $C_5$-$C_{60}$ carbocyclic group, the substituted nitrogen-free $C_1$-$C_{60}$ heterocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ nitrogen-free heterocycloalkyl group, the substituted $C_3$-$C_{10}$ cycloalkenyl group, the substituted $C_1$-$C_{10}$ nitrogen-free heterocycloalkenyl group, the substituted $C_6$-$C_{60}$ aryl group, the substituted $C_7$-$C_{60}$ alkylaryl group, the substituted $C_7$-$C_{60}$ aryl alkyl group, the substituted $C_7$-$C_{60}$ arylalkyloxy group, the substituted $C_7$-$C_{60}$ arylalkylthio group, the substituted $C_8$-$C_{30}$ arylalkenyl group, the substituted $C_8$-$C_{30}$ arylalkynyl group, the substituted $C_6$-$C_{60}$ aryloxy group, the substituted $C_6$-$C_{60}$ arylthio group, the substituted nitrogen-free $C_1$-$C_{60}$ heteroaryl group, the substituted nitrogen-free $C_2$-$C_{60}$ alkylheteroaryl group, the substituted nitrogen-free $C_1$-$C_{60}$ heteroaryloxy group, the substituted nitrogen-free $C_1$-$C_{60}$ heteroarylthio group, the substituted monovalent non-aromatic condensed polycyclic group, and the substituted monovalent non-aromatic condensed heteropolycyclic group is:
deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;
a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ nitrogen-free heterocycloalkyl group, a $C_3$-$C_{10}$ cycloalkenyl group, a $C_1$-$C_{10}$ nitrogen-free heterocycloalkenyl group, Si($Q_{11}$)($Q_{12}$)($Q_{13}$), —N($Q_{11}$)($Q_{12}$), —C(=O)($Q_{11}$), or any combination thereof;
a $C_3$-$C_{10}$ cycloalkyl group, a nitrogen-free $C_1$-$C_{10}$ heterocycloalkyl group, a $C_3$-$C_{10}$ cycloalkenyl group, or a nitrogen-free $C_1$-$C_{10}$ heterocycloalkenyl group;
a $C_3$-$C_{10}$ cycloalkyl group, a nitrogen-free $C_1$-$C_{10}$ heterocycloalkyl group, a $C_3$-$C_{10}$ cycloalkenyl group, or a nitrogen-free $C_1$-$C_{10}$ heterocycloalkenyl group, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a nitrogen-free $C_1$-$C_{10}$ heterocycloalkyl group, a $C_3$-$C_{10}$ cycloalkenyl group, a nitrogen-free $C_1$-$C_{10}$ heterocycloalkenyl group, —Si($Q_{21}$)($Q_{22}$)($Q_{23}$), —N($Q_{21}$)($Q_{22}$), —C(=O)($Q_{21}$), or any combination thereof; and —Si($Q_{31}$)($Q_{32}$)($Q_{33}$), —N($Q_{31}$)($Q_{32}$), or —C(=O)($Q_{31}$), wherein $Q_1$ to $Q_3$, $Q_{11}$ to $Q_{13}$, $Q_{21}$ to $Q_{23}$, and $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and

* indicates a binding site to a neighboring atom.

2. The heterocyclic compound of claim 1, wherein
$L_1$ to $L_4$ and $L_{11}$ are each independently: a single bond, a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthylene group, a heptaphene group, a pyranthrene group, a benzoquinone group, a coumarin group, an anthraquinone group, a fluorenone group, a furan group, a thiene group, a silole group, a benzofuran group, a benzothiene group, a benzosilole group, a dibenzofuran group, a dibenzothiophene group, a dibenzosilole group, a xanthone group, or a thioxanthone group; or
a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphene group, a hexaphene group, a hexacene group, a rubicene group, a trinaphthylene group, a heptaphene group, a pyranthrene group, a benzoquinone group, a coumarin group, an anthraquinone group, a fluorenone group, a furan group, a thiene group, a silole group, a benzofuran group, a benzothiene group, a benzosilole group, a dibenzofuran group, a dibenzothiophene group, a dibenzosilole group, a xanthone group, or a thioxanthone group, each substituted with deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a xanthonenyl group, a thioxanthonyl group, or any combination thereof.

3. The heterocyclic compound of claim 1, wherein
$L_1$ to $L_4$ and $L_{11}$ are each independently a single bond or a group represented by Formulae 3-1 to 3-7 below:

3-1
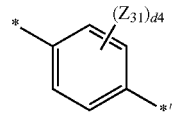

3-2
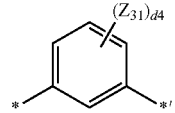

3-3
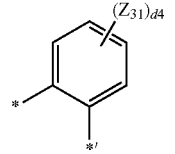

3-4
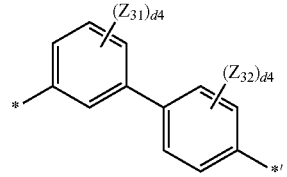

3-5
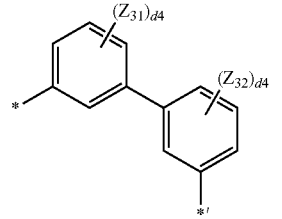

3-6
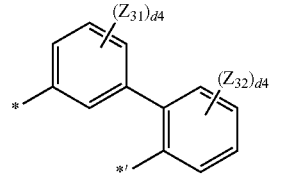

3-7
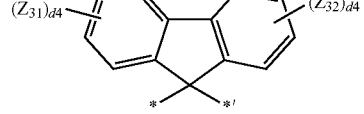

wherein, in Formulae 3-1 to 3-7,
$Z_{31}$ and $Z_{32}$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$),
d4 is an integer from 0 to 4,
$Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and * and *' each indicate a binding site to a neighboring atom.

4. The heterocyclic compound of claim 1, wherein
a2 and a11 are each an integer from 1 to 4, and
a3 and a4 are each 1.

5. The heterocyclic compound of claim 1, wherein
$Ar_1$ and $Ar_{11}$ are each independently a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a xanthonenyl group, or a thioxanthonyl group, or
a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a xanthonenyl group, a thioxanthonyl group, or any combination thereof.

6. The heterocyclic compound of claim 1, wherein
$Ar_1$ and $Ar_{11}$ are each independently a phenyl group, a naphthyl group, a fluorenyl group, a biphenyl group, a terphenyl group, a tetraphenyl group, a dibenzofuranyl group, or a dibenzothiophenyl group; or
a phenyl group, a naphthyl group, a fluorenyl group, a biphenyl group, a terphenyl group, a tetraphenyl group, a dibenzofuranyl group, or a dibenzothiophenyl group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a biphenyl group, a terphenyl group, or any combination thereof.

7. The heterocyclic compound of claim 1, wherein
a moiety represented by *—$(L_1)_{a1}$—$Ar_1$ is a group represented by one of Formulae 4-1 to 4-17 below:

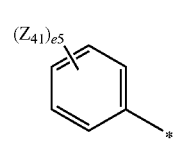

4-1

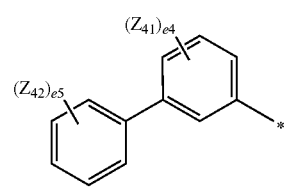

4-2

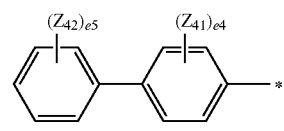

4-3

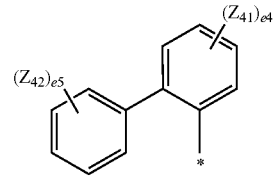

4-4

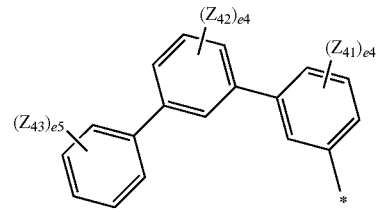

4-5

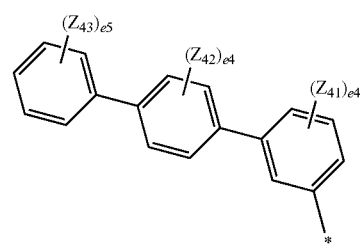

4-6

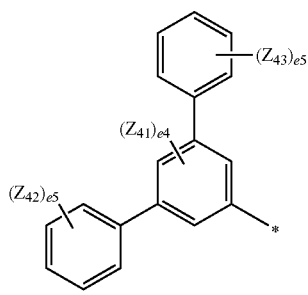
4-7
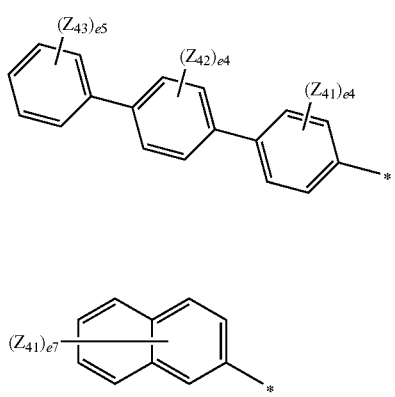
4-8
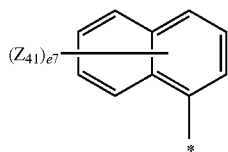
4-9
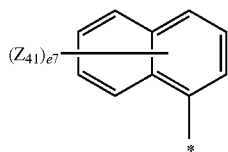
4-10
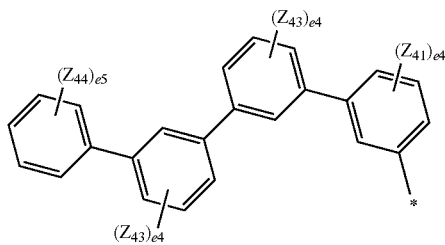
4-11
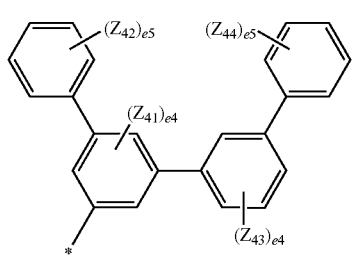
4-12
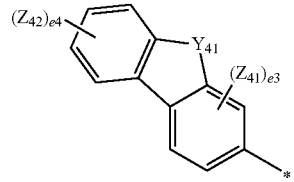
4-13
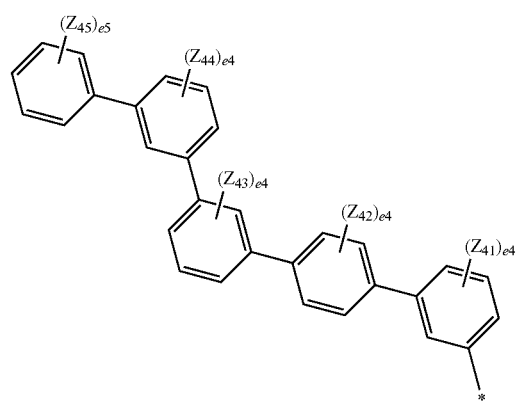
4-14
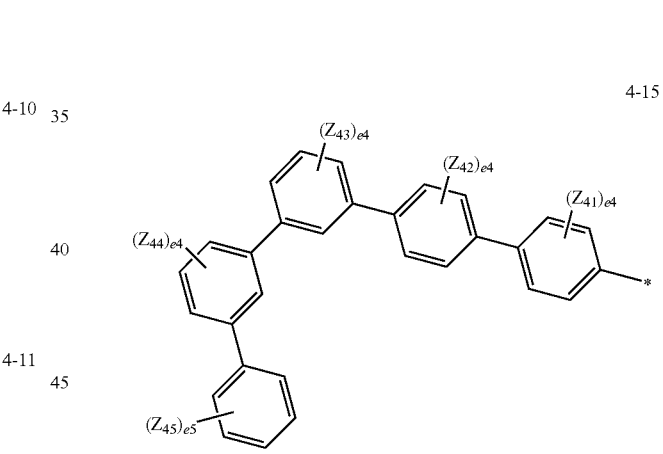
4-15
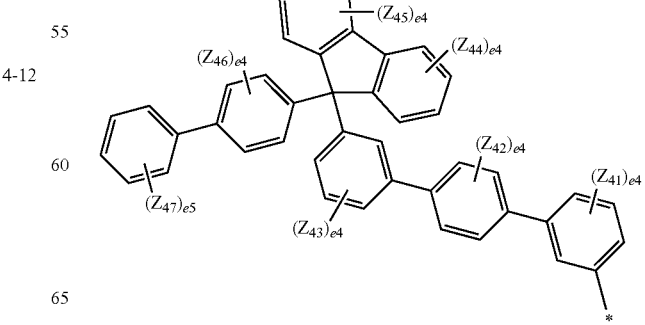
4-16

4-17

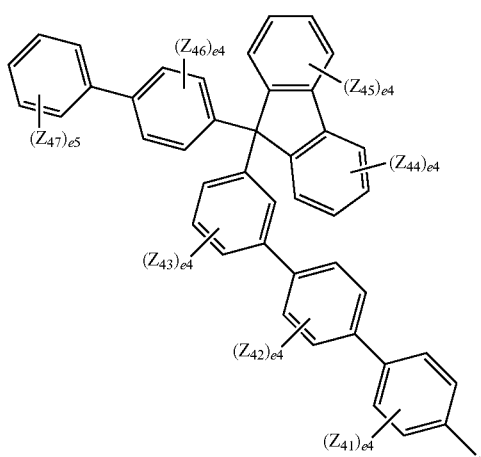

wherein, in Formulae 4-1 to 4-17,
$Y_{41}$ is O, S, or $C(Z_{48})(Z_{49})$,
$Z_{41}$ to $Z_{49}$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —$Si(Q_{31})(Q_{32})(Q_{33})$,
e3 is an integer from 0 to 3,
e4 is an integer from 0 to 4,
e5 is an integer from 0 to 5,
e7 is an integer from 0 to 7,
$Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and
* indicates a binding site to a neighboring atom.

8. The heterocyclic compound of claim 1, wherein the moiety represented by *—$(L_{11})_{a11}$—$Ar_{11}$ is a group represented by one of Formulae 5-1 to 5-13:

5-1

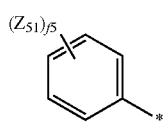

5-2

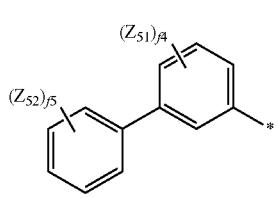

5-3

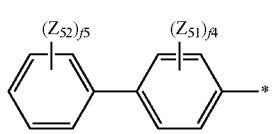

5-4

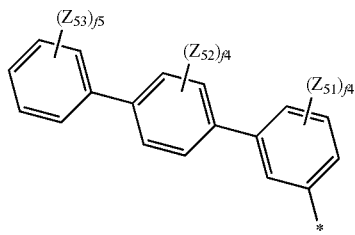

5-5

5-6

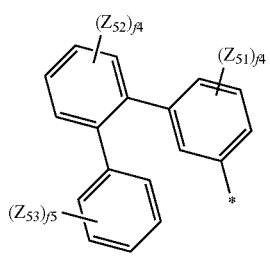

5-7

5-8

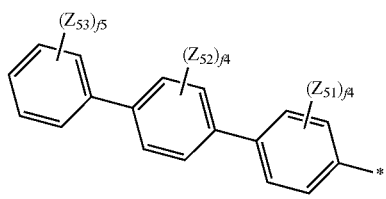

483
-continued 5-9
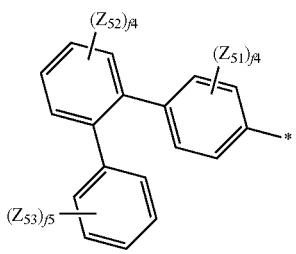

5-10
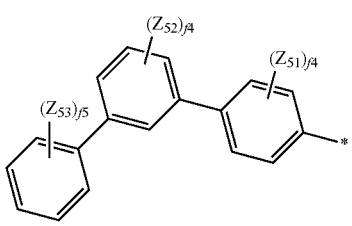

5-11
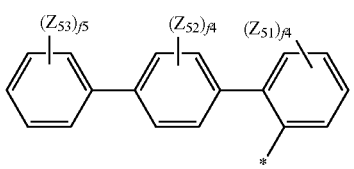

5-12
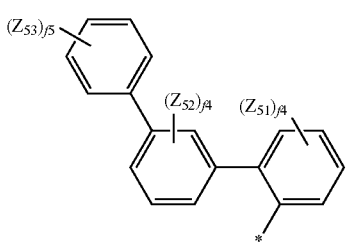

5-13
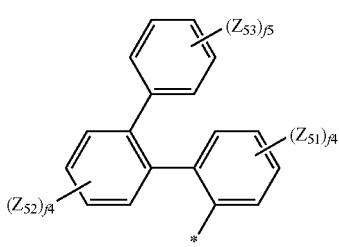

484 wherein, in Formulae 5-1 to 5-13, $Z_{51}$ to $Z_{53}$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —Si($Q_{31}$)($Q_{32}$)($Q_{33}$), f4 is an integer from 0 to 4, f5 is an integer from 0 to 5, $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and

* indicates a binding site to a neighboring atom.

9. The heterocyclic compound of claim 1, wherein $R_1$ to $R_7$, $R_{11}$, and $R_{12}$ are each independently: hydrogen, deuterium, —F, —Cl, —Br, —I, a cyano group, a $C_1$-$C_{20}$ alkyl group, a $C_2$-$C_{20}$ alkenyl group, a $C_2$-$C_{20}$ alkynyl group, and a $C_1$-$C_{20}$ alkoxy group; and a $C_1$-$C_{20}$ alkyl group, a $C_2$-$C_{20}$ alkenyl group, a $C_2$-$C_{20}$ alkynyl group, or $C_1$-$C_{20}$ alkoxy group, each substituted with at least one deuterium, —F, —Cl, —Br, —I, a cyano group, or any combination thereof.

10. The heterocyclic compound of claim 1, wherein the heterocyclic compound is a compound represented by one of Formulae 1(1) to 1(3):

Formula 1(1)
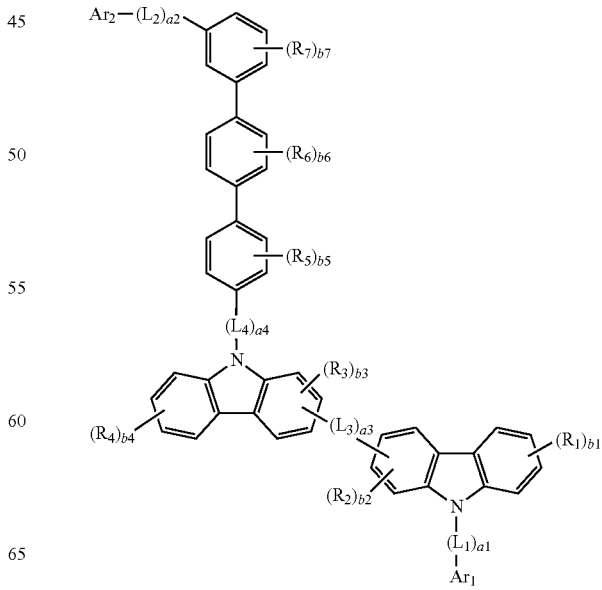

485
-continued
Formula 1(2)
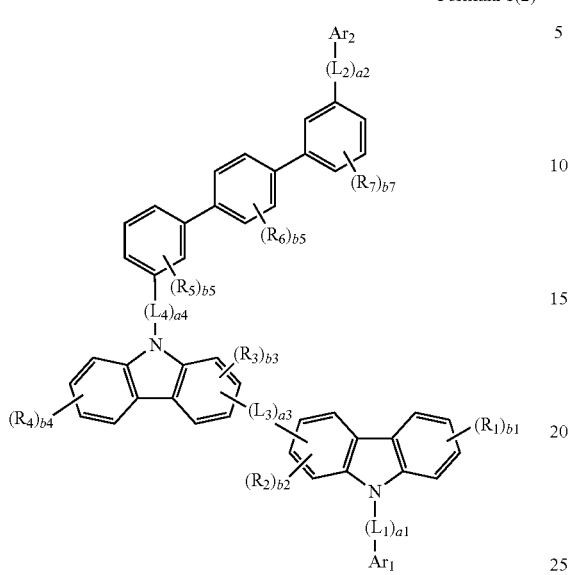
486
-continued
Formula 1(3)
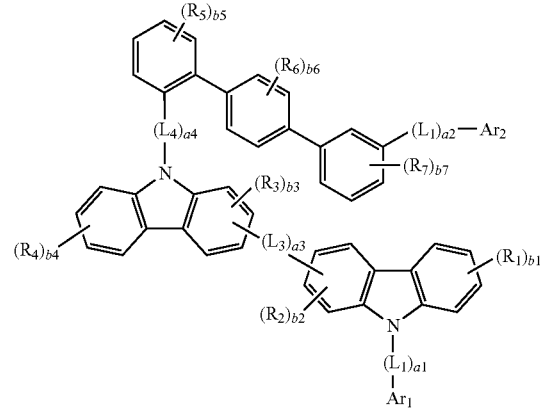
wherein, in Formulae 1(1) to 1(3),
$L_1$ to $L_4$, a1 to a4, $Ar_1$, $Ar_2$, $R_1$ to $R_7$, and b1 to b7 are each understood by referring to the description provided in connection with claim 1.
11. The heterocyclic compound of claim 1, wherein the heterocyclic compound is represented by one of Formulae 1-1 to 1-16:
Formula 1-1
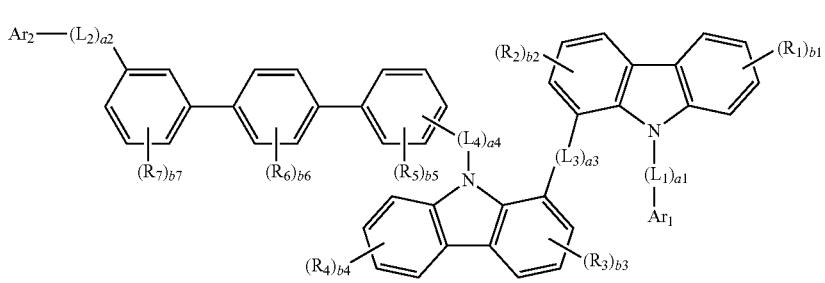
Formula 1-2
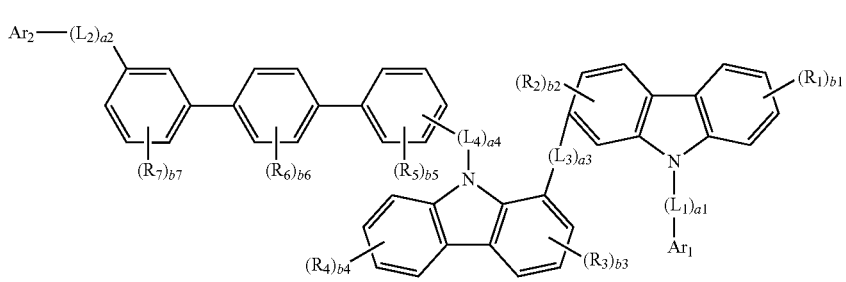
Formula 1-3
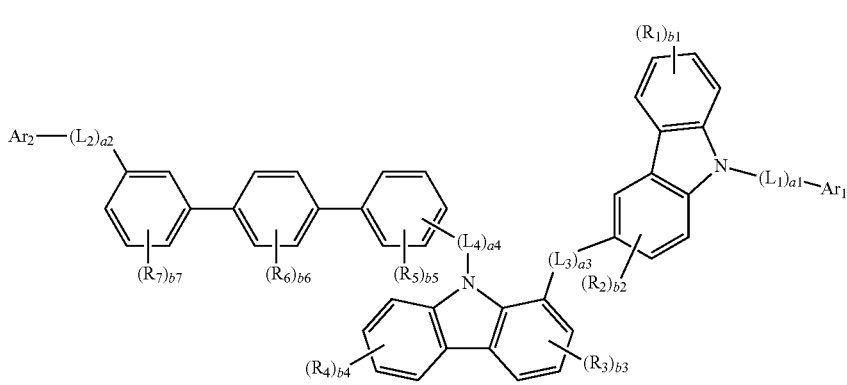

Formula 1-4
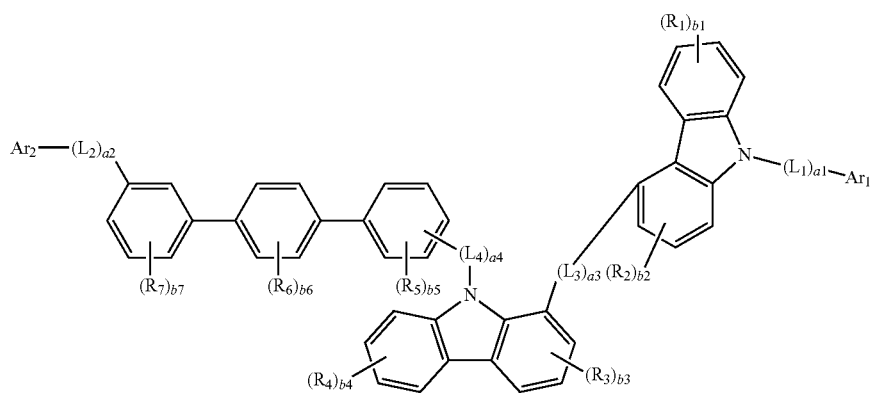
Formula 1-5
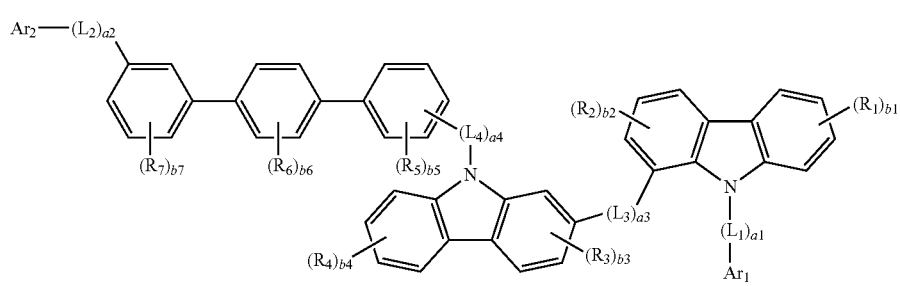
Formula 1-6
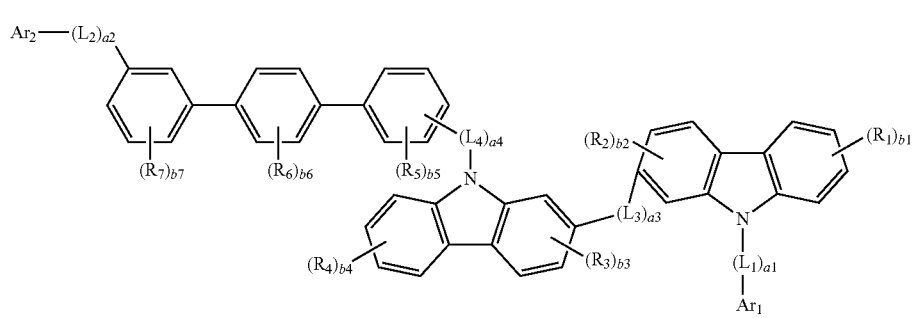
Formula 1-7
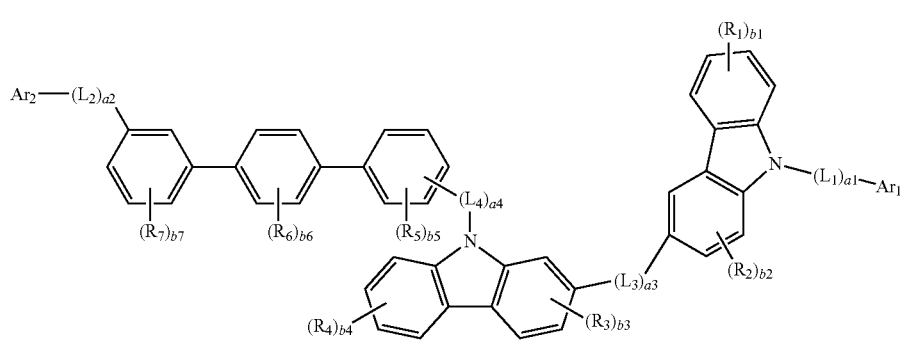
Formula 1-8
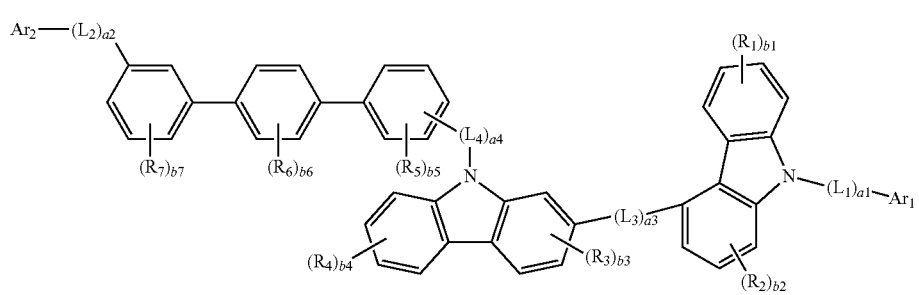

Formula 1-9
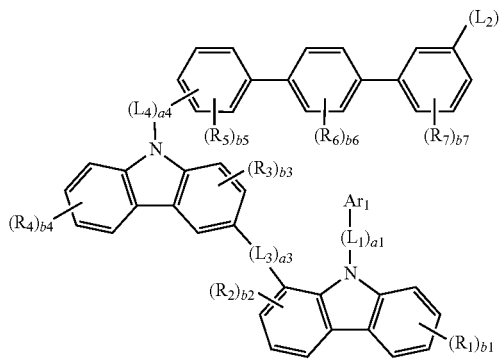
Formula 1-10
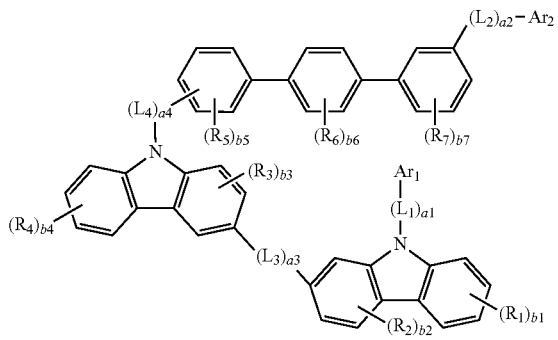
Formula 1-11
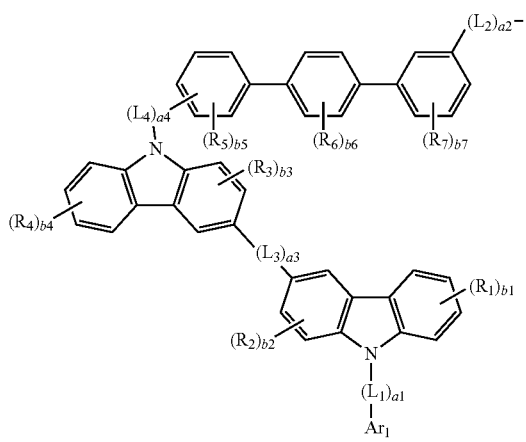
Formula 1-12
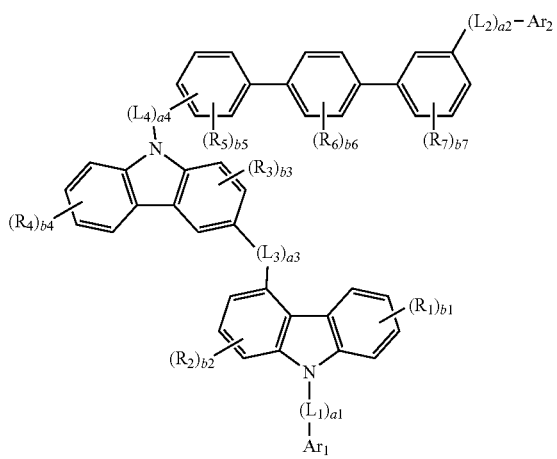
Formula 1-13
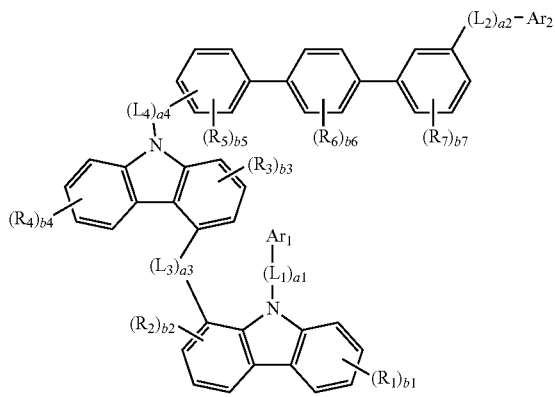
Formula 1-14
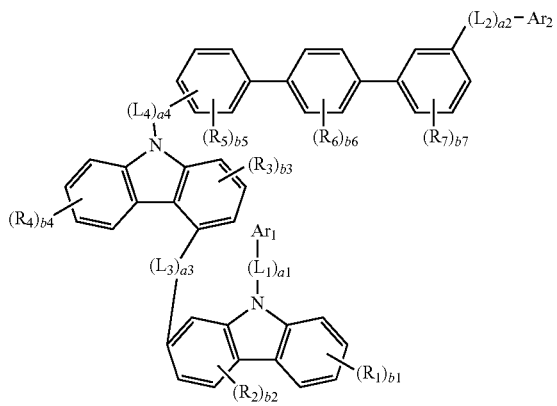

491

-continued

Formula 1-15

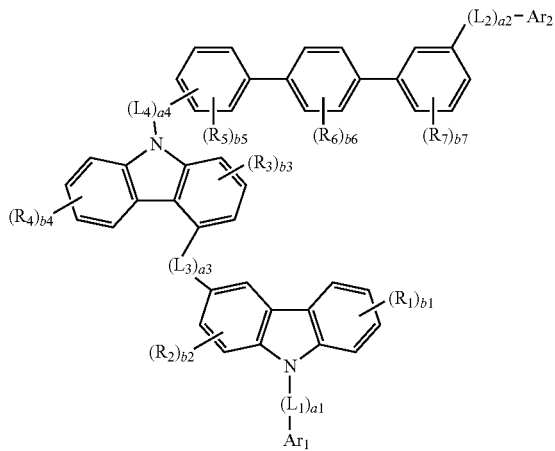

Formula 1-16

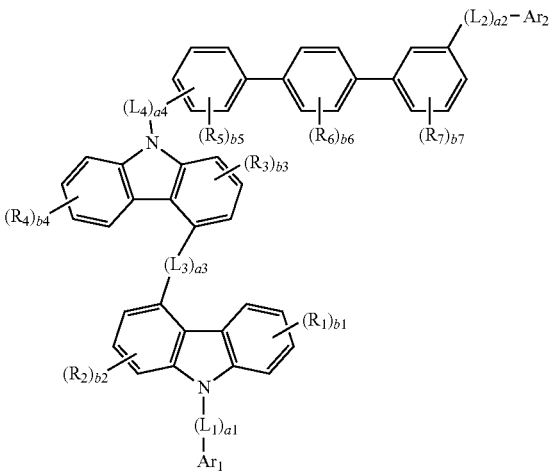

wherein, in Formulae 1-1 to 1-16, $L_1$ to $L_4$, a1 to a4, $Ar_1$, $Ar_2$, $R_1$ to $R_7$, and b1 to b7 are each understood by referring to the description provided in connection with claim 1.

492 the heterocyclic compound has a lowest unoccupied molecular orbital (LUMO) energy level of −2.3 eV or less.

12. The heterocyclic compound of claim 1, wherein

13. The heterocyclic compound of claim 1, wherein the heterocyclic compound is at least one of Compounds A1 to A496:

A1

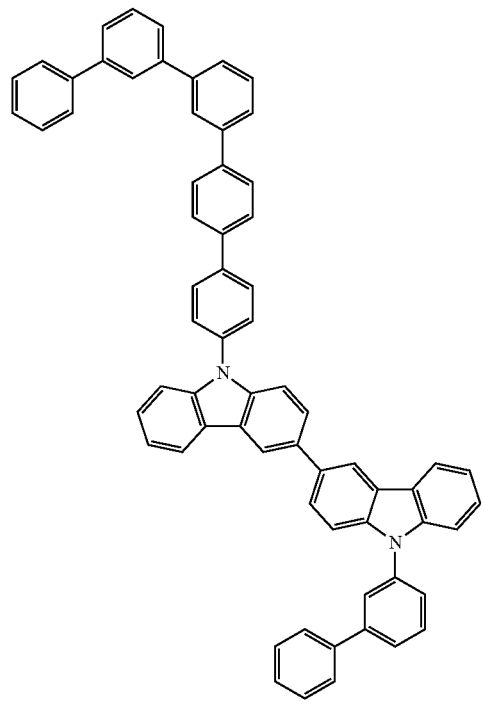

A2

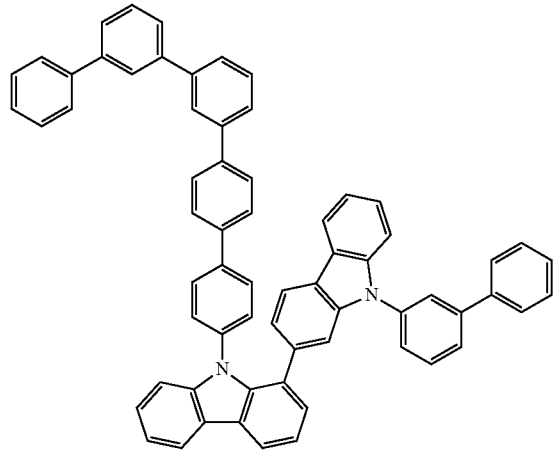

-continued
493 A3
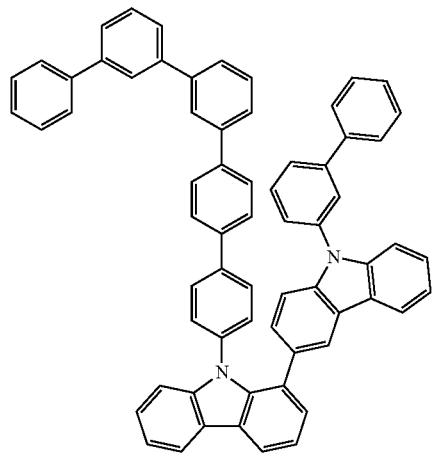
494 A4
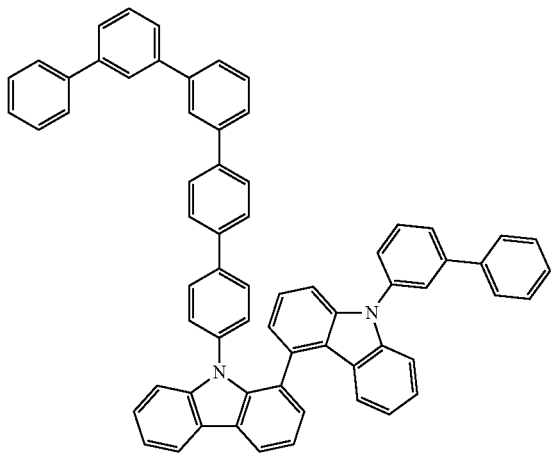
A5
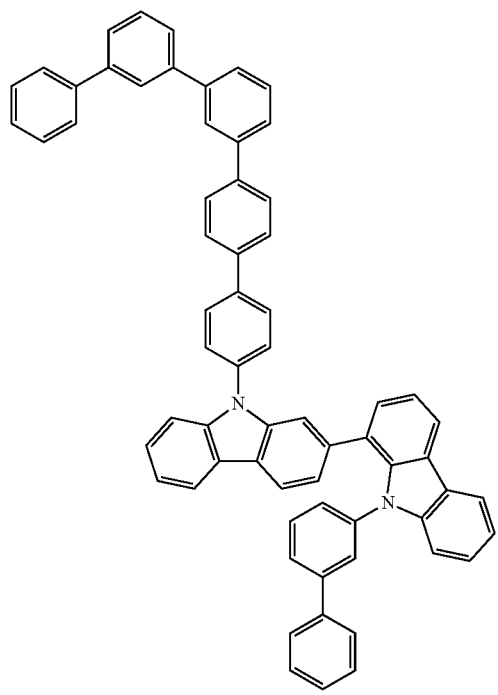
A6
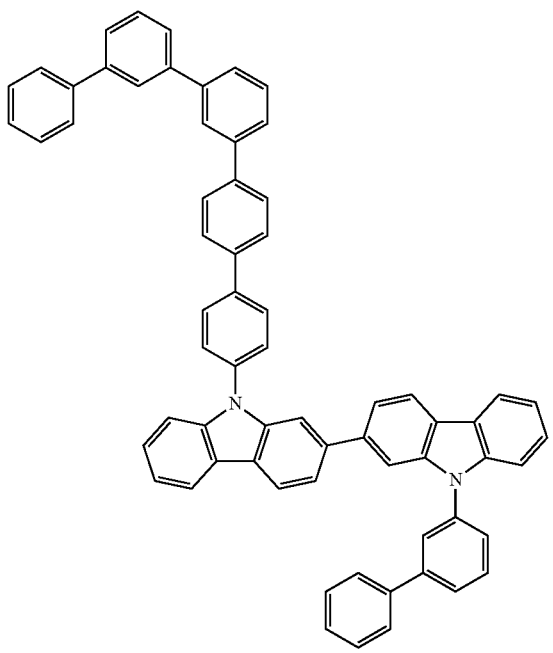
A7
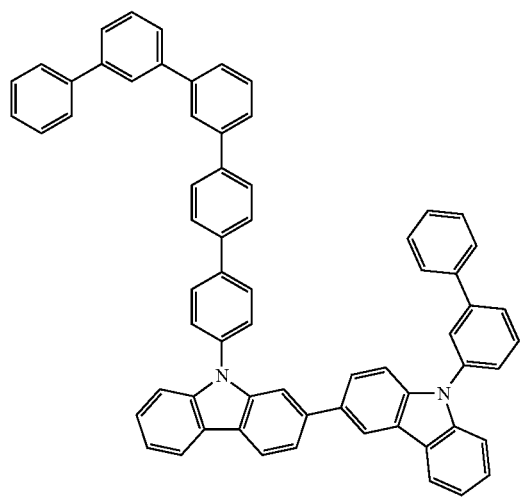
A8
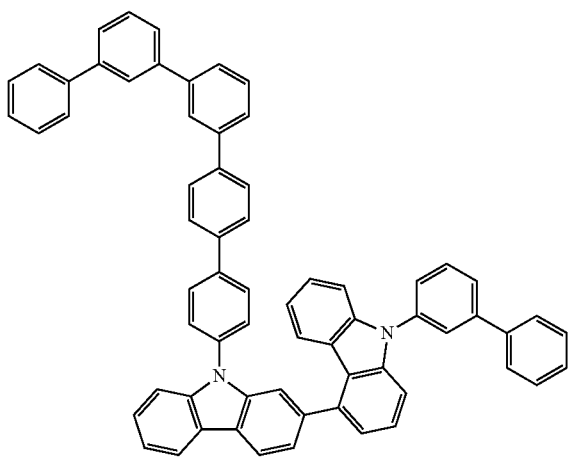

495
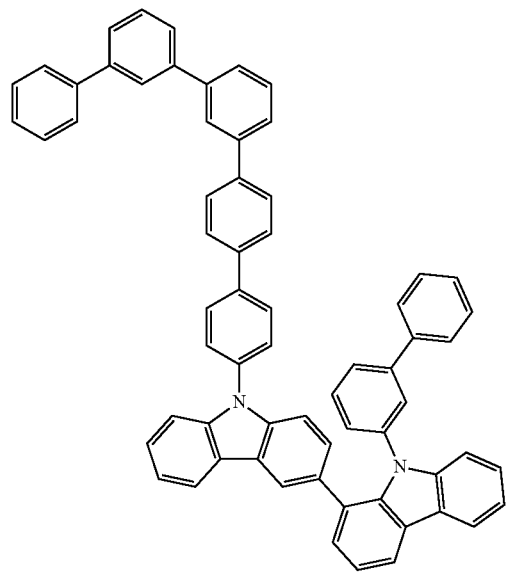
A9
496
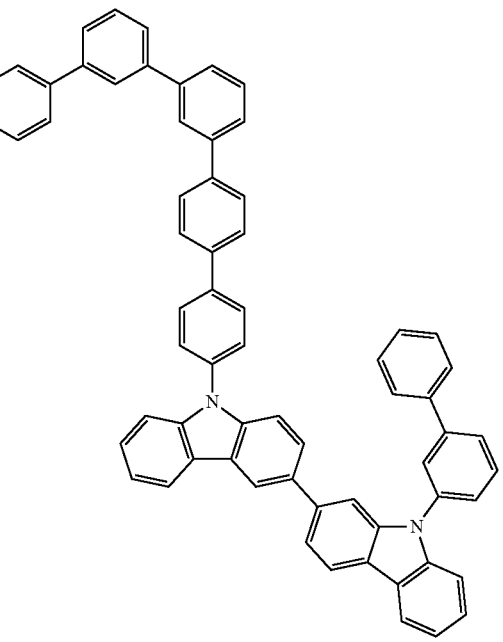
A10
-continued
A11
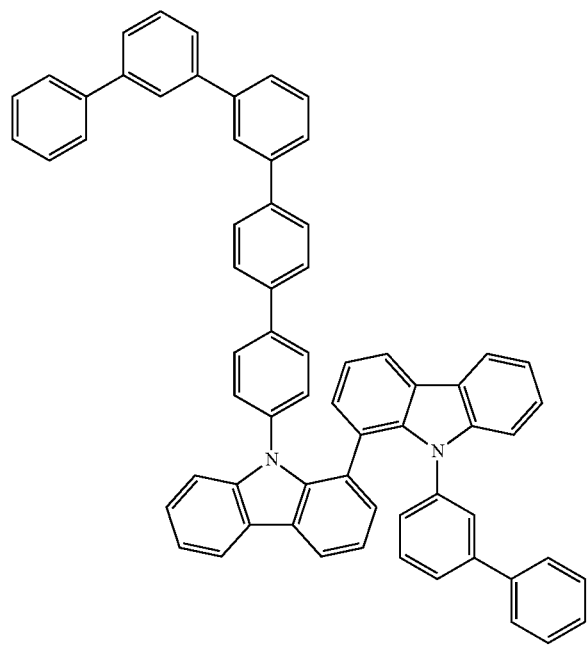
A12
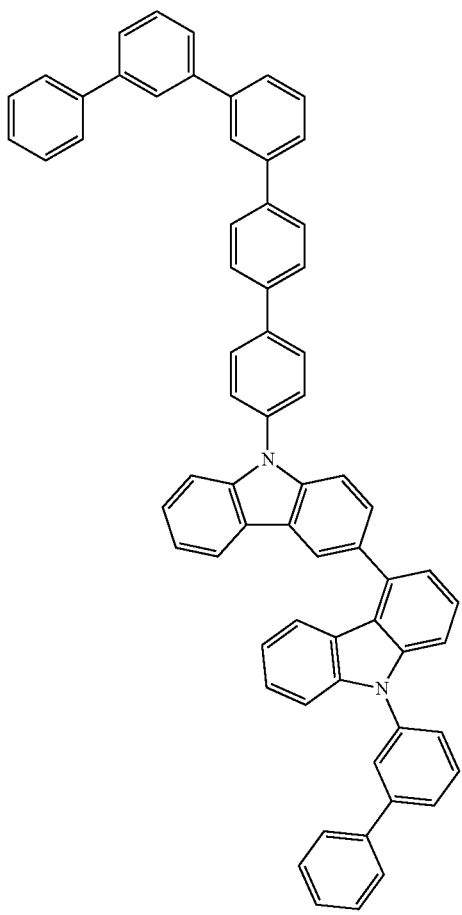

-continued
A13
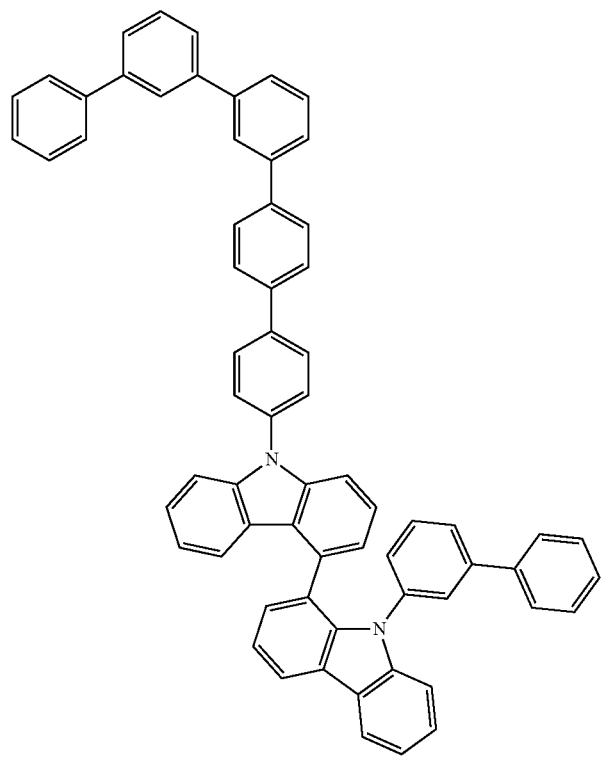
A14
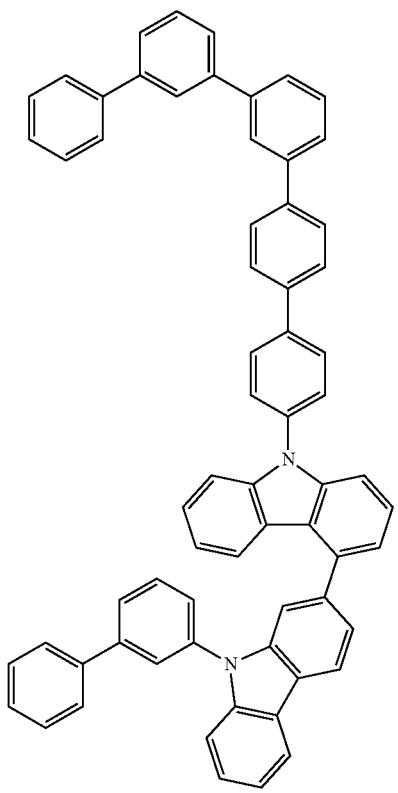

-continued
A15
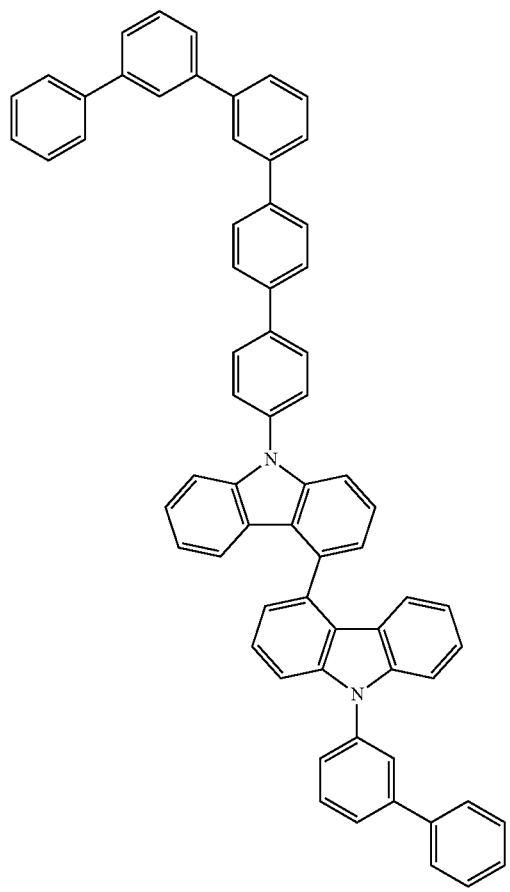
499
A16
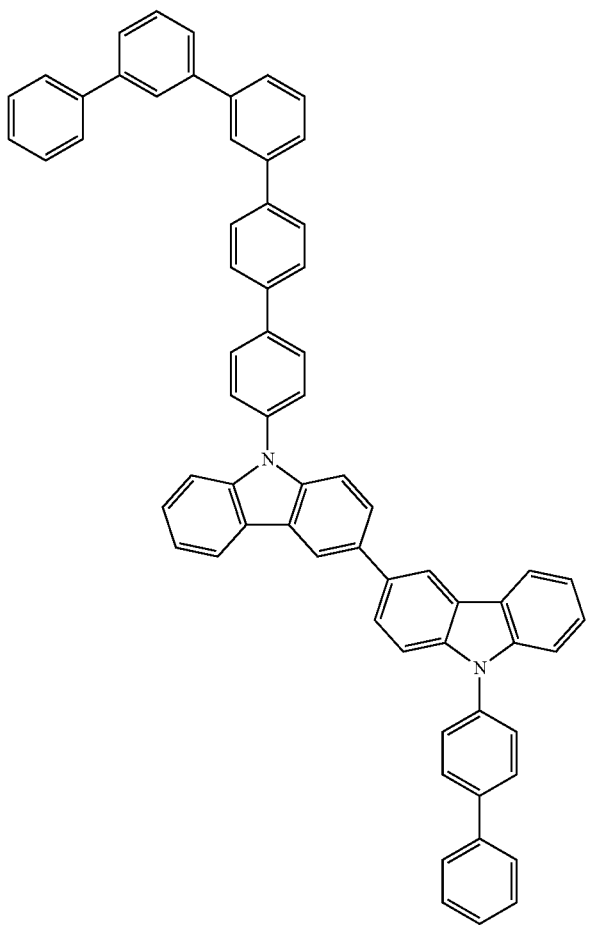
500

-continued
A17
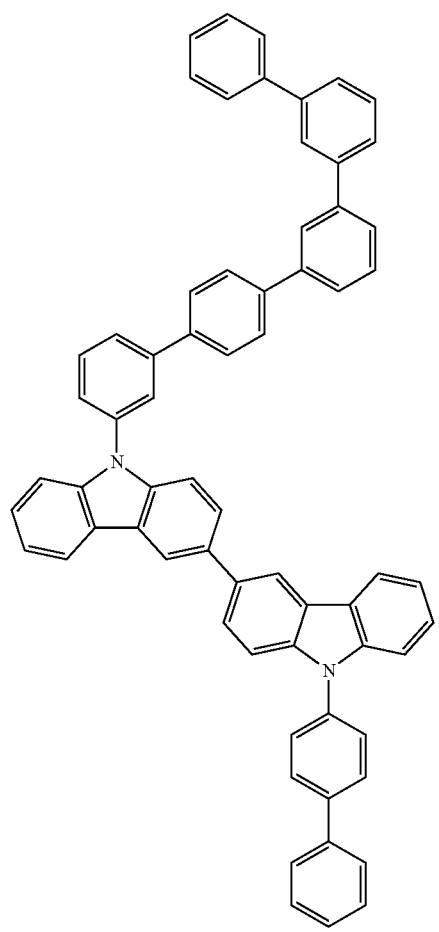
A18
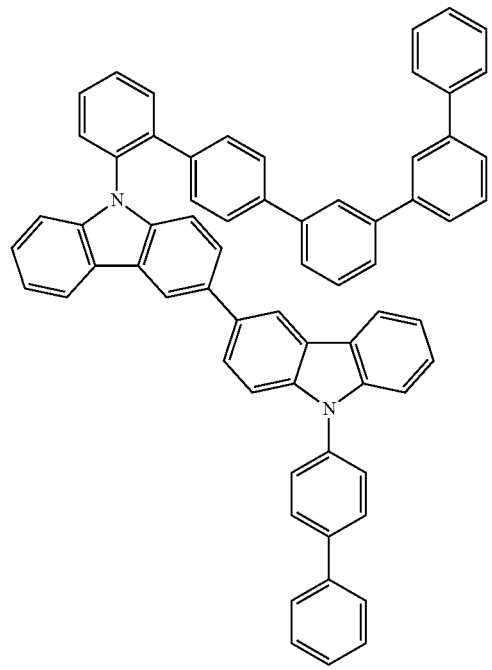
A19
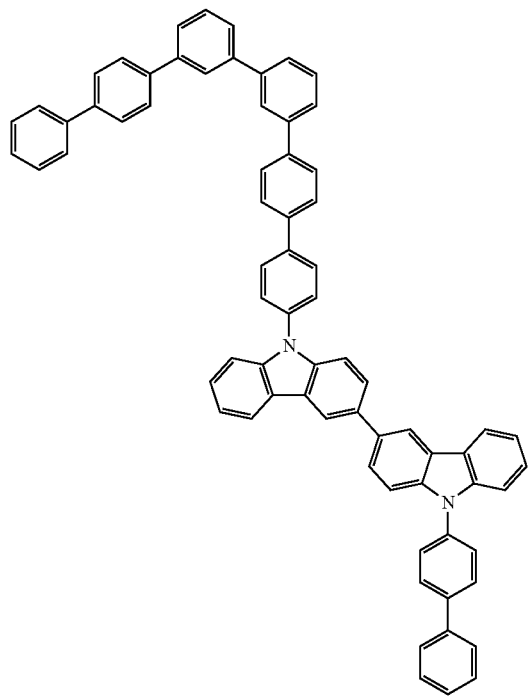
A20
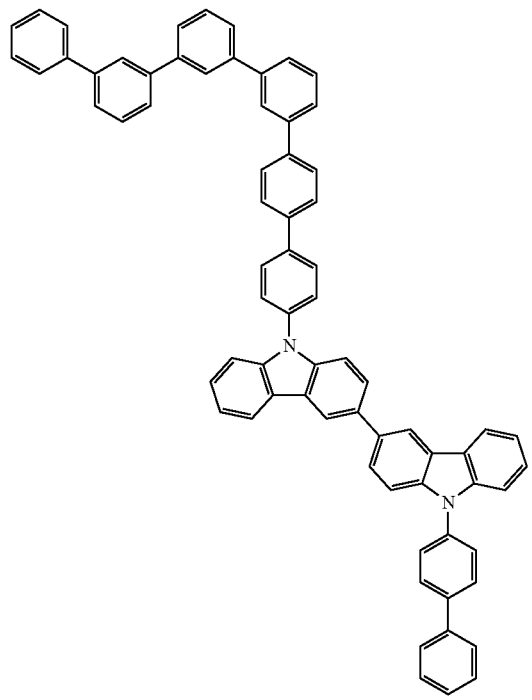

-continued
A21
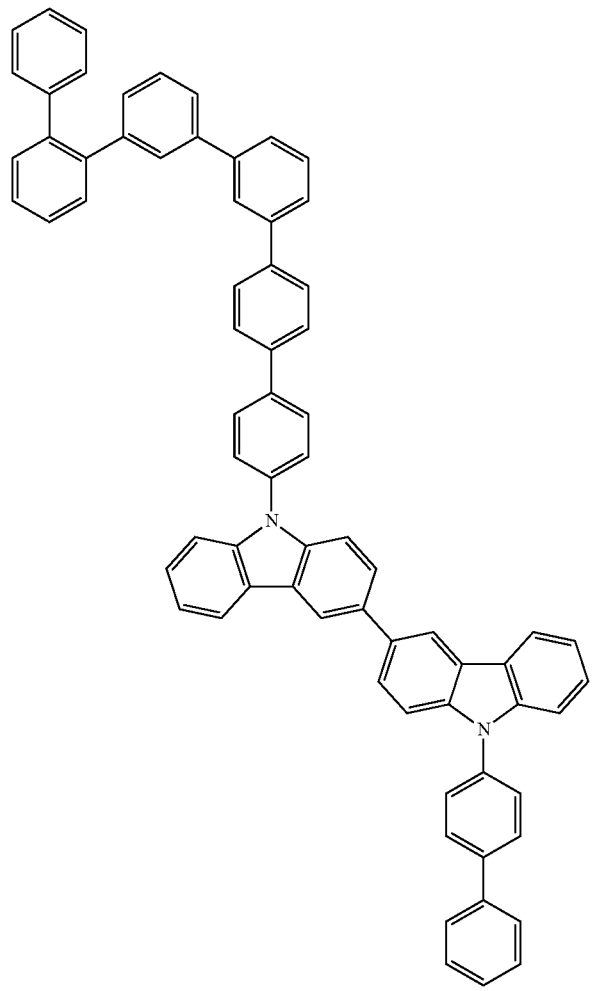
A22
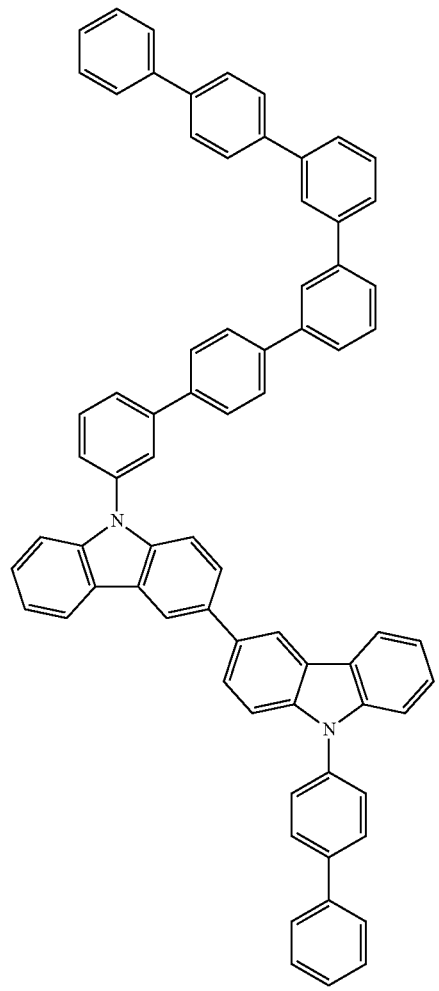

-continued
A23
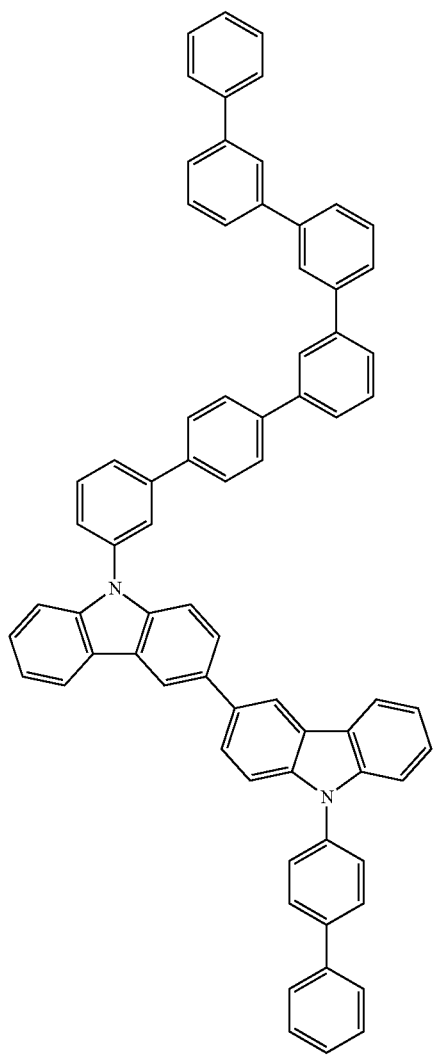
505
A24
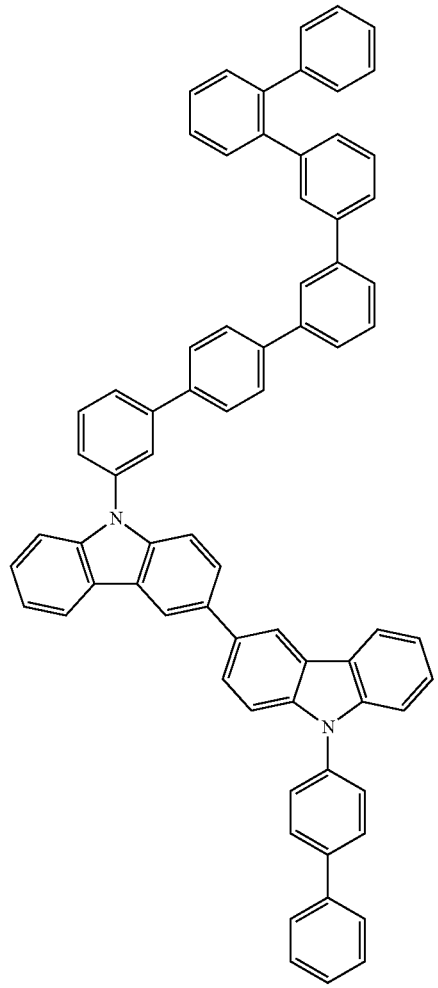
506

-continued
A25
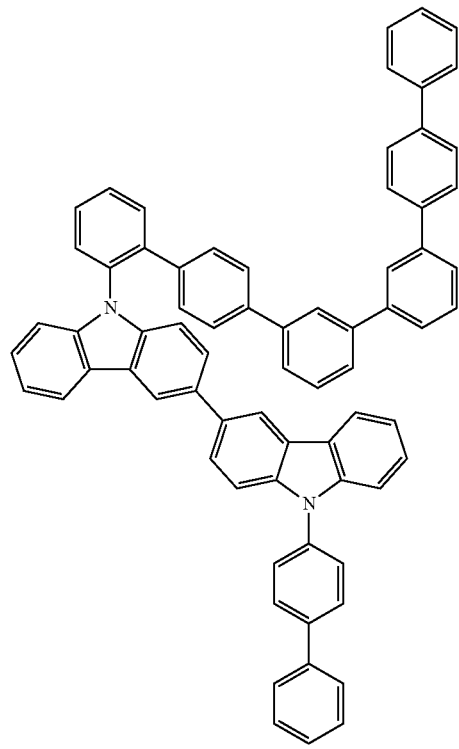
A26
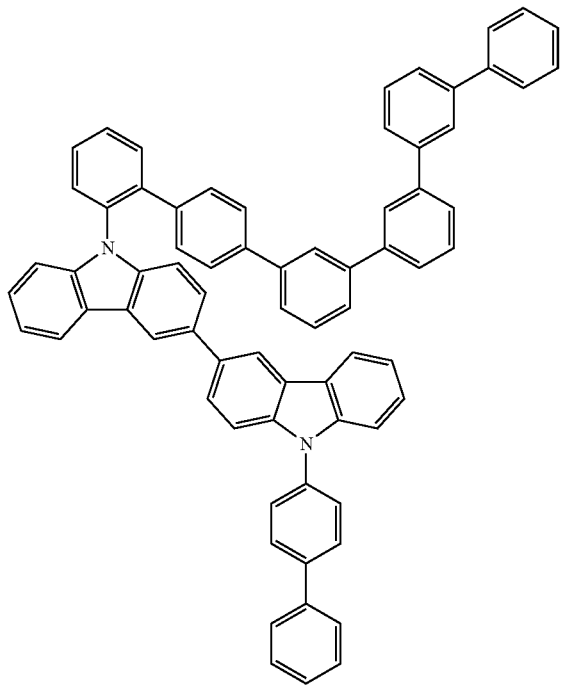
A27
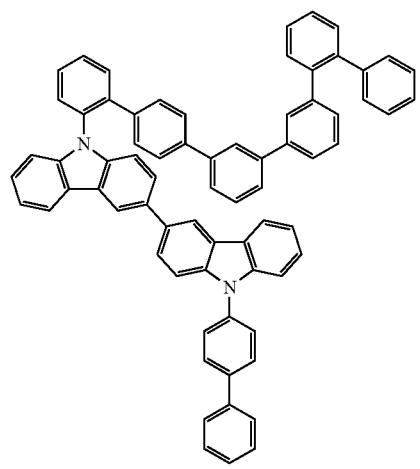
A28
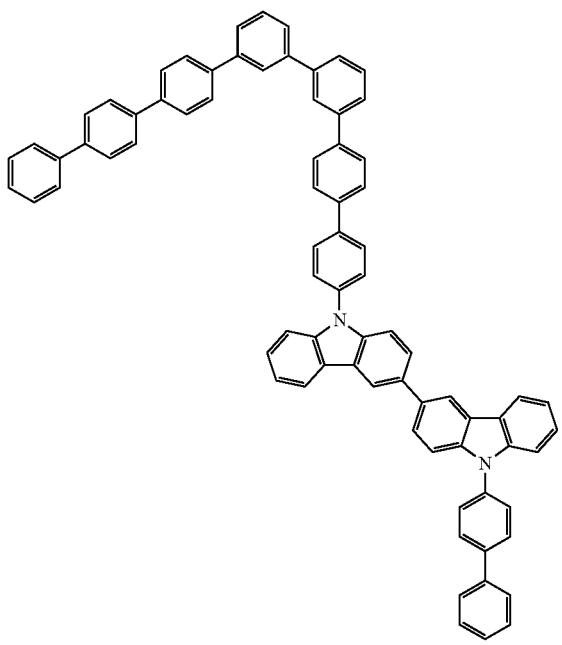

A29
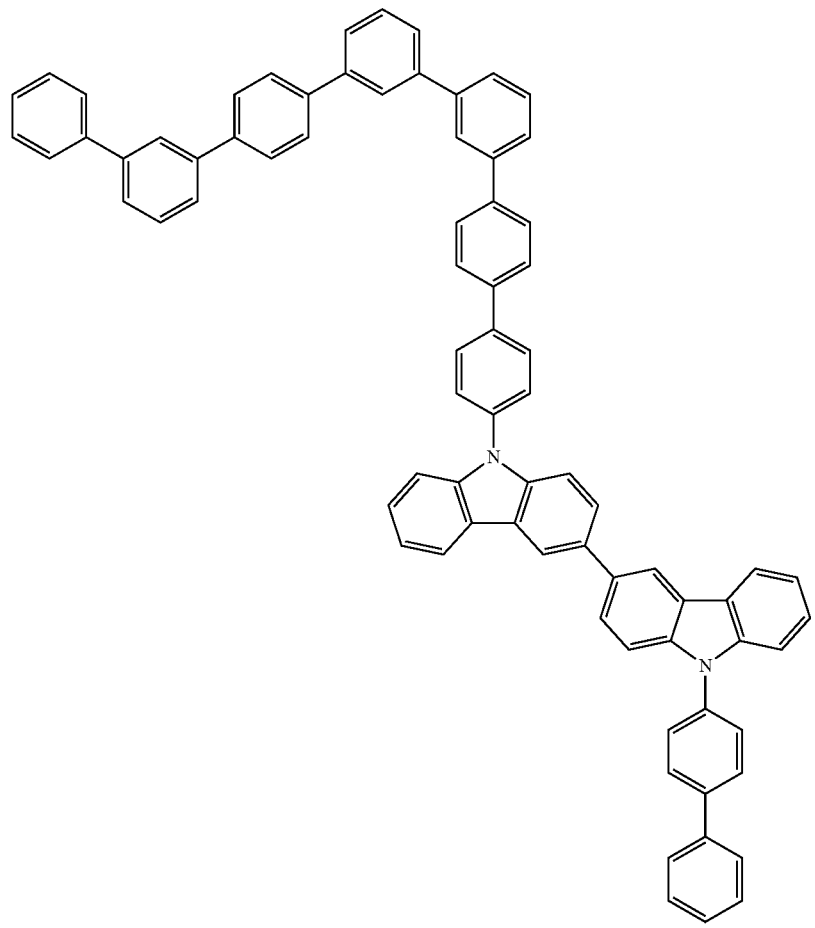

-continued
511
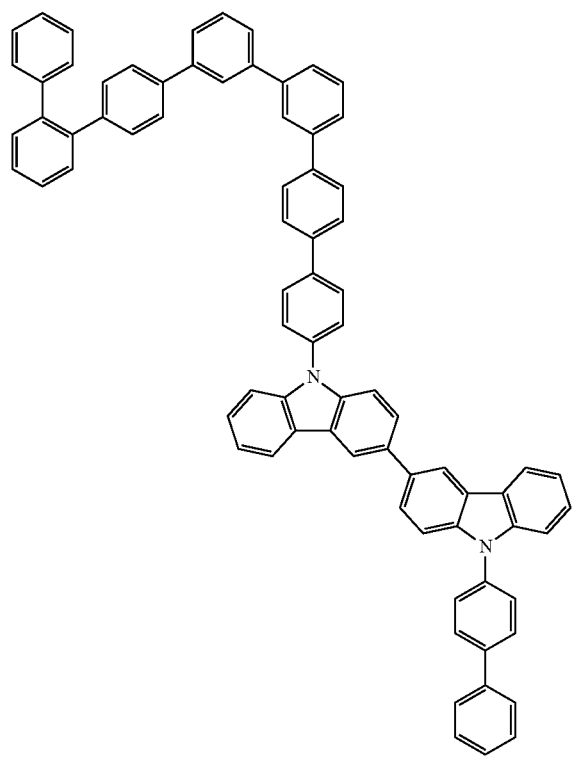
A30
512
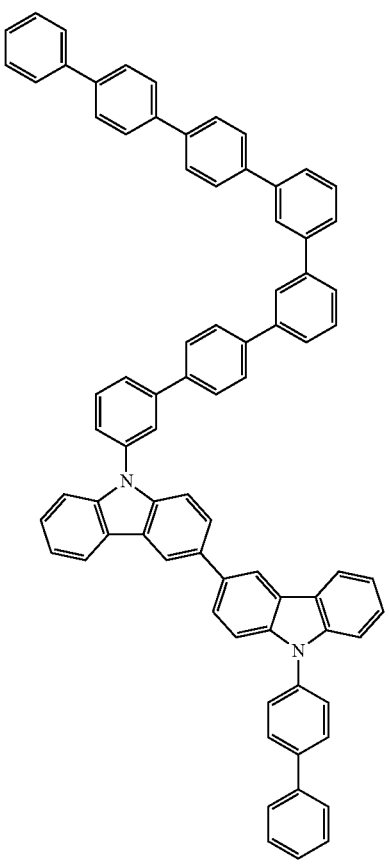
A31

-continued
513
A32
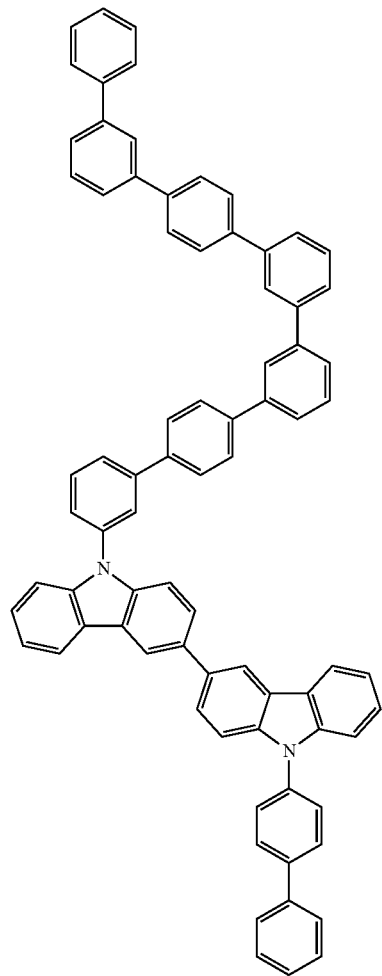
514
A33
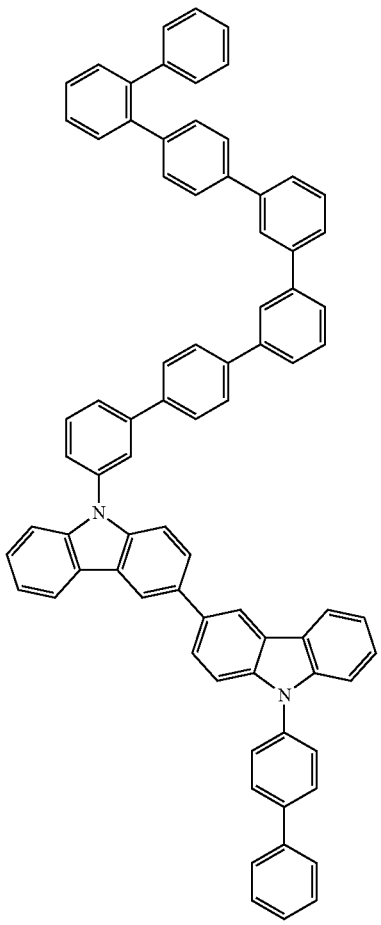

-continued
A34
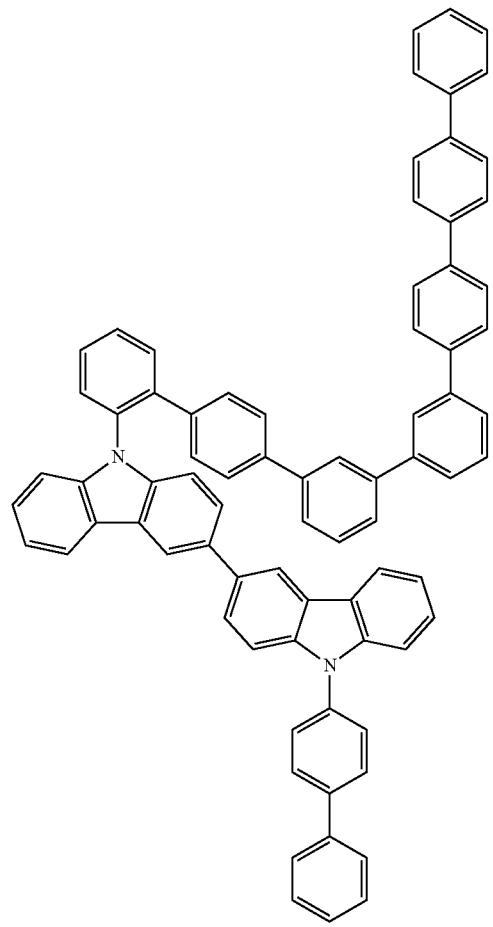
A35
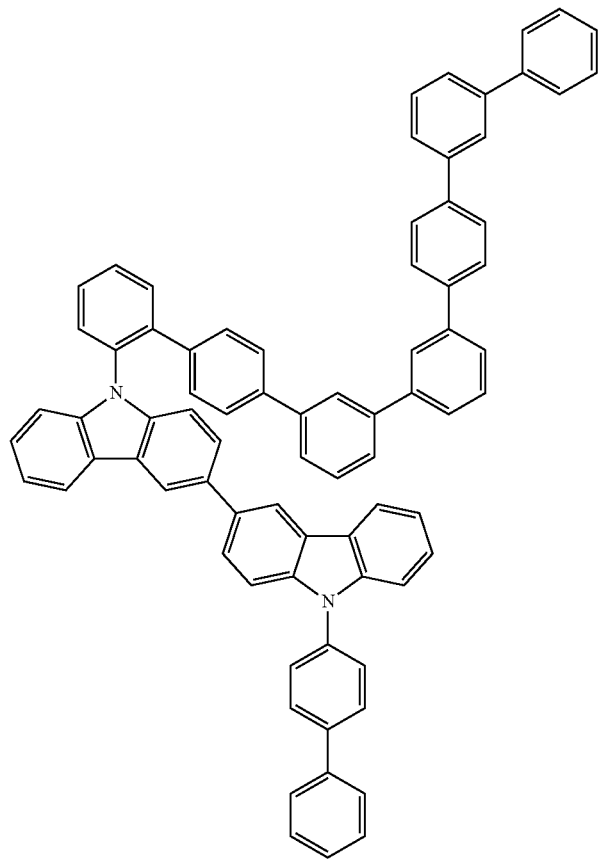

-continued
A36
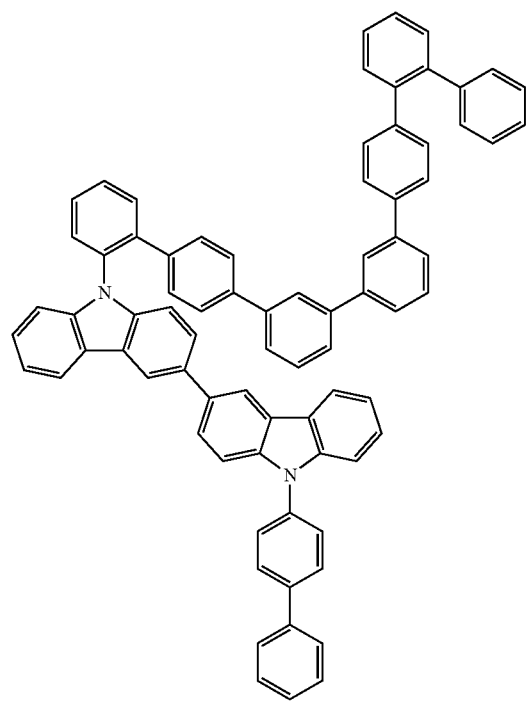
A37
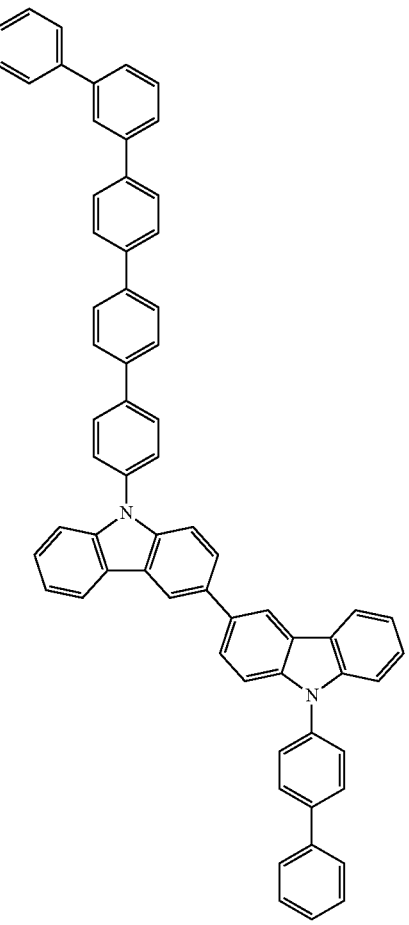

519 520
-continued
A38 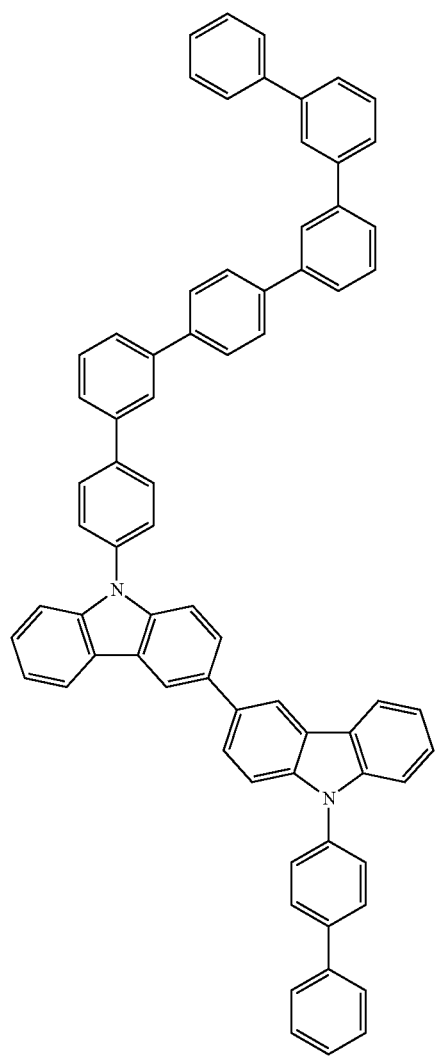 A39

-continued
A40
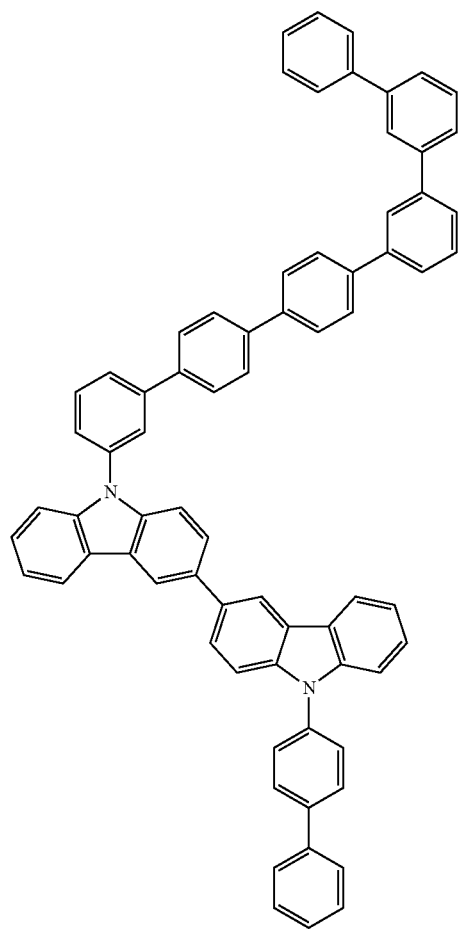
A41
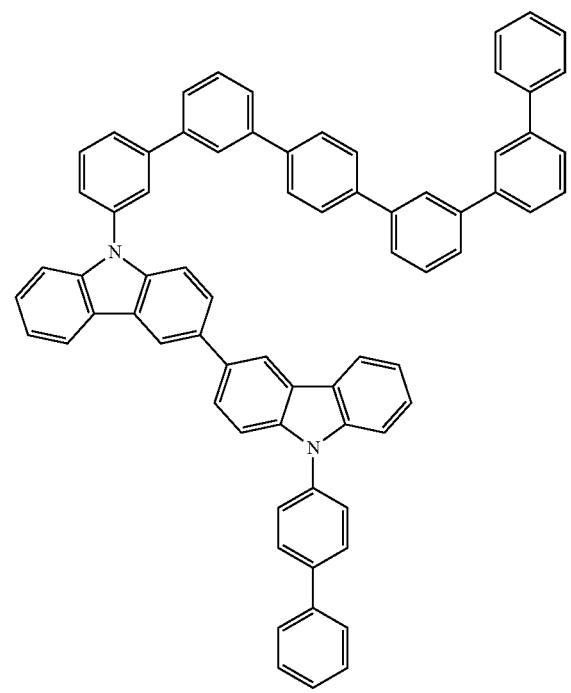
A42
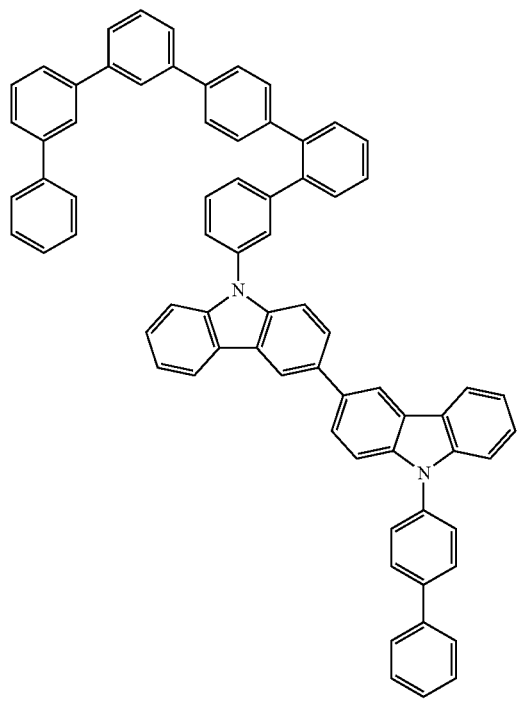
A43
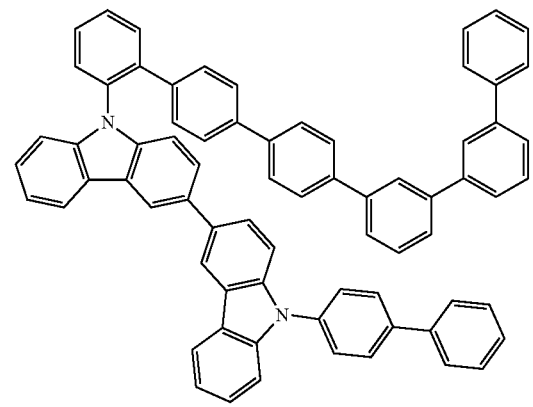

-continued
523 A44
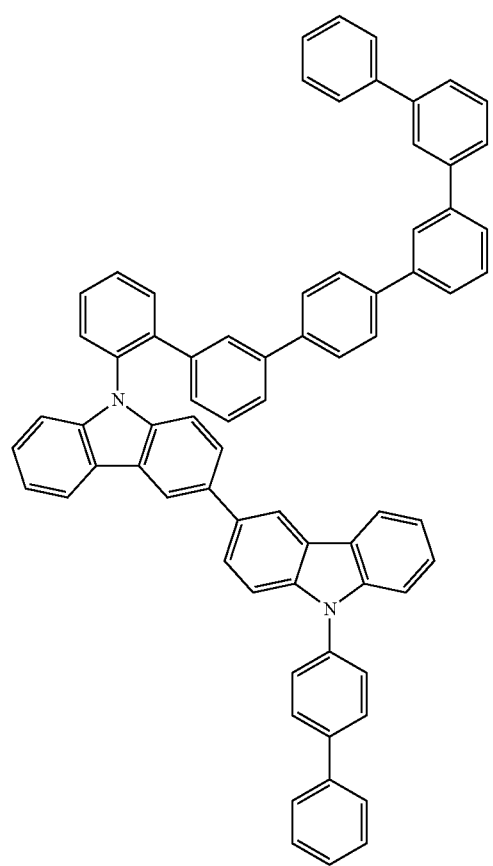
524 A45
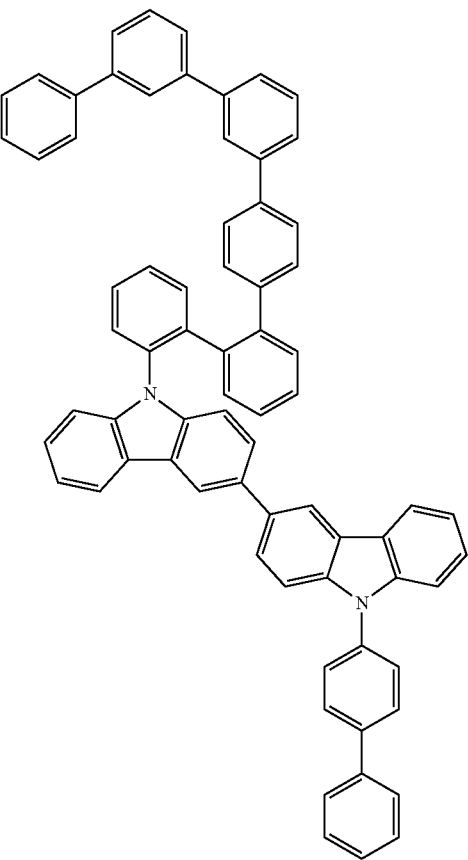

-continued
A46
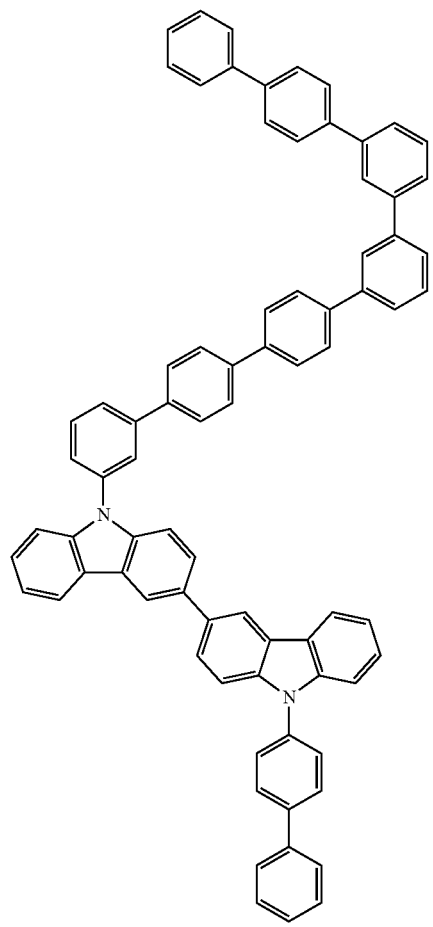
525
A47
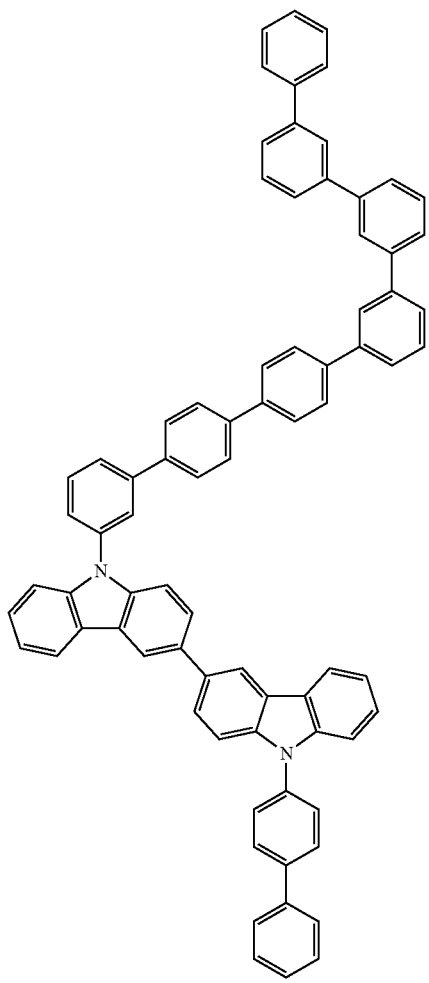
526

-continued
A48
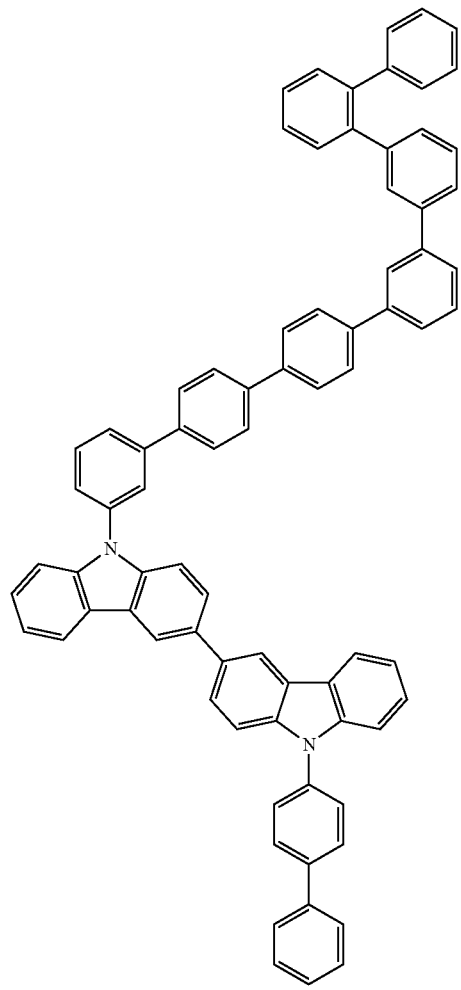
A49
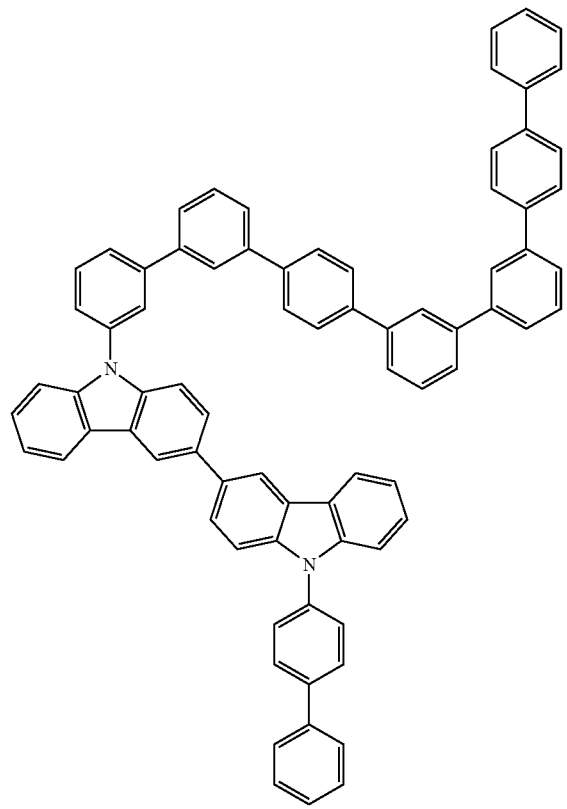
A50
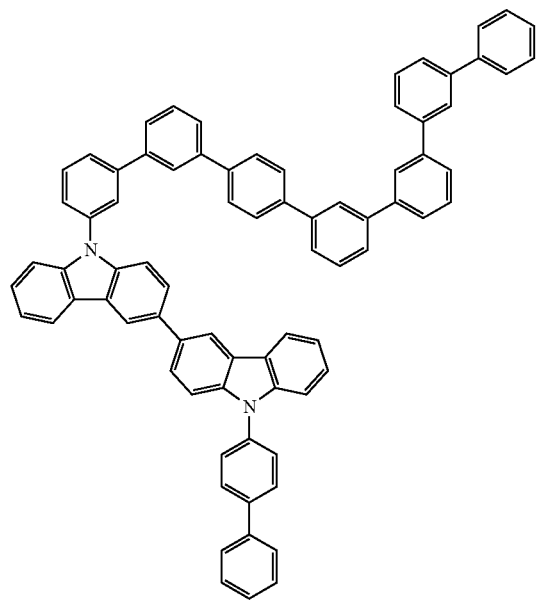
A51
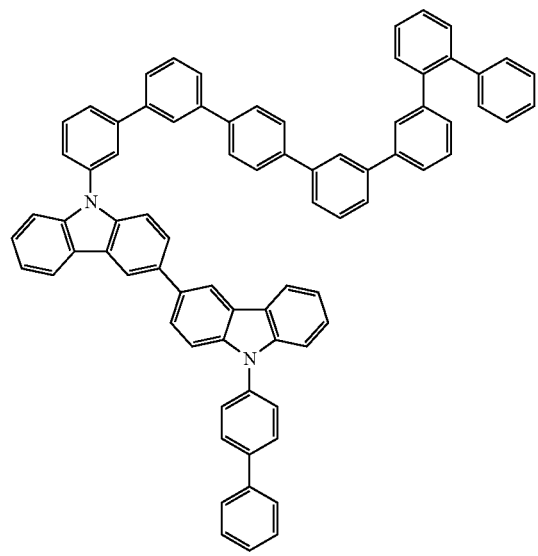

-continued
529
A52
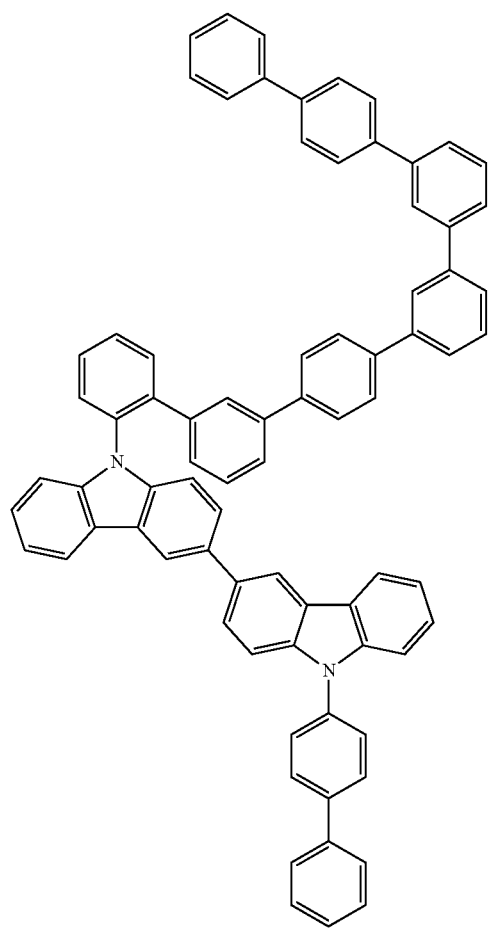
530
A53
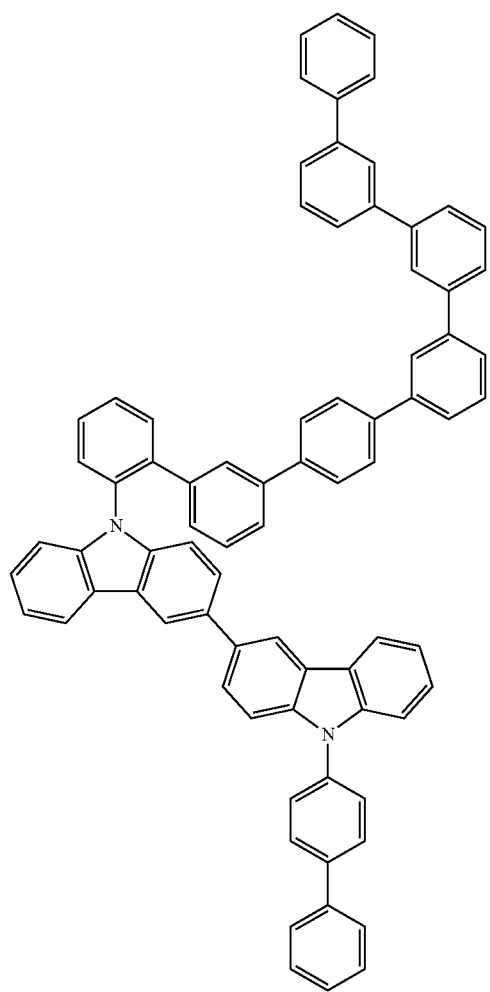

-continued
531
A54
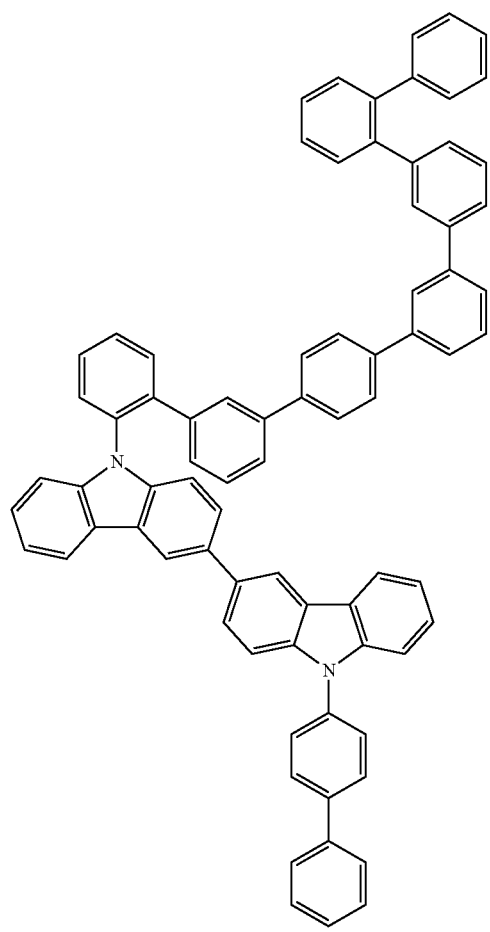
532
A55
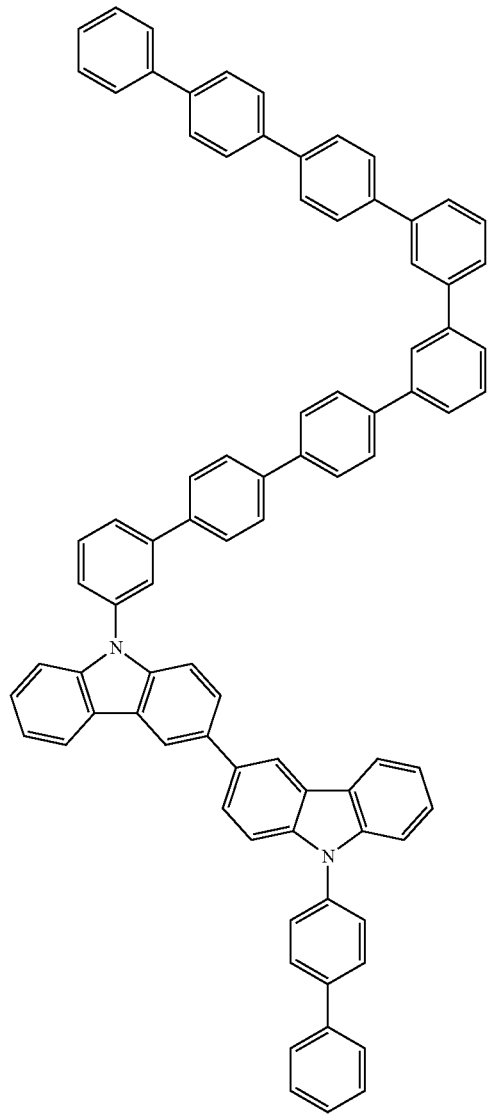

533 A56
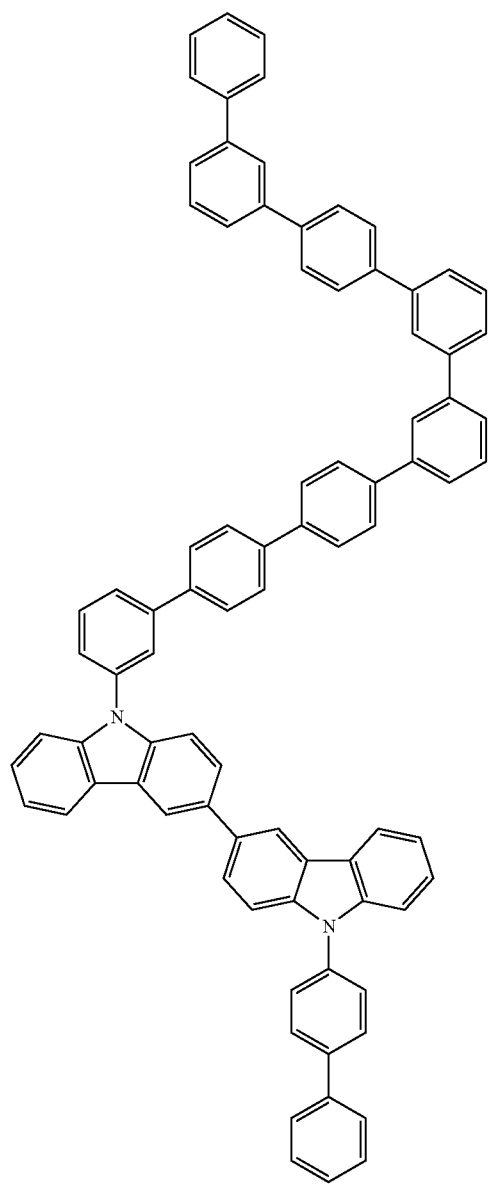
534 A57
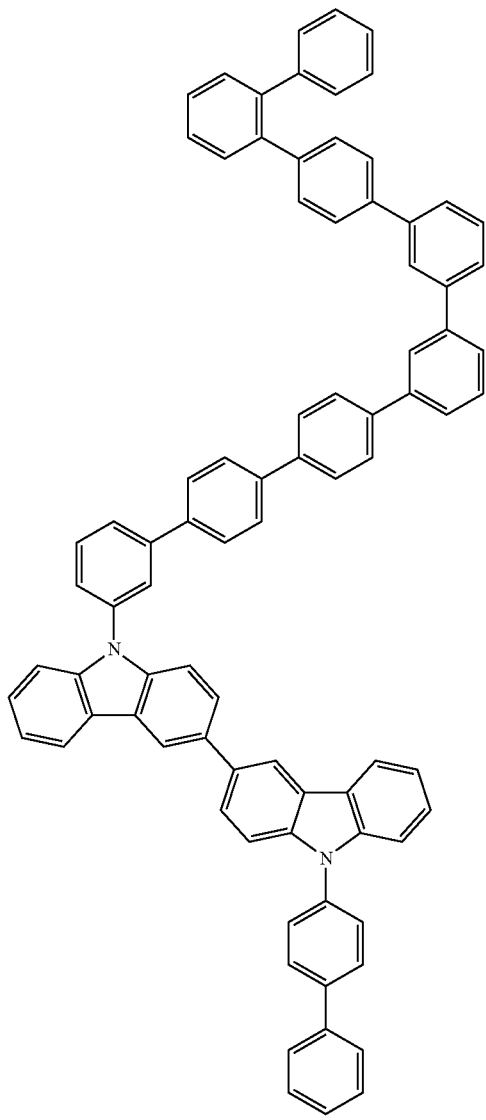

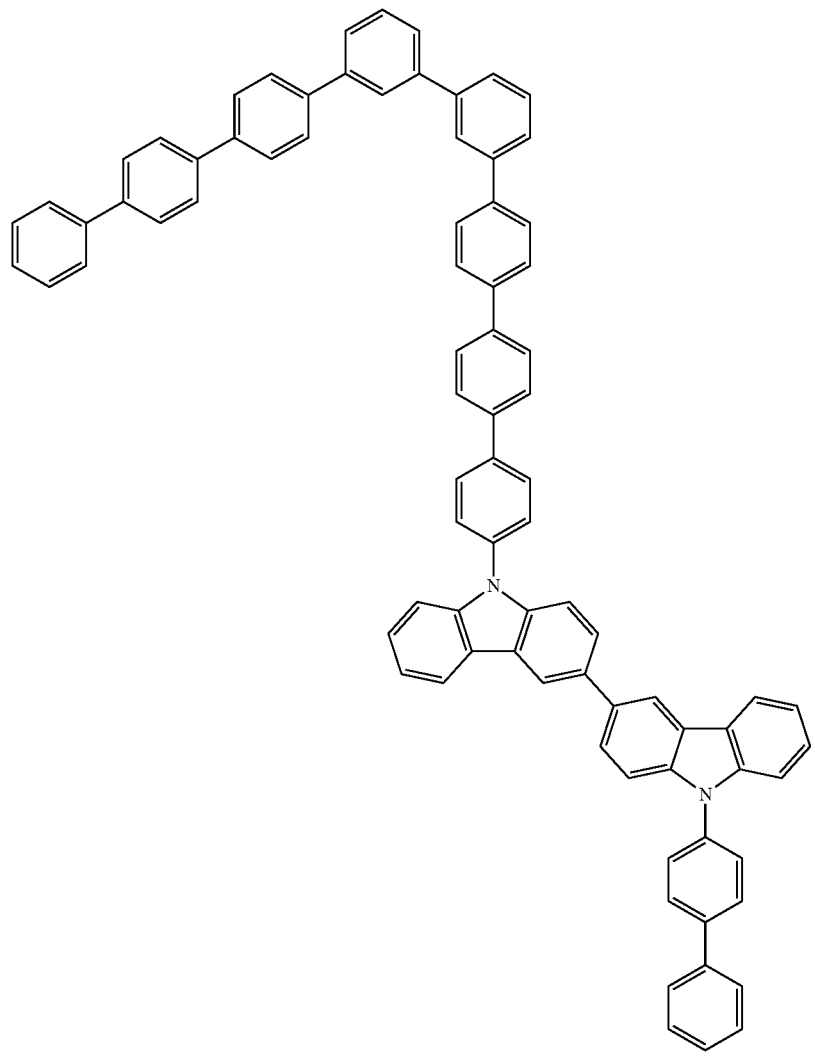
A58

-continued
A59
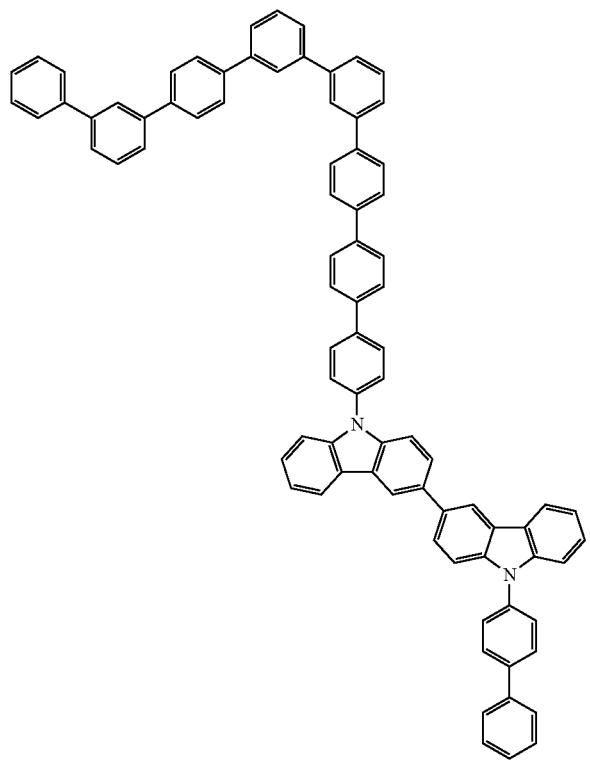
A60
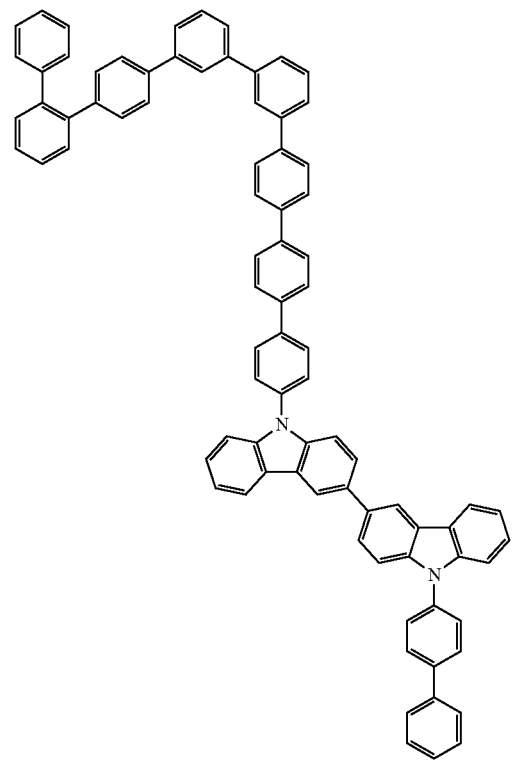
A61
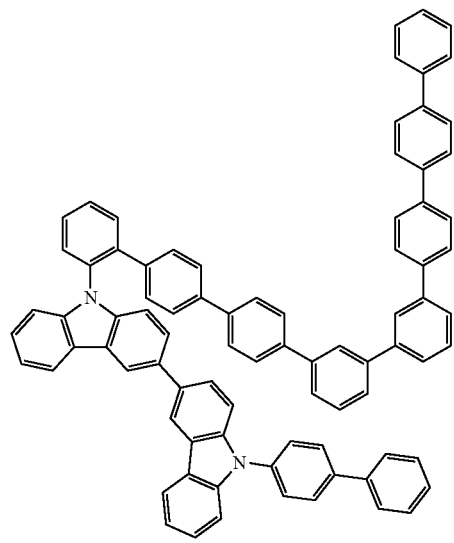
A62
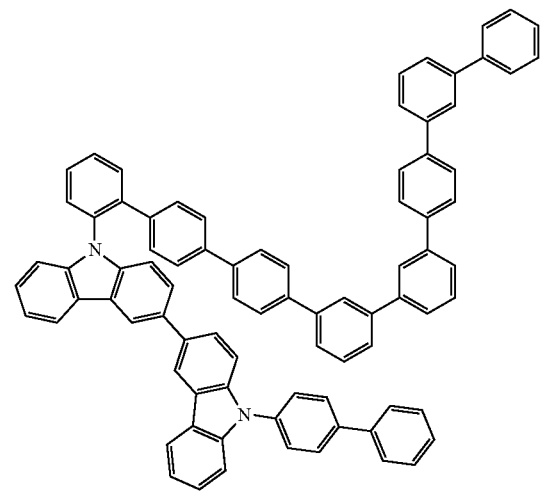

-continued
A63
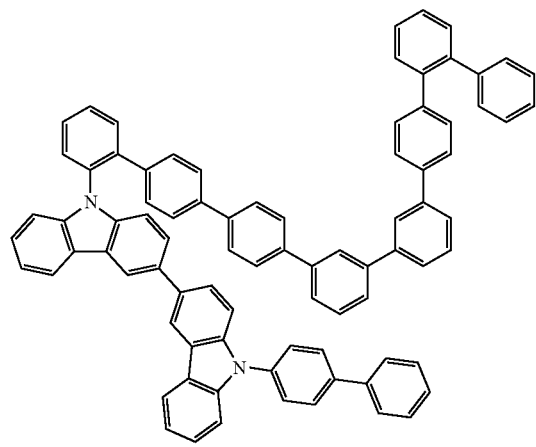
A64
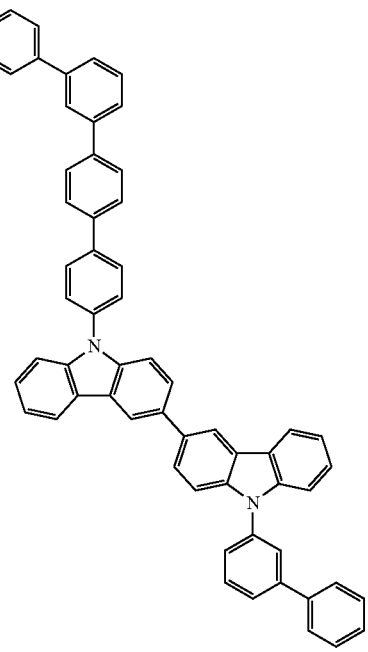
A65
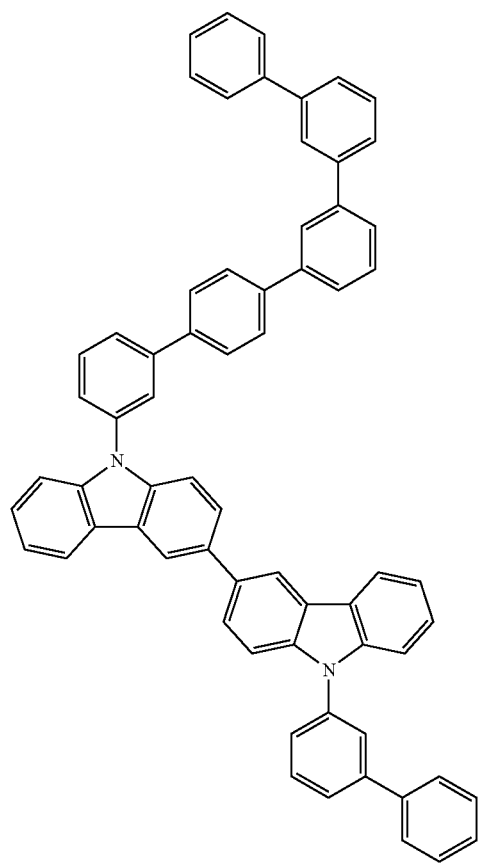
A66
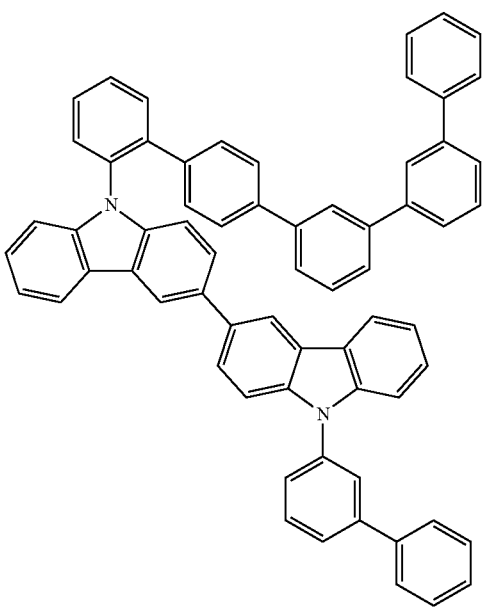

-continued
A67
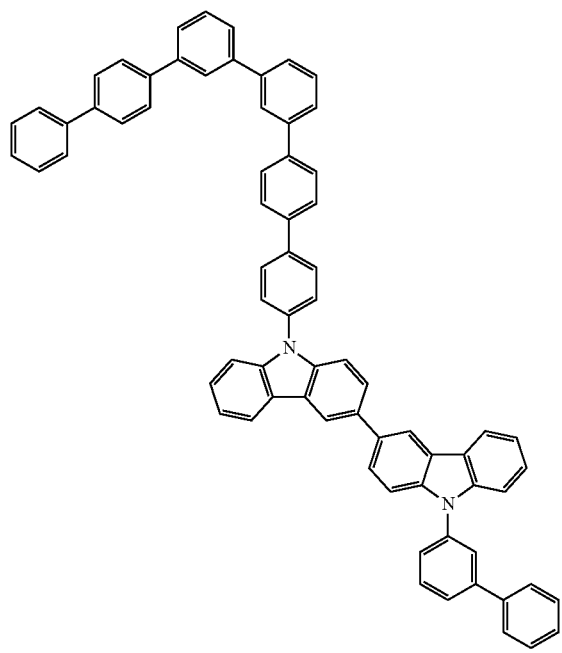
A68
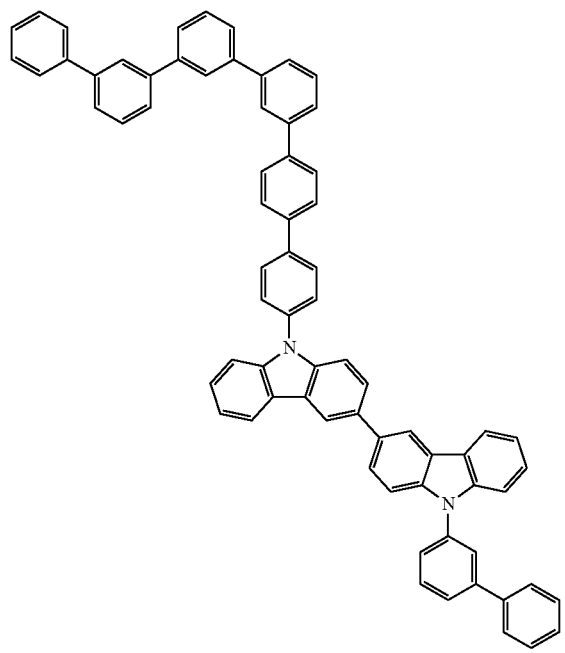
A69
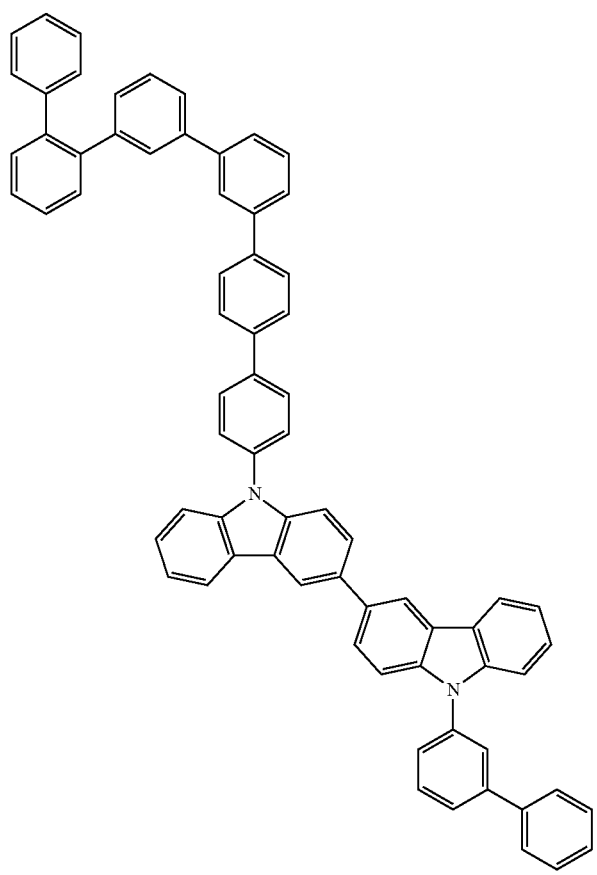
A70
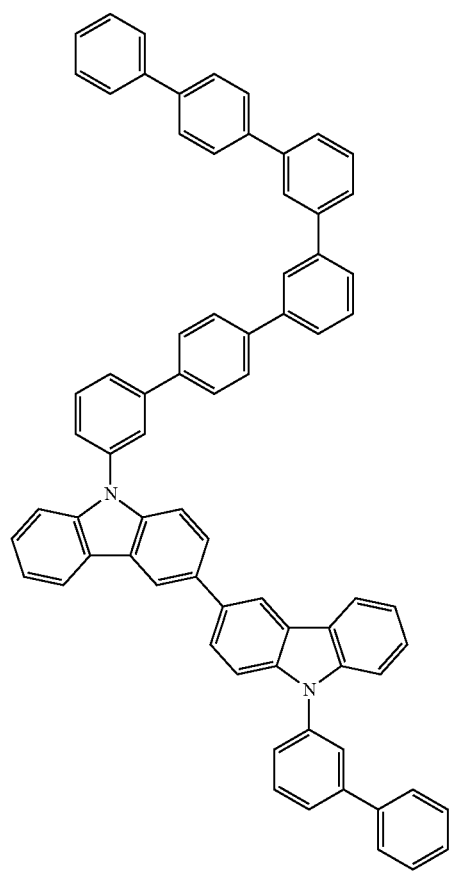

-continued
A71
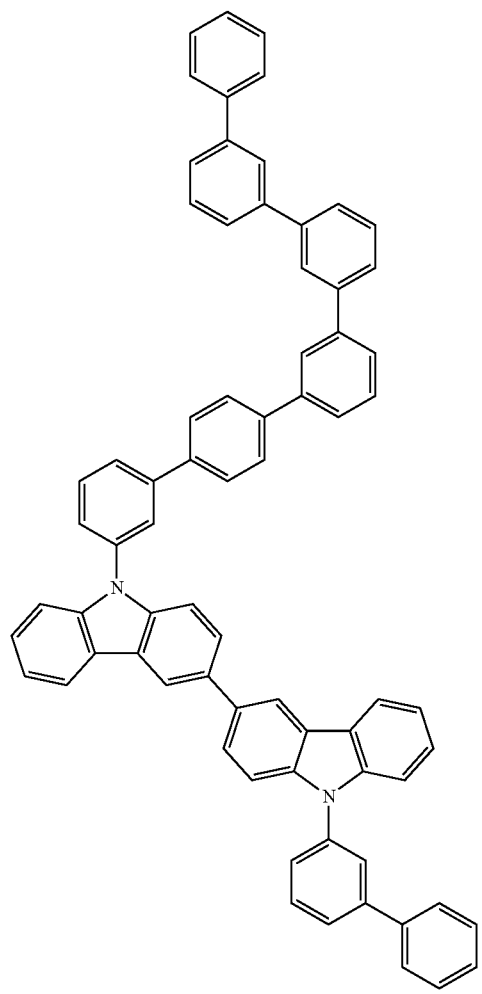
A72
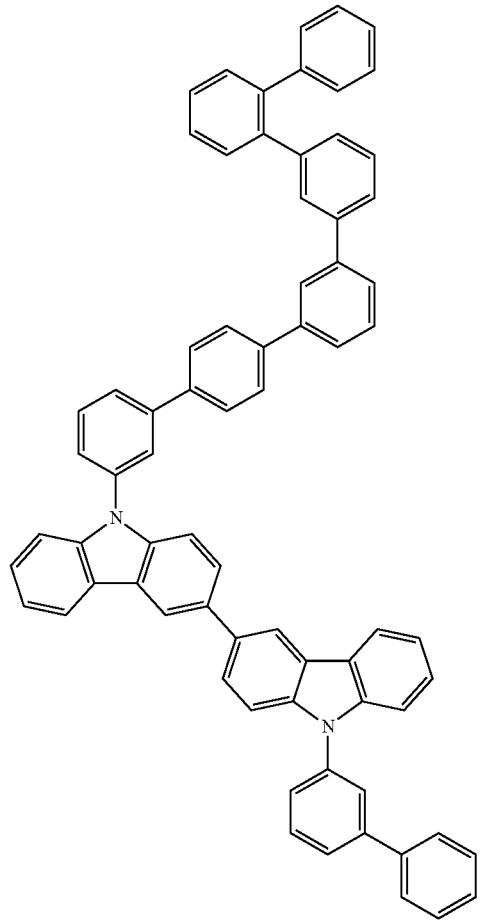
A73
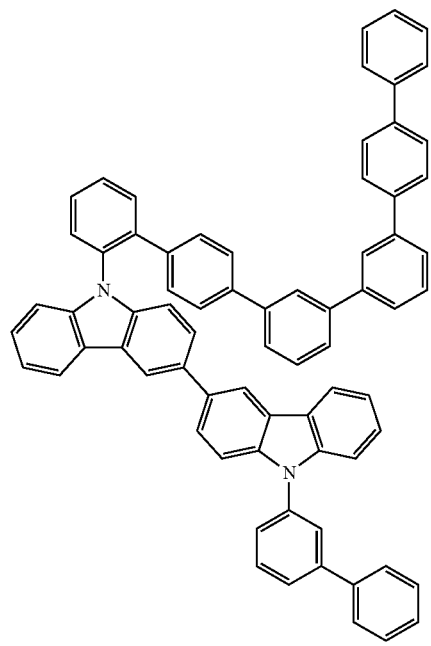
A74
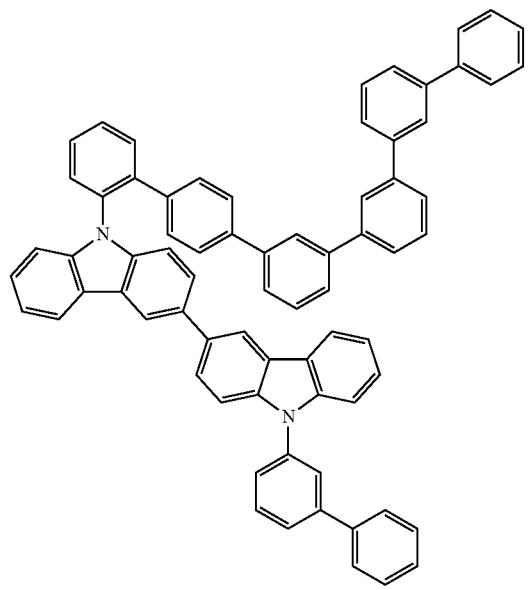

-continued
A75
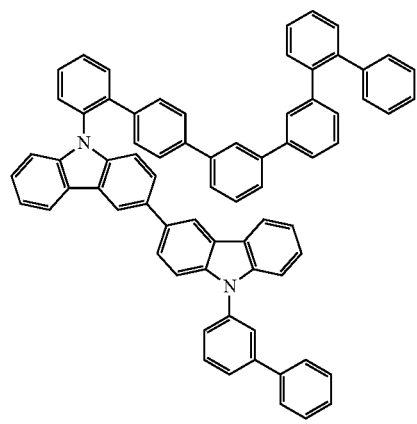
A76
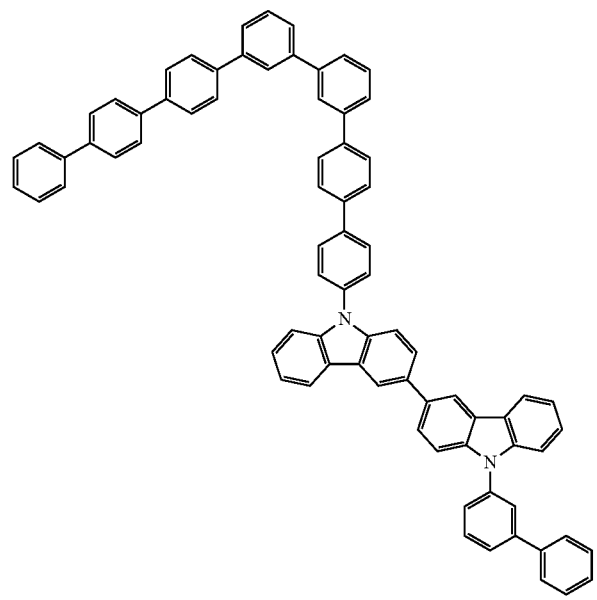
A77
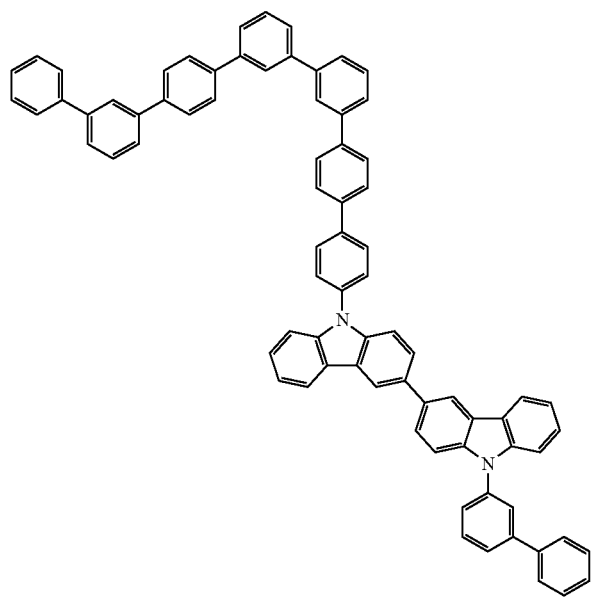
A78
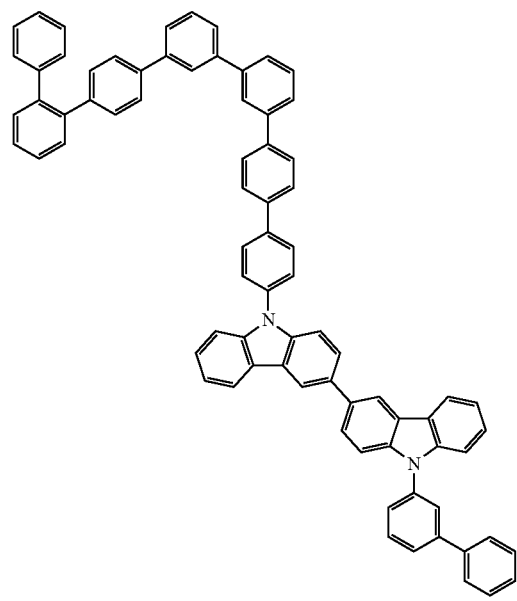

547
548
-continued
A79
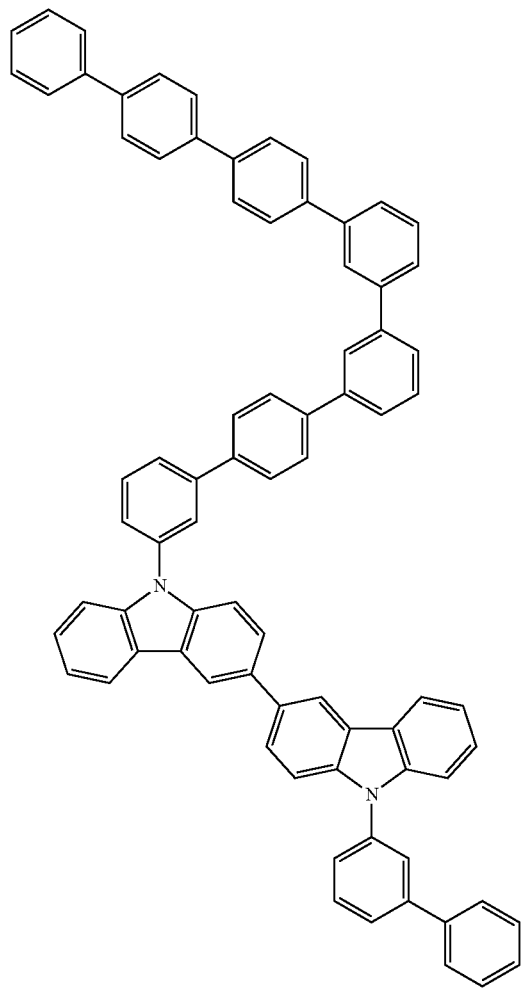
A80
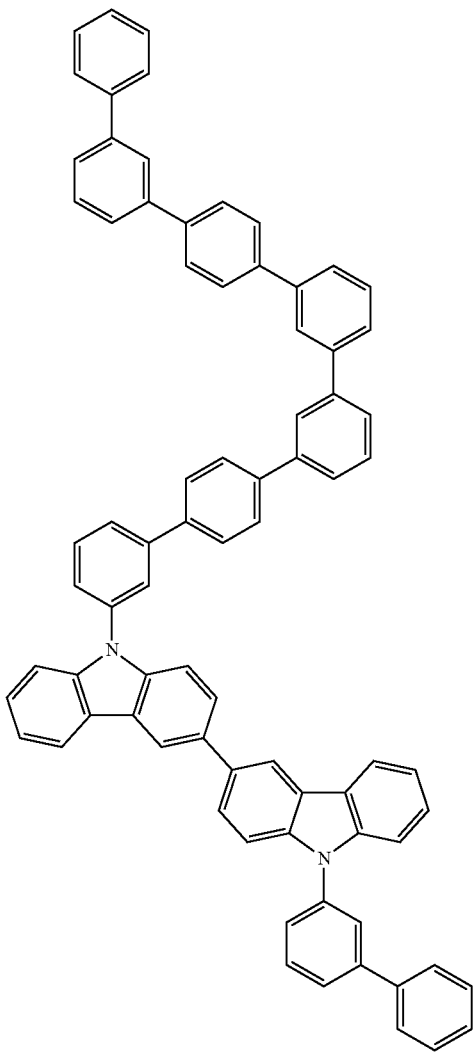

-continued
A81
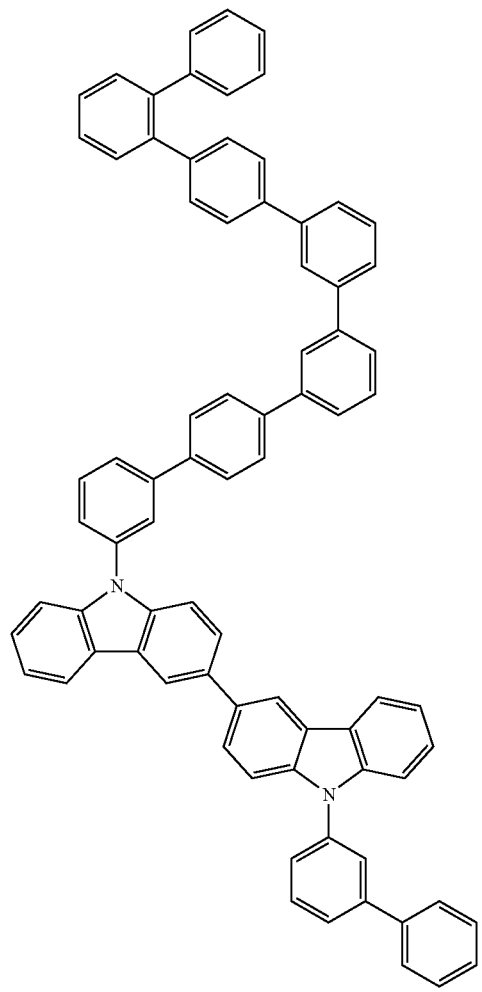
A82
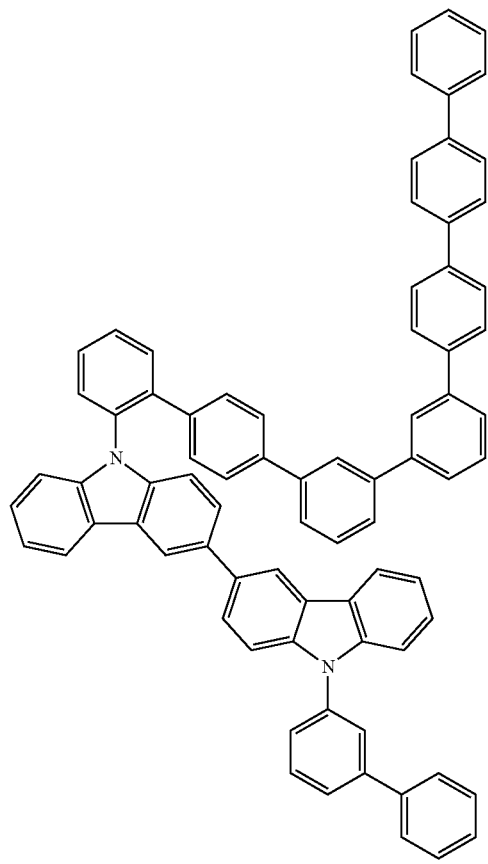
A83
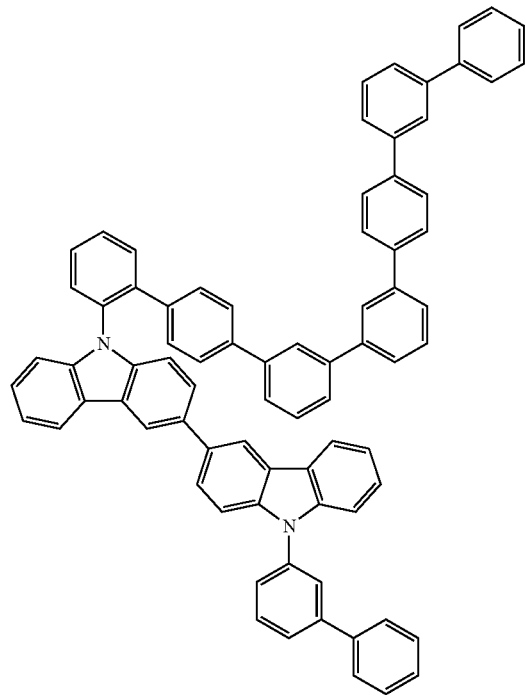
A84
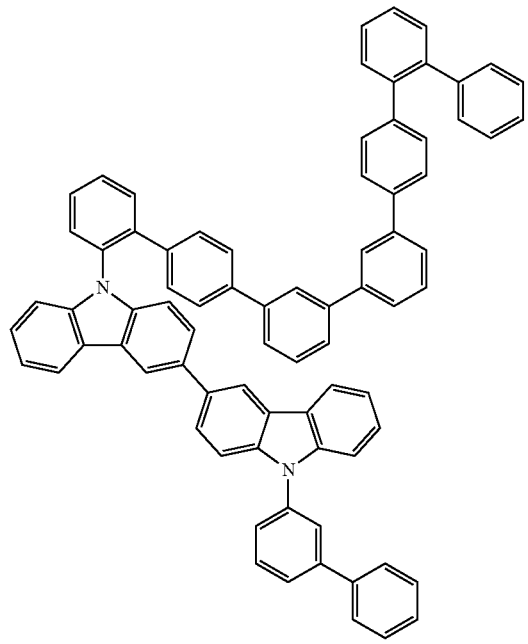

555 556
-continued
A85 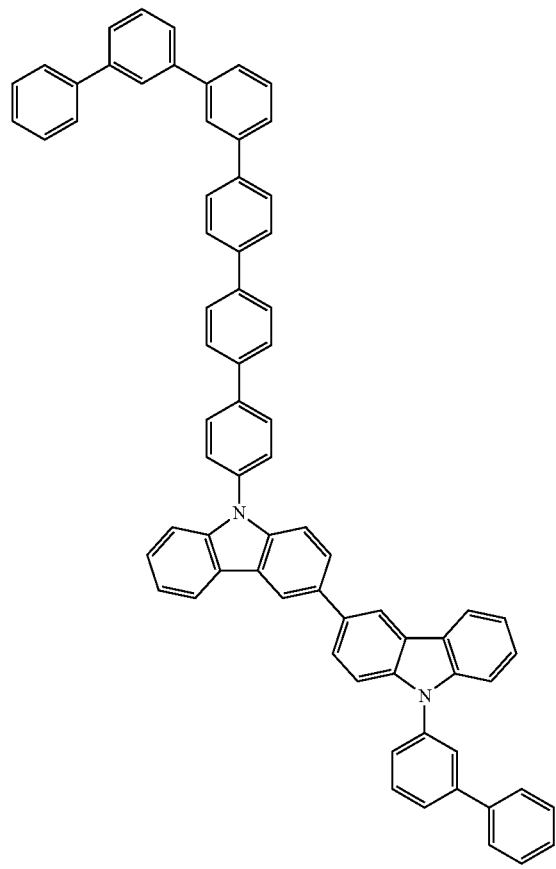 A86 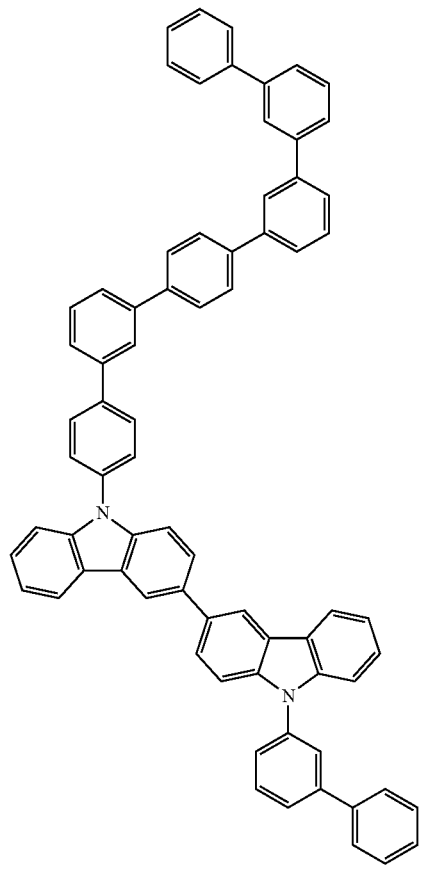

-continued
A87
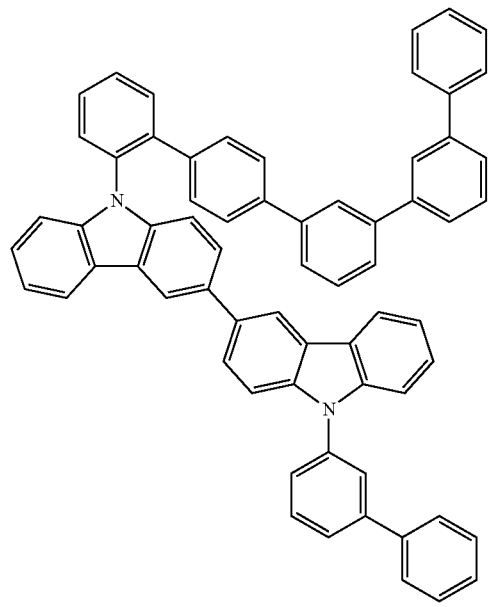
A88
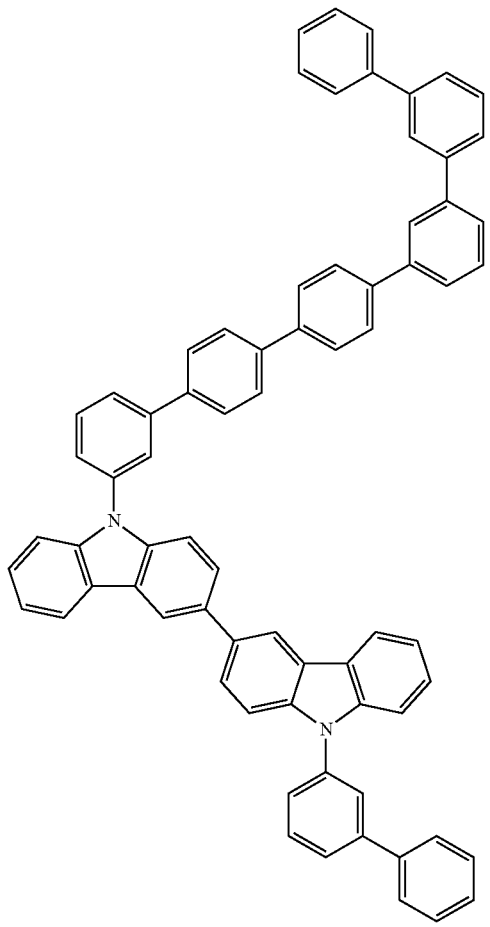
A89
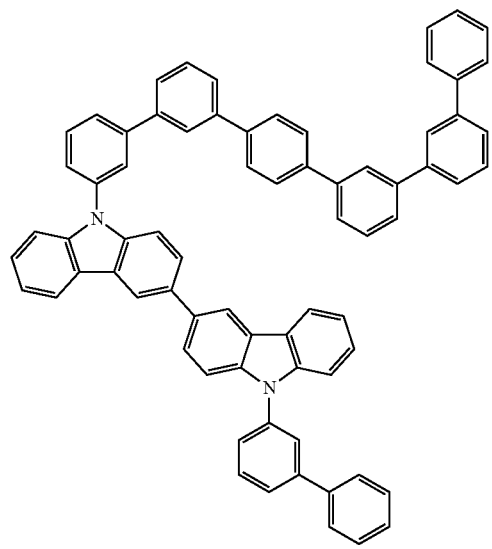
A90
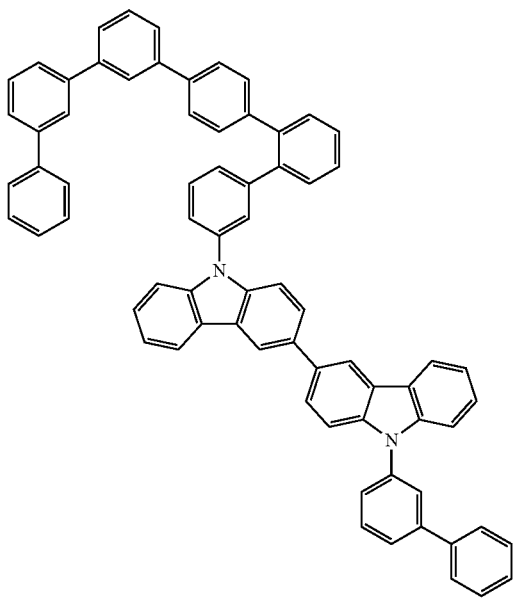

-continued
A91
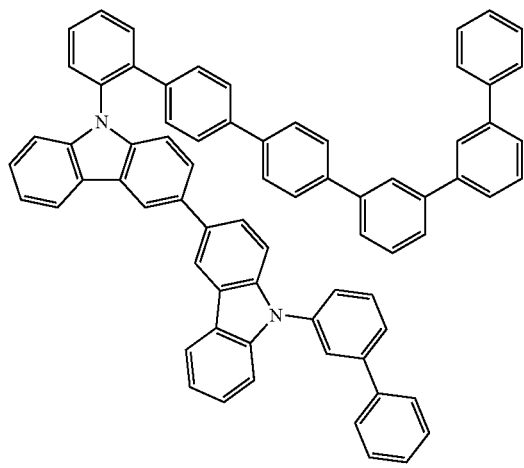
A92
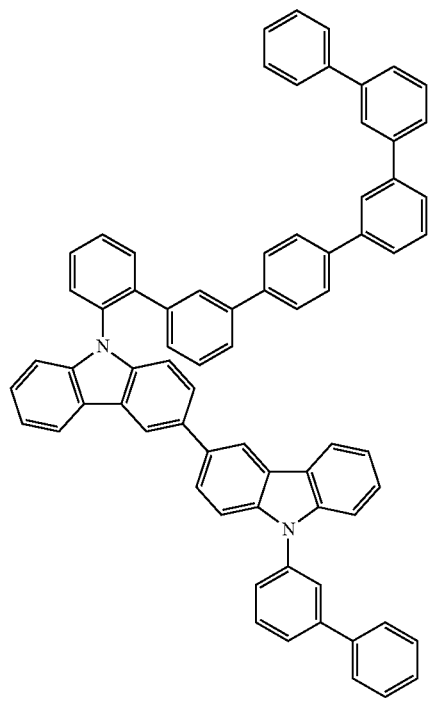
A93
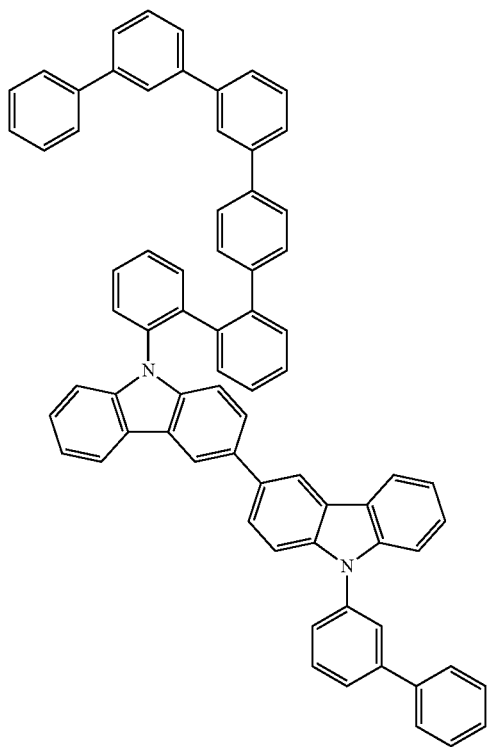
A94
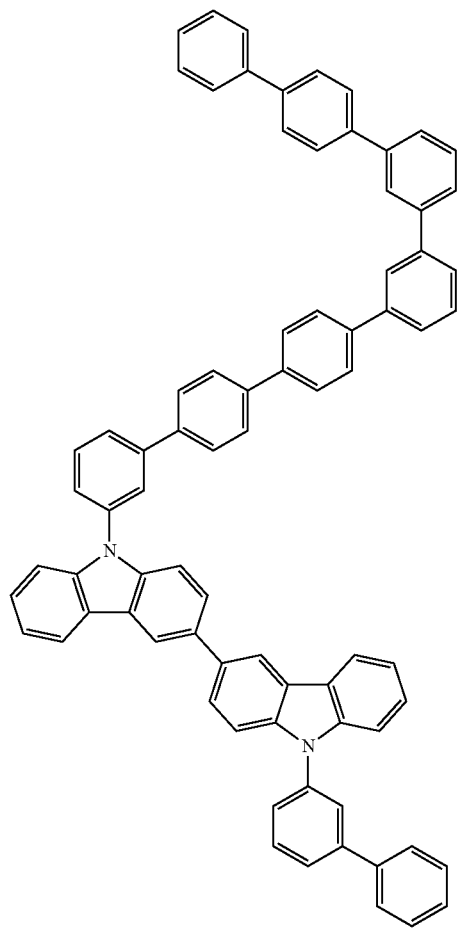

-continued
A95
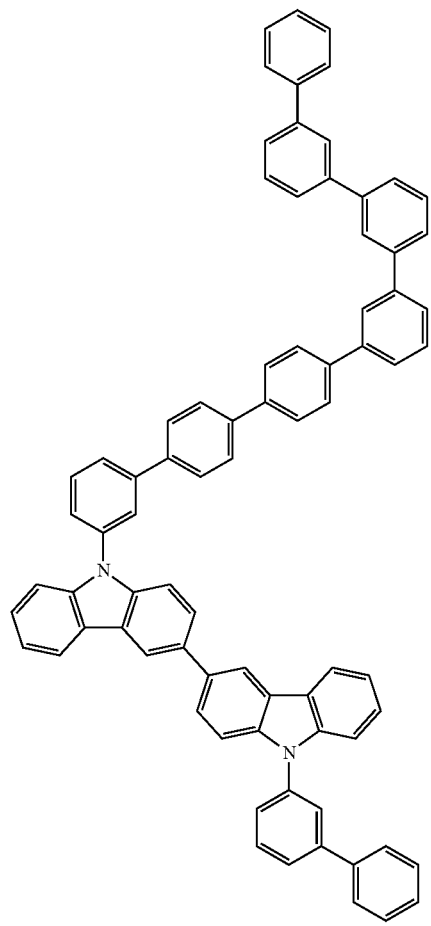
A96
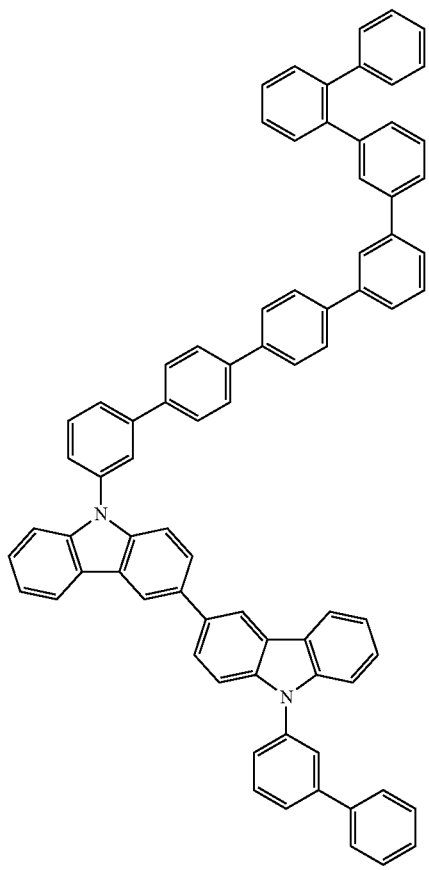
A97
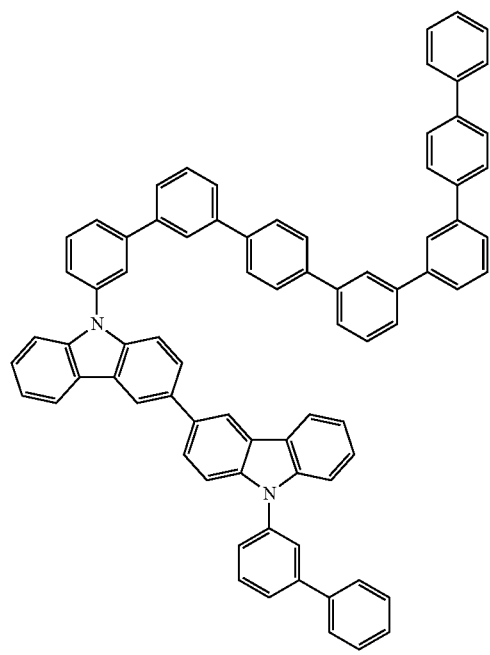
A98
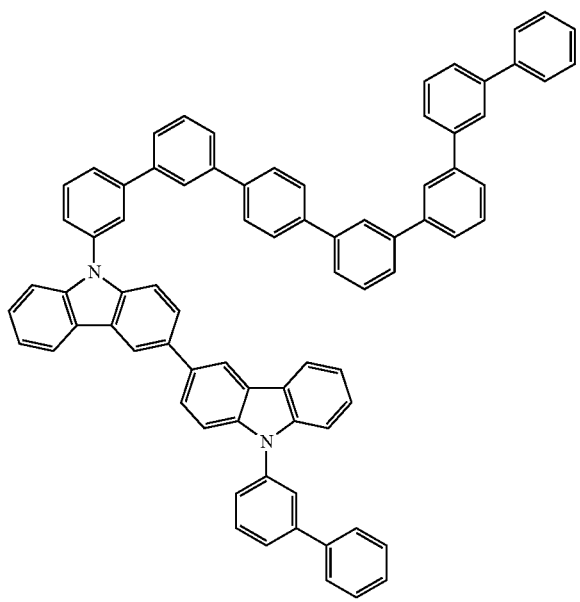

-continued
A99
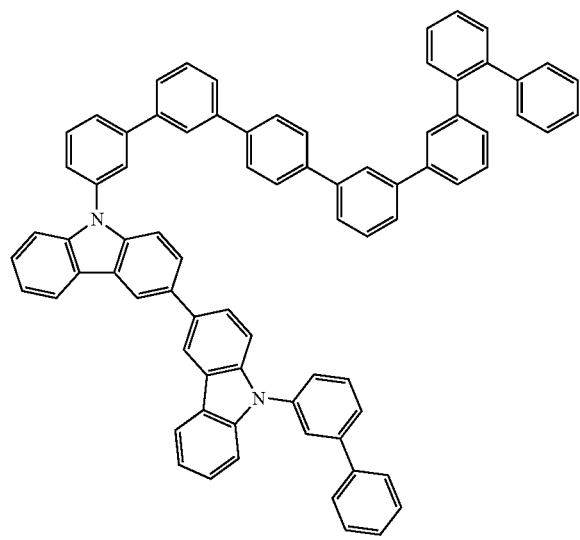
A100
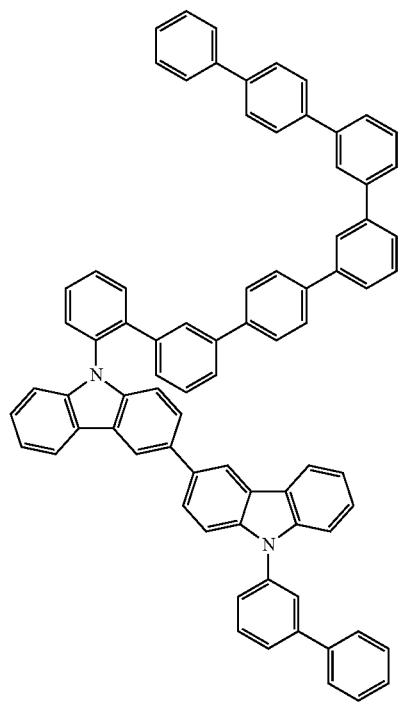
A101
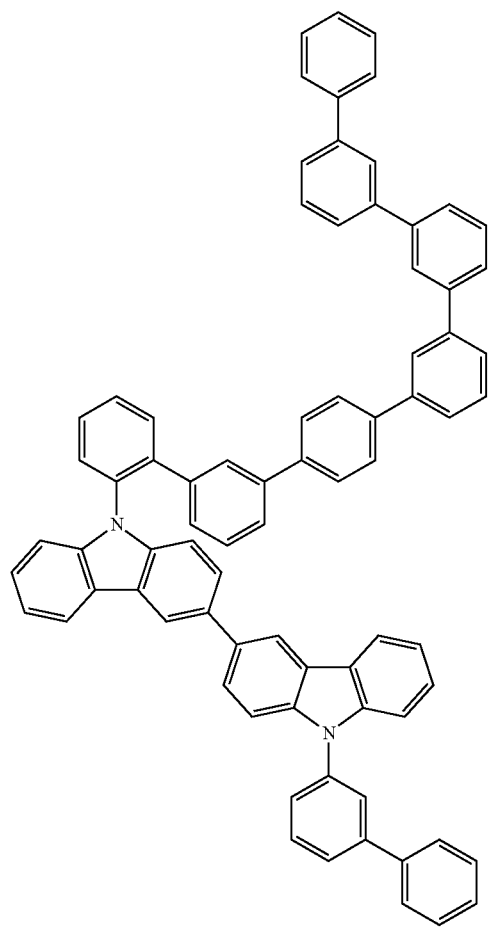
A102
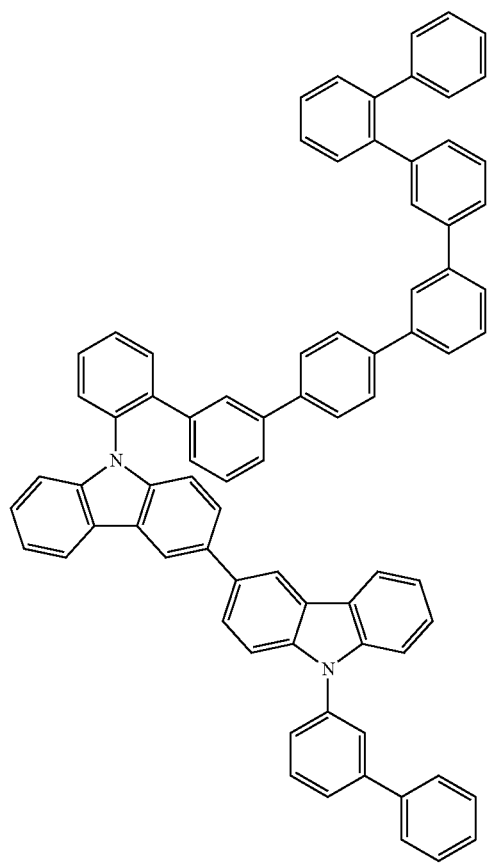

565
A103
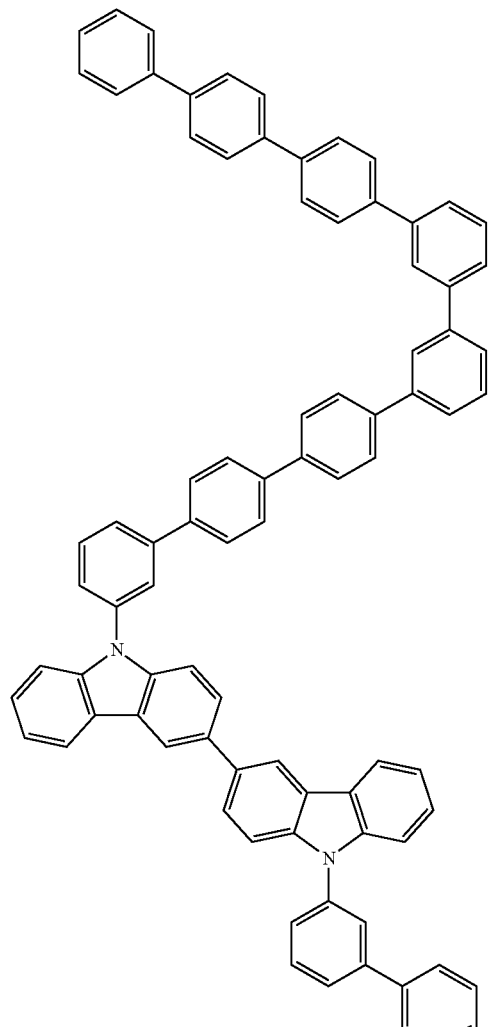
566
A104
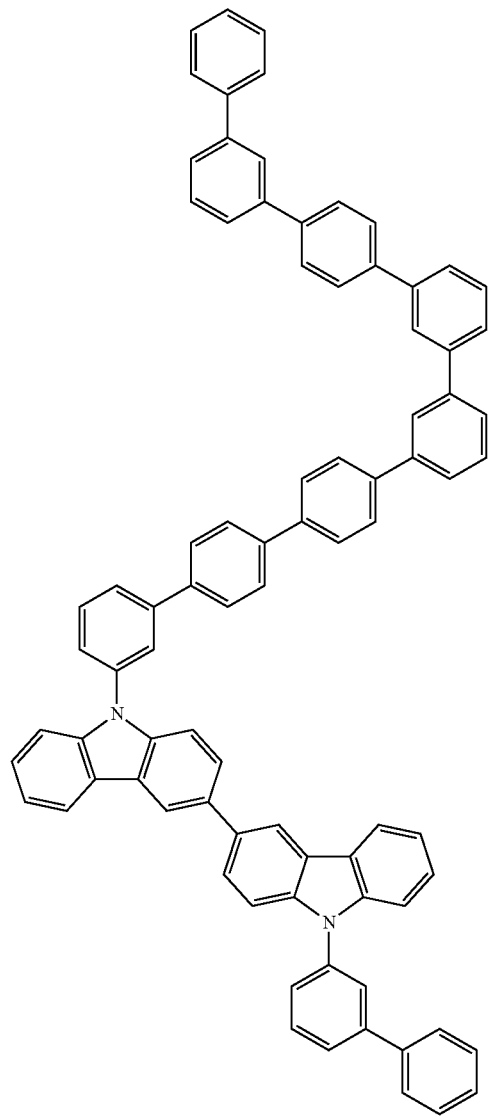

-continued
A105
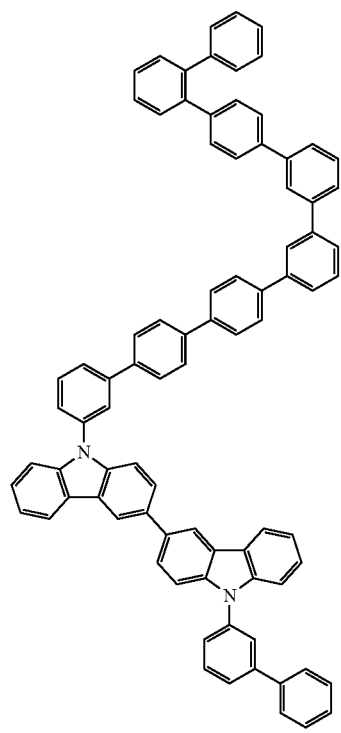
A106
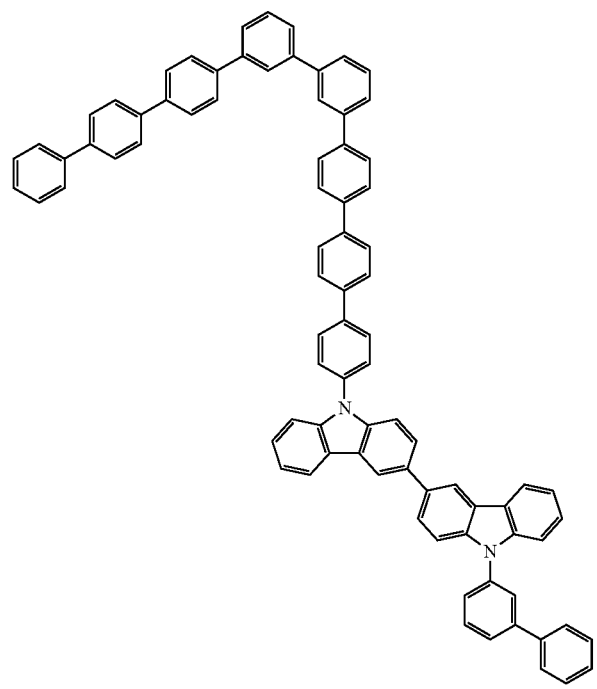
A107
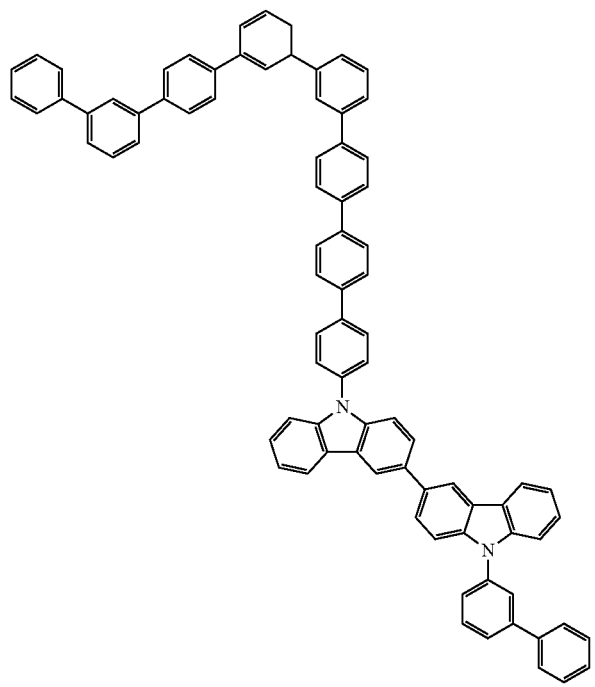
A108
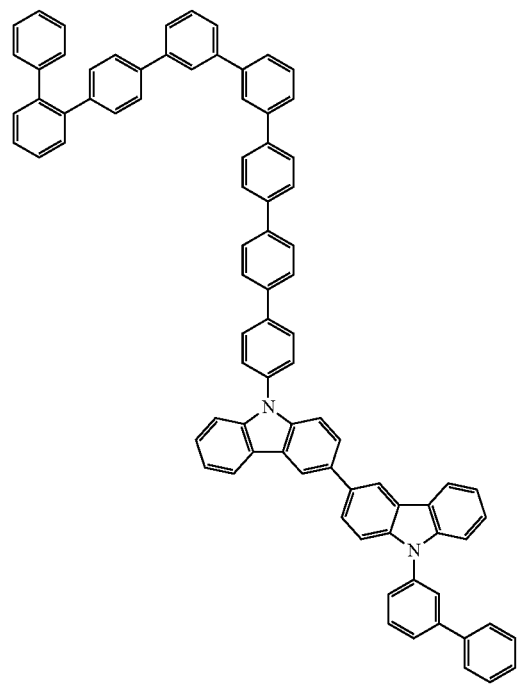

-continued
A109
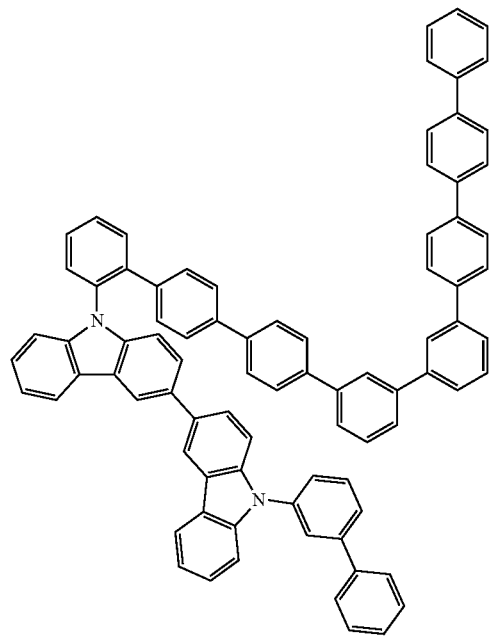
A110
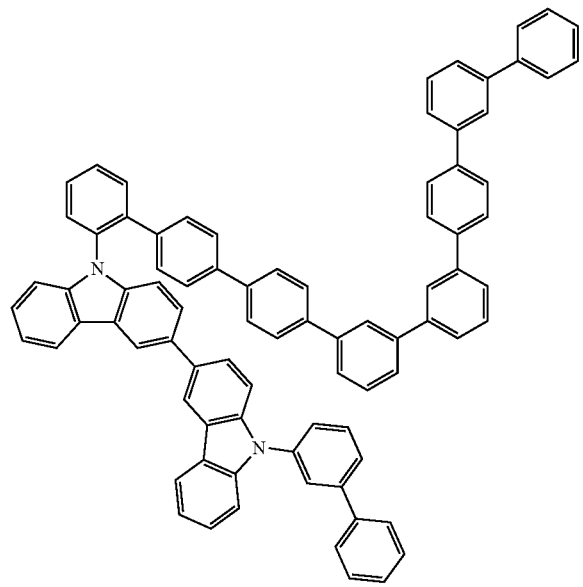
A111
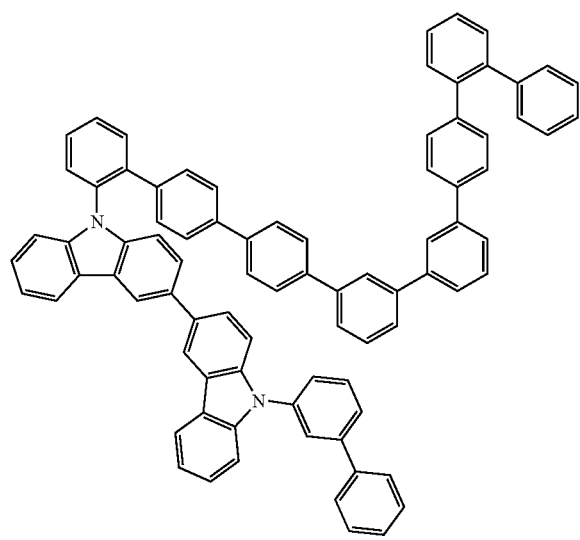
A112
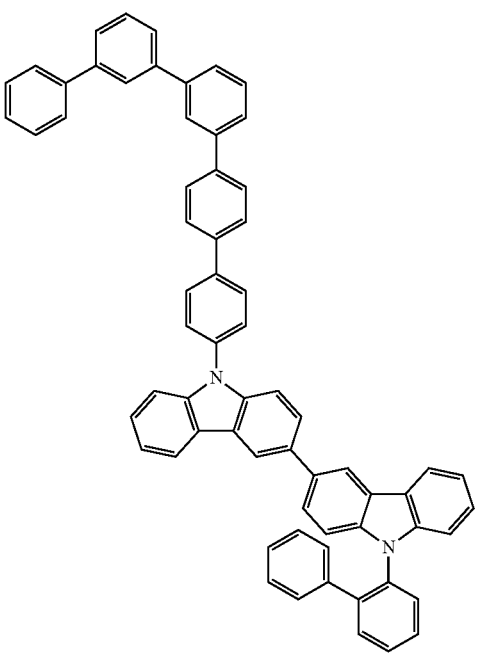

-continued
A113
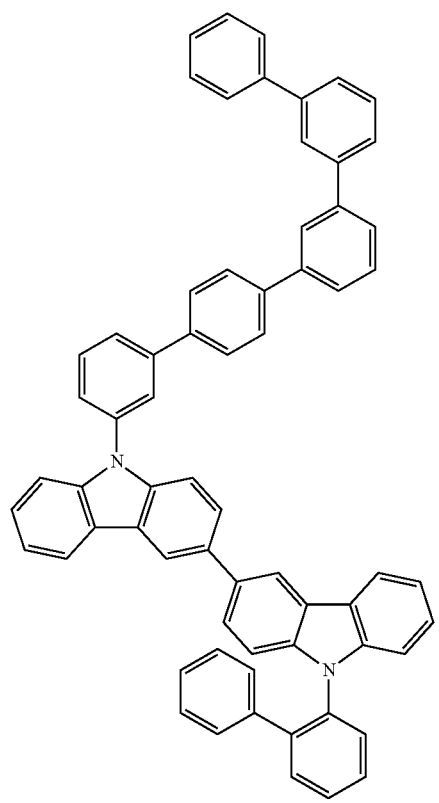
A114
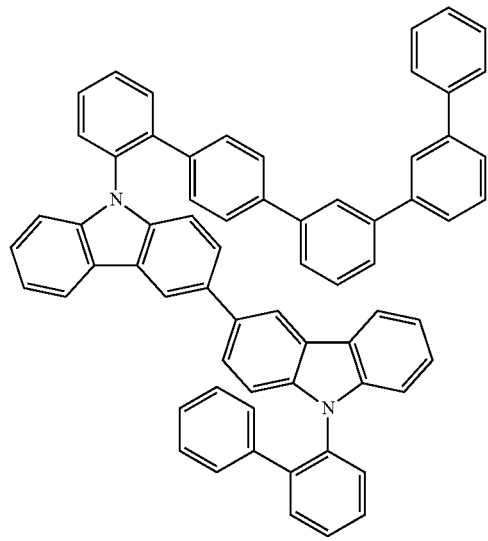
A115
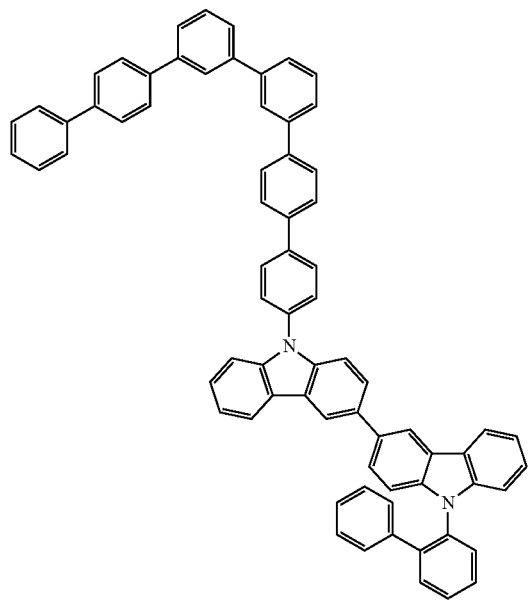
A116
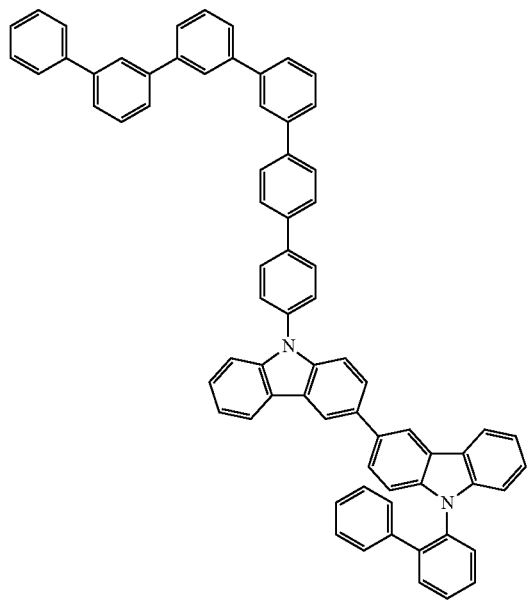

-continued
A117
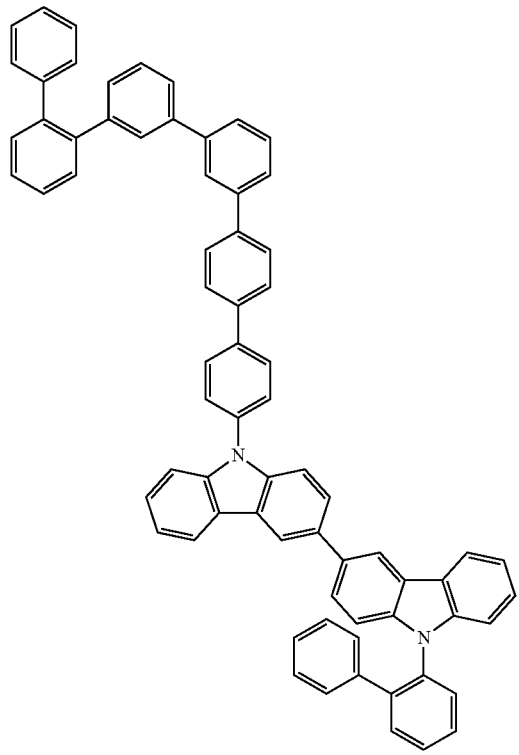
A118
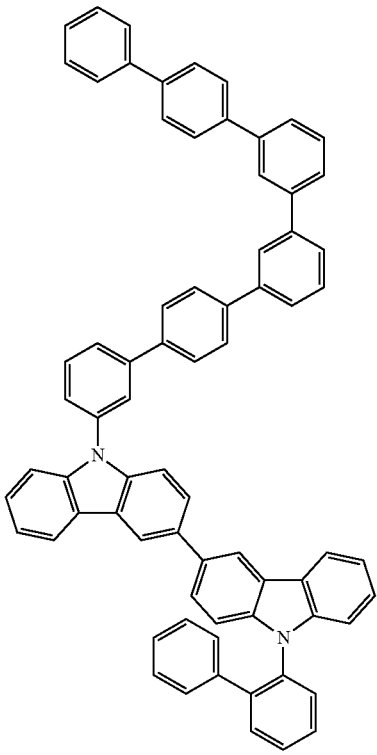
A119
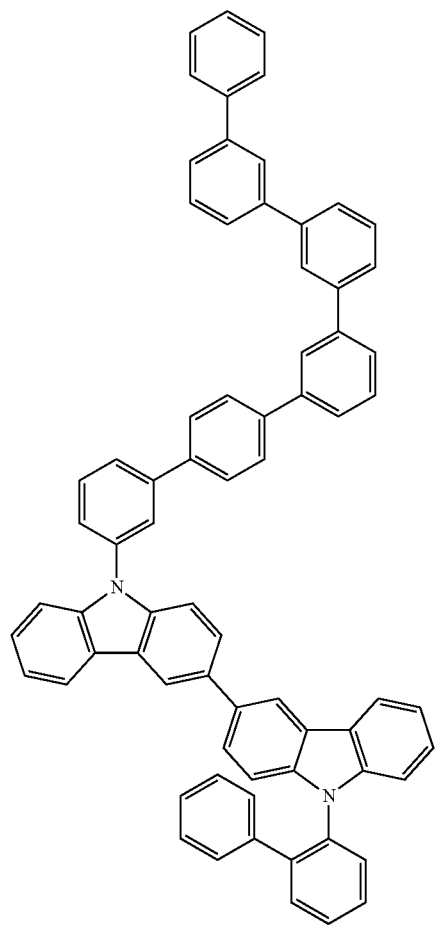
A120
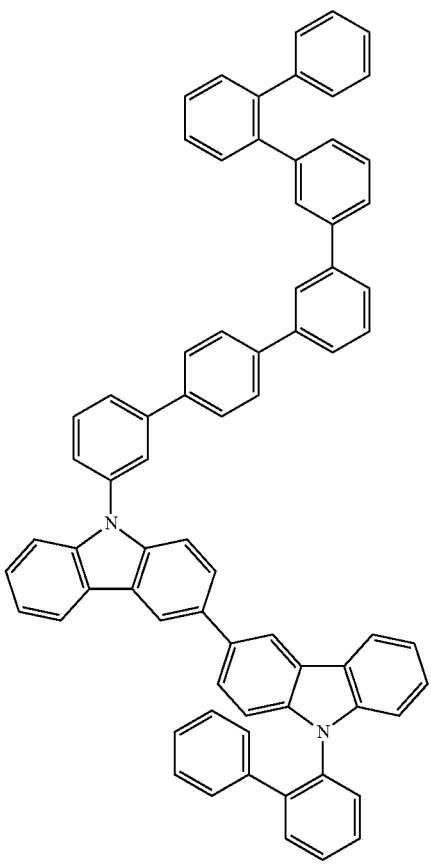

-continued
A121
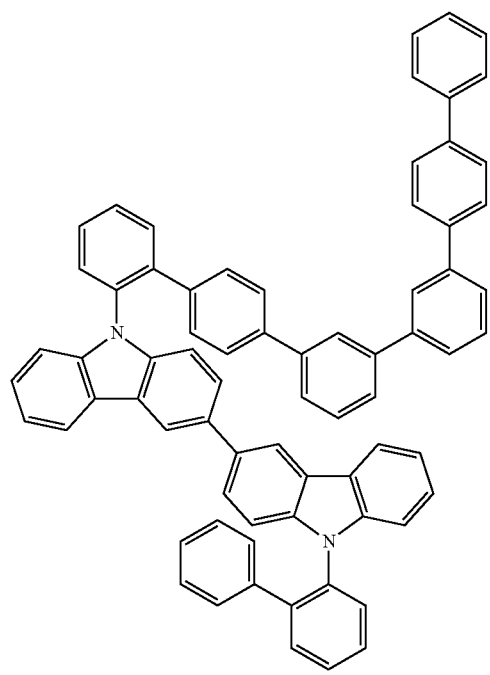
A122
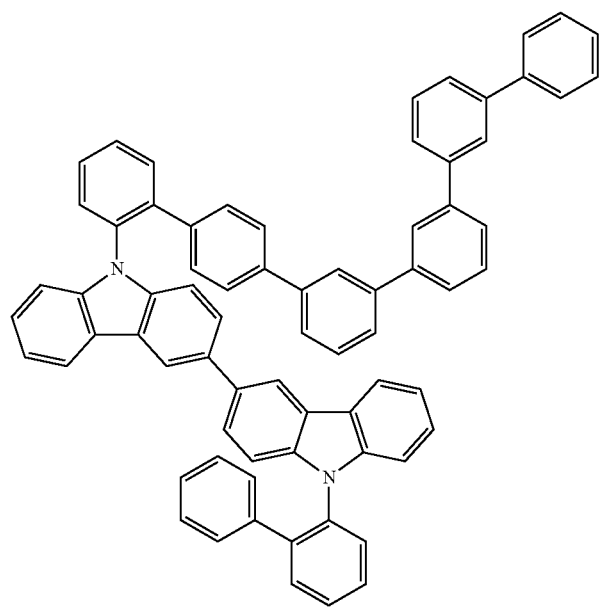
A123
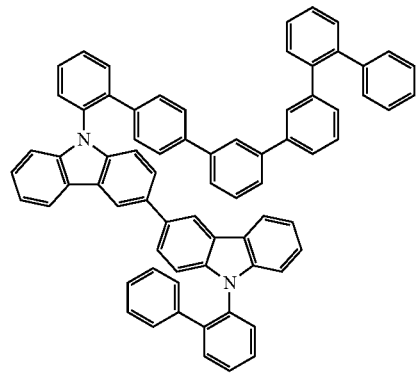
A124
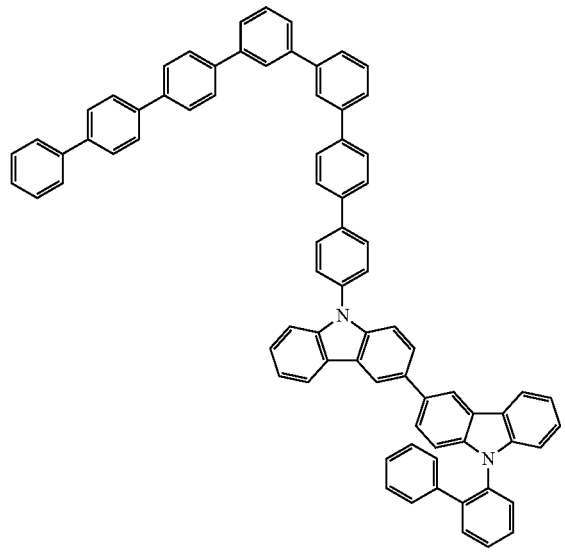

-continued
A125
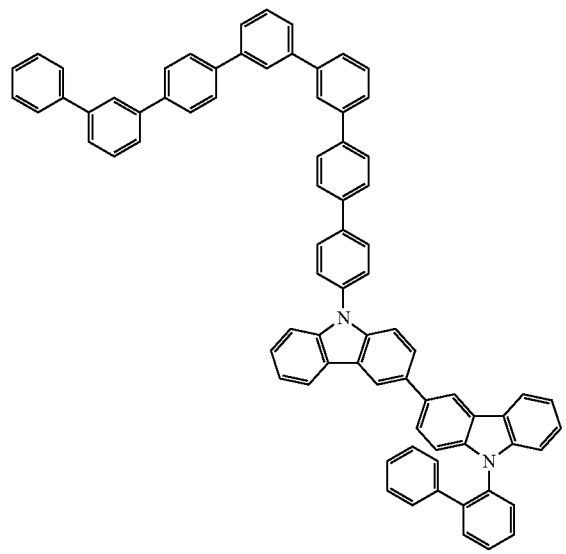
A126
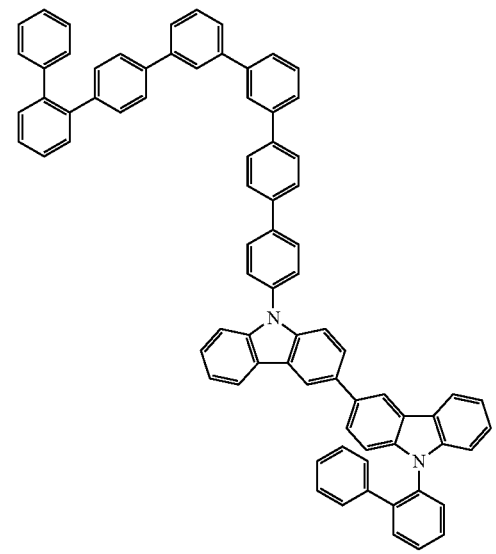
A127
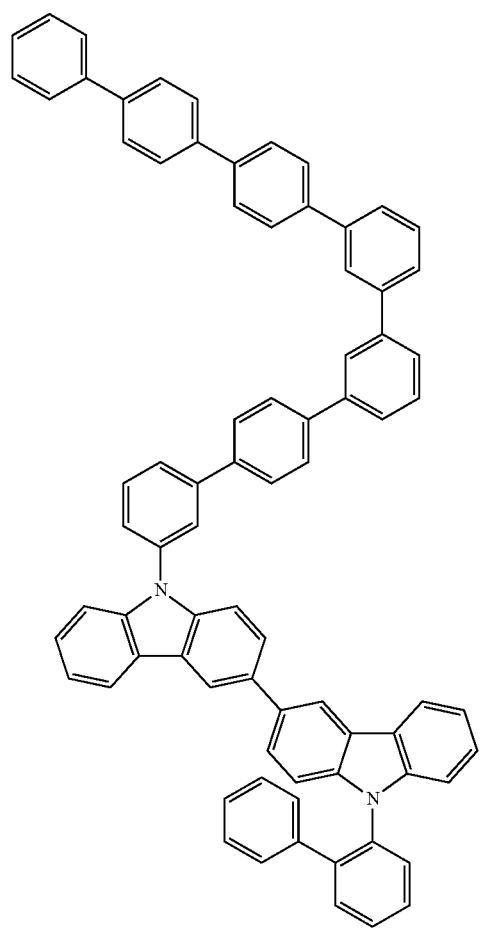
A128
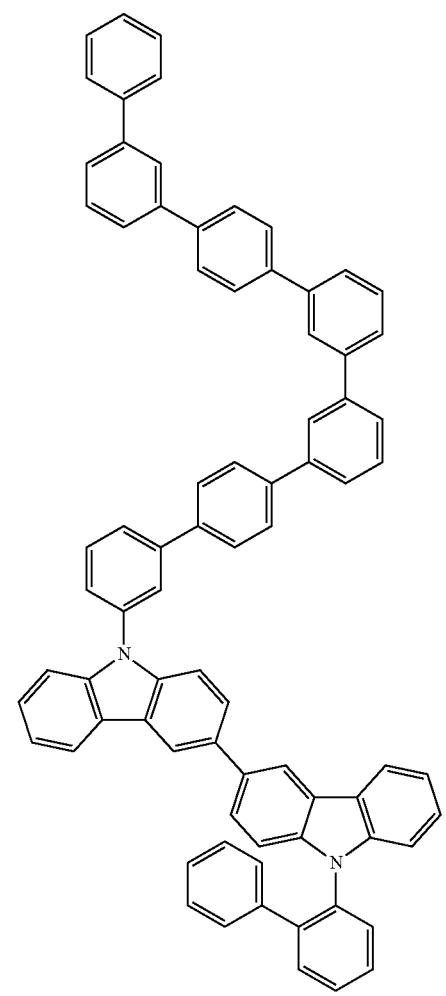

-continued
A129
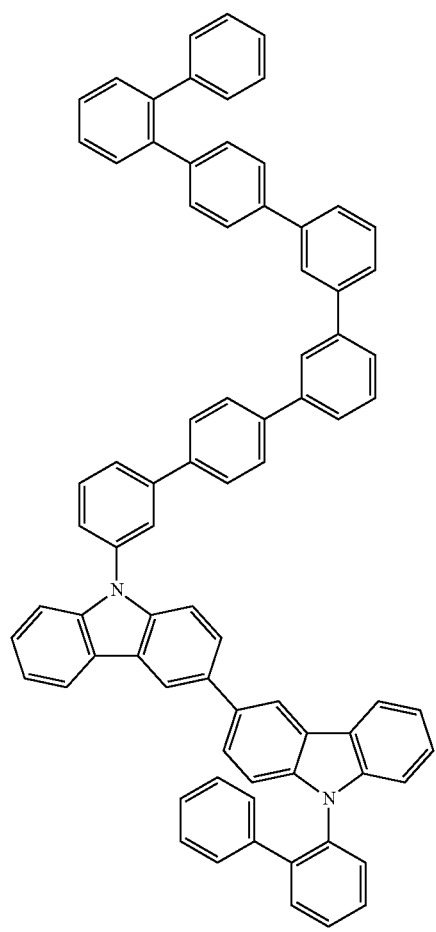
A130
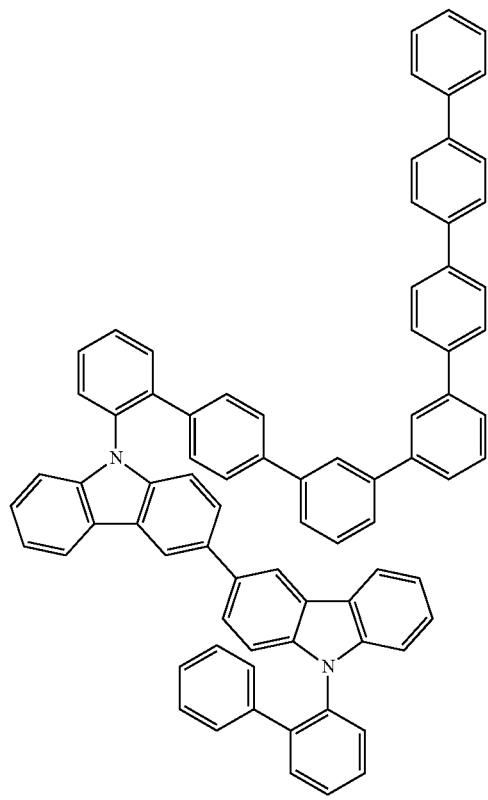
A131
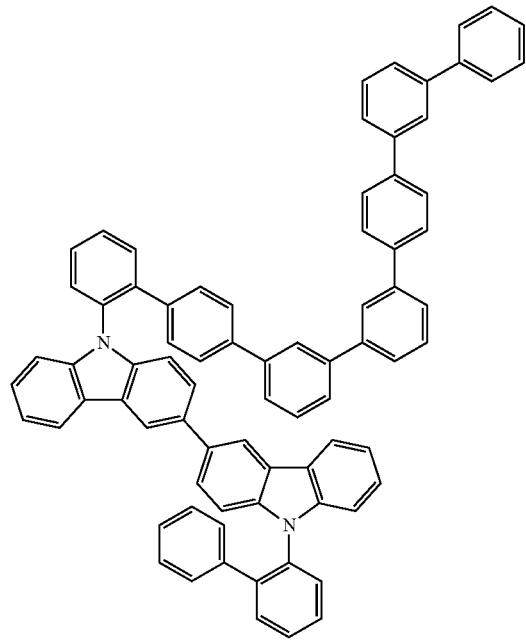
A132
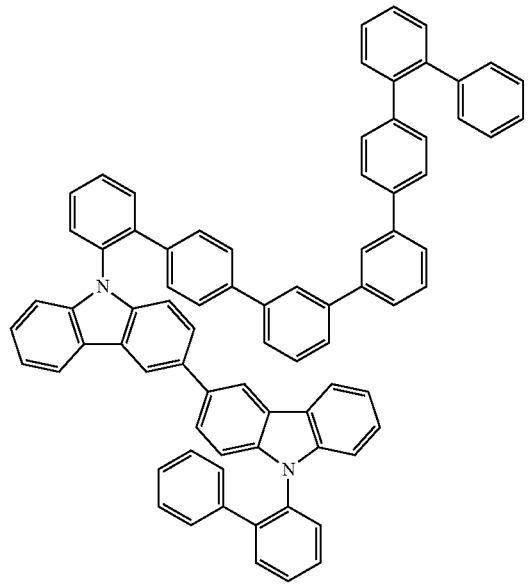

-continued
A133
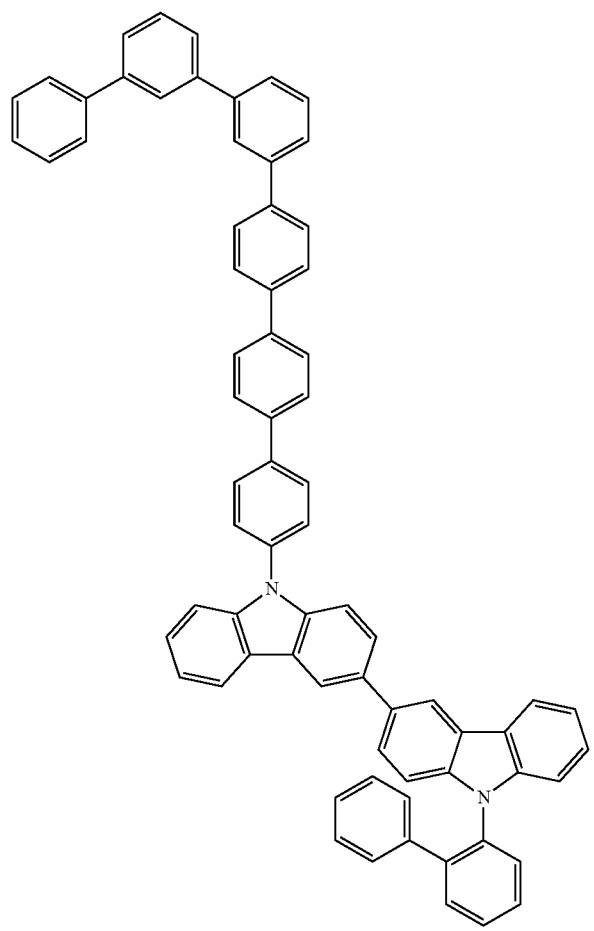
A134
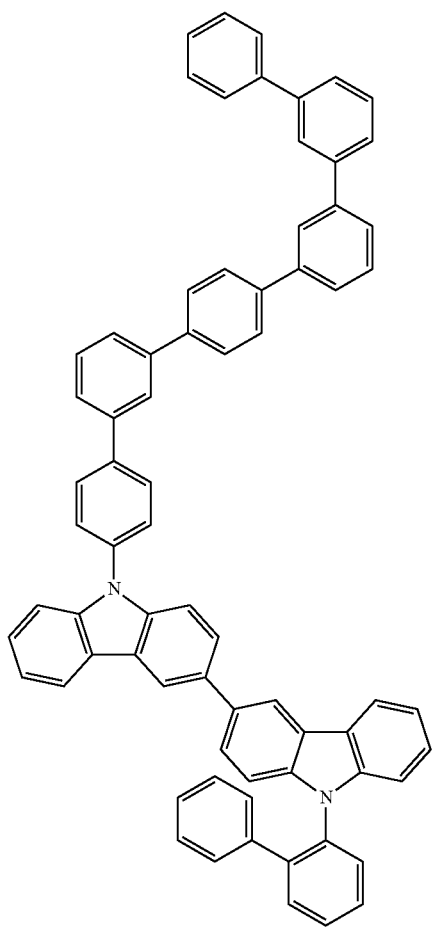

-continued
587  A135
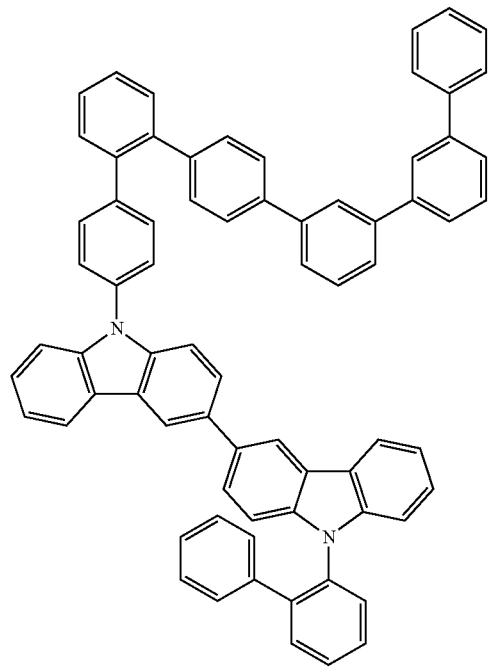
588  A136
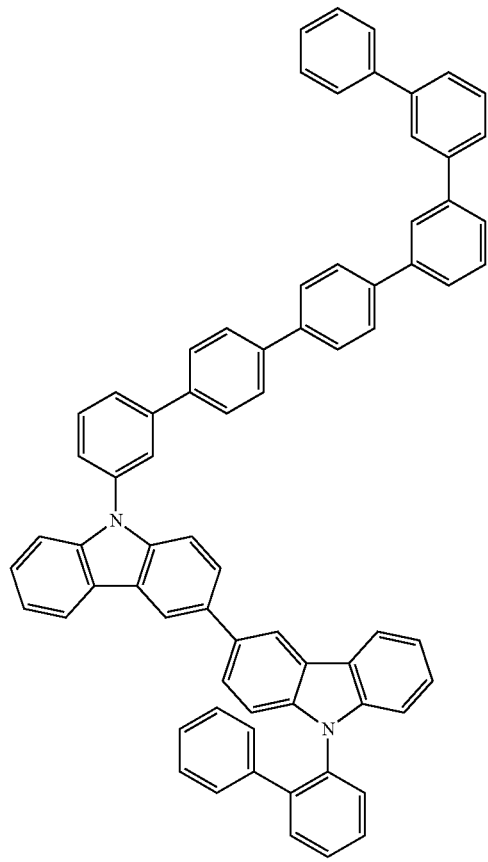
A137
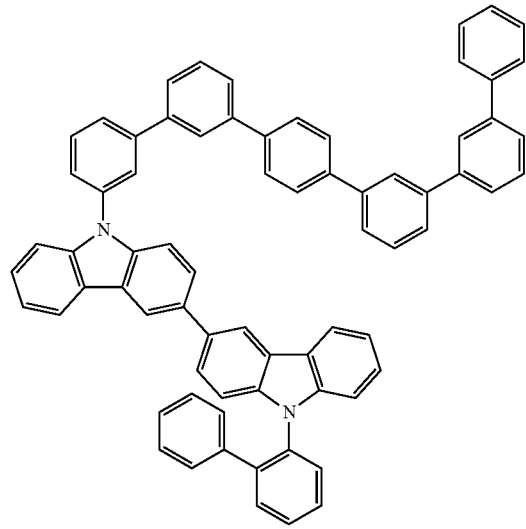
A138
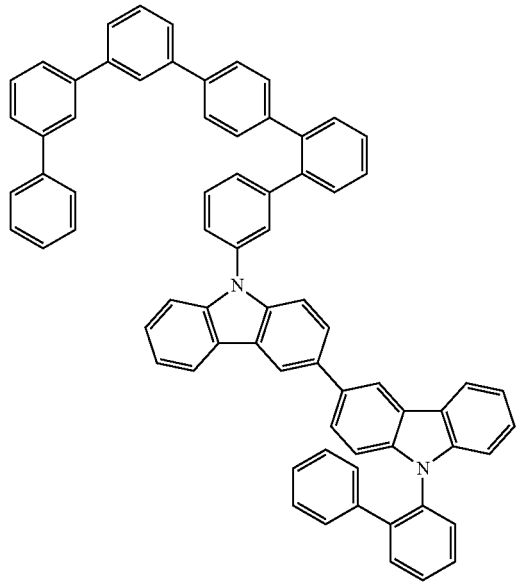

A139
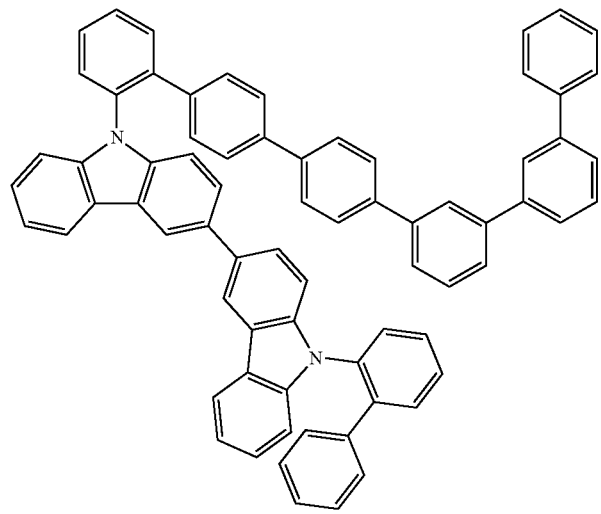
A140
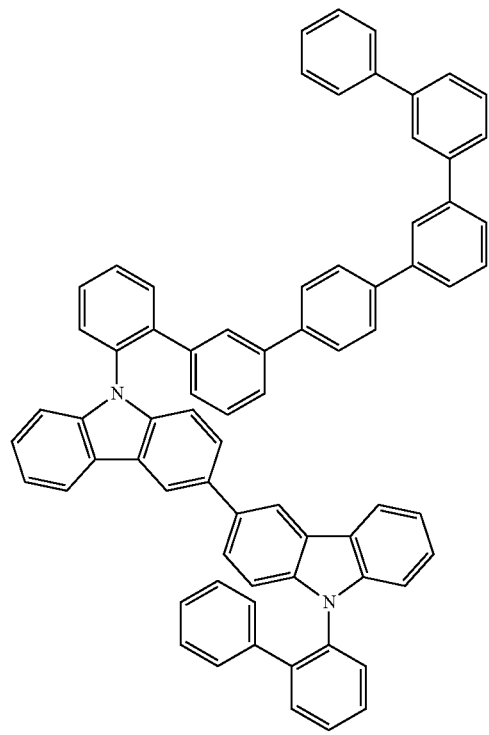
A141
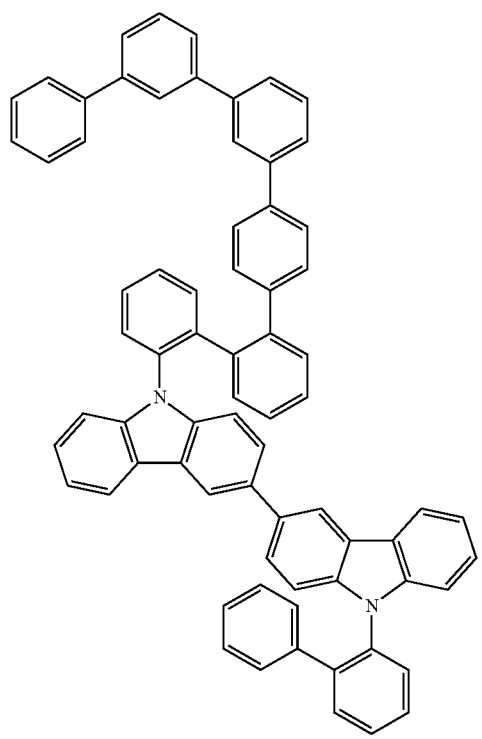
A142
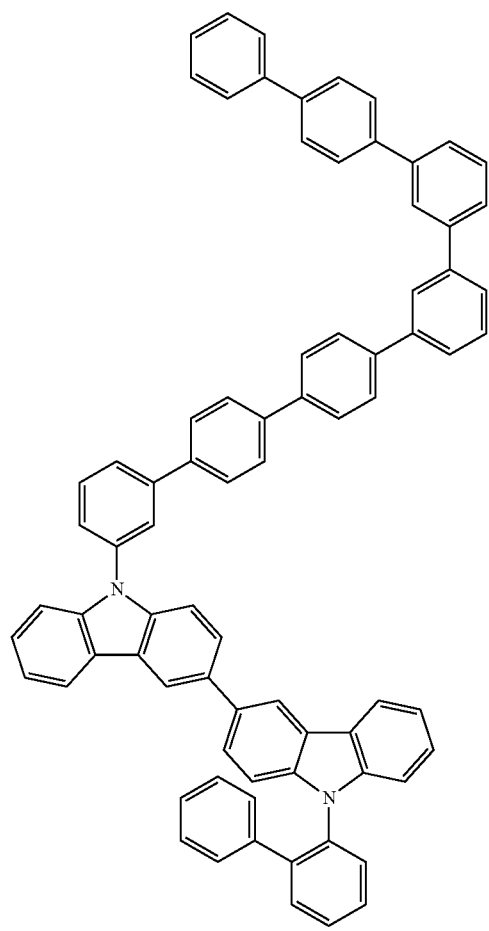

-continued
A143
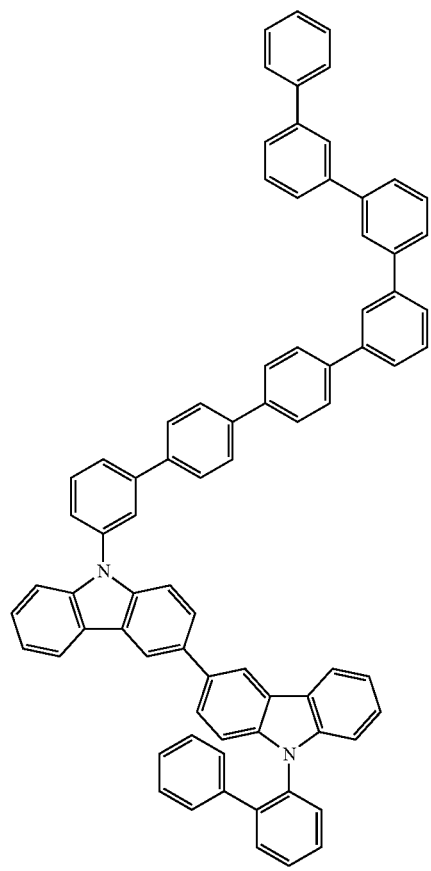
A144
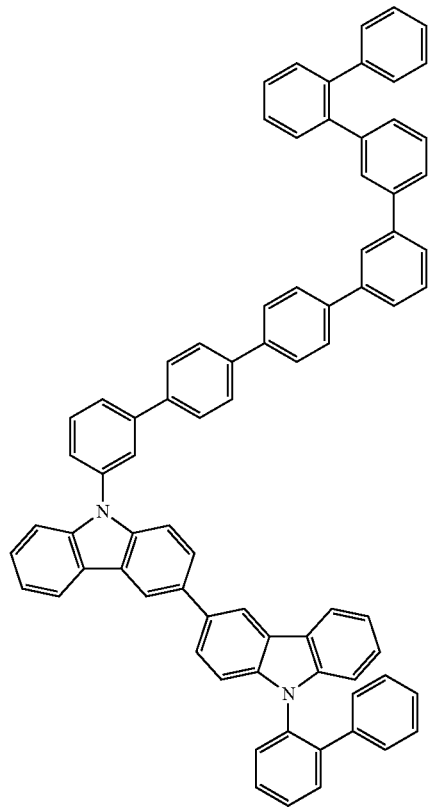
A145
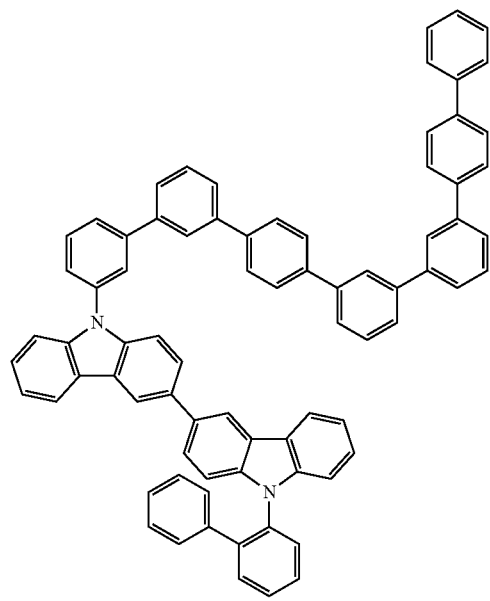
A146
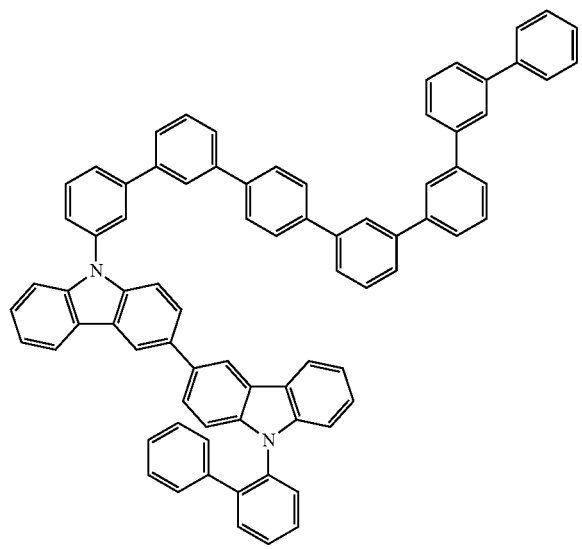

-continued
A147
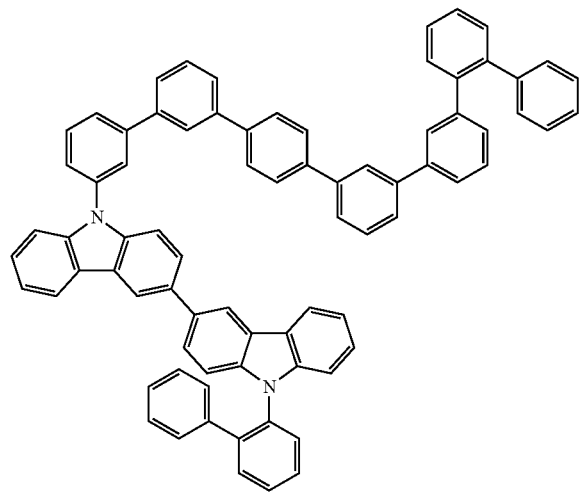
A148
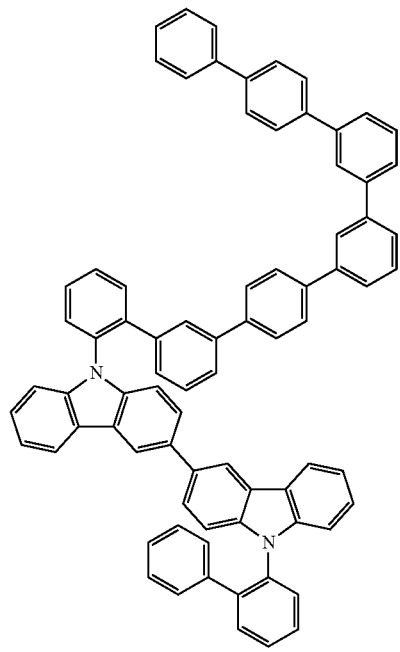
A149
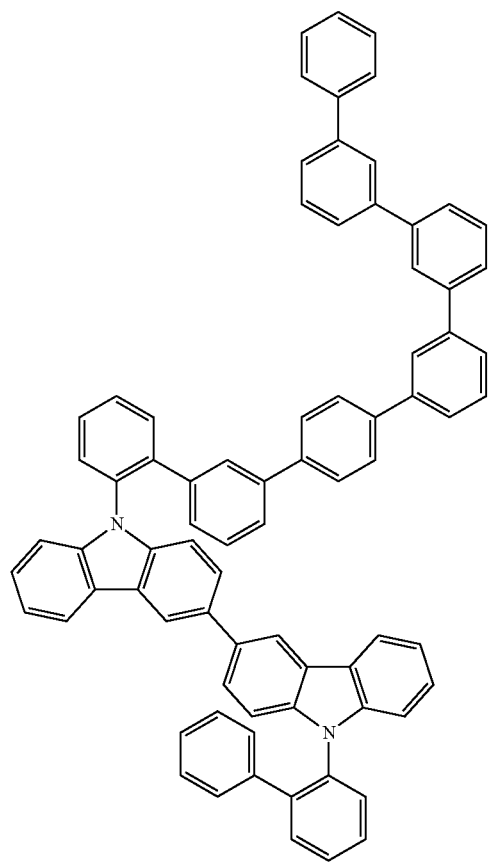
A150
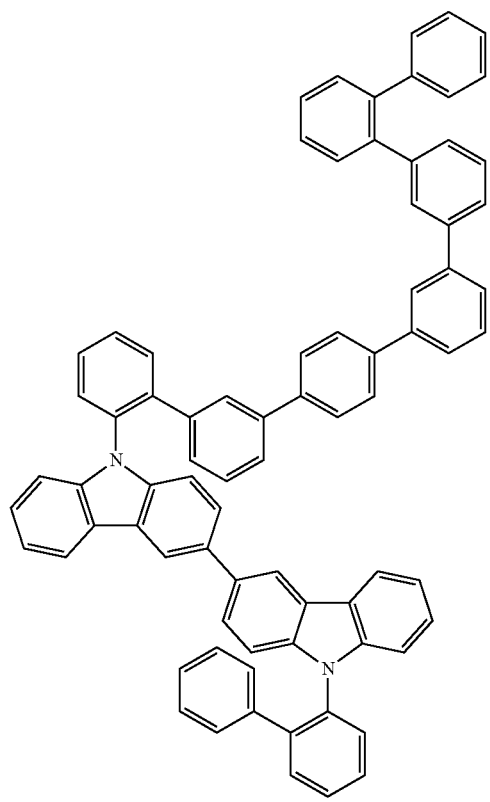

-continued
A151
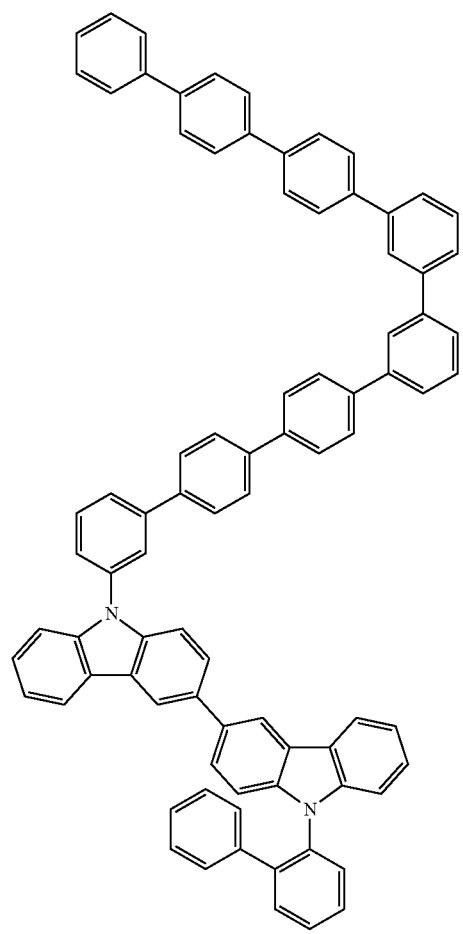
A152
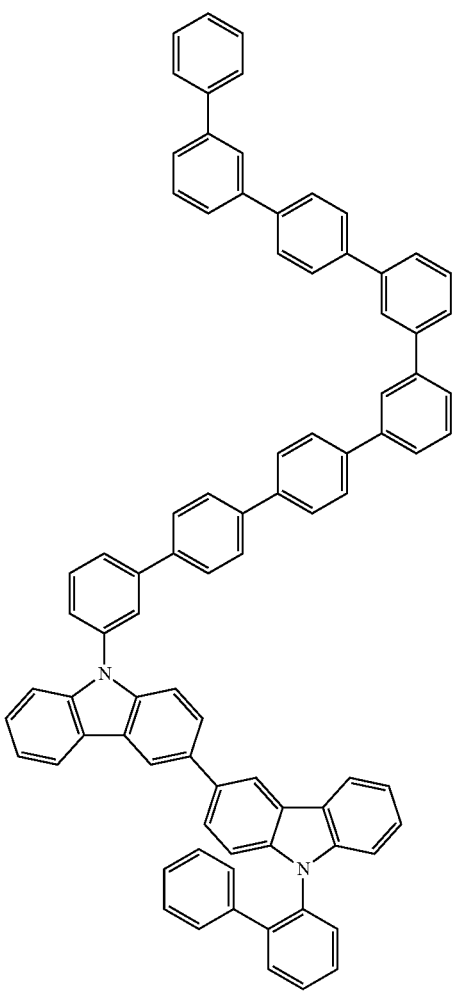
A153
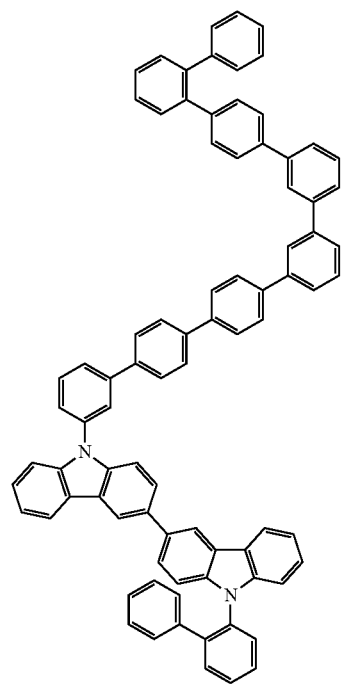
A154
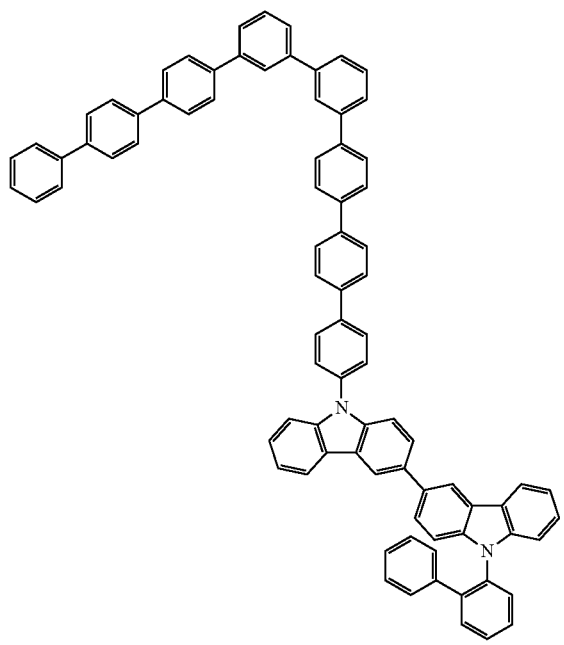

-continued
A155
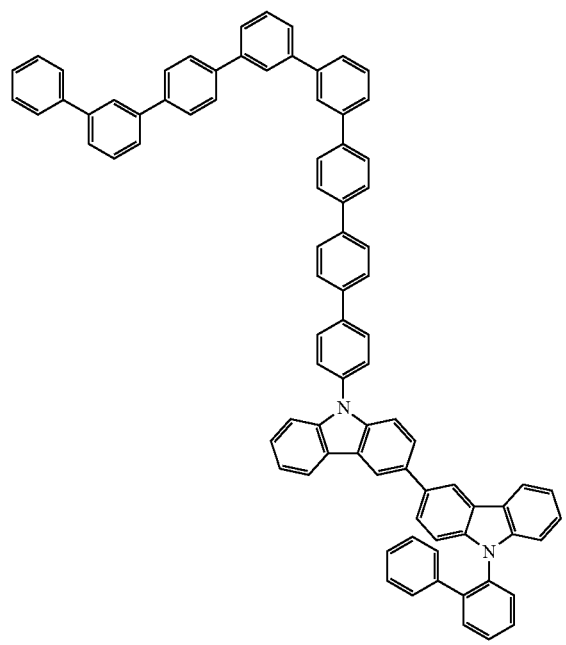
A156
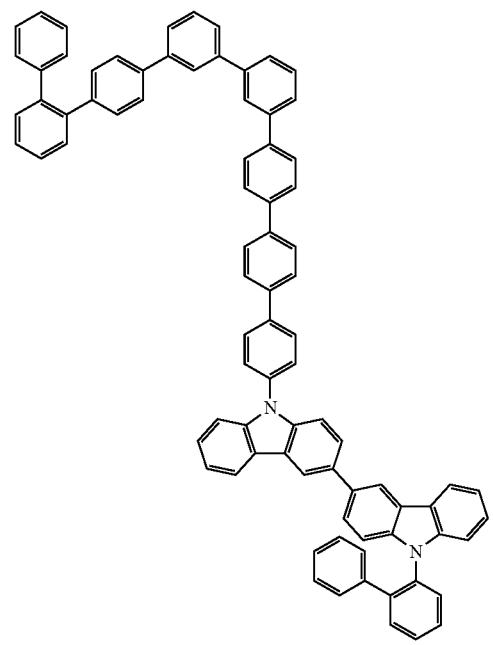
A157
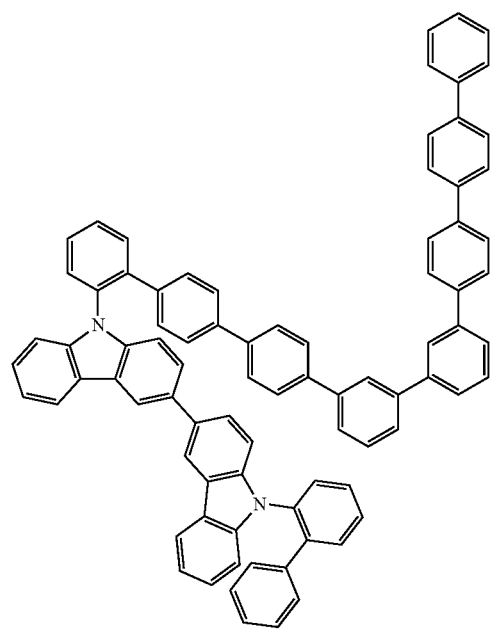
A158
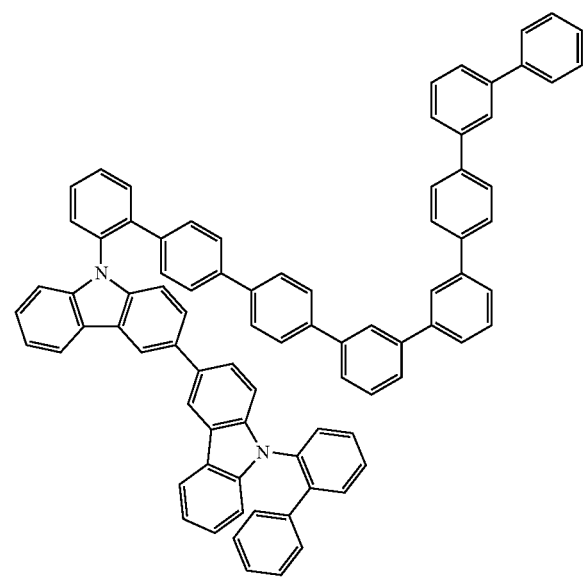

-continued
A159
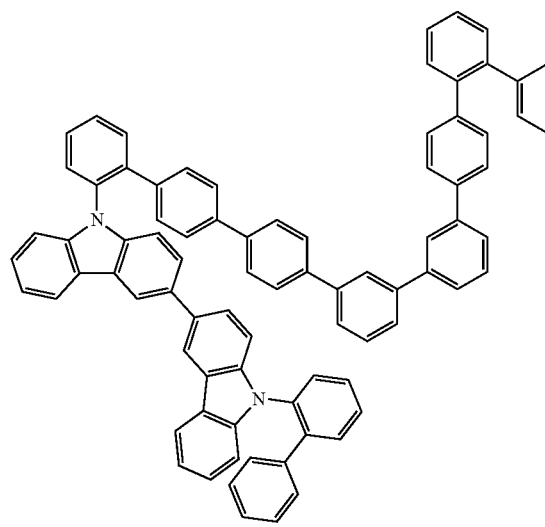
A160
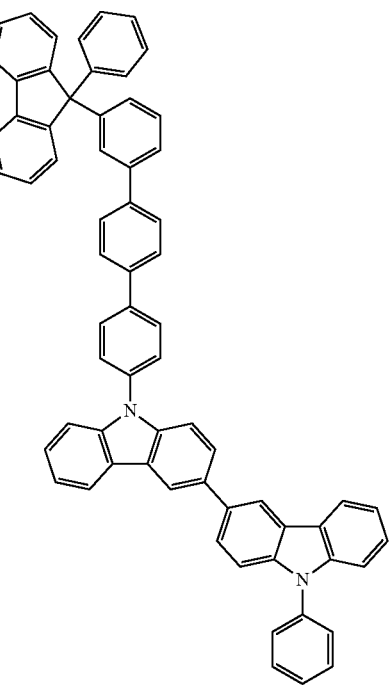
A161
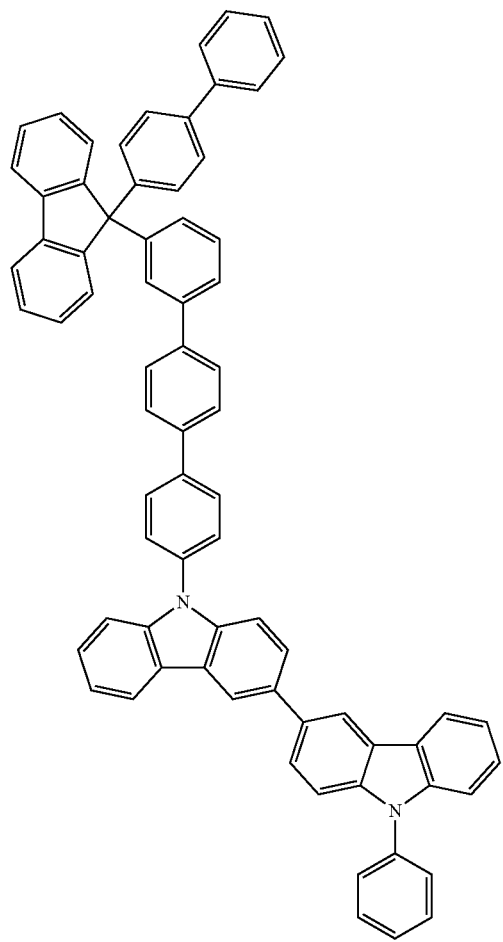
A162
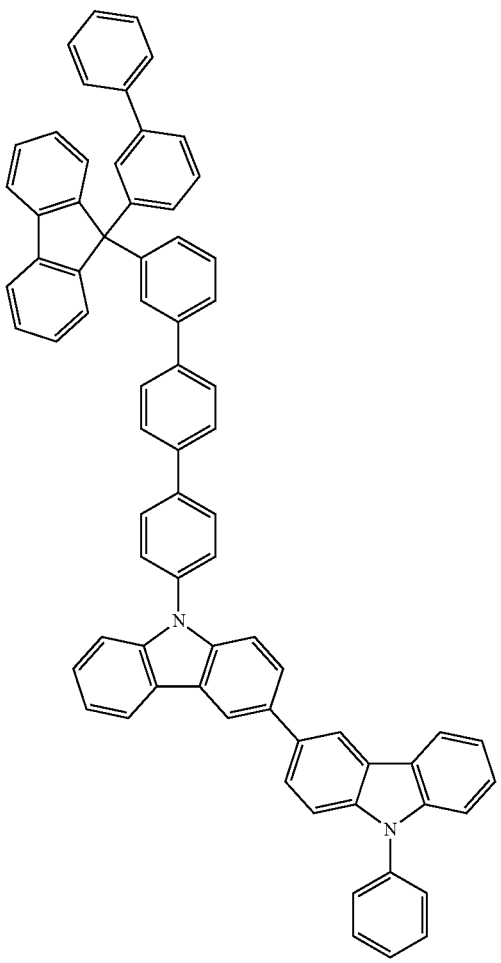

-continued
601 A163
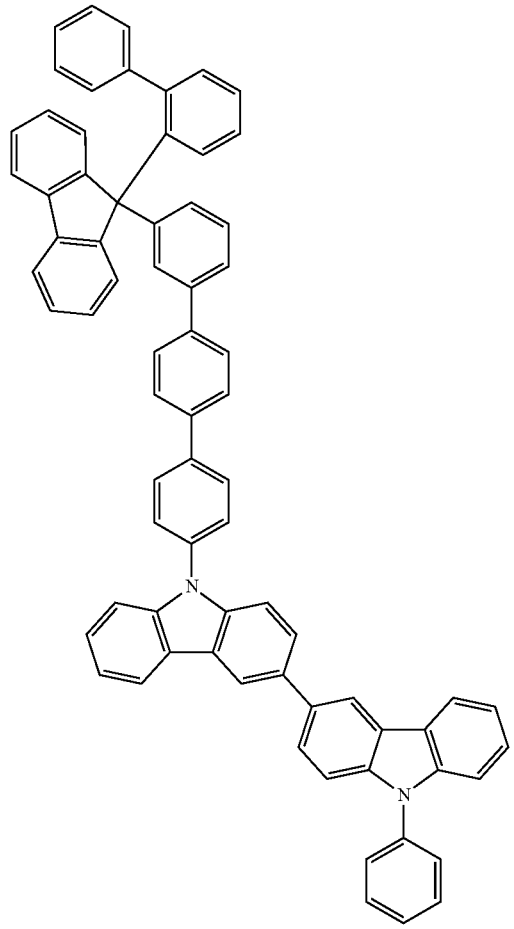
602 A164
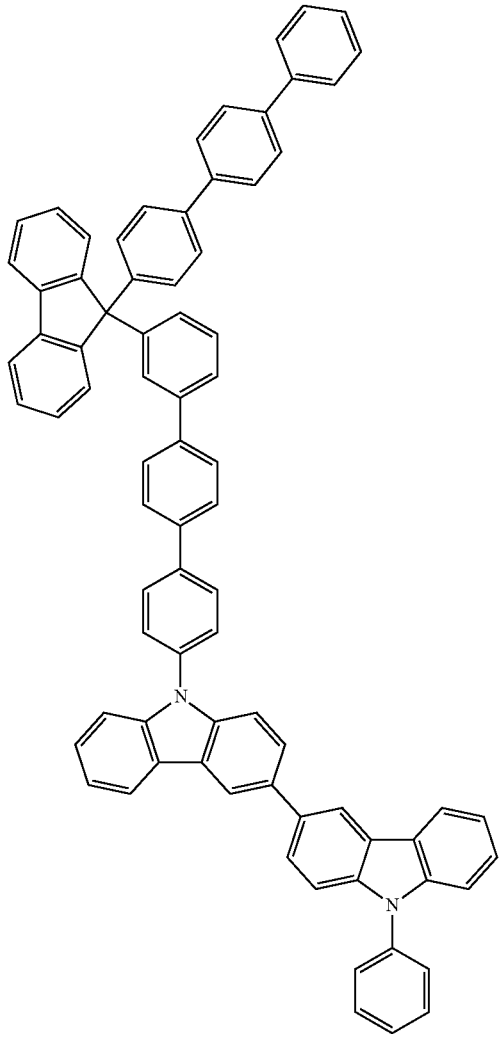

-continued
603 A165
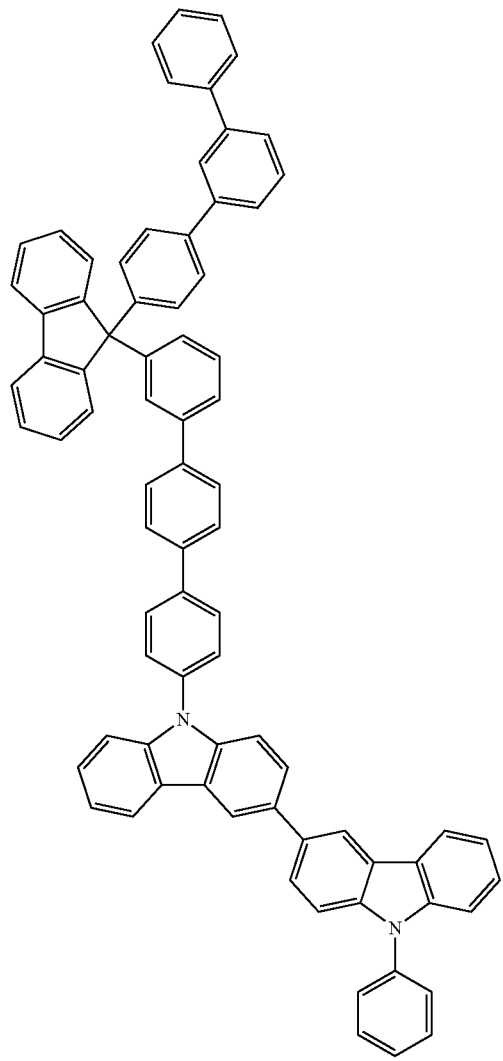
604 A166
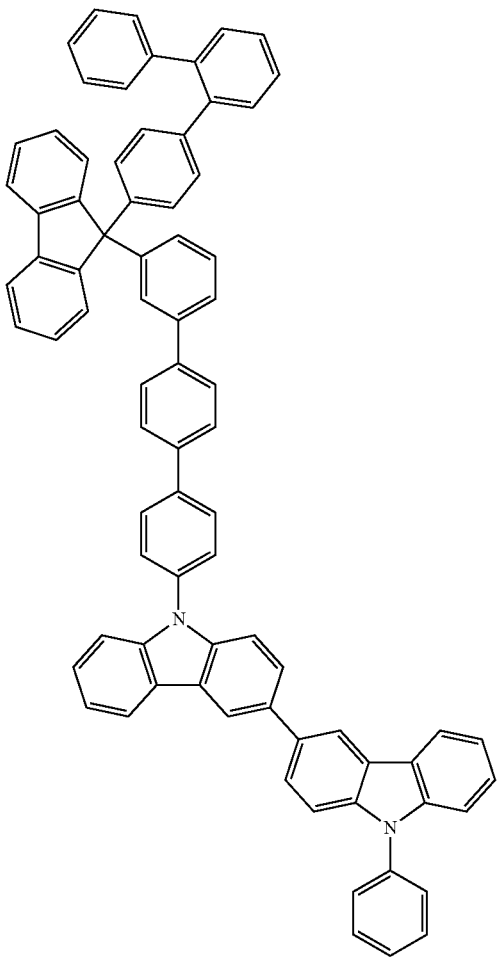

-continued
A167
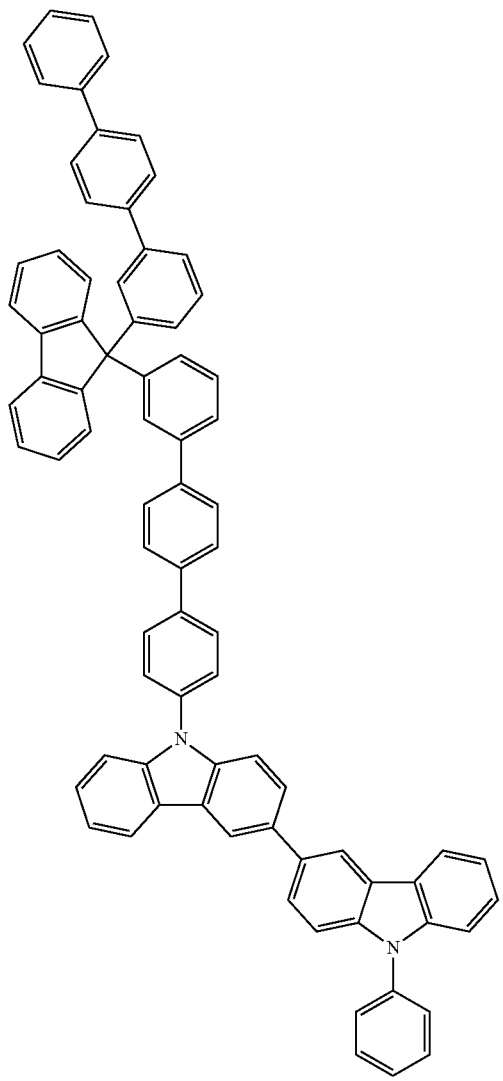
A168
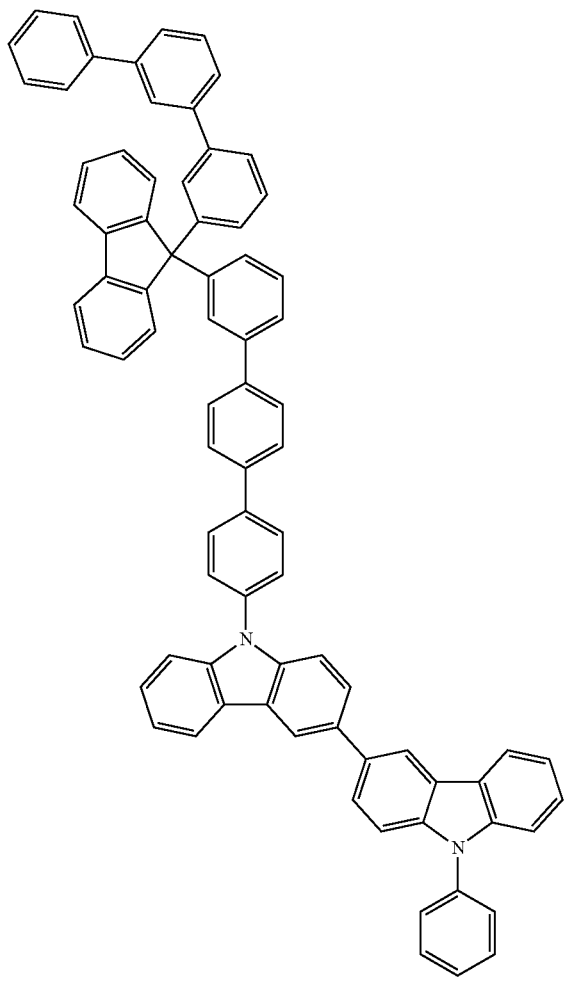

-continued
A169
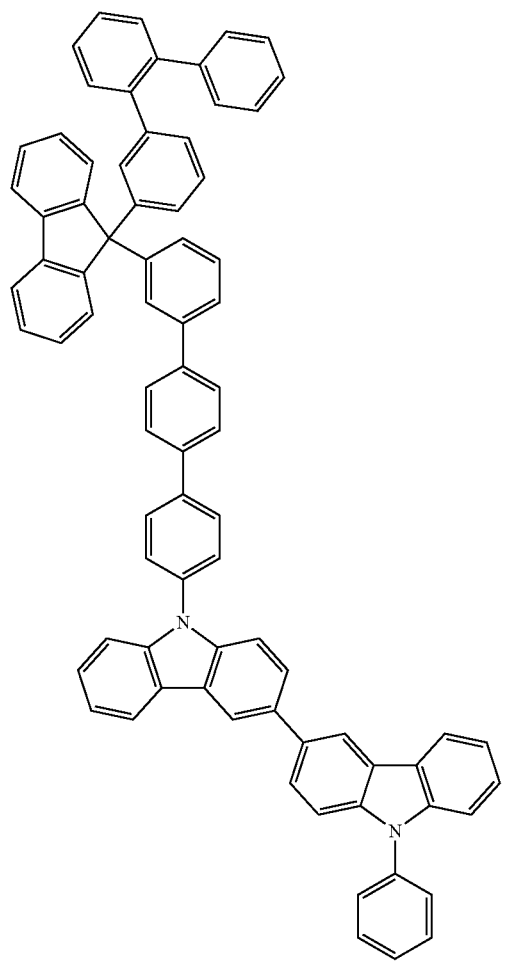
A170
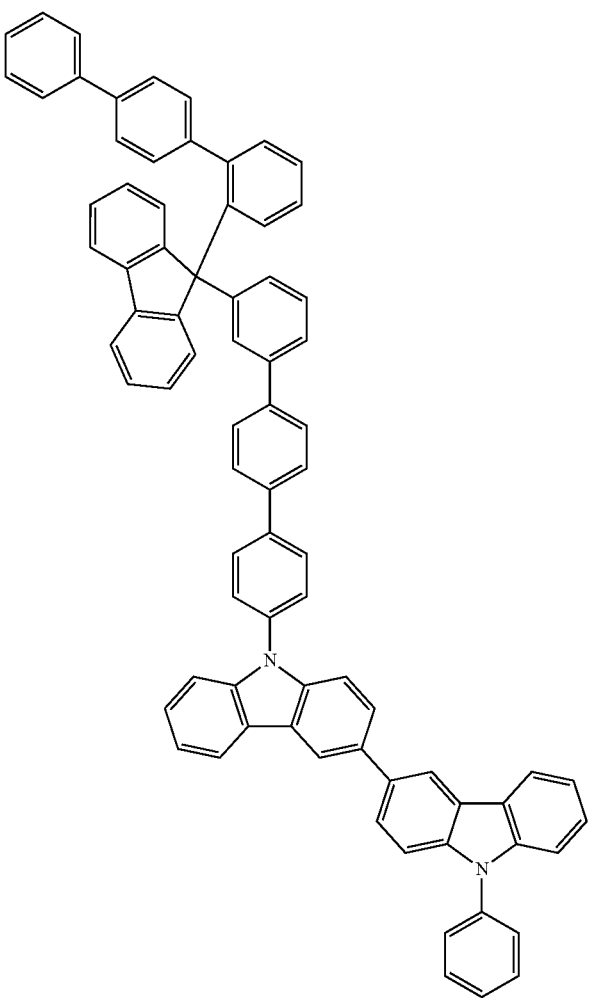

A171
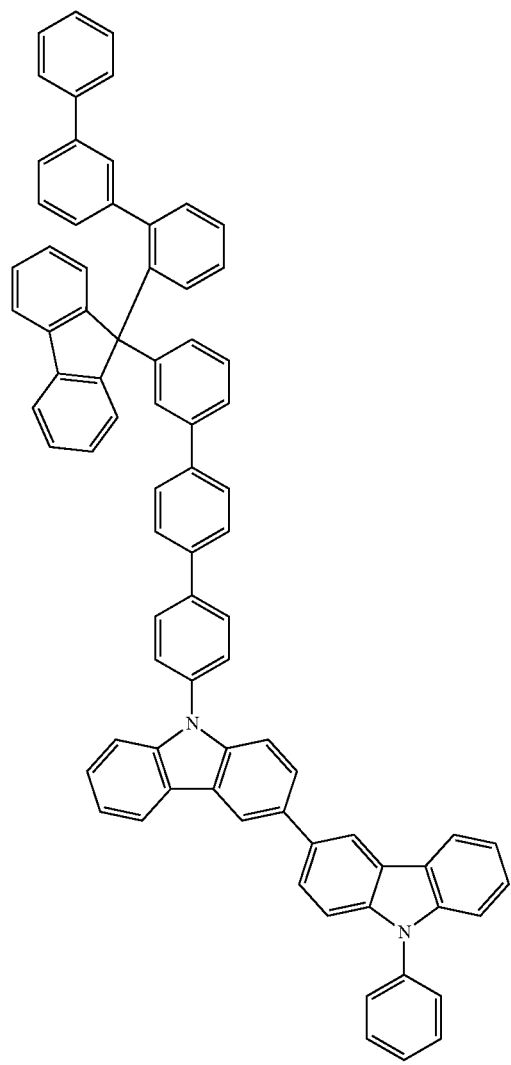
A172
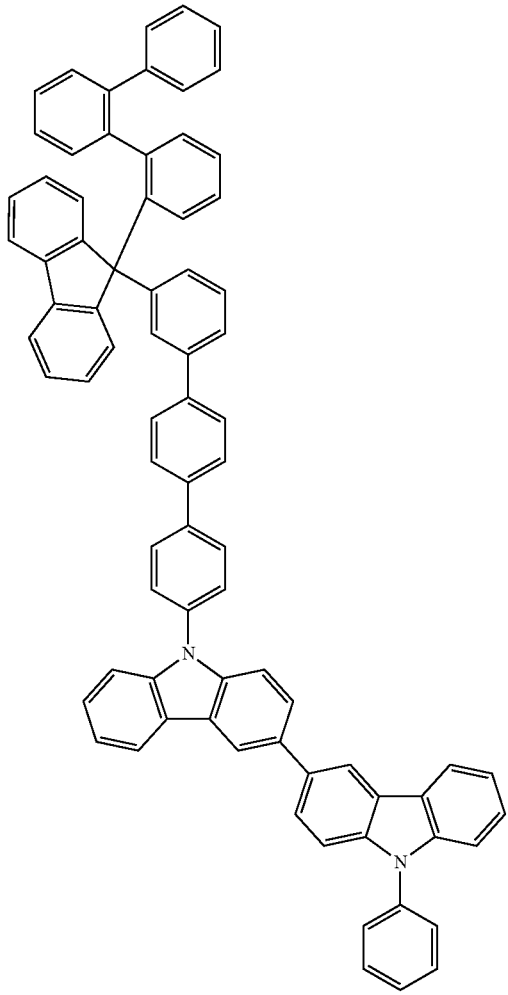

-continued
611
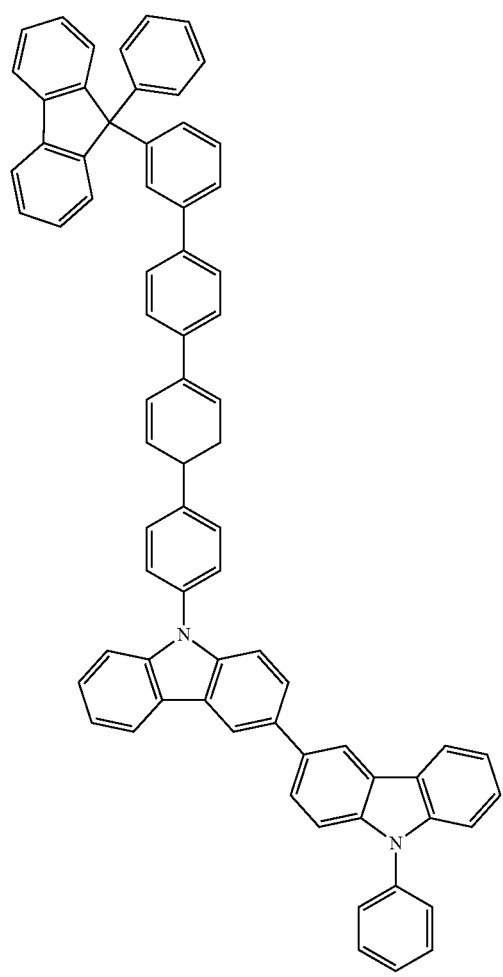
A173
612
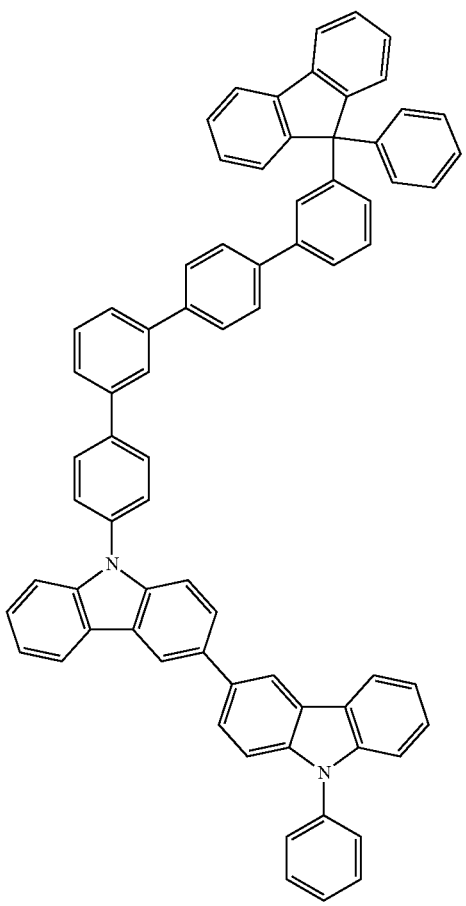
A174

-continued
615
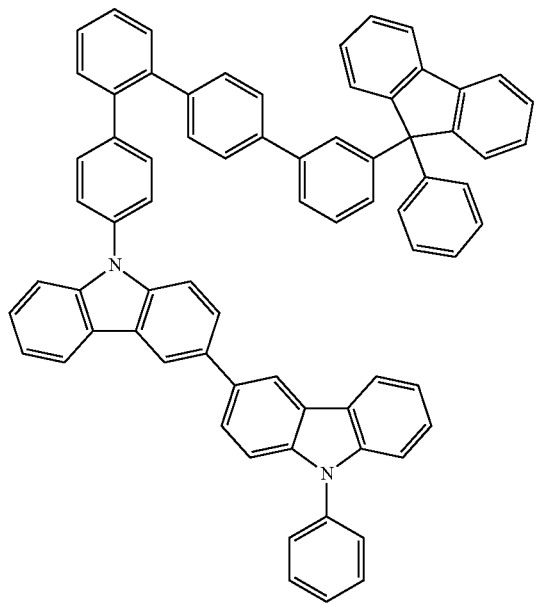
A175
616
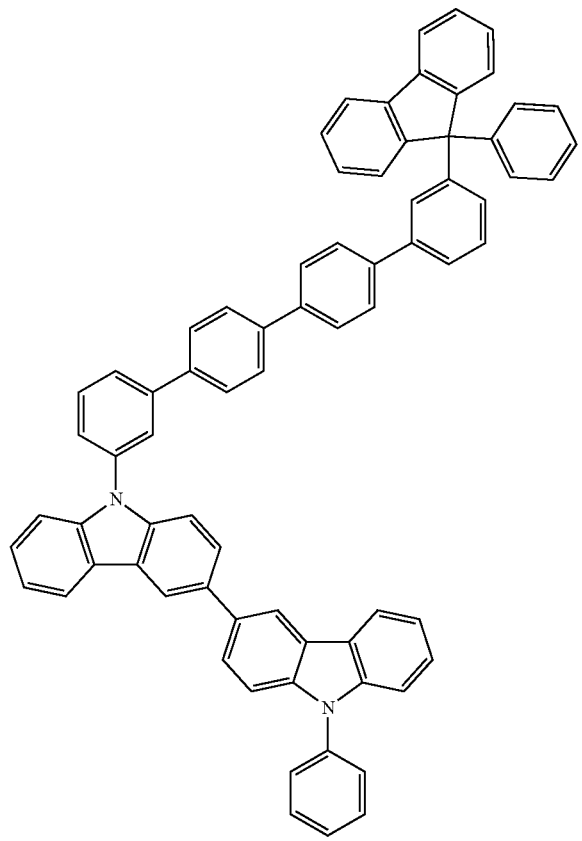
A176
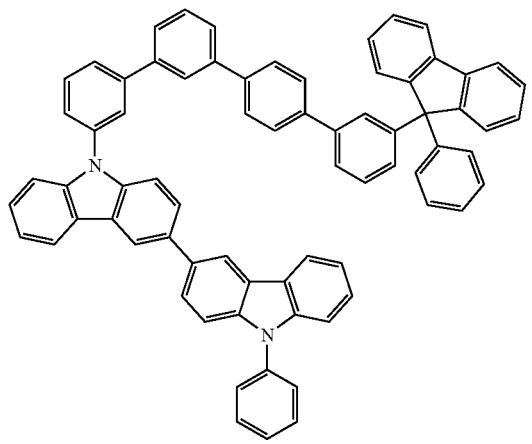
A177
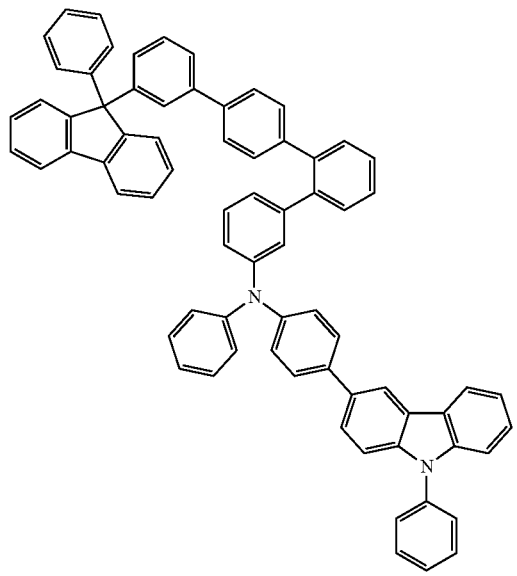
A178

-continued
A179
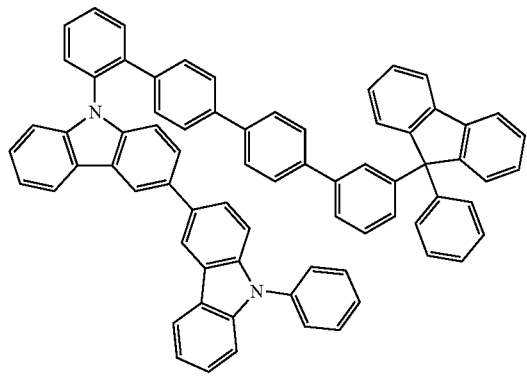
A180
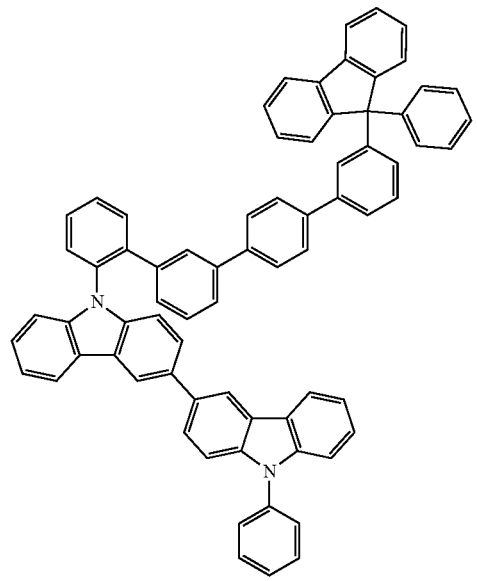
A181
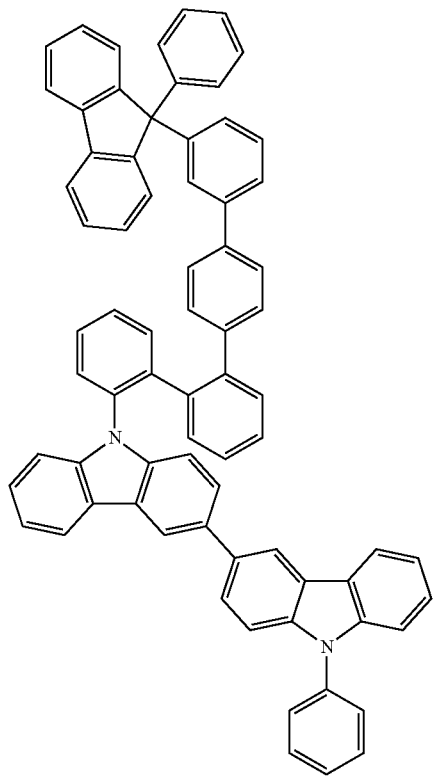
A182
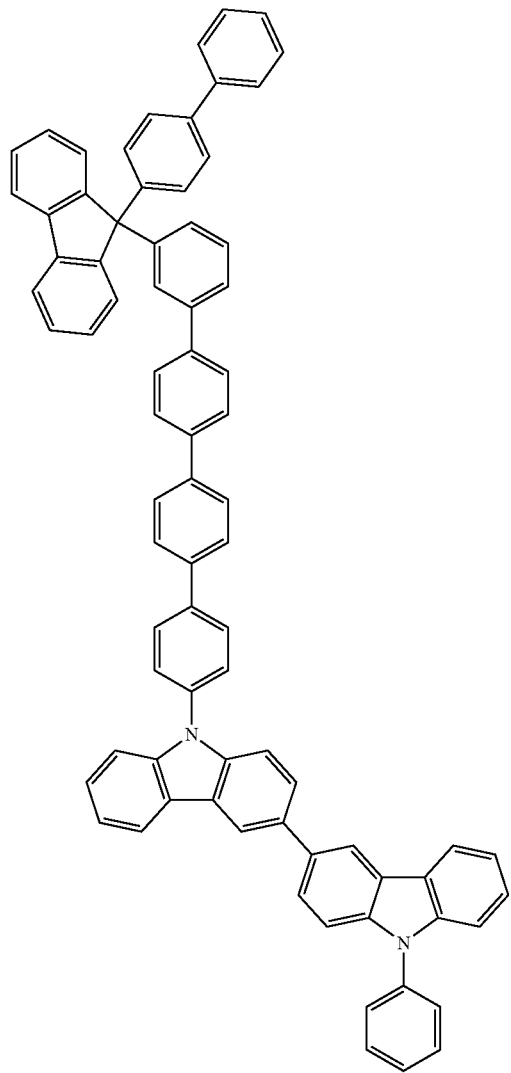

-continued
619
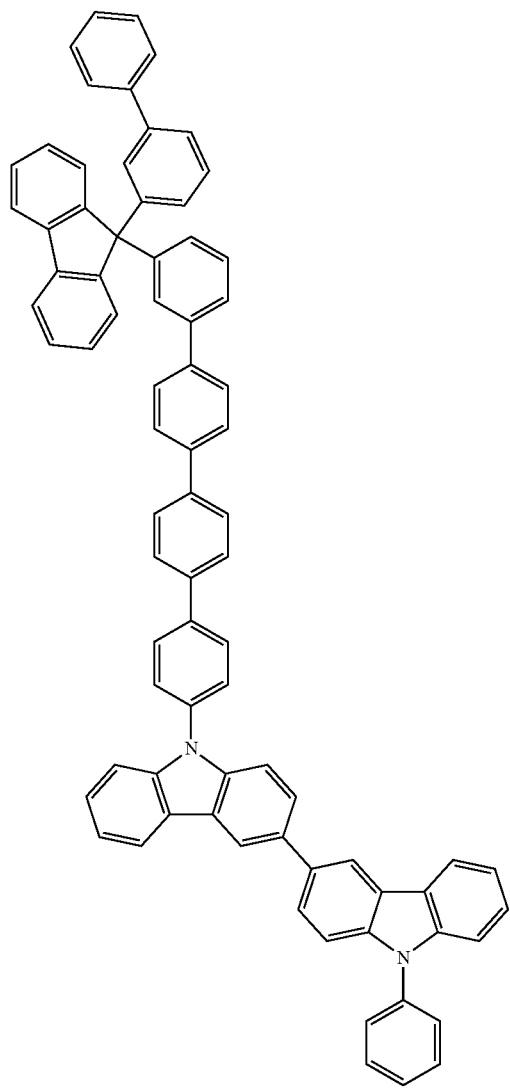
A183
620
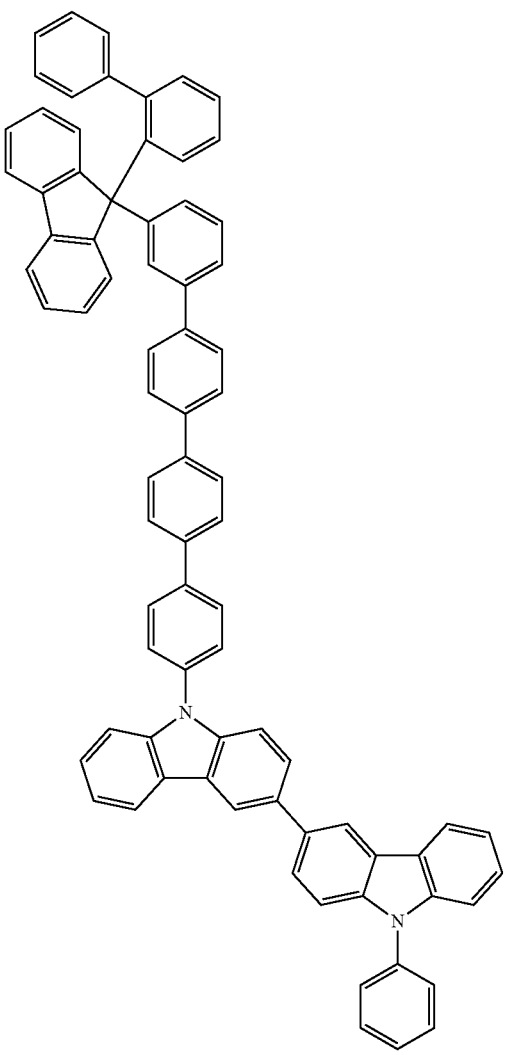
A184

-continued
621 A185
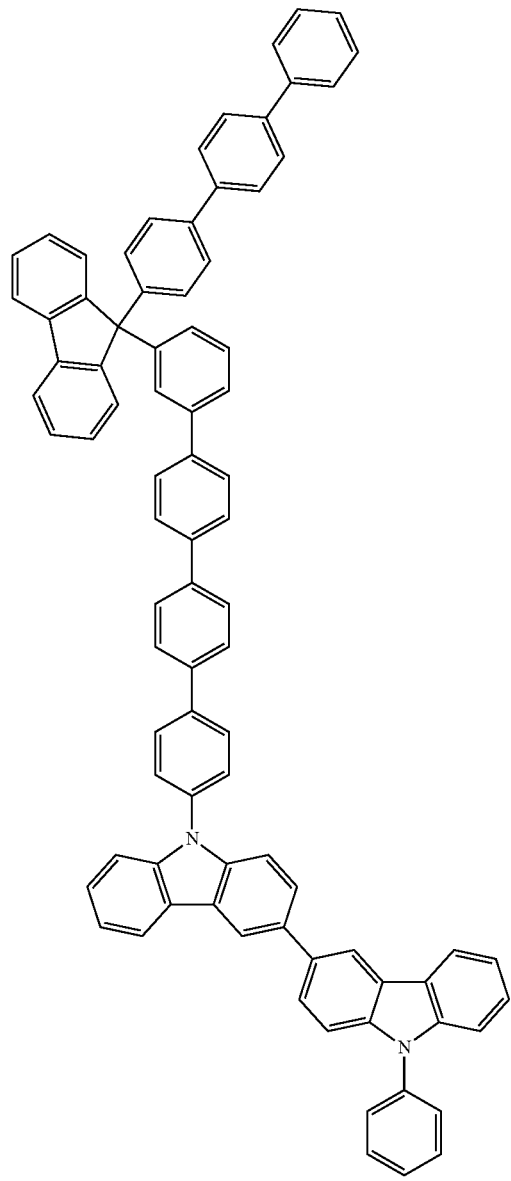
622 A186
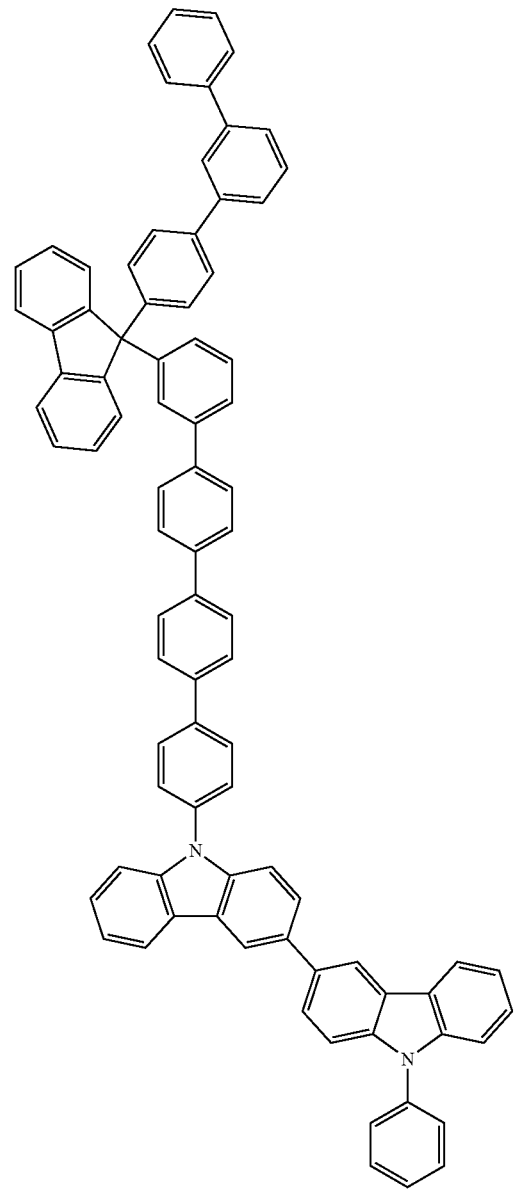

-continued
623
A187
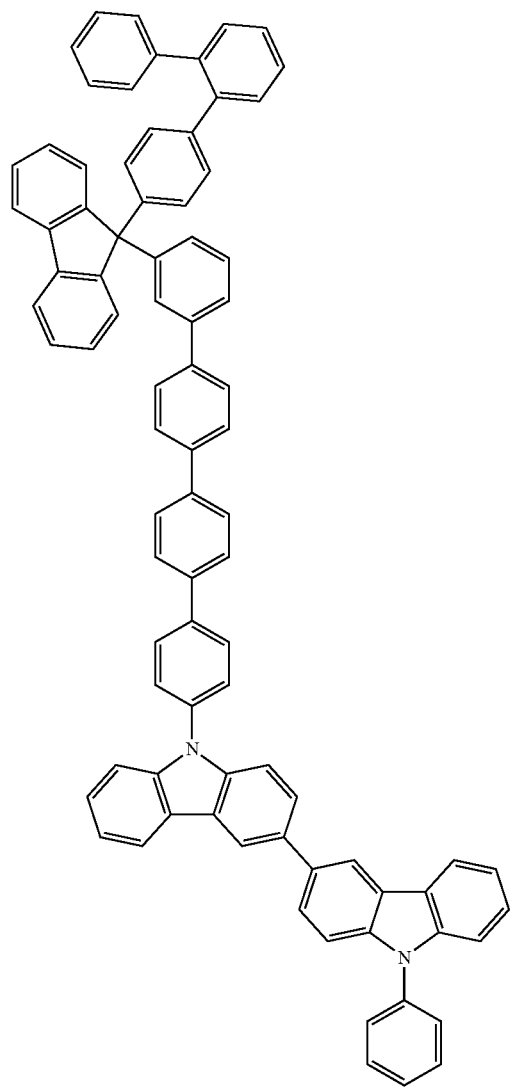
624
A188
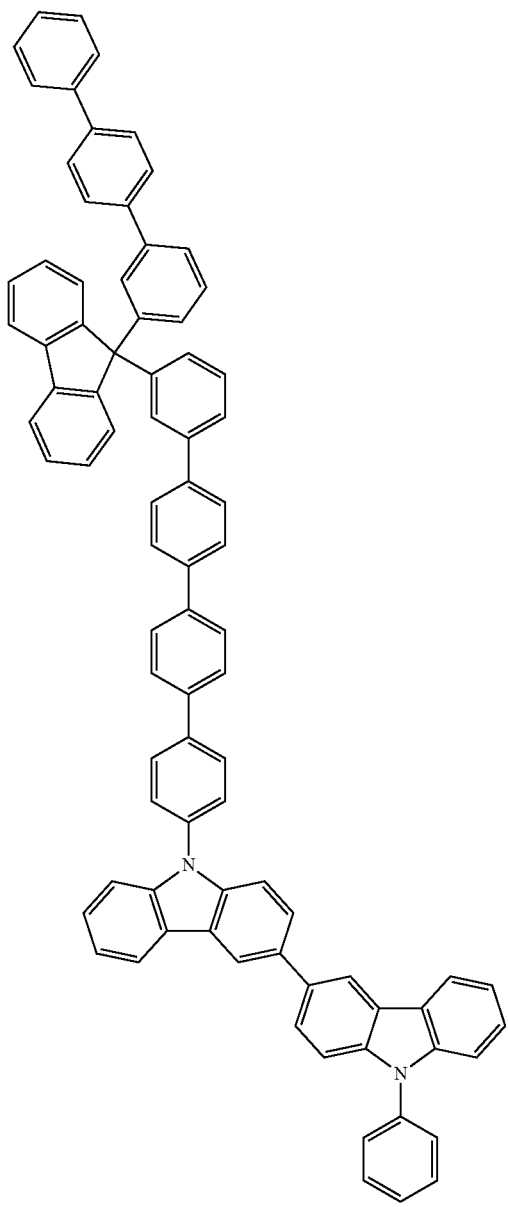

-continued
A189
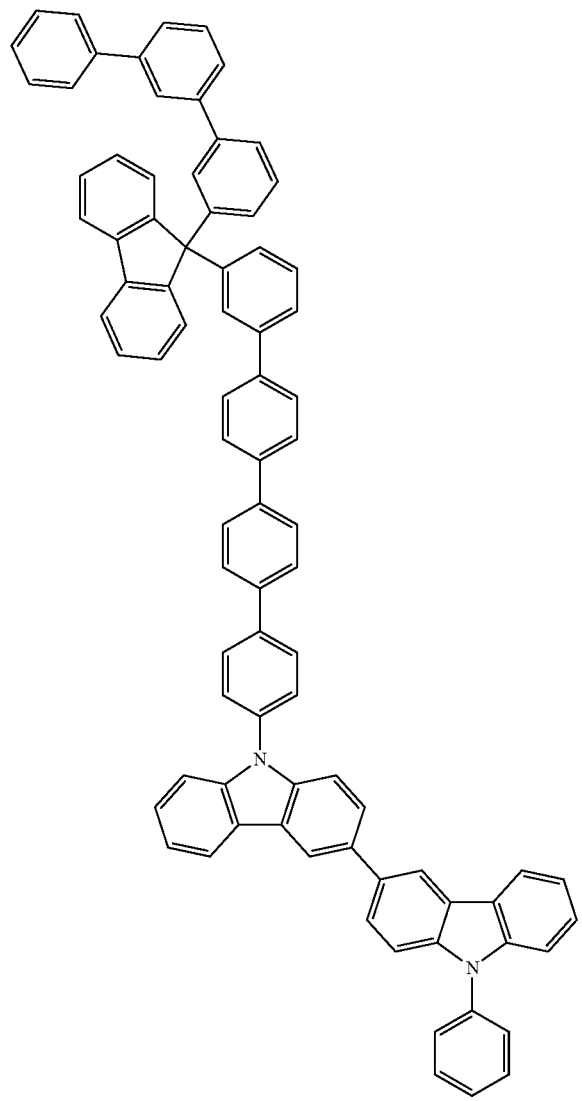
A190
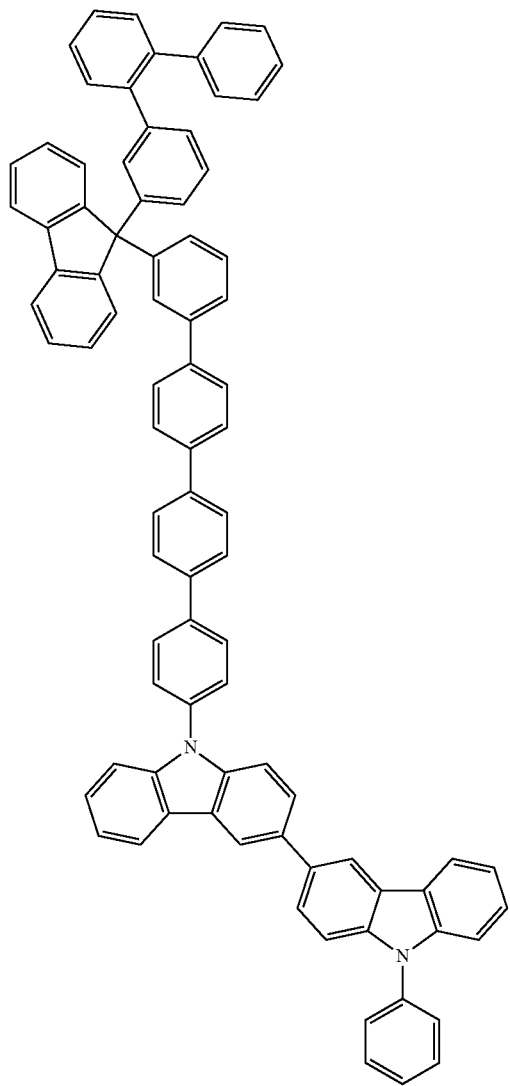

-continued
A191
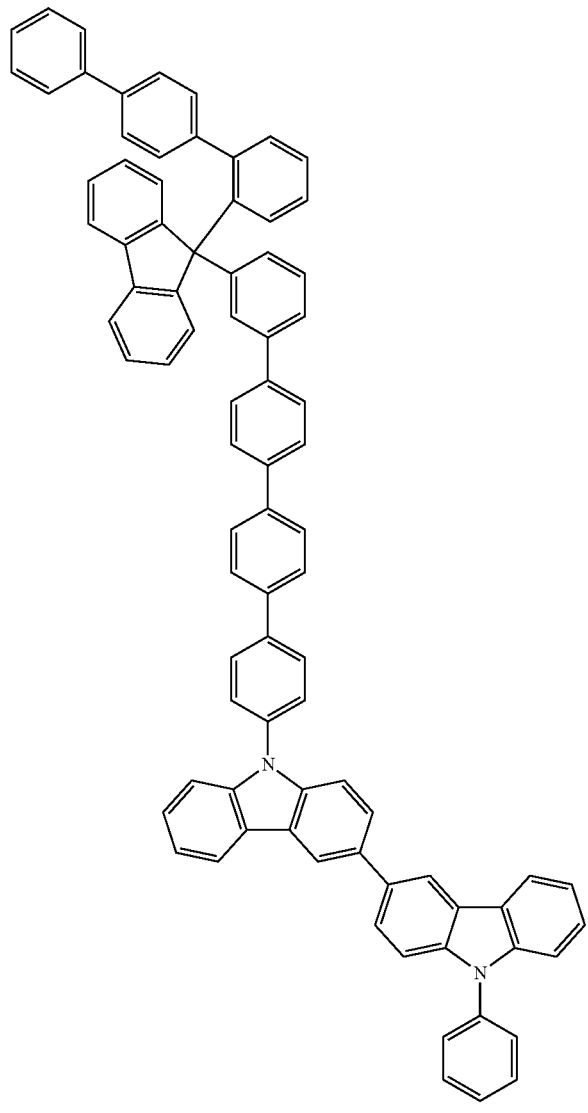
A192
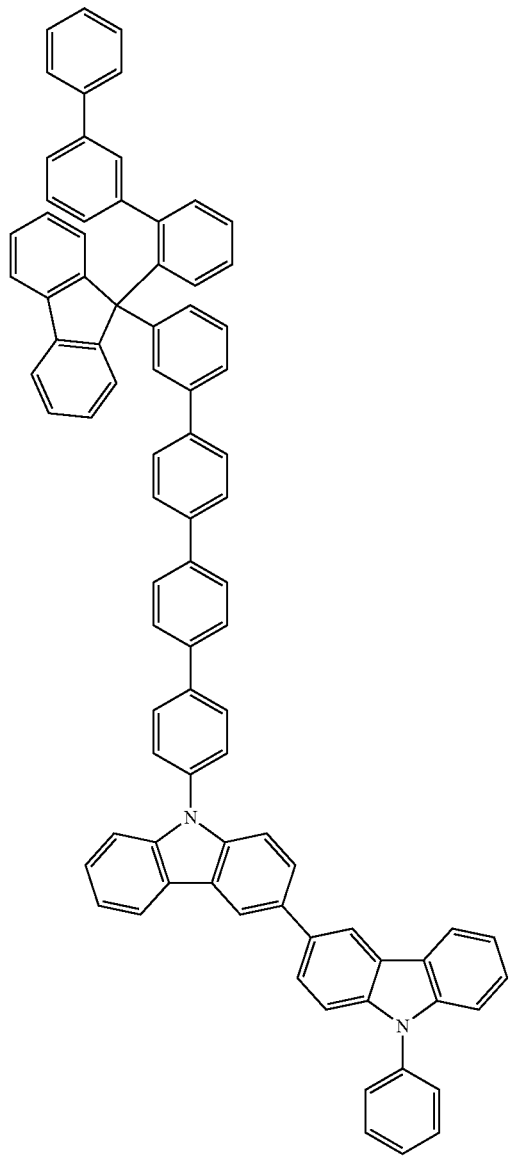

-continued
A193
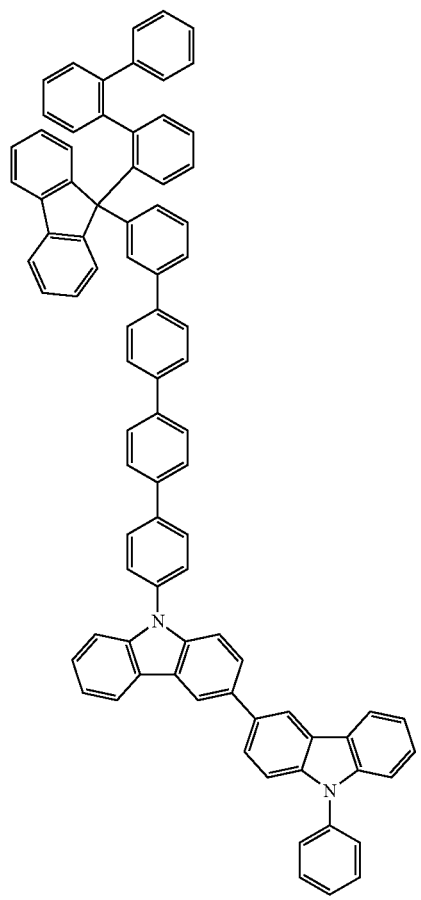
A194
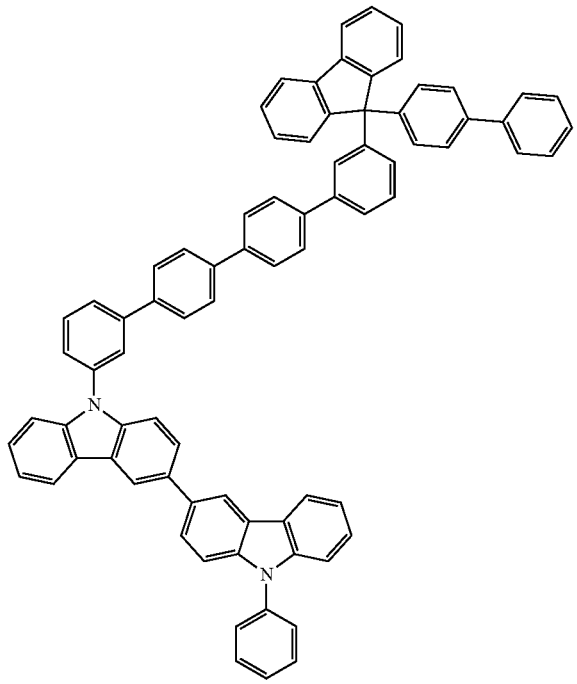
A195
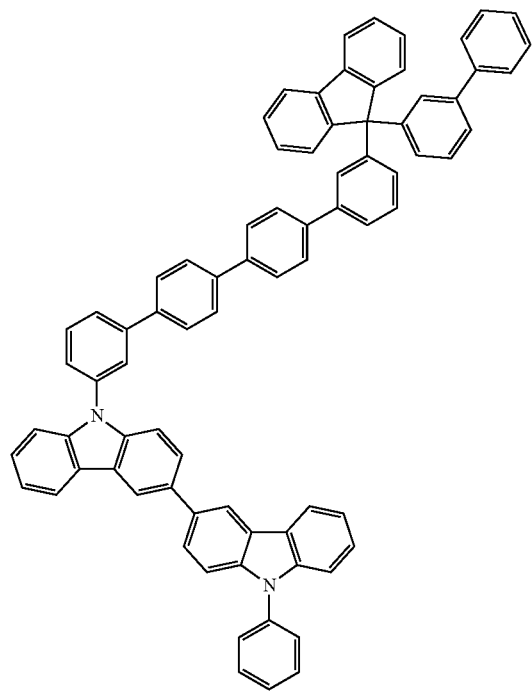
A196
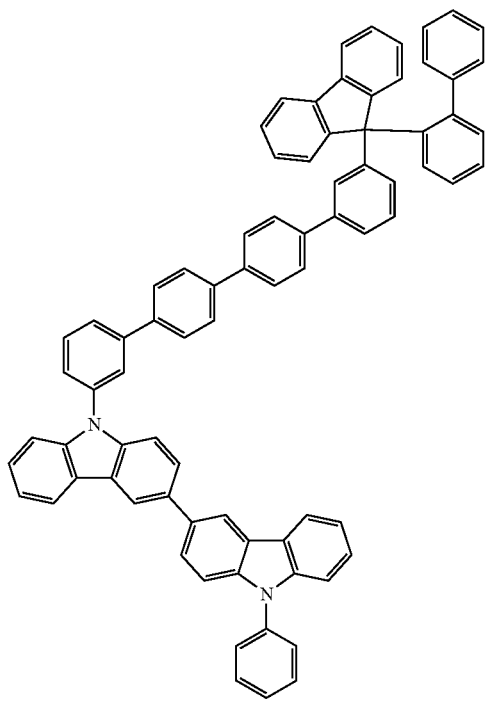

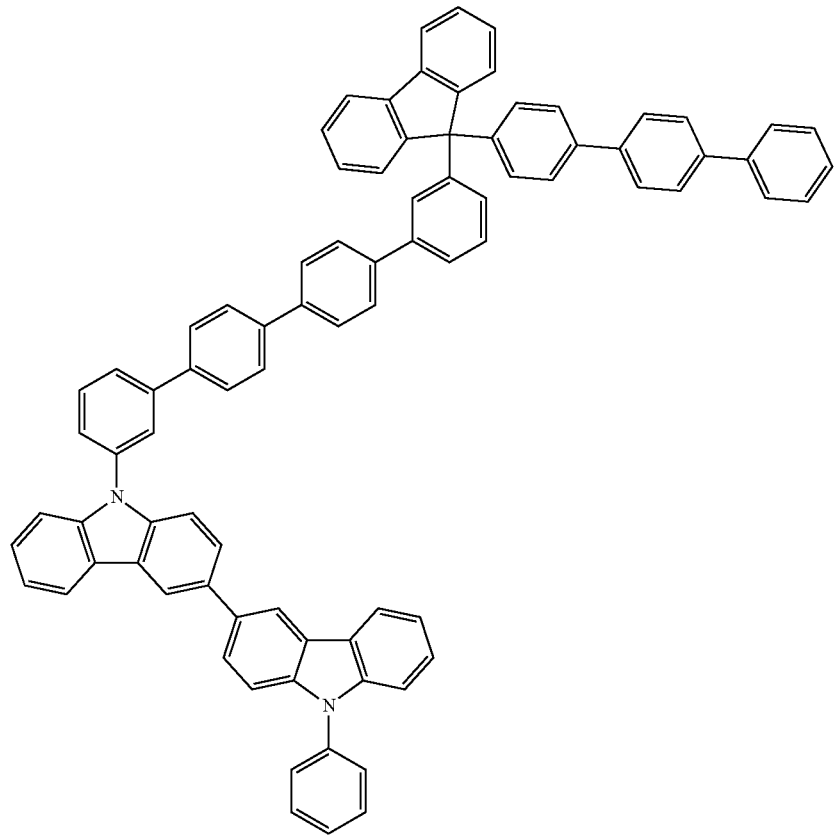
A197
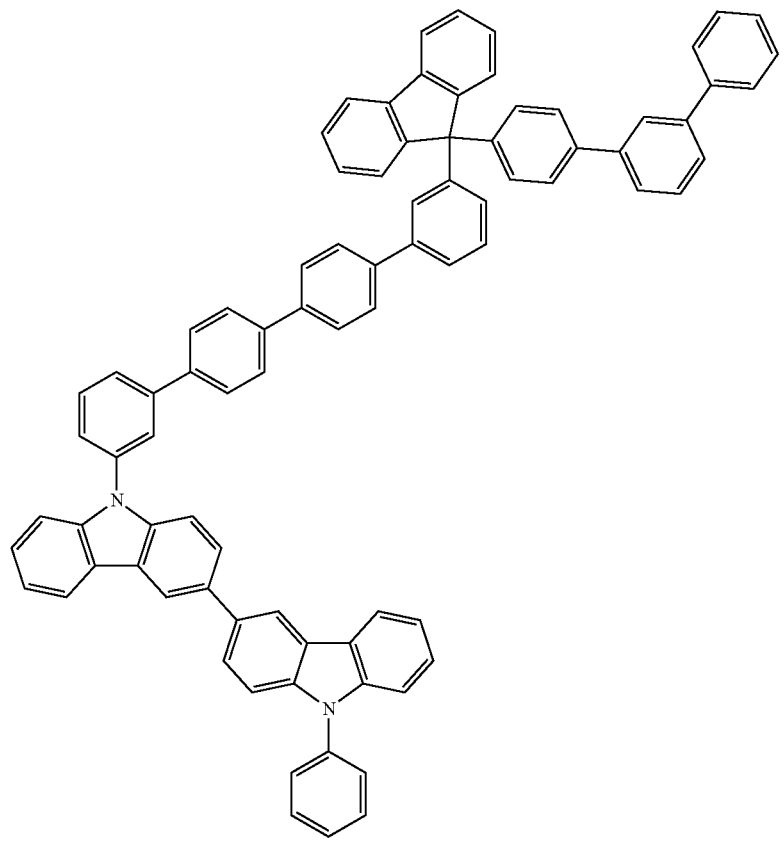
A198

-continued
A199
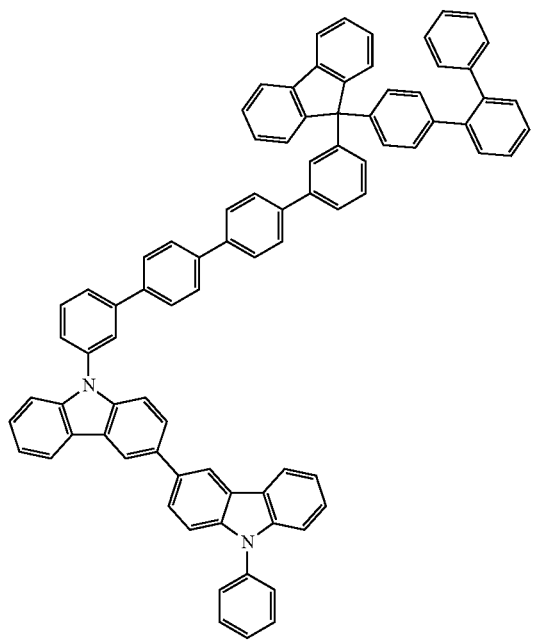
A200
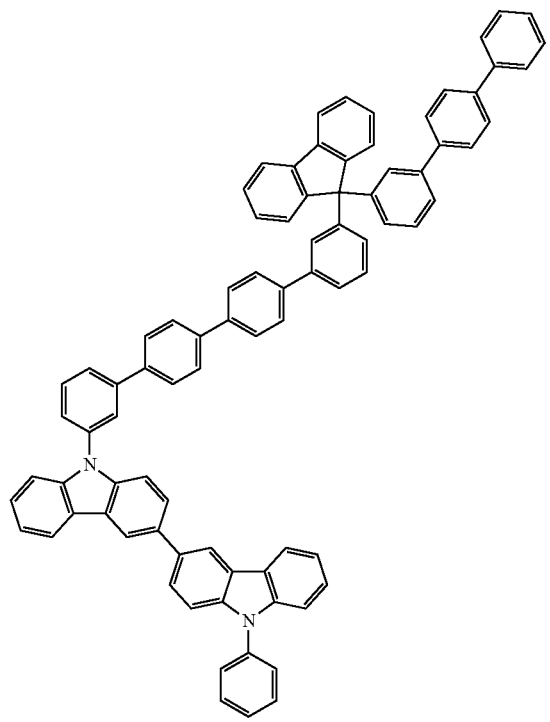
A201
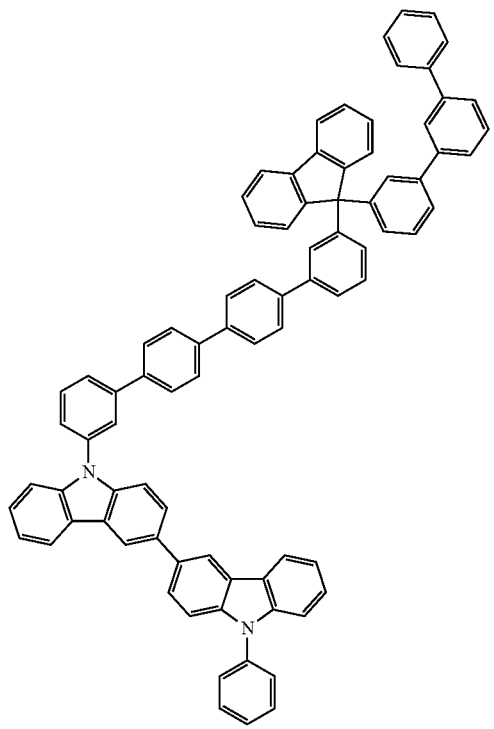
A202
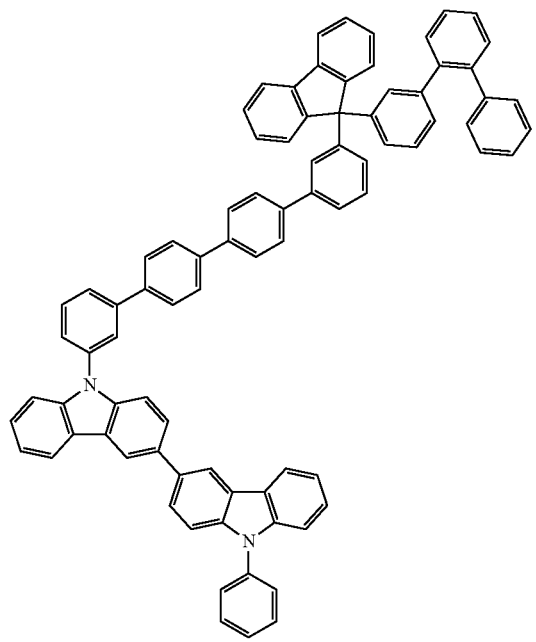

-continued
A203
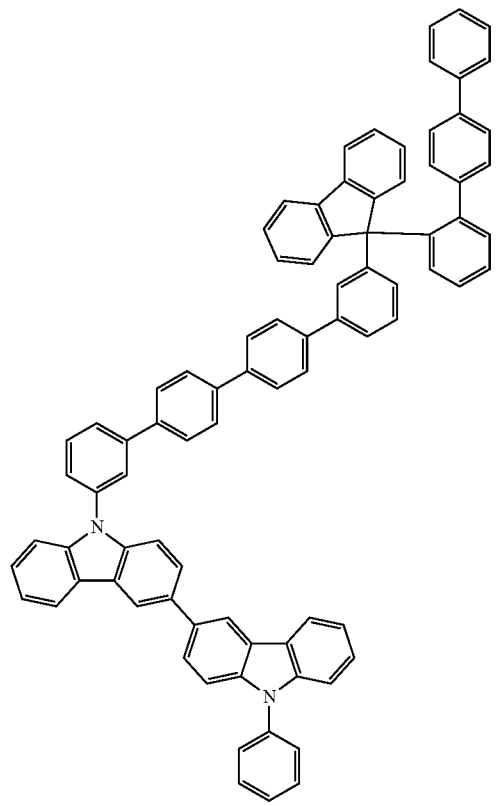
A204
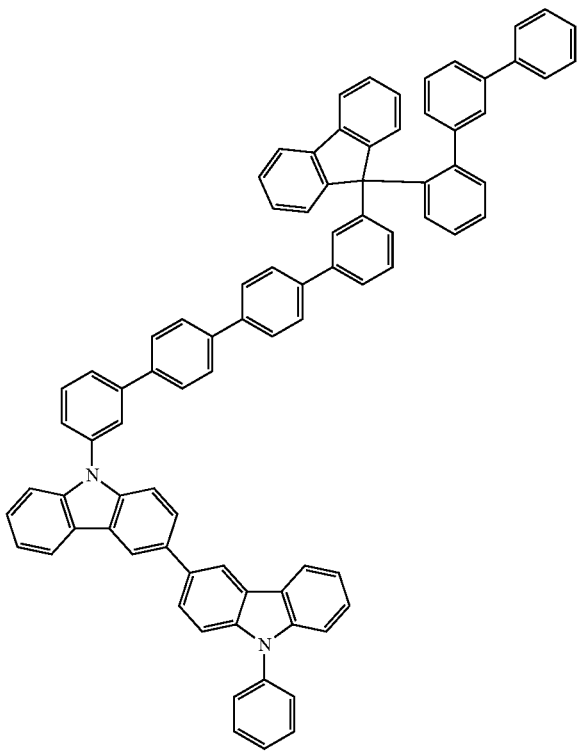
A205
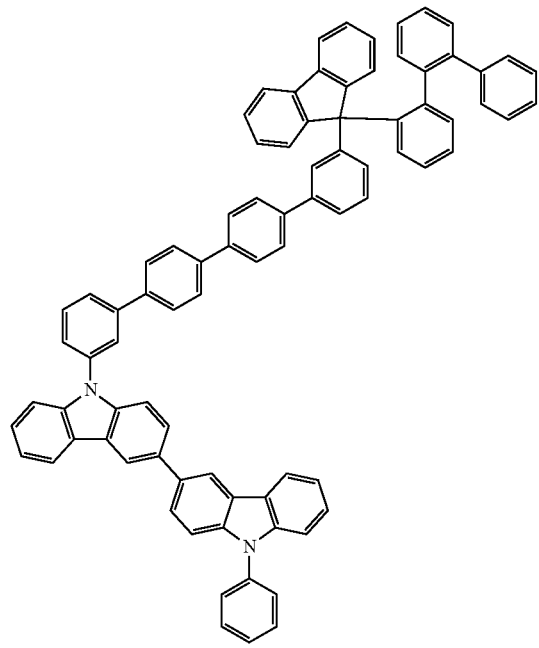
A206

-continued
A207
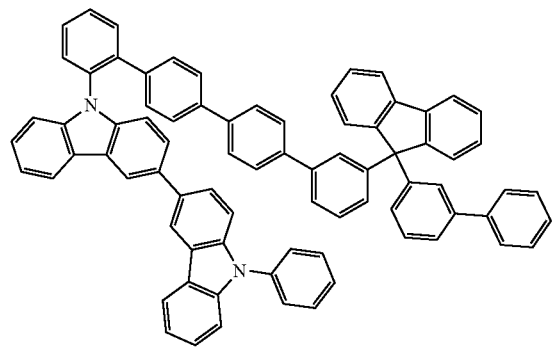
A208
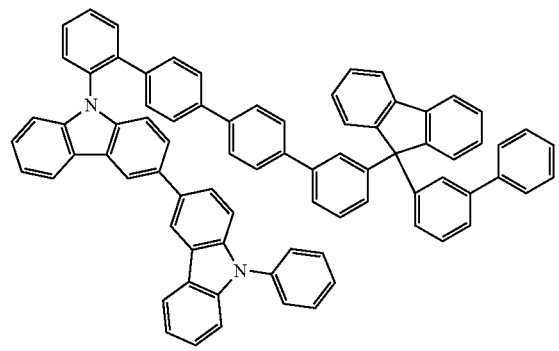
A209
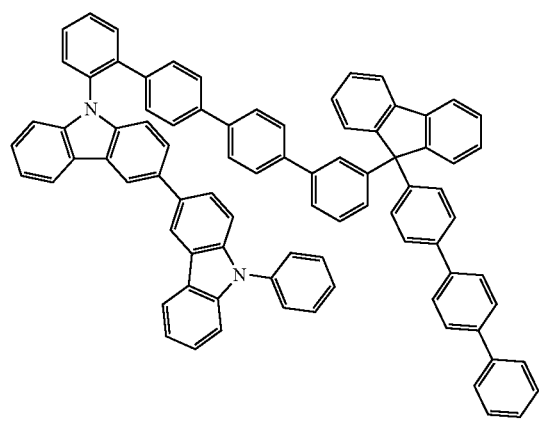
A210
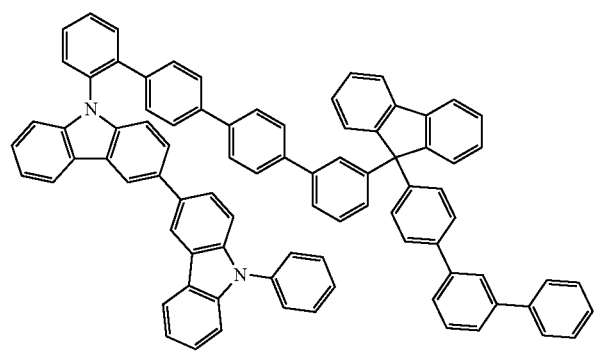
A211
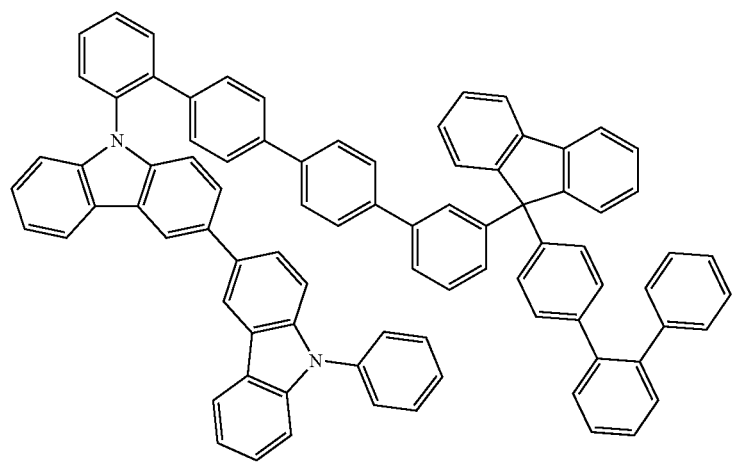

-continued
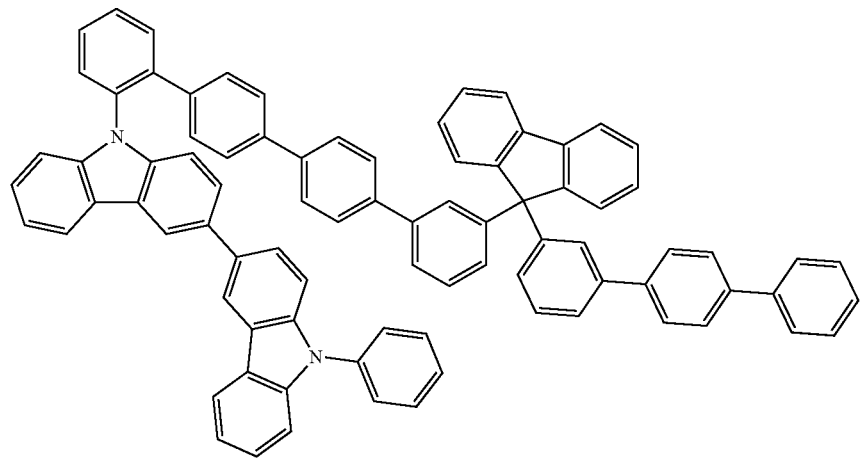
A212
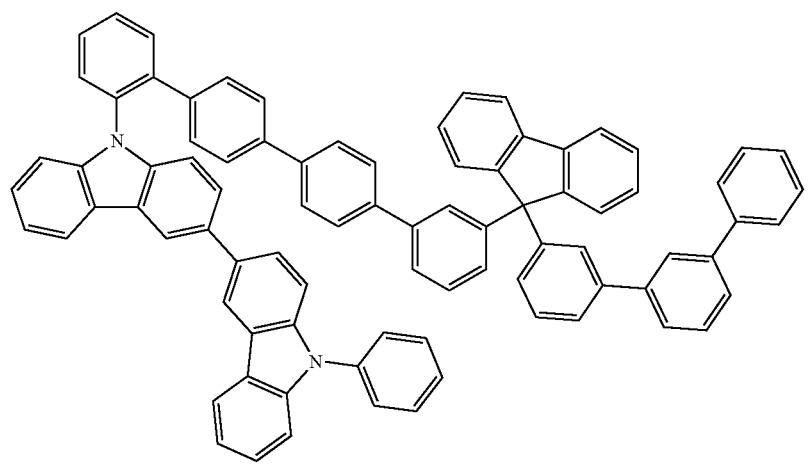
A213
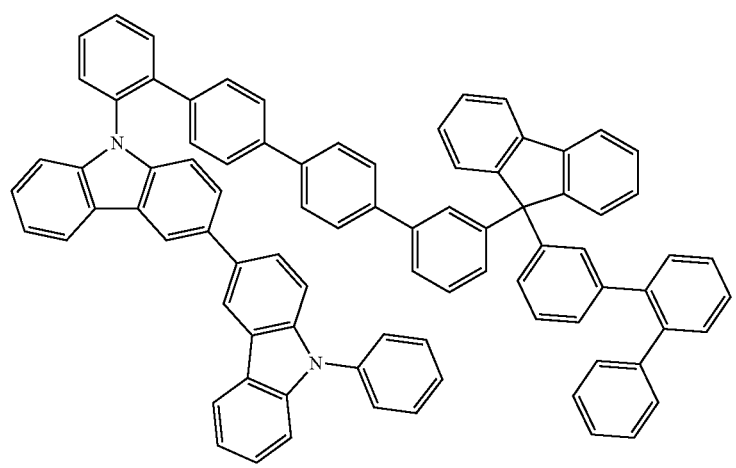
A214

-continued
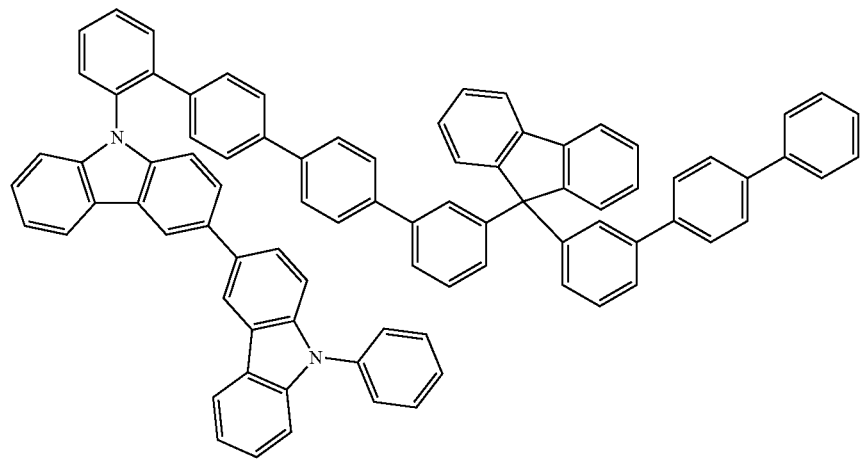
A215
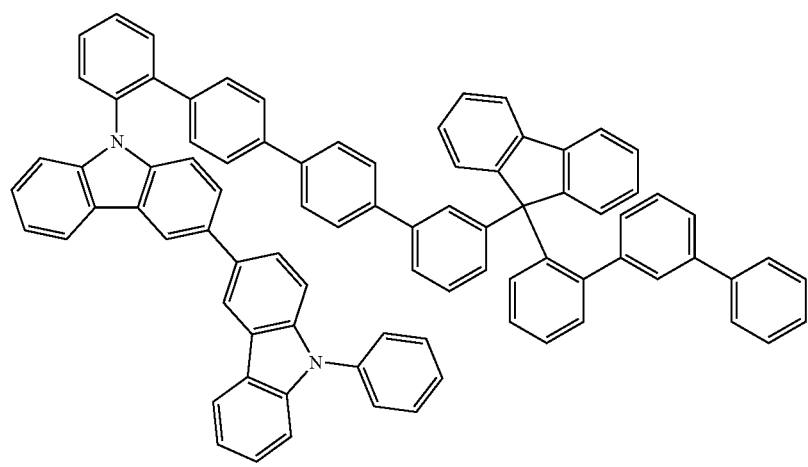
A216
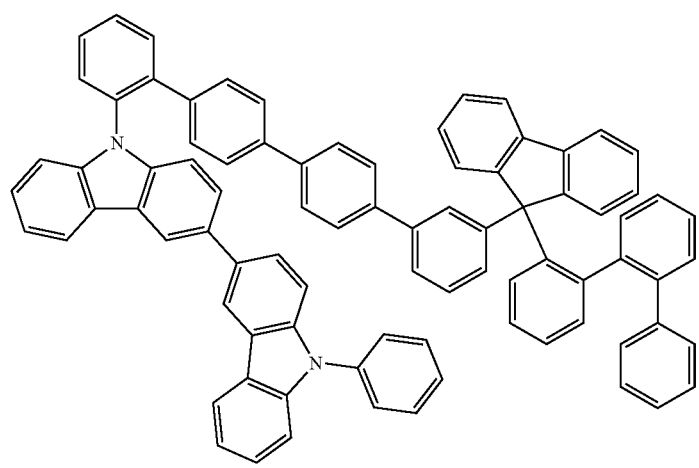
A217

-continued
A218
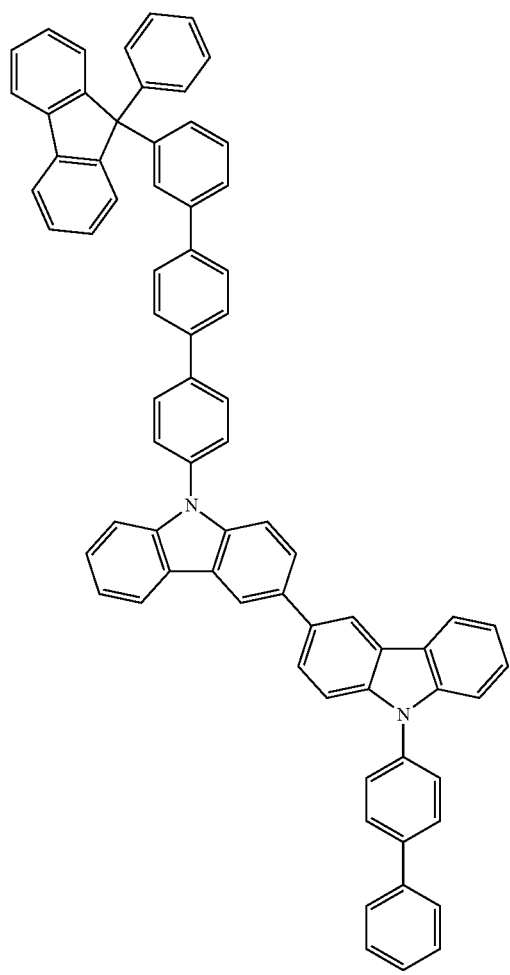
A219
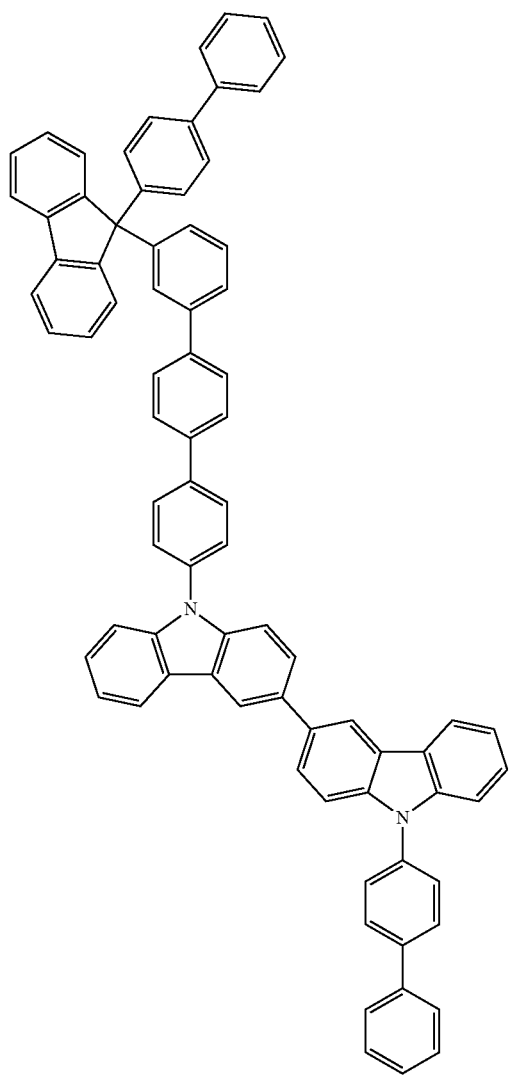

-continued
A220
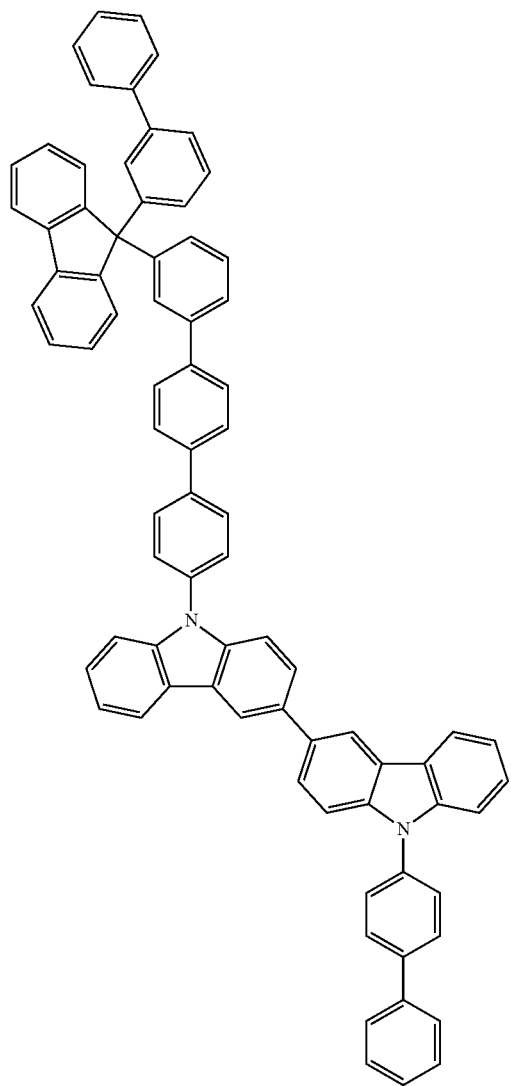
A221
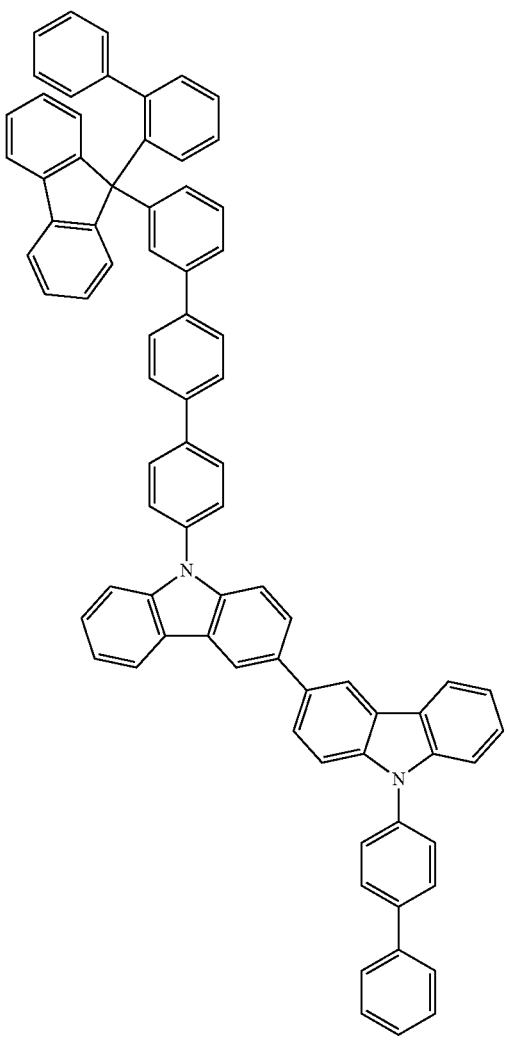

-continued
647
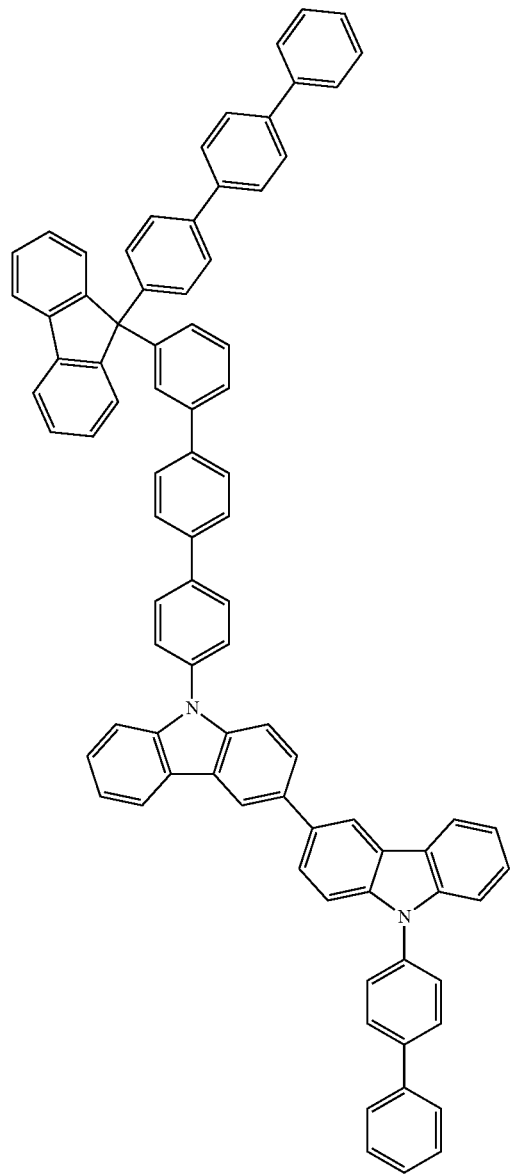
A222
648
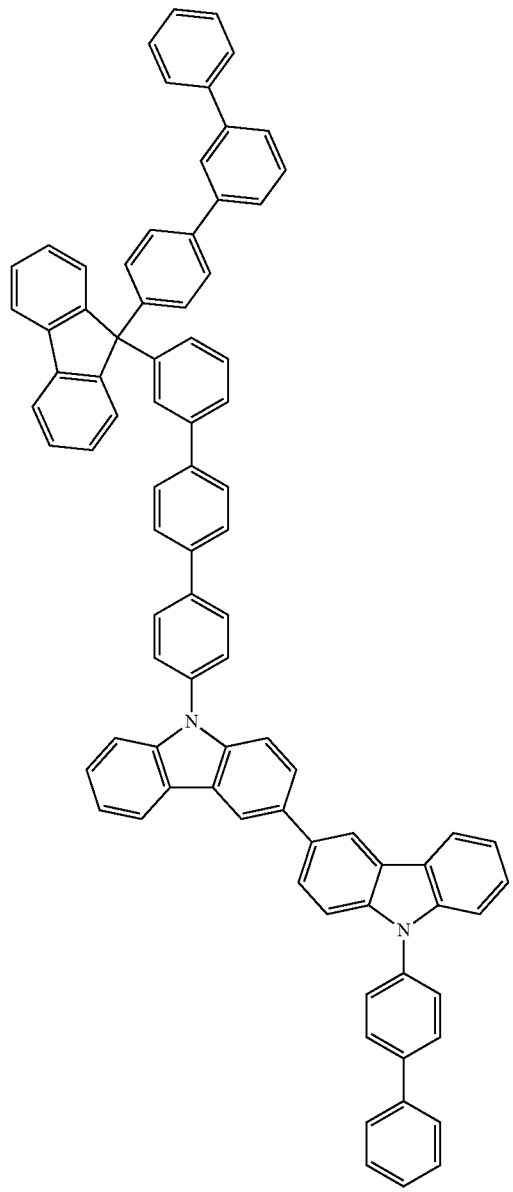
A223

-continued
649
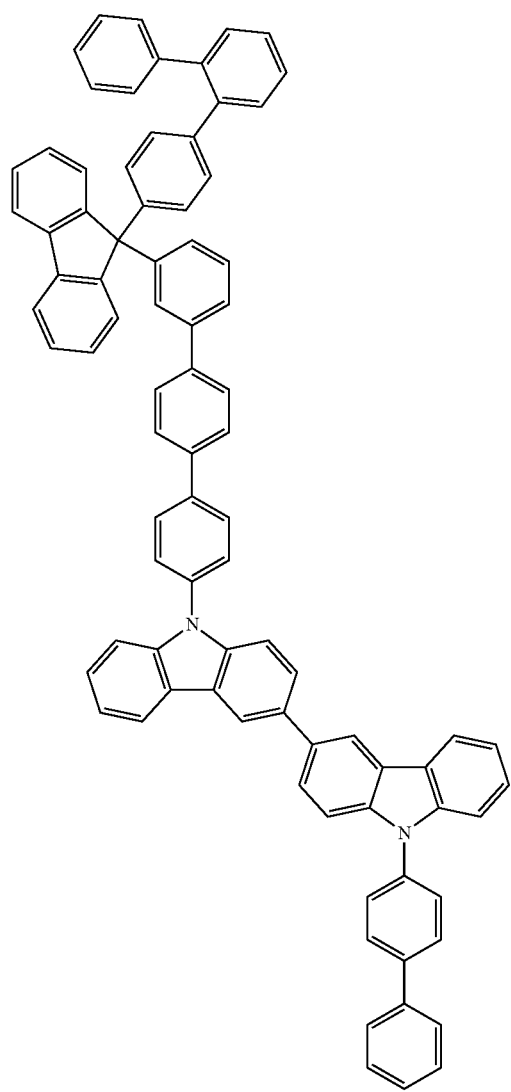
A224
650
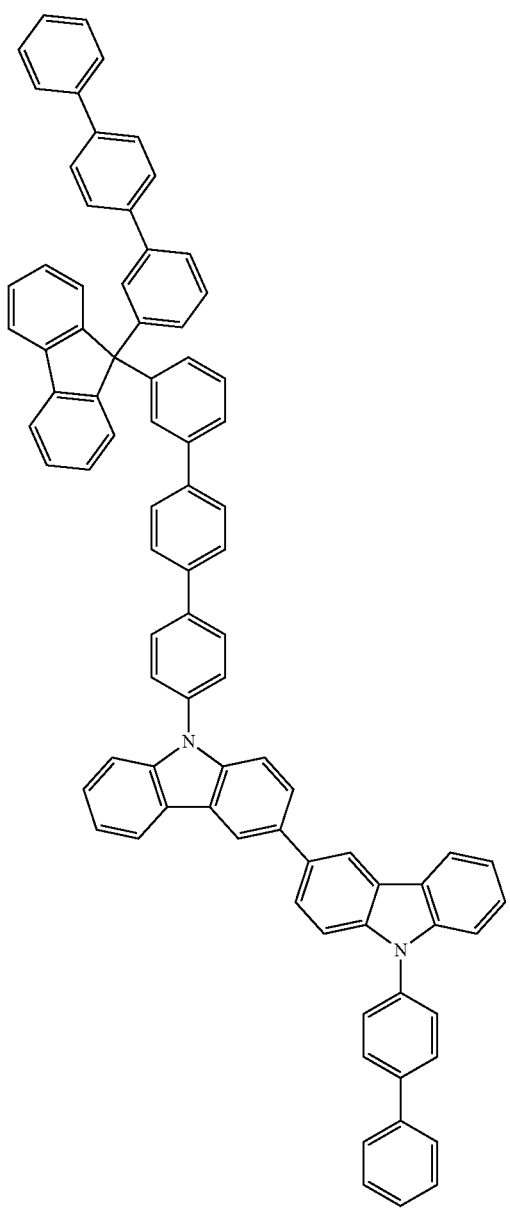
A225

-continued
| 651 | 652 |
|---|---|
| A226 | A227 |
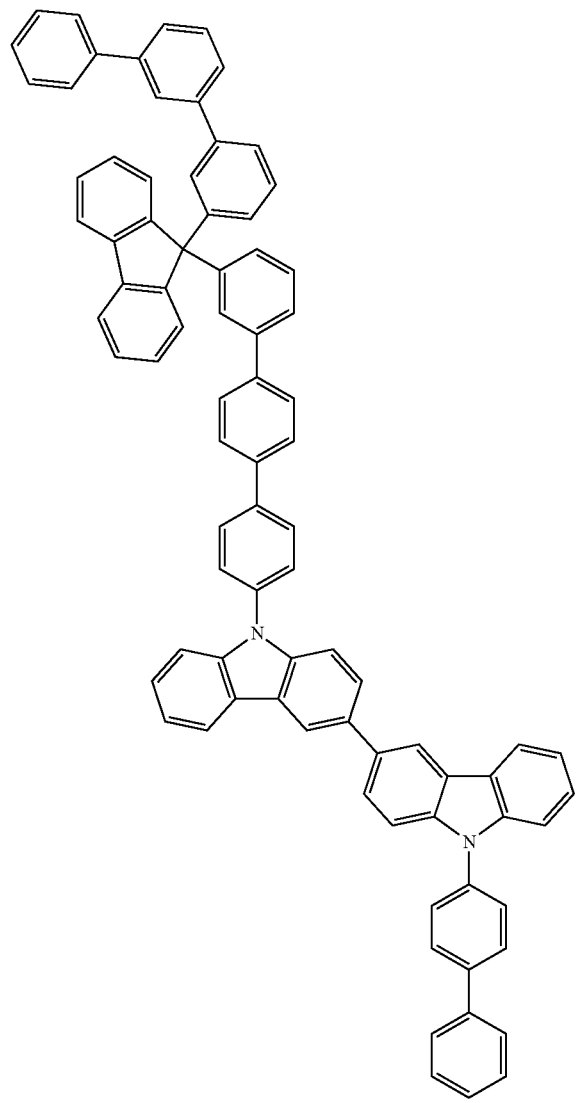
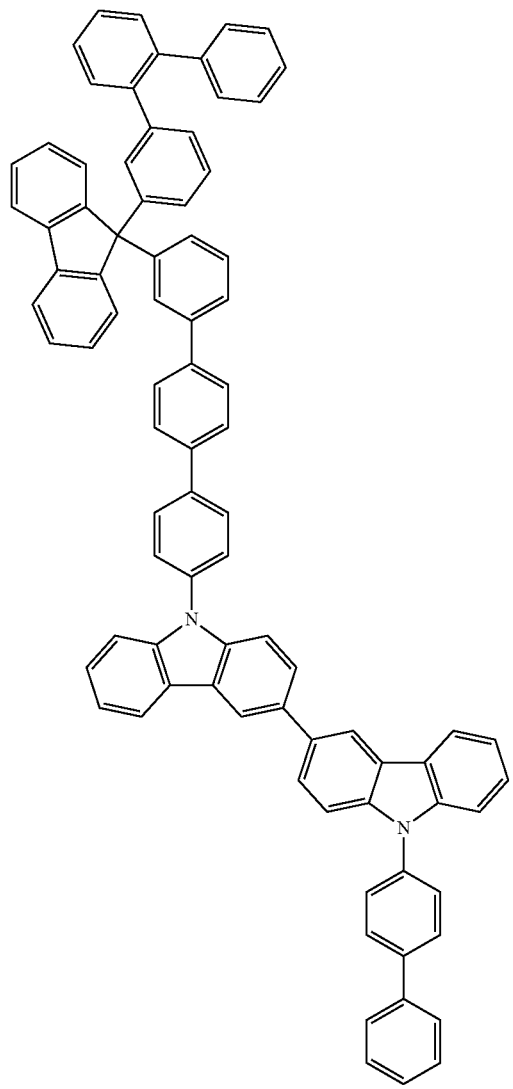

-continued
A228
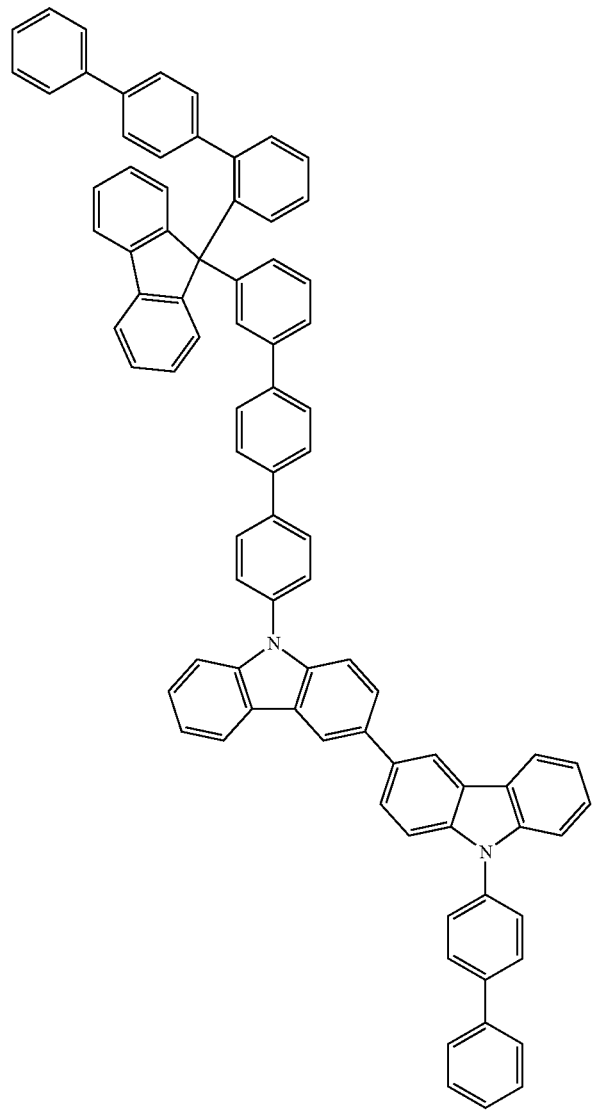
A229
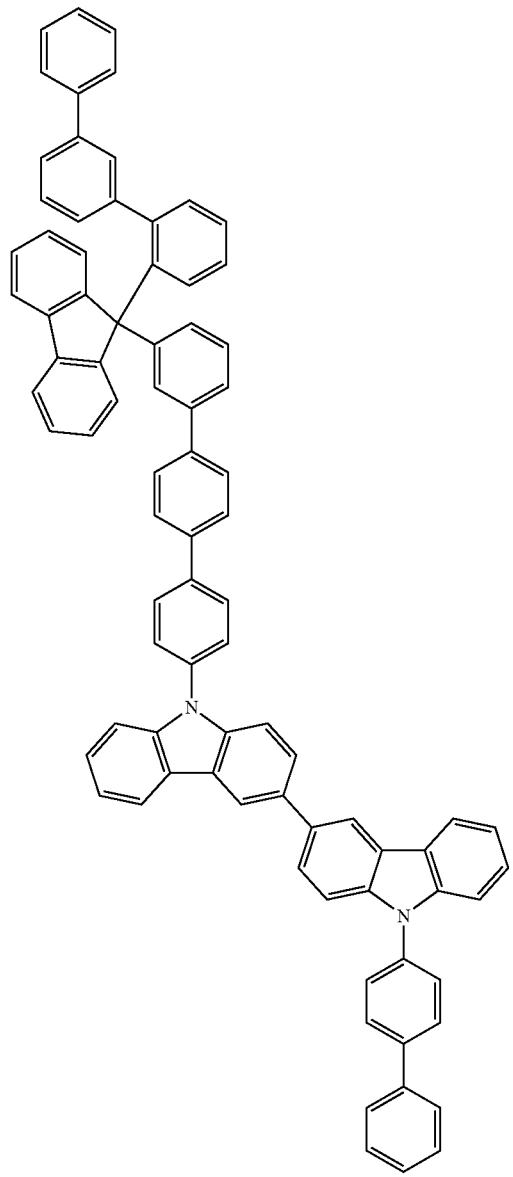

-continued
| 655 | 656 |
|---|---|
| A230 | A231 |
| 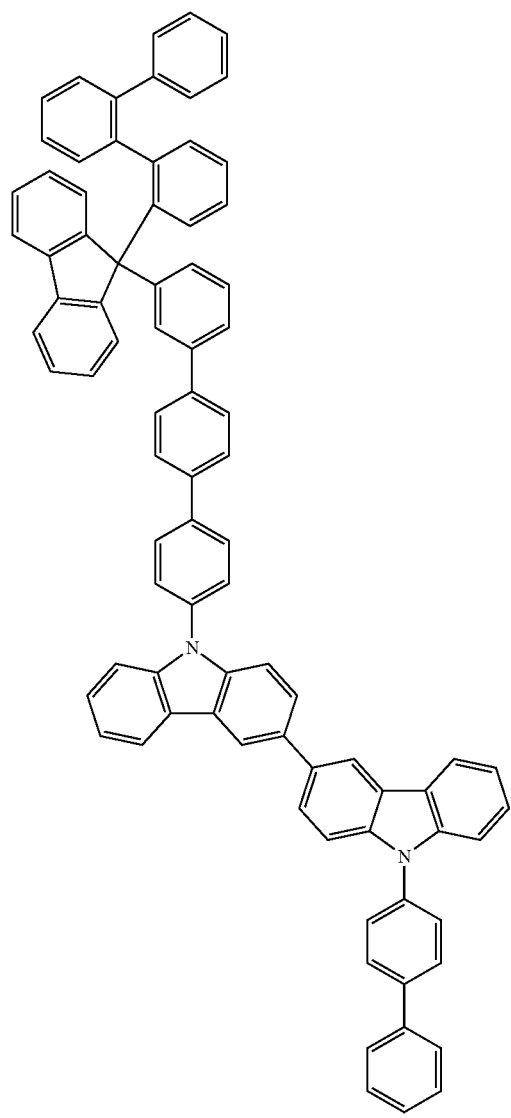 | 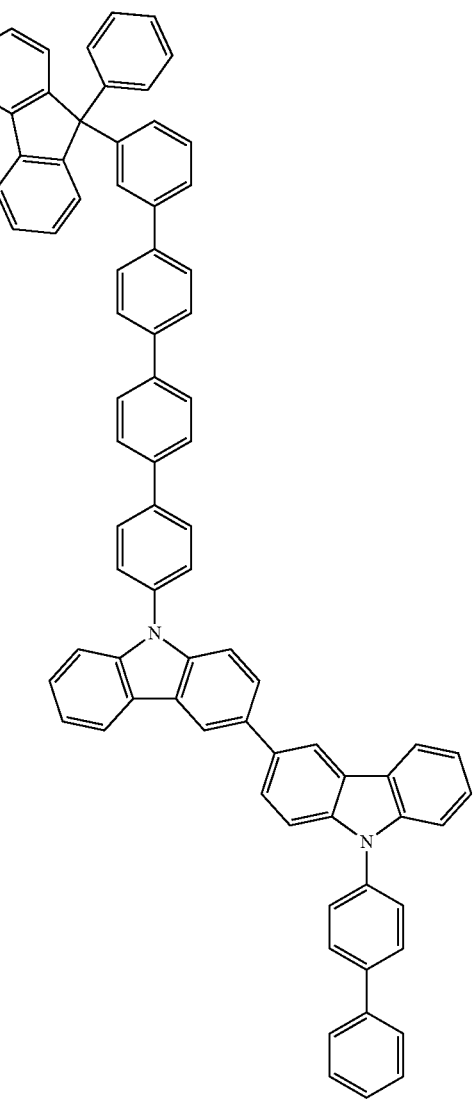 |

-continued
A232
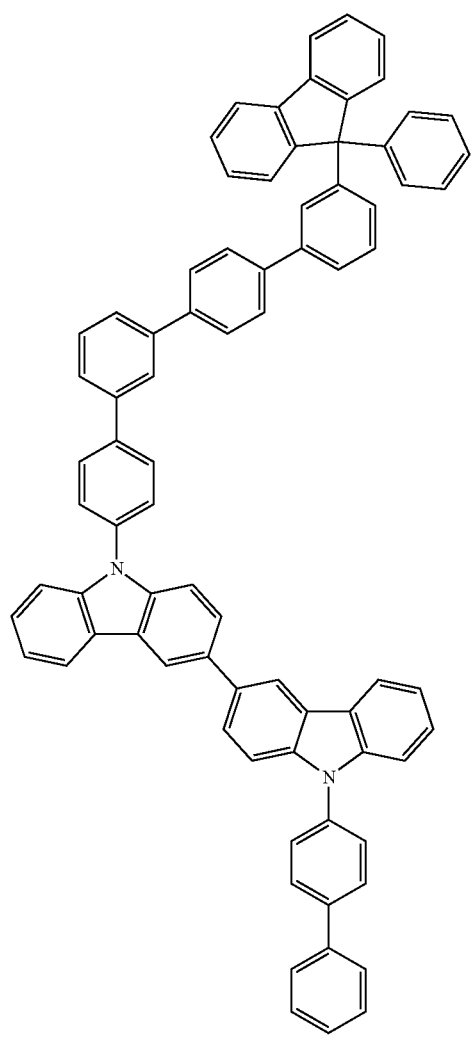
A233
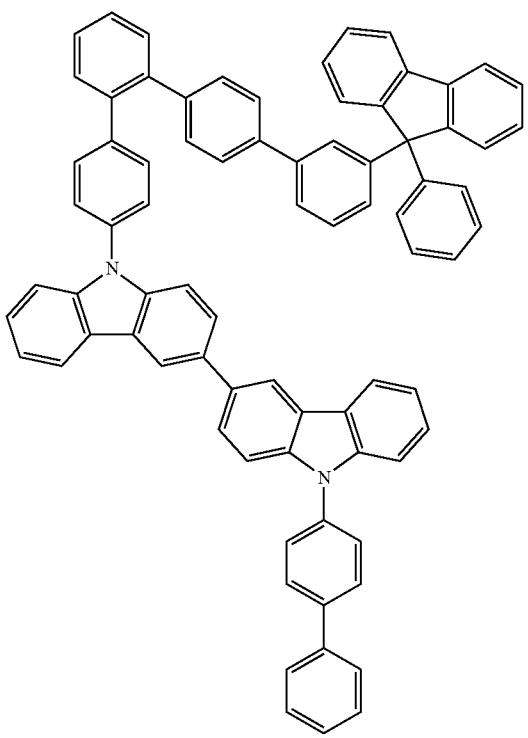

-continued
A234
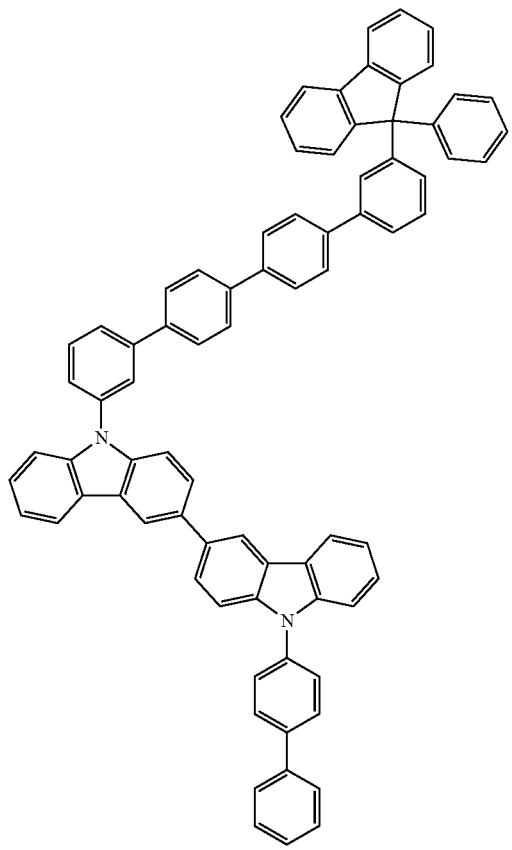
A235
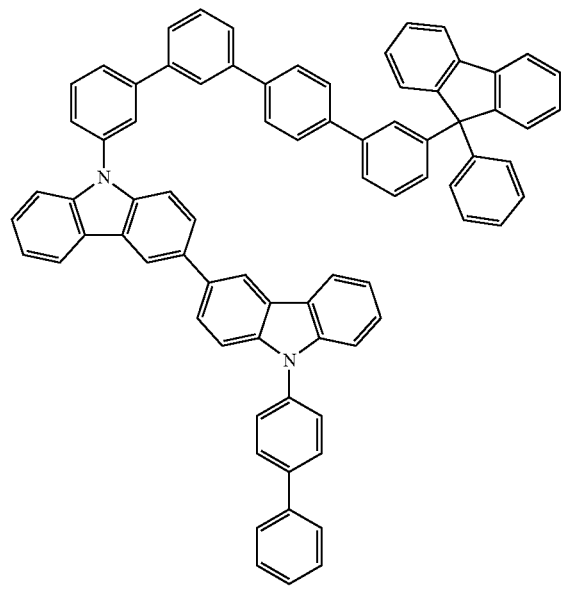
A236
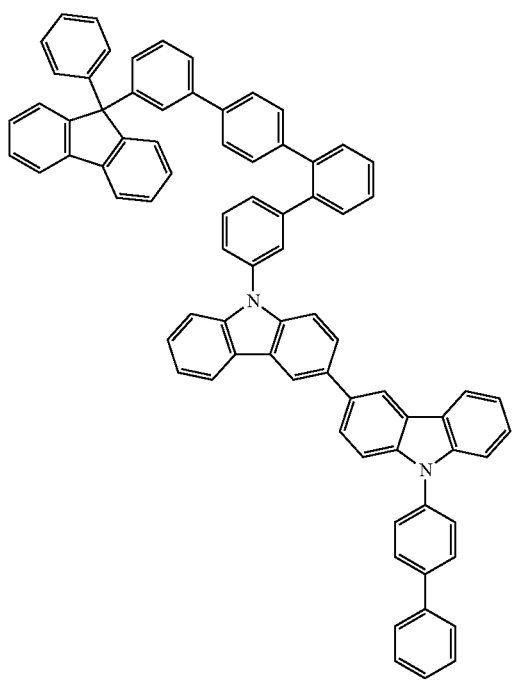
A237
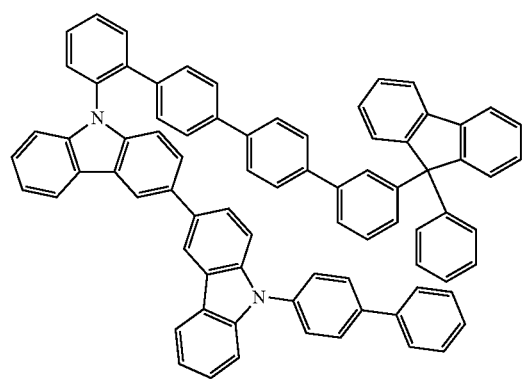

-continued
A238
A239
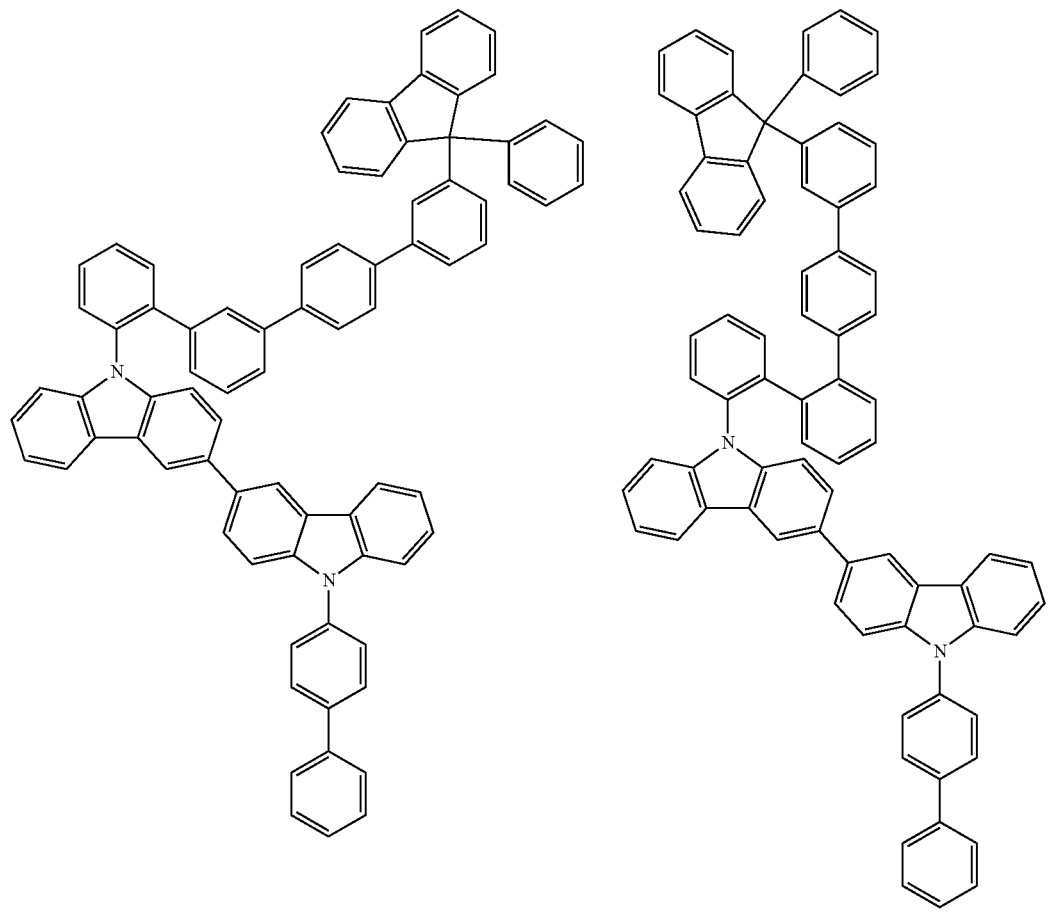

-continued
663
A240
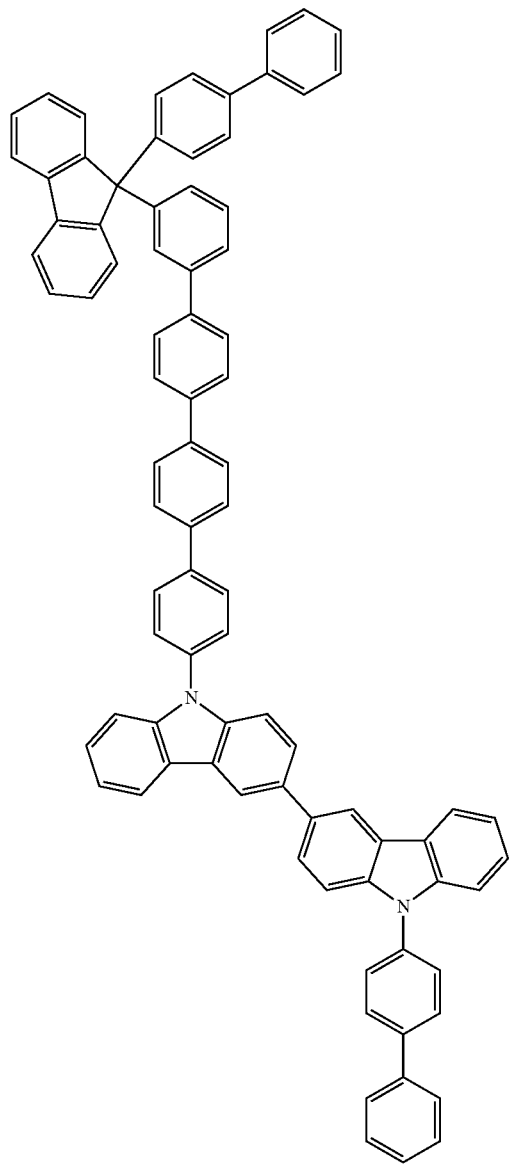
664
A241
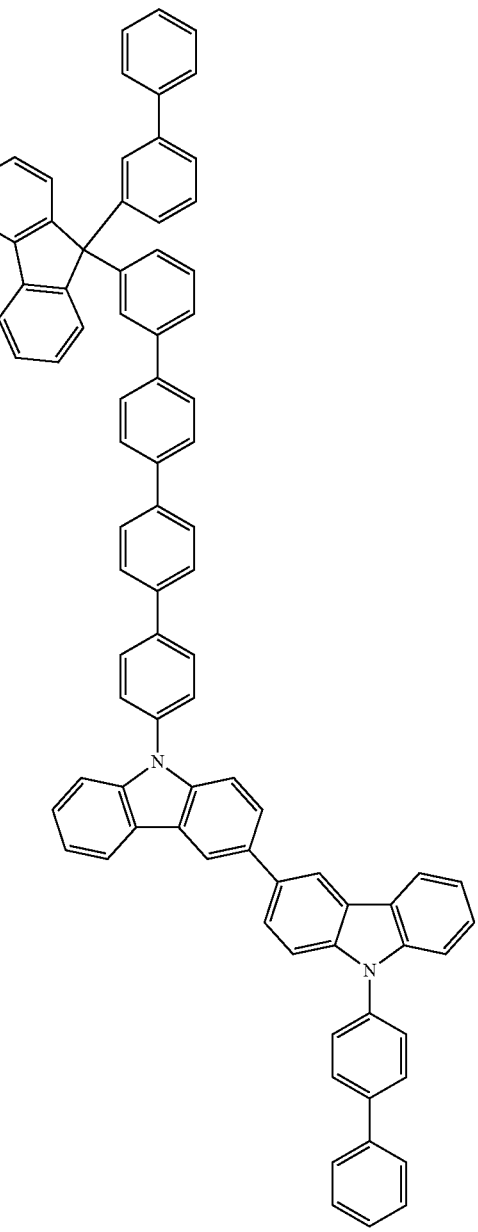

-continued
665 A242
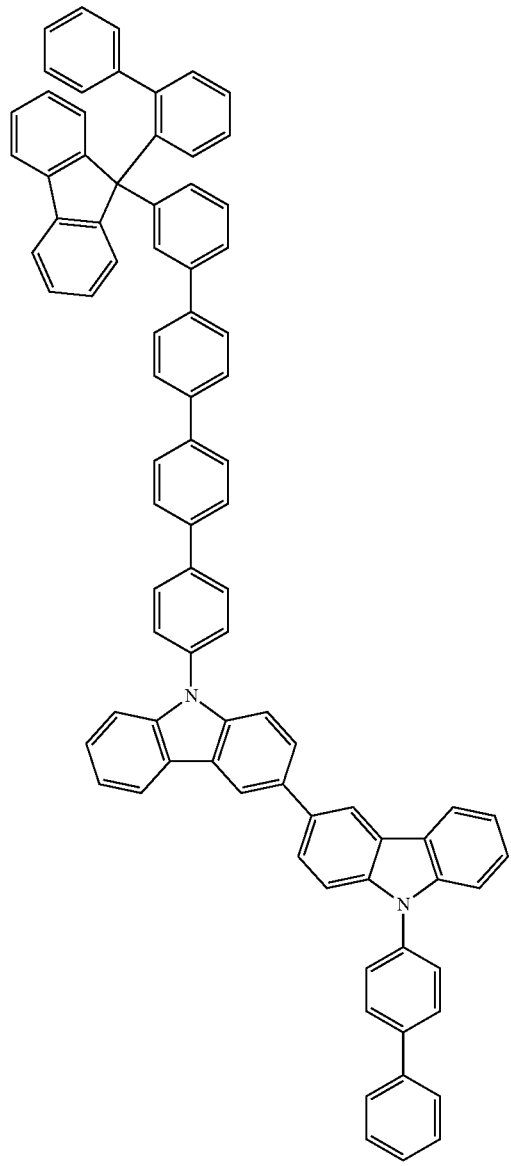
666 A243
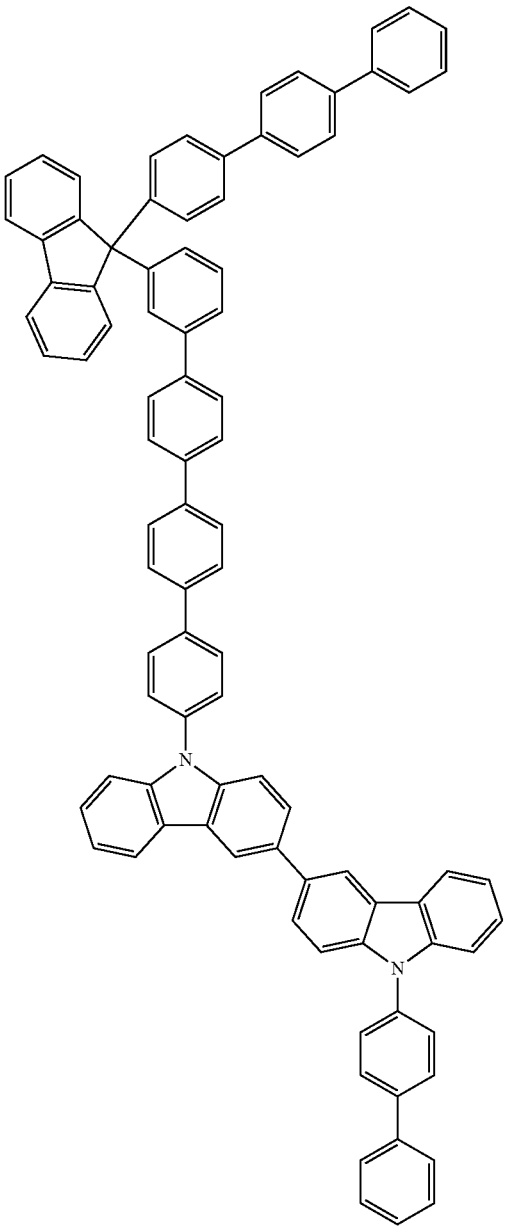

-continued
667
A244
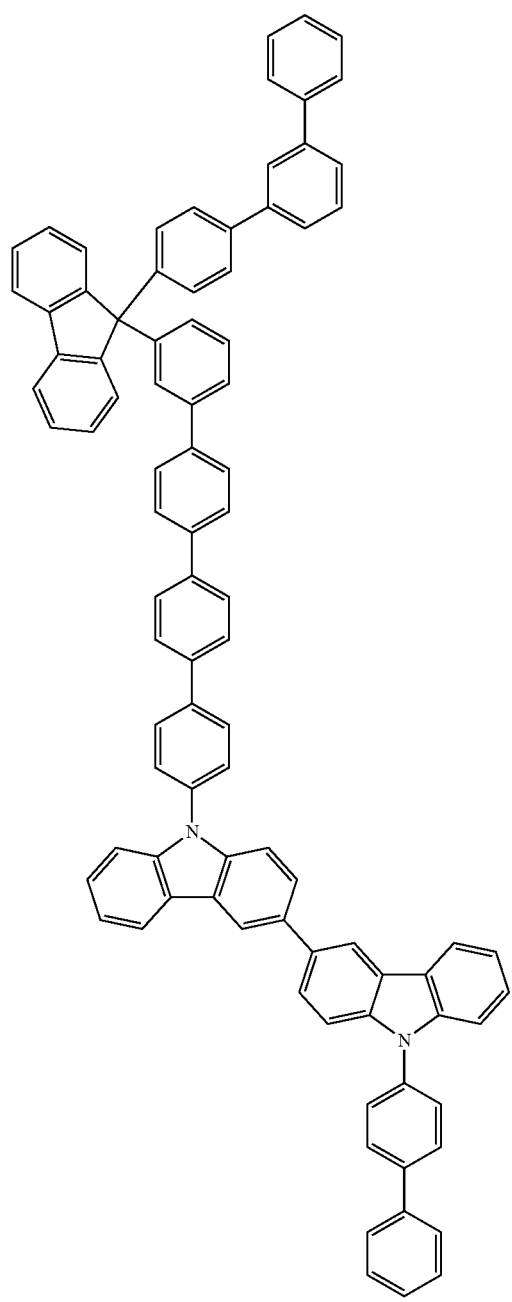
668
A245
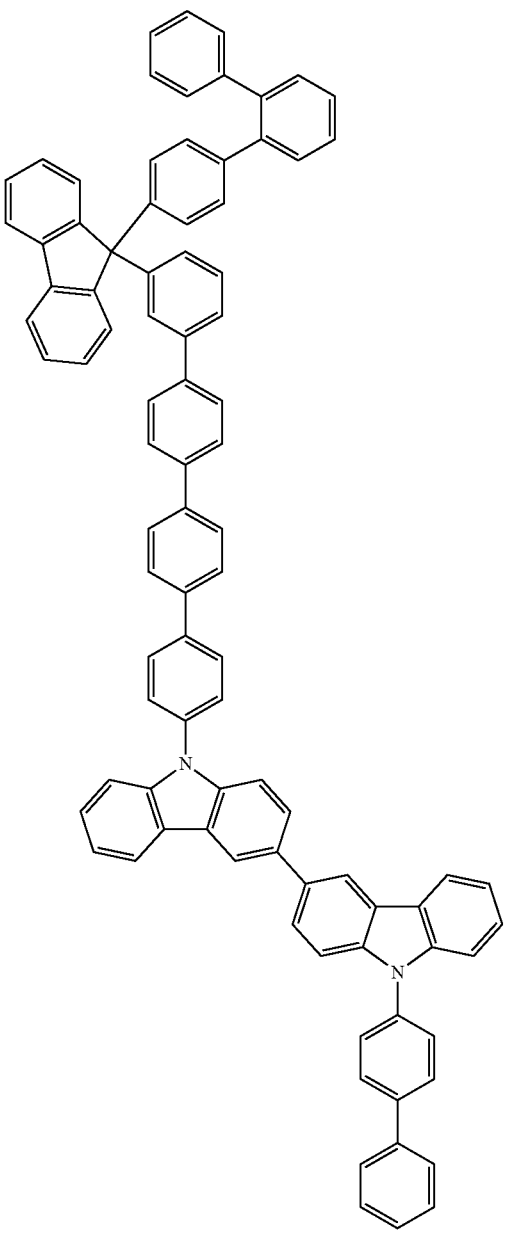

-continued
669
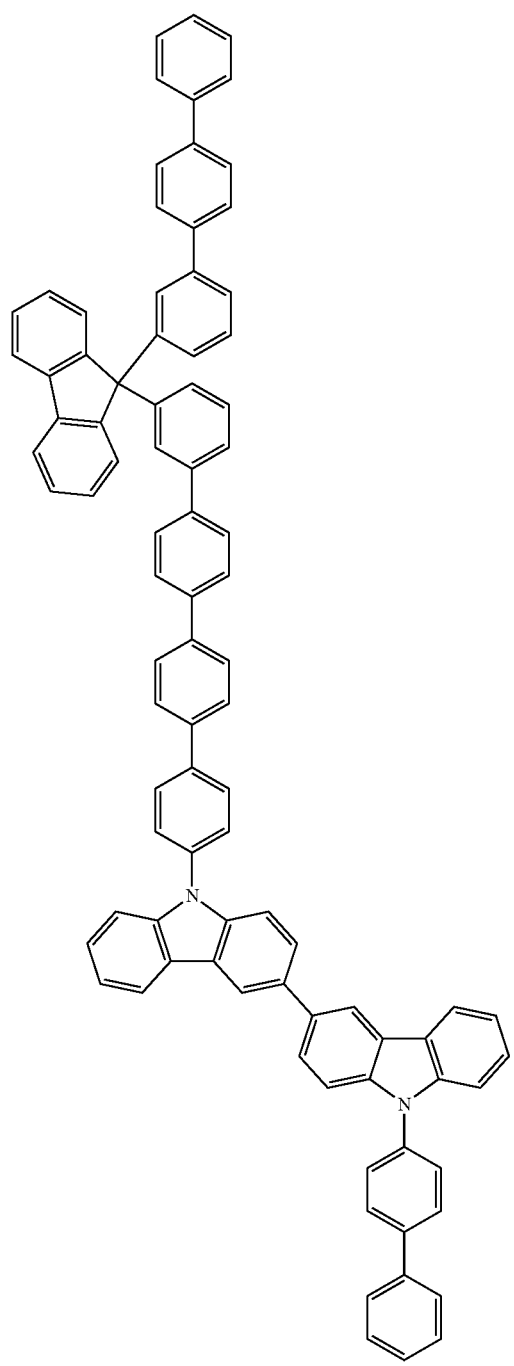
A246
670
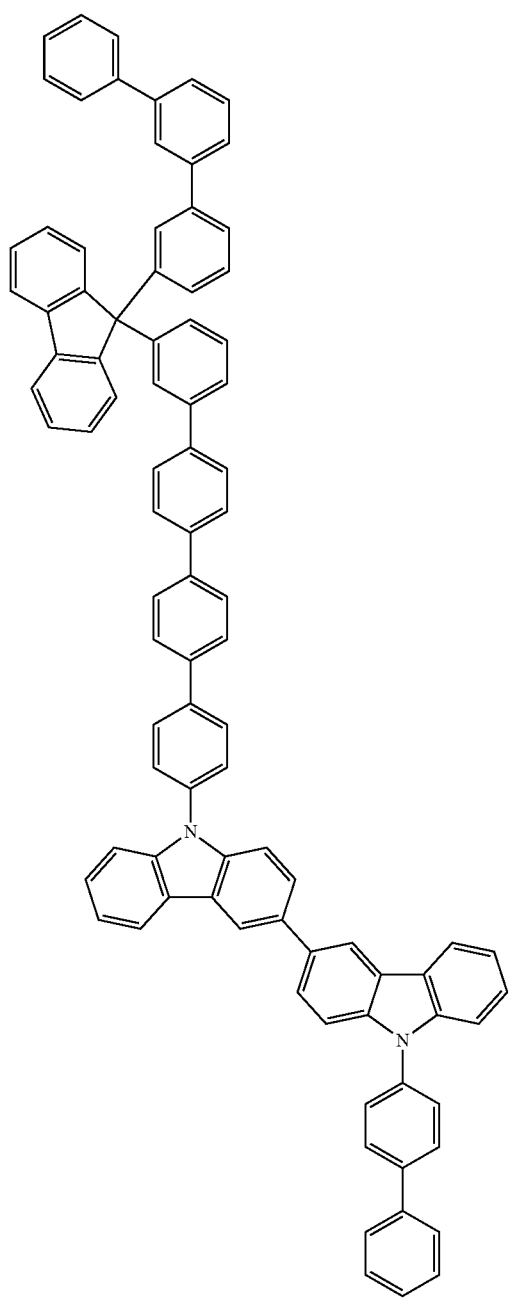
A247

671
672
-continued
A248
A249
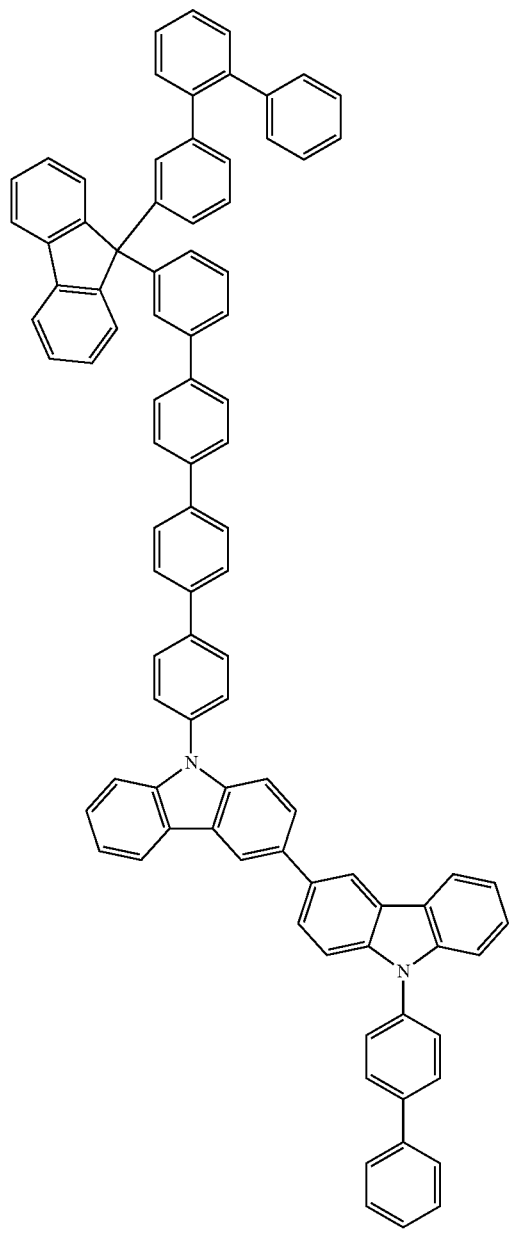
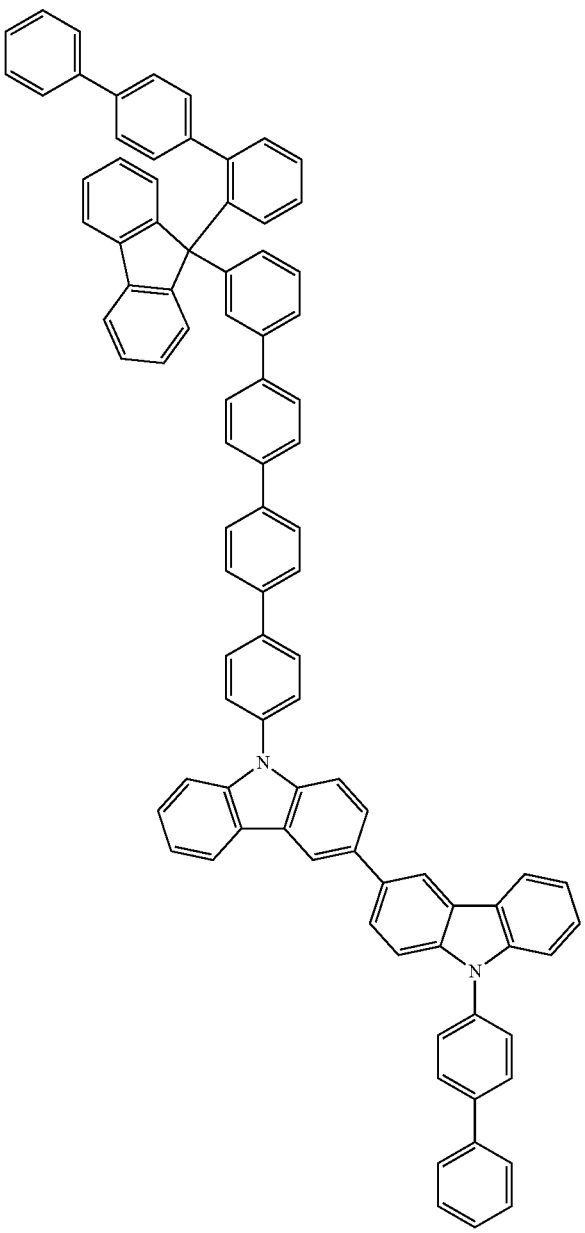

673    674
-continued
A250 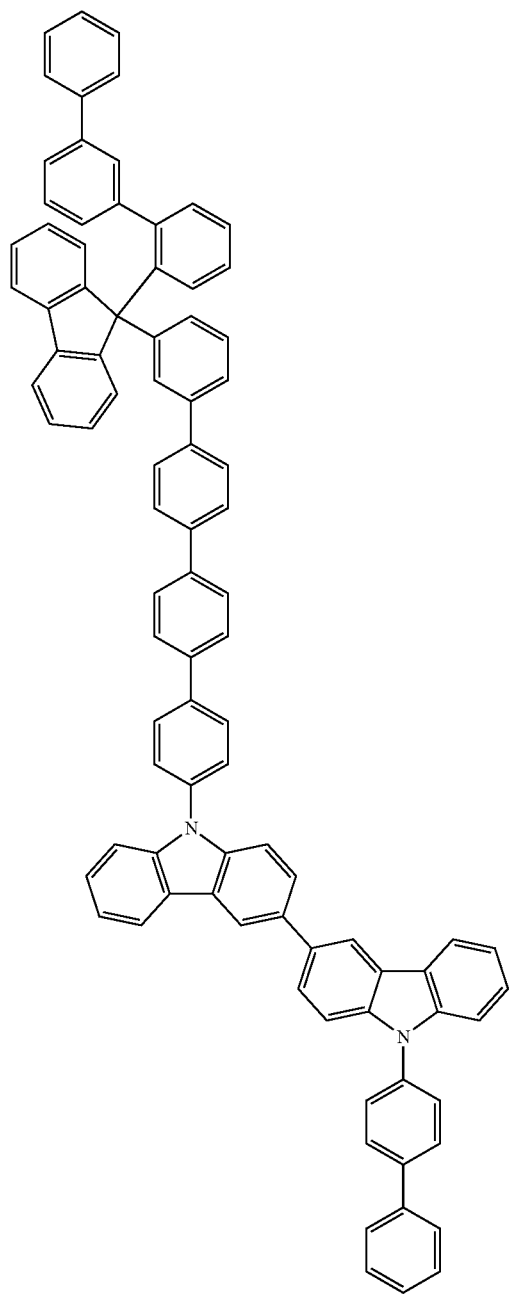 A251 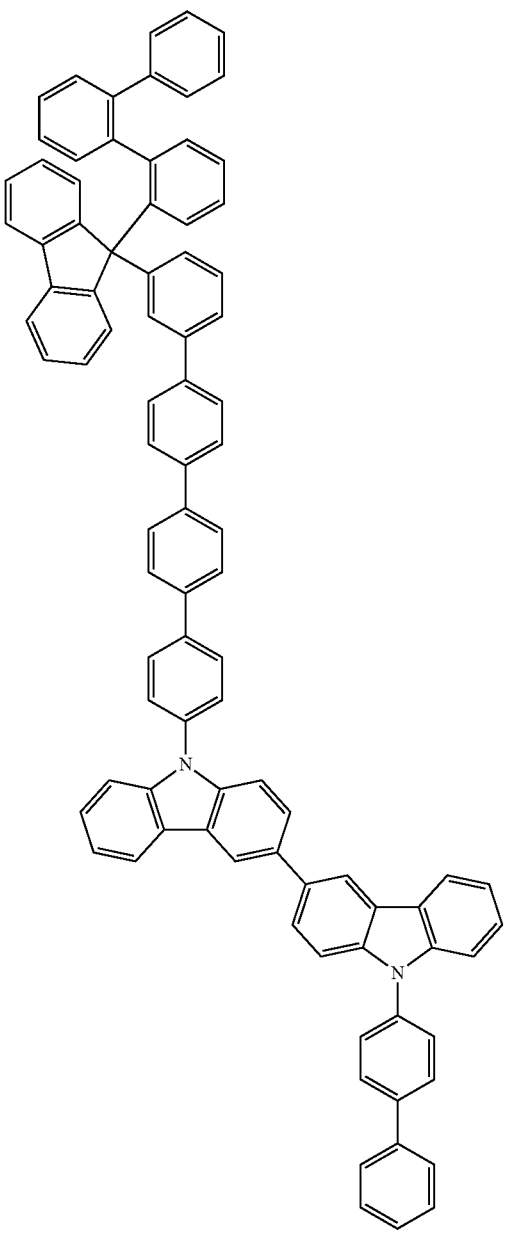

-continued
A252
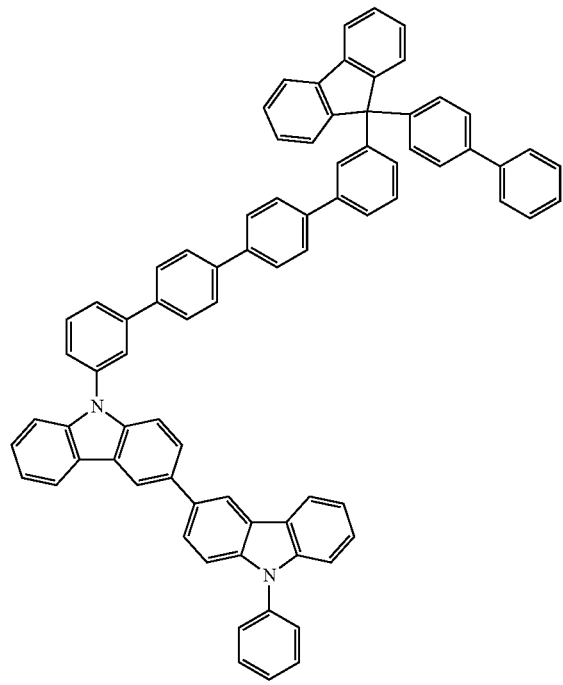
A253
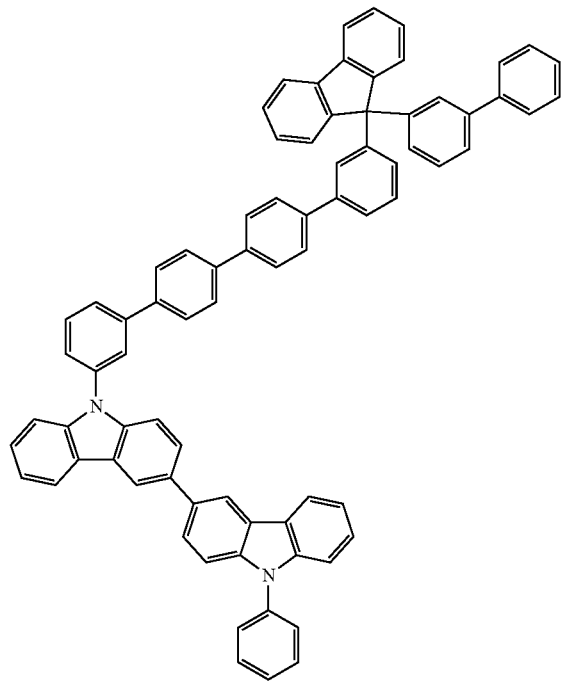
A254
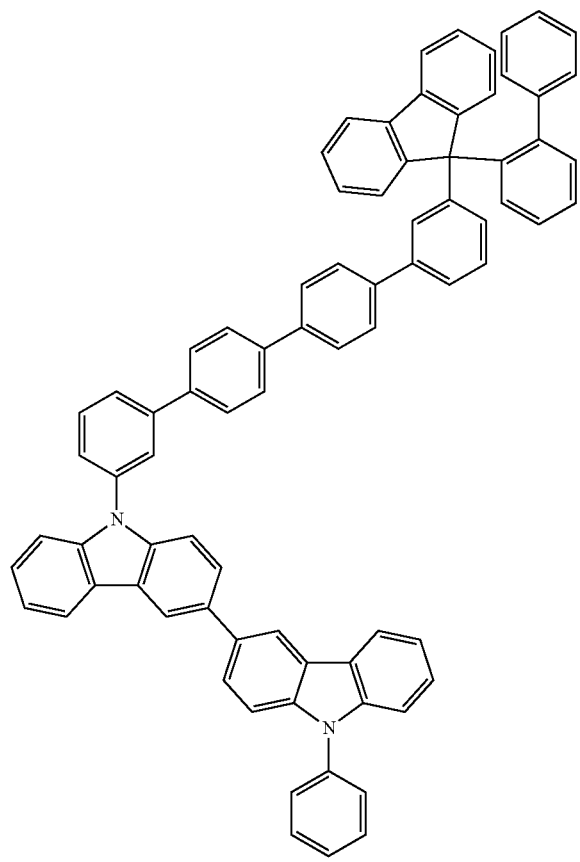

-continued
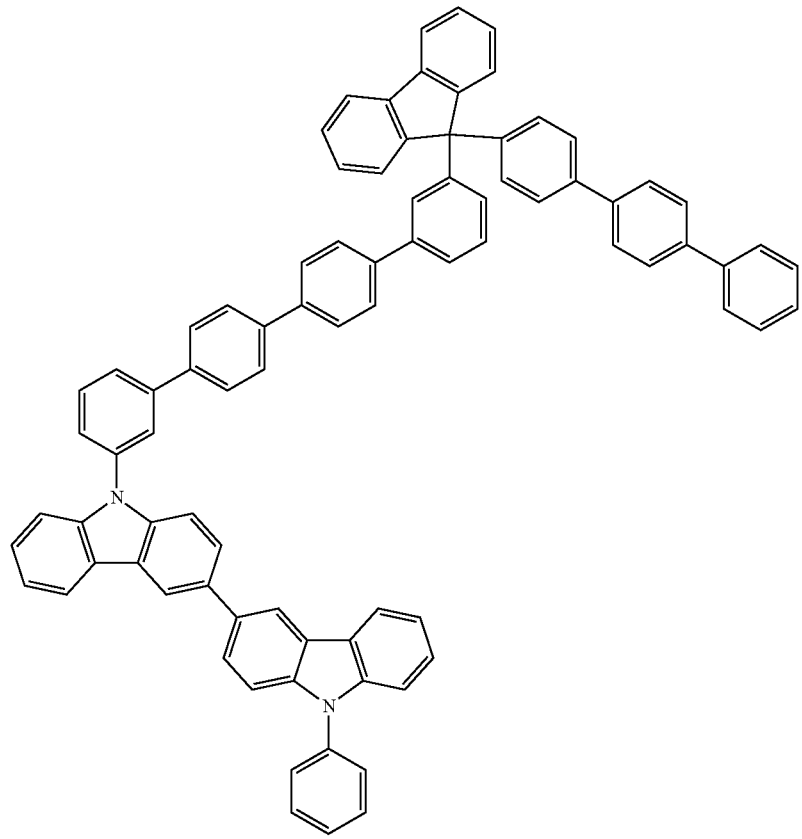
A255
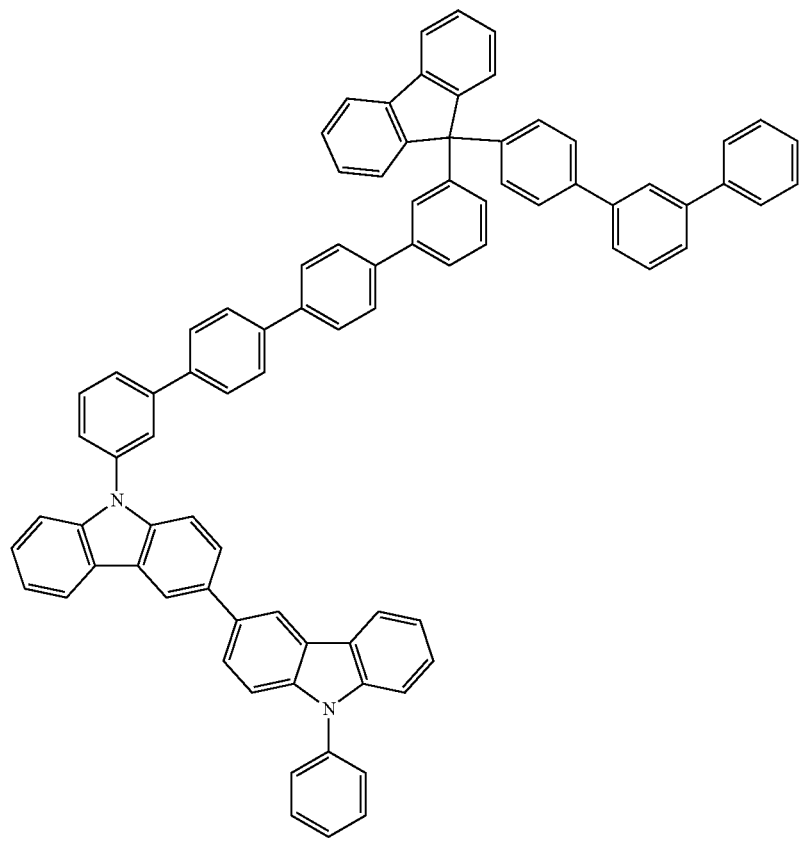
A256

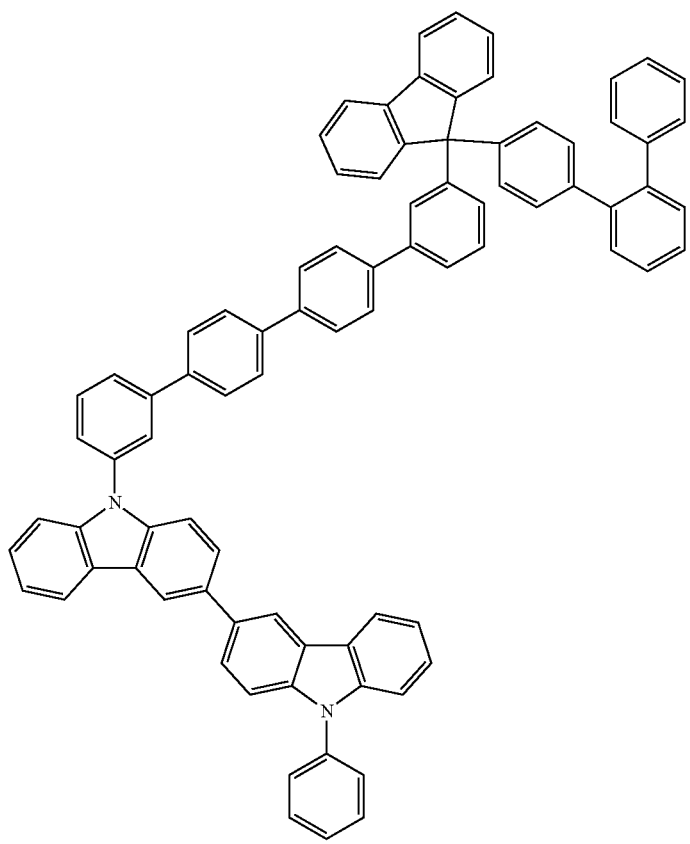
A257

-continued
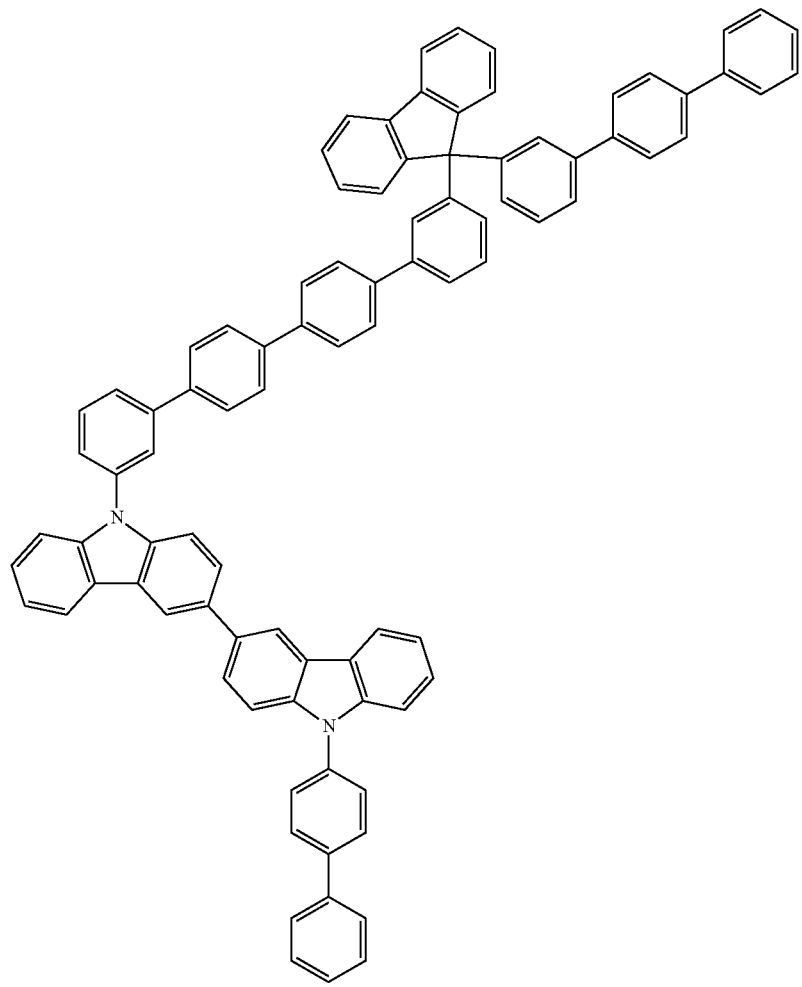
A258

A259
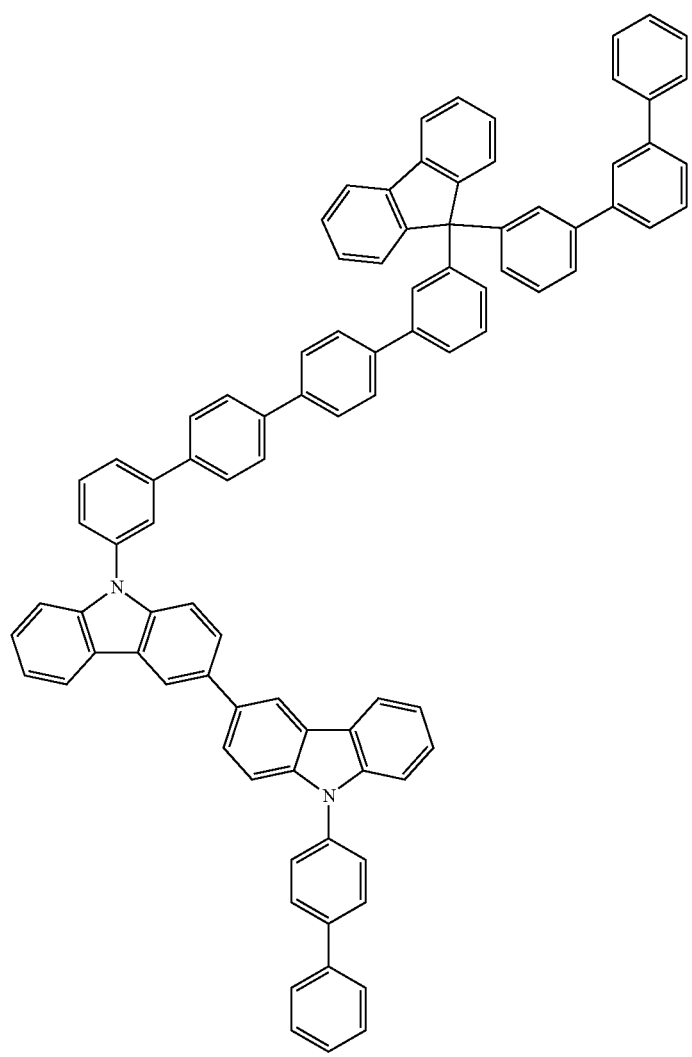

-continued
A260
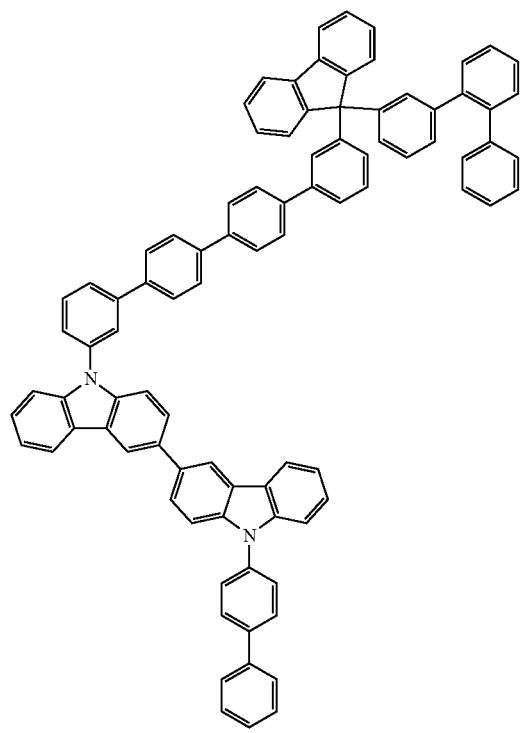
A261
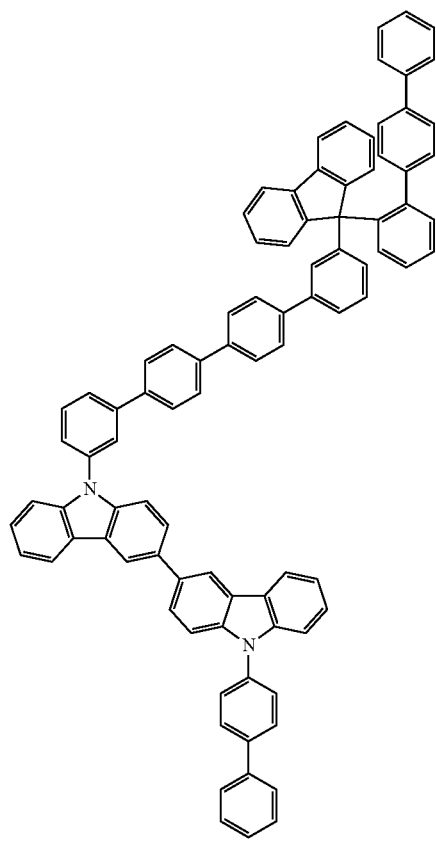
A262
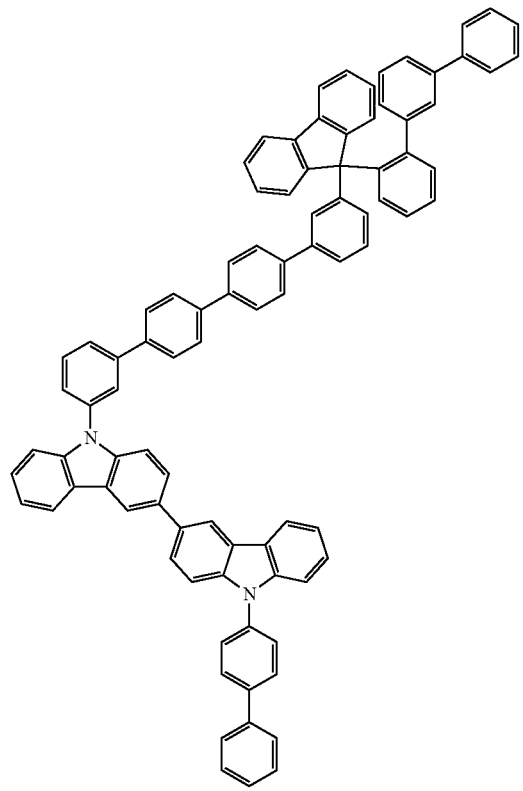
A263
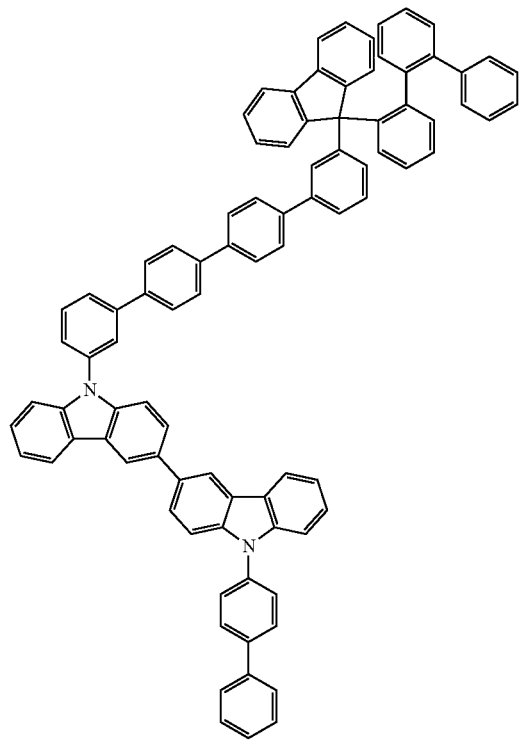

-continued
A264
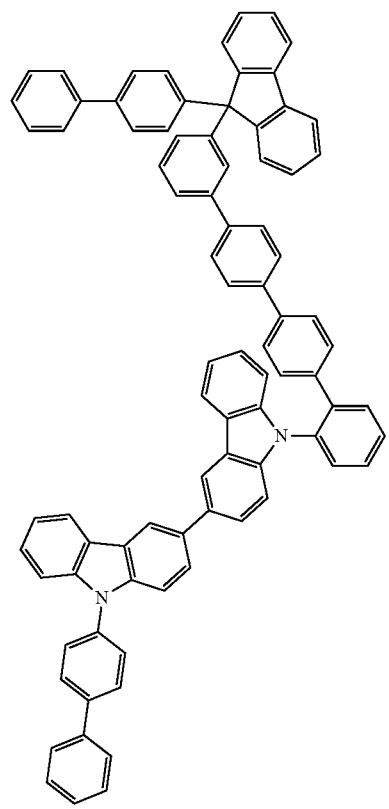
A265
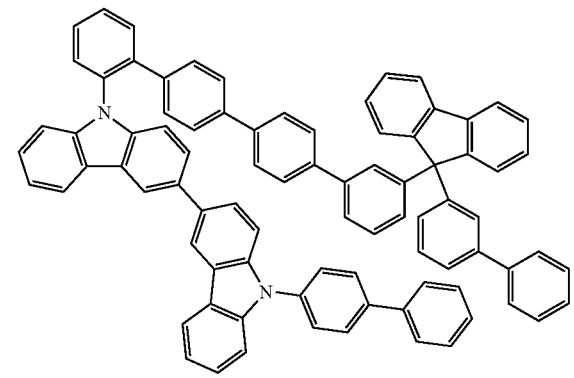
A266
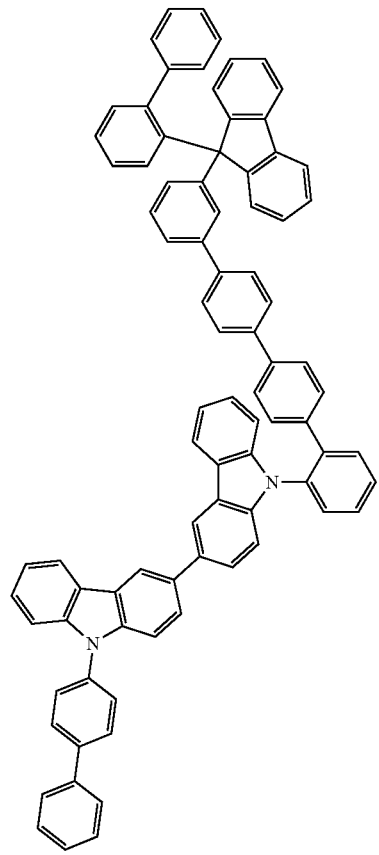
A267
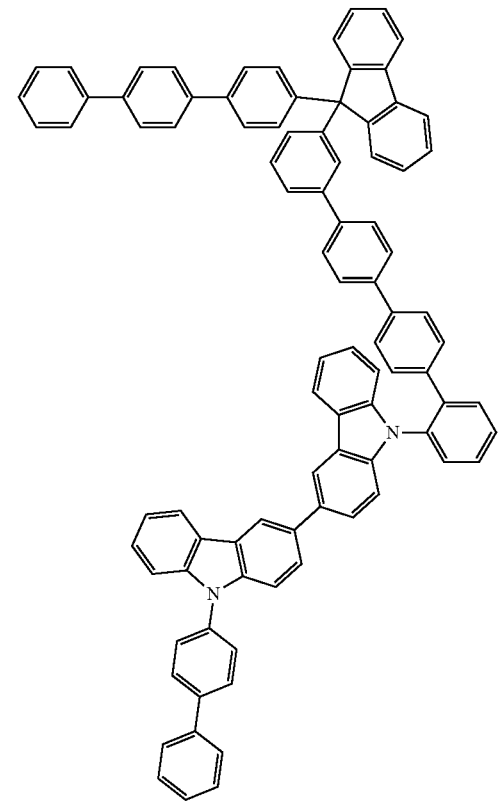

-continued
A268
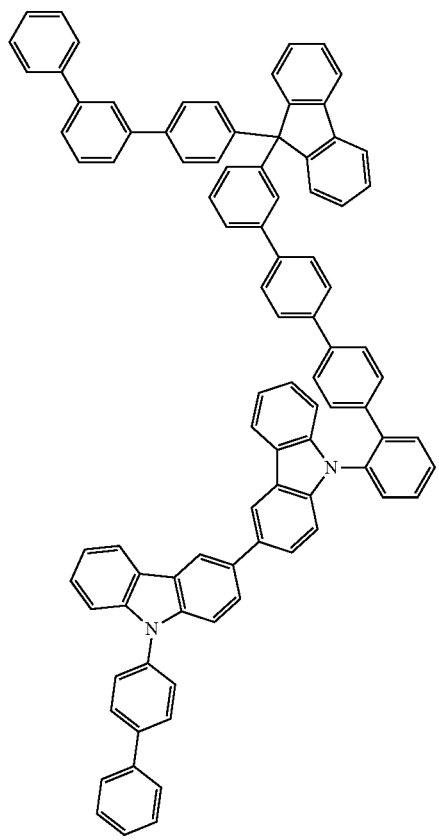
A269
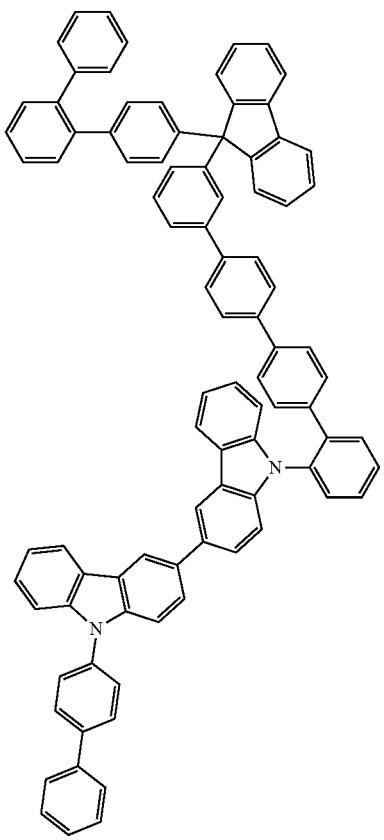
A270
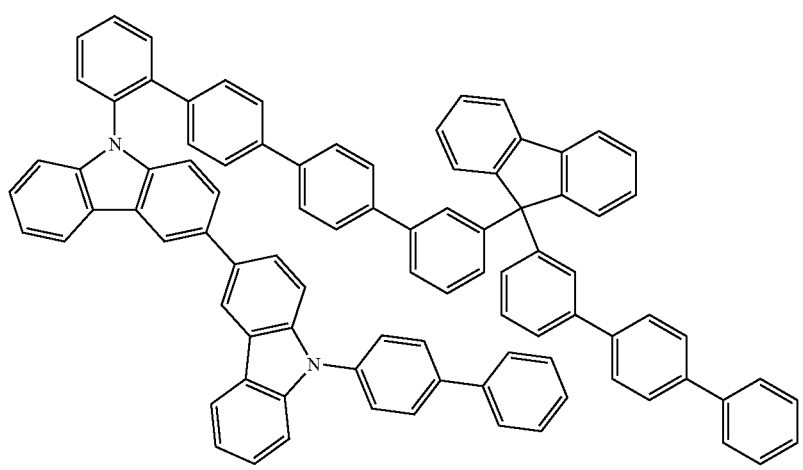

A271
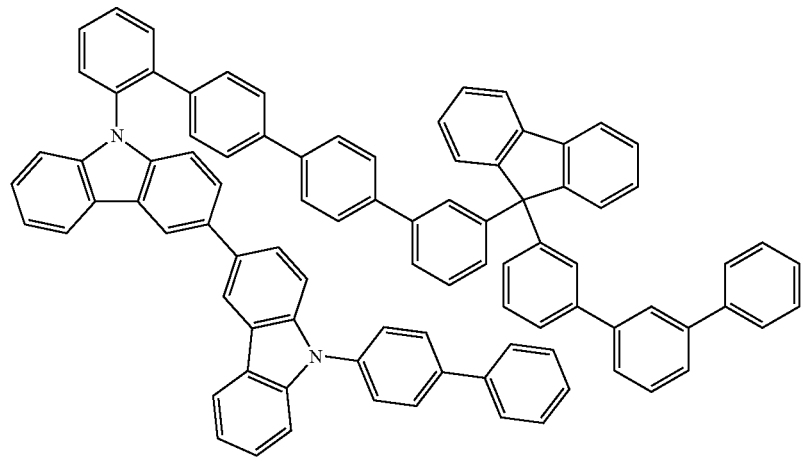
A272
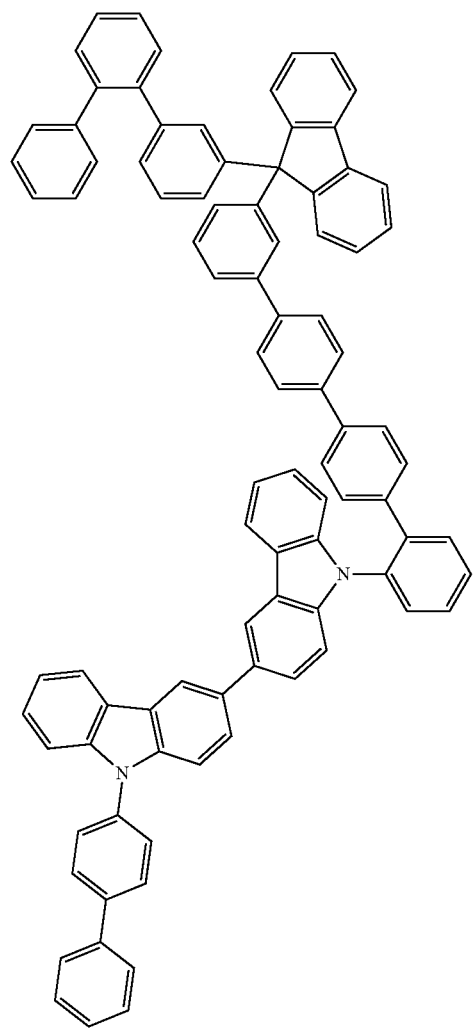
A273
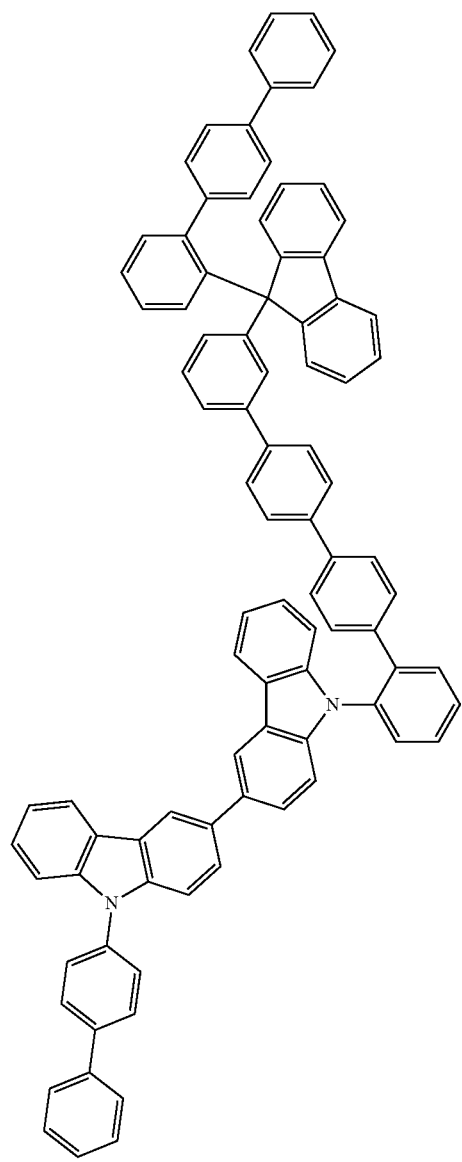

-continued
A274
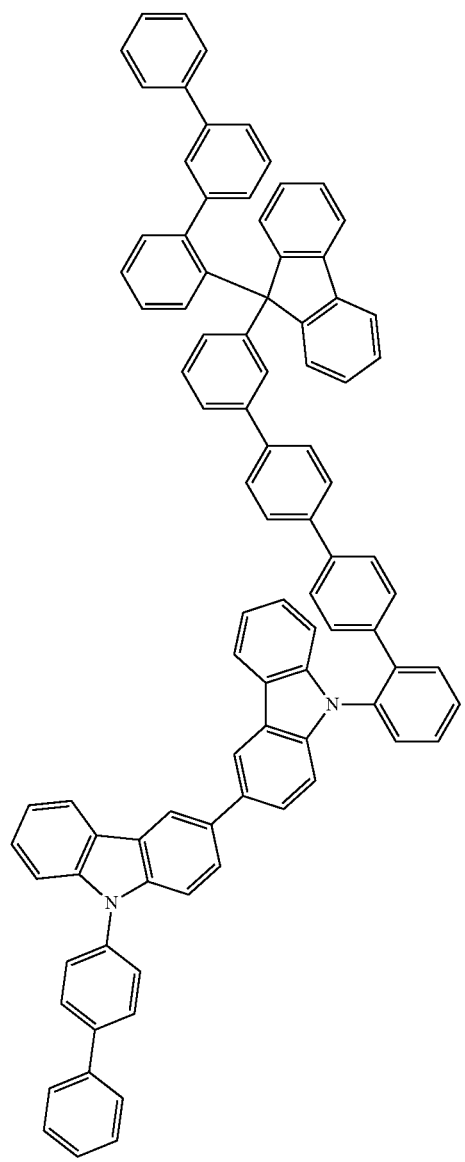
693
A275
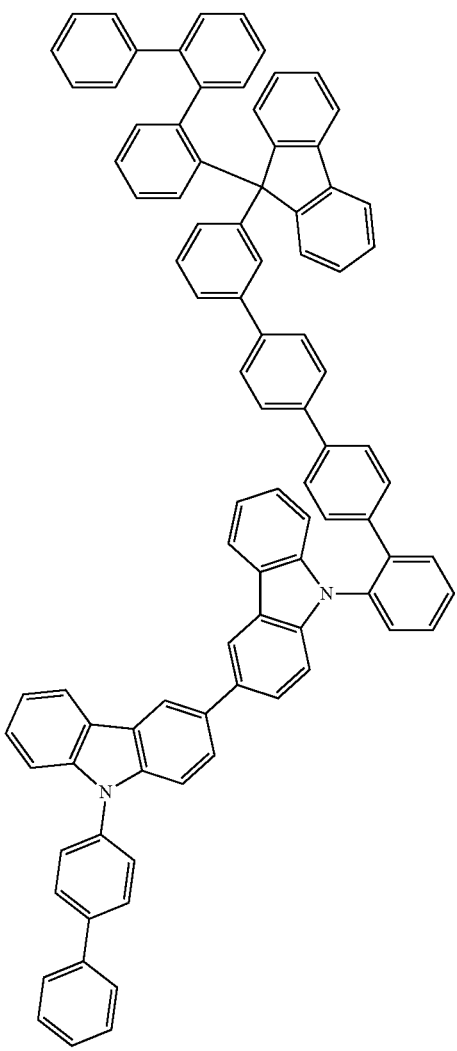
694

-continued
A276
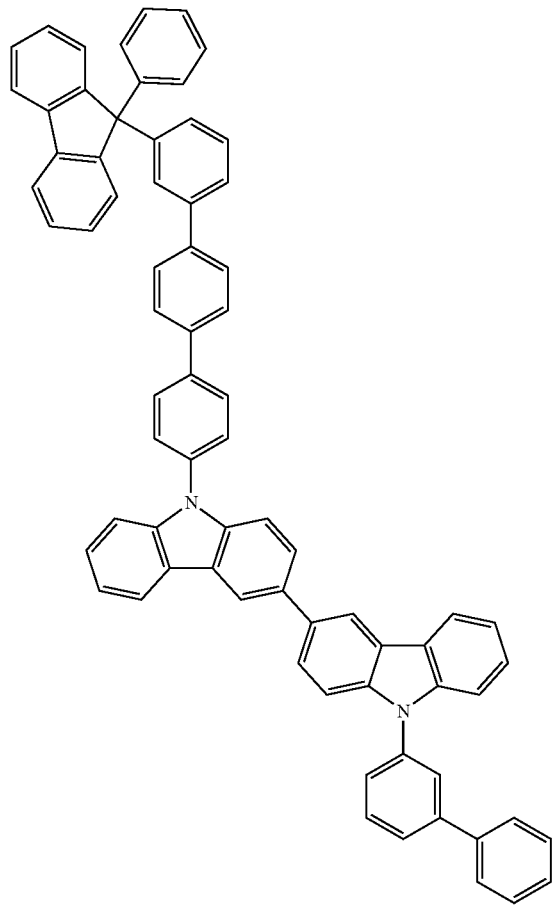
A277
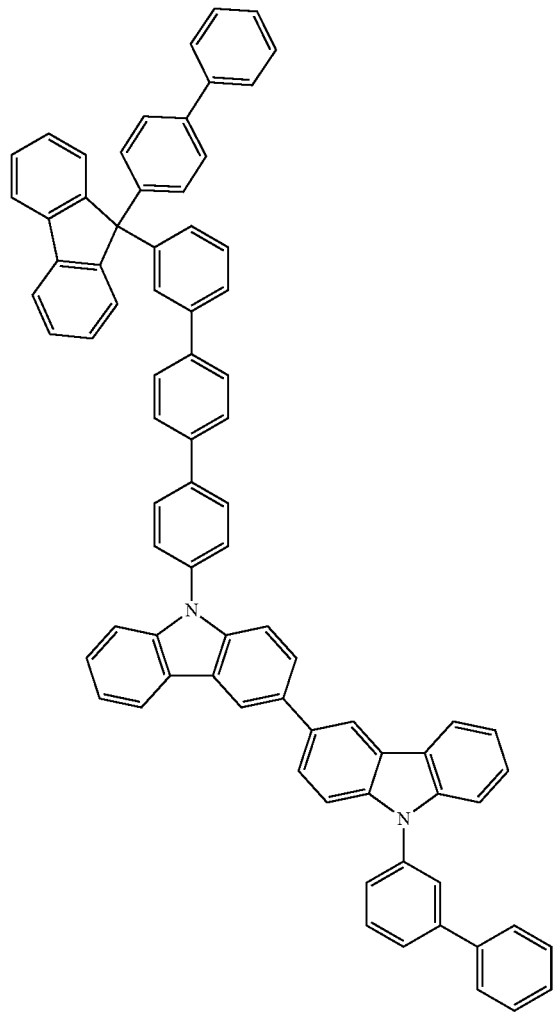

-continued
697
A278
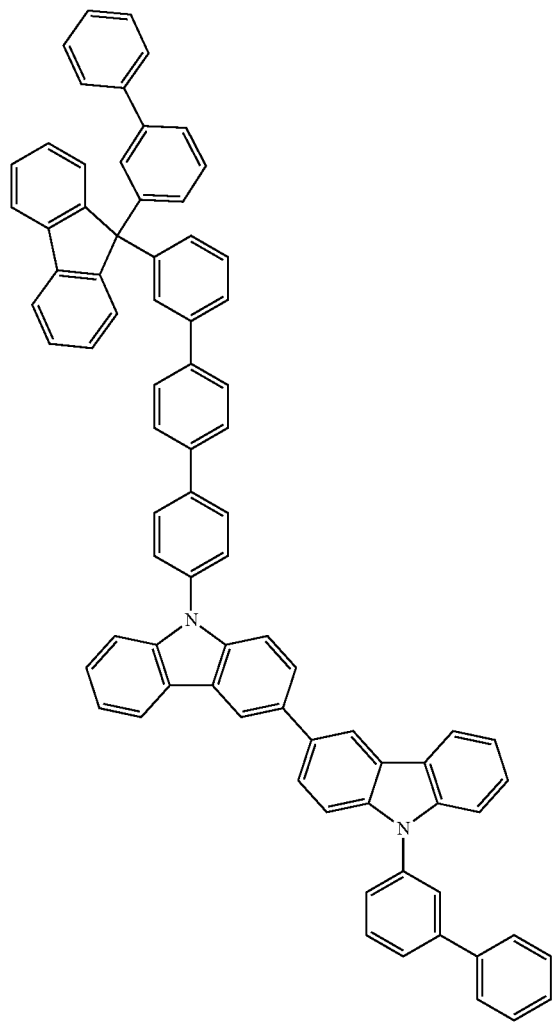
698
A279
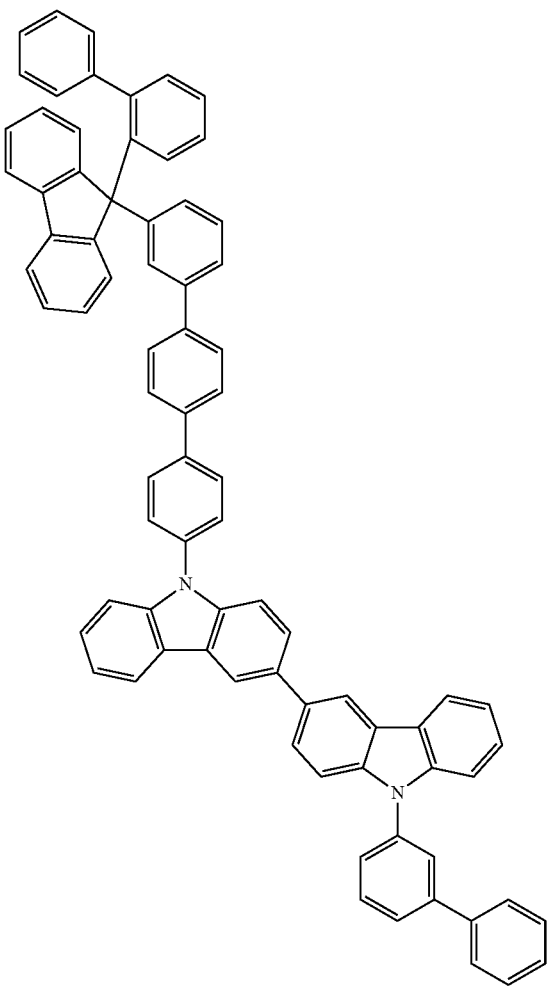

-continued
A280
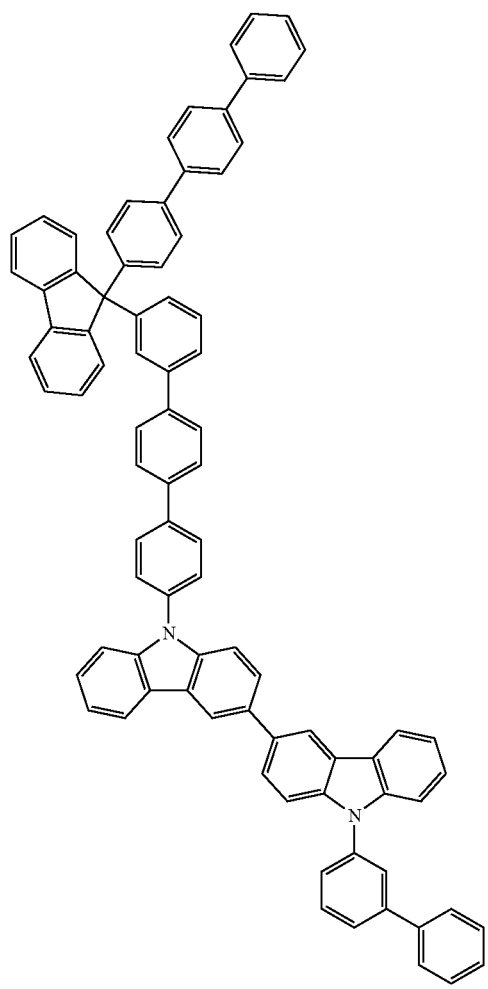
A281
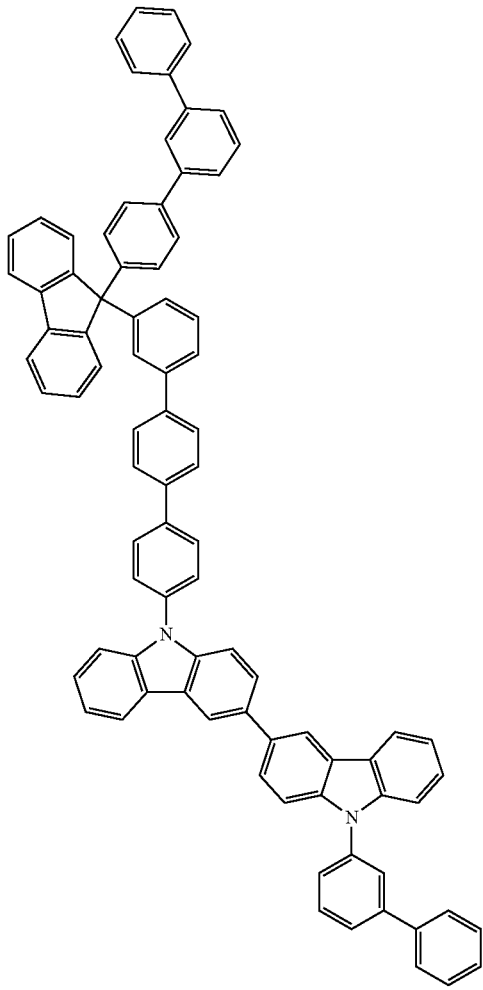

-continued
A282
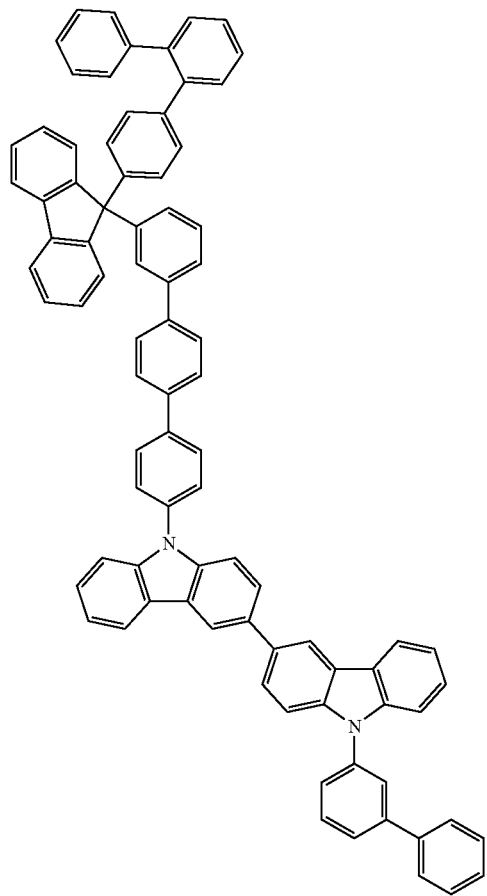
A283
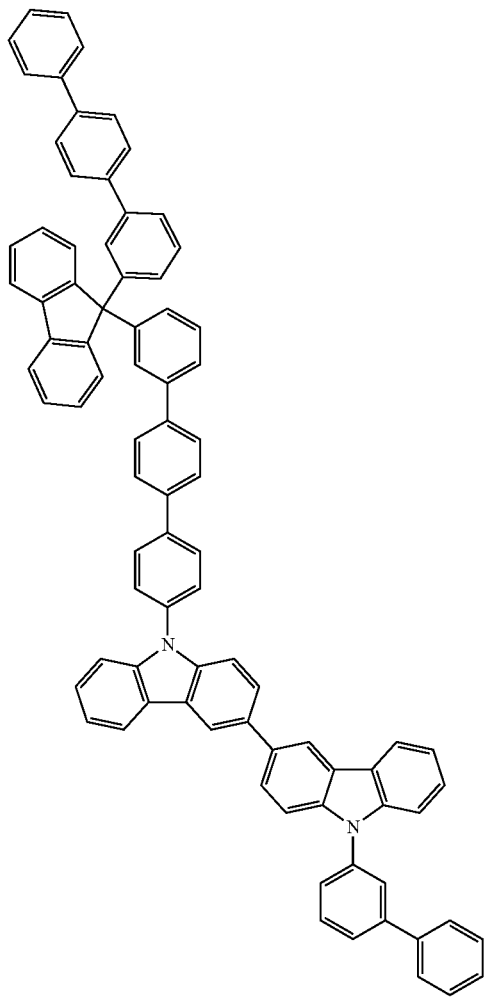

-continued
A284
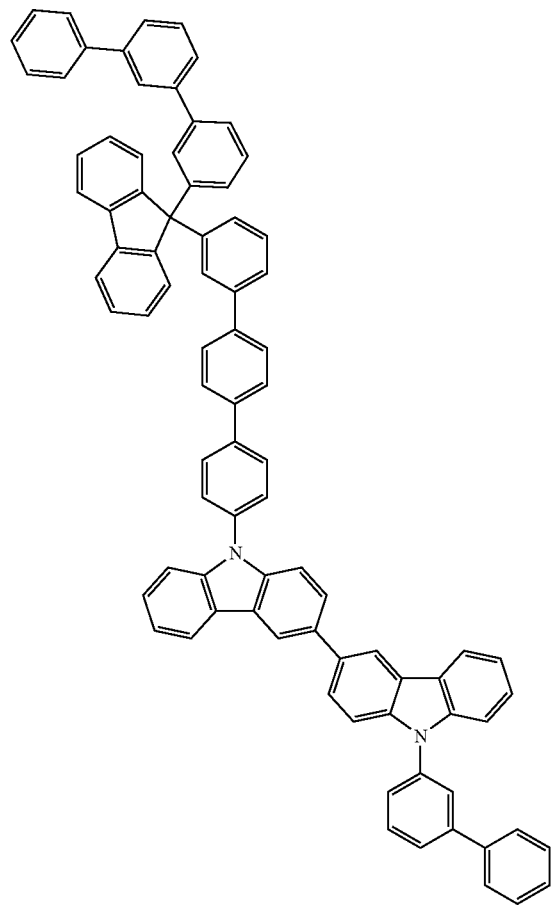
A285
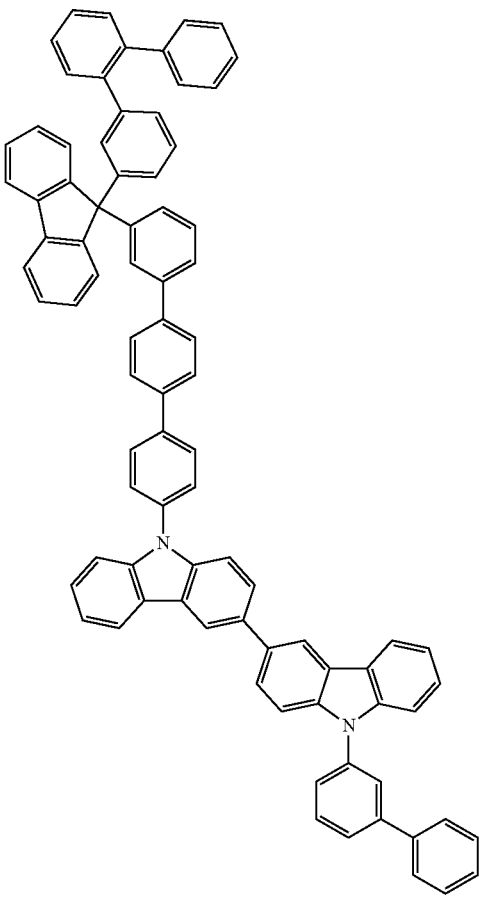

-continued
A286
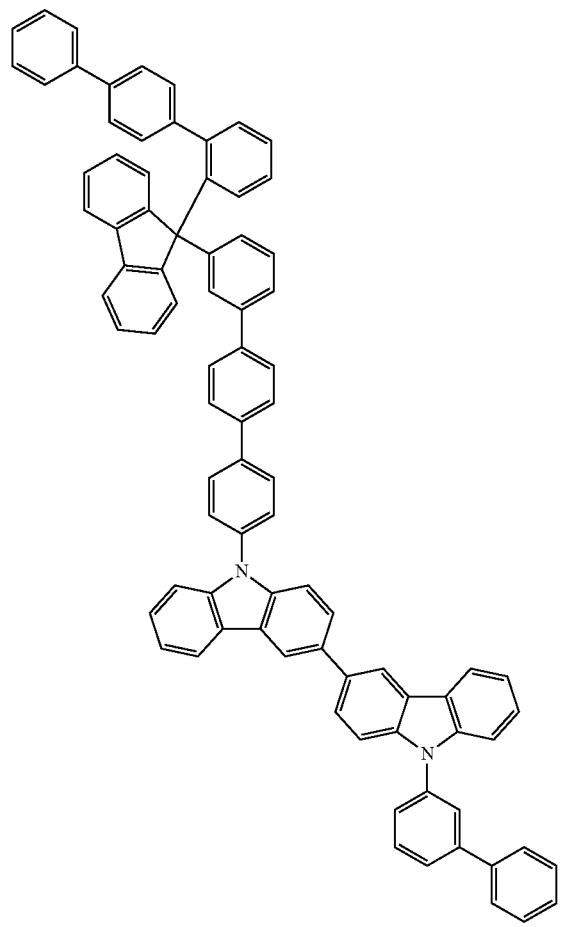
A287
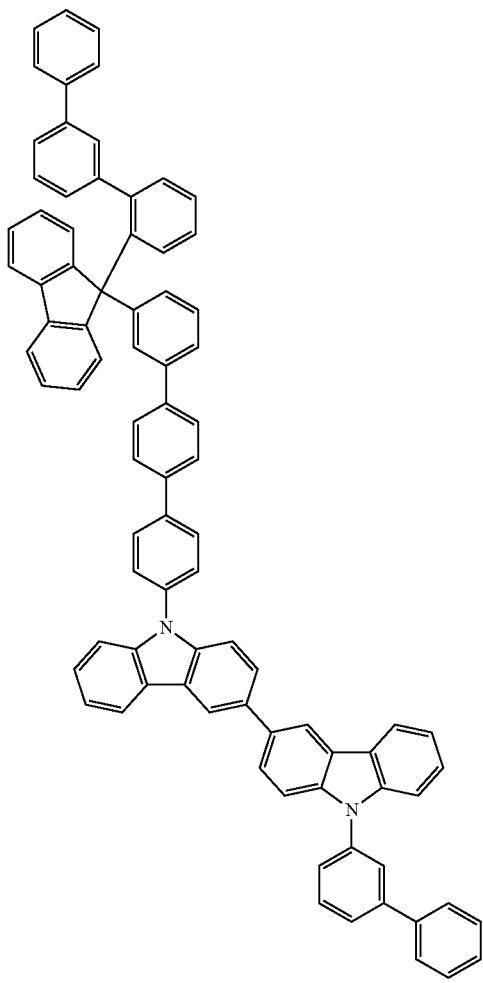

-continued
707
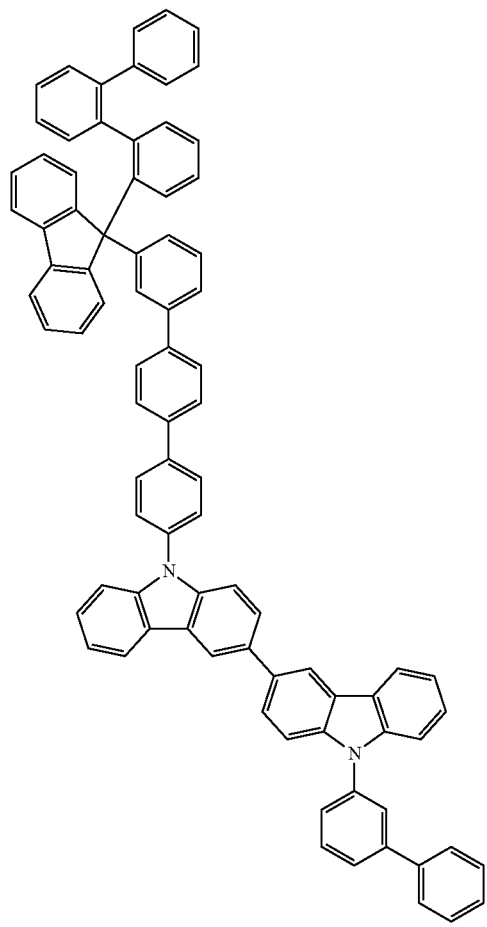
A288
708
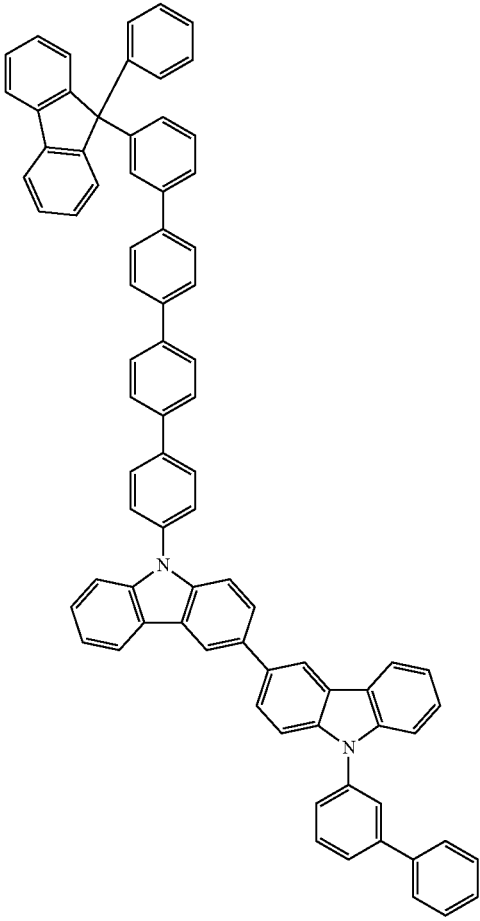
A289

-continued
A290
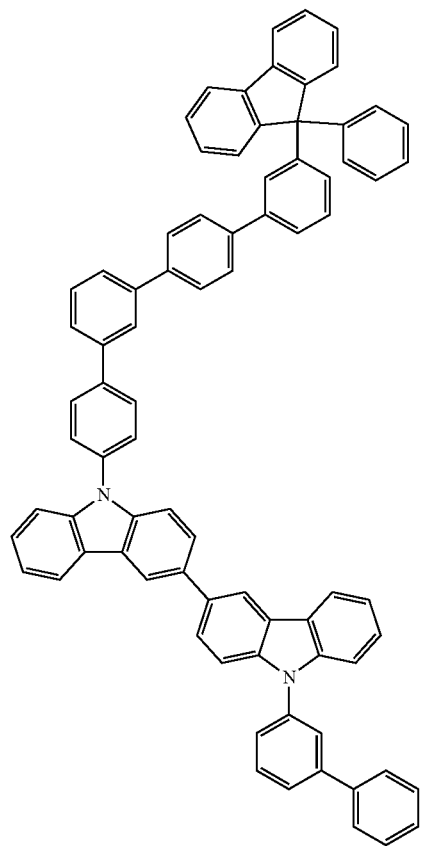
A291
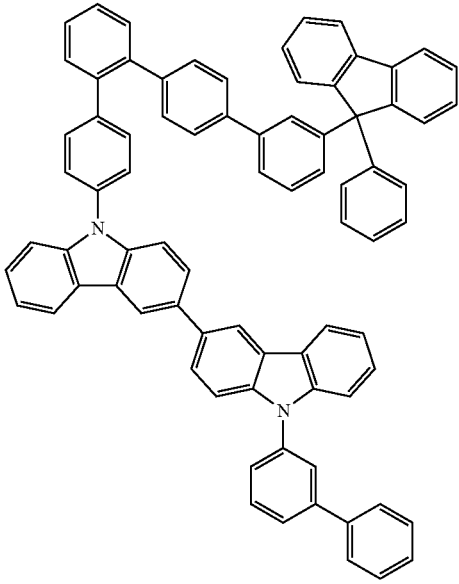
A292
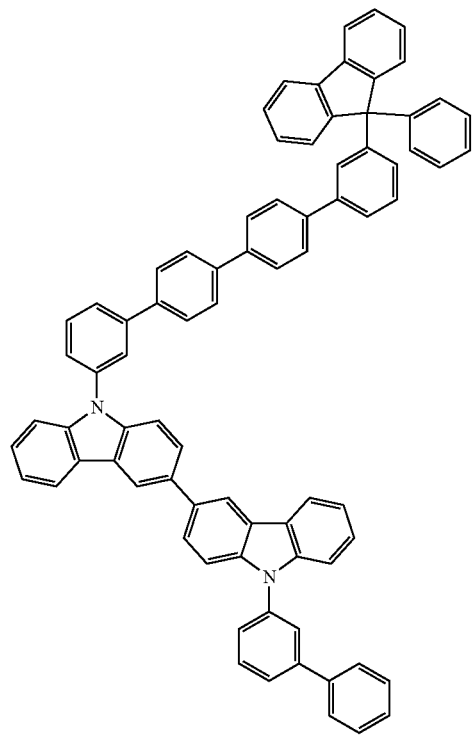
A293
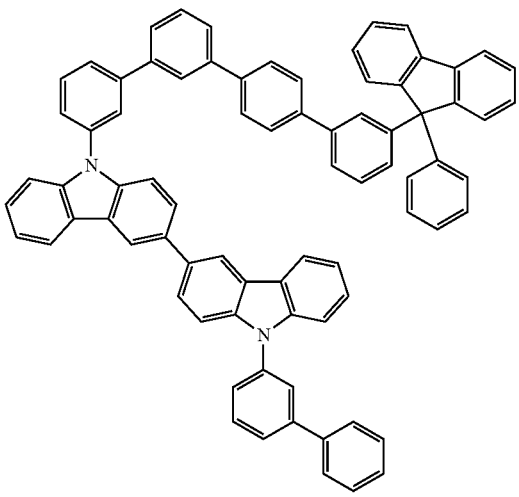

-continued
A294
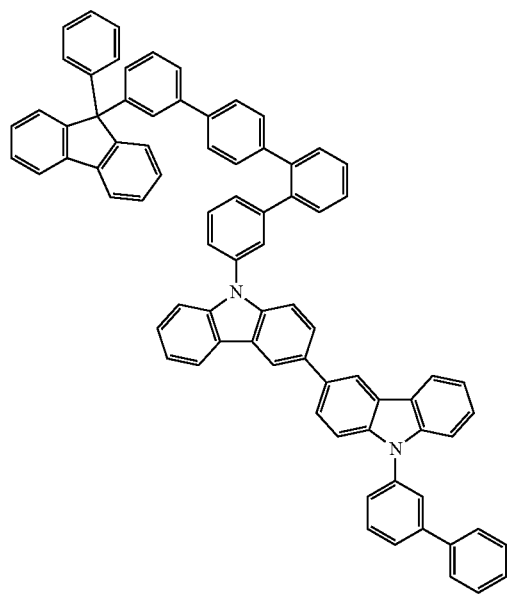
A295
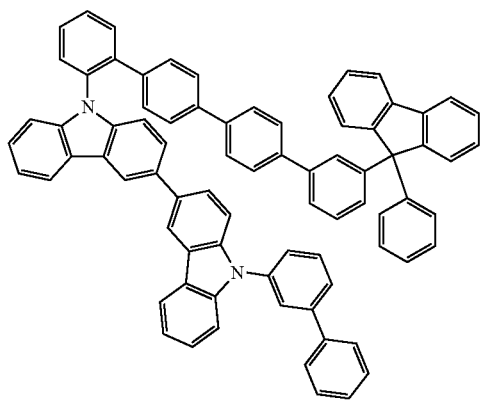
A296
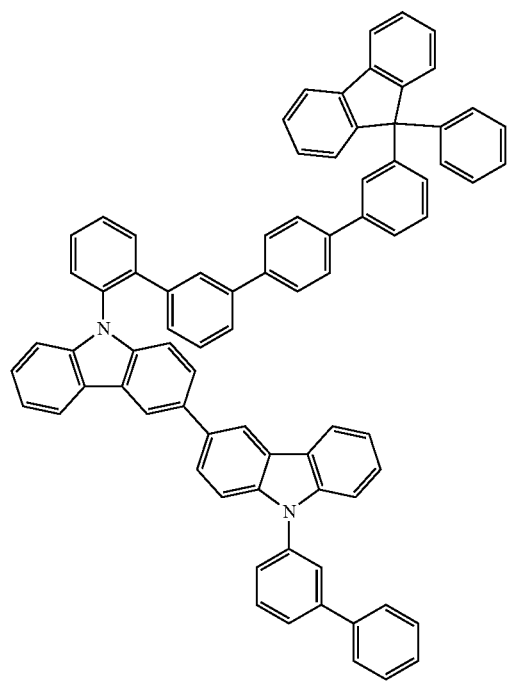
A297
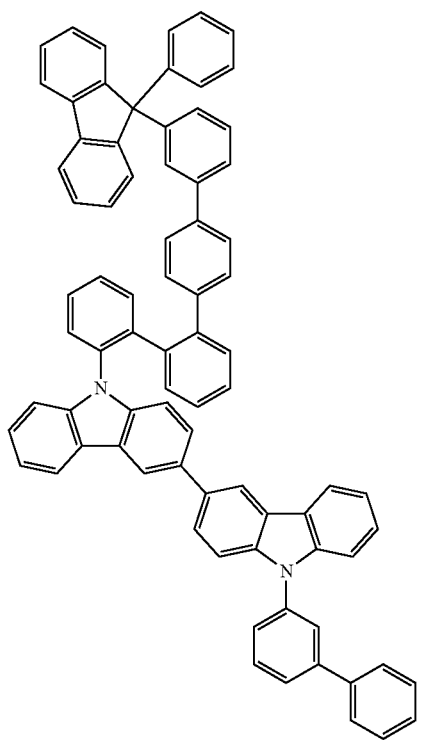

-continued
A298
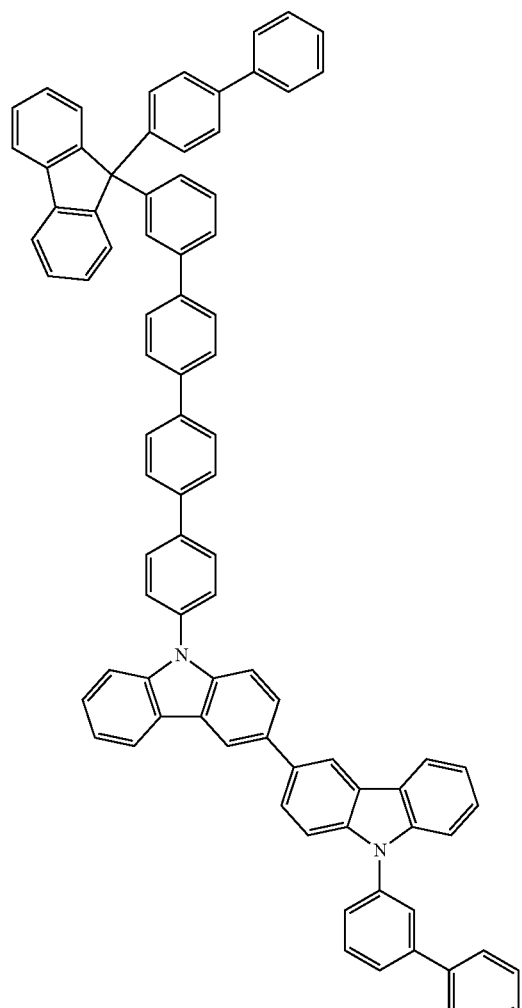
A299
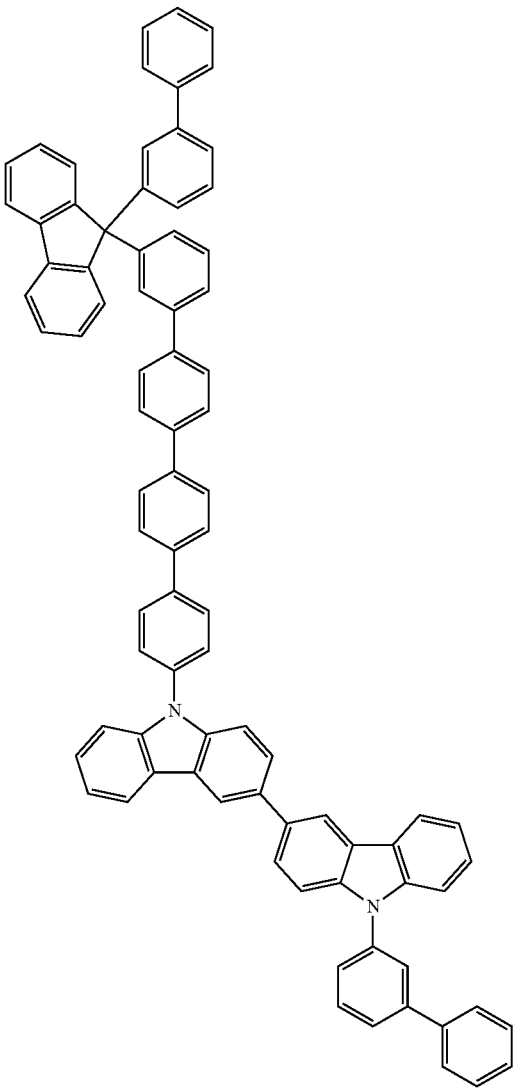

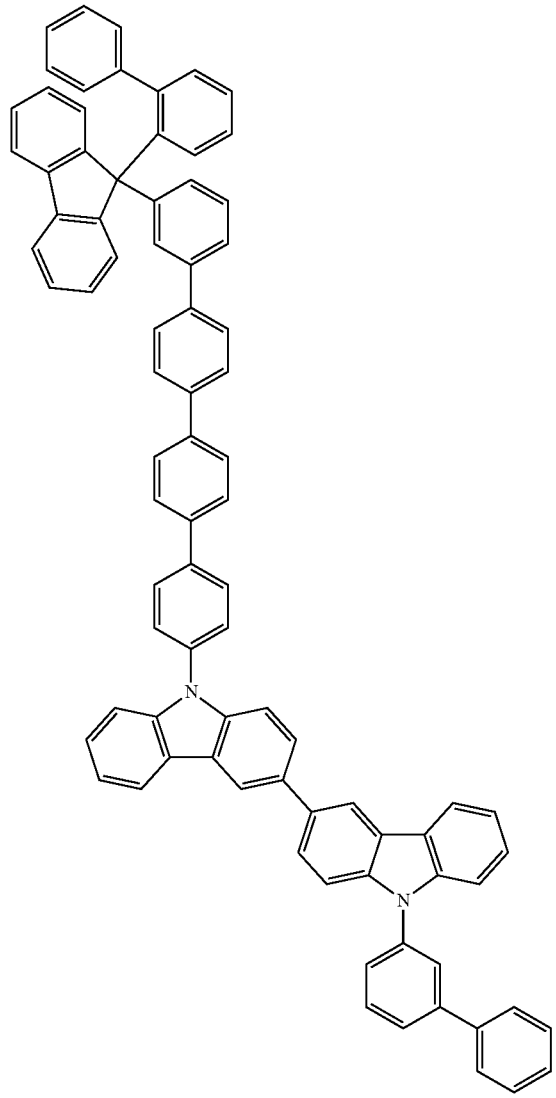
A300

717 718
A301
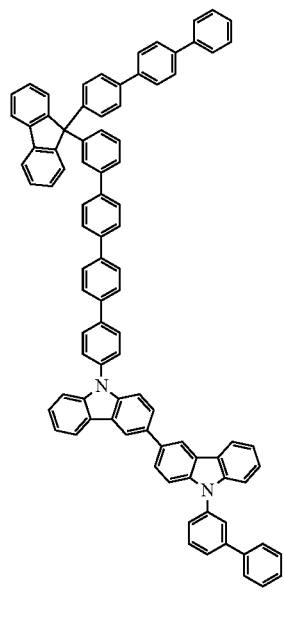
A302
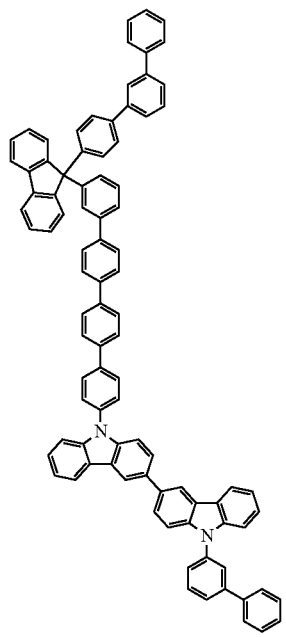
A303
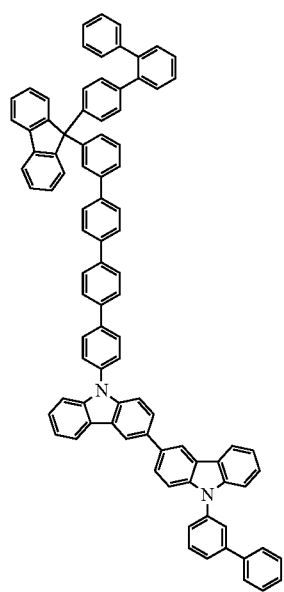
A304
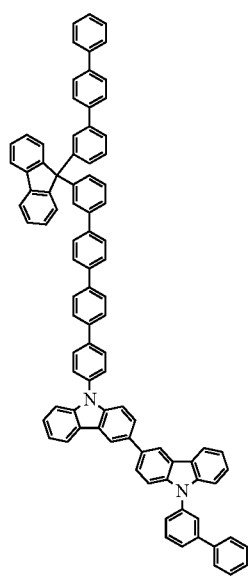

-continued
A305
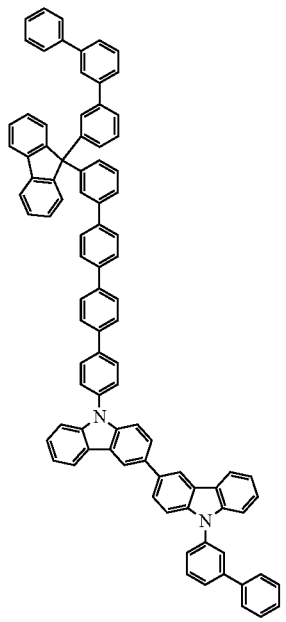
A306
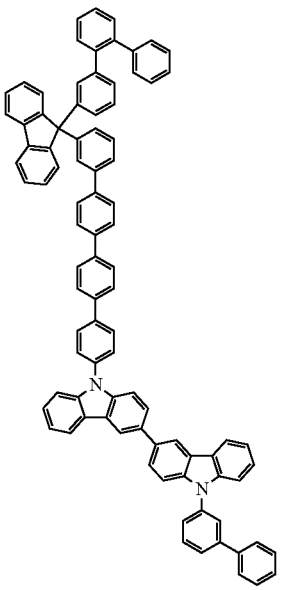
A307
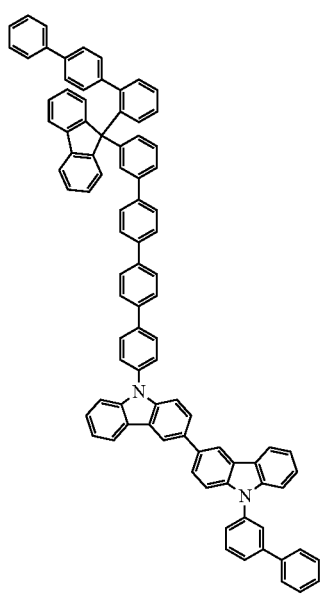
A308
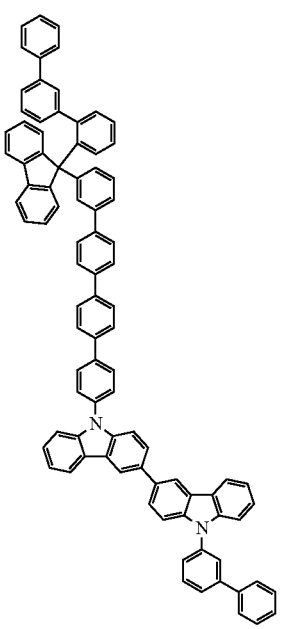

-continued
A309
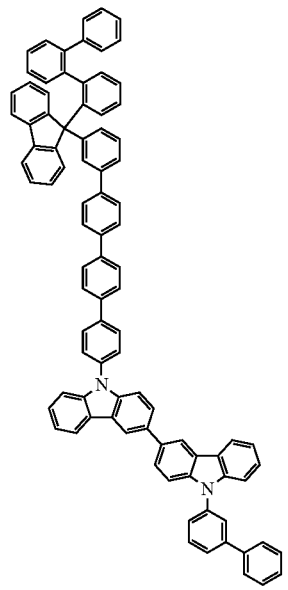
A310
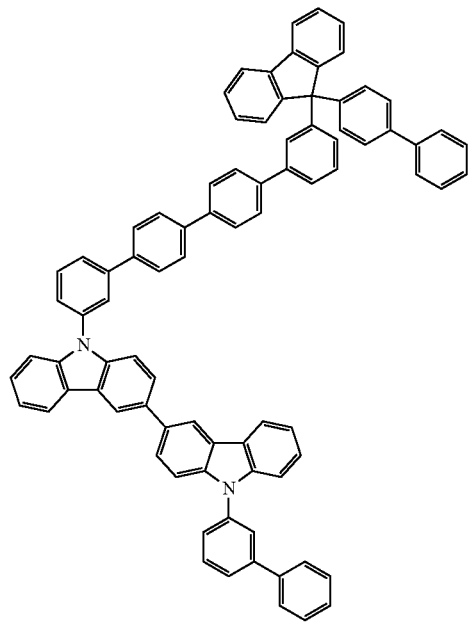
A311
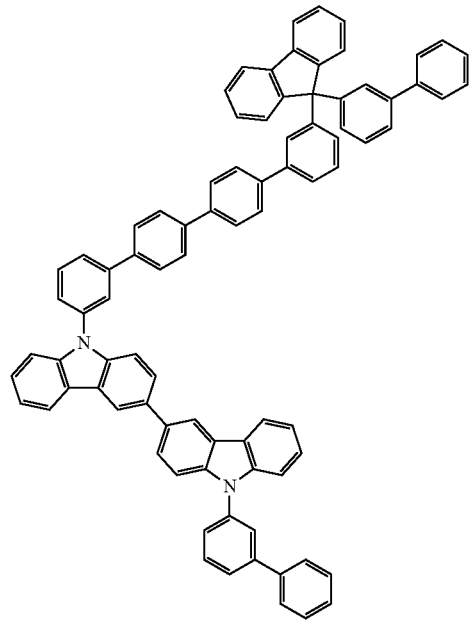
A312
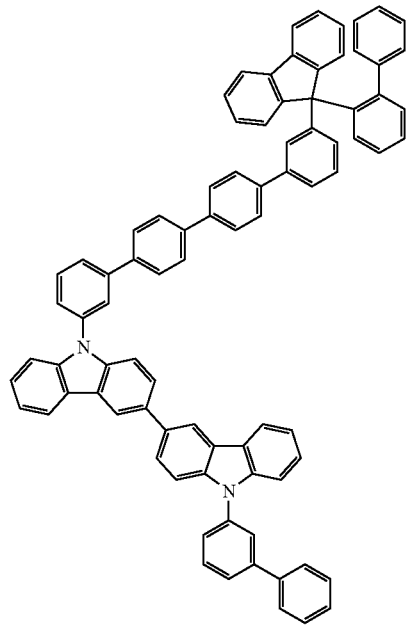

-continued
723 A313
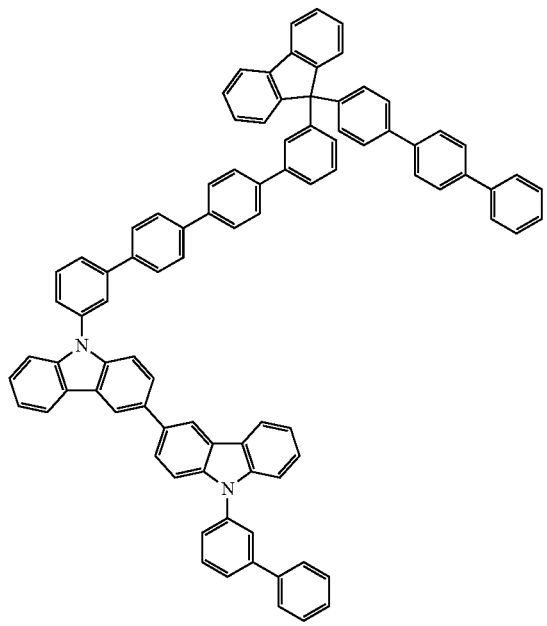
724 A314
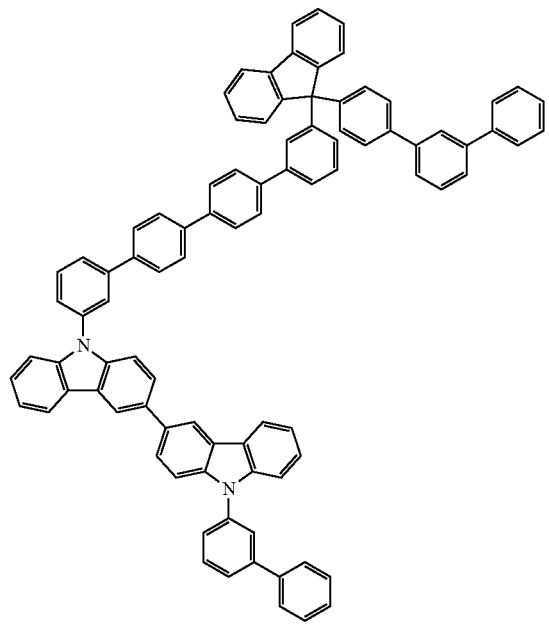
A315
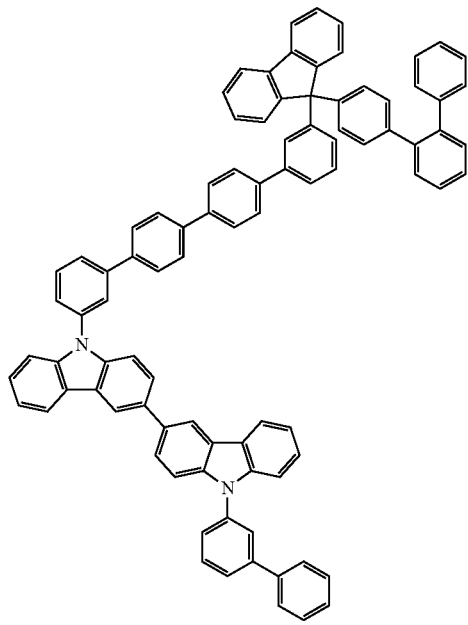
A316
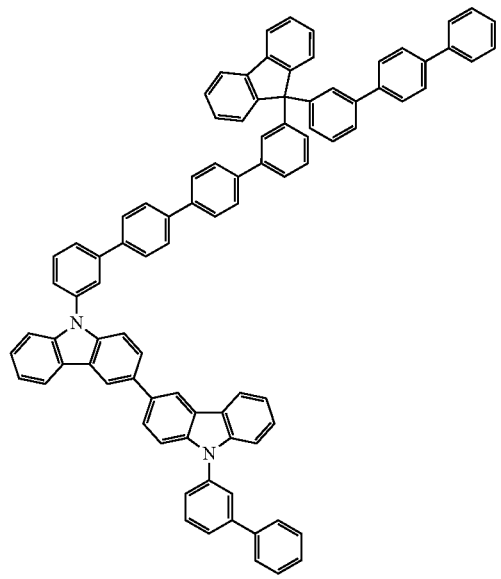

-continued
725 A317
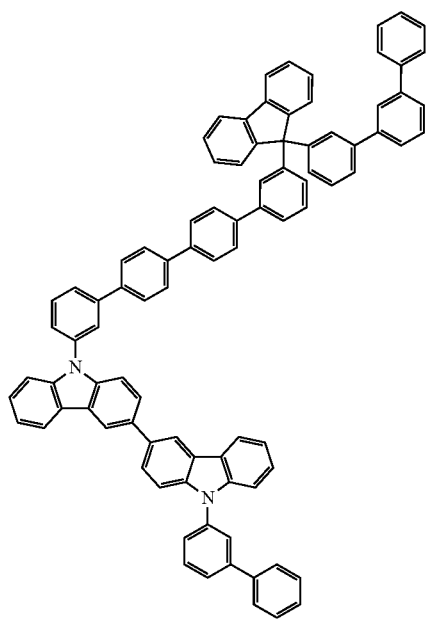
726 A318
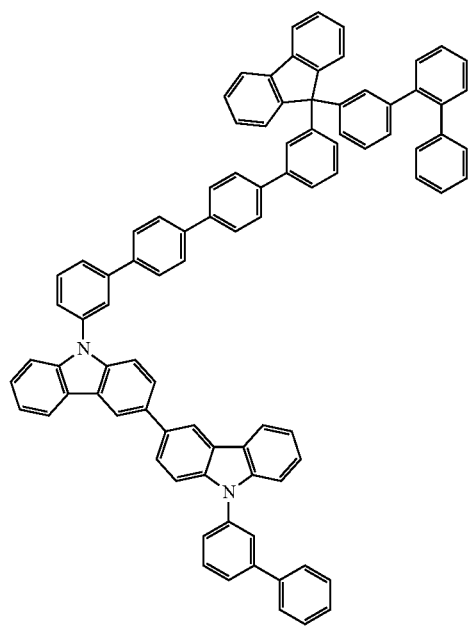
A319
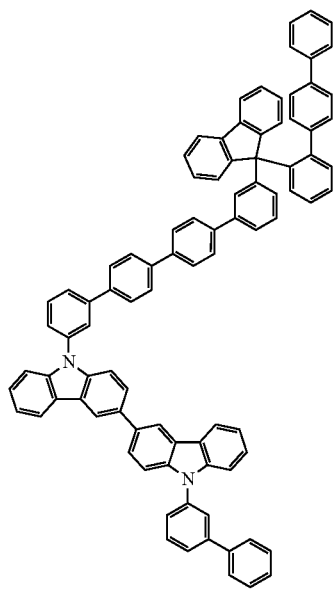
A320
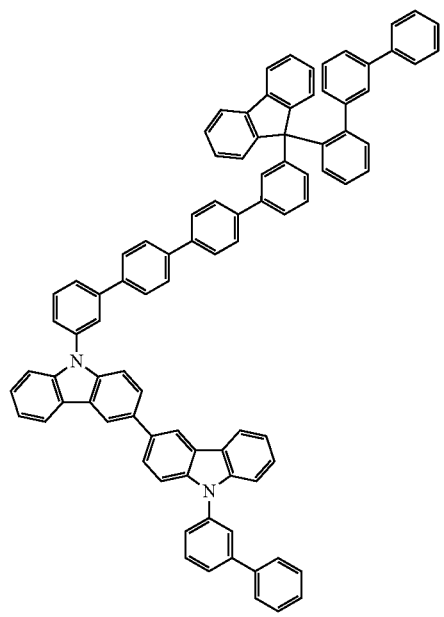

-continued
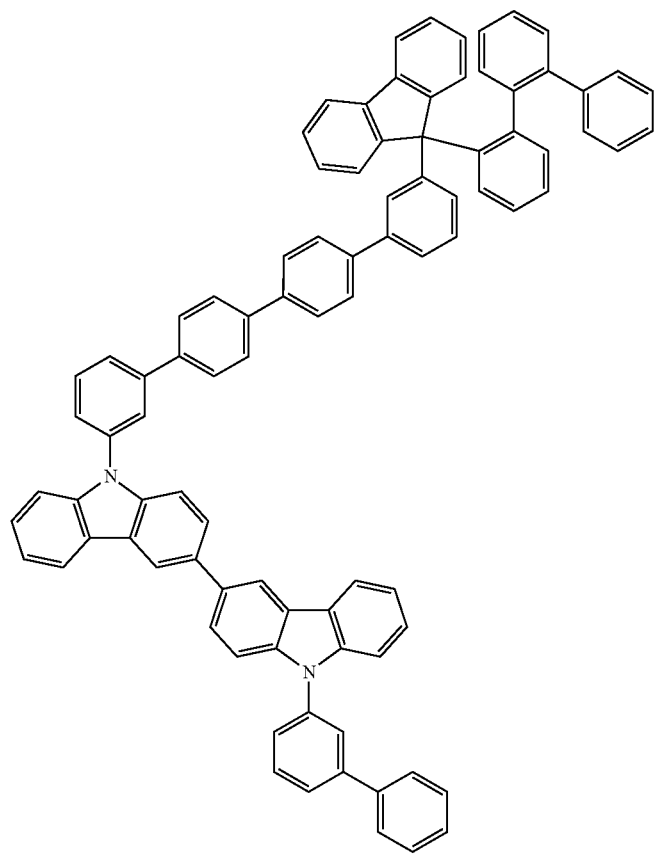
A321
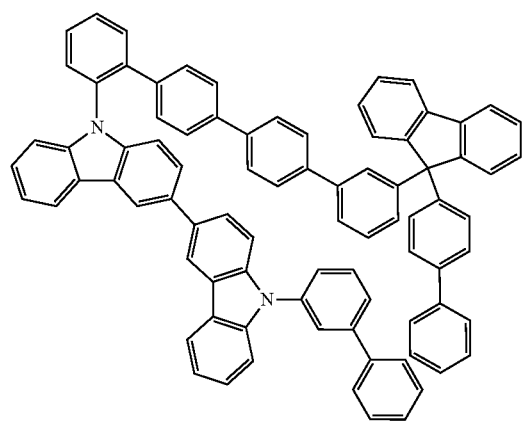
A322
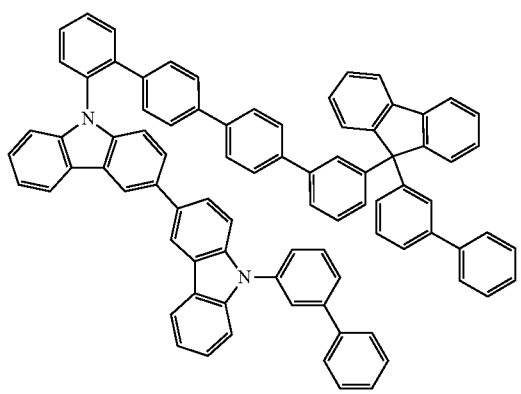
A323

-continued
A324
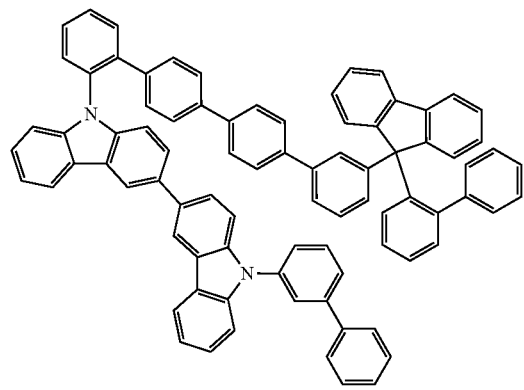
A325
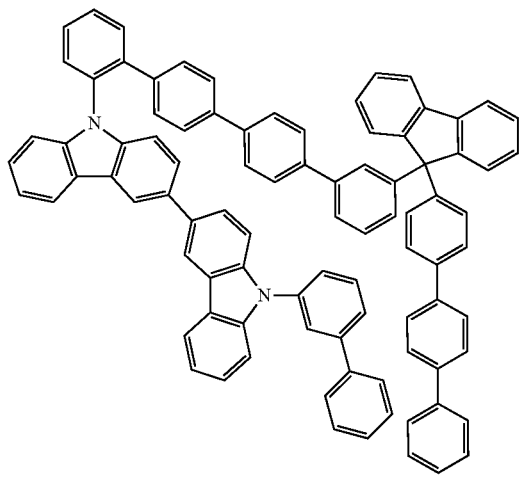
A326
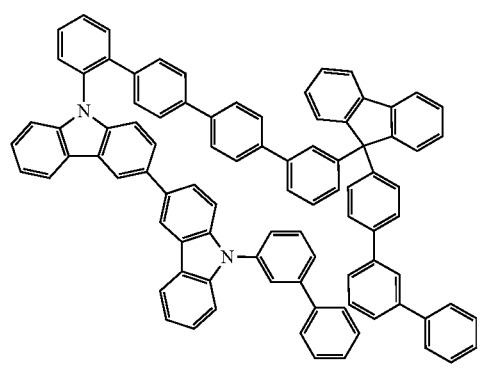
A327
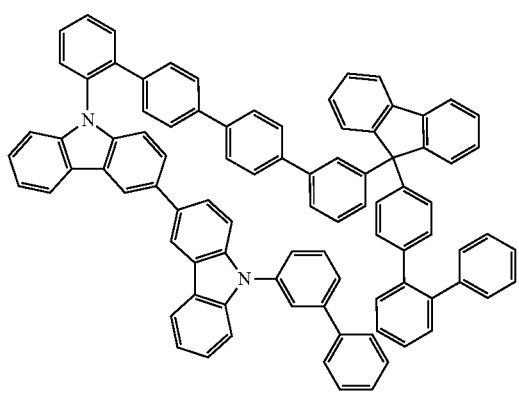
A328
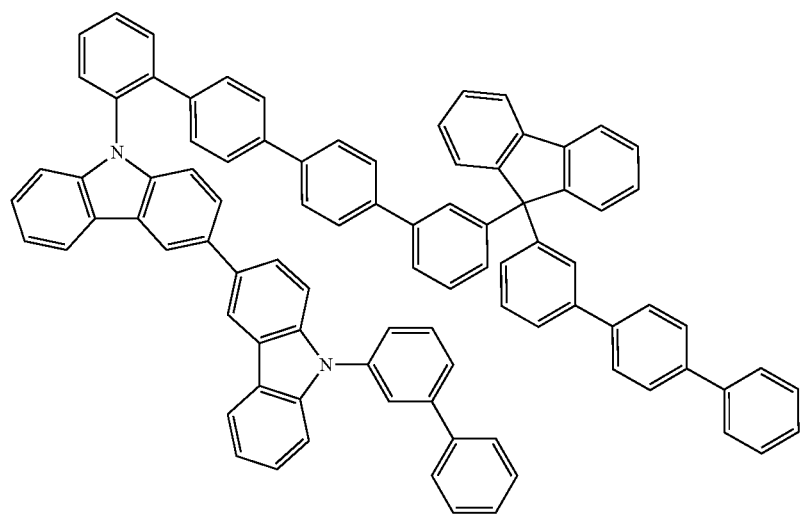

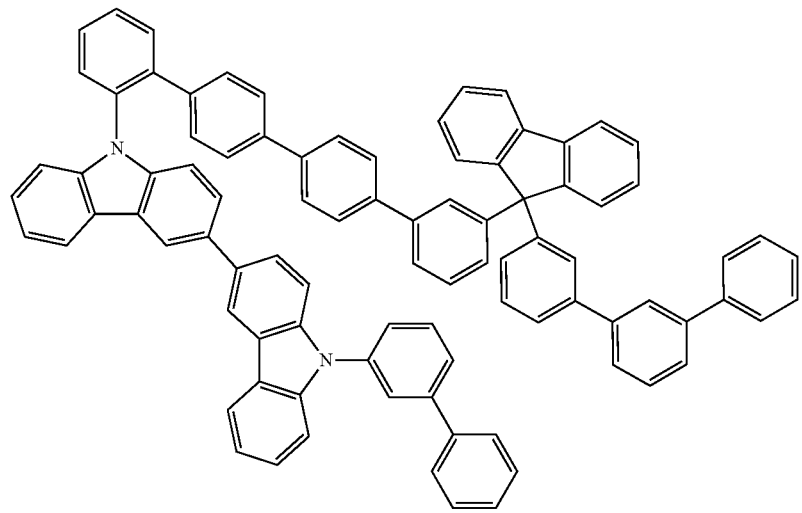
A329
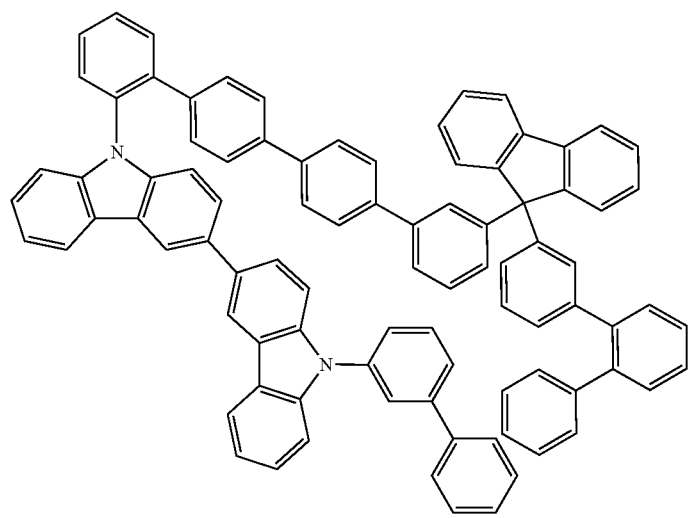
A330
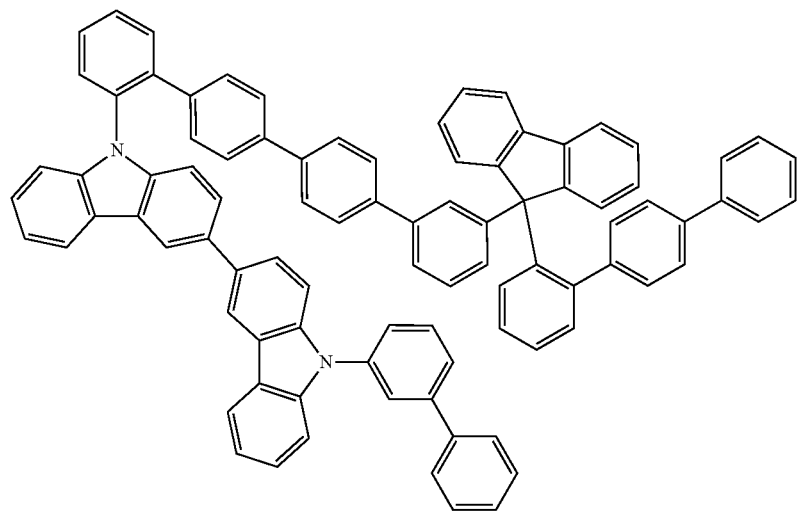
A331

A332
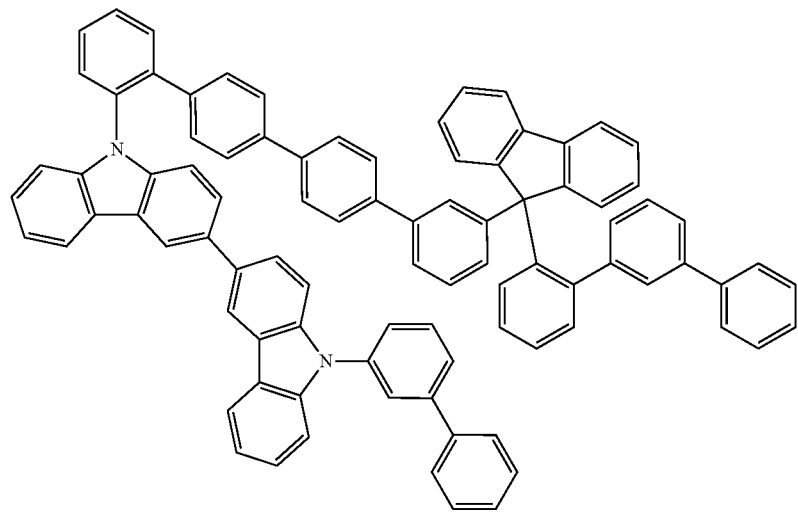
A333
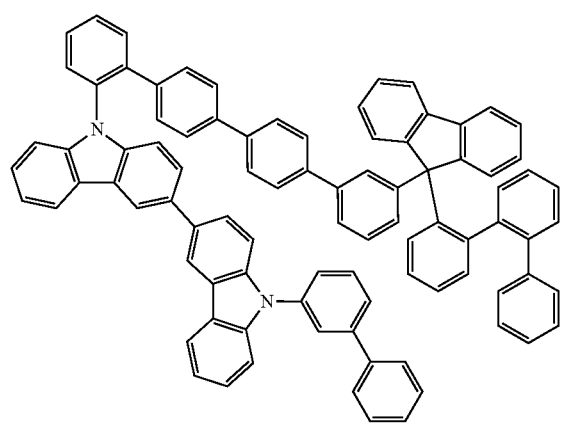
A334
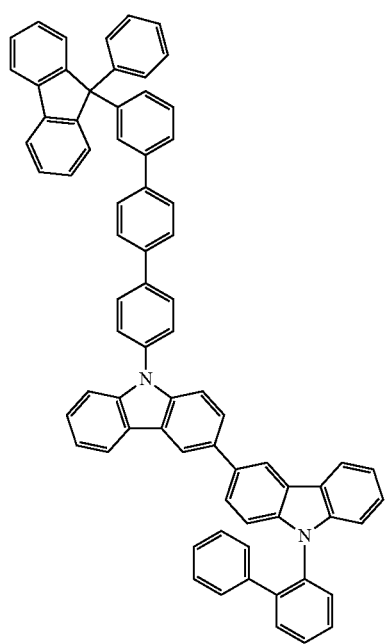

-continued
A335 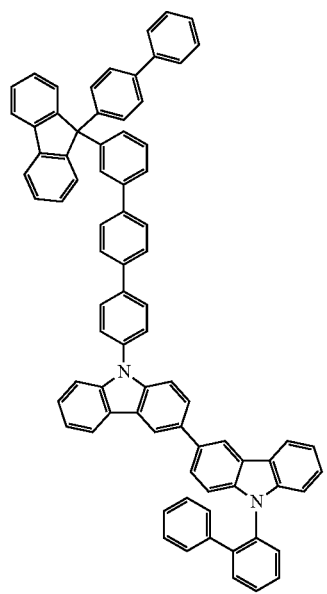 A336 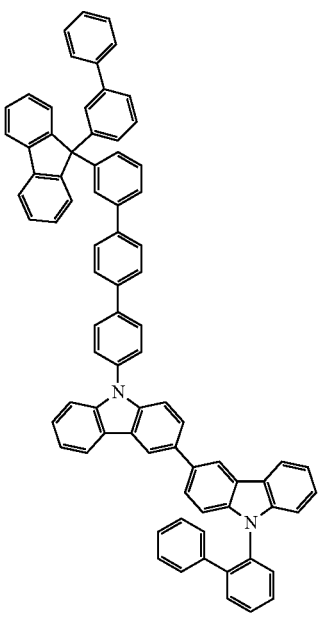
A337 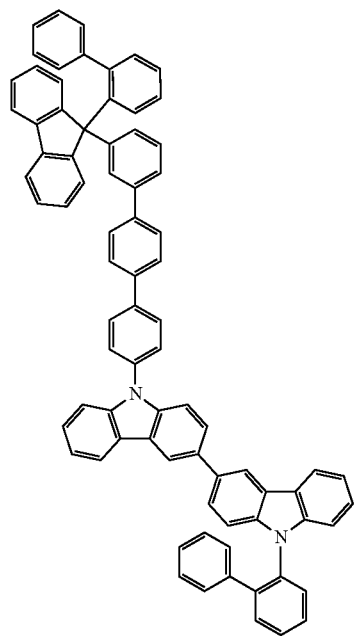 A338 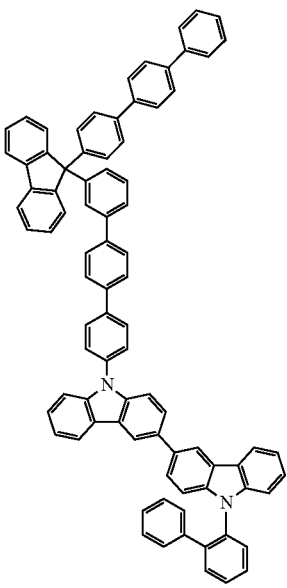

-continued
A339
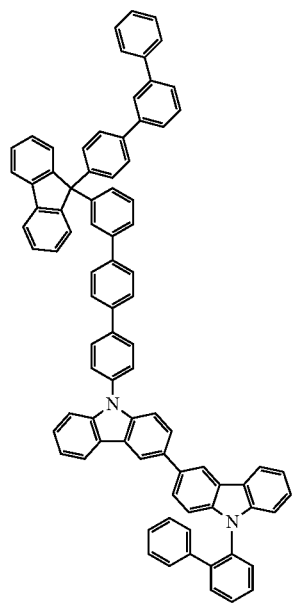
A340
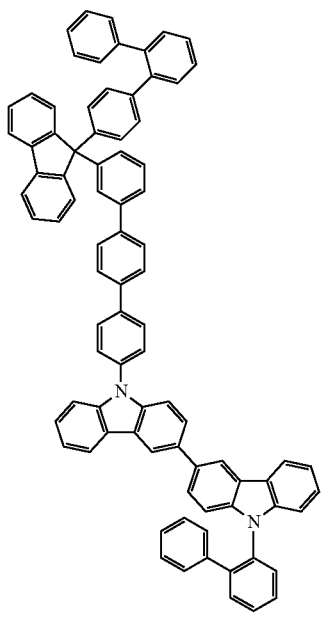
A341
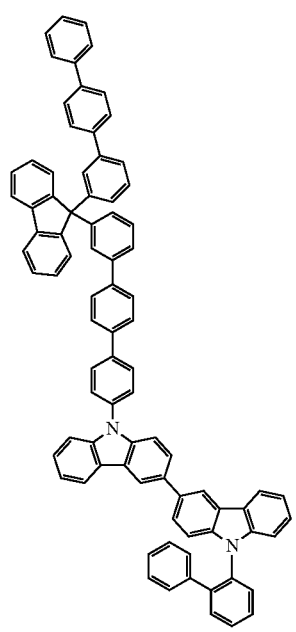
A342
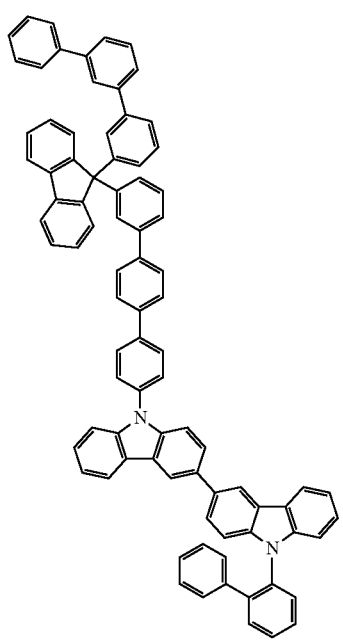

-continued
A343
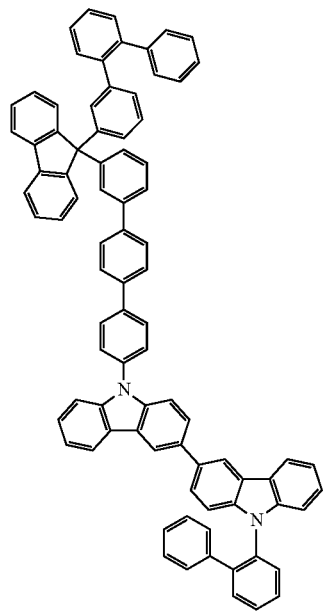
A344
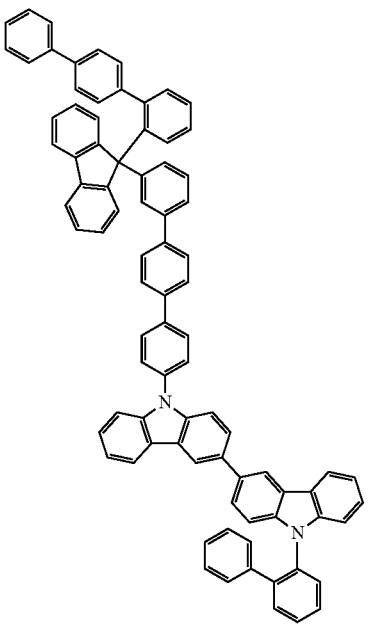
A345
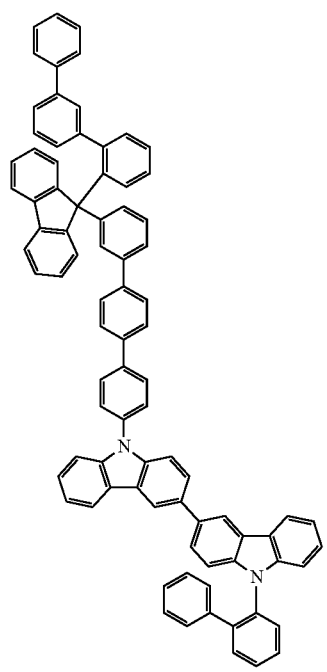
A346
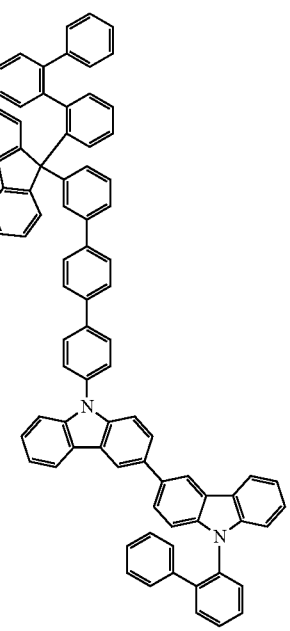

-continued
A347
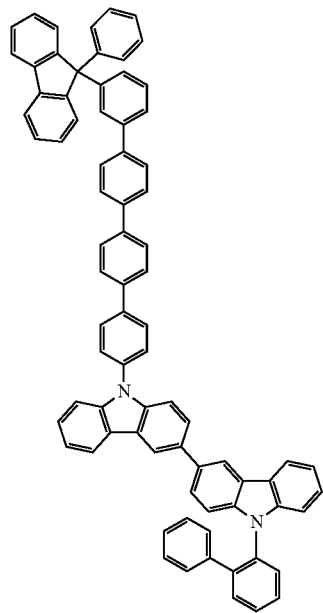
A348
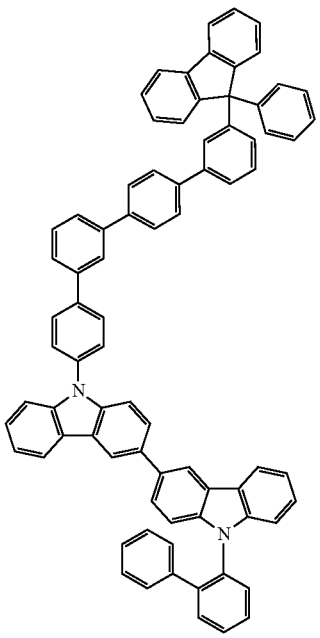
A349
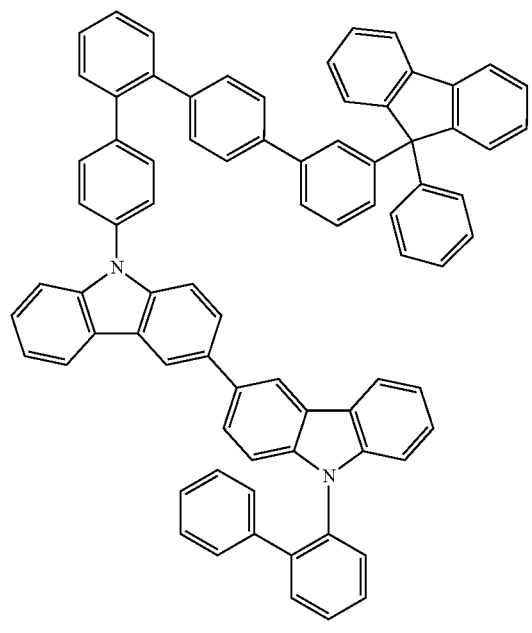
A350
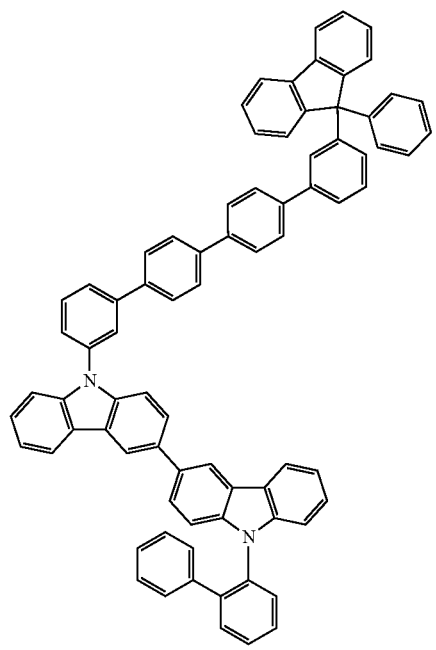

-continued
A351
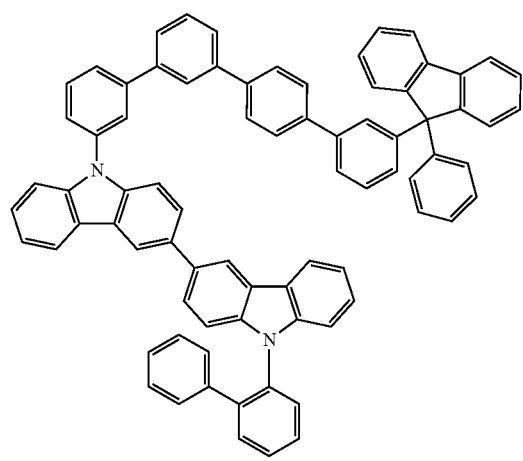
A352
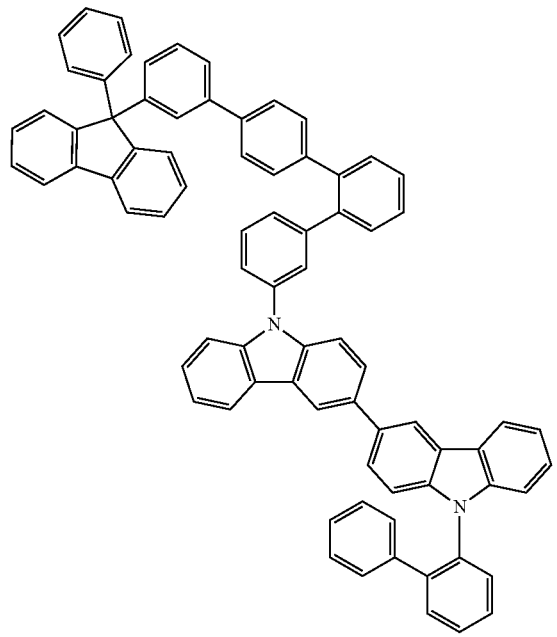
A353
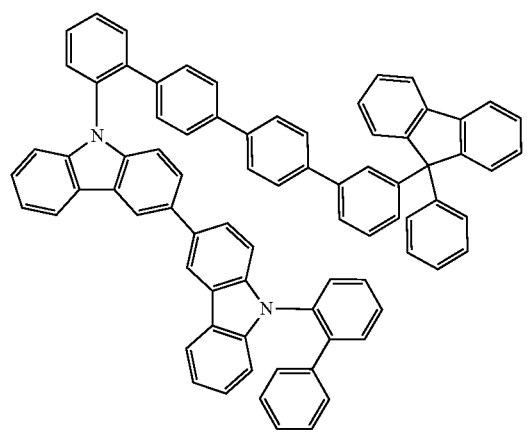
A354
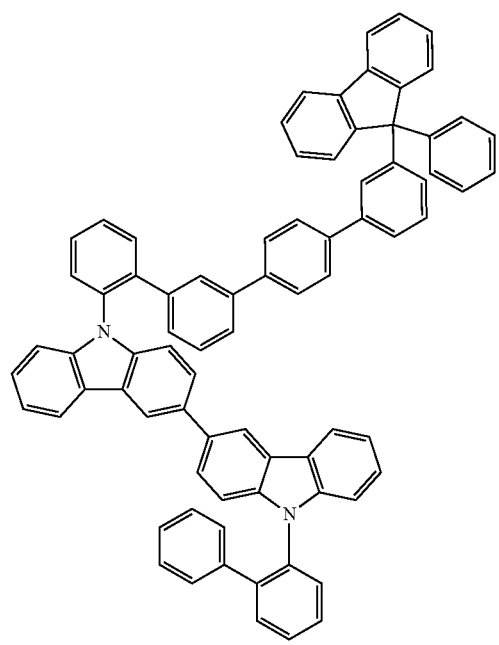

-continued
A355
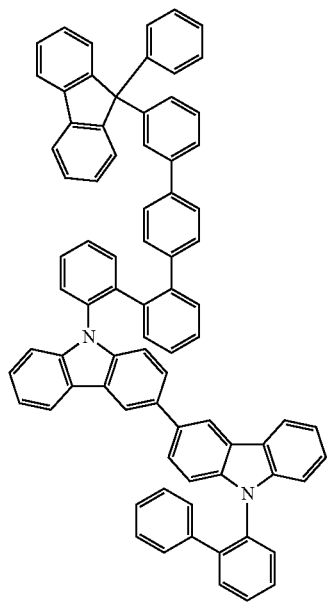
A356
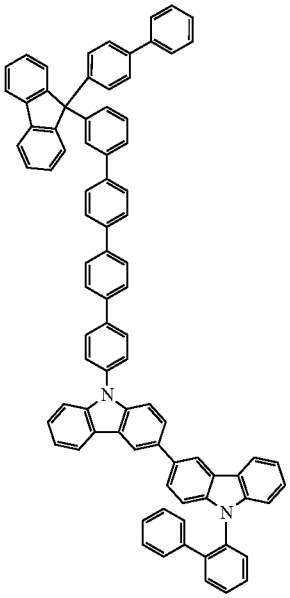
A357
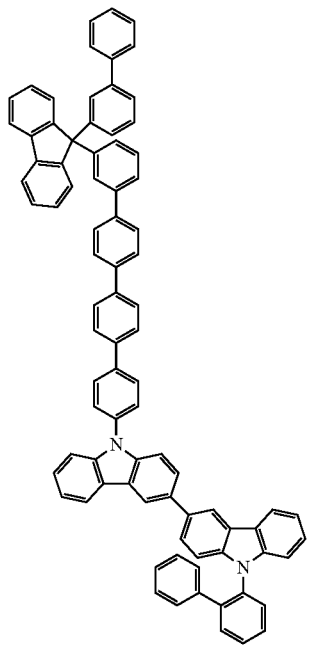
A358
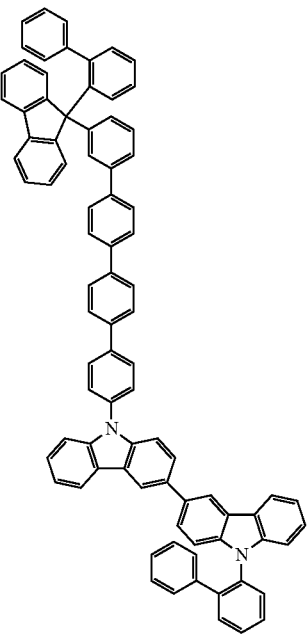

-continued
A359
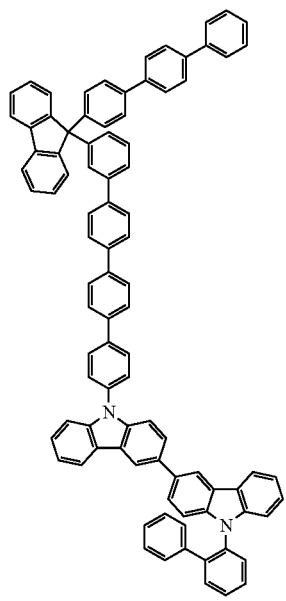
A360
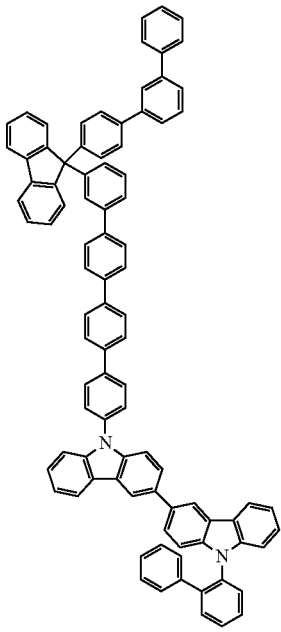
A361
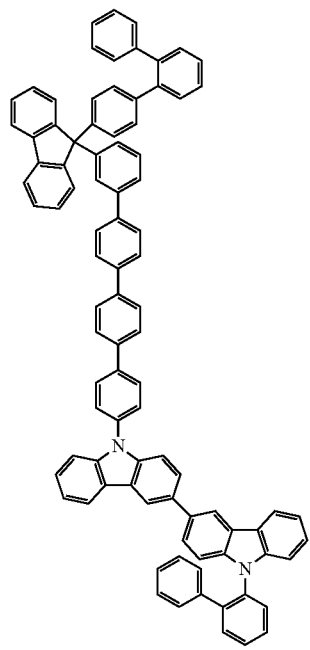
A362
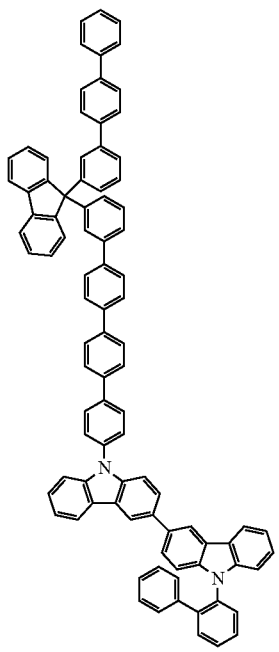

-continued
A363
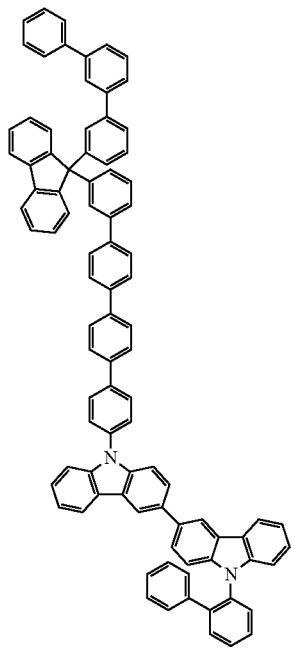
A364
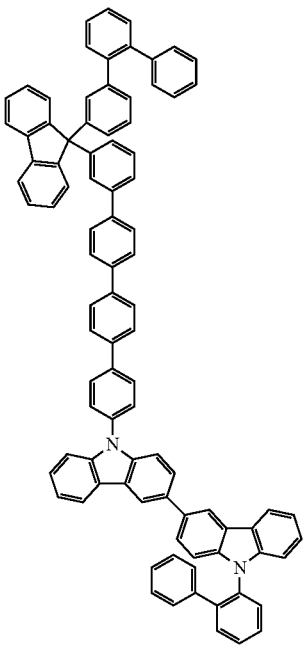
A365
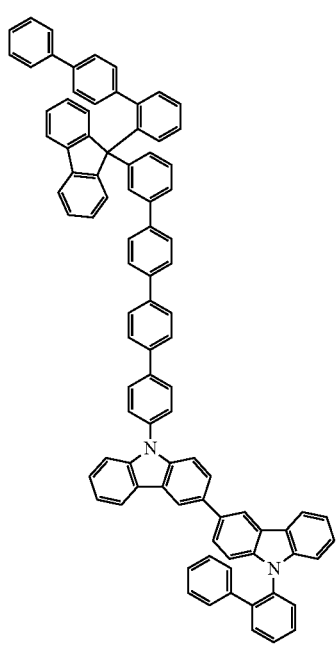
A366
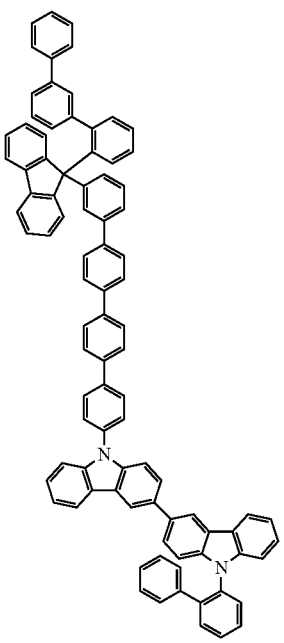

-continued
A367
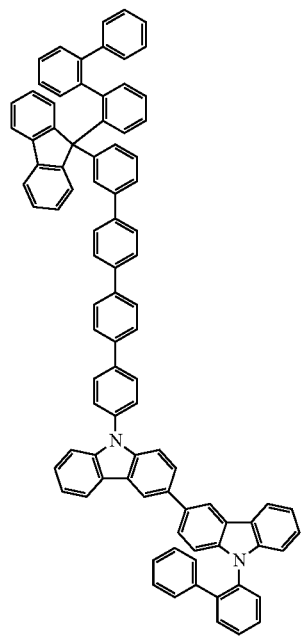
A368
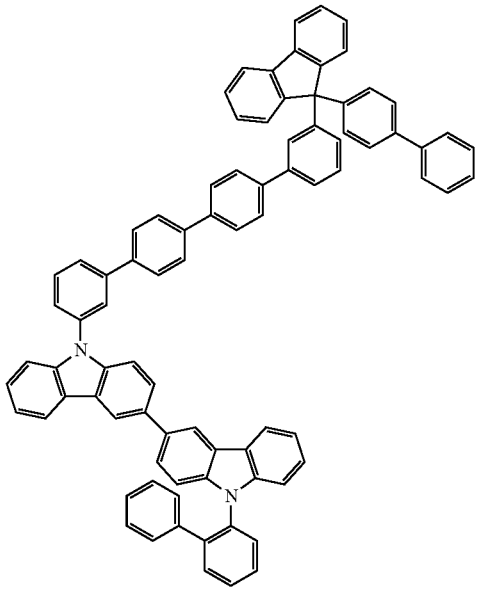
A369
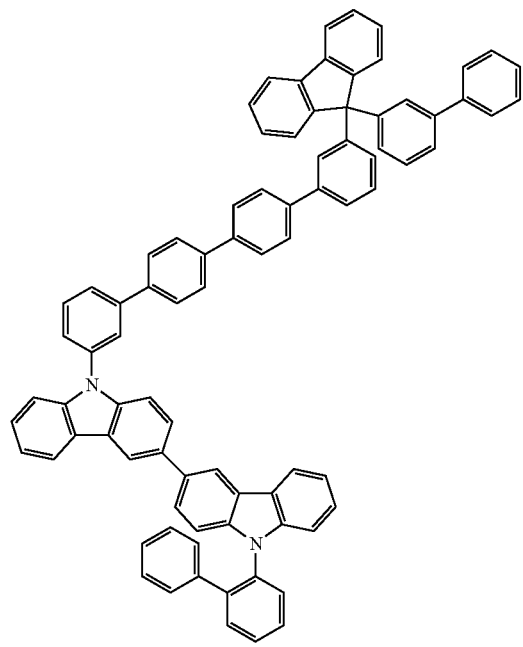
A370
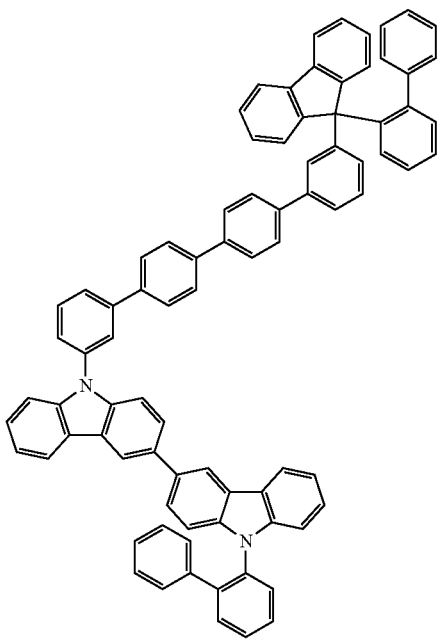

-continued
A371
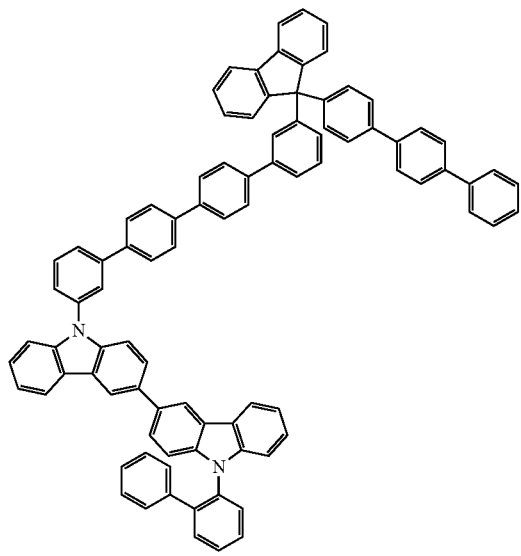
A372
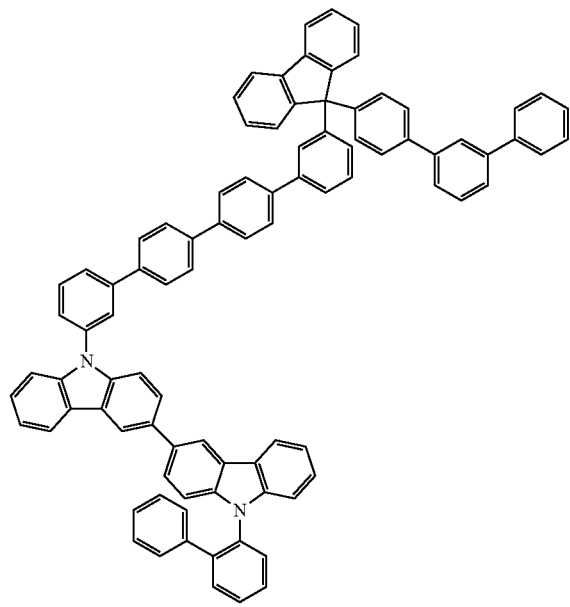
A373
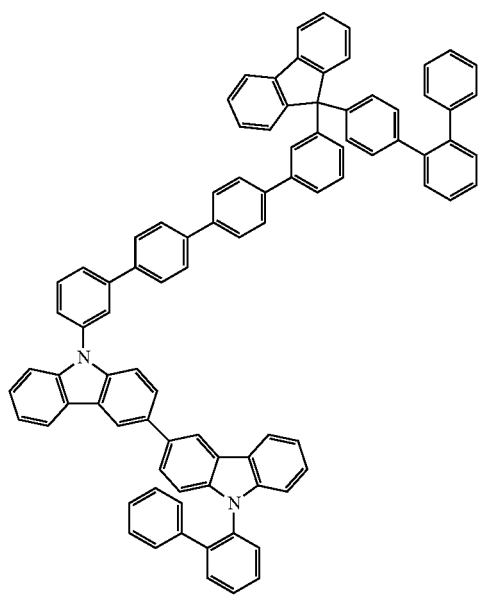
A374
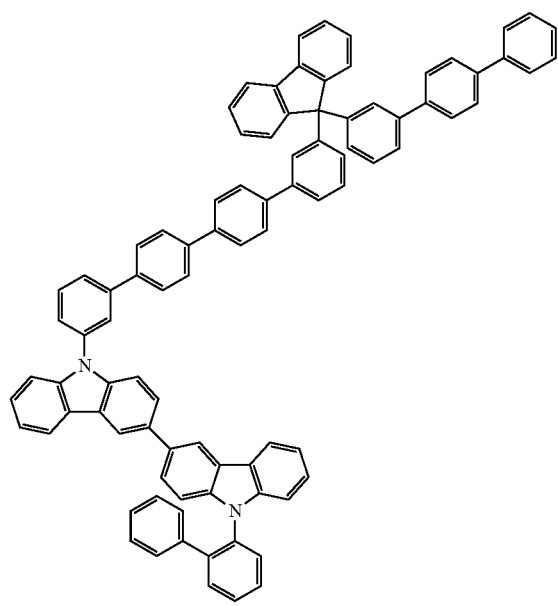

-continued
A375
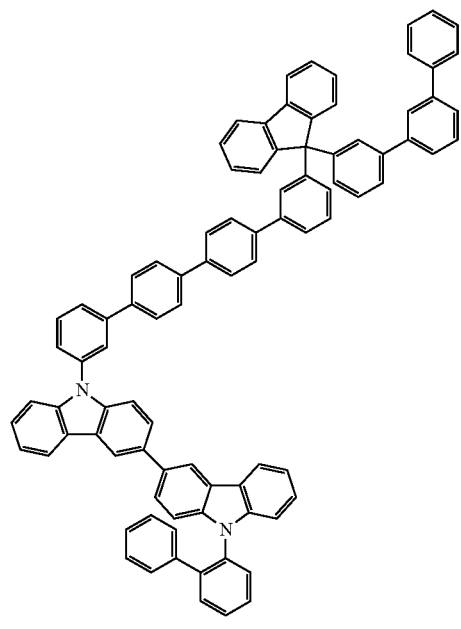
A376
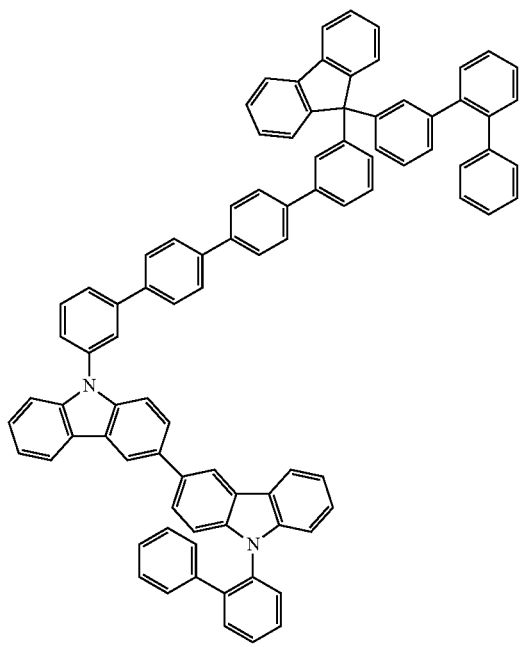
A377
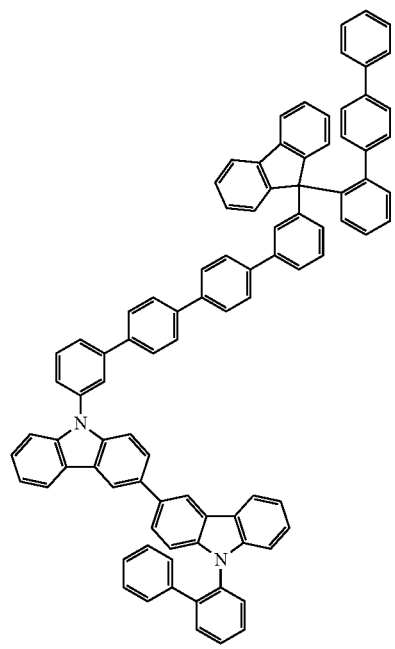
A378
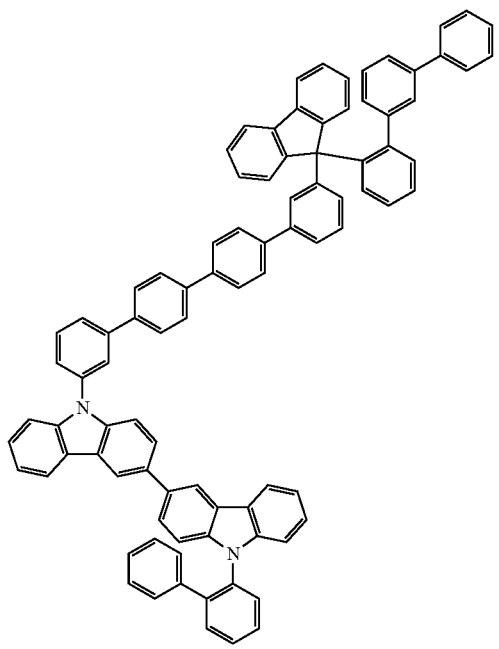

-continued
A379
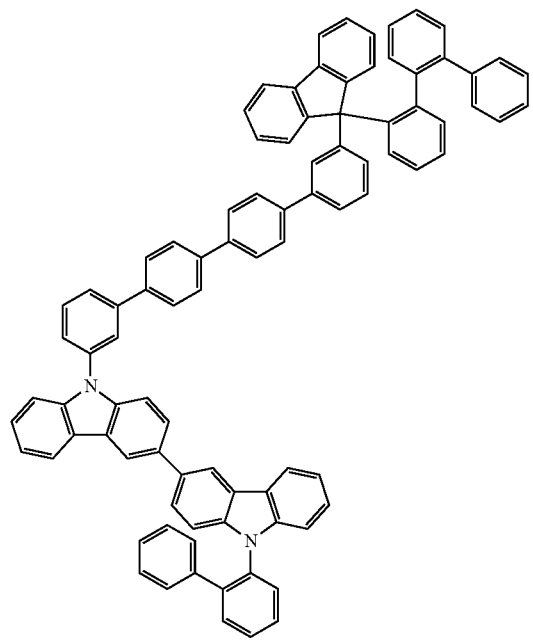
A380
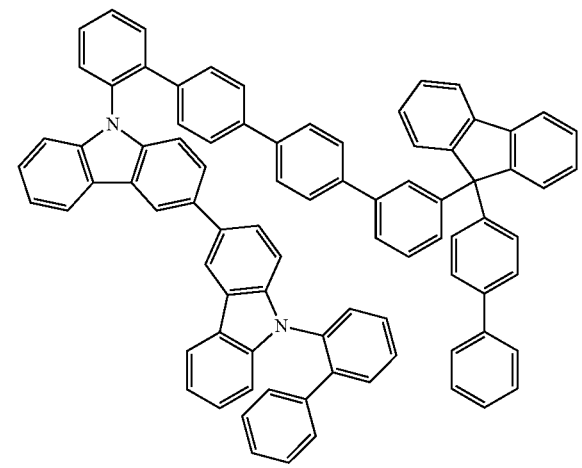
A381
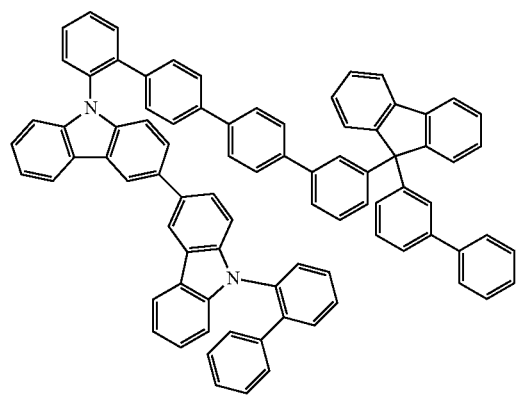
A382
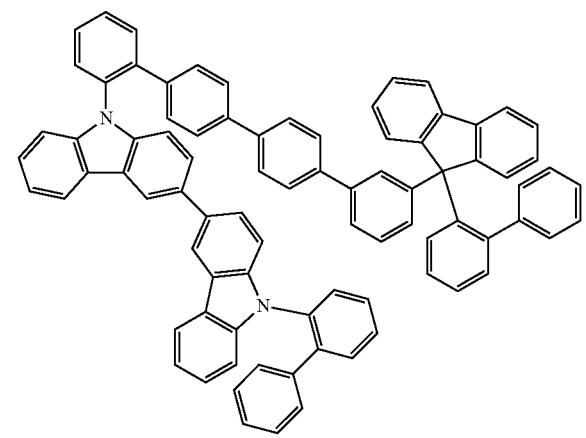
A383
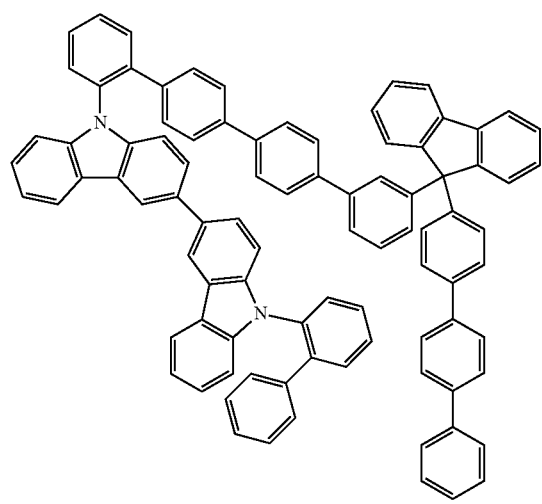

A384
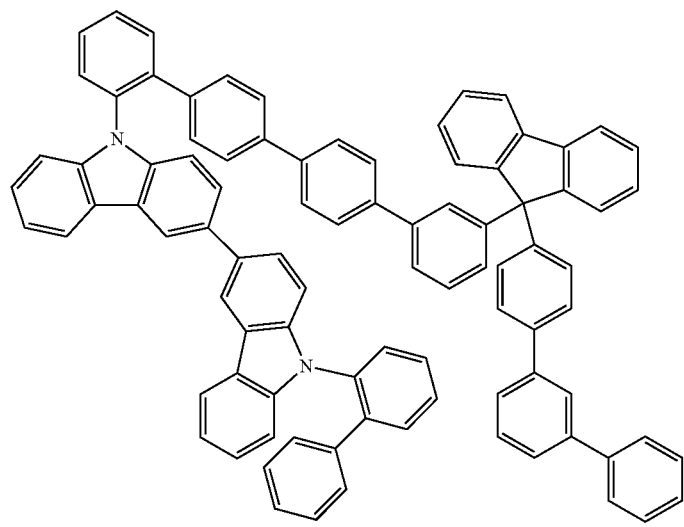
A385
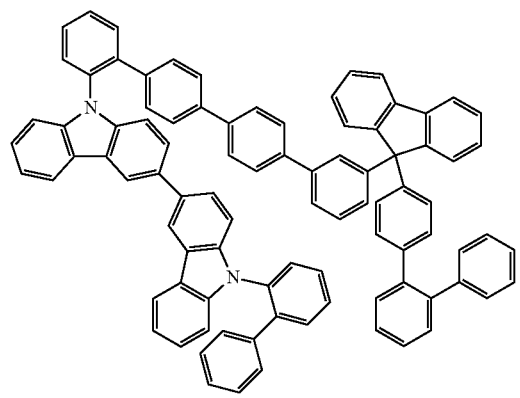
A386
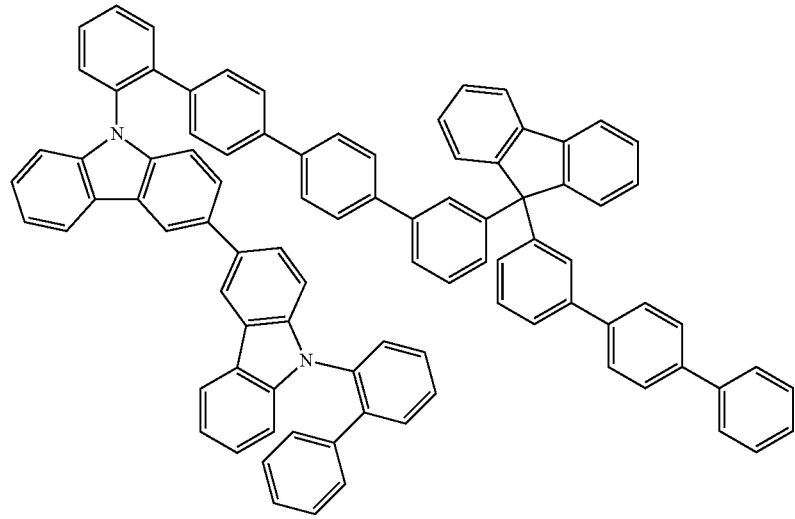

-continued
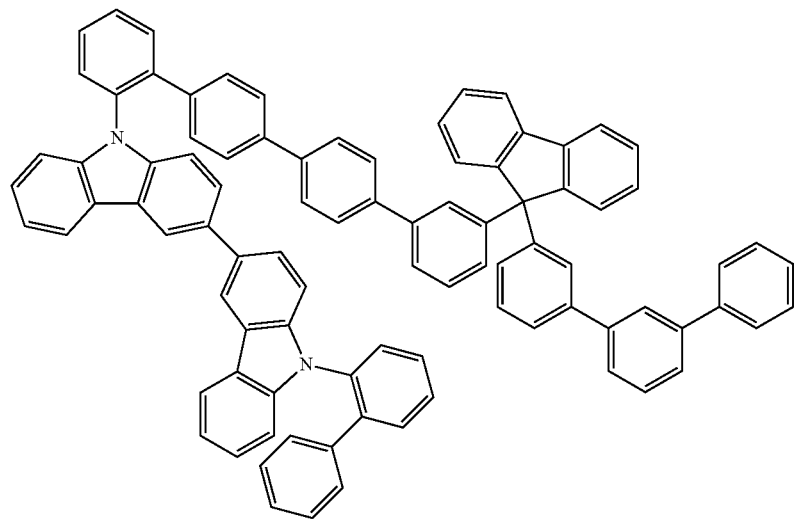
A387
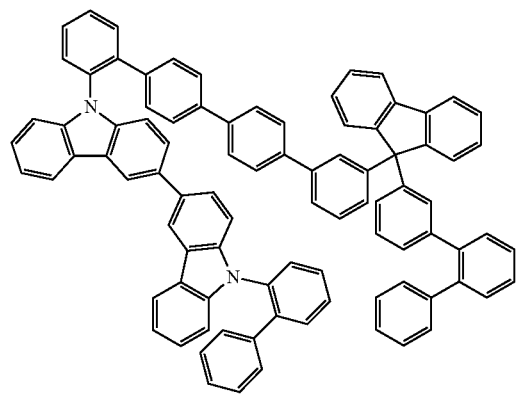
A388
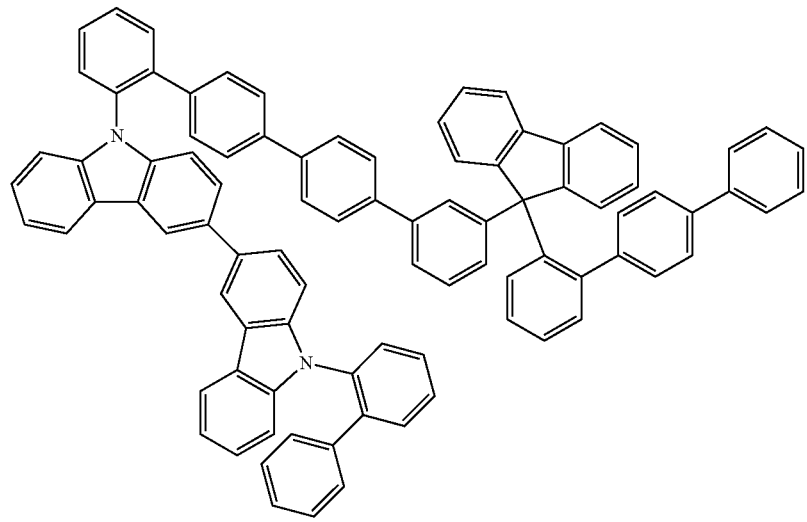
A389

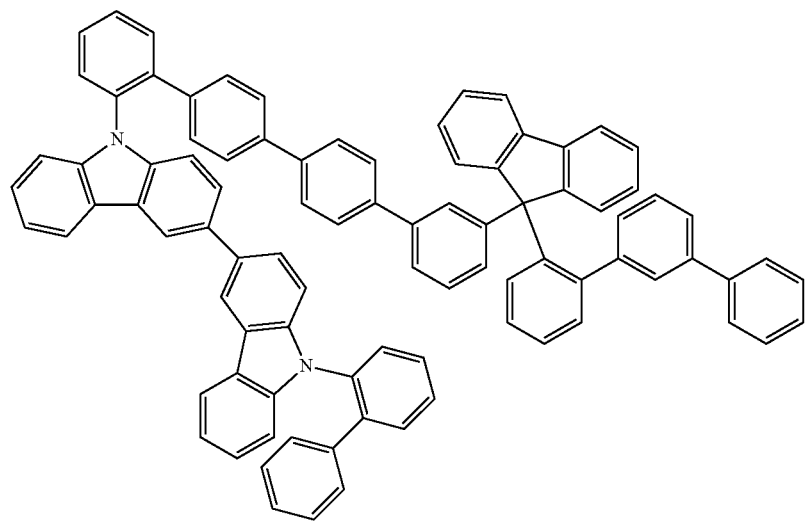
A390
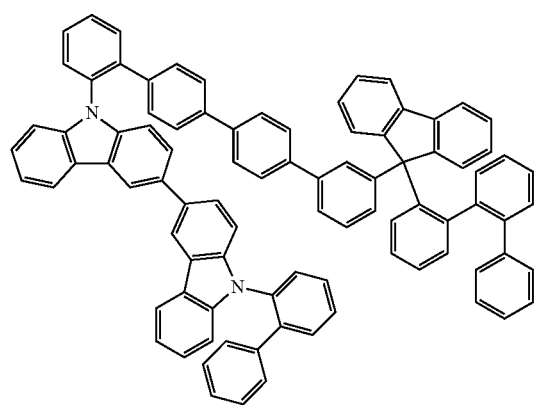
A391
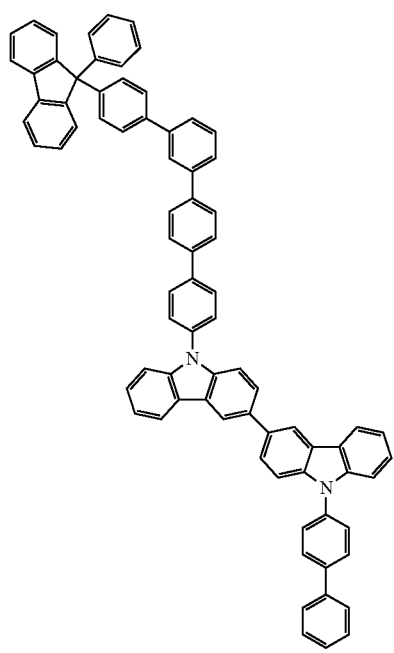
A392

-continued
A393
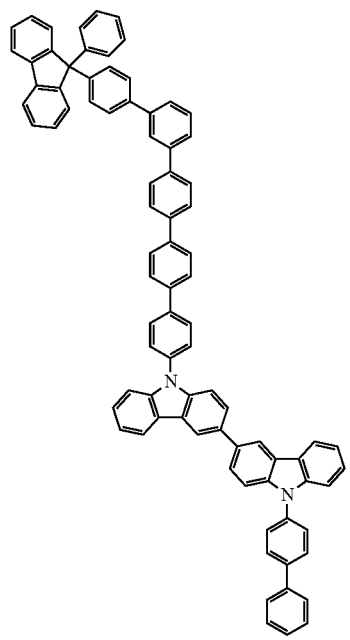
A394
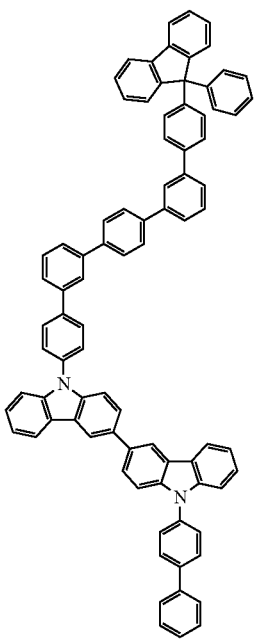
A395
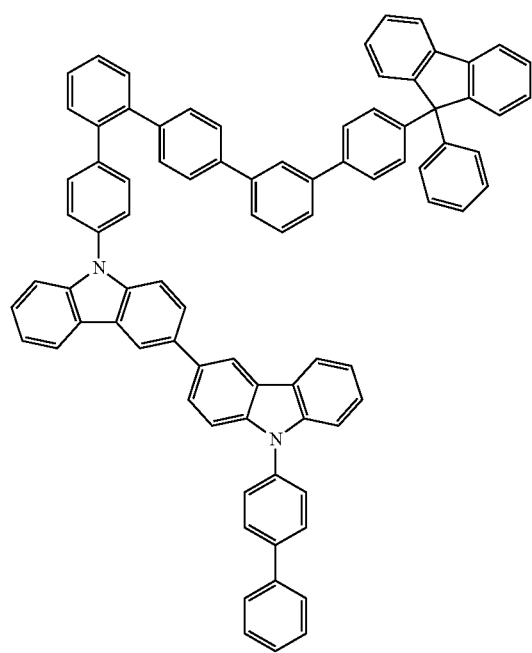
A396
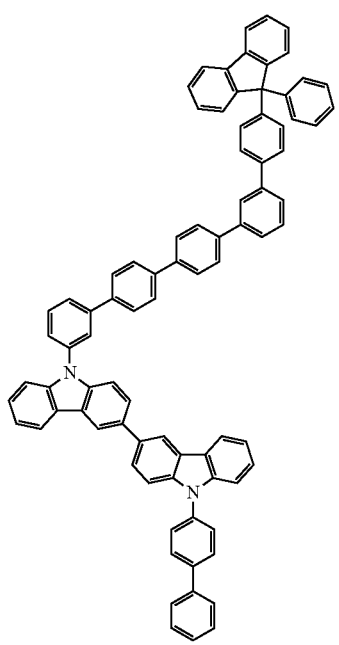

A397
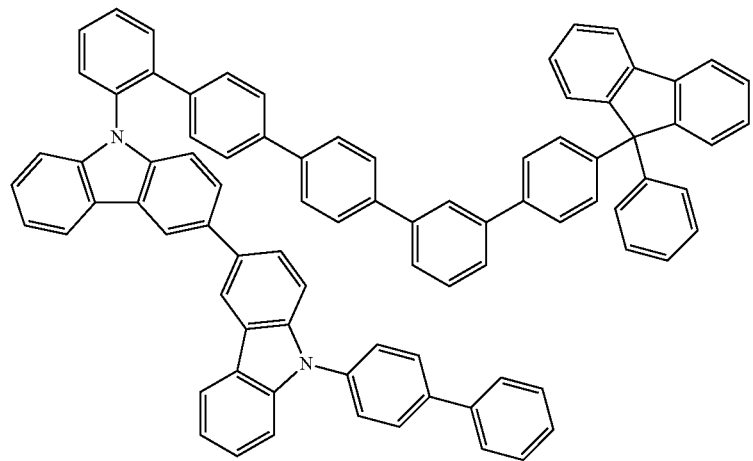
A398
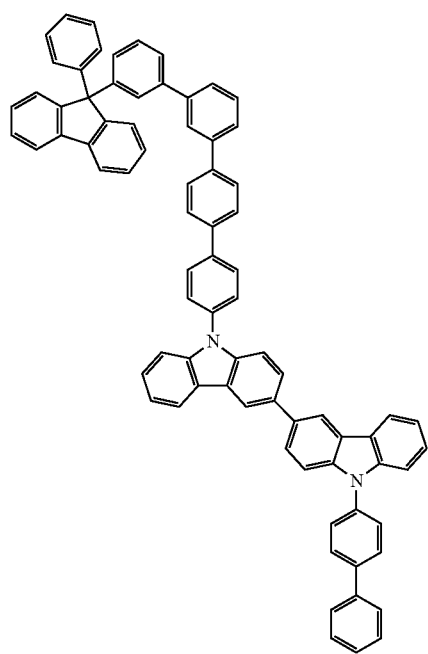
A399
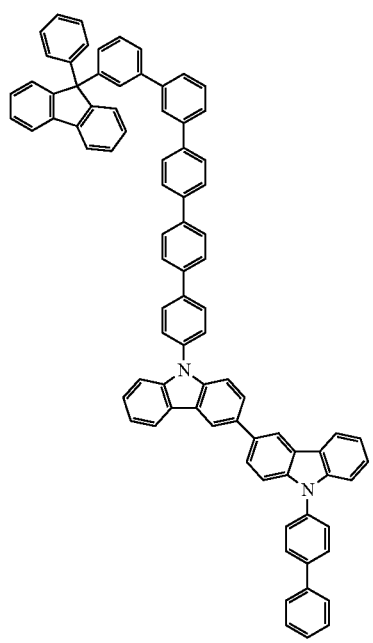

-continued
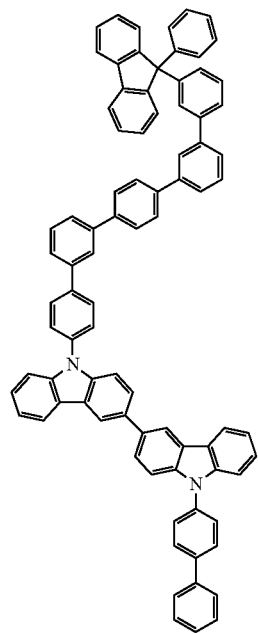
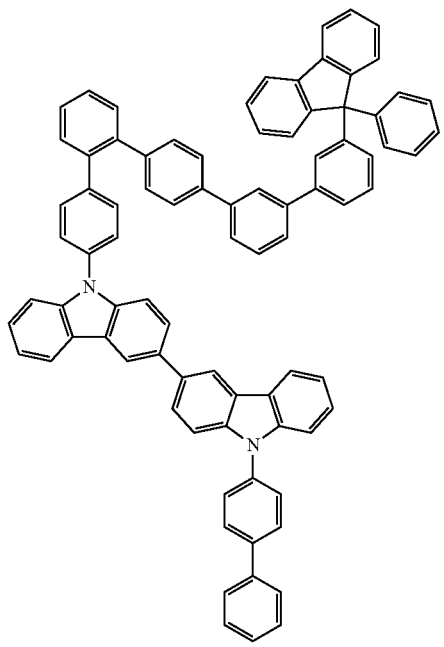
A400
A401
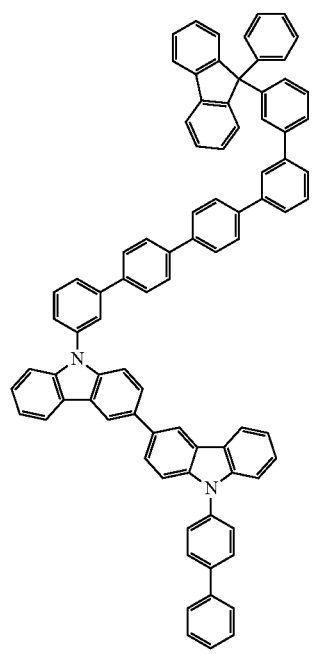
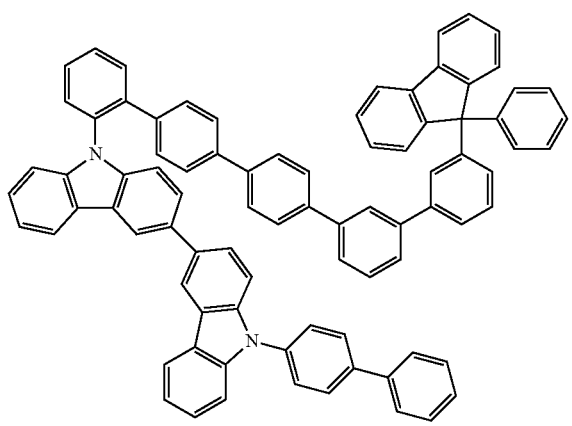
A402
A403

-continued
A404
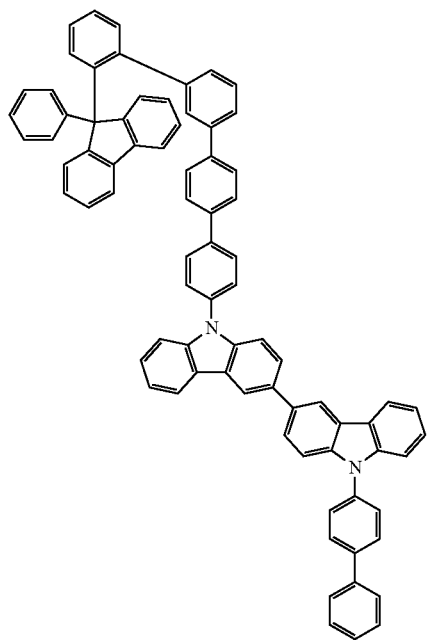
A405
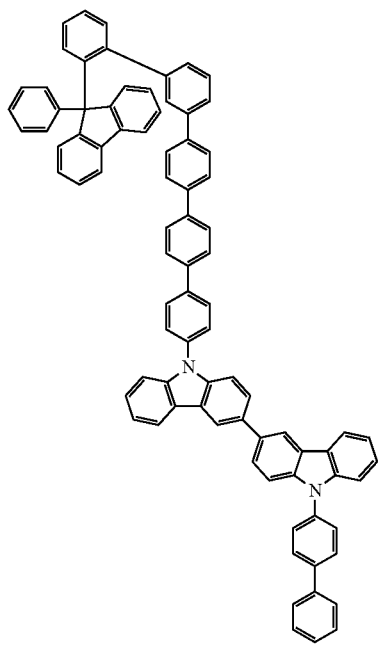
A406
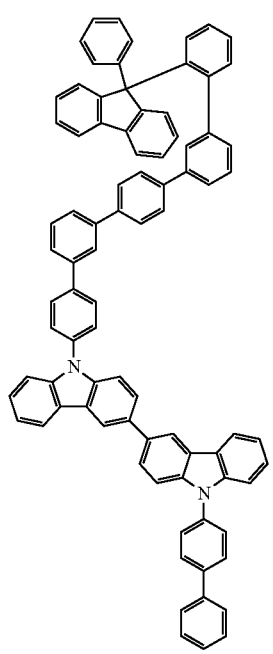
A407
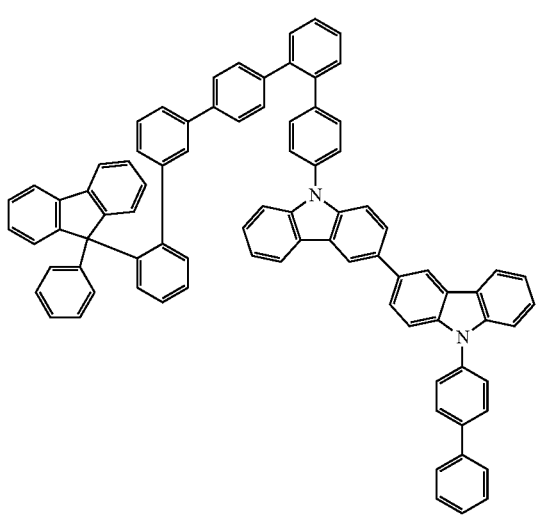

-continued
A408
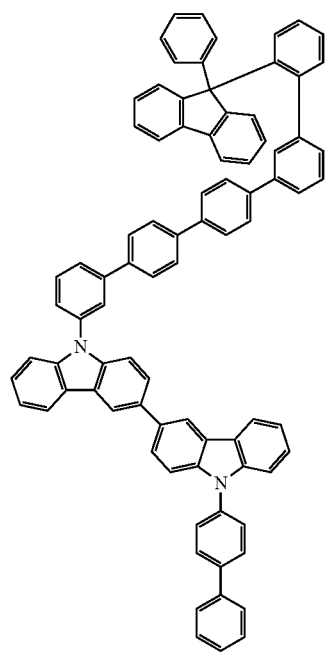
A409
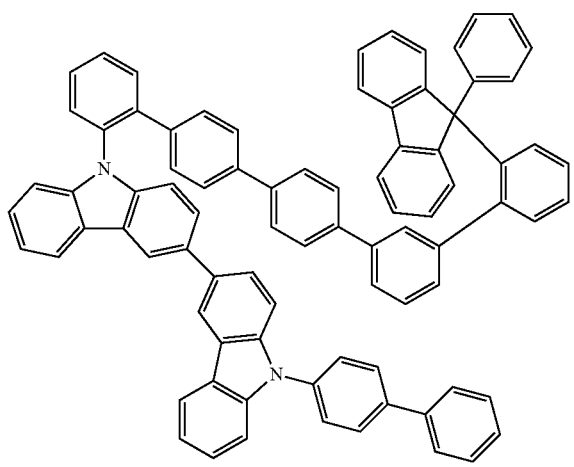
A410
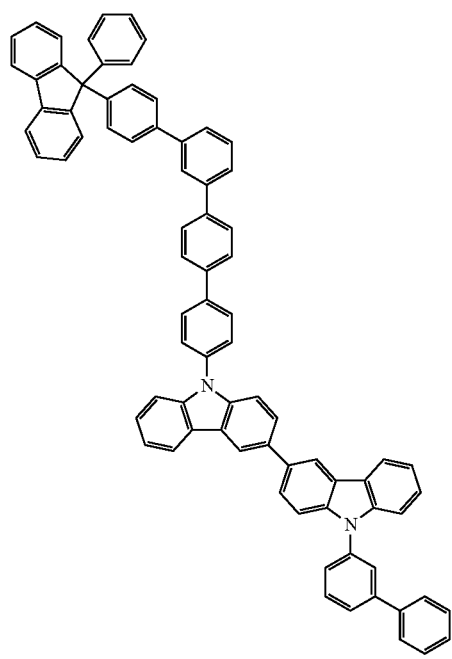
A411
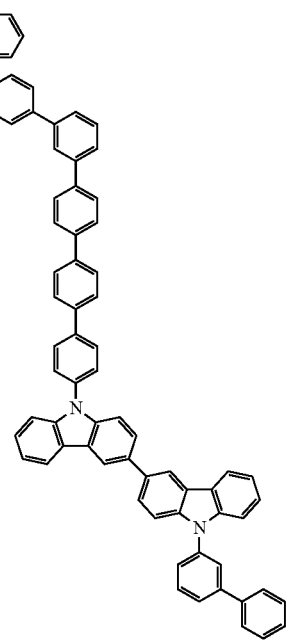

-continued
A412
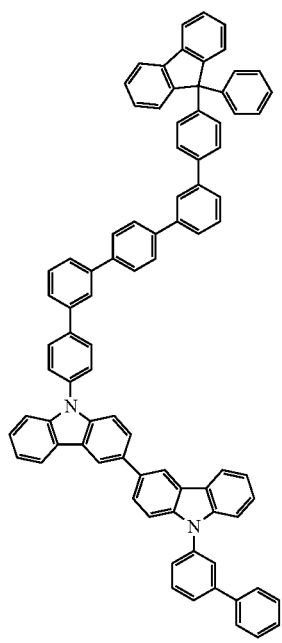
A413
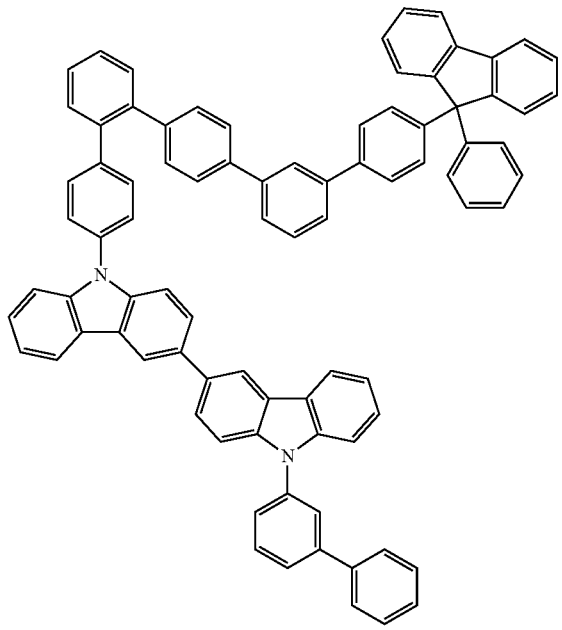
A414
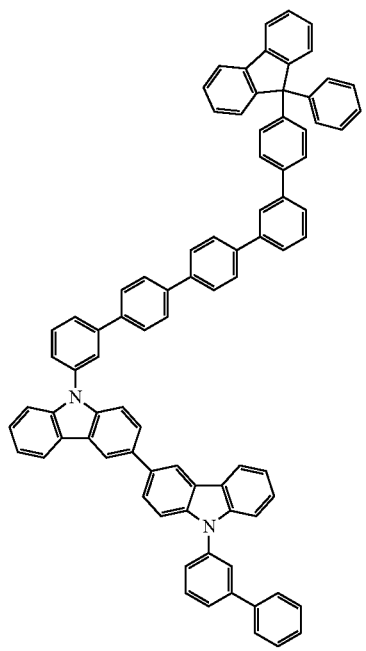
A415
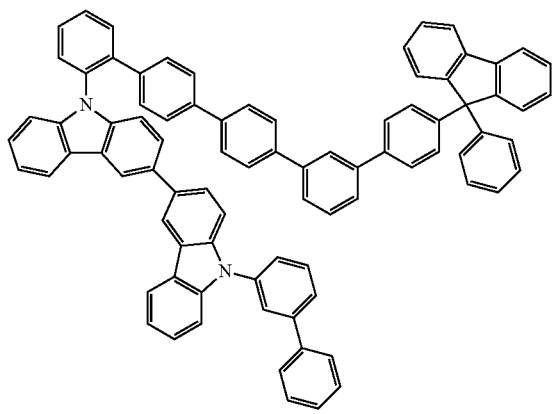

-continued
A416
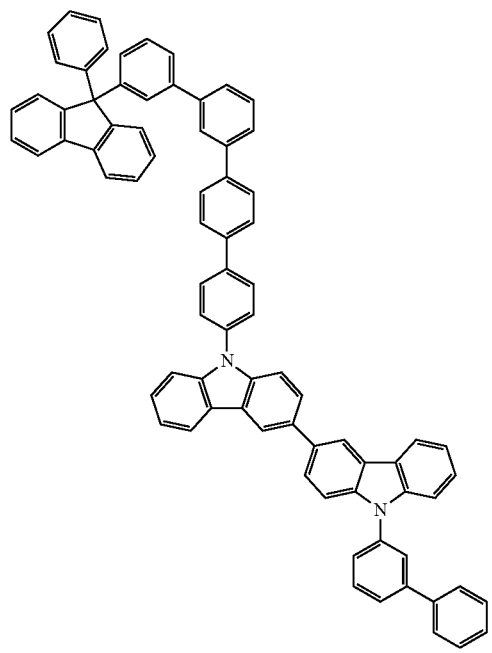
A417
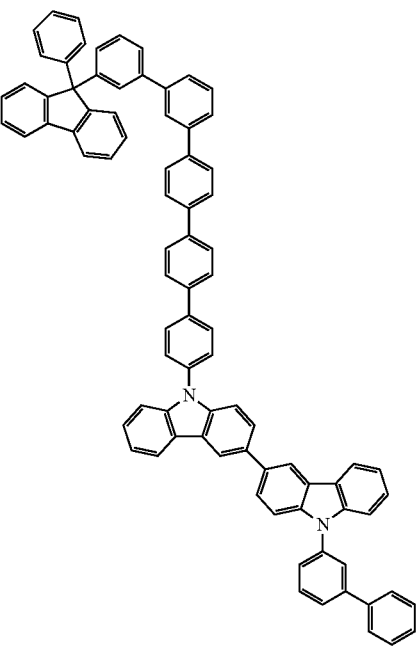
A418
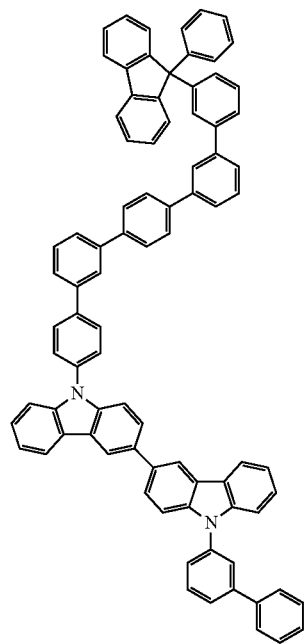
A419
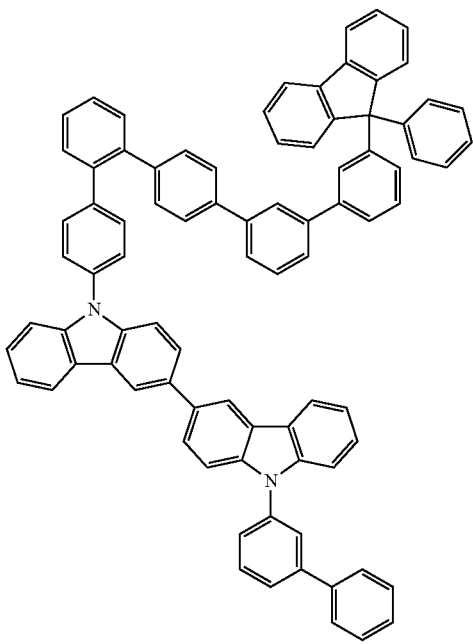

-continued
A420
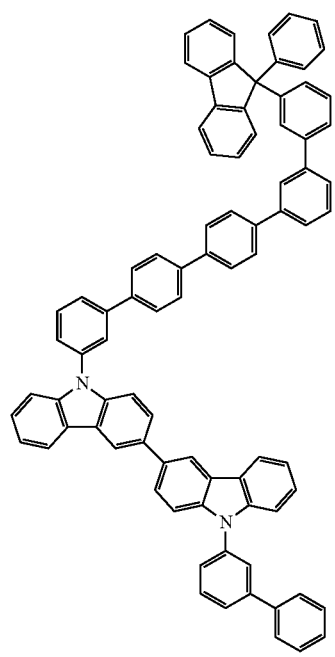
A421
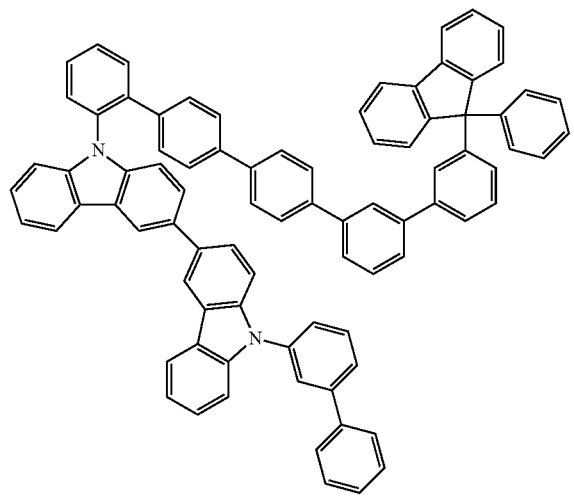
A422
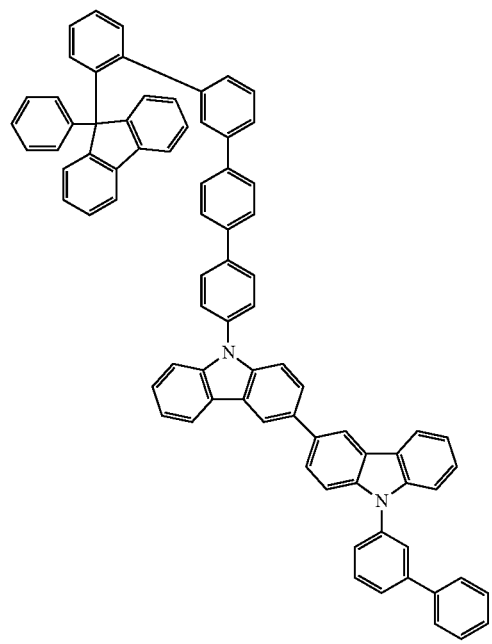
A423
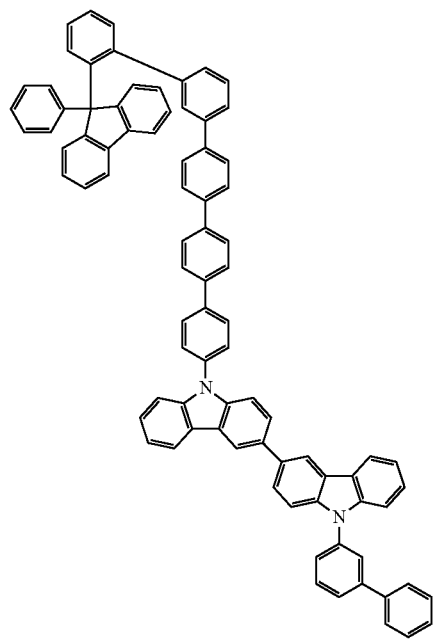

-continued
A424
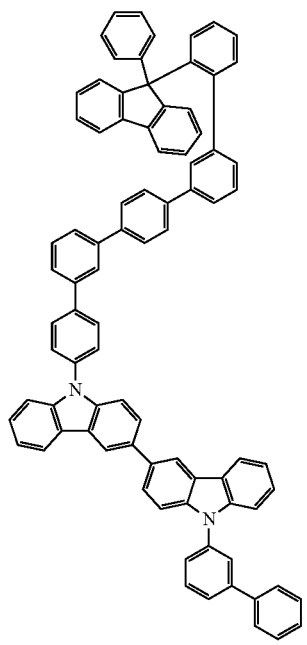
A425
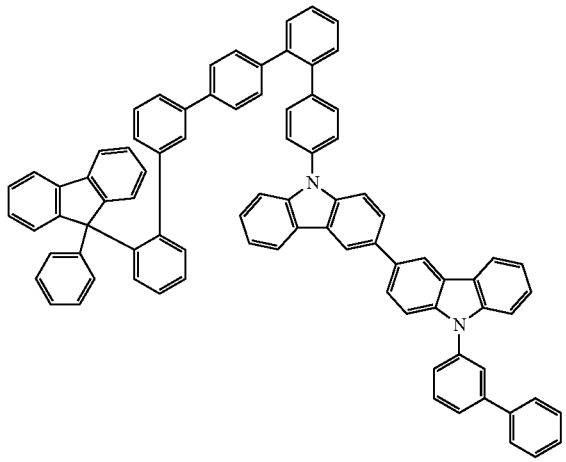
A426
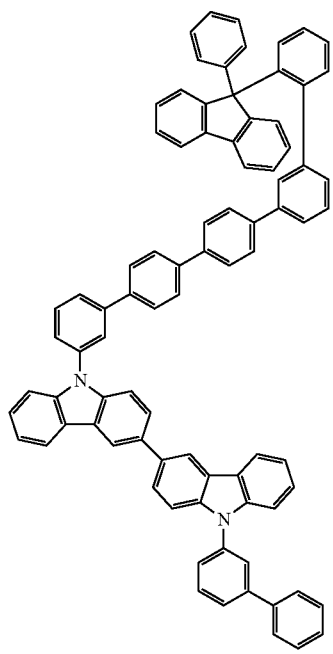
A427
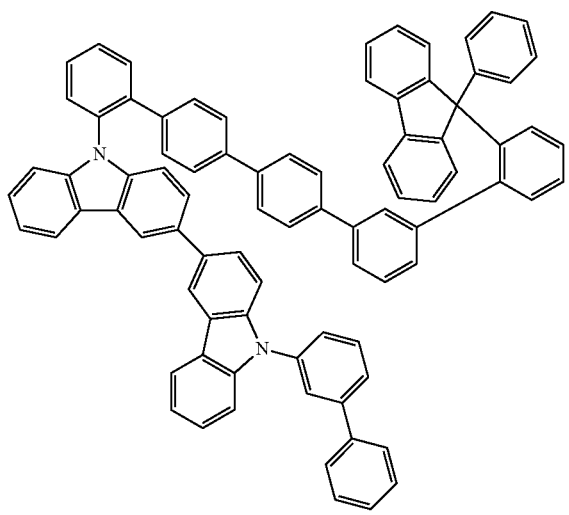

-continued
A428
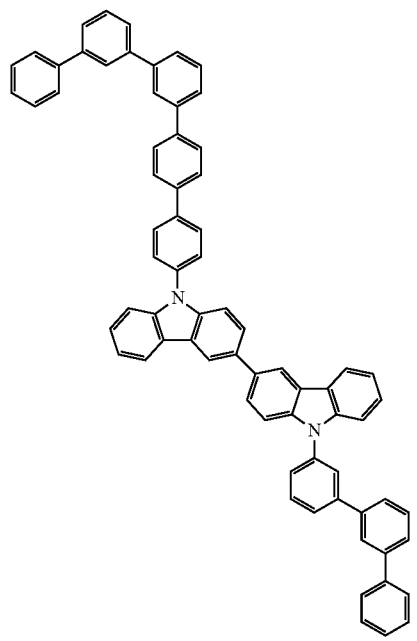
A429
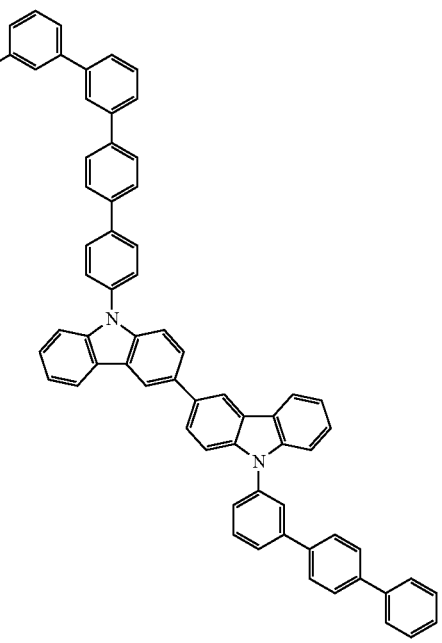
A430
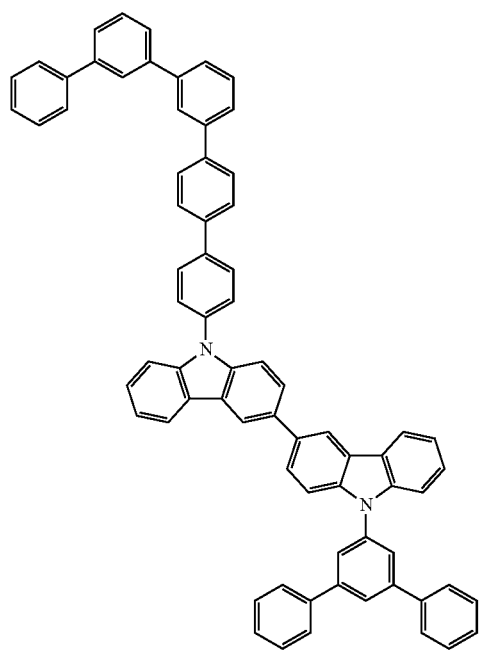
A431
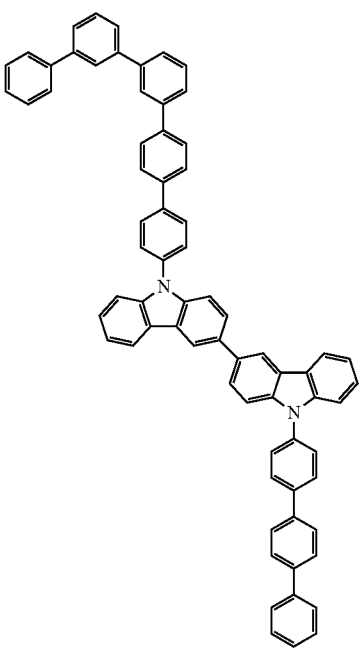

A432
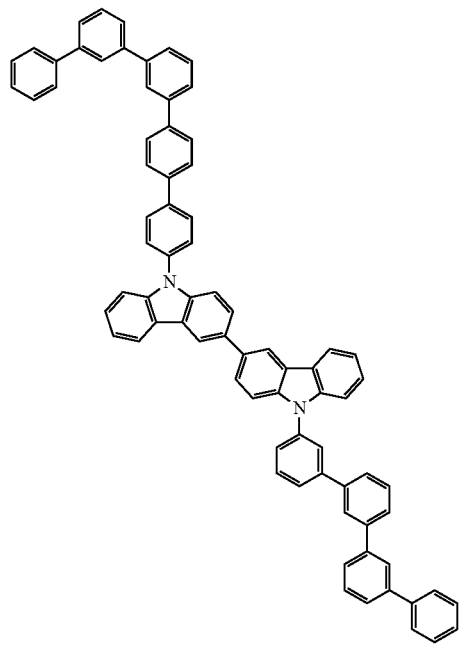
A433
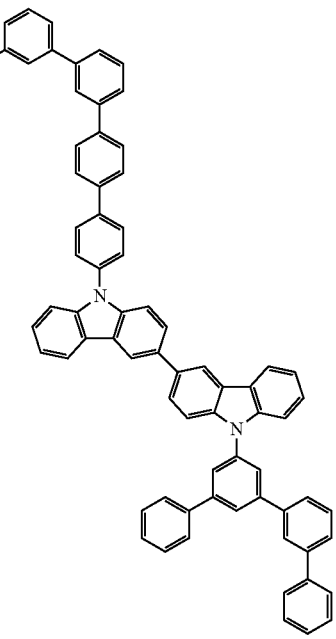
A434
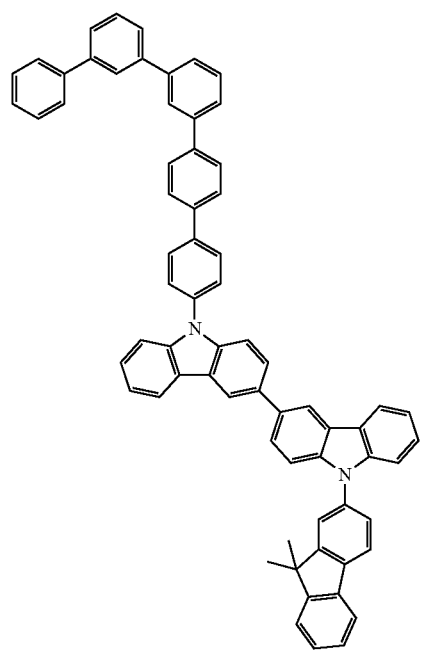
A435

-continued
A436
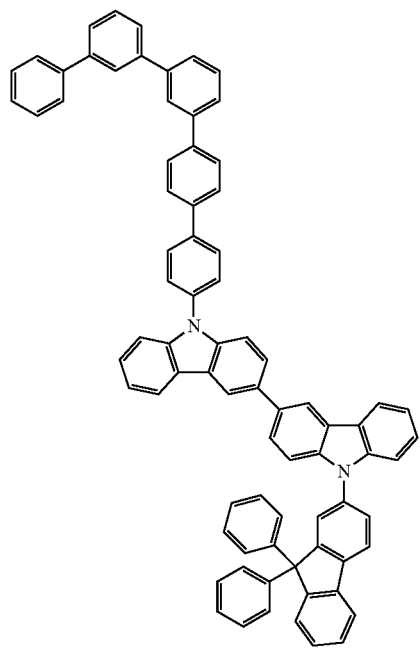
A437
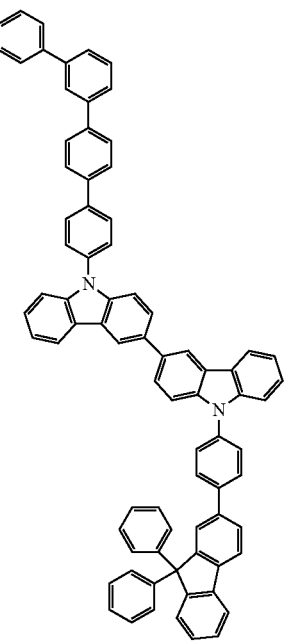
A438
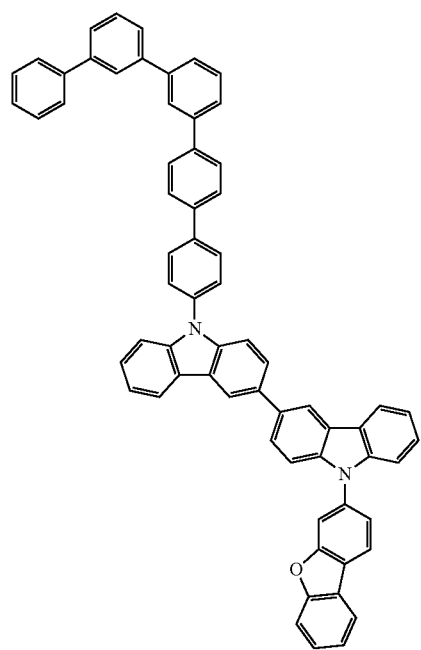
A439
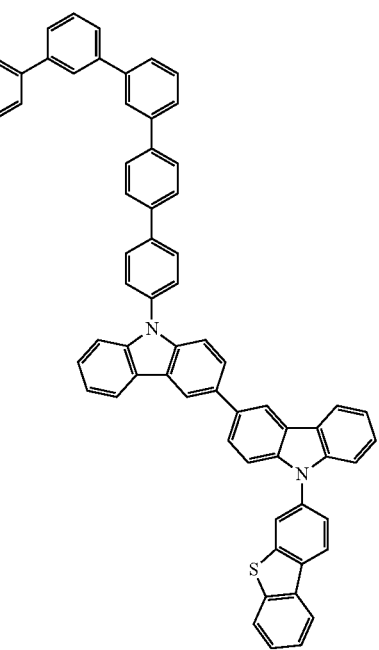

-continued
A440
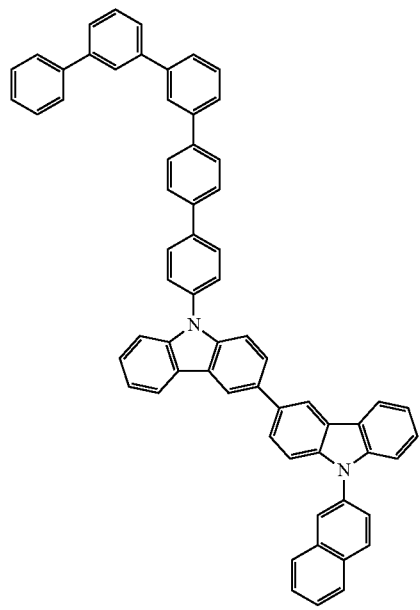
A441
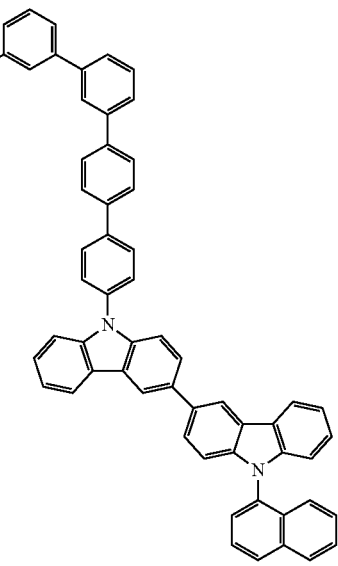
A442
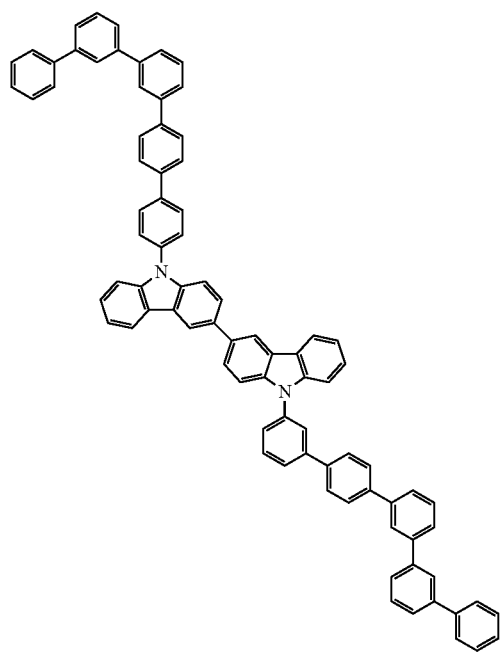
A443
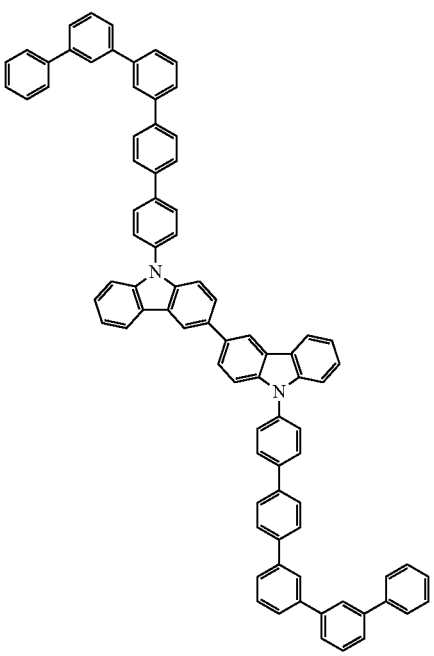

791 792
-continued
A444 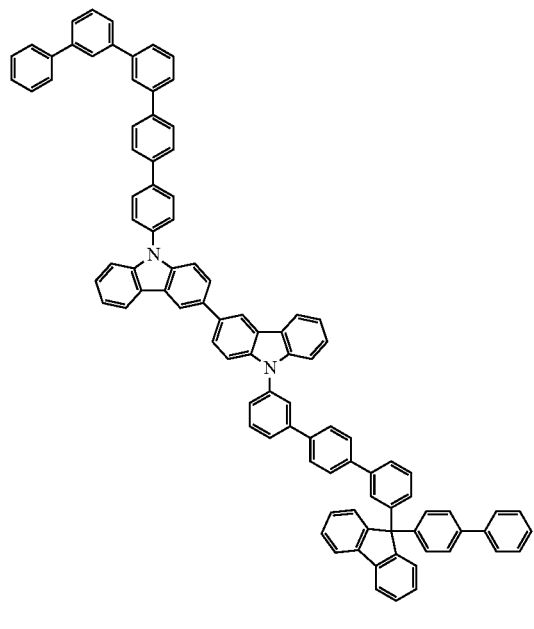 A445 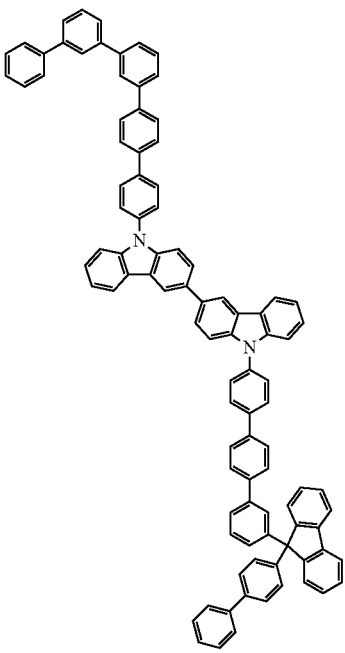
A446 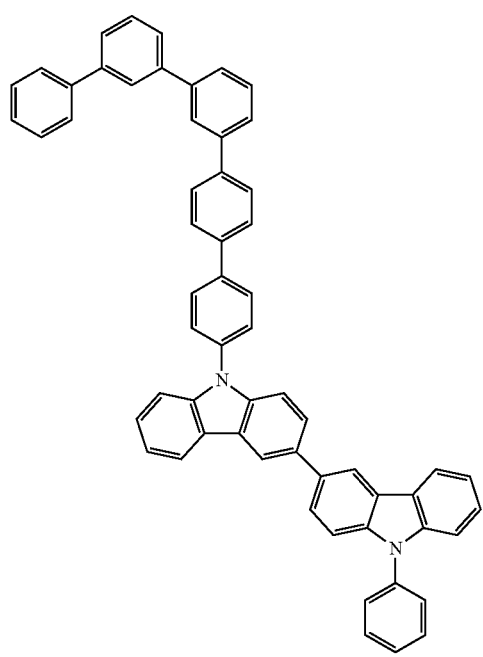 A447 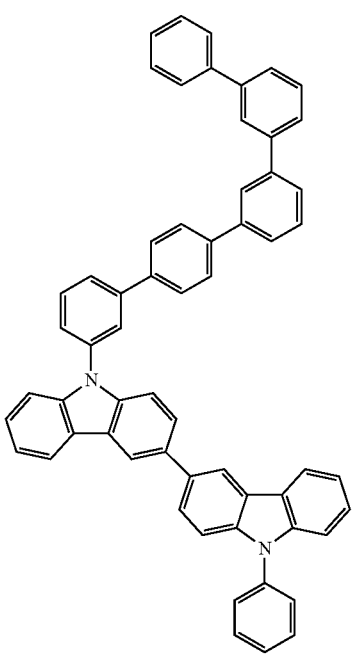

-continued
A448
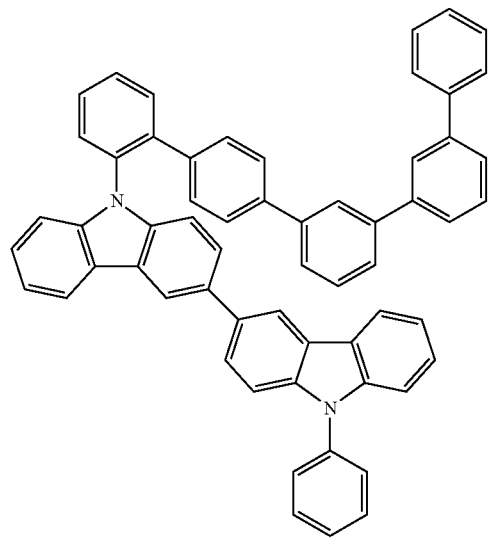
A449
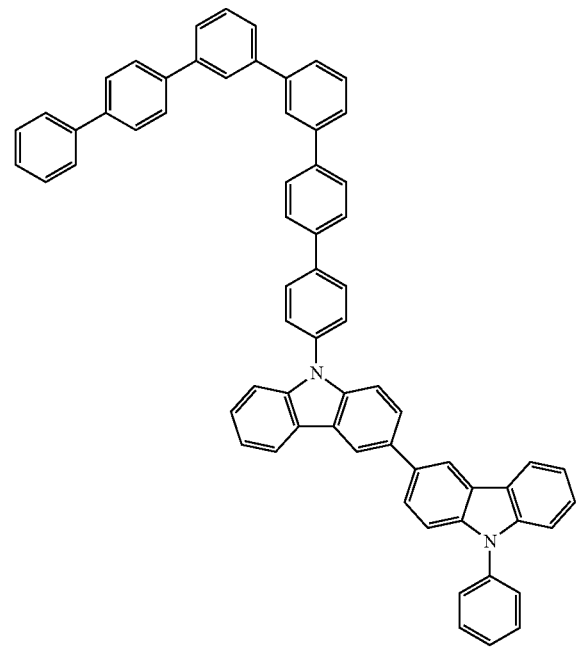
A450
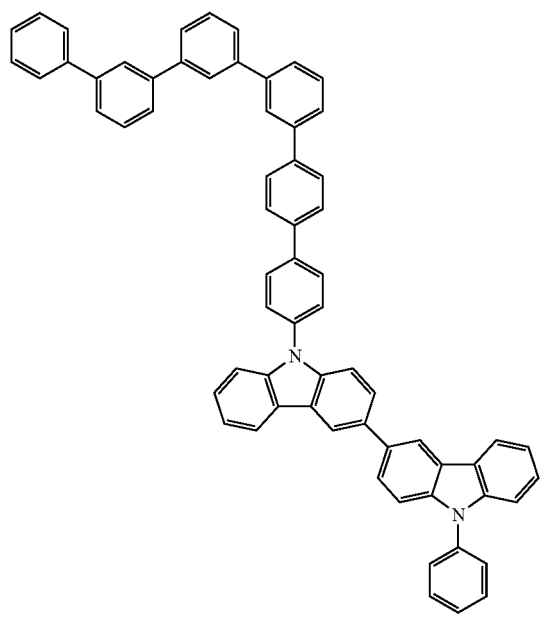
A451
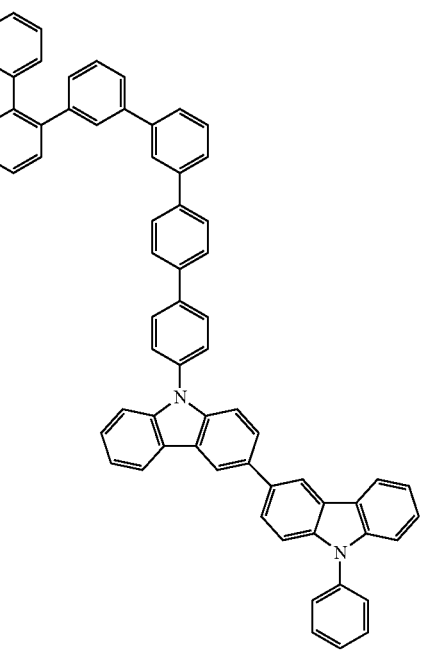

-continued
A452
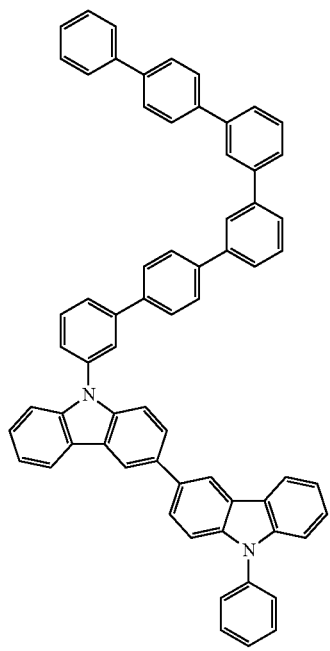
A453
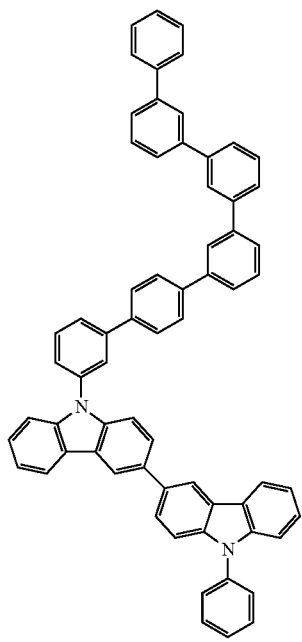
A454
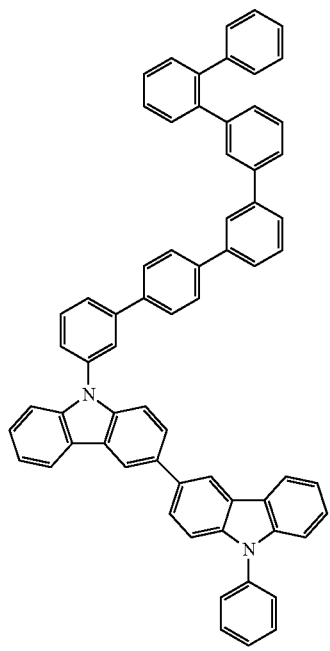
A455
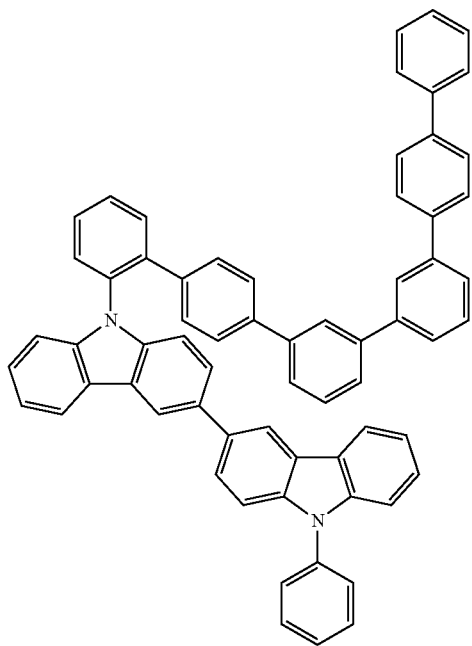

-continued
A456
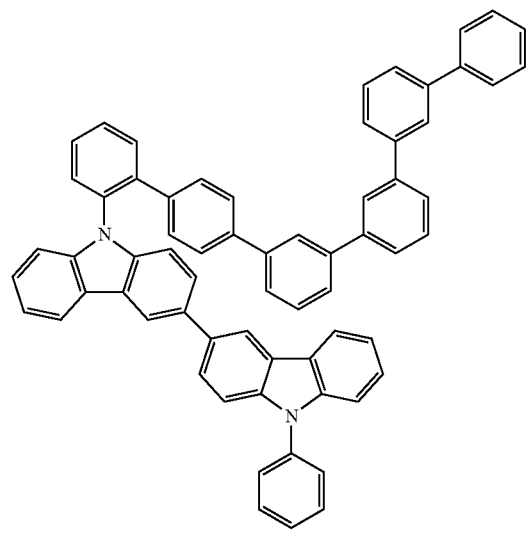
A457
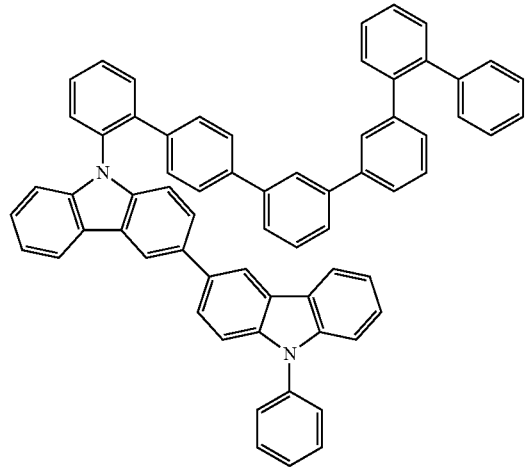
A458
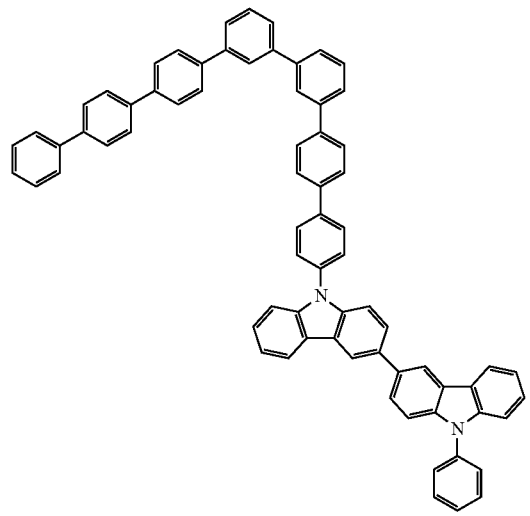
A459
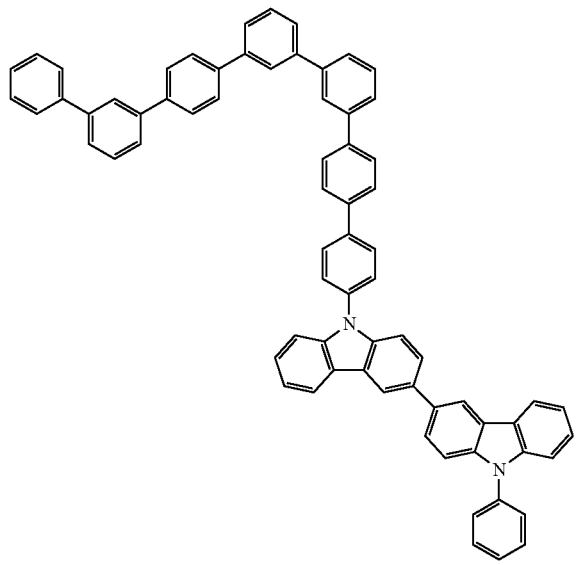

-continued
A460 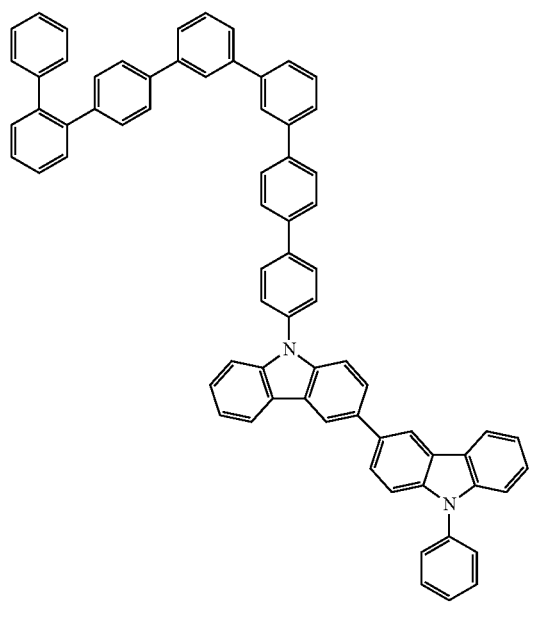
A461 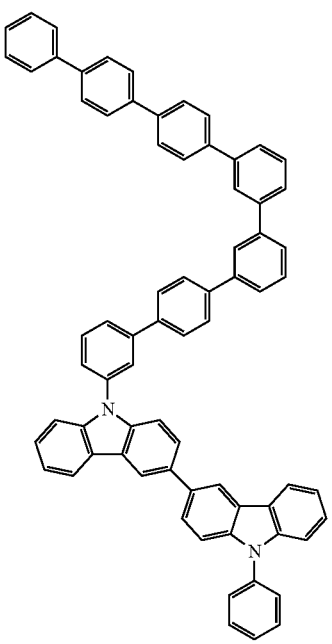
A462 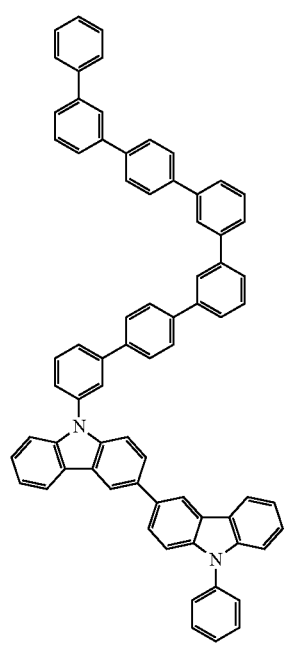
A463 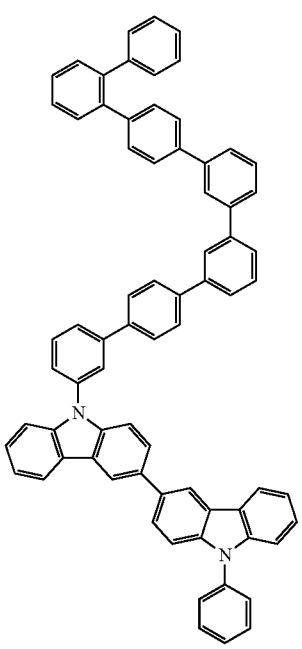

-continued
A464
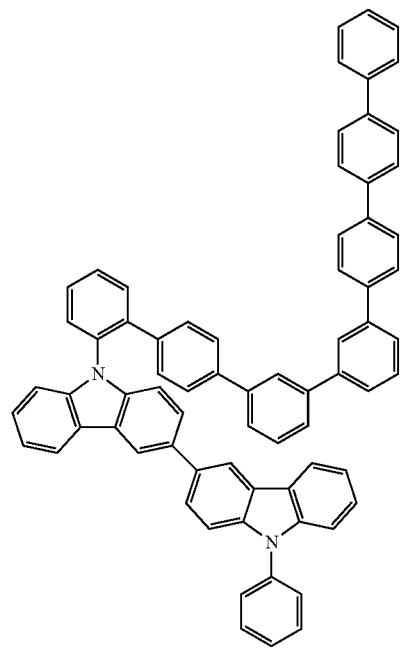
A465
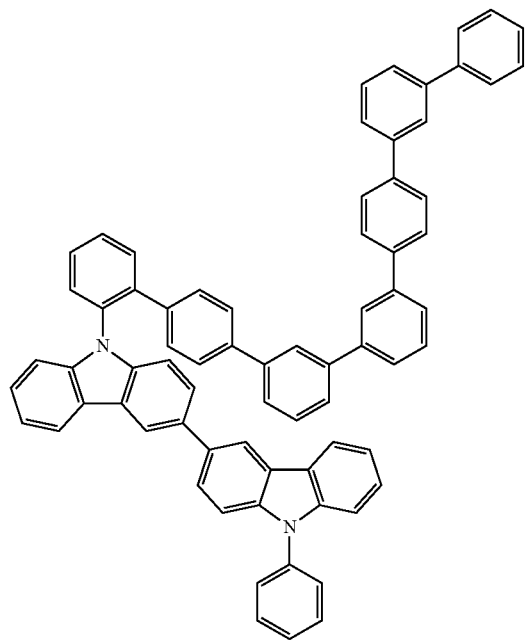
A466
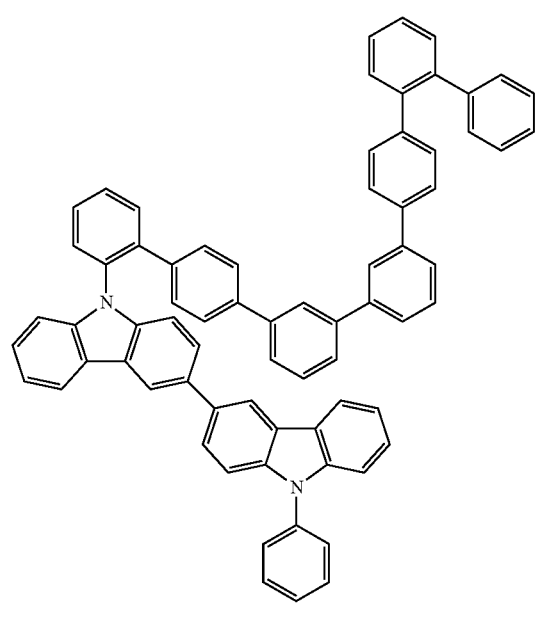
A467
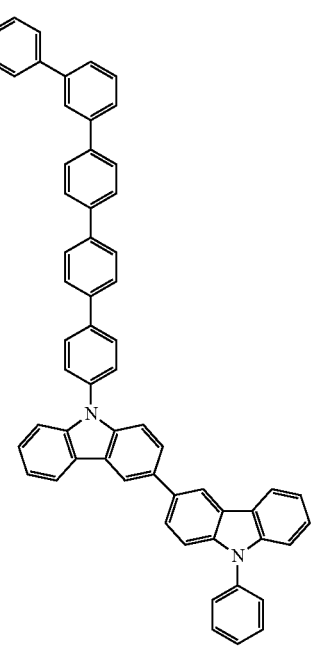

-continued
A468
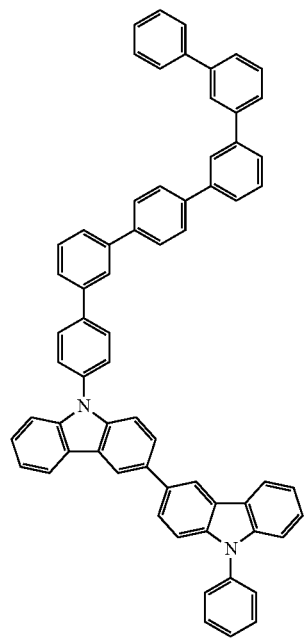
A469
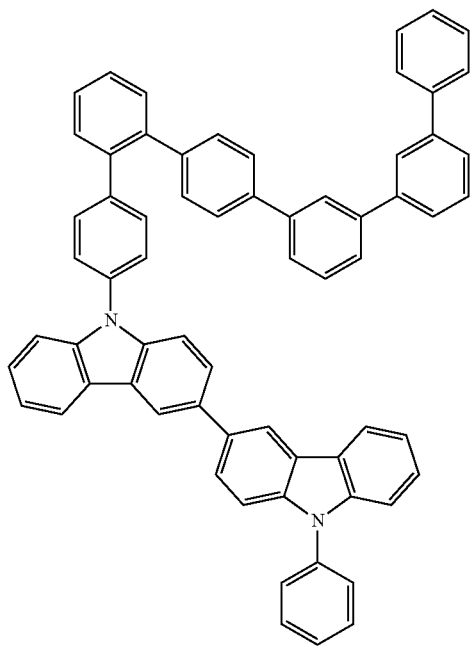
A470
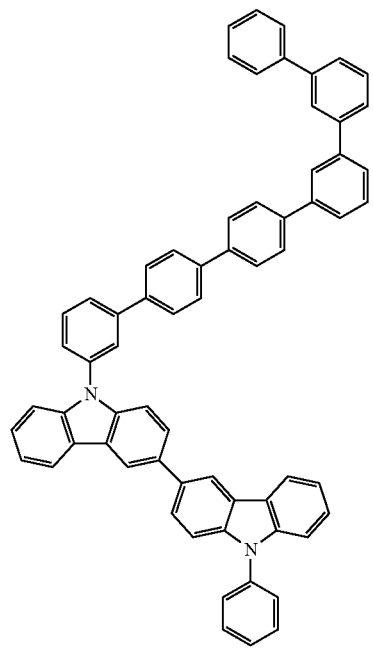
A471
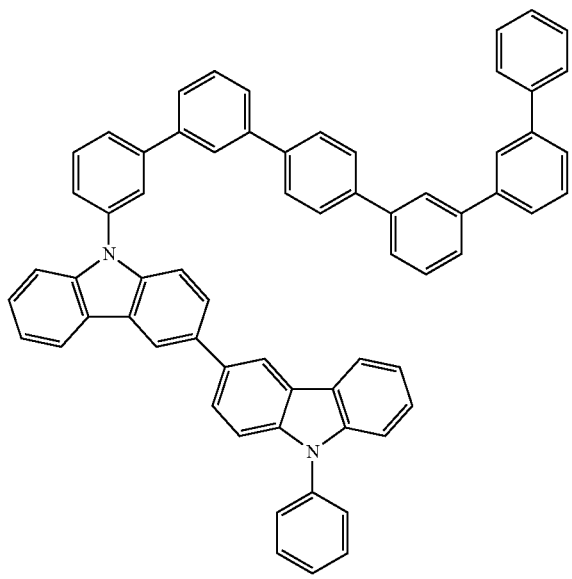

-continued
A472
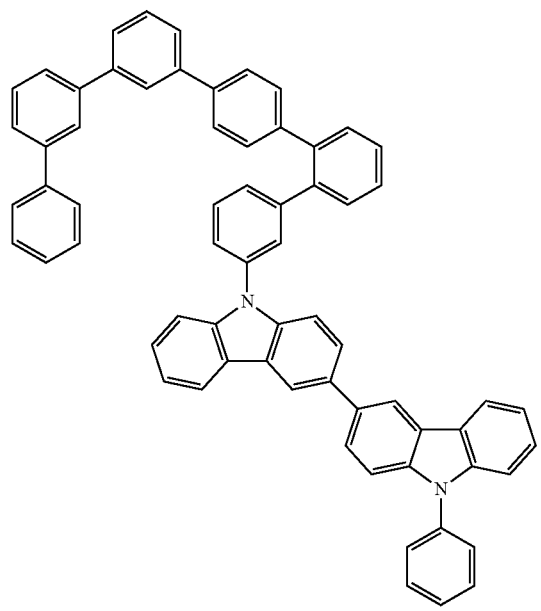
A473
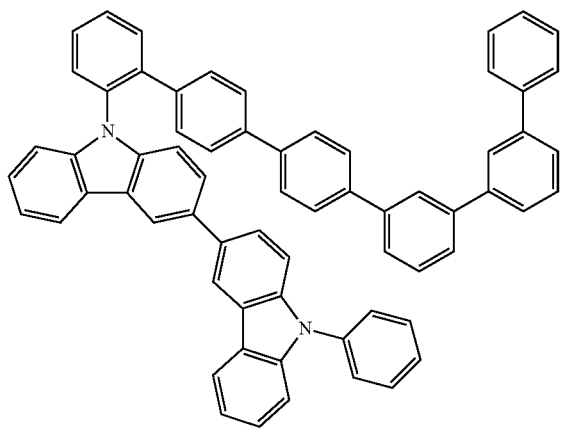
A474
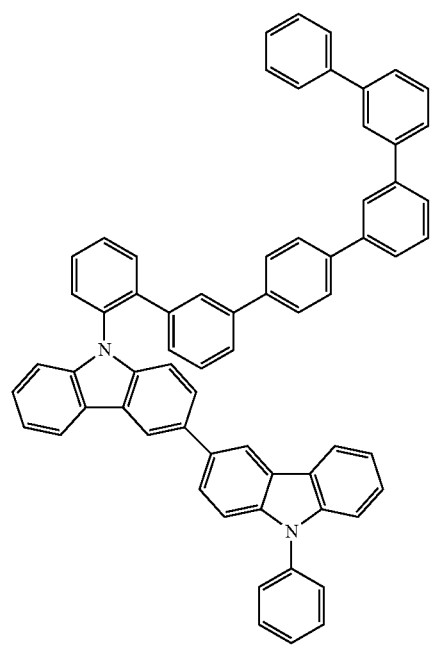
A475
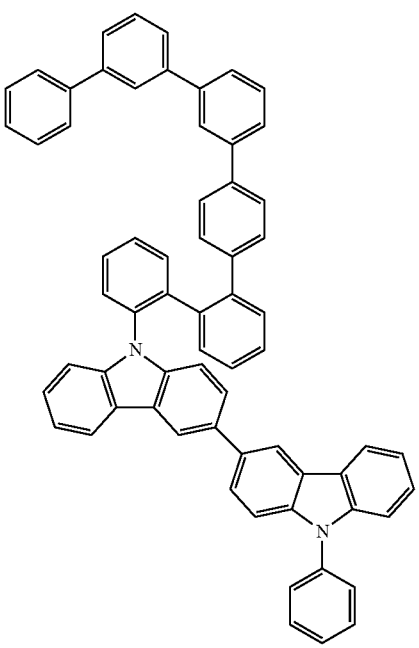

-continued
A476
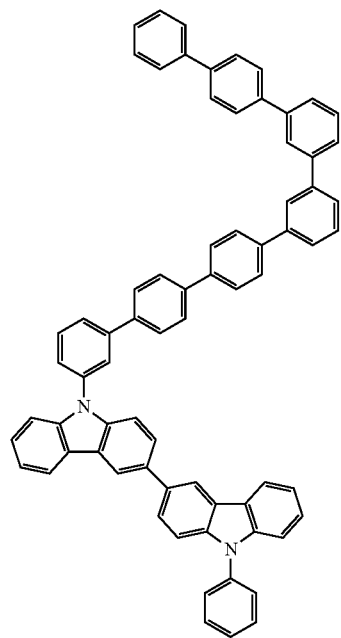
A477
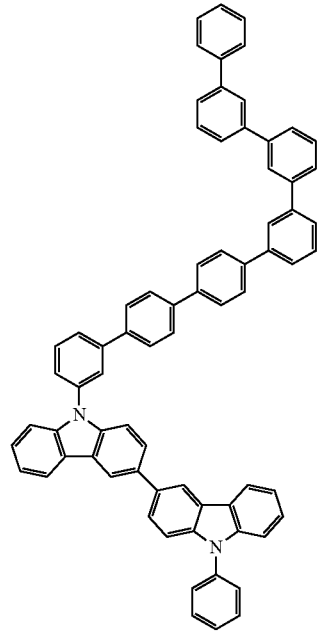
A478
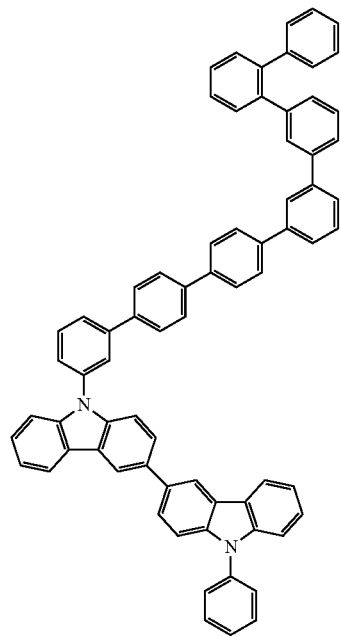
A479
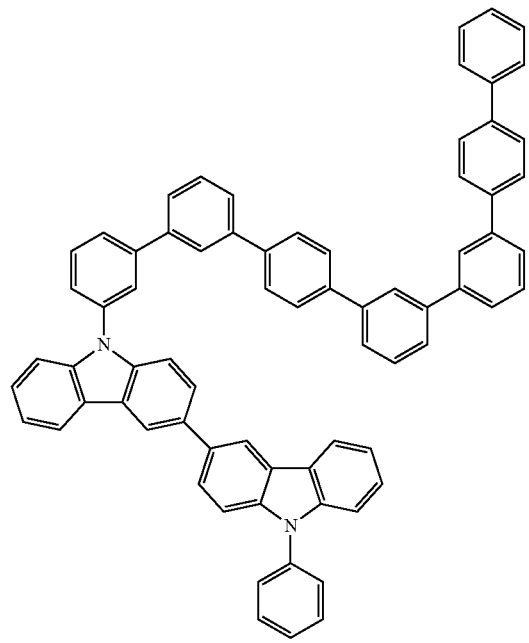

-continued
A480
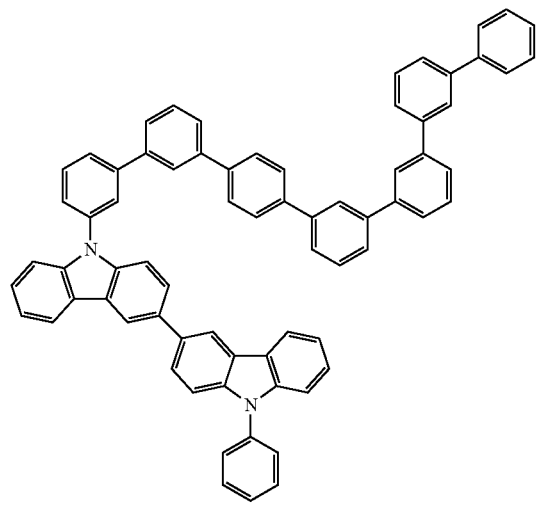
A481
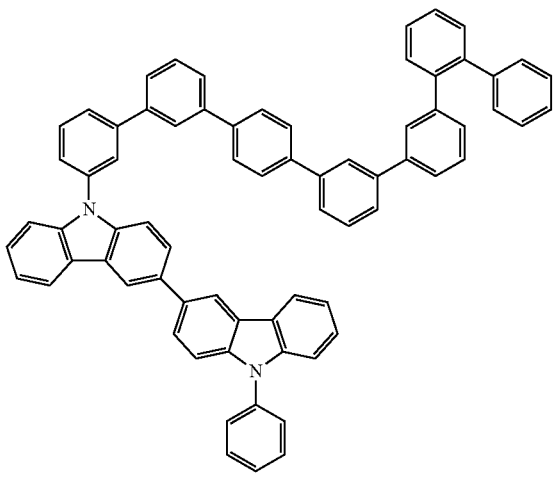
A482
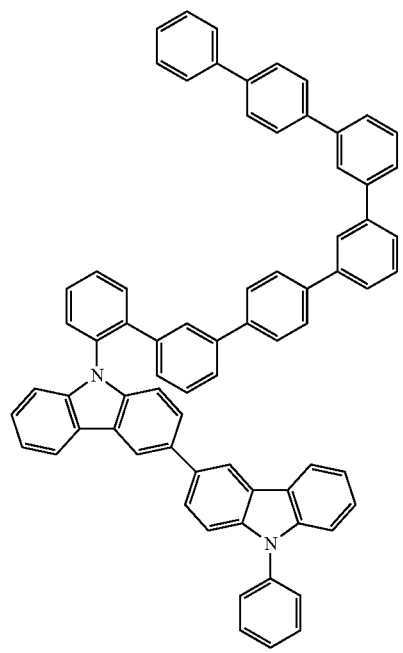
A483
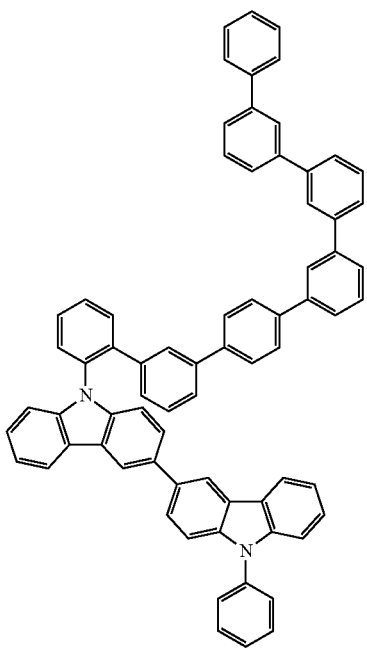

-continued
A484
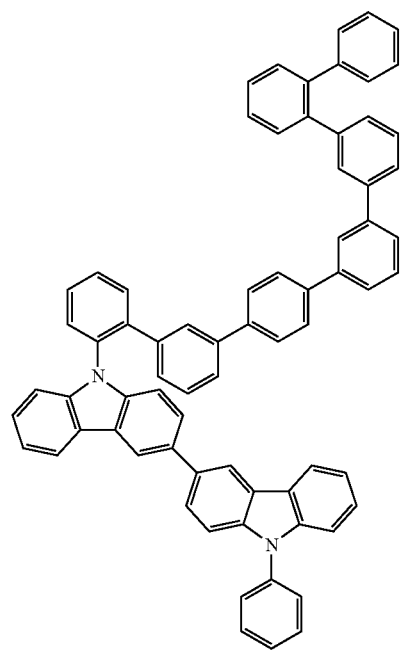
A485
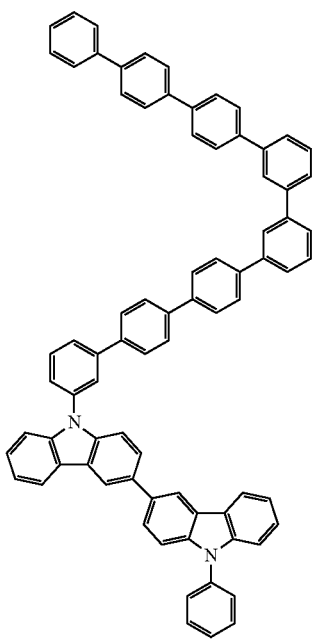
A486
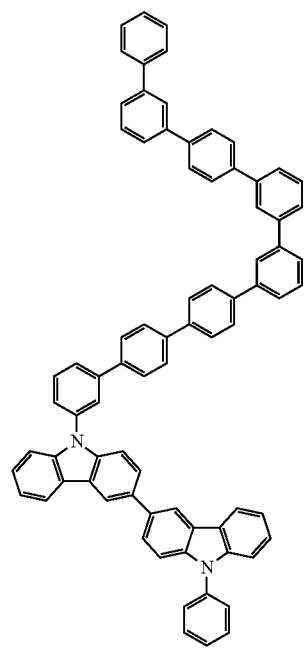
A487
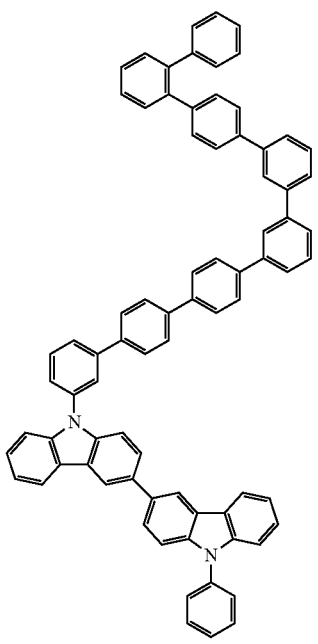

-continued
A488
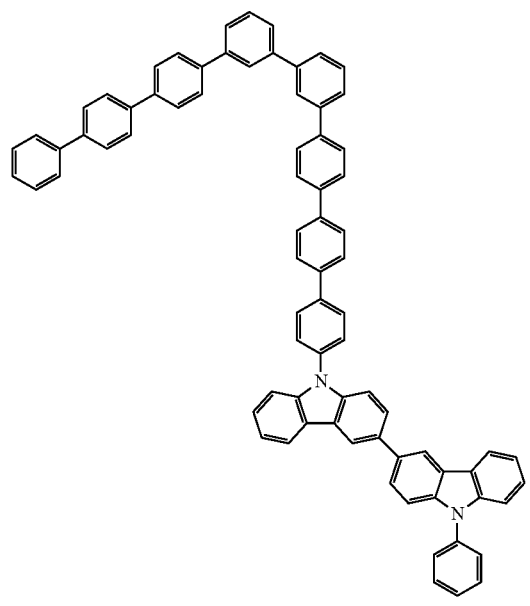
A489
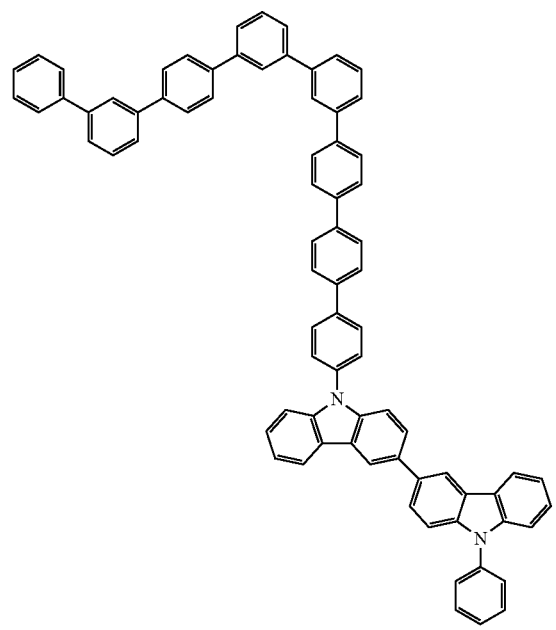
A490
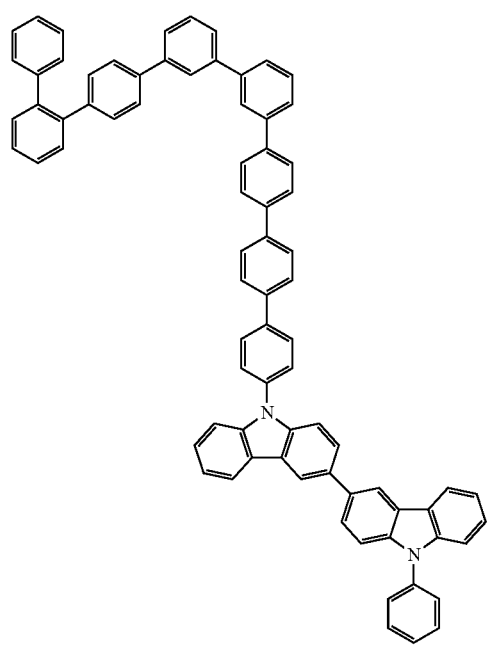
A491
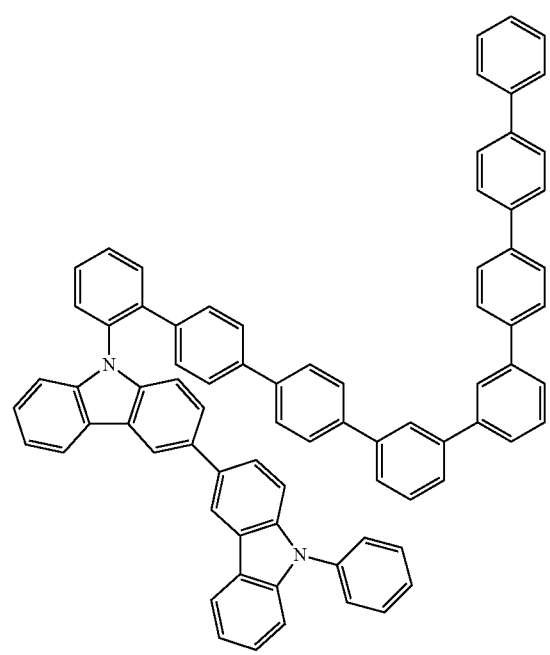

-continued
A492
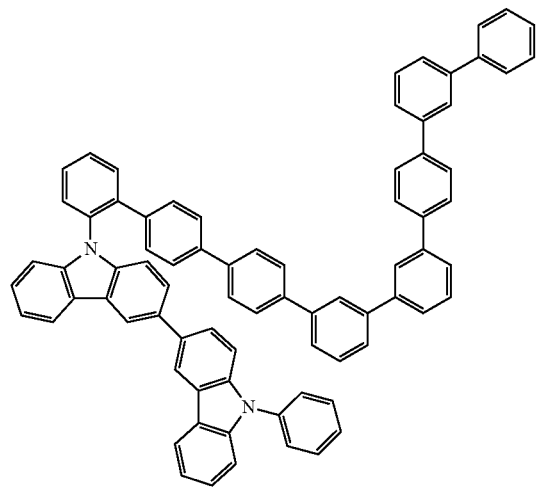
A493
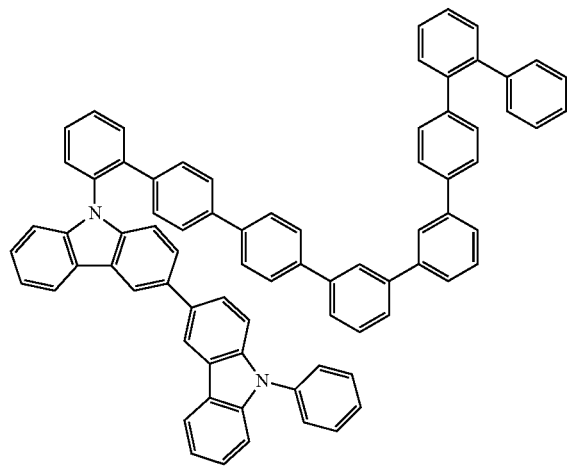
A494
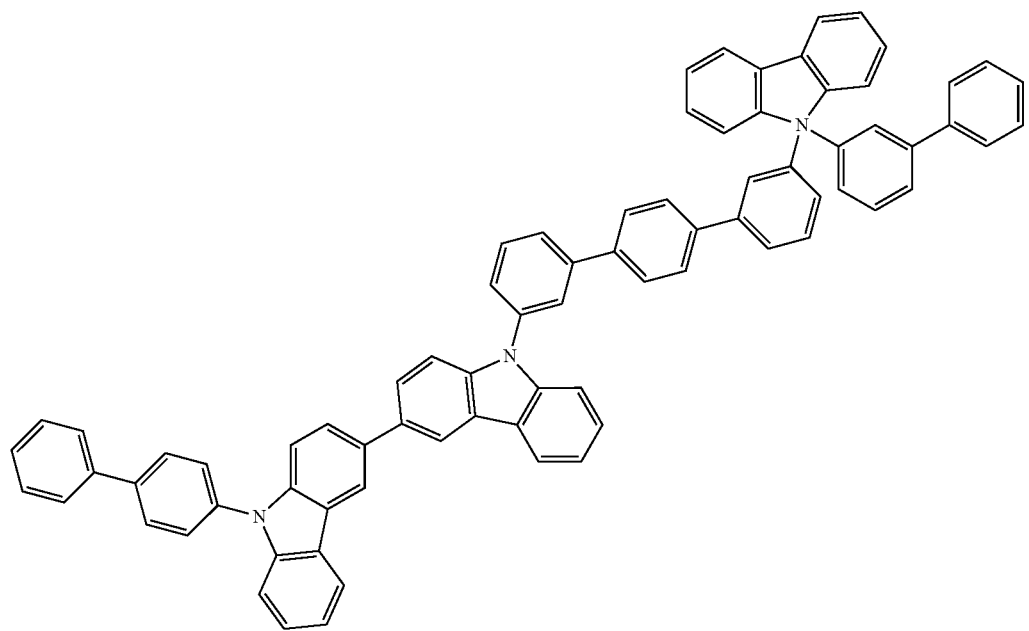

-continued

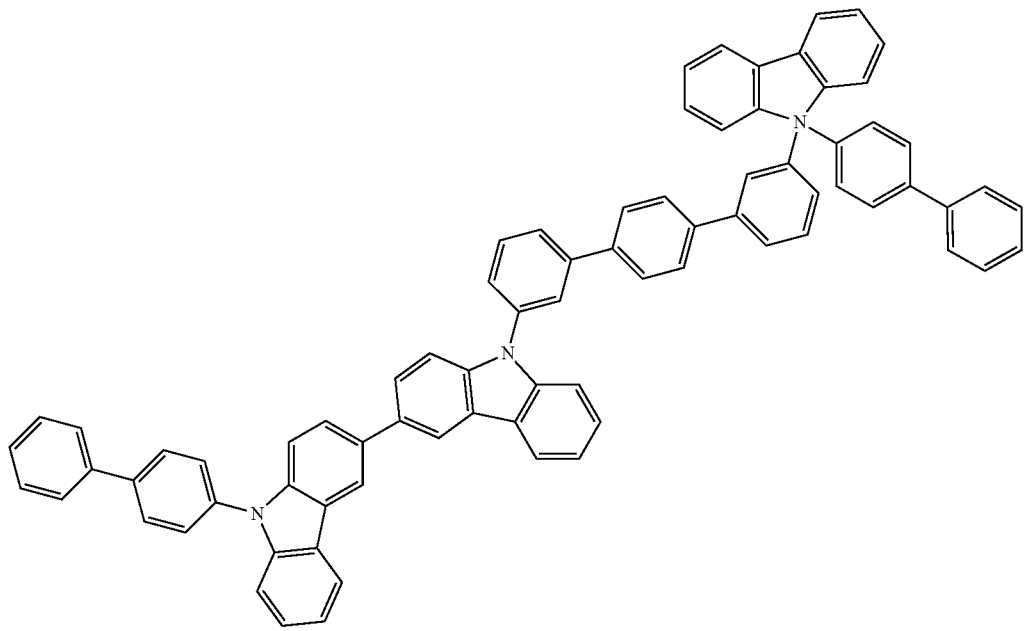

A495

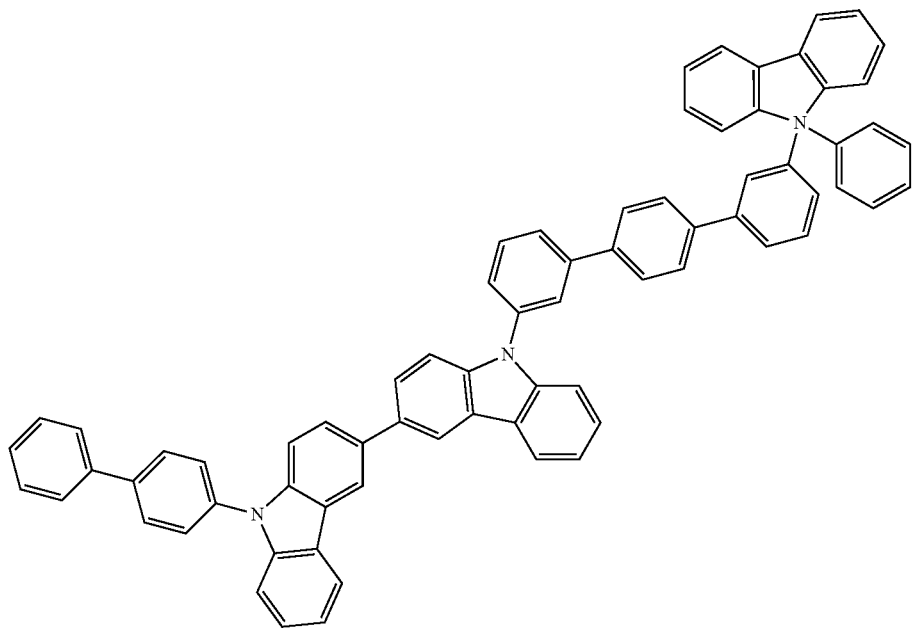

A496

14. A composition comprising at least one heterocyclic compound represented by Formula 1 of claim 1.

15. The composition of claim 14, further comprising one or more of a first compound containing a carbazole-based moiety, a third compound containing an m-phenyl moiety, or a combination thereof.

16. The composition of claim 14, further comprising a second compound comprising an azine-based moiety.

17. The composition of claim 14, further comprising a luminescent material.

18. The composition of claim 14, further comprising a solvent.

19. An organic light-emitting device comprising:
a first electrode;
a second electrode; and
an organic layer located between the first electrode and the second electrode and comprising an emission layer, wherein the organic layer comprises at least one heterocyclic compound represented by Formula 1 of claim 1.

20. The organic light-emitting device of claim 19, wherein the organic layer further comprises a luminescent material, and
the luminescent material emits light from a triplet exciton.

* * * * *